United States Patent
Brubaker et al.

(10) Patent No.: US 11,534,441 B2
(45) Date of Patent: Dec. 27, 2022

(54) MAP4K1 INHIBITORS

(71) Applicant: Blueprint Medicines Corporation, Cambridge, MA (US)

(72) Inventors: Jason D. Brubaker, Cambridge, MA (US); Chandrasekhar V. Miduturu, Cambridge, MA (US); Michael J. Burke, Cambridge, MA (US); Thomas A. Dineen, Cambridge, MA (US); Joseph L. Kim, Cambridge, MA (US); Joshua T. Close, Cambridge, MA (US); Emanuele Perola, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 127 days.

(21) Appl. No.: 17/149,302

(22) Filed: Jan. 14, 2021

(65) Prior Publication Data

US 2022/0323438 A1    Oct. 13, 2022

Related U.S. Application Data

(60) Provisional application No. 62/961,463, filed on Jan. 15, 2020.

(51) Int. Cl.
| | |
|---|---|
| *A61K 31/506* | (2006.01) |
| *C07D 471/04* | (2006.01) |
| *C07D 519/00* | (2006.01) |
| *C07D 401/12* | (2006.01) |
| *A61K 31/4725* | (2006.01) |
| *A61P 35/00* | (2006.01) |
| *A61K 31/4709* | (2006.01) |
| *A61K 31/4375* | (2006.01) |
| *A61K 31/497* | (2006.01) |
| *C07D 491/052* | (2006.01) |

(52) U.S. Cl.
CPC ........ *A61K 31/506* (2013.01); *A61K 31/4375* (2013.01); *A61K 31/4709* (2013.01); *A61K 31/4725* (2013.01); *A61K 31/497* (2013.01); *A61P 35/00* (2018.01); *C07D 401/12* (2013.01); *C07D 471/04* (2013.01); *C07D 491/052* (2013.01); *C07D 519/00* (2013.01)

(58) Field of Classification Search
None
See application file for complete search history.

(56) References Cited

U.S. PATENT DOCUMENTS

| 10,947,201 B2 | 3/2021 | Qian et al. |
| 2008/0306093 A1 | 12/2008 | Servant et al. |
| 2013/0225596 A1 | 8/2013 | Kai et al. |
| 2018/0282328 A1 | 10/2018 | Chan et al. |

FOREIGN PATENT DOCUMENTS

| WO | 2007/125405 A2 | 11/2007 |
| WO | 2009/103966 A1 | 8/2009 |
| WO | 2012/020742 A1 | 2/2012 |
| WO | 2013/083991 A1 | 6/2013 |
| WO | 2015/009812 A2 | 1/2015 |
| WO | 2016/061280 A1 | 4/2016 |
| WO | 2016/133935 A1 | 8/2016 |
| WO | 2019/014513 A1 | 1/2019 |
| WO | 2020/023551 A1 | 1/2020 |
| WO | 2021/133809 A1 | 7/2021 |

OTHER PUBLICATIONS

Degnan et al., Discovery of Orally Active Isofuranones as Potent, Selective Inhibitors of Hematopoetic Progenitor Kinase 1. ACS Med Chem Lett. Feb. 19, 2021;12(3):443-450, pre-publication edition.

You et al., Enhanced antitumor immunity by a novel small molecule HPK1 inhibitor. J Immunother Cancer. Jan. 2021;9(1):e001402, 19 pages.

*Primary Examiner* — Zinna Northington Davis
(74) *Attorney, Agent, or Firm* — McCarter & English, LLP; Steven G. Davis; Paul M. Zagar

(57) ABSTRACT

One embodiment of the disclosure is a compound represented by Formula I or a pharmaceutically acceptable salt thereof. The variables in Formula I are defined herein. Compounds of Formula I are selective MAP4K1 inhibitors, which can be used to treat a diseases or disorders in a subject that benefits from control of MAP4K1 activity.

25 Claims, No Drawings

Specification includes a Sequence Listing.

MAP4K1 INHIBITORS

CROSS-REFERENCE TO RELATED PATENT APPLICATIONS

This application claims the benefit of priority to U.S. Provisional Application No. 62/961,463, filed on Jan. 15, 2020, the entire contents of which is incorporated herein by reference.

SEQUENCE LISTING

This application contains a Sequence Listing which has been submitted electronically in ASCII format and is hereby incorporated by reference in its entirely. Said ASCII copy, created on Jan. 14, 2021, is named 131608-80102_SL.TXT and is 1,052 bytes in size.

FIELD

This application is directed to MAP4K1 inhibitors and methods for their use, such as to control the activity of MAP4K1 in a subject.

BACKGROUND

MAP4K1, also known as hematopoietic progenitor kinase 1 (HPK1), was originally cloned from hematopoietic progenitor cells (Hu, M. C., et al., Genes Dev, 1996. 10(18): p. 2251-64). MAP4K1 is of particular interest as a target, because it is predominantly expressed in hematopoietic cells such as T cells, B cells, macrophages, dendritic cells, neutrophils, and mast cells (Hu, M. C., et al, Genes Dev, 1996. 10(18): p. 2251-64; Kiefer, F., et al, EMBO J, 1996. 15(24): p. 7013-25). MAP4K1 kinase activity has been shown to be induced upon activation of T cell receptors (TCR) (Liou, J., et al., Immunity, 2000. 12(4): p. 399-408), B cell receptors (BCR) (Liou, J., et al., Immunity, 2000. 12(4): p. 399-408), transforming growth factor receptor (TGF-R) (Wang, W., et al, J Biol Chem, 1997. 272(36): p. 22771-5; Zhou, G., et al, J Biol Chem, 1999. 274(19): p. 13133-8), or $G_s$-coupled $PGE_2$ receptors (EP2 and EP4) (Ikegami, R, et al, J Immunol, 2001. 166(7): p. 4689-96). As such, MAP4K1 regulates diverse functions of various immune cells.

MAP4K1 is important in regulating the functions of various immune cells and it has been implicated in autoimmune diseases and anti-tumor immunity (Shui, J. W., et al, Nat Immunol, 2007. 8(1): p. 84-91; Wang, X., et al, J Biol Chem, 2012. 287(14): p. 11037-48). Those observations suggested that attenuation of MAP4K1 activity may contribute to autoimmunity in patients. Furthermore, MAP4K1 may also control anti-tumor immunity via T cell-dependent mechanisms. In the PGE2-producing Lewis lung carcinoma tumor model, the tumors developed more slowly in MAP4K1 knockout mice as compared to wild-type mice (see US 2007/0087988). In addition, it was shown that adoptive transfer of MAP4K1 deficient T cells was more effective in controlling tumor growth and metastasis than wild-type T cells (Alzabin, S., et al., Cancer Immunol Immunother, 2010. 59(3): p. 419-29). Similarly, bone marrow derived dendritic cells (BMDCs) from MAP4K1 knockout mice were more efficient to mount a T cell response to eradicate Lewis lung carcinoma as compared to wild-type BMDCs (Alzabin, S., et al., J Immunol, 2009. 182(10): p. 6187-94). Data obtained from MAP4K1 kinase dead mice demonstrated that MAP4K1 kinase activity is critical in conferring suppressive functions of MAP4K1 in a wide range of immune cells including CD4+, CD8+, DC, NK to T regulatory cells (Tregs) and inactivation of kinase domain was sufficient to elict robust anti-tumor immune responses. Liu et at, PLoS ONE 14(3):e0212670 https://doi.org/10.1371/journal.pone.0212670. Moreover, loss of MAP4K1 kinase function suppresses tumor growth in preclinical tumor models and therapeutic co-blockade of MAP4K1 kinase and PD-L1 enhances anti-tumor responses. Hernandez S. et al., Cell Reports 2018 25: p. 80-94. Recently presented results show tumor growth inhibition in a CT-26 syngeneic mouse model using a small molecule (Seungmook, L., Cancer research.AACR Journal, 2019, Abstract 4150). These data have validated MAP4K1 as a novel drug target for enhancing antitumor immunity. Accordingly, there is a need for new compounds that modulate MAP4K1 activity for the treatment of MAP4K1-dependent diseases or disorders such as cancer, viral infection, and other diseases and disorders.

SUMMARY

Provided herein are compounds and compositions which inhibit MAP4K1, thereby enhancing an immune response in a subject. For example, the $IC_{50}$ values for inhibition of MAP4K1 provided in Example 19 demonstrate that these compounds are potent inhibitors of MAP4K1. Compounds provided here in are selective inhibitors of MAP4K1. Also disclosed are methods of using the compounds and compositions described herein for treating cancer and viral infection One embodiment of the disclosure is a compound represented by Formula I:

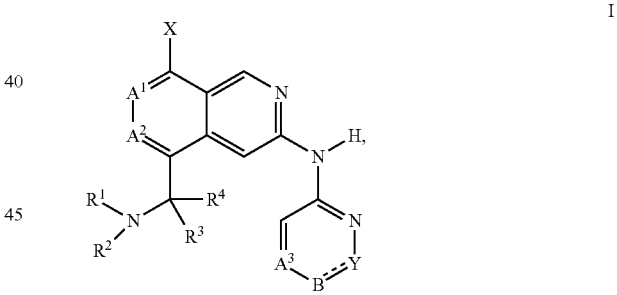

or a pharmaceutically acceptable salt thereof,
wherein:
$A^1$ and $A^2$ are selected from N and CH;
$A^3$ is selected from CH and N;
X is selected from $C_{1-3}$ alkyl, $OR^6$, $NHR^7$ and halogen;
B is selected from $CR^{11}$ and N, Y is selected from N and $CR^{12}$, and the bond between Y and B is a double bond; or
B is C(O), Y is $NR^{14}$, and the bond between Y and B is a single bond; or Y and B taken together form a 5 to 7-membered heterocycle or $C_{5-6}$ cycloalkyl, and the bond between Y and B is a double bond, wherein said heterocycle or cycloalkyl is optionally substituted with 1-6 $R^8$;
each $R^8$ is independently selected from $C_{1-3}$ alkyl and OH, or
  two $R^8$ attached to the same carbon form an oxo, or
  two $R^8$ attached to the same carbon atom taken together with the carbon atom to which they are attached a form a $C_{3-5}$ cycloalkyl, or two $R^8$ attached to two adjacent carbon atoms taken together with the two adjacent carbon atoms to which they are attached form a $C_{3-6}$ cycloalkyl, wherein said alkyl and cycloalkyl are optionally substituted with 1-6 halogen;

$R^1$ and $R^2$ are each independently selected from hydrogen, $C_{1-4}$ alkyl, $C_{3-5}$ cycloalkyl, and 3 to 5-membered heterocycle, wherein said alkyl and cycloalkyl are optionally substituted with OH, $C_{1-6}$ alkoxy or 1-6 halogen; or $R^1$ and $R^2$, taken together with the atoms to which they are attached, form a 4 to 6-membered heterocycle or $C_{3-6}$ cycloalkyl;

$R^3$ and $R^4$ are each independently selected from hydrogen, $C_{1-6}$ alkyl, $C_{1-6}$ alkyl substituted with $OR^{16}$, $C_{3-6}$ cycloalkyl and 4 to 6-membered heterocycle; or $R^3$ and $R^4$ taken together with the atoms to which they are attached, form a $C_{3-6}$ cycloalkyl or 4 to 6-membered heterocycle; or $R^1$ and $R^3$, taken together with the atoms to which they are attached, form a 3 to 6-membered heterocycle;

$R^6$ is selected from $C_{1-3}$ alkyl, $C_{3-6}$ cycloalkyl and 4 to 6-membered heterocycle, wherein said alkyl, cycloalkyl, and heterocycle are optionally substituted with 1-3 $R^9$;

$R^7$ is selected from hydrogen, $C_{1-3}$ alkyl, $C_{3-5}$ cycloalkyl and 4 to 6-membered heterocycle, wherein said alkyl, cycloalkyl, and heterocycle are optionally substituted with 1-3 $R^9$;

$R^9$ is selected from $C_{1-3}$ alkyl, $C_{3-6}$ cycloalkyl substituted with halogen, halogen, $SO_2Me$, $C_{1-3}$ alkoxy and OH;

$R^{11}$ is selected from hydrogen, COON, CN, halogen, and $C_{1-3}$ alkoxy;

$R^{12}$ is selected from $C_{1-5}$ alkyl, $C_{4-6}$ cycloalkyl, 3 to 6-membered heterocycle, $NHR^{13}$, $NR^{13}R^{13}$ and $OR^{13}$, wherein said alkyl, cycloalkyl or heterocycle is optionally substituted with OH, $NH_2$, 1-4 halogen or $R^{15}$;

each $R^{13}$ is independently selected from $C_{1-6}$ alkyl and $C_{3-6}$ cycloalkyl, wherein said alkyl or cycloalkyl is optionally substituted with halogen;

$R^{14}$ is selected from $C_{1-6}$ alkyl, $C_{3-6}$ cycloalkyl and 4 to 6-membered heterocycle, wherein said alkyl, cycloalkyl or heterocycle is optionally substituted with 1-6 halogen;

$R^{15}$ is OH, $C_{1-3}$ alkyl or $C_{3-5}$ cycloalkyl; and $R^{16}$ is H or $C_{1-3}$ alkyl.

Another embodiment of the disclosure is a pharmaceutical composition comprising a pharmaceutically acceptable carrier or excipient and a compound disclosed herein or a pharmaceutically acceptable salt thereof.

Another embodiment of the disclosure is a method of treating a MAP4K1-dependent disorder or disease (e.g., treating a cancer or viral infection), comprising administering to the subject an effective amount of a compound disclosed herein or a pharmaceutically acceptable salt thereof or a pharmaceutical composition comprising the compound(s).

Another embodiment of the disclosure is the use of a compound disclosed herein or a pharmaceutically acceptable salt thereof or a pharmaceutical composition comprising the compound(s), for the preparation of a medicament for treating a MAP4K1-dependent disorder or disease (e.g., treating a cancer or viral infection).

Another embodiment of the disclosure is a compound disclosed herein or a pharmaceutically acceptable salt thereof or a pharmaceutical composition comprising the compound(s), for use in treating a MAP4K1-dependent disorder or disease (e.g., treating a cancer or viral infection).

DETAILED DESCRIPTION

The disclosed compounds are MAP4K1 inhibitors, which can be used for treating a MAP4K1-dependent disorder or disease. Such diseases or disorders include cancer and viral infection.

Compound Embodiments

Example embodiments include:

First embodiment: a compound represented by Formula I, or a pharmaceutically acceptable salt thereof. The variables in Formula I are described above in the summary.

Second embodiment: a compound represented by Formula I, or a pharmaceutically acceptable salt thereof, wherein:

X is selected from $OR^6$, $NHR^7$ and halogen;

$R^3$ and $R^4$ are each independently selected from hydrogen, $C_{1-6}$ alkyl substituted with OH, $C_{1-6}$ alkyl, $C_{3-6}$ cycloalkyl and 4 to 6-membered heterocycle; or $R^3$ and $R^4$, taken together with the atoms to which they are attached, form a $C_{3-6}$ cycloalkyl or 4 to 6-membered heterocycle; or $R^1$ and $R^3$, taken together with the atoms to which they are attached, form a 3 to 6-membered heterocycle; and the remainder of the variables in Formula I are described above in the first embodiment.

Third embodiment: a compound represented by Formula I, or a pharmaceutically acceptable salt thereof, wherein:

$R^1$ and $R^2$ are each independently selected from hydrogen, $C_{1-4}$ alkyl optionally substituted with OH, cyclobutyl, and oxetanyl;

$R^3$ and $R^4$ are each independently selected from hydrogen, $C_{1-6}$ alkyl and $C_{3-6}$ cycloalkyl; or $R^1$ and $R^3$, taken together with the atoms to which they are attached, form a 3 to 6-membered heterocycle;

each $R^8$ is independently $C_{1-3}$ alkyl; or two $R^8$ attached to the same carbon form an oxo; or two $R^8$ attached to the same carbon atom taken together with the carbon atom to which they are attached form a $C_{3-5}$ cycloalkyl; or two $R^8$ attached to two adjacent carbon atoms taken together with the two adjacent carbon atoms to which they are attached form $C_{3-6}$ cycloalkyl;

$R^6$ is selected from $C_{1-3}$ alkyl and $C_{3-6}$ cycloalkyl, wherein said alkyl and cycloalkyl are optionally substituted with 1 to 3 $R^9$;

$R^7$ is selected from $C_{1-3}$ alkyl and $C_{3-6}$ cycloalkyl;

$R^{11}$ is selected from COOH and CN;

$R^{12}$ is selected from $C_{1-5}$ alkyl, $C_{4-6}$ cycloalkyl, 3 to 6-membered heterocycle and $OR^{13}$, wherein said alkyl, cycloalkyl, or heterocycle is optionally substituted with OH, $NH_2$, 1 to 4 halogen or $R^{15}$;

$R^{13}$ is $C_{1-6}$ alkyl;

$R^{14}$ is $C_{1-6}$ alkyl; and $R^{15}$ is $C_{1-3}$ alkyl; and the remainder of the variables in Formula I are described above in the first and/or second embodiments.

Fourth embodiment: a compound represented by Formula II:

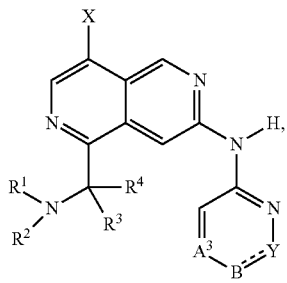

II or a pharmaceutically acceptable salt thereof. The variables in Formula II are described above in the first, second and/or the third embodiments.

Fifth embodiment: a compound represented by Formula III:

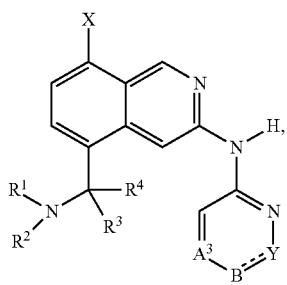

III or a pharmaceutically acceptable salt thereof. The variables in Formula III are described above in the first, second and/or the third embodiments.

Sixth embodiment: a compound represented by Formula IV:

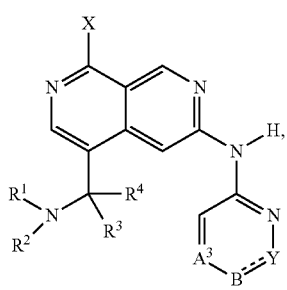

IV or a pharmaceutically acceptable salt thereof. The variables in Formula IV are described above in the first, second and/or the third embodiments.

Seventh embodiment: a compound represented by Formula V or VI:

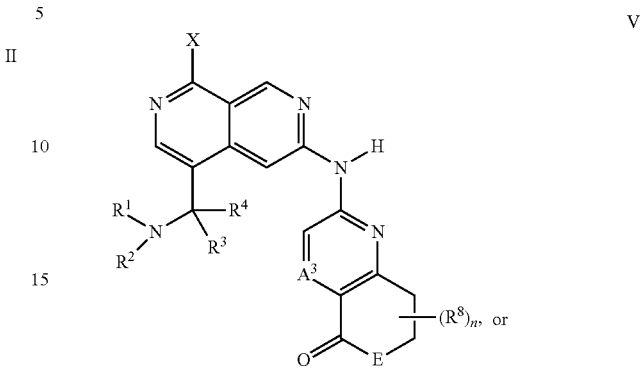

V

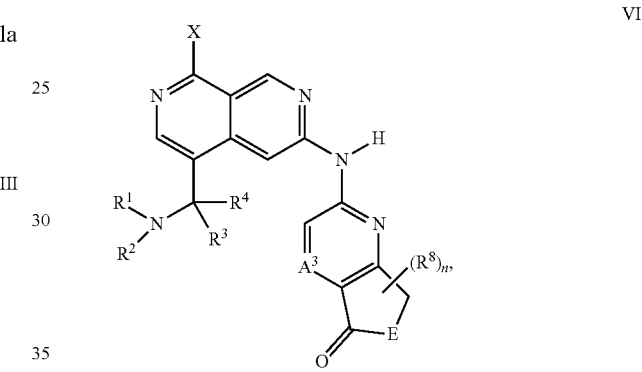

VI or a pharmaceutically acceptable salt thereof, wherein E is $CH_2$, NH, or O; each $R^8$ is $C_{1-3}$ alkyl, and n is 0 to 4; two $R^8$ attached to the same carbon atom taken together with the carbon atom to which they are attached form a $C_{3-5}$ cycloalkyl; or two $R^8$ attached to two adjacent carbon atoms taken together with the two adjacent carbon atoms to which they are attached form a $C_{4-6}$ cycloalkyl. Alternatively, E is NH. In another alternative, E is O. The remainder of the variables in Formulas V and VI are described above in the first, second and/or the third embodiments.

Eighth embodiment: a compound represented by Formula V(A) or VI(A):

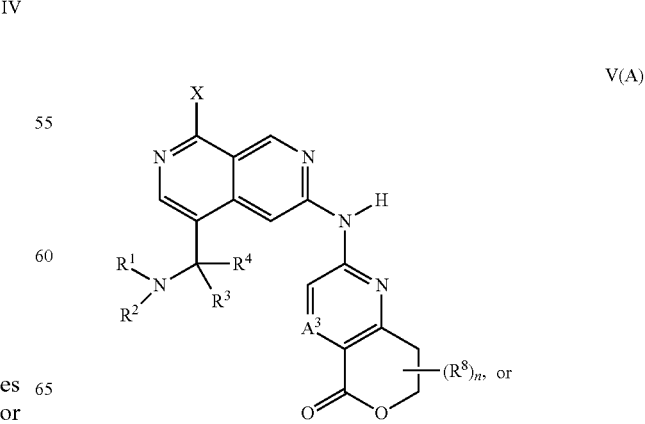

V(A)

-continued

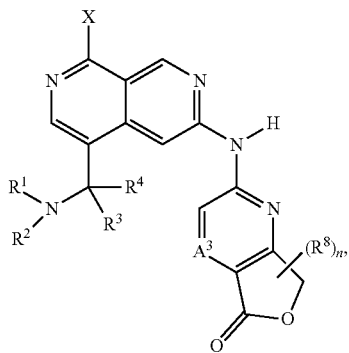

VI(A)

or a pharmaceutically acceptable salt thereof. The variables in Formulas V(A) and VI(A) are described above in the first, second, third and/or the seventh embodiments.

Ninth embodiment: a compound represented by Formula V(B) or VI(B):

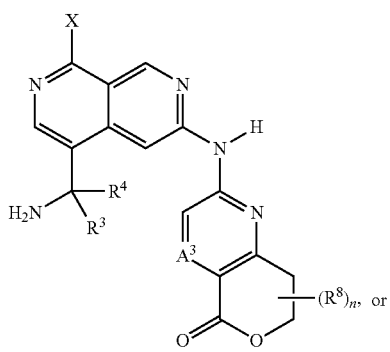

V(B)

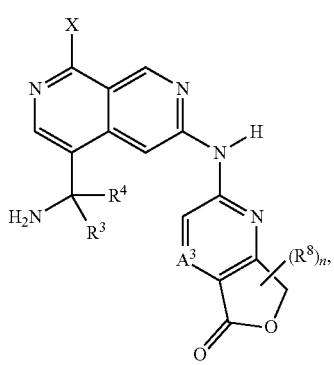

VI(B)

or a pharmaceutically acceptable salt thereof. The variables in Formulas V(B) and VI(B) are described above in the first, second, third and/or the seventh embodiments.

Tenth embodiment: a compound represented by Formula V(C) or VI(C):

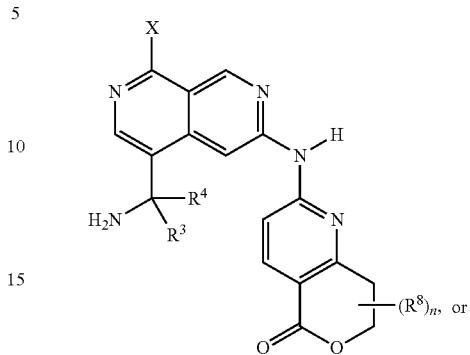

V(C)

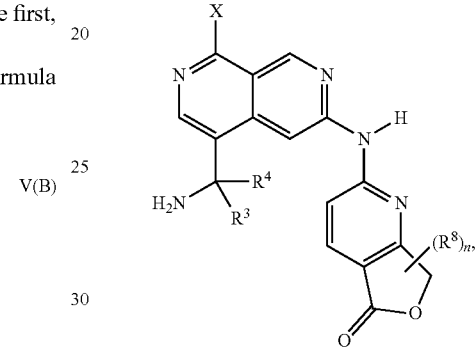

VI(C)

or a pharmaceutically acceptable salt thereof. The variables in Formulas V(C) and VI(C) are described above in the first, second, third and/or the seventh embodiments.

Eleventh embodiment: a compound represented by any one of Formulas I, V, VI, V(A), VI(A), V(B), VI(B), V(C) and VI(C), or a pharmaceutically acceptable salt thereof, wherein $R^8$ is methyl and n is 0, 1, 2, 3 or 4. Alternatively, $R^8$ is methyl and n is 1; $R^8$ is methyl and n is 2; $R^8$ is methyl and n is 3; $R^8$ is methyl and n is 4; $R^8$ is ethyl and n is 0, 1, 2, or 3; $R^8$ is ethyl and n is 1; $R^8$ is ethyl and n is 2; or $R^8$ is ethyl and n is 3 The remainder of the variables in Formulas I, V, VI, V(A), VI(A), V(B), VI(B), V(C) and VI(C) are as described above in the first, second, third and/or the seventh embodiments.

Twelfth embodiment: a compound represented by any one of Formulas I, V, VI, V(A), VI(A), V(B), VI(B), V(C) and VI(C), or a pharmaceutically acceptable salt thereof, wherein two $R^8$ attached to the same carbon atom taken together with the carbon atom to which they are attached form a cyclopropyl; or two $R^8$ attached to two adjacent carbon atoms taken together with the two adjacent carbon atoms to which they are attached form a cyclopentyl. Alternatively, two $R^8$ attached to the same carbon atom taken together with the carbon atom to which they are attached form a cyclobutyl. In another alternative, two $R^8$ attached to the same carbon atom taken together with the carbon atom to which they are attached form a cyclopentyl. In another alternative, two $R^8$ attached to two adjacent carbon atoms taken together with the two adjacent carbon atoms to which they are attached form a cyclobutyl. In yet another embodiment, two $R^8$ attached to two adjacent carbon atoms taken together with the two adjacent carbon atoms to which they are attached form a cyclopropyl. The remainder of the variables in Formulas I, V, VI, V(A), VI(A), V(B), VI(B), V(C) and VI(C) are as described above in the first, second, third and/or the seventh embodiments.

Thirteenth embodiment: a compound represented by Formula VII, VIII or IX:

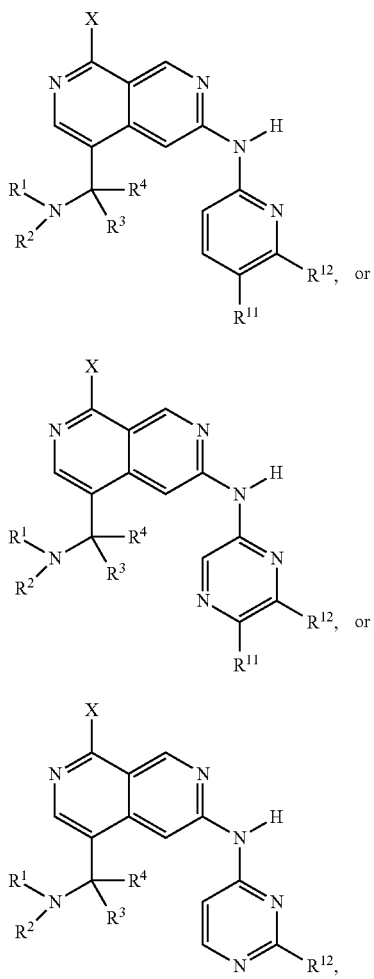

VII

VIII

IX or a pharmaceutically acceptable salt thereof. The variables in Formulas VII, VIII and IX are as described above in the first, second and/or the third embodiments.

Fourteenth embodiment: a compound represented by Formula VII(A), VIII(A) or IX(A):

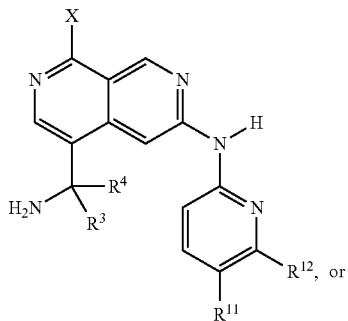

VII(A)

VIII(A)

IX(A)

or a pharmaceutically acceptable salt thereof. The variables in Formulas VII(A), VIII(A) and IX(A) are as described above in the first, second and/or the third embodiments.

Fifteenth embodiment: a compound represented by any one of Formulas I-IV, VII-IX and VII(A)-IX(A), or a pharmaceutically acceptable salt thereof, wherein $R^{11}$ is CN. The remainder of the variables in Formulas I-IV, VII-IX and VII(A)-IX(A) are as described above in the first, second and/or the third embodiments.

Sixteenth embodiment: a compound represented by any one of Formulas I-IV, VII-IX and VII(A)-IX(A), or a pharmaceutically acceptable salt thereof, wherein $R^{12}$ is selected from isopropyl, fluoropropyl, trifluoroisopropyl, isobutyl, tert-butyl, isopropyloxy, methylpyrrolidine, methylazetidine, and hydroxycyclohexyl. The remainder of the variables in Formulas I-IV, VII-IX and VII(A)-IX(A) are as described above in the first, second, third and/or the fifteenth embodiments.

Seventeenth embodiment: a compound represented by Formula X:

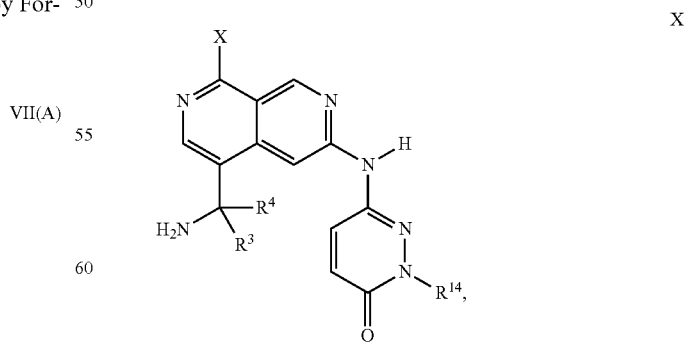

X or a pharmaceutically acceptable salt thereof. The variables in Formula X are as described above in the first, second and/or the third embodiments.

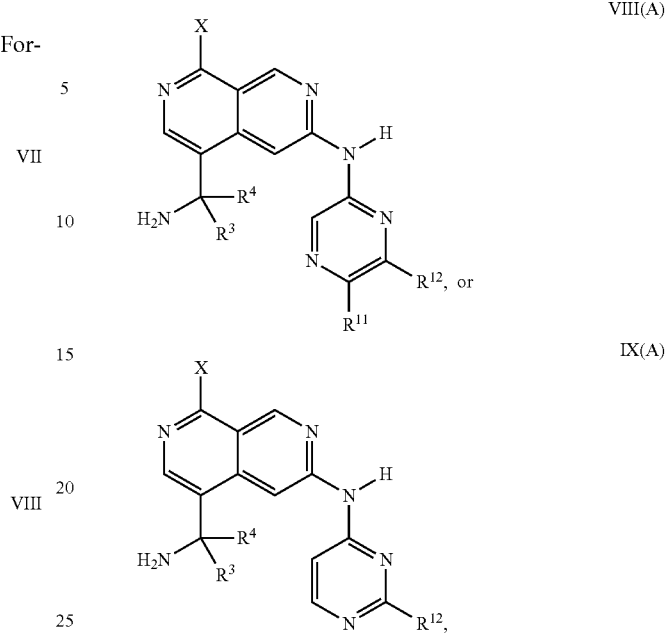

Eighteenth embodiment: a compound represented by any one of Formulas I-IV and X, or a pharmaceutically acceptable salt thereof, wherein $R^{14}$ is isobutyl. The remainder of the variables in Formulas I-IV and X are as described above in the first, second and/or the third embodiments.

Nineteenth embodiment: a compound represented by any one of Formulas I-IV, V(A)-V(C), VI(A)-VI(C), VII-IX, VII(A)-IX(A) and X, or a pharmaceutically acceptable salt thereof, wherein X is $OR^6$, and $R^6$ is selected from methyl, ethyl, propyl, isopropyl, trifluoroethyl, trifluoroisopropyl, difluoroethyl, difluoropropyl, difluoroisopropyl, oxetanyl, tetrahydrofuranyl, cyclobutyl, and cyclopropyl, wherein cyclopropyl is optionally substituted with methyl or one or two fluoro, wherein cyclobutyl is optionally substituted with OH, wherein oxetanyl is optionally substituted with methyl. The remainder of the variables in Formulas I-IV and X are as described above in the first, second, third, seventh, eleventh, twelfth, fifteenth, sixteenth and/or the eighteenth embodiments.

Twentieth embodiment: a compound represented by any one of Formulas I-IV, V(A)-V(C), VI(A)-VI(C), VII-IX, VII(A)-IX(A) and X, or a pharmaceutically acceptable salt thereof, wherein X is $OR^6$, and $R^6$ is selected from methyl, ethyl, propyl, isopropyl, trifluoroethyl, trifluoroisopropyl, difluoroethyl, difluoropropyl, difluoroisopropyl, oxetanyl, tetrahydrofuranyl, cyclobutyl, and cyclopropyl, wherein cyclopropyl is optionally substituted with methyl or one or two fluoro. Alternatively, $R^6$ is methyl; in another alternative, $R^6$ is ethyl; in another alternative, $R^6$ is trifluoroethyl; in another alternative, $R^6$ is difluoroethyl; in another alternative, $R^6$ is propyl; in another alternative, $R^6$ is difluoropropyl; in another alternative, $R^6$ is isopropyl; in another alternative, $R^6$ is trifluoroisopropyl; in another alternative, $R^6$ is difluoroisopropyl; in another alternative, $R^6$ is methylsulfonylethyl; in another alternative, $R^6$ is cyclopropyl; in another alternative, $R^6$ is cyclobutyl; in another alternative, $R^6$ is optionally substituted with $R^9$, wherein $R^9$ is $C_{1-3}$ alkyl, $C_{3-6}$ cycloalkyl substituted with halogen, halogen, $C_{1-3}$alkoxy, and OH; in another alternative, $R^6$ is cyclopropyl substituted with $R^9$, wherein $R^9$ is methyl or one or two fluoro; in another alternative $R^6$ is oxetanyl; in another alternative $R^6$ is tetrahydropyranyl; in another alternative $R^6$ is tetrahydrofuranyl; and in yet another alternative $R^6$ is cyclopropyl substituted with methyl. The remainder of the variables in Formulas I-IV, V(A)-V(C), VI(A)-VI(C), VII-IX, VII(A)-IX(A) and X are as described above in the first, second, third, seventh, eleventh, twelfth, fifteenth, sixteenth and/or eighteenth embodiments.

Twenty-first embodiment: a compound represented by any one of Formulas I-IV, V(A)-V(C), VI(A)-VI(C), VII-IX, VII(A)-IX(A) and X, or a pharmaceutically acceptable salt thereof, wherein X is $NHR^7$, and $R^7$ is selected from methyl, ethyl, cyclopropyl and cyclobutyl. The remainder of the variables in Formulas I-IV, V(A)-V(C), VI(A)-VI(C), VII-IX, VII(A)-IX(A) and X are described above in the first, second, third, seventh, eleventh, twelfth, fifteenth, sixteenth and/or eighteenth embodiments.

Twenty-second embodiment: a compound represented by any one of Formulas I-IV, V(A)-V(C), VI(A)-VI(C), VII-IX, VII(A)-IX(A) and X, or a pharmaceutically acceptable salt thereof, wherein X is methyl. The remainder of the variables in Formulas I-IV, V(A)-V(C), VI(A)-VI(C), VII-IX, VII(A)-IX(A) and X are described above in the first, second, third, seventh, eleventh, twelfth, fifteenth, sixteenth and/or eighteenth embodiments.

Twenty-third embodiment: a compound represented by any one of Formulas I-IV, V(A)-V(C), VI(A)-VI(C), VII-IX, VII(A)-IX(A) and X, or a pharmaceutically acceptable salt thereof, wherein $R^3$ and $R^4$ are each independently selected from hydrogen, methyl, methyl substituted with $OCH_3$, ethyl, hydroxymethyl, cyclopropyl and cyclobutyl. The remainder of the variables in Formulas I-IV, V(A)-V(C), VI(A)-VI(C), VII-IX, VII(A)-IX(A) and X are described above in the first, second, third, seventh, eleventh, twelfth, fifteenth, sixteenth, eighteenth, nineteenth, twentieth, twentyfirst and/or twentysecond embodiments.

Twenty-fourth embodiment: a compound represented by any one of Formulas I-IV, V(A)-V(C), VI(A)-VI(C), VII-IX, VII(A)-IX(A) and X, or a pharmaceutically acceptable salt thereof, wherein $R^3$ and $R^4$ are each independently selected from hydrogen, methyl, hydroxymethyl, ethyl, cyclopropyl and cyclobutyl. Alternatively, $R^3$ and $R^4$ are each independently selected from $C_{1-6}$ alkyl and $C_{3-6}$cycloalkyl; in another alternative, $R^3$ and $R^4$ are each independently selected from $C_{1-3}$ alkyl and cyclopropyl; in another alternative, $R^3$ is methyl and $R^4$ is methyl; in another alternative, $R^3$ is H and $R^4$ is methyl; in another alternative $R^3$ is ethyl and $R^4$ is methyl; in another alternative $R^3$ is $CH_2OH$ and $R^4$ is methyl; in another alternative, $R^3$ is methyl and $R^4$ is cyclopropyl; in another alternative, and in yet another alternative $R^3$ is methyl and $R^4$ is cyclobutyl. The remainder of the variables in Formulas I-IV, V(A)-V(C), VI(A)-VI(C), VII-IX, VII(A)-IX(A) and X are described above in the first, second, third, seventh, eleventh, twelfth, fifteenth, sixteenth, eighteenth, nineteenth, twentieth and/or twentyfirst embodiments.

The disclosure also includes the compounds depicted in Table 1 and prepared in the Exemplification. The synthetic protocol used to prepare compounds in Table 1 is listed in the last column of Table 1 and full details for each synthetic protocol are described in Schemes 1-17 in the General Synthetic Methods and Intermediates section.

TABLE 1

| # | Structure | LCMS (M + 1) | NMR | Synthetic Protocol |
|---|---|---|---|---|
| 1 | | 357 | ¹H-NMR (400 MHz, CD$_3$OD): δ ppm 9.23 (br s, 1H), 8.74 (br s, 1H), 8.30 (br s, 1H), 8.09 (br d, J = 3.2 Hz, 1H), 7.08 (br s, 1H), 4.60 (br s, 1H), 4.02 (br d, J = 4.0 Hz, 3H), 1.84-1.61 (m, 6H), 1.49 (br s, 3H), 1.19 (br s, 1H) | 1 Second eluting isomer |
| 2 | 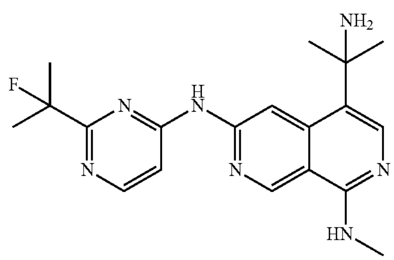 [SMILES: CNc1ncc(C(C)(C)N)c2cc(Nc3ccnc(C(C)(C)F)n3)ncc12] | 366 | ¹H-NMR (400 MHz, CD$_3$OD): δ ppm 9.56 (s, 1H), 8.53 (d, J = 7.2 Hz, 1H), 8.39 (d, J = 6.8 Hz, 1H), 8.05 (s, 1H), 7.61 (s, 1H), 3.25 (s, 3H), 1.97 (s, 6H), 1.50 (s, 9H) | 3 |
| 3 | 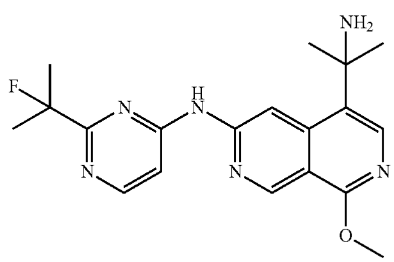 [SMILES: COc1ncc(C(C)(C)N)c2cc(Nc3ccnc(C(C)(C)F)n3)ncc12] | 367 | ¹H-NMR (400 MHz, CD$_3$OD): δ ppm 9.39 (s, 1H), 8.58 (s, 1H), 8.34 (d, J = 5.6 Hz, 1H), 8.19 (s, 1H), 7.47 (d, J = 6.0 Hz, 1H), 4.12 (s, 3H), 1.76 (s, 6H), 1.45 (s, 9H). | 2 |
| 4 | 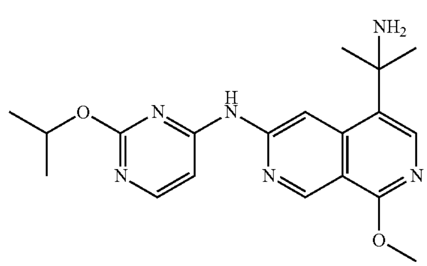 [SMILES: COc1ncc(C(C)(C)N)c2cc(Nc3ccnc(OC(C)C)n3)ncc12] | 369 | ¹H-NMR (400 MHz, CD$_3$OD): δ ppm 9.51 (s, 1H), 8.39 (s, 1H), 8.25 (d, J = 6.8 Hz, 1H), 8.05 (s, 1H), 7.74-7.67 (m, 1H), 5.41-5.48 (m, 1H), 4.18 (s, 3H), 2.00 (s, 6H), 1.46 (d, J = 6.4 Hz, 6H) | 3 |

TABLE 1-continued

| # | Structure | LCMS (M + 1) | NMR | Synthetic Protocol |
|---|---|---|---|---|
| 5 | 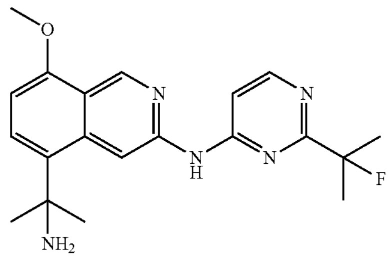 [SMILES: COc1ccc(C(C)(C)N)c2cc(Nc3ccnc(C(C)(C)F)n3)ncc12] | 370 | ¹H-NMR (400 MHz, CD₃OD): δ ppm 9.42 (s, 1H), 9.03 (s, 1H), 8.35 (d, 1H, J = 6.0 Hz), 7.76 (d, 1H, J = 8.4 Hz), 7.28 (d, 1H, J = 5.6 Hz), 6.85 (d, 1H, J = 8.4 Hz), 4.05 (s, 3H), 1.80 (t, 13H, J = 10.8 Hz). | 4 |
| 6 | 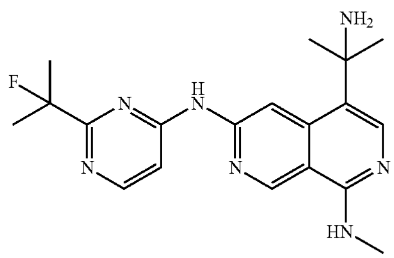 [SMILES: CNc1ncc(C(C)(C)N)c2cc(Nc3ccnc(C(C)(C)F)n3)ncc12] | 370 | ¹H-NMR (400 MHz, CD₃OD): δ ppm 9.22 (s, 1H), 8.89 (s, 1H), 8.37 (d, J = 6.0 Hz, 1H), 8.04 (s, 1H), 7.32 (d, J = 6.0 Hz, 1H), 3.05 (s, 3H), 1.81 (s, 3H), 1.76 (s, 3H), 1.74 (s, 6H) | 5 |
| 7 | 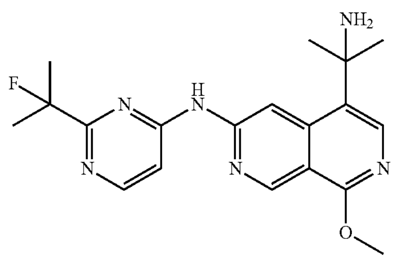 [SMILES: COc1ncc(C(C)(C)N)c2cc(Nc3ccnc(C(C)(C)F)n3)ncc12] | 371 | ¹H-NMR (400 MHz, CD₃OD): δ ppm 9.38 (s, 1H), 9.12 (s, 1H), 8.40 (d, J = 6.0 Hz, 1H), 8.14 (s, 1H), 7.25 (d, J = 6.0 Hz, 1H), 4.13 (s, 3H), 1.83 (s, 6H), 1.82 (s, 3H), 1.77 (s, 3H) | 3 |
| 8 | 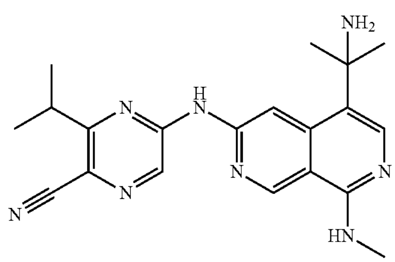 [SMILES: CNc1ncc(C(C)(C)N)c2cc(Nc3cnc(C#N)c(C(C)C)n3)ncc12] | 377 | ¹H-NMR (400 MHz, CD₃OD): δ ppm 9.49 (s, 1H), 9.08 (s, 1H), 8.28 (s, 1H), 7.56 (s, 1H), 3.55-3.46 (m, 1H), 3.24 (s, 3H), 2.00 (s, 6H), 1.42 (d, J = 7.2 Hz, 6H) | 6 |
| 9 | 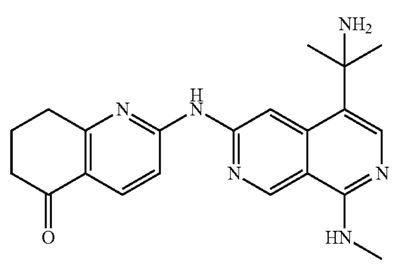 [SMILES: CNc1ncc(C(C)(C)N)c2cc(Nc3ccc4c(n3)CCCC4=O)ncc12] | 378 | ¹H-NMR (400 MHz, CD₃OD): δ ppm 9.52 (s, 1H), 9.32 (d, J = 0.8 Hz, 1H), 8.20 (s, 1H), 8.12 (d, J = 8.8 Hz, 1H), 7.07 (d, J = 8.8 Hz, 1H), 4.13 (s, 3H), 3.16 (t, J = 6.0 Hz, 2H), 2.73-2.62 (m, 2H), 2.22 (m, 2H), 1.84 (s, 6H) | 3 |
| 10 | 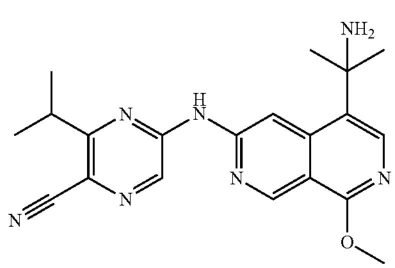 [SMILES: COc1ncc(C(C)(C)N)c2cc(Nc3cnc(C#N)c(C(C)C)n3)ncc12] | 378 | ¹H-NMR (400 MHz, CD₃OD): δ ppm 9.49 (s, 1H), 8.81 (s, 1H), 8.49 (s, 1H), 8.00 (s, 1H), 4.72-4.63 (m, 1H), 4.18 (s, 3H), 3.57-3.45 (m, 1H), 2.03 (s, 6H), 1.44 (d, J = 7.2 Hz, 6H) | 3 |

TABLE 1-continued

| # | Structure | LCMS (M + 1) | NMR | Synthetic Protocol |
|---|---|---|---|---|
| 11 | 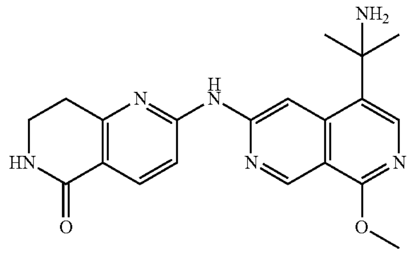 [SMILES: COc1ncc(C(C)(C)N)c2cc(Nc3ccc4c(n3)CCNC4=O)ncc12] | 379 | ¹H-NMR (400 MHz, CD₃OD): δ ppm 9.44 (s, 1H), 9.34 (s, 1H), 8.18 (s, 1H), 8.12 (d, J = 8.8 Hz, 1H), 7.15 (d, J = 8.8 Hz, 1H), 4.14 (s, 3H), 3.64 (t, J = 6.8 Hz, 2H), 3.17 (t, J = 6.8 Hz, 2H), 1.83 (s, 6H) | 3 |
| 12 | 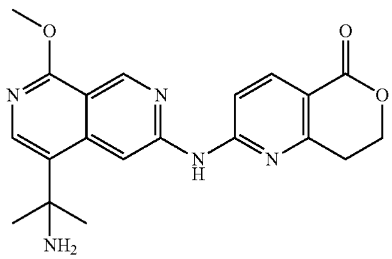 [SMILES: COc1ncc(C(C)(C)N)c2cc(Nc3ccc4c(n3)CCOC4=O)ncc12] | 380 | ¹H NMR (400 MHz, DMSO-d₆): δ ppm 10.71 (s, 1H), 9.61 (s, 1H), 9.30 (s, 1H), 8.20 (s, 1H), 9.09 (d, J = 8.8 Hz, 1H), 7.30 (d, J = 8.8 Hz, 1H), 4.59 (t, J = 6.0 Hz, 2H), 4.06 (s, 3H), 3.16 (t, J = 5.6 Hz, 2H), 1.91 (s, 2H), 1.69 (s, 6H) | 3 |
| 13 | 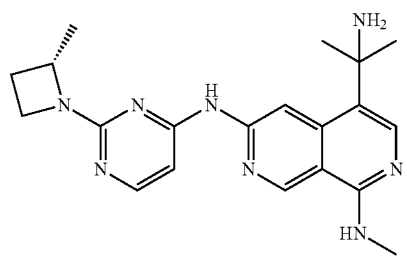 [SMILES: CNc1ncc(C(C)(C)N)c2cc(Nc3ccnc(N4CC[C@@H]4C)n3)ncc12] | 380 | ¹H-NMR (400 MHz, CD₃OD): δ ppm 9.34 (s, 1H), 8.59 (s, 1H), 8.17 (s, 1H), 7.98 (d, J = 5.6 Hz, 1H), 6.74 (d, J = 5.6 Hz, 1H), 4.60-4.51 (m, 1H), 4.23-4.15 (m, 1H), 4.11 (s, 3H), 4.08-4.00 (m, 1H), 2.58-2.47 (m, 1H), 2.05-1.95 (m, 1H), 1.73 (d, J = 1.6 Hz, 6H), 1.51 (d, J = 6.4 Hz, 3H) | 3 |
| 14 | Or | 383 | ¹H-NMR (400 MHz, CD₃OD): δ ppm 9.36 (s, 1H), 8.34 (s, 1H), 8.11 (s, 1H), 7.65 (d, J = 9.6 Hz, 1H), 7.01 (d, J = 9.6 Hz, 1H), 5.18-5.09 (m, 1H), 4.13 (s, 1H), 2.16-2.04 (m, 1H), 1.85 (d, J = 3.6 Hz, 6H), 1.83-1.79 (m, 1H), 1.47 (d, J = 6.4 Hz, 3H), 0.88 (t, J = 7.2 Hz, 3H) | 3 Intermediate 3 |
| 15 | 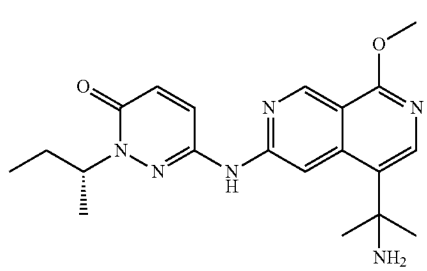 | 383 | ¹H-NMR (400 MHz, CD₃OD): δ ppm 9.36 (s, 1H), 8.34 (s, 1H), 8.11 (s, 1H), 7.65 (d, J = 9.6 Hz, 1H), 7.01 (d, J = 9.6 Hz, 1H), 5.18-5.09 (m, 1H), 4.13 (s, 1H), 2.16-2.04 (m, 1H), 1.85 (d, J = 3.6 Hz, 6H), 1.83-1.79 (m, 1H), 1.47 (d, J = 6.4 Hz, 3H), 0.88 (t, J = 7.2 Hz, 3H) | 3 Intermediate 4 |

TABLE 1-continued

| # | Structure | LCMS (M + 1) | NMR | Synthetic Protocol |
|---|---|---|---|---|
| | Or (structure) | | | |
| 16 | (structure) | 385 | ¹H-NMR (400 MHz, CD$_3$OD): δ ppm 9.39 (s, 1H), 9.08 (s, 1H), 8.39 (d, J = 6.0 Hz, 1H), 8.17 (s, 1H), 7.28 (d, J = 5.6 Hz, 1H), 4.60-4.53 (m, 2H), 1.82 (s, 3H), 1.77 (s, 9H), 1.51 (t, J = 6.8 Hz, 3H) | 3 |
| 17 | (structure) | 385 | ¹H-NMR (400 MHz, CD$_3$OD): δ ppm 9.37 (s, 1 H), 9.31 (s, 1 H), 8.39 (d, J = 6.0 Hz, 1 H), 8.03 (s, 1 H), 7.29 (d, J = 6.0 Hz, 1 H), 4.13 (s, 3 H), 2.07 (s, 3 H), 1.83 (s, 3 H) 1.78 (s, 3 H), 1.69 (s, 6 H) | 10 |
| 18 | (structure) Or (structure) | 391 | ¹H-NMR (400 MHz, CD$_3$OD): δ ppm 9.43 (s, 1H), 8.42 (s, 1H), 7.96 (s, 1H), 7.89 (d, J = 8.8 Hz, 1H), 7.56 (d, J = 8.8 Hz, 1H), 4.16 (s, 3H), 3.30-3.22 (m, 1H), 2.02 (d, J = 3.2 Hz, 6H), 2.00-1.93 (m, 1H), 1.84-1.73 (m, 1H), 1.41 (d, J = 6.8 Hz, 3H), 0.91 (t, J = 7.2 Hz, 3H) | 3 Intermediate 7 |

TABLE 1-continued
| # | Structure | LCMS (M + 1) | NMR | Synthetic Protocol |
|---|---|---|---|---|
| 19 | 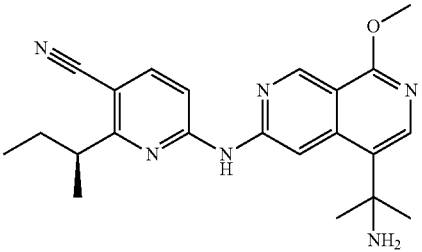 Or 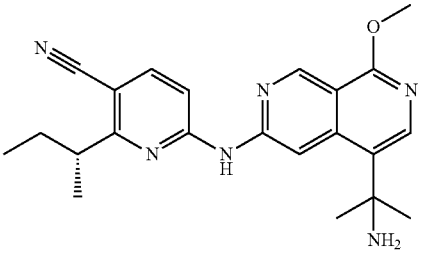 | 391 | ¹H-NMR (400 MHz, CD₃OD): δ ppm 9.37 (s, 1H), 8.70 (s, 1H), 8.17 (s, 1H), 7.86 (d, J = 8.8 Hz, 1H), 7.47 (d, J = 8.8 Hz, 1H), 4.12 (s, 3H), 3.29-3.20 (m, 1H), 2.08-1.96 (m, 1H), 1.83-1.75 (m, 7H), 1.41 (d, J = 6.8 Hz, 3H), 0.90 (t, J = 7.2 Hz, 3H) | 3 Intermediate 8 |
| 20 | 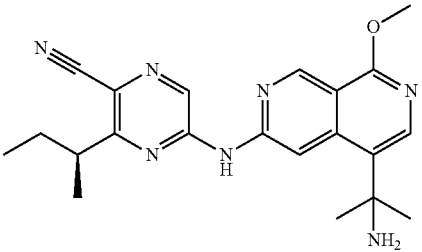 Or 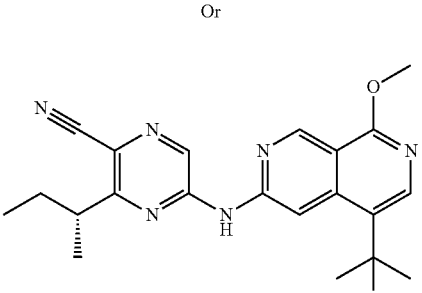 | 392 | ¹H-NMR (400 MHz, CD₃OD): δ ppm 9.49 (s, 1H), 8.76 (s, 1H), 8.54 (s, 1H), 7.99 (s, 1H), 4.18 (s, 3H), 3.28-3.23 (m, 1H), 2.02 (d, J = 3.2 Hz, 6H), 2.00-1.92 (m, 1H), 1.87-1.78 (m, 1H), 1.42 (d, J = 6.8 Hz, 3H), 0.94 (t, J = 7.6 Hz, 3H). | 3 Intermediate 29 |

TABLE 1-continued
| # | Structure | LCMS (M + 1) | NMR | Synthetic Protocol |
|---|-----------|--------------|-----|--------------------|
| 21 | 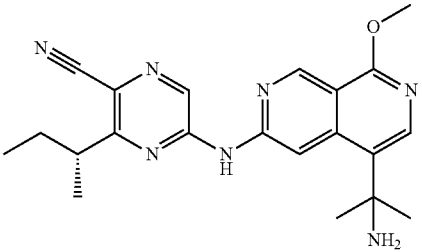<br>Or<br>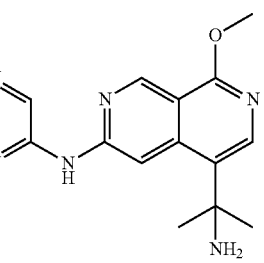 | 392 | ¹H-NMR (400 MHz, CD₃OD): δ ppm 9.49 (s, 1H), 8.76 (s, 1H), 8.54 (s, 1H), 7.99 (s, 1H), 4.18 (s, 3H), 3.28-3.23 (m, 1H), 2.02 (d, J = 3.2 Hz, 6H), 2.00-1.92 (m, 1H), 1.87-1.78 (m, 1H), 1.42 (d, J = 6.8 Hz, 3H), 0.94 (t, J = 7.6 Hz, 3H). | 3 Intermediate 30 |
| 22 | 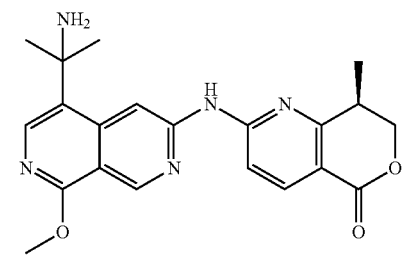<br>Or<br>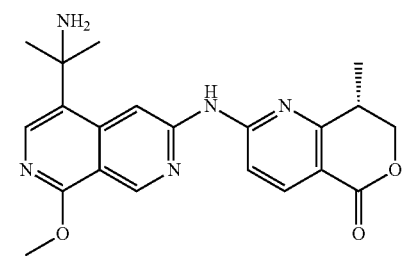 | 394 | ¹H-NMR (400 MHz, CD₃OD): δ ppm 9.36 (s, 1H), 9.23 (s, 1H), 8.15 (d, J = 8.8 Hz, 1H), 8.10 (s, 1H), 7.25 (d, J = 8.4 Hz, 1H), 4.71-4.67 (m, 1H), 4.44-4.41 (m, 1H), 4.14 (s, 3H), 3.20-3.14 (m, 1H), 1.93 (s, 3H), 1.91 (s, 3H), 1.49 (d, J = 7.2 Hz, 3H) | 3, first eluting isomer |

TABLE 1-continued
| # | Structure | LCMS (M + 1) | NMR | Synthetic Protocol |
|---|---|---|---|---|
| 23 | 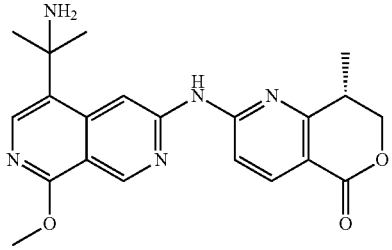 Or 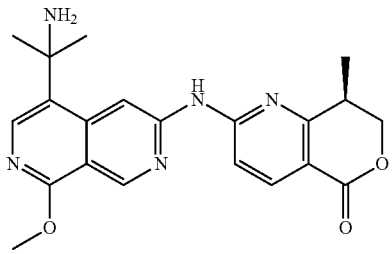 | 394 | ¹H-NMR (400 MHz, CD₃OD): δ ppm 9.35 (s, 1H), 9.25 (s, 1H), 8.14 (d, J = 9.2 Hz, 1H), 8.13 (s, 1H), 7.24 (d, J = 8.4 Hz, 1H), 4.71-4.67 (m, 1H), 4.44-4.40 (m, 1H), 4.13 (s, 3H), 3.20-3.14 (m, 1H), 1.90 (s, 3H), 1.88 (s, 3H), 1.48 (d, J = 7.2 Hz, 3H) | 3, second eluting isomer |
| 24 | 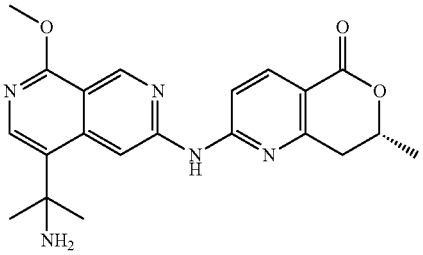 Or 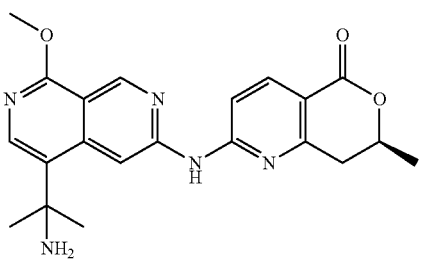 | 394 | ¹H NMR (400 MHz, DMSO-d₆): δ ppm 10.69 (s, 1H), 9.56 (s, 1H), 9.29 (d, J = 0.8 Hz, 1H), 8.18 (s, 1H), 8.07 (d, J = 8.8 Hz, 1H), 7.31 (d, J = 8.8 Hz, 1H), 4.87-4.77 (m, 1H), 4.05 (s, 3H), 3.10-3.01 (m, 2H), 1.68 (d, J = 2.0 Hz, 6H), 1.46 (d, J = 6.4 Hz, 3H) | 3, first eluting isomer |

TABLE 1-continued

| # | Structure | LCMS (M + 1) | NMR | Synthetic Protocol |
|---|---|---|---|---|
| 25 | | 394 | ¹H NMR (400 MHz, DMSO-d₆): δ ppm 10.70 (s, 1H), 9.57 (s, 1H), 9.29 (s, 1H), 8.19 (s, 1H), 8.08 (d, J = 8.8 Hz, 1H), 7.31 (d, J = 8.8 Hz, 1H), 4.89-4.77 (m, 1H), 4.06 (s, 3H), 3.11-3.03 (m, 2H), 1.68 (d, J = 2.0 Hz, 6H), 1.47 (d, J = 6.4 Hz, 3H) | 3, second eluting isomer |
| | Or | | | |
| 26 | 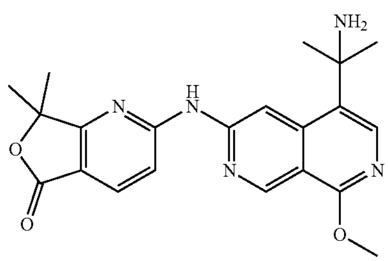 [SMILES: COc1ncc(C(C)(C)N)c2cc(Nc3ccc4c(n3)C(C)(C)OC4=O)ncc12] | 394 | ¹H-NMR (400 MHz, CD₃OD): δ ppm 9.40 (s, 2H), 8.25 (s, 1H), 8.01 (d, J = 8.4 Hz, 1H), 7.29 (d, J = 8.4 Hz, 1H), 4.15 (s, 3H), 1.86 (s, 6H), 1.78 (s, 6H) | 3 |
| 27 | 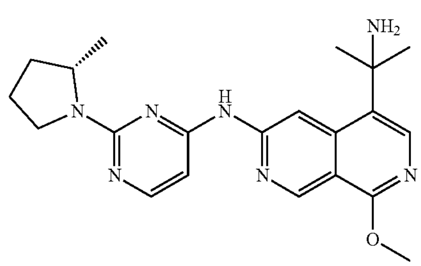 [SMILES: COc1ncc(C(C)(C)N)c2cc(Nc3ccnc(N4CCC[C@@H]4C)n3)ncc12] | 394 | ¹H-NMR (400 MHz, CD₃OD): δ ppm 9.32 (s, 1H), 8.54 (s, 1H), 8.16 (s, 1H), 7.97 (d, J = 6.0 Hz, 1H), 6.71 (s, 1H), 4.43-4.33 (m, 1H), 4.10 (s, 3H), 3.79-3.69 (m, 1H), 3.65-3.56 (m, 1H), 2.20-2.08 (m, 2H), 2.06-1.96 (m, 1H), 1.79-1.75 (m, 1H), 1.72 (s, 6H), 1.25 (d, J = 6.4 Hz, 3H) | 3 |
| 28 | 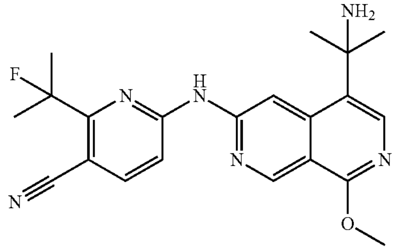 [SMILES: COc1ncc(C(C)(C)N)c2cc(Nc3ccc(C#N)c(C(C)(C)F)n3)ncc12] | 395 | ¹H-NMR (400 MHz, DMSO-d₆): δ ppm 10.65 (s, 1H), 9.31 (s, 1H), 9.09 (s, 1H), 8.14 (s, 1H), 8.08 (d, J = 8.8 Hz, 1H), 7.58 (d, J = 9.2 Hz, 1H), 4.05 (s, 3H), 1.86 (s, 3H), 1.81 (s, 3H), 1.62 (s, 6H) | 3 |

TABLE 1-continued

| # | Structure | LCMS (M + 1) | NMR | Synthetic Protocol |
|---|---|---|---|---|
| 29 | 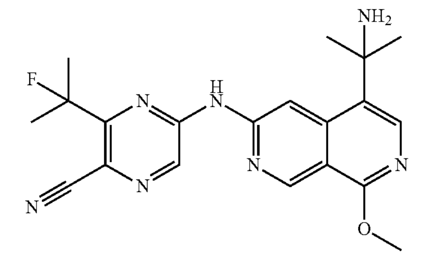 [SMILES: COc1ncc(C(C)(C)N)c2cc(Nc3cnc(C#N)c(C(C)(C)F)n3)ncc12] | 396 | ¹H-NMR (400 MHz, CD₃OD): δ ppm 9.51 (s, 1H), 9.07 (d, J = 4.4 Hz, 1H), 8.40-8.33 (m, 1H), 8.00 (s, 1H), 4.18 (s, 3H), 1.99 (s, 6H), 1.93-1.82 (m, 6H) | 3 |
| 30 | Or | 396 | ¹H-NMR (400 MHz, CD₃OD): δ ppm 9.42 (s, 1H), 9.20 (s, 1H), 8.65 (s, 1H), 8.25 (s, 1H), 5.80-5.65 (m, 1H), 4.15 (s, 3H), 2.29-2.11 (m, 2H), 1.81 (d, J = 4.4 Hz, 6H), 1.14 (t, J = 7.6 Hz, 3H) | 3, Intermediate 26 first eluting isomer |
| 31 | Or | 396 | ¹H-NMR (400 MHz, CD₃OD): δ ppm 9.29 (s, 1H), 9.06 (s, 1H), 8.51 (s, 1H), 8.10 (s, 1H), 5.68-5.53 (m, 1H), 4.03 (s, 3H), 2.19-1.95 (m, 2H), 1.72-1.66 (m, 6H), 1.03 (t, J = 7.6 Hz, 3H) | 3, second eluting isomer |

TABLE 1-continued

| # | Structure | LCMS (M + 1) | NMR | Synthetic Protocol |
|---|---|---|---|---|
| 32 | 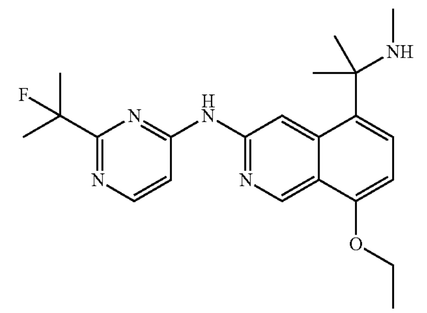 [SMILES: CCOc1ccc(C(C)(C)NC)c2cc(Nc3ccnc(C(C)(C)F)n3)ncc12] | 399 | ¹H-NMR (400 MHz, CD₃OD): δ ppm 9.38 (s, 1H), 9.30 (s, 1H), 8.38 (d, J = 6.0 Hz, 1H), 8.07 (s, 1H), 7.28 (d, J = 6.0 Hz, 1H), 4.60-4.52 (m, 2H), 2.06 (s, 3H), 1.82 (s, 3H), 1.77 (s, 3H), 1.68 (s, 6H), 1.51 (t, J = 6.8 Hz, 3H) | 10 |
| 33 | 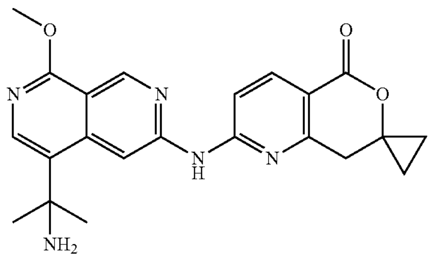 [SMILES: COc1ncc(C(C)(C)N)c2cc(Nc3ccc4c(n3)CC3(CC3)OC4=O)ncc12] | 406 | ¹H-NMR (400 MHz, CD₃OD): δ ppm 9.35 (d, J = 9.6 Hz, 2H), 8.17 (t, J = 4.8 Hz, 2H), 7.22 (d, J = 8.8 Hz, 1H), 4.12 (s, 3H), 3.26 (s, 2H), 1.78 (s, 6H), 1.14-1.09 (m, 2H), 0.89-0.84 (m, 2H) | 3 |
| 34 | 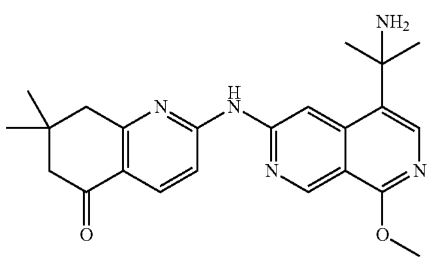 [SMILES: COc1ncc(C(C)(C)N)c2cc(Nc3ccc4c(n3)CC(C)(C)CC4=O)ncc12] | 406 | ¹H-NMR (400 MHz, CD₃OD): δ ppm 9.47 (s, 1 H), 9.33 (s, 1 H), 8.19 (s, 1 H), 8.11 (d, J = 8.8 Hz, 1 H), 7.09 (d, J = 8.8 Hz, 1 H), 4.12 (s, 3 H), 3.04 (s, 2 H), 2.53 (s, 2 H), 1.84 (s, 6 H), 1.14 (s, 6H) | 3 |
| 35 | 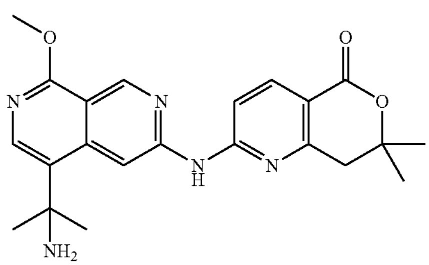 | 407 | ¹H-NMR (400 MHz, CD₃OD): δ ppm 9.24 (s, 1H), 9.20-9.17 (m, 1H), 8.12 (d, J = 8.8 Hz, 1H), 8.03 (s, 1H), 7.19 (d, J = 8.8 Hz, 1H), 3.21 (s, 2H), 3.05 (s, 3H), 1.77 (s, 6H), 1.53 (s, 6H) | 5 |
| 36 | 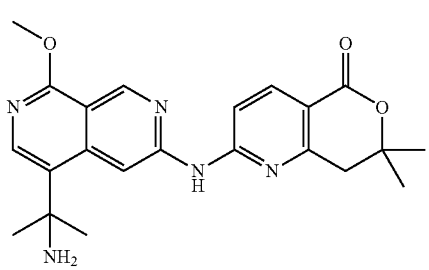 [SMILES: COc1ncc(C(C)(C)N)c2cc(Nc3ccc4c(n3)CC(C)(C)OC4=O)ncc12] | 408 | ¹H-NMR (400 MHz, CD₃OD): δ ppm 9.36 (s, 1H), 9.31 (s, 1H), 817 (s, 1H), 8.12 (d, J = 8.4 Hz, 1H), 7.17 (d, J = 8.4 Hz, 1H), 4.11 (s, 3H), 3.21 (s, 2H), 1.80 (s, 6H), 1.53 (s, 6H) | 3 |

TABLE 1-continued

| # | Structure | LCMS (M + 1) | NMR | Synthetic Protocol |
|---|---|---|---|---|
| 37 | 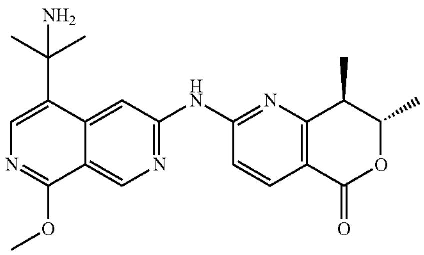 [SMILES: COc1ncc(C(C)(C)N)c2cc(Nc3ccc4c(n3)[C@@H](C)[C@H](C)OC4=O)ncc12] | 408 | ¹H-NMR (400 MHz, CD₃OD): δ ppm 9.36 (s, 1H), 9.19 (s, 1H), 8.19 (s, 1H), 8.14 (d, J = 8.8 Hz, 1H), 7.31 (d, J = 8.8 Hz, 1H), 4.69-4.63 (m, 1H), 4.12 (s, 3H), 3.08-2.99 (m, 1H), 1.79 (d, J = 4.4 Hz, 6H), 1.51 (d, J = 7.2 Hz, 3H), 1.46 (d, J = 6.4 Hz, 3H) | 3 Intermediate 17 |
| 38 | 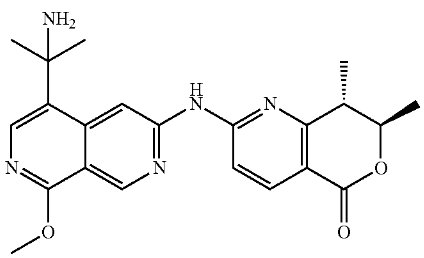 [SMILES: COc1ncc(C(C)(C)N)c2cc(Nc3ccc4c(n3)[C@H](C)[C@@H](C)OC4=O)ncc12] | 408 | ¹H-NMR (400 MHz, CD₃OD): δ ppm 9.35 (d, J = 0.8 Hz, 1H), 9.19 (s, 1H), 8.19 (s, 1H), 8.14 (d, J = 8.4 Hz, 1H), 7.31 (d, J = 8.4 Hz, 1H), 4.69-4.61 (m, 1H), 4.12 (s, 3H), 3.07-3.00 (m, 1H), 1.79 (d, J = 4.8 Hz, 6H), 1.51 (d, J = 7.2 Hz, 3H), 1.46 (d, J = 6.4 Hz, 3H) | 3 Intermediate 18 |
| 39 | Or | 408 | ¹H-NMR (400 MHz, CD₃OD): δ ppm 9.42 (s, 1H), 9.34 (s, 1H), 8.16 (s, 1H), 8.13 (d, J = 8.8 Hz, 1H), 7.16 (d, J = 8.8 Hz, 1H), 4.93-4.89 (m, 1H), 4.12 (s, 3H), 3.06-2.99 (m, 1H), 1.84 (d, J = 9.6 Hz, 6H), 1.51 (d, J = 6.8 Hz, 3H), 1.32 (d, J = 7.2 Hz, 3H) | 3 first eluting isomer |
| 40 | Or | 408 | ¹H-NMR (400 MHz, CD₃OD): δ ppm 9.42 (s, 1H), 9.27 (s, 1H), 8.18 (d, J = 8.8 Hz, 1H), 7.98 (s, 1H), 7.22 (d, J = 8.8 Hz, 1H), 4.95-4.92 (m, 1H), 4.17 (s, 3H), 3.03-2.96 (m, 1H), 2.06 (d, J = 13.2 Hz, 6H), 1.52 (d, J = 6.8 Hz, 3H), 1.34 (d, J = 7.2 Hz, 3H) | 3 second eluting isomer |

TABLE 1-continued
| # | Structure | LCMS (M + 1) | NMR | Synthetic Protocol |
|---|---|---|---|---|
| 41 | 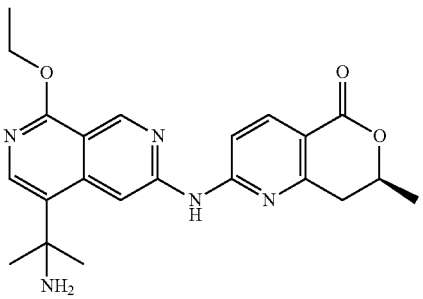 Or 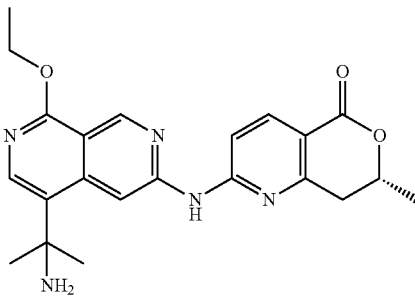 | 408 | ¹H-NMR (400 MHz, CD₃OD): δ ppm 9.40 (s, 1H), 9.33 (s, 1H), 8.17 (d, J = 8.8 Hz, 1H), 8.09 (s, 1H), 7.23 (d, J = 8.8 Hz, 1H), 4.84 (s, 1H), 4.61 (q, J = 7.2 Hz, 2H), 3.14 (d, J = 6.8 Hz, 2H), 1.95 (d, J = 5.6 Hz, 6H), 1.58 (d, J = 6.4 Hz, 3H), 1.53 (t, J = 7.2 Hz, 3H) | 3, first eluting isomer |
| 42 | 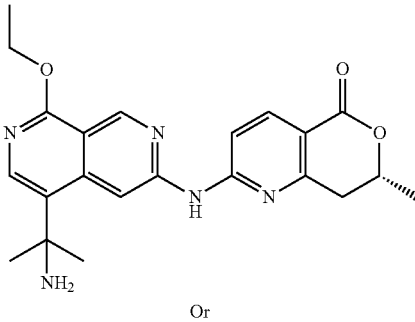 Or 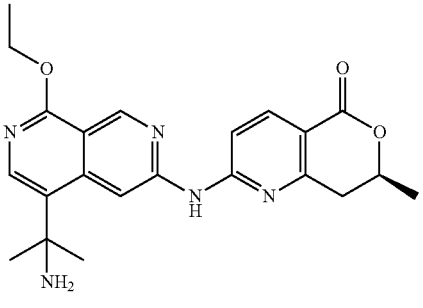 | 408 | ¹H-NMR (400 MHz, CD₃OD): δ ppm 9.39 (s, 1H), 9.35 (s, 1H), 8.17 (d, J = 8.8 Hz, 1H), 8.10 (s, 1H), 7.22 (d, J = 8.8 Hz, 1H), 4.84 (s, 1H), 4.63-4.57 (m, 2H), 3.14 (d, J = 7.2 Hz, 2H), 1.93 (d, J = 5.6 Hz, 6H), 1.58 (d, J = 6.4 Hz, 3H), 1.53 (t, J = 7.2 Hz, 3H) | 3, second eluting isomer |
| 43 | 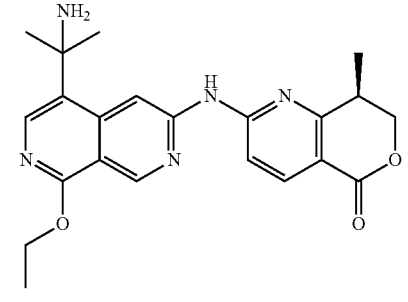 | 408 | ¹H-NMR (400 MHz, CD₃OD): δ ppm 9.35 (s, 1H), 9.33 (s, 1H), 8.18 (s, 1H), 8.14 (d, J = 8.8 Hz, 1H), 7.22 (d, J = 8.8 Hz, 1H), 4.72-4.66 (m, 1H), 4.60-4.52 (m, 2H), 4.46-4.38 (m, 1H), 3.23-3.15 (m, 1H), 1.80 (d, J = 6.0 Hz, 6H), 1.54-1.47 (m, 6H) | 3, first eluting isomer |

TABLE 1-continued

| # | Structure | LCMS (M + 1) | NMR | Synthetic Protocol |
|---|---|---|---|---|
| | Or | | | |
| 44 | | 408 | ¹H-NMR (400 MHz, CD₃OD): δ ppm 9.35 (s, 1H), 9.30 (s, 1H), 8.15 (s, 1H), 8.13 (d, J = 8.4 Hz, 1H), 7.22 (d, J = 8.8 Hz, 1H), 4.73-4.66 (m, 1H), 4.60-4.52 (m, 2H), 4.45-4.40 (m, 1H), 3.22-3.13 (m, 1H), 1.83 (d, J = 6.8 Hz, 6H), 1.53-1.47 (m, 6H) | 3 second eluting isomer |
| | Or | | | |
| 45 | 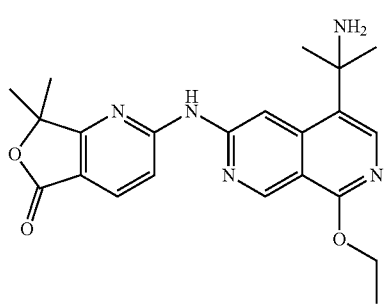 [SMILES: CCOc1ncc(C(C)(C)N)c2cc(Nc3ccc4c(n3)C(C)(C)OC4=O)ncc12] | 408 | ¹H-NMR (400 MHz, CD₃OD): δ ppm 9.39 (d, J = 1.6 Hz, 2H), 8.23 (s, 1H), 8.00 (d, J = 8.4 Hz, 1H), 7.28 (d, J = 8.4 Hz, 1H), 4.59 (d, J = 7.2 Hz, 2H), 1.85 (s, 6H), 1.78 (s, 6H), 1.53 (d, J = 7.2 Hz, 3H) | 4 |
| 46 | 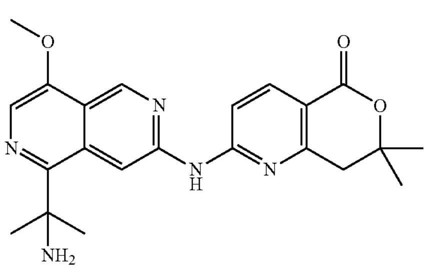 | 408 | ¹H-NMR (400 MHz, CD₃OD): δ ppm 9.43 (s, 1H), 8.14 (d, J = 8.8 Hz, 1H), 8.06 (s, 1H), 7.17 (d, J = 8.4 Hz, 1H), 4.13 (s, 3H), 3.22 (s, 2H), 1.92 (s, 6H), 1.54 (s, 6H) | 7 |

TABLE 1-continued

| # | Structure | LCMS (M + 1) | NMR | Synthetic Protocol |
|---|---|---|---|---|
| 47 | 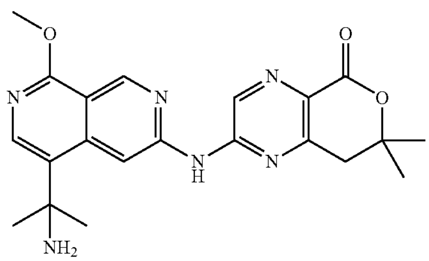 [SMILES: COc1ncc(C(C)(C)N)c2cc(Nc3cnc4c(n3)CC(C)(C)OC4=O)ncc12] | 409 | ¹H-NMR (400 MHz, CD₃OD): δ ppm 9.44 (s, 1H), 9.24 (s, 1H), 8.63 (s, 1H), 8.16 (s, 1H), 4.17 (s, 3H), 3.32 (s, 2H), 1.93 (s, 6H), 1.59 (s, 6H) | 3 |
| 48 | 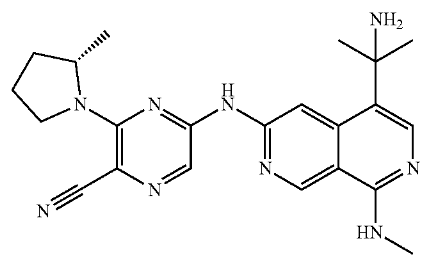 [SMILES: CNc1ncc(C(C)(C)N)c2cc(Nc3cnc(C#N)c(N4CCC[C@@H]4C)n3)ncc12] | 418 | ¹H-NMR (400 MHz, CD₃OD): δ ppm 9.43 (s, 1H), 8.80 (s, 1H), 7.79 (s, 1H), 7.53 (s, 1H), 4.69-4.56 (m, 1H), 4.04-3.92 (m, 1H), 3.84-3.70 (m, 1H), 3.20 (s, 3H), 2.20-2.11 (m, 2H), 2.06-2.00 (m, 1H), 1.95 (s, 6H), 1.83-1.73 (m, 1H), 1.33 (d, J = 6.4 Hz, 3H) | 6 |
| 49 | 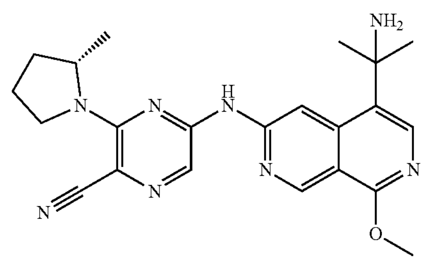 [SMILES: COc1ncc(C(C)(C)N)c2cc(Nc3cnc(C#N)c(N4CCC[C@@H]4C)n3)ncc12] | 419 | ¹H-NMR (400 MHz, CD₃OD): δ ppm 9.46 (s, 1H), 8.56 (s, 1H), 7.96 (s, 1H), 7.95 (s, 1H), 4.72-4.63 (m, 1H), 4.16 (s, 3H), 4.03-3.95 (m, 1H), 3.82-3.73 (m, 1H), 2.22-2.11 (m, 2H), 2.08-2.01 (m, 1H), 1.97 (s, 6H), 1.85-1.78 (m, 1H), 1.32 (d, J = 6.0 Hz, 3H) | 3 |
| 50 | 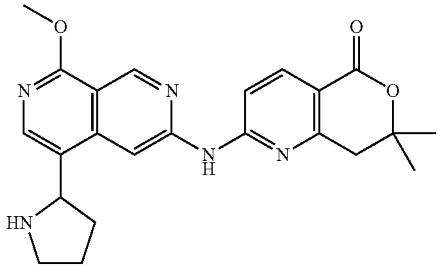 [SMILES: COc1ncc(C2CCCN2)c2cc(Nc3ccc4c(n3)CC(C)(C)OC4=O)ncc12] | 420 | ¹H NMR (400 MHz, DMSO-d₆): δ ppm 10.64 (s, 1H), 9.18 (d, J = 0.8 Hz, 1H), 8.49 (s, 1H), 8.05 (d, J = 8.7 Hz, 1H), 7.38-7.31 (m, 2H), 4.22 (t, J = 6.7 Hz, 1H), 4.06 (s, 3H), 3.21 (s, 2H), 3.15 (s, 1H), 3.09 (dt, J = 10.4, 6.4 Hz, 1H), 2.98 (dt, J = 10.1, 6.7 Hz, 1H), 2.24-2.09 (m, 1H), 1.84-1.70 (m, 3H), 1.43 (s, 6H). | 11 |
| 51 | Or | 420 | ¹H-NMR (400 MHz, CD₃OD): δ ppm 9.43 (s, 1H), 9.32 (s, 1H), 8.19 (s, 1H), 8.13 (d, J = 8.8 Hz, 1H), 7.12 (d, J = 8.0 Hz, 1H), 5.17-5.15 (m, 1H), 4.12 (s, 3H), 3.29-3.24 (m, 1H), 2.46-2.37 (m, 1H), 2.24-2.14 (m, 2H), 2.12-2.01 (m, 1H), 1.99-1.91 (m, 1H), 1.90-1.87 (m, 1H), 1.82 (d, J = 8.0 Hz, 6H) | 3 Intermediate 12 |

TABLE 1-continued

| # | Structure | LCMS (M + 1) | NMR | Synthetic Protocol |
|---|---|---|---|---|
| | [Structure image] | | | |
| 52 | [Structure image] Or [Structure image] | 520 | ¹H NMR (400 MHz, CD₃OD): δ ppm 9.44 (s, 1H), 9.33 (s, 1H), 8.19 (s, 1H), 8.14 (d, J = 8.8 Hz, 1H), 7.12 (d, J = 4.8 Hz, 1H), 5.18-5.15 (m, 1H), 4.12 (s, 4H), 3.29-3.24 (m, 1H), 2.46-2.37 (m, 1H), 2.25-2.18 (m, 2H), 2.11-2.02 (m, 1H), 1.98-1.90 (m, 1H), 1.92-1.84 (m, 1H), 1.82 (d, J = 7.6 Hz, 6H) | 3 Intermediate 13 |
| 53 | [Structure image] | 421 | ¹H-NMR (400 MHz, CD₃OD): δ ppm 9.24 (s, 1H), 9.23 (s, 1H), 8.12 (d, J = 8.8 Hz, 1H), 8.02 (s, 1H), 7.19 (d, J = 8.8 Hz, 1H), 3.59-3.51 (m, 2H), 3.21 (s, 2H), 1.77 (s, 6H), 1.53 (s, 6H), 1.32 (t, J = 7.2 Hz, 3H) | 5 |
| 54 | [Structure image] | 422 | ¹H-NMR (400 MHz, CD₃OD): δ ppm 9.36 (d, J = 9.2 Hz, 2H), 8.17-8.13 (m, 2H), 7.20 (d, J = 8.4 Hz, 1H), 4.59-4.53 (m, 2H), 3.22 (s, 2H), 1.83 (s, 6H), 1.53 (s, 6H), 1.52-1.48 (m, 3H) | 3 |

TABLE 1-continued

| # | Structure | LCMS (M + 1) | NMR | Synthetic Protocol |
|---|---|---|---|---|
| 55 | 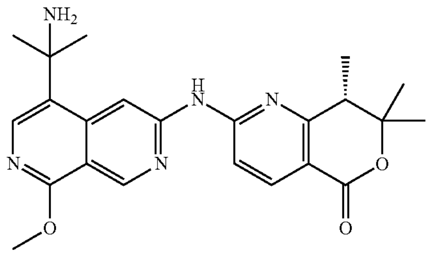 [SMILES: COc1ncc(C(C)(C)N)c2cc(Nc3ccc4c(n3)[C@H](C)C(C)(C)OC4=O)ncc12] | 422 | $^1$H-NMR (400 MHz, CD$_3$OD): δ ppm 9.35 (s, 1H), 9.32 (s, 1H), 8.16 (s, 1H), 8.13 (d, J = 8.8 Hz, 1H), 7.23 (d, J = 8.8 Hz, 1H), 4.13 (s, 3H), 3.07-3.00 (m, 1H), 1.83 (d, J = 8.0 Hz, 6H), 1.54 (s, 3H), 1.45 (s, 3H), 1.40 (d, J = 7.2 Hz, 3H) | 3 Intermediate 21 |
| 56 | 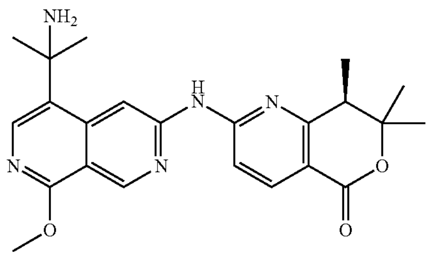 [SMILES: COc1ncc(C(C)(C)N)c2cc(Nc3ccc4c(n3)[C@@H](C)C(C)(C)OC4=O)ncc12] | 422 | $^1$H-NMR (400 MHz, CD$_3$OD): δ ppm 9.36 (s, 1H), 9.31 (s, 1H), 8.15 (s, 1H), 8.14 (d, J = 8.8 Hz, 1H), 7.24 (d, J = 8.8 Hz, 1H), 4.13 (s, 3H), 3.07-3.00 (m, 1H), 1.85 (d, J = 8.4 Hz, 6H), 1.54 (s, 3H), 1.45 (s, 3H), 1.40 (d, J = 7.2 Hz, 3H) | 3 Intermediate 20 |
| 57 | 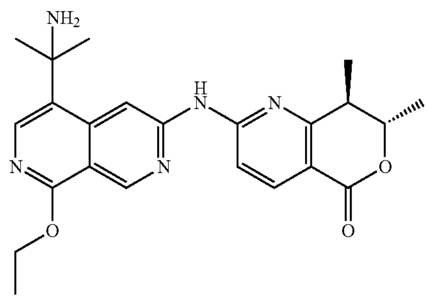 [SMILES: CCOc1ncc(C(C)(C)N)c2cc(Nc3ccc4c(n3)[C@@H](C)[C@H](C)OC4=O)ncc12] | 422 | $^1$H-NMR (400 MHz, CD$_3$OD): δ ppm 9.36 (s, 1H), 9.18 (s, 1H), 8.17 (s, 1H), 8.14 (d, J = 8.8 Hz, 1H), 7.30 (d, J = 8.8 Hz, 1H), 4.69-4.62 (m, 1H), 4.59-4.53 (m, 2H), 3.07-2.99 (m, 1H), 1.79 (d, J = 4.8 Hz, 6H), 1.53-1.48 (m, 6H), 1.46 (d, J = 6.4 Hz, 3H) | 3 Intermediate 17 |
| 58 | 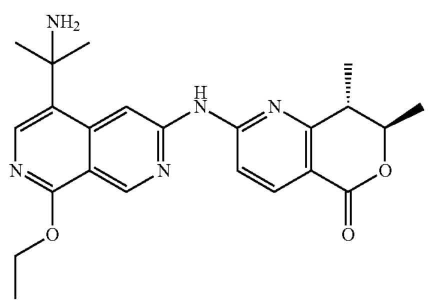 [SMILES: CCOc1ncc(C(C)(C)N)c2cc(Nc3ccc4c(n3)[C@H](C)[C@@H](C)OC4=O)ncc12] | 422 | $^1$H-NMR (400 MHz, CD$_3$OD): δ ppm 9.37 (d, J = 0.8 Hz, 1H), 9.18 (s, 1H), 8.17 (s, 1H), 8.15 (d, J = 8.8 Hz, 1H), 7.31 (d, J = 8.8 Hz, 1H), 4.70-4.63 (m, 1H), 4.59-4.53 (m, 2H), 3.07-2.99 (m, 1H), 1.79 (d, J = 4.8 Hz, 6H), 1.53-1.49 (m, 6H), 1.46 (d, J = 6.4 Hz, 3H) | 3 Intermediate 18 |
| 59 | 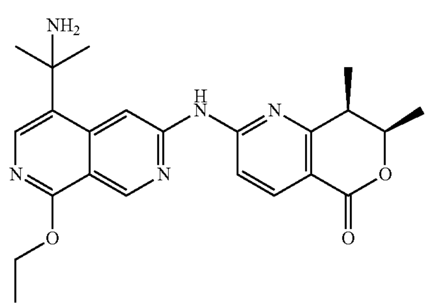 | 422 | $^1$H-NMR (400 MHz, CD$_3$OD): δ ppm 9.43 (s, 1H), 9.32 (s, 1H), 8.17 (s, 1H), 8.11 (d, J = 8.8 Hz, 1H), 7.12 (d, J = 8.4 Hz, 1H), 4.91-4.88 (m, 1H), 4.58-4.51 (m, 2H), 3.06-3.02 (m, 1H), 1.80 (d, J = 8.8 Hz, 6H), 1.54-1.46 (m, 6H), 1.32 (d, J = 7.2 Hz, 3H) | 3 Intermediate 19 first eluting isomer |

Or

TABLE 1-continued

| # | Structure | LCMS (M + 1) | NMR | Synthetic Protocol |
|---|---|---|---|---|
| | [structure] | | | |
| 60 | [structure] Or [structure] | 422 | ¹H-NMR (400 MHz, CD$_3$OD): δ ppm 9.44 (s, 1H), 9.33 (d, J = 0.6 Hz, 1H), 8.17 (s, 1H), 8.11 (d, J = 8.8 Hz, 1H), 7.13 (d, J = 8.8 Hz, 1H), 4.92-4.88 (m, 1H), 4.58-4.51 (m, 2H), 3.06-2.99 (m, 1H), 1.80 (d, J = 8.8 Hz, 6H), 1.54-1.47 (m, 6H), 1.32 (d, J = 7.2 Hz, 3H) | 3 Intermediate 19 second eluting isomer |
| 61 | [structure] Or [structure] | 422 | ¹H-NMR (400 MHz, CD$_3$OD): δ ppm 9.34 (d, J = 3.2 Hz, 2H), 8.15 (s, 1H), 8.13 (d, J = 8.8 Hz, 1H), 7.19 (d, J = 8.8 Hz, 1H), 4.12 (s, 3H), 3.21 (s, 2H), 2.42-2.12 (m, 2H), 1.75 (s, 3H), 1.53 (s, 6H), 0.74 (t, J = 7.6 Hz, 3H) | 3 first eluting isomer |

TABLE 1-continued
| # | Structure | LCMS (M + 1) | NMR | Synthetic Protocol |
|---|---|---|---|---|
| 62 | 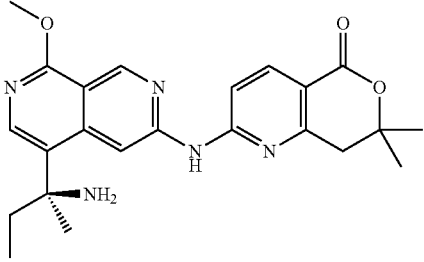 Or 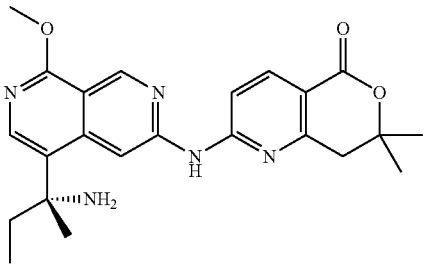 | 422 | ¹H-NMR (400 MHz, CD₃OD): δ ppm 9.34 (d, J = 2.4 Hz, 2H), 8.16 (s, 1H), 8.13 (d, J = 8.8 Hz, 1H), 7.19 (d, J = 8.4 Hz, 1H), 4.13 (s, 3H), 3.21 (s, 2H), 2.43-2.12 (m, 2H), 1.75 (s, 3H), 1.53 (s, 6H), 0.74 (t, J = 7.6 Hz, 3H) | 3, second eluting isomer |
| 63 | 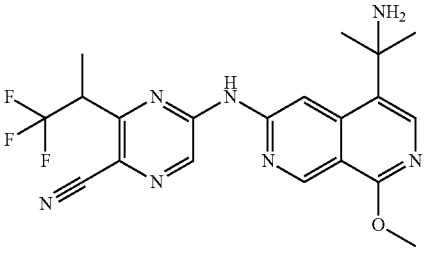 [SMILES: COc1ncc(C(C)(C)N)c2cc(Nc3cnc(C#N)c(C(C)C(F)(F)F)n3)ncc12] | 432 | ¹H-NMR (400 MHz, CD₃OD): δ ppm 9.45 (s, 1H), 9.03 (s, 1H), 8.65 (s, 1H), 8.26 (s, 1H), 4.22-4.18 (m, 1H), 4.15 (s, 3H), 1.76-1.74 (m, 9H) | 3 |
| 64 | 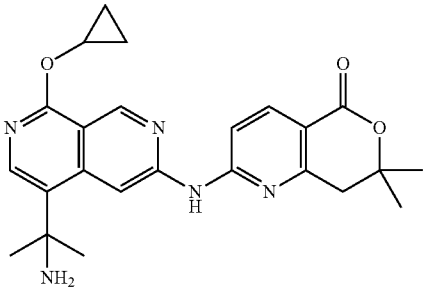 [SMILES: CC1(C)Cc2nc(Nc3cc4c(C(C)(C)N)cnc(OC5CC5)c4cn3)ccc2C(=O)O1] | 434 | | 8 |
| 65 | 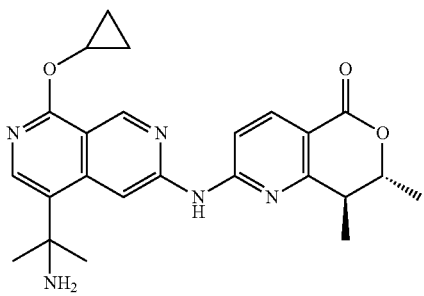 [SMILES: C[C@H]1OC(=O)c2ccc(Nc3cc4c(C(C)(C)N)cnc(OC5CC5)c4cn3)nc2[C@@H]1C] | 434 | ¹H NMR (400 MHz, DMSO-d₆): δ ppm 10.62 (s, 1H), 9.36 (s, 1H), 9.19 (s, 1H), 8.20 (s, 1H), 8.06 (d, J = 8.7 Hz, 1H), 7.37 (d, J = 8.7 Hz, 1H), 4.63-4.53 (m, 1H), 4.52-4.43 (m, 1H), 3.03-2.92 (m, 1H), 1.66 (d, J = 2.5 Hz, 6H), 1.42 (d, J = 7.0 Hz, 3H), 1.36 (d, J = 6.5 Hz, 3H), 0.88-0.79 (m, 4H). | 8 Intermediate 18 |

TABLE 1-continued

| # | Structure | LCMS (M + 1) | NMR | Synthetic Protocol |
|---|---|---|---|---|
| 66 | 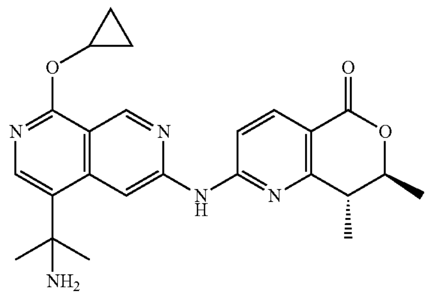 [SMILES: C[C@@H]1OC(=O)c2ccc(Nc3cc4c(C(C)(C)N)cnc(OC5CC5)c4cn3)nc2[C@H]1C] | 434 | $^1$H NMR (400 MHz, DMSO-d$_6$): δ ppm 10.61 (s, 1H), 9.38 (s, 1H), 9.19 (d, J = 0.7 Hz, 1H), 8.20 (s, 1H), 8.06 (d, J = 8.7 Hz, 1H), 7.36 (d, J = 8.7 Hz, 1H), 5.73 (s, 1H), 4.63-4.52 (m, 1H), 4.52-4.43 (m, 1H), 3.03-2.92 (m, 1H), 1.64 (d, J = 2.0 Hz, 6H), 1.39 (dd, J = 24.8, 6.8 Hz, 6H), 0.85-0.78 (m, 4H). | 8 Intermediate 17 |
| 67 | 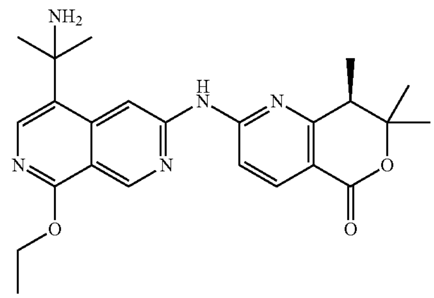 [SMILES: CCOc1ncc(C(C)(C)N)c2cc(Nc3ccc4c(n3)[C@@H](C)C(C)(C)OC4=O)ncc12] | 436 | $^1$H-NMR (400 MHz, CD$_3$OD): δ ppm 9.36 (d, J = 2.4 Hz, 2H), 8.17 (s, 1H), 8.13 (d, J = 8.8 Hz, 1H), 7.22 (d, J = 8.8 Hz, 1H), 4.60-4.52 (m, 2H), 3.08-3.00 (m, 1H), 1.80 (d, J = 7.2 Hz, 6H), 1.54 (s, 3H), 1.51 (t, J = 7.2 Hz, 3H), 1.45 (s, 3H), 1.40 (d, J = 7.2 Hz, 3H) | 3 Intermediate 20 |
| 68 | 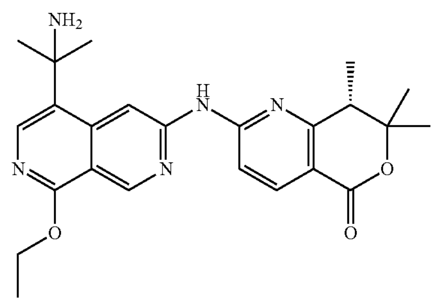 [SMILES: CCOc1ncc(C(C)(C)N)c2cc(Nc3ccc4c(n3)[C@H](C)C(C)(C)OC4=O)ncc12] | 436 | $^1$H-NMR (400 MHz, CD$_3$OD): δ ppm 9.34 (s, 2H), 8.17 (s, 1H), 8.12 (d, J = 8.8 Hz, 1H), 7.20 (d, J = 8.8 Hz, 1H), 4.59-4.51 (m, 2H), 3.07-3.00 (m, 1H), 1.79 (d, J = 7.2 Hz, 6H), 1.53 (s, 3H), 1.50 (t, J = 7.2 Hz, 3H), 1.45 (s, 3H), 1.39 (d, J = 7.2 Hz, 3H) | 3 Intermediate 21 |
| 69 | 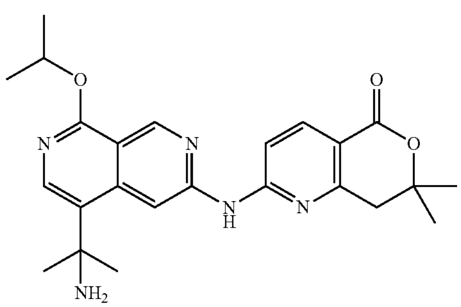 [SMILES: CC(C)Oc1ncc(C(C)(C)N)c2cc(Nc3ccc4c(n3)CC(C)(C)OC4=O)ncc12] | 436 | $^1$H-NMR (400 MHz, CD$_3$OD): δ ppm 9.36 (s, 1H), 9.32 (d, J = 0.8 Hz, 1H), 8.16 (s, 1H), 8.13 (d, J = 8.4 z, 1H), 7.19 (d, J = 8.8 Hz, 1H), 5.58-5.48 (m, 1H), 3.21 (s, 2H), 1.80 (s, 6H), 1.53 (s, 6H), 1.46 (d, J = 6.0 Hz, 6H) | 3 |
| 70 | 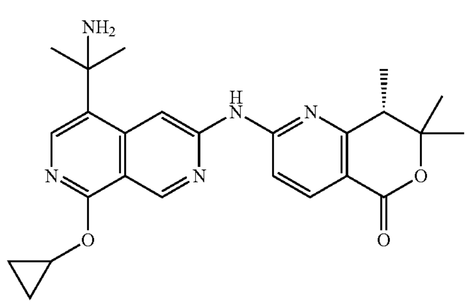 [SMILES: C[C@H]1c2nc(Nc3cc4c(C(C)(C)N)cnc(OC5CC5)c4cn3)ccc2C(=O)OC1(C)C] | 448 | $^1$H NMR (400 MHz, DMSO-d$_6$): δ ppm 10.65 (s, 1H), 9.52 (s, 1H), 9.18 (s, 1H), 8.21 (s, 1H), 8.04 (d, J = 8.7 Hz, 1H), 7.29 (d, J = 8.7 Hz, 1H), 4.47 (td, J = 6.5, 5.6, 3.5 Hz, 1H), 2.98 (q, J = 7.1 Hz, 1H), 1.66 (d, J = 2.3 Hz, 6H), 1.42 (s, 3H), 1.38-1.27 (m, 6H), 0.88-0.79 (m, 4H). | 8 Intermediate 21 |

TABLE 1-continued

| # | Structure | LCMS (M + 1) | NMR | Synthetic Protocol |
|---|---|---|---|---|
| 71 | 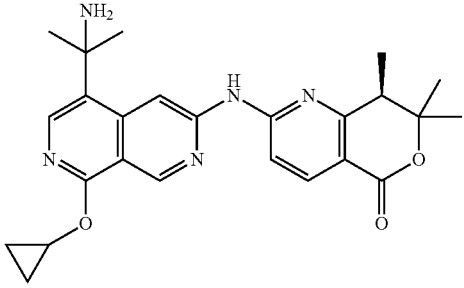 [SMILES: C[C@@H]1c2nc(Nc3cc4c(C(C)(C)N)cnc(OC5CC5)c4cn3)ccc2C(=O)OC1(C)C] | 448 | ¹H NMR (400 MHz, DMSO-d₆): δ ppm 10.65 (s, 1H), 9.53 (s, 1H), 9.18 (s, 1H), 8.21 (s, 1H), 8.04 (d, J = 8.6 Hz, 1H), 7.29 d, J = 8.6 Hz, 1H), 4.52-4.43 (m, 1H), 2.98 (q, J = 7.1 Hz, 1H), 2.02 (s, 1H), 1.65 (d, J = 2.1 Hz, 6H), 1.42 (s, 3H), 1.38-1.27 (m, 6H), 0.86-0.79 (m, 4H). | 3 Intermediate 20 |
| 72 | 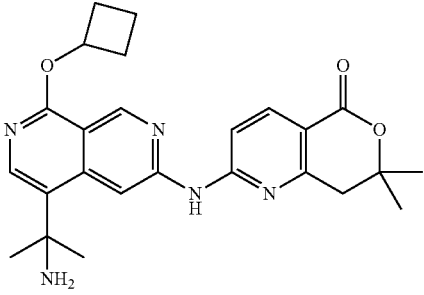 [SMILES: CC1(C)Cc2nc(Nc3cc4c(C(C)(C)N)cnc(OC5CCC5)c4cn3)ccc2C(=O)O1] | 408 | ¹H-NMR (400 MHz, CD₃OD): δ ppm 9.37 (s, 1H), 9.32 (s, 1H), 8.15 (d, J = 8.8 Hz, 1H), 8.10 (s, 1H), 7.21 (d, J = 8.8 Hz, 1H), 5.48-5.35 (m, 1H), 3.22 (s, 2H), 2.62-2.51 (m, 2H), 2.34-2.22 (m, 2H), 1.96-1.91 (m, 1H), 1.85 (s, 6H), 1.82-1.74 (m, 1H), 1.53 (s, 6H) | 9 |
| 73 | 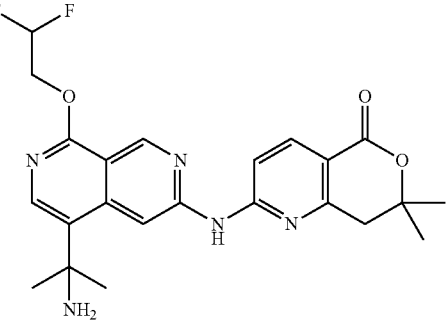 | 458 | ¹H-NMR (400 MHz, CD₃OD): δ ppm 9.42 (s, 1H), 9.37 (s, 1H), 8.20 (s, 1H), 8.13 (d, J = 8.4 Hz, 1H), 7.18 (d, J = 8.8 Hz, 1H), 6.52-6.18 (m, 1H), 4.80-4.69 (m, 2H), 3.22 (s, 2H), 1.80 (s, 6H), 1.53 (s, 6H) | 3 |
| 74 | 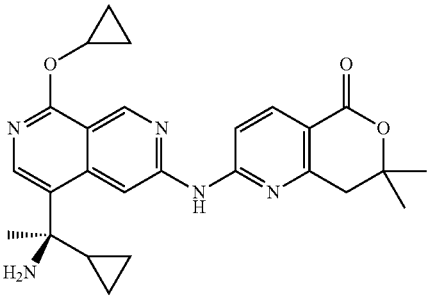 | 460 | ¹H NMR (400 MHz, CD₃OD): δ ppm 9.27 (s, 1 H), 9.19 (s, 1 H), 8.52 (s, 1 H), 8.15-8.11 (m, 2 H), 7.24 (d, J = 8.8 Hz, 1 H), 4.54-4.46 (m, 1 H), 3.18 (d, J = 0.8 Hz, 2 H), 1.84 (s, 3 H), 1.65-1.56 (m, 1 H), 1.52 (d, J = 7.6 Hz, 6 H), 0.94-0.86 (m, 4 H), 0.84-0.67 (m, 3 H), 0.65-0.54 (m, 1 H). | 3 second eluting isomer after Step 4 Example 3B |
| 75 | 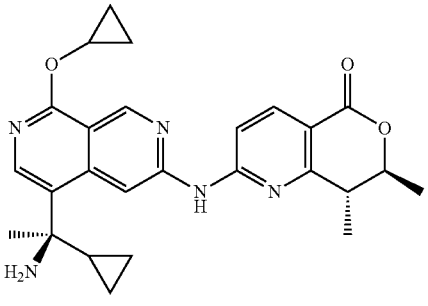 [SMILES: C[C@@H]1OC(=O)c2ccc(Nc3cc4c([C@](C)(N)C5CC5)cnc(OC5CC5)c4cn3)nc2[C@H]1C] | 460 | ¹H NMR (400 MHz, CD₃OD): δ ppm 10.62 (s, 1H), 9.52 (s, 1H), 9.21 (s, 1H), 8.38 (s, 1H), 8.07 (d, J = 8.8 Hz, 1H), 7.38 (d, J = 8.8 Hz, 1H), 4.63-4.54 (m, 1H), 4.53-4.43 (m, 1H), 3.02-2.92 (m, 1H), 1.64-1.60 (m, 1H), 1.56 (s, 3H), 1.44 (d, J = 7.2 Hz, 3H), 1.37 (d, J = 6.4 Hz, 3H), 0.88-1.80 (m, 4H), 0.62-0.53 (m, 1H), 0.50-0.38 (m, 3H). | 3 second eluting isomer after Step 4 Example 3B and Intermediate 17 |

TABLE 1-continued

| # | Structure | LCMS (M + 1) | NMR | Synthetic Protocol |
|---|---|---|---|---|
| 76 | 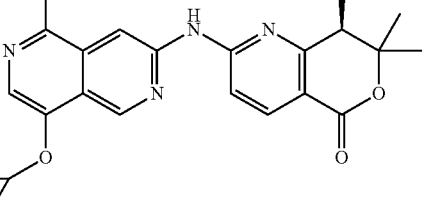 | 474 | $^1$H NMR (400 MHz, CD$_3$OD): δ ppm 9.32 (s, 1H), 9.29 (s, 1H), 8.23 (s, 1H), 8.15 (d, J = 8.8 Hz, 1H), 7.30 (d, J = 8.8 Hz, 1H), 4.55-4.44 (m, 1H), 3.08-2.94 (m, 1H), 1.79 (s, 3H), 1.72-1.62 (m, 1H), 1.58-1.44 (m, 6H), 1.40 (d, J = 7.2 Hz, 3H), 0.96-0.87 (m, 4H), 0.75-0.49 (m, 4H) | 3 second eluting isomer after Step 3 Example 3B and Intermediate 20 |
| 77 | 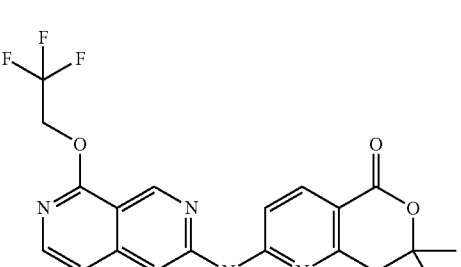 | 476 | $^1$H NMR (400 MHz, DMSO-d$_6$): δ ppm 10.75 (s, 1H), 9.63 (s, 1H), 9.27 (s, 1H), 8.18 (s, 1H), 8.07 (d, J = 8.7 Hz, 1H), 7.30 (d, J = 8.7 Hz, 1H), 5.20 (q, J = 9.0 Hz, 2H), 3.15 (s, 2H), 1.67 (s, 5H), 1.44 (s, 6H). | 8 |
| 78 | 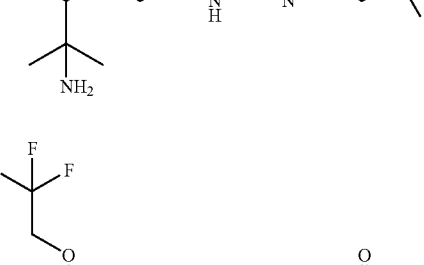 | 476 | $^1$H NMR (400 MHz, DMSO-d$_6$): δ ppm 10.71 (s, 1H), 9.46 (s, 1H), 9.28 (s, 1H), 8.19 (s, 1H), 8.08 (d, J = 8.7 Hz, 1H), 7.38 (d, J = 8.7 Hz, 1H), 5.20 (q, J = 9.1 Hz, 2H), 4.65-4.53 (m, 1H), 3.05-2.93 (m, 1H), 2.04 (s, 1H), 1.65 (d, J = 2.4 Hz, 6H), 1.40 (dd, J = 25.7, 6.8 Hz, 6H). | 8 Intermediate 17 |
| 79 | 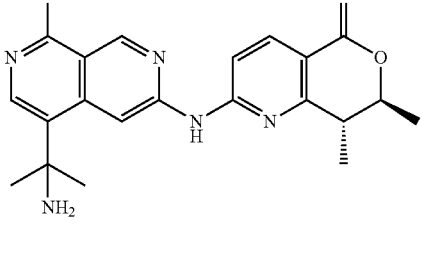 | 491 | $^1$H NMR (500 MHz, DMSO-d$_6$): δ ppm 10.78 (s, 1H), 9.64 (s, 1H), 9.30 (d, J = 0.8 Hz, 1H), 8.21 (s, 1H), 8.08 (d, J = 8.7 Hz, 1H), 7.33 (d, J = 8.7 Hz, 1H), 5.22 (q, J = 9.1 Hz, 2H), 3.01 (q, J = 7.1 Hz, 1H), 1.68 (d, J = 3.3 Hz, 7H), 1.45 (s, 3H), 1.37 (s, 3H), 1.32 (d, J = 7.1 Hz, 3H). | 8 Intermediate 20 |

TABLE 1-continued
| # | Structure | LCMS (M + 1) | NMR | Synthetic Protocol |
|---|---|---|---|---|
| 80 | 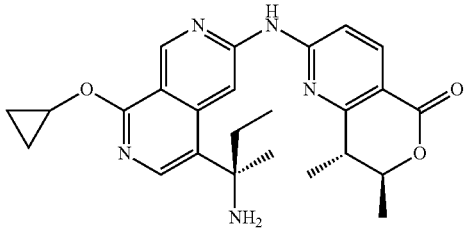  Or  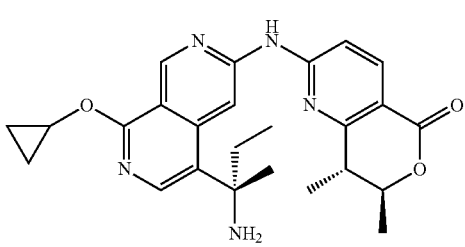 [SMILES: C[C@@H]1OC(=O)c2ccc(Nc3cc4c(C(C)(C)N)cnc(OC5(C)CC5)c4cn3)nc2[C@H]1C] | 448 | ¹H NMR (400 MHz, CD₃OD): δ ppm 9.22 (s, 1H), 9.14 (s, 1H), 8.17 (s, 1H), 8.11 (d, J = 8.8 Hz, 1H), 7.27 (d, J = 8.8 Hz, 1H), 4.69-4.60 (m, 1H), 4.49-4.41 (m, 1H), 3.06-2.96 (m, 1H), 2.42-2.30 (m, 1H), 2.21-2.08 (m, 1H), 1.74 (s, 3H), 1.51-1.42 (m, 6H), 0.92-0.83 (m, 4H), 0.73 (t, J = 7.2 Hz, 3H). | 3 Intermediate 17 and Intermediate 33 |
| 81 | 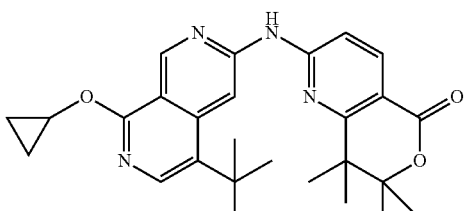 | | | |
| 82 | 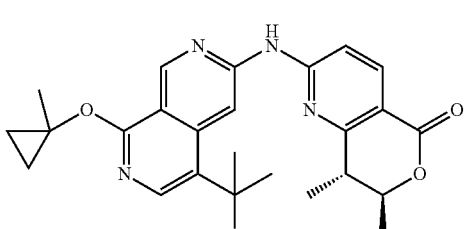 | 448 | ¹H-NMR (400 MHz, CD₃OD): δ ppm 9.27 (s, 1 H), 9.17 (s, 1 H), 8.22 (s, 1 H), 8.14 (d, J = 8.4 Hz, 1 H), 7.30 (d, J = 8.8 Hz, 1 H), 4.69-4.63 (m, 1 H), 3.06-3.00 (m, 1 H), 1.80 (d, J = 4.8 Hz, 6 H), 1.75 (s, 3H), 1.51 (d, J = 7.2 Hz, 3 H), 1.46 (d, J = 6.4 Hz, 3 H), 1.33-1.28 (m, 1 H), 1.08-1.05 (m, 2 H), 0.86-0.83 (m, 2 H). | 3 Intermediate 17 |
| 83 | 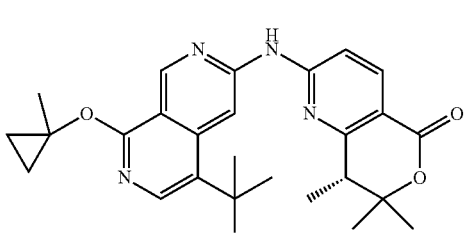 | 462 | ¹H-NMR (400 MHz, CD₃OD): δ ppm 9.30 (d, J = 20.4 Hz, 2 H), 8.20 (s, 1 H), 8.13 (d, J = 8.8 Hz, 1 H), 7.22 (d, J = 8.4 Hz, 1 H), 3.06-3.01 (m, 1 H), 1.83 (d, J = 8 Hz, 6 H), 1.75 (s, 3 H), 1.54 (s, 3 H), 1.45 (s, 3 H), 1.40 (d, J = 7.2 Hz, 3 H), 1.29 (d, J = 4.8 Hz, 1 H), 1.08-1.05 (m, 2 H), 0.86-0.83 (m, 2 H). | 3 Intermediate 20 |

TABLE 1-continued
| # | Structure | LCMS (M + 1) | NMR | Synthetic Protocol |
|---|---|---|---|---|
| 84 | 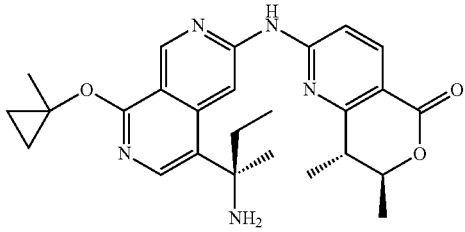 Or 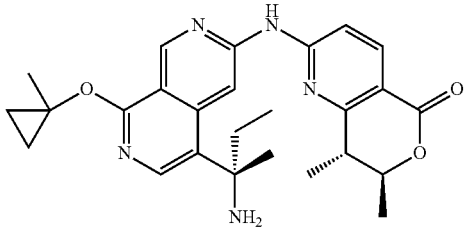 | 462 | ¹H-NMR (400 MHz, CDCl₃): δ ppm 9.30 (s, 1H), 9.19 (s, 1H), 8.23 (d, J = 9.2 Hz, 3H), 7.26 (d, J = 8.8 Hz, 1H), 4.58-4.52 (m, 1H), 3.01-2.94 (m, 1H), 2.18-2.04 (m, 2H), 1.78 (s, 3H), 1.70 (s, 3H), 1.53-1.50 (m, 6H), 1.10-1.07 (m, 2H), 0.86-0.83 (m, 2H), 0.82-0.78 (m, 3H). | 3 Intermediate 38 and Intermediate 17 |
| 85 | 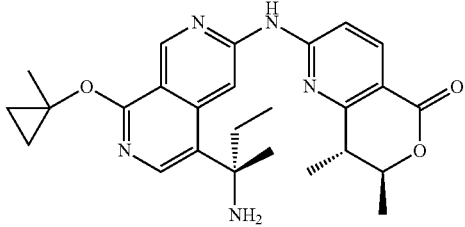 Or 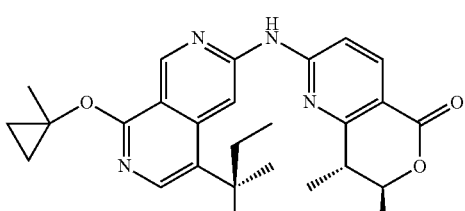 | 462 | ¹H-NMR (400 MHz, CDCl₃): δ ppm 9.31 (s, 1H), 9.19 (s, 1H), 8.24-8.21 (m, 2H), 8.07 (s, 1H), 7.24 (d, J = 8.8 Hz, 1H), 4.58-4.52 (m, 1H), 3.02-2.95 (m, 1H), 2.25-2.00 (m, 2H), 1.78 (s, 3H), 1.69 (s, 3H), 1.53-1.50 (m, 6H), 1.10-1.07 (m, 2H), 0.86-0.83 (m, 2H), 0.81-0.77 (m, 3H). | 3 Intermediate 37 and Intermediate 17 |

TABLE 1-continued
| # | Structure | LCMS (M + 1) | NMR | Synthetic Protocol |
|---|---|---|---|---|
| 86 | 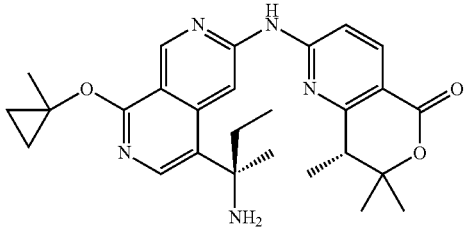 [SMILES: C[C@@H]1c2nc(Nc3cc4c(C(C)(C)N)cnc(OC5(C)CC5)c4cn3)ccc2C(=O)OC1(C)C] Or 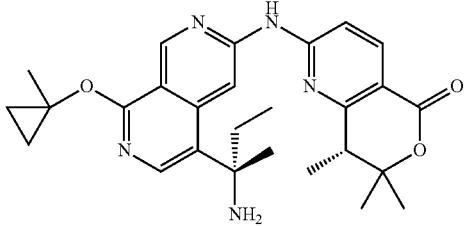 | 476 | ¹H-NMR (400 MHz, CD₃OD): δ ppm 9.32-9.27 (m, 2H), 8.20 (s, 1H), 8.15 (d, J = 8.8 Hz, 1H), 7.24 (d, J = 8.8 Hz, 1H), 3.03 (q, J = 7.2 Hz, 1H), 2.55-2.39 (m, 1H), 2.23-2.09 (m, 1H), 1.86-1.73 (m, 6H), 1.56 (s, 3H), 1.46 (s, 3H), 1.42 (d, J = 6.8 Hz, 3H), 1.12-1.05 (m, 2H), 0.90-0.84 (m, 2H), 0.78 (t, J = 7.2 Hz, 3H) | 3 Intermediate 38 and Intermediate 20 |
| 87 | 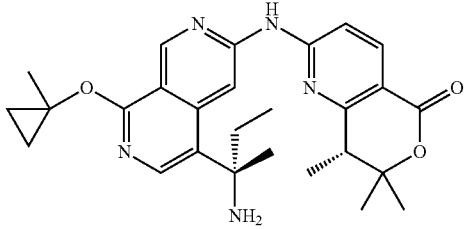 Or 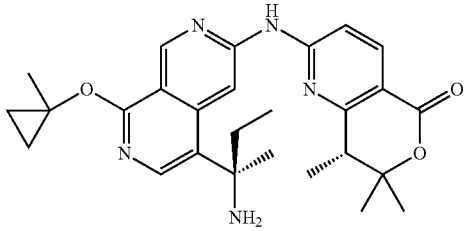 | 476 | ¹H-NMR (400 MHz, CD₃OD): δ ppm 9.33 (s, 1H), 9.30 (s, 1H), 8.21-8.11 (m, 2H), 7.24 (d, J = 8.8 Hz, 1H), 3.08-2.97 (m, 1H), 2.53-2.36 (m, 1H), 2.31-2.19 (m, 1H), 1.84-1.76 (m, 6H), 1.56 (s, 3H), 1.47 (s, 3H), 1.43-1.38 (m, 3H), 1.12-1.06 (m, 2H), 0.89-0.84 (m, 2H), 0.79 (t, J = 7.2 Hz, 3H) | 3 Intermediate 37 and Intermediate 20 |

TABLE 1-continued

| # | Structure | LCMS (M + 1) | NMR | Synthetic Protocol |
|---|---|---|---|---|
| 88 | | 474 | ¹H-NMR (400 MHz, CDCl₃): δ ppm 9.31 (s, 1 H), 9.26 (s, 1 H), 8.51 (s, 1 H), 8.24 (d, J = 8.8 Hz, 1 H), 7.95 (s, 1 H), 7.38-7.32 (m, 1 H), 4.57-4.44 (m, 1 H), 3.03-2.86 (m, 1 H), 1.79 (s, 3 H), 1.54-1.49 (m, 11 H), 1.12-1.06 (m, 2 H), 0.89-0.83 (m, 2 H), 0.70-0.60 (m, 2 H), 0.52-0.43 (m, 2 H). | 3 Intermediate 39 and Intermediate 17 |
| 89 | | 474 | ¹H-NMR (400 MHz, CDCl₃): δ ppm 9.31 (d, J = 2.4 Hz, 2 H), 8.55-8.50 (m, 1 H), 8.23 (d, J = 8.4 Hz, 1 H), 8.07 (s, 1 H), 7.32 (d, J = 8.8 Hz, 1 H), 4.60-4.44 (m, 1 H), 3.07-2.92 (m, 1 H), 1.79 (s, 3 H), 1.62-1.61 (m, 1 H), 1.54-1.48 (m, 10 H), 1.12-1.06 (m, 2 H), 0.89-0.82 (m, 2 H), 0.73-0.59 (m, 2 H), 0.55-0.42 (m, 2 H). | 3 Intermediate 40 and Intermediate 17 |

TABLE 1-continued
| # | Structure | LCMS (M + 1) | NMR | Synthetic Protocol |
|---|---|---|---|---|
| 90 | 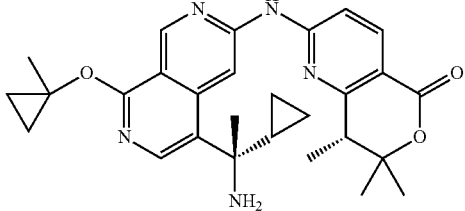 Or 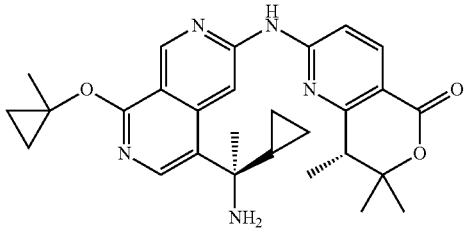 | 488 | ¹H-NMR (400 MHz, CDCl₃): δ ppm 9.38 (s, 1H), 9.32 (s, 1H), 8.52 (s, 1H), 8.21 (d, J = 8.8 Hz, 1H), 8.12 (s, 1H), 7.25 (d, J = 8.4 Hz, 1H), 3.02-2.97 (m, 1H), 1.79 (m, 3H), 1.54 (s, 3H), 1.53-1.51 (m, 1H), 1.49 (s, 6H), 1.41 (d, J = 7.2 Hz, 1H), 1.11-1.07 (m, 2H), 0.87-0.83 (m, 2H), 0.70-0.59 (m, 2H), 0.54-0.43 (m, 2H). | 3 Intermediate 40 and Intermediate 20 |
| 91 | 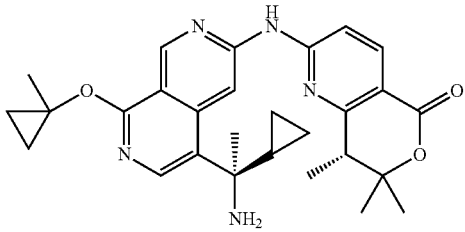 Or 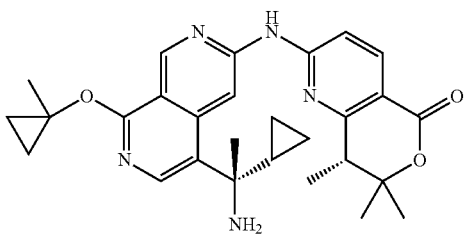 | 488 | ¹H-NMR (400 MHz, CDCl₃): δ ppm 9.36 (s, 1H), 9.32 (s, 1H), 8.50 (s, 1H), 8.24 (s, 1H), 8.20 (d, J = 8.8 Hz, 1H), 7.27 (d, J = 8.8 Hz, 1H), 2.99-2.94 (m, 1H), 1.78 (s, 3H), 1.58-1.56 (m, 1H), 1.48 (s, 3H), 1.47 (s, 3H), 1.42 (d, J = 7.2 Hz, 1H), 1.10-1.07 (m, 2H), 0.91-0.83 (m, 2H), 0.65-0.61 (m, 2H), 0.51-0.42 (m, 2H). | 3 Intermediate 39 and Intermediate 20 |

TABLE 1-continued

| # | Structure | LCMS (M + 1) | NMR | Synthetic Protocol |
|---|---|---|---|---|
| 92 | | 462 | ¹H-NMR (400 MHz, CDCl₃): δ ppm 9.38 (s, 1H), 9.22 (s, 1H), 8.16-7.78 (m, 3H), 6.95 (d, J = 8.0 Hz, 1H), 7.50 (d, J = 8.8 Hz, 1H), 4.79-4.74 (m, 1H), 2.93-2.87 (m, 1H), 2.14-2.04 (m, 2H), 1.71 (s, 3H), 1.62 (s, 3H), 1.45-1.43 (m, 3H), 1.27-1.25 (m, 3H), 1.01 (s, 2H), 0.77-0.69 (m, 5H). | 3 Intermediate 37 and Intermediate 41 |

TABLE 1-continued
| # | Structure | LCMS (M + 1) | NMR | Synthetic Protocol |
|---|---|---|---|---|
| 93 | 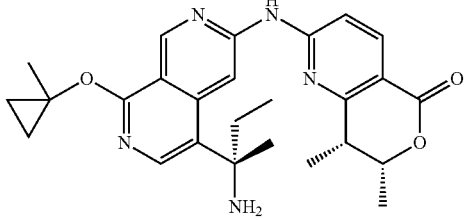<br>Or<br>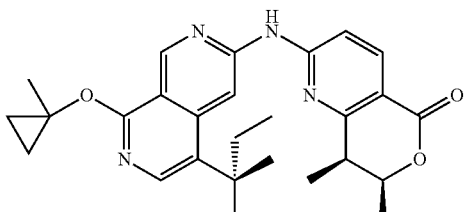<br>Or<br>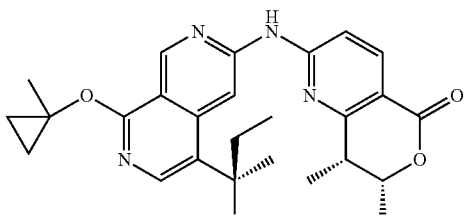<br>Or<br>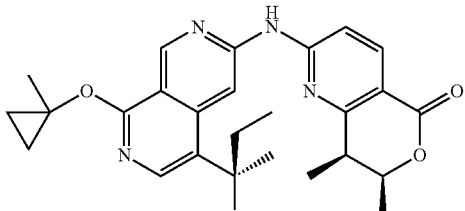 | 462 | ¹H-NMR (400 MHz, CDCl₃): δ ppm 9.34 (s, 1H), 9.23 (s, 1H), 8.18-8.12 (m, 2H), 8.01 (s, 1H), 6.98 (d, J = 8.4 Hz, 1H), 4.79-4.73 (m, 1H), 2.91-2.87 (m, 1H), 2.09 (t, J = 7.6 Hz, 2H), 1.71 (s, 3H), 1.64-1.60 (m, 3H), 1.44 (d, J = 6.4 Hz, 3H), 1.28 (d, J = 7.6 Hz, 3H), 1.01-0.99 (m, 2H), 0.79-0.71 (m, 5H), 1.52-1.39 (m, 2H), 1.25-1.13 (m, 1H). | 3 Intermediate 38 and Intermediate 41 |

TABLE 1-continued
| # | Structure | LCMS (M + 1) | NMR | Synthetic Protocol |
|---|---|---|---|---|
| 94 | 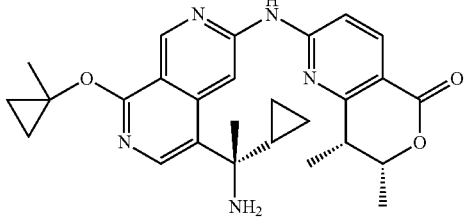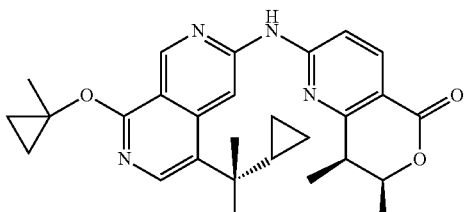 Or 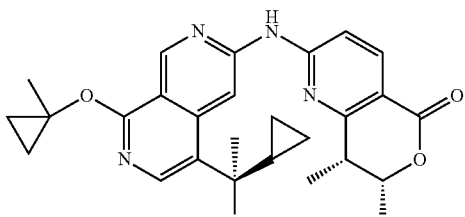 Or 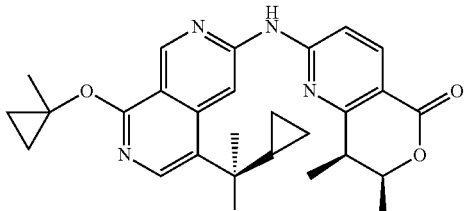 Or | 474 | ¹H-NMR (400 MHz, CDCl₃): δ ppm 9.43 (s, 1H), 9.23 (s, 1H), 8.43 (s, 1H), 8.14 (d, J = 8.8 Hz, 1H), 7.87 (s, 1H), 7.09 (d, J = 8.8 Hz, 1H), 4.75 (dd, J = 2.8, 6.4 Hz, 1H), 2.87 (dd, J = 2.8, 7.2 Hz, 1H), 1.71 (s, 3H), 1.50 (s, 4H), 1.44 (d, J = 6.4 Hz, 4H), 1.28 (d, J = 7.2 Hz, 3H), 1.22-1.14 (m, 1H), 1.02 (s, 2H), 0.81-0.75 (m, 2H), 0.56 (d, J = 6.0 Hz, 2H), 0.45-0.37 (m, 2H) | 3 Intermediate 39 and Intermediate 41 |

TABLE 1-continued
| # | Structure | LCMS (M + 1) | NMR | Synthetic Protocol |
|---|-----------|--------------|-----|--------------------|
| 95 | 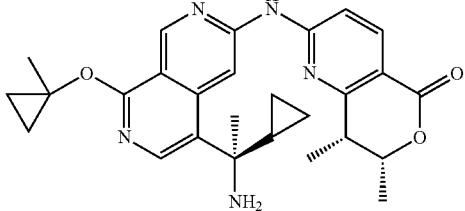<br>Or<br>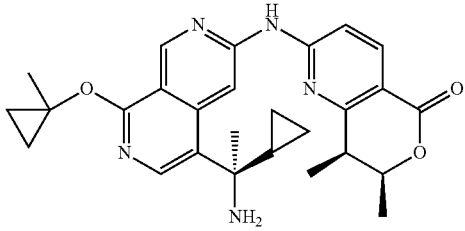<br>Or<br>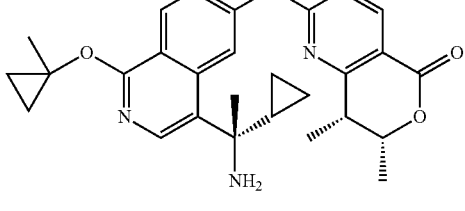<br>Or<br>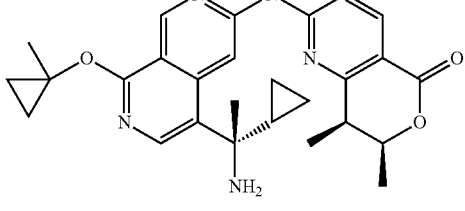 | 474 | ¹H-NMR (400 MHz, CDCl₃): δ ppm 9.47 (s, 1H), 9.23 (s, 1H), 8.48-8.43 (m, 1H), 8.13 (d, J = 8.8 Hz, 1H), 7.97-7.89 (m, 1H), 7.07 (d, J = 8.8 Hz, 1H), 4.75 (dd, J = 3.2, 6.4 Hz, 1H), 2.89 (dd, J = 3.2, 7.2 Hz, 1H), 1.71 (s, 3H), 1.49 (s, 4H), 1.44 (d, J = 6.8 Hz, 4H), 1.25 (d, J = 7.2 Hz, 3H), 1.21-1.14 (m, 1H), 1.05-0.99 (m, 2H), 0.83-0.74 (m, 2H), 0.57 (ddd, J = 4.4, 8.4, 16.8 Hz, 2H), 0.49-0.36 (m, 2H) | 3 Intermediate 40 and Intermediate 41 |
| 96 | 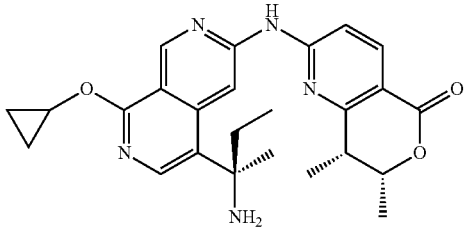<br>Or | 448 | ¹H-NMR (400 MHz, CD₃OD): δ ppm 9.49 (s, 1H), 9.27 (s, 1H), 8.21 (s, 1H), 8.15 (d, J = 8.8 Hz, 1H), 7.17 (d, J = 8.8 Hz, 1H), 4.93 (dd, J = 3.2, 6.4 Hz, 1H), 4.52-4.46 (m, 1H), 3.05 (dd, J = 2.8, 7.2 Hz, 1H), 2.47-2.36 (m, 1H), 2.27-2.17 (m, 1H), 1.77 (s, 3H), 1.54 (d, J = 6.8 Hz, 3H), 1.34 (d, J = 7.2 Hz, 3H), 0.94-0.89 (m, 4H), 0.76 (t, J = 7.2 Hz, 3H) | 3 Intermediate 33 Intermediate 41 |

TABLE 1-continued
| # | Structure | LCMS (M + 1) | NMR | Synthetic Protocol |
|---|---|---|---|---|
| | 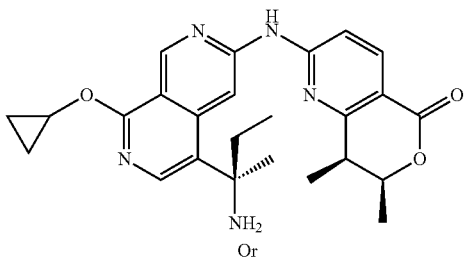 | | | |
| 97 | 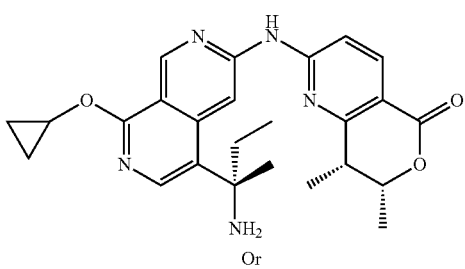 | 420 | ¹H-NMR (400 MHz, CDCl₃): δ ppm 9.31 (s, 1 H), 9.18 (s, 1 H), 8.52 (s, 1 H), 8.24 (d, J = 8.4 Hz, 1 H), 8.03-7.93 (m, 1 H), 7.42 (d, J = 8.8 Hz, 1 H), 4.58-4.40 (m, 2 H), 1.53 (s, 1 H), 1.50 (s, 3 H), 1.46 (d, J = 6.8 Hz, 3 H), 0.95-0.89 (m, 4 H), 0.72-0.59 (m, 2 H), 0.52-0.41 (m, 2 H). | 3 Intermediate 43 |
| 98 | 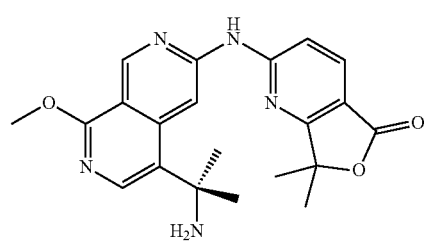 | 420 | ¹H-NMR (400 MHz, CD₃OD): δ ppm 9.56 (s, 1H), 9.36 (s, 1H), 8.31 (s, 1H), 7.98 (d, J = 8.8 Hz, 1H), 7.29 (d, J = 8.8 Hz, 1H), 4.13 (s, 3H), 1.76 (s, 3H), 1.75 (s, 3H), 1.73 (s, 3H), 1.72-1.68 (m, 1H), 0.64-0.56 (m, 2H), 0.54-0.41 (m, 2H). | 3 Intermediate 44 |

| # | Structure | LCMS (M + 1) | NMR | Synthetic Protocol |
|---|---|---|---|---|
| | | | | |
| 99 | | 434 | ¹H-NMR (400 MHz, CDCl₃): δ ppm 9.72 (s, 1 H), 9.39 (s, 1 H), 8.48 (s, 1 H), 8.12 (s, 1 H), 7.99 (d, J = 8.44 Hz, 1 H), 7.12 (d, J = 8.4 Hz, 1 H), 4.27-4.08 (m, 3 H), 1.77 (s, 3 H), 1.74 (s, 3 H), 1.58-1.55 (m, 4 H), 0.72-0.59 (m, 2 H), 0.54-0.43 (m, 2 H). | 3 Intermediate 43 and Intermediate 17 |
| 100 | | 434 | ¹H-NMR (400 MHz, CD₃OD): δ ppm 9.36 (s, 1H), 9.31 (s, 1H), 8.30 (s, 1H), 8.15 (d, J = 8.8 Hz, 1H), 7.36 (d, J = 8.8 Hz, 1H), 4.70-4.61 (m, 1H), 4.13 (s, 3H), 3.07-3.00 (m, 1H), 1.71 (s, 3H), 1.67-1.60 (m, 1H), 1.52-1.46 (m, 6H), 0.66-0.59 (m, 2H), 0.58-0.44 (m, 2H). | 3 Intermediate 44 and Intermediate 17 |

US 11,534,441 B2

TABLE 1-continued

| # | Structure | LCMS (M + 1) | NMR | Synthetic Protocol |
|---|-----------|--------------|-----|--------------------|
| 101 | 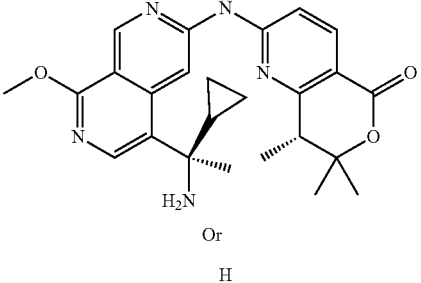 Or 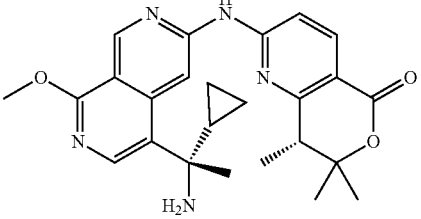 | 448 | ¹H-NMR (400 MHz, CDCl₃): δ ppm 9.41 (s, 2 H), 8.44 (s, 1 H), 8.23 (d, J = 8.4 Hz, 1 H), 8.02-7.96 (m, 1 H), 7.30 (s, 1 H), 4.15 (s, 3 H), 3.08-2.89 (m, 1 H), 1.56 (s, 3 H), 1.55-1.53 (m, 1 H), 1.49 (d, J = 5.2 Hz, 6 H), 1.45-1.41 (m, 3 H), 1.37-1.36 (m, 1 H), 0.73-0.57 (m, 2 H), 0.55-0.40 (m, 2 H). | 3 Intermediate 43 and Intermediate 20 |
| 102 | 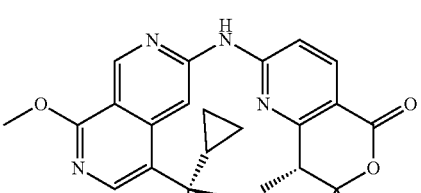 Or 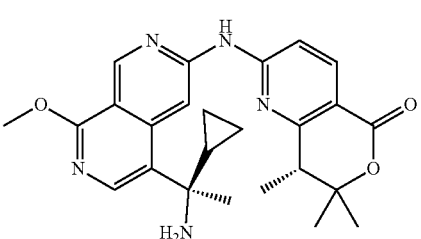 | 448 | ¹H-NMR (400 MHz, CD₃OD): δ ppm 9.46 (s, 1H), 9.36 (s, 1H), 8.31 (s, 1H), 8.13 (d, J = 8.4 Hz, 1H), 7.26 (d, J = 8.4 Hz, 1H), 4.13 (s, 3H), 3.10-3.02 (m, 1H), 1.73 (s, 3H), 1.70-1.61 (m, 1H), 1.54 (s, 3H), 1.46 (s, 3H), 1.39 (d, J = 8.8 Hz, 3H), 0.66-0.58 (m, 2H), 0.57-0.45 (m, 2H). | 3 Intermediate 44 and Intermediate 20 |
| 103 | 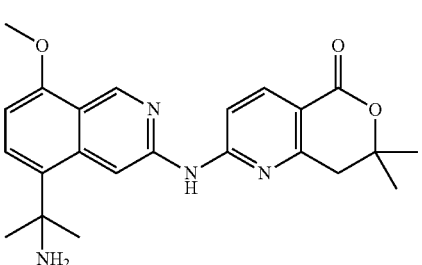 | 407 | ¹H-NMR (400 MHz, CD₃OD): δ ppm 9.44 (s, 1H), 9.25 (s, 1H), 8.54 (s, 1H), 8.13 (d, J = 8.8 Hz, 1H), 7.52 (d, J = 8.4 Hz, 1H), 7.19 (d, J = 8.8 Hz, 1H), 6.91 (d, J = 8.4 Hz, 1H), 4.08 (s, 3H), 3.21 (s, 2H), 2.07 (s, 6H), 1.54 (s, 6H) | 4 |
| 104 | 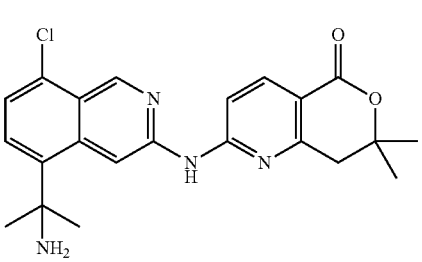 [SMILES: CC1(C)Cc2nc(Nc3cc4c(C(C)(C)N)ccc(Cl)c4cn3)ccc2C(=O)O1] | 411 | ¹H-NMR (400 MHz, CD₃OD): δ ppm 9.61 (s, 1H), 9.42 (s, 1H), 8.12 (d, J = 8.8 Hz, 1H), 7.79 (d, J = 8.0 Hz, 1H), 7.48 (d, J = 8.0 Hz, 1H), 7.14 (d, J = 8.8 Hz, 1H), 3.24 (s, 2H), 1.87 (s, 6H), 1.55 (s, 6H) | 12 |

TABLE 1-continued

| # | Structure | LCMS (M + 1) | NMR | Synthetic Protocol |
|---|---|---|---|---|
| 105 | 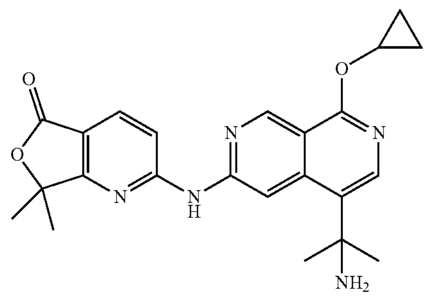 [SMILES: CC(C)(N)c1cnc(OC2CC2)c2cnc(Nc3ccc4c(n3)C(C)(C)OC4=O)cc12] | 420 | ¹H-NMR (400 MHz, 6d-DMSO): δ ppm 10.97-10.89 (m, 1 H), 9.67 (s, 1 H), 9.22 (s, 1 H), 8.30-8.17 (m, 1 H), 8.02 (d, J = 8.8 Hz, 1 H), 7.39-7.23 (m, 1 H), 4.53-4.45 (m, 1 H), 2.06 (d, J = 4.4 Hz, 1 H), 1.68 (d, J = 1.6 Hz, 12 H), 0.90-0.74 (m, 4 H). | 3 |
| 106 | 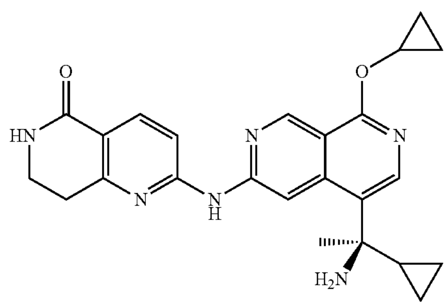 [SMILES: C[C@](N)(c1cnc(OC2CC2)c2cnc(Nc3ccc4c(n3)CCNC4=O)cc12)C1CC1] | 431 | ¹H-NMR (400 MHz, CD₃OD): δ ppm 9.45 (s, 1H), 9.24 (s, 1H), 8.24 (s, 1H), 8.10 (d, J = 8.8 Hz, 1H), 7.15 (d, J = 8.4 Hz, 1H), 4.52-4.40 (m, 1H), 3.61 (d, J = 7.2 Hz, 2H), 3.14 (d, J = 6.8 Hz, 2H), 1.76 (s, 3H), 1.67-1.61 (m, 1H), 0.91-0.88 (m, 4H), 0.75-0.45 (m, 4H). | 3 second eluting isomer after Step 3 Example 3B |
| 107 | 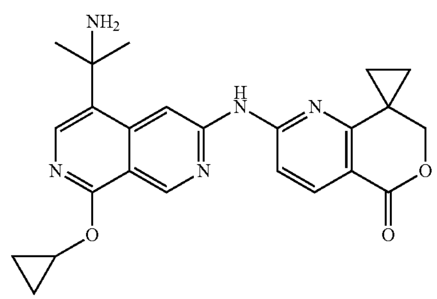 [SMILES: CC(C)(N)c1cnc(OC2CC2)c2cnc(Nc3ccc4c(n3)C3(CC3)COC4=O)cc12] | 432 | ¹H-NMR (400 MHz, CD₃OD): δ ppm 9.26 (s, 1H), 8.61 (s, 1H), 8.20 (s, 1H), 8.14 (d, J = 8.8 Hz, 1H), 7.45 (d, J = 8.8 Hz, 1H), 4.47-4.43 (m, 1H), 4.42 (s, 2H), 1.75 (s, 6H), 1.65-1.60 (m, 2H), 1.20-1.16 (m, 2H), 0.90-0.96 (m, 4H). | 3 |
| 108 | 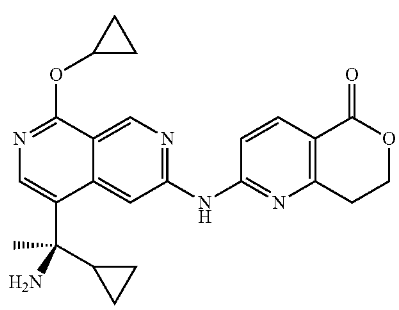 [SMILES: C[C@](N)(c1cnc(OC2CC2)c2cnc(Nc3ccc4c(n3)CCOC4=O)cc12)C1CC1] | 432 | | 3 second eluting isomer after Step 3 Example 3B |
| 109 | 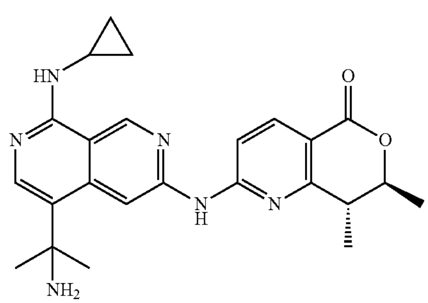 [SMILES: C[C@@H]1OC(=O)c2ccc(Nc3cc4c(C(C)(C)N)cnc(NC5CC5)c4cn3)nc2[C@H]1C] | 433 | ¹H-NMR (400 MHz, 6d-DMSO): δ ppm 10.46 (s, 1H), 9.35-9.23 (m, 2H), 8.12 (s, 1H), 8.05 (d, J = 8.8 Hz, 1H), 7.69 (d, J = 2.8 Hz, 1H), 7.35 (d, J = 8.8 Hz, 1H), 4.63-4.53 (m, 1H), 3.03-2.85 (m, 2H), 1.62 (s, 6H), 1.47-1.33 (m, 6H), 0.79-0.69 (m, 2H), 0.62-0.52 (m, 2H). | 5 Intermediate 17 |

TABLE 1-continued
| # | Structure | LCMS (M + 1) | NMR | Synthetic Protocol |
|---|---|---|---|---|
| 110 | 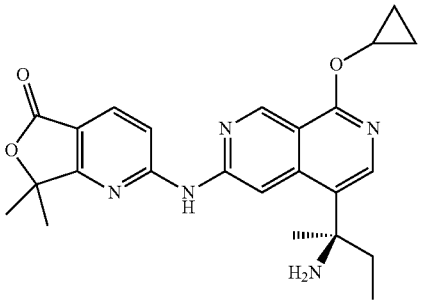 Or 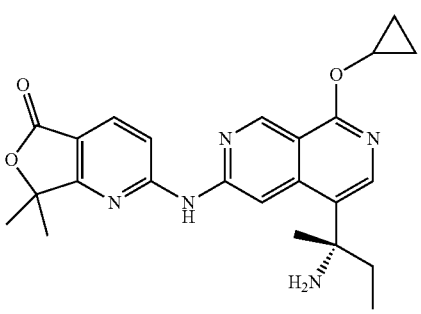 | 434 | ¹H-NMR (400 MHz, CD₃OD): δ ppm 9.36 (s, 1H), 9.29 (s, 1H), 8.23 (s, 1H), 7.98 (d, J = 8.4 Hz, 1H), 7.25 (d, J = 8.4 Hz, 1H), 4.53-4.42 (m, 1H), 2.55-2.45 (m, 1H), 2.18-2.08 (m, 1H), 1.77 (s, 3H), 1.76 (d, J = 2.0 Hz, 6H), 0.93-0.87 (m, 4H), 0.72 (t, J = 7.2 Hz, 3H). | 3 Intermediate 33 |
| 111 | 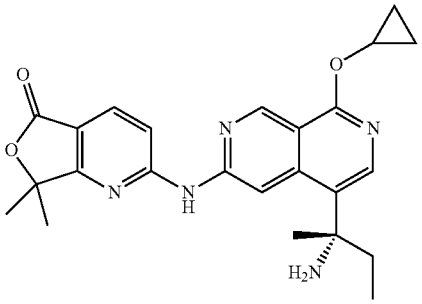 Or 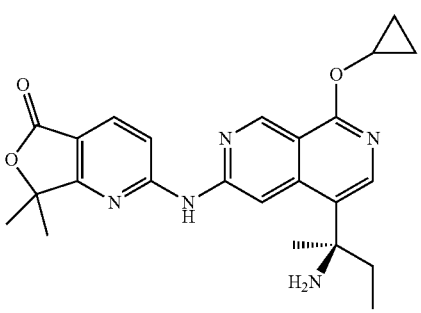 | 434 | ¹H-NMR (400 MHz, CD₃OD): δ ppm 9.36 (s, 1H), 9.29 (s, 1H), 8.23 (s, 1H), 7.98 (d, J = 8.4 Hz, 1H), 7.25 (d, J = 8.8 Hz, 1H), 4.52-4.44 (m, 1H), 2.55-2.45 (m, 1H), 2.19-2.08 (m, 1H), 1.79 (s, 3H), 1.76 (d, J = 2.4 Hz, 6H), 0.93-0.87 (m, 4H), 0.72 (t, J = 7.6 Hz, 3H). | 3 Intermediate 34 |
| 112 | 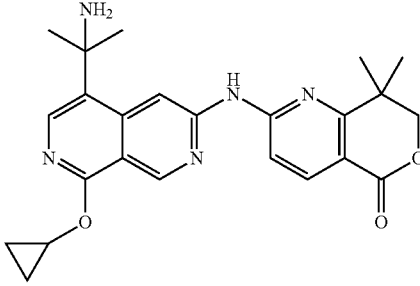 | 434 | ¹H-NMR (400 MHz, CD₃OD): δ ppm 9.30 (s, 1H), 8.78 (s, 1H), 8.23 (s, 1H), 8.19-8.11 (m, 1H), 7.50 (d, J = 8.8 Hz, 1H), 4.51-4.44 (m, 1H), 4.33 (s, 2H), 1.80 (s, 6H), 1.48 (s, 6H), 0.94-0.88 (m, 4H) | 3 |

TABLE 1-continued
| # | Structure | LCMS (M + 1) | NMR | Synthetic Protocol |
|---|---|---|---|---|
| 113 | 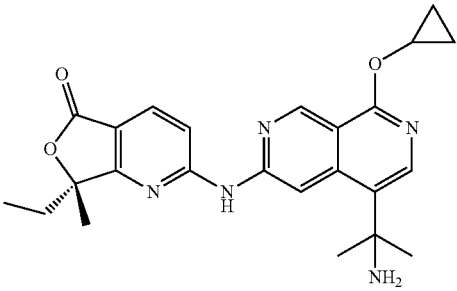  Or | 434 | ¹H-NMR (400 MHz, CD$_3$OD): δ ppm 9.36 (s, 1H), 9.27 (s, 1H), 8.27 (s, 1H), 7.99 (d, J = 8.8 Hz, 1H), 7.26 (d, J = 8.8 Hz, 1H), 4.46 (dd, J = 3.2, 6.0 Hz, 1H), 2.26-2.15 (m, 2H), 1.83 (d, J = 4.4 Hz, 6H), 1.74 (s, 3H), 0.95-0.85 (m, 4H), 0.77 (d, J = 7.2 Hz, 3H) | 3 Intermediate 47 |
| 114 | 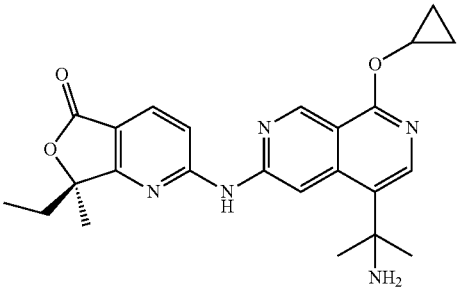  Or | 434 | ¹H-NMR (400 MHz, CD$_3$OD): δ ppm 9.37 (s, 1H), 9.28 (d, J = 0.8 Hz, 1H), 8.27 (s, 1H), 8.00 (d, J = 8.8 Hz, 1H), 7.27 (d, J = 8.8 Hz, 1H), 4.47 (dd, J = 3.2, 6.0 Hz, 1H), 2.26-2.15 (m, 2H), 1.83 (d, J = 4.4 Hz, 6H), 1.75 (s, 3H), 0.95-0.86 (m, 4H), 0.78 (d, J = 7.6 Hz, 3H) | 3 Intermediate 46 |

TABLE 1-continued

| # | Structure | LCMS (M + 1) | NMR | Synthetic Protocol |
|---|---|---|---|---|
| 115 | 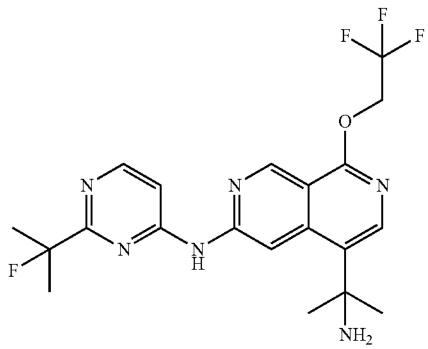 [SMILES: CC(C)(N)c1cnc(OCC(F)(F)F)c2cnc(Nc3ccnc(C(C)(C)F)n3)cc12] | 439 | ¹H-NMR (400 MHz, CD₃OD): δ ppm 9.37 (s, 1H), 9.17 (s, 1H), 8.40 (d, J = 6.0 Hz, 1H), 8.23 (s, 1H), 7.27 (d, J = 5.6 Hz, 1H), 5.18-5.01 (m, 2H), 1.82 (s, 3H), 1.80-1.75 (m, 9H). | 3 |
| 116 | 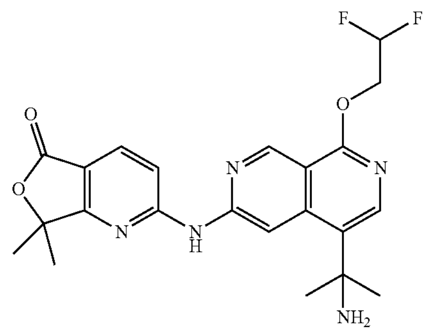 [SMILES: CC(C)(N)c1cnc(OCC(F)F)c2cnc(Nc3ccc4c(n3)C(C)(C)OC4=O)cc12] | 444 | | 3 |
| 117 | | 446 | ¹H-NMR (400 MHz, CD₃OD): δ ppm 9.45 (s, 1H), 9.25 (s, 1H), 8.31 (s, 1H), 8.14 (d, J = 8.8 Hz, 1H), 7.27 (d, J = 8.8 Hz, 1H), 4.73-4.64 (m, 1H), 4.49-4.38 (m, 2H), 3.21-3.11 (m, 1H) 1.73-1.64 (m, 4H), 1.48 (d, J = 7.2 Hz, 3H), 0.93-0.85 (m, 4H), 0.66-0.43 (m, 4H). | 3 second eluting isomer after Step 3 Example 3B and Intermediate 48 |

TABLE 1-continued
| # | Structure | LCMS (M + 1) | NMR | Synthetic Protocol |
|---|-----------|--------------|-----|--------------------|
| 118 | 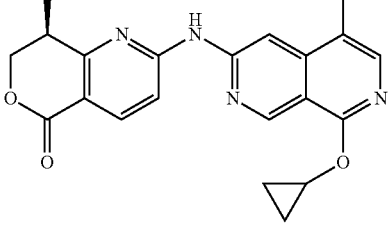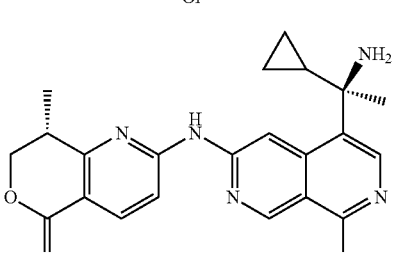 Or | 446 | ¹H-NMR (400 MHz, CD₃OD): δ ppm 9.35 (s, 1H), 9.27 (s, 1H), 8.25 (s, 1H), 8.14 (d, J = 8.8 Hz, 1H), 7.29 (d, J = 8.8 Hz, 1H), 4.64-4.68 (m, 1H), 4.51-4.45 (m, 1H), 4.44-4.38 (m, 1H), 3.24-3.14 (m, 1H), 1.80 (s, 3H), 1.71-1.62 (m, 1H), 1.47 (d, J = 7.2 Hz, 3H), 0.93-0.87 (m, 4H), 0.72-0.57 (m, 3H), 0.51-0.43 (m, 1H). | 3 second eluting isomer after Step 3 Example 3B and Intermediate 49 |
| 119 | 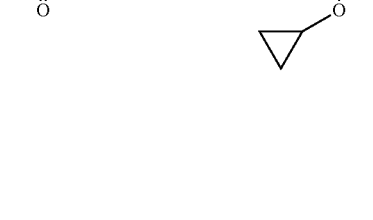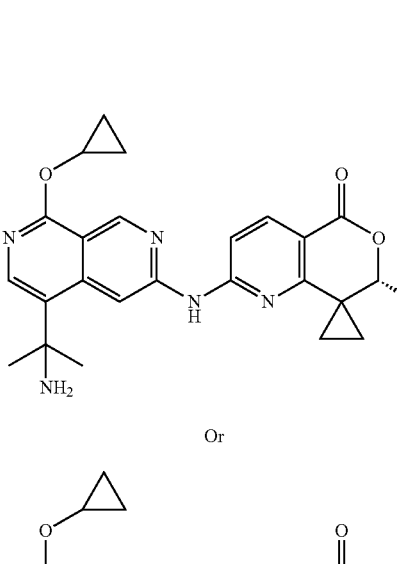 Or | 446 | ¹H-NMR (400 MHz, CD₃OD): δ ppm 9.27 (s, 1H), 8.57 (s, 1H), 8.20 (s, 1H), 8.15 (d, J = 8.8 Hz, 1H), 7.49 (d, J = 8.8 Hz, 1H), 4.68-4.61 (m, 1H), 4.50-4.42 (m, 1H), 1.76 (s, 6H), 1.90-1.63 (m, 1H), 1.56-1.51 (m, 1H), 1.37 (d, J = 6.4 Hz, 3H), 1.26-1.18 (m, 2H), 0.92-0.86 (m, 4H). | 3 Intermediate 50 |

TABLE 1-continued
| # | Structure | LCMS (M + 1) | NMR | Synthetic Protocol |
|---|---|---|---|---|
| 120 | 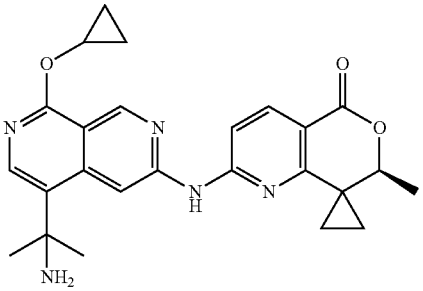<br>Or<br>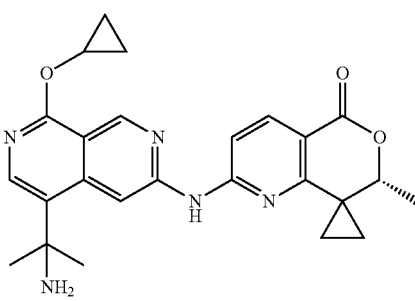 | 446 | ¹H-NMR (400 MHz, CD₃OD): δ ppm 9.26 (s, 1H), 8.56 (s, 1H), 8.19 (s, 1H), 8.14 (d, J = 8.8 Hz, 1H), 7.49 (d, J = 8.8 Hz, 1H), 4.67-4.60 (m, 1H), 4.50-4.41 (m, 1H), 1.76 (s, 6H), 1.69-1.62 (m, 1H), 1.56-1.51 (m, 1H), 1.37 (d, J = 6.4 Hz, 3H), 1.27-1.18 (m, 2H), 0.91-0.86 (m, 4H). | 3 Intermediate 51 |
| 121 | 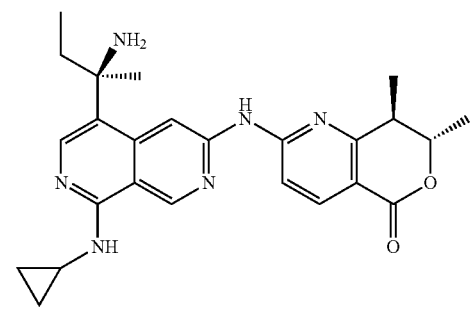<br>Or<br>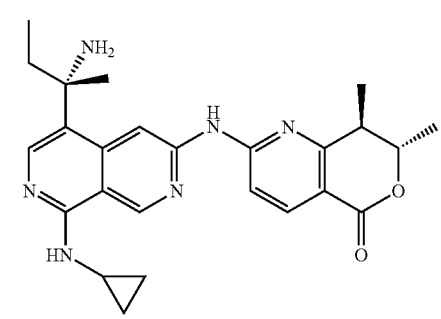 | 448 | ¹H-NMR (400 MHz, CD₃OD): δ ppm 9.21 (s, 1H), 9.01 (s, 1H), 8.12 (d, J = 8.4 Hz, 1H), 8.05 (s, 1H), 7.30 (d, J = 8.8 Hz, 1H), 4.68-4.62 (m, 1H), 3.06-2.94 (m, 1H), 2.87-2.77 (m, 1H), 2.43-2.24 (m, 1H), 2.16-2.03 (m, 1H), 1.77-1.67 (m, 3H), 1.54-1.40 (m, 6H), 0.92-0.83 (m, 2H), 0.73 (t, J = 7.4 Hz, 3H), 0.67-0.61 (m, 2H). | 5 Intermediate 53 and Intermediate 17 |

TABLE 1-continued

| # | Structure | LCMS (M + 1) | NMR | Synthetic Protocol |
|---|---|---|---|---|
| 122 | 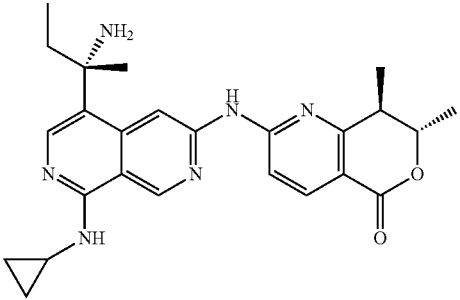 Or 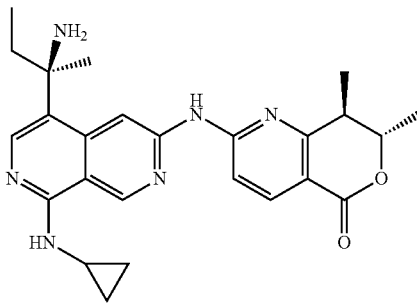 | 447 | ¹H-NMR (400 MHz, CD₃OD): δ ppm 9.22 (s, 1H), 9.05 (s, 1H), 8.13 (d, J = 8.8 Hz, 1H), 8.05 (s, 1H), 7.30 (d, J = 8.4 Hz, 1H), 4.68-4.65 (m, 1H), 3.07-2.96 (m, 1H), 2.87-2.79 (m, 1H), 2.40-2.25 (m, 1H), 2.22-2.09 (m, 1H), 1.75-1.68 (m, 3H), 1.51-1.42 (m, 6H), 0.91-0.84 (m, 2H), 0.74 (t, J = 7.4 Hz, 3H), 0.68-0.62 (m, 2H). | 5 Intermediate 52 and Intermediate 17, |
| 123 | 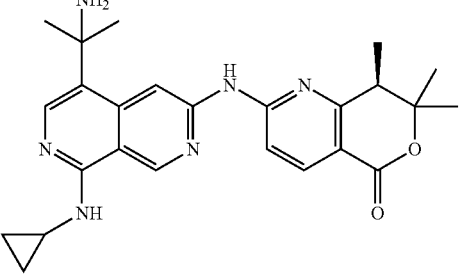 | 447 | ¹H-NMR (400 MHz, CD₃OD): δ ppm 9.25 (d, J = 4.4 Hz, 2H), 8.13 (d, J = 8.8 Hz, 1H), 8.15-8.11 (m, 1H), 8.10 (s, 1H), 7.23 (d, J = 8.8 Hz, 1H), 3.05 (q, J = 7.2 Hz, 1H), 2.85 (dd, J = 3.6, 7.2 Hz, 1H), 1.80 (d, J = 7.2 Hz, 6H), 1.55 (s, 3H), 1.46 (s, 3H), 1.40 (d, J = 7.2 Hz, 3H), 0.94-0.86 (m, 2H), 0.69-0.63 (m, 2H) | 5 Intermediate 20 |
| 124 | 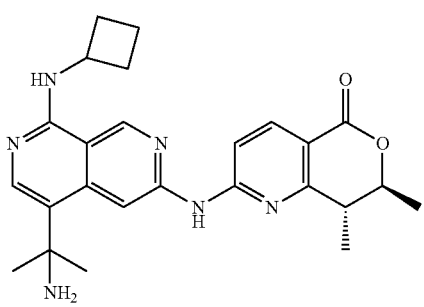 [SMILES: C[C@@H]1OC(=O)c2ccc(Nc3cc4c(C(C)(C)N)cnc(NC5CCC5)c4cn3)nc2[C@H]1C] | 447 | ¹H-NMR (400 MHz, CD₃OD): δ ppm 9.33 (s, 1H), 9.05 (s, 1H), 8.15 (d, J = 8.8 Hz, 1H), 8.04 (s, 1H), 7.34 (d, J = 8.7 Hz, 1H), 4.70-4.65 (m, 1H), 4.65-4.59 (m, 1H), 3.07-3.02 (m, 1H), 2.53-2.45 (m, 2H), 2.17-2.09 (m, 2H), 1.88-1.81 (m, 2H), 1.77 (d, J = 4.6 Hz, 6H), 1.53-1.49 (m, 3H), 1.47 (d, J = 6.5 Hz, 3H) | 5 Intermediate 17 |
| 125 | 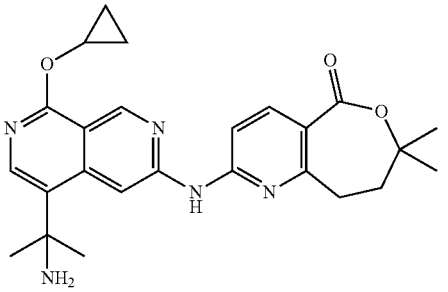 [SMILES: CC1(C)CCc2nc(Nc3cc4c(C(C)(C)N)cnc(OC5CC5)c4cn3)ccc2C(=O)O1] | 448 | ¹H-NMR (400 MHz, CD₃OD): δ ppm 9.34 (s, 1H), 9.13 (s, 1H), 8.10 (s, 1H), 7.97 (d, J = 8.8 Hz, 1H), 7.04 (d, J = 8.8 Hz, 1H), 4.37-4.33 (m, 1H), 3.18-3.14 (m, 2H), 2.22-2.18 (m, 2H), 1.71 (s, 6H), 1.32 (s, 6H), 0.81-0.76 (m, 4H). | 3 |

TABLE 1-continued

| # | Structure | LCMS (M + 1) | NMR | Synthetic Protocol |
|---|-----------|--------------|-----|--------------------|
| 126 | Intentionally Omitted | | | |
| 127 | | 448 | ¹H-NMR (400 MHz, CD₃OD): δ ppm 9.31 (s, 1H), 8.72 (s, 1H), 8.33-8.11 (m, 2H), 7.55 (d, J = 8.8 Hz, 1H), 4.61-4.59 (m, 1H), 4.52-4.44 (m, 1H), 1.81 (d, J = 0.8 Hz, 6H), 1.55 (s, 3H), 1.48 (d, J = 6.8 Hz, 3H), 1.33 (s, 3H), 0.94-0.88 (m, 4H) | 3 Intermediate 56 |
| 128 | | 448 | ¹H-NMR (400 MHz, CD₃OD): δ ppm 9.32-9.25 (m, 2H), 8.19-8.16 (m, 2H), 7.28 (d, J = 8.8 Hz, 1H), 4.96-4.94 (m, 2H), 4.50 (t, J = 3.2 Hz, 1H), 2.97 (s, 1H), 2.06-1.99 (m, 1H), 1.89-1.86 (m, 6H), 1.57 (t, J = 6.4 Hz, 3H), 0.95-0.90 (m, 7H). | 3 Intermediate 58 |

TABLE 1-continued

| # | Structure | LCMS (M + 1) | NMR | Synthetic Protocol |
|---|-----------|--------------|-----|--------------------|
| 129 | | 448 | ¹H-NMR (400 MHz, CD₃OD): δ ppm 8.30 (d, J = 2.4 Hz, 1H), 7.86 (d, J = 7.6 Hz, 1H), 7.57 (s, 1H), 7.06 (d, J = 2.4 Hz, 1H), 7.02 (s, 1H), 6.61 (d, J = 7.6 Hz, 1H), 4.34 (s, 2H), 4.27-4.12 (m, 2H), 4.10 (s, 3H), 4.06 (s, 2H), 4.00 (d, J = 2.8 Hz, 1H), 3.9 (s, 3H), 3.55-3.48 (m, 2H), 3.19-3.12 (m, 2H). | 3 Intermediate 33 Intermediate 46 |

Or

Or

Or

TABLE 1-continued
| # | Structure | LCMS (M + 1) | NMR | Synthetic Protocol |
|---|---|---|---|---|
| 130 | 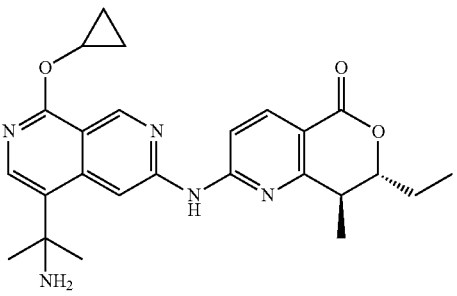 Or 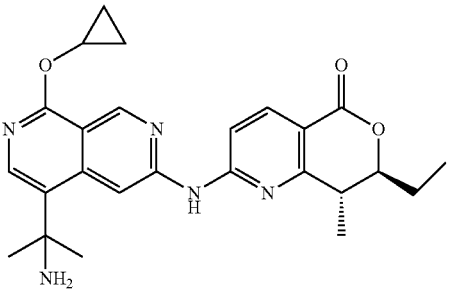 | 448 | ¹H-NMR (400 MHz, CD₃OD): δ ppm 9.30 (s, 1H), 9.15 (s, 1H), 8.52 (s, 1H), 8.16 (d, J = 8.8 Hz, 1H), 8.09 (s, 1H), 7.29 (d, J = 8.4 Hz, 1H), 4.54-4.42 (m, 2H), 3.12-3.05 (m, 1H), 1.94 (d, J = 2.4 Hz, 6H), 1.83-1.71 (m, 2H), 1.51 (d, J = 7.2 Hz, 3H), 1.08-1.05 (m, 3H), 0.92-0.89 (m, 4H) | 3 Intermediate 60 |
| 131 | 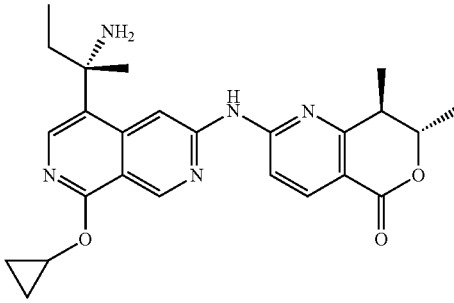 Or 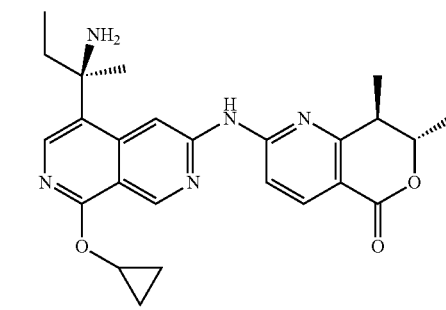 | 448 | ¹H-NMR (400 MHz, CD₃OD): δ ppm 9.28 (s, 1H), 9.16 (s, 1H), 8.19 (s, 1H), 8.15 (d, J = 8.4 Hz, 1H), 7.31 (d, J = 8.4 Hz, 1H), 4.71-4.64 (m, 1H), 4.52-4.43 (m, 1H), 3.06-2.98 (m, 1H), 2.48-2.36 (m, 1H), 2.20-2.05 (m, 1H), 1.77 (s, 3H), 1.51 (d, J = 7.2 Hz, 3H), 1.46 (d, J = 6.8 Hz, 3H), 0.92-0.88 (m, 4H), 0.75 (t, J = 7.2 Hz, 3H). | 3 Intermediate 34 and Intermediate 17 |

TABLE 1-continued
| # | Structure | LCMS (M + 1) | NMR | Synthetic Protocol |
|---|---|---|---|---|
| 132 | 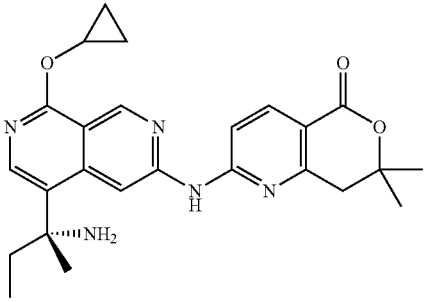 Or 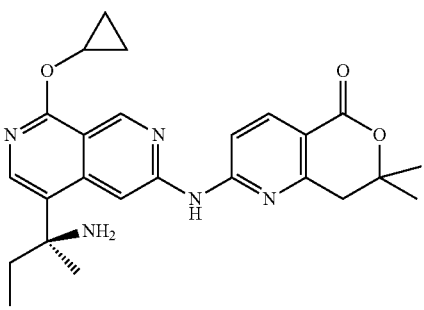 | 448 | ¹H-NMR (400 MHz, CD₃OD): δ ppm 9.36 (s, 1H), 9.26 (s, 1H), 8.18 (s, 1H), 8.14 (d, J = 8.4 Hz, 1H), 7.19 (d, J = 8.8 Hz, 1H), 4.50-4.44 (m, 1H), 3.22 (s, 2H), 2.43-2.32 (m, 1H), 2.25-2.13 (m, 1H), 1.77 (s, 3H), 1.53 (s, 6H), 0.93-0.87 (m, 4H), 0.76 (t, J = 7.2 Hz, 3H). | 3 Intermediate 33 |
| 133 | 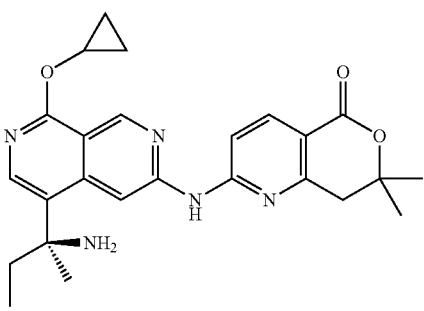 Or 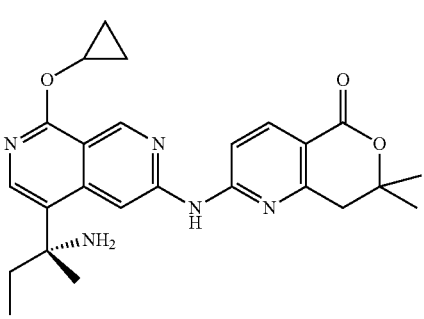 | 448 | ¹H-NMR (400 MHz, CD₃OD): δ ppm 9.35 (s, 1H), 9.26 (s, 1H), 8.16 (s, 1H), 8.14 (d, J = 8.8 Hz, 1H), 7.19 (d, J = 8.8 Hz, 1H), 4.51-4.44 (m, 1H), 3.22 (s, 2H), 2.46-2.35 (m, 1H), 2.25-2.15 (m, 1H), 1.79 (s, 3H), 1.53 (s, 6H), 0.92-0.87 (m, 4H), 0.77 (t, J = 7.2 Hz, 3H). | 3 Intermediate 34 |

TABLE 1-continued

| # | Structure | LCMS (M + 1) | NMR | Synthetic Protocol |
|---|---|---|---|---|
| 134 | | 448 | ¹H-NMR (400 MHz, CD₃OD): δ ppm 9.34 (s, 1H), 9.09 (s, 1H), 8.50 (s, 1H), 8.16 (d, J = 8.4 Hz, 1H), 8.05 (s, 1H), 7.31 (d, J = 8.4 Hz, 1H), 4.55-4.45 (m, 2H), 3.08-3.06 (m, 1H), 2.00 (d, J = 2.4 Hz, 6H), 1.85-1.70 (m, 2H), 1.51 (d, J = 7.2 Hz, 3H), 1.08-1.05 (m, 3H), 0.92-0.90 (m, 4H) | 3 Intermediate 61 |
| | Or | | | |
| 135 | 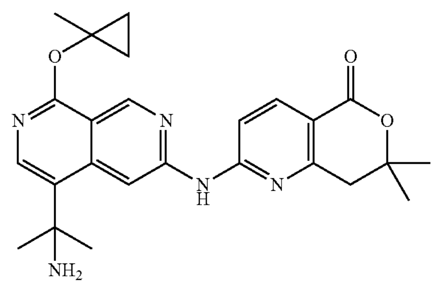 [SMILES: CC1(C)Cc2nc(Nc3cc4c(C(C)(C)N)cnc(OC5(C)CC5)c4cn3)ccc2C(=O)O1] | 448 | ¹H-NMR (400 MHz, CD₃OD): δ ppm 9.37 (s, 1H), 9.25 (s, 1H), 8.21 (s, 1H), 8.13 (d, J = 8.8 Hz, 1H), 7.18 (d, J = 8.4 Hz, 1H), 3.21 (s, 2H), 1.80 (s, 6H), 1.74 (s, 3H), 1.53 (s, 6H), 1.10-1.01 (m, 2H), 0.88-0.80 (m, 2H). | 3 |
| 136 | | 448 | ¹H-NMR (400 MHz, CD₃OD): δ ppm 9.32 (s, 1H), 8.66 (s, 1H), 8.23-8.14 (m, 2H), 7.55 (d, J = 8.8 Hz, 1H), 4.54-4.45 (m, 1H), 4.33 (s, 2H), 2.50-2.37 (m, 1H), 2.23-2.11 (m, 1H), 1.79 (s, 3H), 1.48 (s, 6H), 0.94-0.88 (m, 4H), 0.80-0.72 (m, 3H). | 3 Intermediate 33 |
| | Or | | | |

TABLE 1-continued
| # | Structure | LCMS (M + 1) | NMR | Synthetic Protocol |
|---|---|---|---|---|
| 137 | 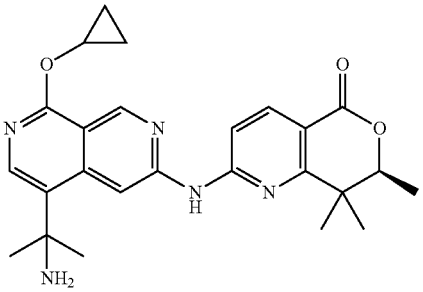 Or 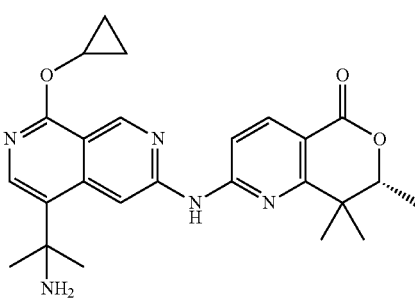 | 448 | ¹H-NMR (400 MHz, CD₃OD): δ ppm 9.31 (s, 1H), 8.72 (s, 1H), 8.23-8.14 (m, 2H), 7.56 (d, J = 8.4 Hz, 1H), 4.59-4.58 (m, 1H), 4.53-4.43 (m, 1H), 1.81 (s, 6H), 1.56 (s, 3H), 1.48 (d, J = 6.4 Hz, 3H), 1.33 (s, 3H), 0.96-0.88 (m, 4H) | 3 Intermediate 57 |
| 138 | 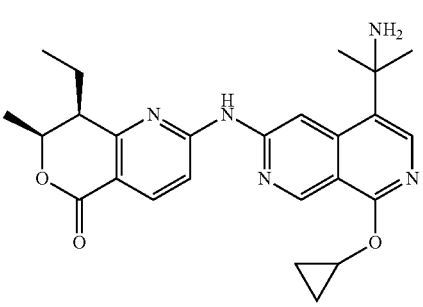 Or 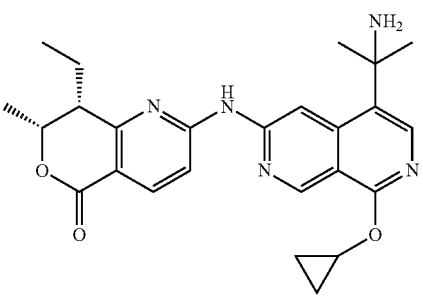 | 448 | ¹H-NMR (400 MHz, CD₃OD): δ ppm 9.29-9.24 (m, 2H), 8.18-8.13 (m, 2H), 7.28 (d, J = 8.8 Hz, 1H), 4.97-4.92 (m, 2H), 4.51-4.47 (m, 1H), 2.98-2.94 (m, 1H), 2.04-2.00 (m, 1H), 1.90-1.87 (m, 6H), 1.57 (t, J = 6.8 Hz, 3H), 0.95-0.91 (m, 7H) | 3 Intermediate 59 |

TABLE 1-continued

| # | Structure | LCMS (M + 1) | NMR | Synthetic Protocol |
|---|---|---|---|---|
| 139 | | 450 | ¹H-NMR (400 MHz, CD₃OD): δ ppm 9.33 (s, 1H), 8.92 (s, 1H), 8.18 (d, J = 8.8 Hz, 1H), 8.01 (s, 1H), 7.35 (d, J = 8.4 Hz, 1H), 4.68-4.65 (m, 1H), 4.54 (m, 1H), 4.42-4.38 (m, 1H), 4.11-4.08 (m, 1H), 3.03-3.01 (m, 1H), 1.99 (s, 3H), 1.53-1.45 (m, 6H), 0.91 (m, 4H). | Example 13 1st eluting isomer |
| 140 | | 450 | ¹H-NMR (400 MHz, CD₃OD): δ ppm 9.33 (s, 1H), 8.94 (s, 1H), 8.18 (d, J = 8.8 Hz, 1H), 8.01 (s, 1H), 7.34 (d, J = 8.4 Hz, 1H), 4.69-4.67 (m, 1H), 4.55-4.50 (m, 1H), 4.39-4.36 (m, 1H), 4.16-4.13 (m, 1H), 3.06-3.03 (m, 1H), 1.99 (s, 3H), 1.51-1.46 (m, 6H), 0.91 (m, 4H). | Example 13, 2nd eluting isomer |

TABLE 1-continued

| # | Structure | LCMS (M + 1) | NMR | Synthetic Protocol |
|---|---|---|---|---|
| 141 | 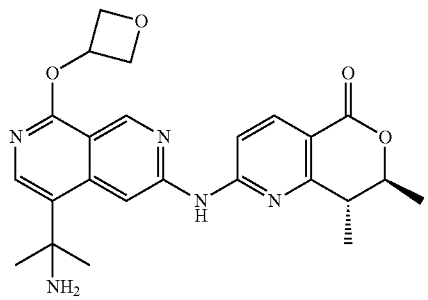 | 450 | ¹H-NMR (400 MHz, CD₃OD): δ ppm 9.44 (s, 1H), 9.19 (s, 1H), 8.16-8.12 (m, 2H), 7.31 (d, J = 8.8 Hz, 1H), 5.85-5.79 (m, 1H), 5.11-5.06 (m, 2H), 4.83-4.81 (m, 2H), 4.67-4.64 (m, 1H), 3.06-2.99 (m, 1H), 1.81-1.72 (m, 6H), 1.52-1.45 (m, 6H). | 9 Intermediate 17 |
| 142 | Or | 450 | | 3 Intermediate 17 and Intermediate 33, isolated during the final step of synthesis of Compound 80 |

TABLE 1-continued
| # | Structure | LCMS (M + 1) | NMR | Synthetic Protocol |
|---|---|---|---|---|
| 143 | 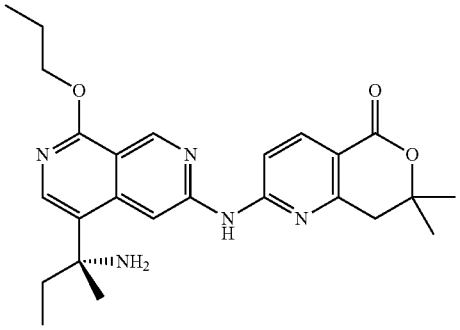 Or 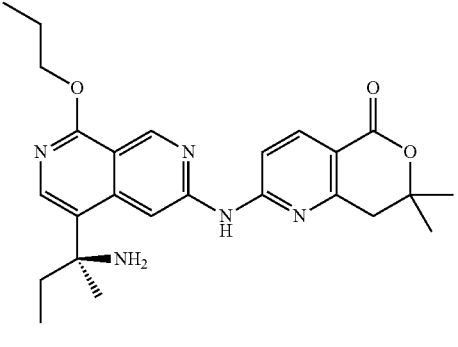 | 450 | ¹H-NMR (400 MHz, CD₃OD): δ ppm 9.31 (s, 1H), 9.03 (s, 1H), 8.49 (s, 1H), 8.17 (d, J = 8.8 Hz, 1H), 7.47 (s, 1H), 7.29 (d, J = 8.8 Hz, 1H), 4.05-3.98 (m, 2H), 3.20 (s, 2H), 2.46-2.36 (m, 1H), 2.31-2.17 (m, 1H), 1.90-1.80 (m, 5H), 1.53 (d, J = 2.8 Hz, 6H), 1.01 (t, J = 7.6 Hz, 3H), 0.84 (t, J = 7.6 Hz, 3H). | 3 Intermediate 33, isolated during the final step Compound 132 |
| 144 | 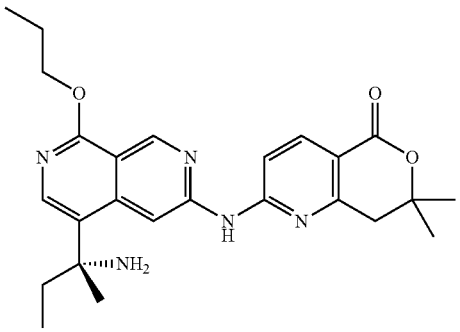 Or | 450 | ¹H-NMR (400 MHz, CD₃OD): δ ppm 9.31 (s, 1H), 9.04 (s, 1H), 8.49 (s, 1H), 8.17 (d, J = 8.4 Hz, 1H), 7.47 (s, 1H), 7.28 (d, J = 8.8 Hz, 1H), 4.05-3.98 (m, 2H), 3.20 (s, 2H), 2.46-2.36 (m, 1H), 2.30-2.17 (m, 1H), 1.88-1.79 (m, 5H), 1.53 (d, J = 2.0 Hz, 6H), 1.01 (t, J = 7.2 Hz, 3H), 0.84 (t, J = 7.2 Hz, 3H). | 3 Intermediate 34, isolated during the final step Compound 133 |

TABLE 1-continued

| # | Structure | LCMS (M + 1) | NMR | Synthetic Protocol |
|---|---|---|---|---|
| 145 | | 450 | ¹H-NMR (400 MHz, CD₃OD): δ ppm 9.32 (s, 1H), 8.82 (s, 1H), 8.51 (s, 1H), 8.17 (d, J = 8.8 Hz, 1H), 7.48 (s, 1H), 7.44 (d, J = 8.8 Hz, 1H), 4.69-4.64 (m, 1H), 4.05-3.97 (m, 2H), 3.04-2.95 (m, 1H), 2.47-2.35 (m, 1H), 2.16-2.06 (m, 1H), 1.90-1.81 (m, 2H), 1.76 (s, 3H), 1.471.51-1.44 (m, 6H), 1.00 (t, J = 7.2 Hz, 3H), 0.80 (t, J = 7.6 Hz, 3H). | 3 Intermediate 17 and Intermediate 34, isolated during the final step of synthesis of Compound 131 |
| | Or | | | |
| 146 | 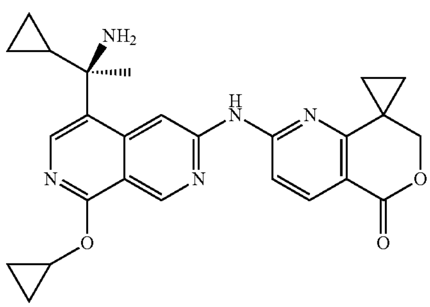 [SMILES: C[C@](N)(c1cnc(OC2CC2)c2cnc(Nc3ccc4c(n3)C3(CC3)COC4=O)cc12)C1CC1] | 458 | ¹H-NMR (400 MHz, CD₃OD): δ ppm 9.24 (s, 1 H), 8.78-8.73 (m, 1 H), 8.27 (s, 1 H), 8.13 (d, J = 8.8 Hz, 1 H), 7.49 (d, J = 8.8 Hz, 1 H), 4.47-4.43 (m, 1 H), 4.41 (s, 2 H), 1.68-1.63 (m, 4 H), 1.62-1.53 (m, 2 H), 1.19-1.11 (m, 2 H), 0.92-0.86 (m, 4 H), 0.73-0.56 (m, 3 H), 0.51-0.43 (m, 1 H). | 3 second eluting isomer after Step 3 Example 3B |
| 147 | 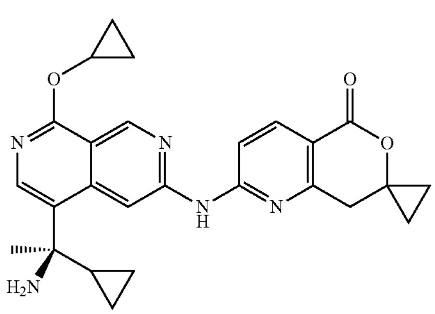 [SMILES: C[C@](N)(c1cnc(OC2CC2)c2cnc(Nc3ccc4c(n3)CC3(CC3)OC4=O)cc12)C1CC1] | 458 | ¹H-NMR (400 MHz, CD₃OD): δ ppm 9.47 (s, 1H), 9.28 (s, 1H), 8.56 (s, 1H), 8.32 (s, 1H), 8.19 (d, J = 8.8 Hz, 1H), 7.26 (d, J = 8.4 Hz, 1H), 4.53-4.44 (m, 1H), 3.26 (s, 2H), 1.70 (s, 3H), 1.65-1.55 (m, 1H), 1.19-1.06 (m, 2H), 0.97-0.82 (m, 6H), 0.73-0.42 (m, 4H) | 3 second eluting isomer after Step 3 Example 3B |

TABLE 1-continued

| # | Structure | LCMS (M + 1) | NMR | Synthetic Protocol |
|---|---|---|---|---|
| 148 | 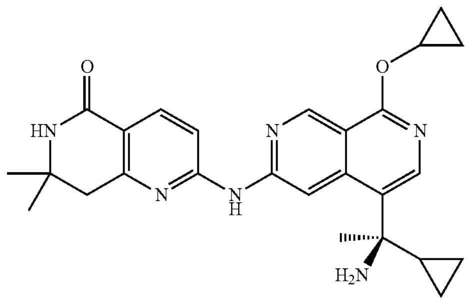 [SMILES: CC1(C)Cc2nc(Nc3cc4c([C@](C)(N)C5CC5)cnc(OC5CC5)c4cn3)ccc2C(=O)N1] | 459 | ¹H-NMR (400 MHz, CD₃OD): δ ppm 9.43 (s, 1H), 9.24 (s, 1H), 8.26 (s, 1H), 8.10 (d, J = 8.8 Hz, 1H), 7.16 (d, J = 8.4 Hz, 1H), 4.49-4.43 (m, 1H), 3.07 (s, 2H), 1.73 (s, 3H), 1.68-1.58 (m, 1H), 1.38 (s, 6H), 0.92-0.86 (m, 4H), 0.73-0.49 (m, 4H) | 3 second eluting isomer after Step 3 Example 3B |
| 149 | | 459 | ¹H-NMR (400 MHz, CD₃OD): δ ppm 9.24 (s, 1H), 9.16 (s, 1H), 8.22 (s, 1H), 8.15 (d, J = 8.8 Hz, 1H), 7.38 (d, J = 8.8 Hz, 1H), 4.68-4.64 (m, 1H), 3.07-2.99 (m, 1H), 2.85 (dd, J = 3.6, 6.8 Hz, 1H), 1.66 (s, 3H), 1.62-1.57 (m, 1H), 1.49 (dd, J = 6.8, 11.6 Hz, 6H), 0.93-0.87 (m, 2H), 0.71-0.65 (m, 2H), 0.64-0.45 (m, 4H) | 5 Intermediate 43 and Intermediate 17 |
| 150 | | 459 | ¹H-NMR (400 MHz, CD₃OD): δ ppm 9.23 (s, 1H), 9.19 (s, 1H), 8.24 (s, 1H), 8.18-8.12 (m, 1H), 7.37 (d, J = 8.8 Hz, 1H), 4.65 (dd, J = 4.8, 6.4 Hz, 1H), 3.10-2.99 (m, 1H), 2.84 (dd, J = 3.6, 7.2 Hz, 1H), 1.69 (s, 3H), 1.64-1.57 (m, 1H), 1.49 (d, J = 6.4 Hz, 6H), 0.94-0.86 (m, 2H), 0.69-0.65 (m, 2H), 0.64-0.47 (m, 4H) | 5 Intermediate 44 and Intermediate 17 |

TABLE 1-continued

| # | Structure | LCMS (M + 1) | NMR | Synthetic Protocol |
|---|---|---|---|---|
| 151 | 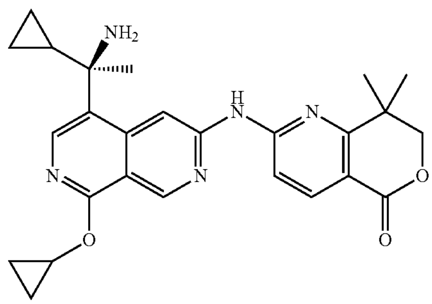 [SMILES: CC1(C)COC(=O)c2ccc(Nc3cc4c([C@](C)(N)C5CC5)cnc(OC5CC5)c4cn3)nc21] | 460 | ¹H-NMR (400 MHz, CD₃OD): δ ppm 9.30 (s, 1H), 8.97 (s, 1H), 8.34 (s, 1H), 8.17 (d, J = 8.8 Hz, 1H), 7.56 (d, J = 8.8 Hz, 1H), 4.51-4.43 (m, 1H), 4.33 (s, 2H), 1.69 (s, 3H), 1.67-1.61 (m, 1H), 1.48 (d, J = 4.8 Hz, 6H), 0.96-0.88 (m, 5H), 0.70-0.56 (m, 3H), 0.52-0.45 (m, 1H) | 3 second eluting isomer after Step 3 Example 3B |
| 152 | Or | 460 | ¹H-NMR (400 MHz, CD₃OD): δ ppm 9.46 (s, 1 H), 9.28 (d, J = 0.8 Hz, 1 H), 8.29 (s, 1 H), 8.06-7.92 (m, 1 H), 7.30 (d, J = 8.8 Hz, 1 H), 4.52-4.45 (m, 1 H), 2.20-2.14 (m, 2 H), 1.80 (s, 3 H), 1.73 (s, 3 H), 0.92-0.88 (m, 5 H), 0.77-0.73 (m, 3 H), 0.67-0.59 (m, 2 H), 0.58-0.50 (m, 1 H), 0.48-0.40 (m, 1 H). | 3 second eluting isomer after Step 3 Example 3B and Intermediate 46 |
| 153 | 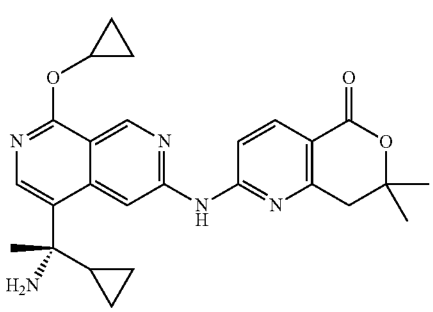 [SMILES: CC1(C)Cc2nc(Nc3cc4c([C@@](C)(N)C5CC5)cnc(OC5CC5)c4cn3)ccc2C(=O)O1] | 460 | ¹H-NMR (400 MHz, CD₃OD): δ ppm 9.28 (s, 1 H), 9.17 (s, 1 H), 8.52 (s, 1 H), 8.15 (d, J = 8.4 Hz, 1 H), 8.11 (s, 1 H), 7.25 (d, J = 8.4 Hz, 1 H), 4.57-4.46 (m, 1 H), 3.19 (d, J = 2.4 Hz, 2 H), 1.86 (s, 3 H), 1.65-1.57 (m, 1 H), 1.52 (d, J = 8.4 Hz, 6 H), 0.94-0.86 (m, 4 H), 0.85-0.70 (m, 3 H), 0.66-0.55 (m, 1 H). | 3 first eluting isomer after Step 3 Example 3B |

US 11,534,441 B2

TABLE 1-continued

| # | Structure | LCMS (M + 1) | NMR | Synthetic Protocol |
|---|---|---|---|---|
| 154 | (structure shown) Or (structure shown) | 460 | ¹H-NMR (400 MHz, CD₃OD): δ ppm 9.57 (s, 1 H), 9.24 (s, 1 H), 8.29 (s, 1 H), 8.12 (d, J = 8.4 Hz, 1 H), 7.18 (d, J = 8.8 Hz, 1 H), 4.64-4.54 (m, 1 H), 4.44-4.41 (m, 1 H), 3.05-2.96 (m, 1 H), 1.77-1.65 (m, 4 H), 1.50 (d, J = 6.4 Hz, 3 H), 1.32 (d, J = 7.2 Hz, 3 H), 0.95-0.82 (m, 4 H), 0.68-0.44 (m, 4 H). | 3 second eluting isomer after Step 3 Example 3B and Intermediate 41 |
| 155 | (structure shown) Or (structure shown) | 460 | ¹H-NMR (400 MHz, 6d-DMSO): δ ppm 10.69 (s, 1 H), 9.80 (s, 1 H), 9.19 (s, 1 H), 8.40-8.36 (m, 1 H), 8.06 (d, J = 8.8 Hz, 1 H), 7.28 (s, 1 H), 4.92-4.85 (m, 1 H), 4.53-4.46 (m, 1 H), 3.02-2.95 (m, 1 H), 1.61 (s, 4 H), 1.41 (d, J = 6.4 Hz, 3 H), 1.19 (d, J = 7.2 Hz, 3 H), 0.86-0.82 (m, 4 H), 0.64-0.39 (m, 4 H). | 3 second eluting isomer after Step 3 Example 3B and Intermediate 42 |

TABLE 1-continued
| # | Structure | LCMS (M + 1) | NMR | Synthetic Protocol |
|---|---|---|---|---|
| 156 | 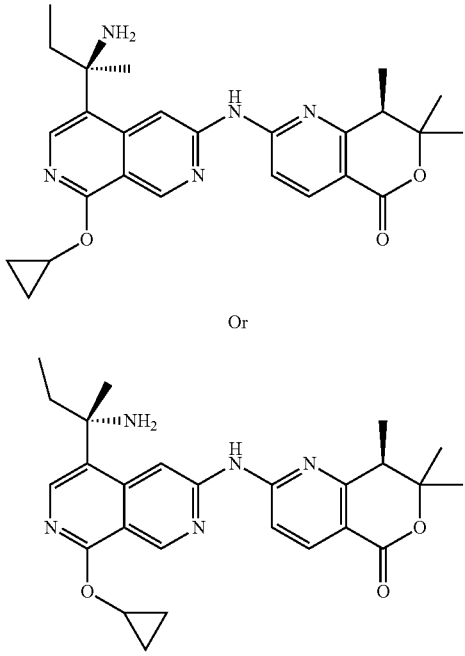 Or | 462 | ¹H-NMR (400 MHz, CD₃OD): δ ppm 9.39 (s, 1H), 9.28 (s, 1H), 8.21 (s, 1H), 8.14 (d, J = 8.7 Hz, 1H), 7.22 (d, J = 8.6 Hz, 1H), 4.55-4.43 (m, 1H), 3.05 (q, J = 7.1 Hz, 1H), 2.44-2.32 (m, 1H), 2.26-2.16 (m, 1H), 1.76 (s, 3H), 1.56 (s, 3H), 1.47 (s, 3H), 1.41 (d, J = 7.2 Hz, 3H), 0.95-0.88 (m, 4H), 0.76 (t, J = 7.5 Hz, 3H). | 3 Intermediate 20 and Intermediate 33 |
| 157 | 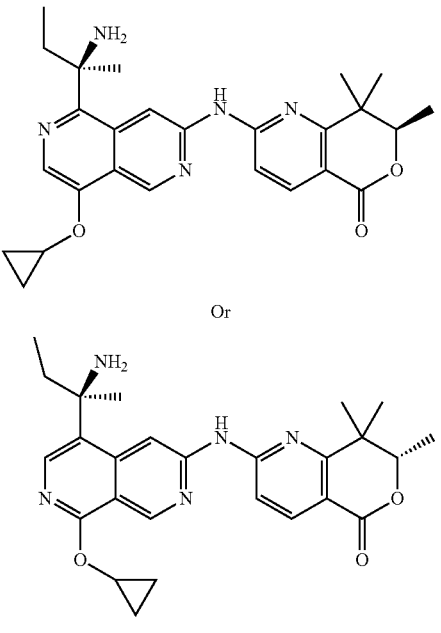 Or | 462 | ¹H-NMR (400 MHz, CD₃OD): δ ppm 9.32 (s, 1H), 8.64 (s, 1H), 8.26-8.11 (m, 2H), 7.58 (d, J = 8.8 Hz, 1H), 4.61-4.57 (m, 1H), 4.53-4.46 (m, 1H), 2.46-2.33 (m, 1H), 2.20-2.08 (m, 1H), 1.77 (s, 3H), 1.54 (s, 3H), 1.48 (d, J = 6.8 Hz, 3H), 1.33 (s, 3H), 0.97-0.87 (m, 4H), 0.80-0.70 (m, 3H) | 3 Intermediate 33 and Intermediate 56 |

TABLE 1-continued
| # | Structure | LCMS (M + 1) | NMR | Synthetic Protocol |
|---|---|---|---|---|
| | 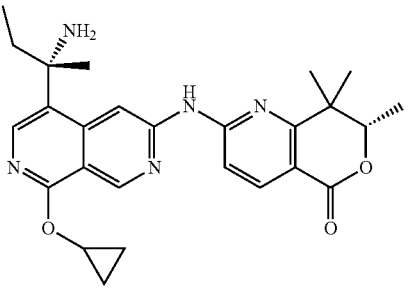Or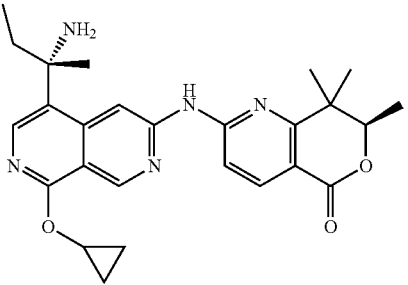 | | | |
| 158 | 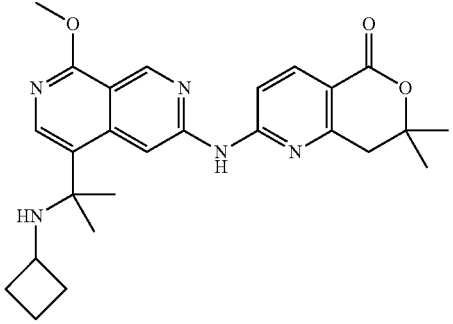 [SMILES: COc1ncc(C(C)(C)NC2CCC2)c2cc(Nc3ccc4c(n3)CC(C)(C)OC4=O)ncc12] | 462 | ¹H-NMR (400 MHz, 6d-DMSO): δ ppm 10.80 (s, 1H), 9.38 (s, 1H), 9.14 (s, 2H), 8.83 (s, 1H), 8.17-8.13 (m, 2H), 7.41-7.39 (m, 1H), 4.11 (s, 3H), 3.09 (s, 2H), 2.52 (s, 1H), 2.12-2.05 (m, 2H), 1.99 (s, 5H), 1.92-1.87 (m, 2H), 1.69-1.58 (m, 2H), 1.45 (s, 6H). | 14 |
| 159 | 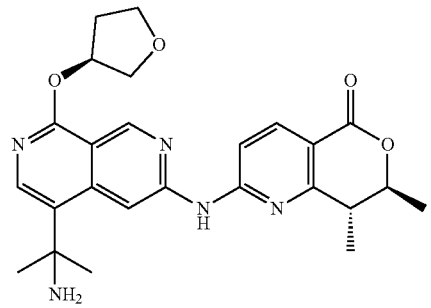 [SMILES: C[C@@H]1OC(=O)c2ccc(Nc3cc4c(C(C)(C)N)cnc(O[C@H]5CCOC5)c4cn3)nc2[C@H]1C] | 464 | ¹H-NMR (400 MHz,CD₃OD): δ ppm 9.35 (s, 1H), 9.15 (s, 1H), 8.17 (s, 1H), 8.14 (d, J = 8.4 Hz, 1H), 7.30 (d, J = 8.8 Hz, 1H), 5.82-5.75 (m, 1H), 4.70-4.65 (m, 1H), 4.16-3.99 (m, 3H), 3.98-3.91 (m, 1H), 3.08-2.97 (m, 1H), 2.45-2.34 (m, 1H), 2.33-2.23 (m, 1H), 1.82 (d, J = 4.8 Hz, 6H), 1.50 (d, J = 7.2 Hz, 3H), 1.46 (d, J = 6.4 Hz, 3H). | 3 Intermediate 17 and Intermediate 36h |

TABLE 1-continued

| # | Structure | LCMS (M + 1) | NMR | Synthetic Protocol |
|---|---|---|---|---|
| 160 | 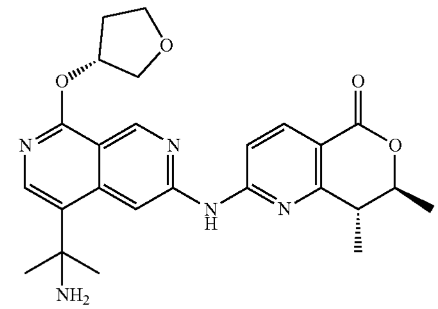 [SMILES: C[C@@H]1OC(=O)c2ccc(Nc3cc4c(C(C)(C)N)cnc(O[C@@H]5CCOC5)c4cn3)nc2[C@H]1C] | 464 | ¹H-NMR (400 MHz, CD₃OD): δ ppm 9.38 (s, 1H), 9.11 (s, 1H), 8.18-8.11 (m, 2H), 7.32 (d, J = 8.8 Hz, 1H), 5.83-5.75 (m, 1H), 4.71-4.62 (m, 1H), 4.13-4.00 (m, 3H), 3.99-3.89 (m, 1H), 3.06-2.98 (m, 1H), 2.45-2.34 (m, 1H), 2.33-2.25 (m, 1H), 1.86 (d, J = 5.6 Hz, 6H), 1.51 (d, J = 7.2 Hz, 3H), 1.46 (d, J = 6.4 Hz, 3H). | 3 Intermediate 17 and Intermediate 36g |
| 161 | 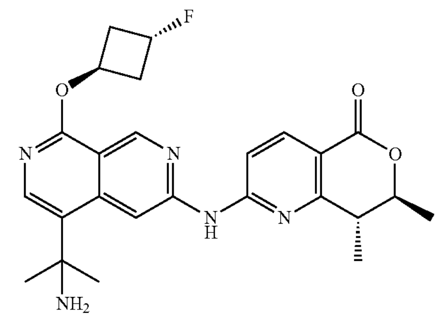 [SMILES: C[C@@H]1OC(=O)c2ccc(Nc3cc4c(C(C)(C)N)cnc(O[C@H]5C[C@H](F)C5)c4cn3)nc2[C@H]1C] | 466 | ¹H-NMR (400 MHz, CD₃OD): δ ppm 9.30 (s, 1H), 8.98 (s, 1H), 8.08-8.04 (m, 1H), 7.99 (s, 1H), 7.25 (d, J = 8.8 Hz, 1H), 5.55 (dt, J = 3.2, 7.2 Hz, 1H), 5.35-5.31 (m, 1H), 5.21-5.17 (m, 1H), 4.59-4.54 (m, 1H), 2.95-2.91 (m, 1H), 2.74-2.65 (m, 2H), 2.63-2.55 (m, 2H), 1.79 (d, J = 5.4 Hz, 6H), 1.41 (d, J = 7.2 Hz, 3H), 1.36 (d, J = 6.6 Hz, 3H) | 3 Intermediate 17 and Intermediate 36i |
| 162 | 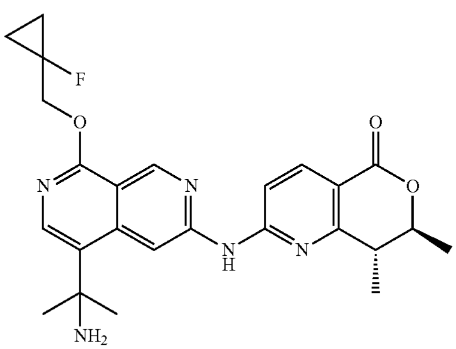 [SMILES: C[C@@H]1OC(=O)c2ccc(Nc3cc4c(C(C)(C)N)cnc(OCC5(F)CC5)c4cn3)nc2[C@H]1C] | 466 | ¹H-NMR (400 MHz, CD₃OD): δ ppm 9.45 (s, 1H), 9.09 (s, 1H), 8.17 (d, J = 8.8 Hz, 1H), 8.08 (s, 1H), 7.34 (d, J = 8.8 Hz, 1H), 4.85-4.80 (m, 2H), 4.71-4.64 (m, 1H), 3.07-2.989 (m, 1H), 1.91 (d, J = 5.4 Hz, 6H), 1.52 (d, J = 5.6 Hz, 3H), 1.46 (d, J = 7.6 Hz, 3H), 1.24-1.14 (m, 2H), 1.00-0.92 (m, 2H) | 3 Intermediate 17 |
| 163 | 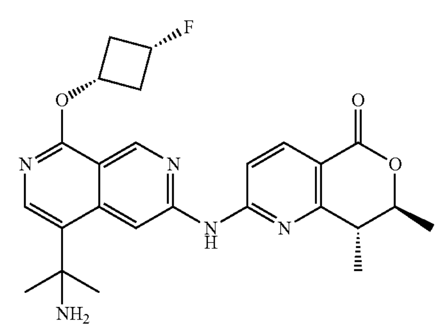 [SMILES: C[C@@H]1OC(=O)c2ccc(Nc3cc4c(C(C)(C)N)cnc(O[C@H]5C[C@@H](F)C5)c4cn3)nc2[C@H]1C] | 466 | ¹H-NMR (400 MHz, CD₃OD): δ ppm 9.38 (s, 1H), 9.17 (s, 1H), 8.24-8.03 (m, 2H), 7.31 (d, J = 8.8 Hz, 1H), 5.08-4.93 (m, 2H), 4.70-4.61 (m, 1H), 3.16-3.07 (m, 2H), 3.05-2.98 (m, 1H), 2.56-2.32 (m, 2H), 1.79 (d, J = 4.8 Hz, 6H), 1.50 (d, J = 7.2 Hz, 3H), 1.45 (d, J = 6.4 Hz, 3H). | 3 Intermediate 17 and Intermediate 36j |

TABLE 1-continued

| # | Structure | LCMS (M + 1) | NMR | Synthetic Protocol |
|---|-----------|--------------|-----|--------------------|
| 164 | | 472 | ¹H-NMR (400 MHz, CD₃OD): δ ppm 9.39 (s, 1 H), 9.35 (s, 1 H), 8.17 (s, 1 H), 8.14 (d, J = 8.8 Hz, 1 H), 7.22-7.16 (m, 1 H), 6.32-5.98 (m, 1 H), 5.77-5.59 (m, 1 H), 3.21 (s, 2 H), 1.83 (s, 3 H), 1.53 (s, 6 H), 1.28 (s, 6 H). | 3<br>1ˢᵗ eluting isomer from SFC (column: Daicel Chiralpak IG (250 mm × 50 mm, 10 um); mobile phase: [EtOH with 0.1% NH₄OH] |
| 165 | | 472 | ¹H-NMR (400 MHz, CD₃OD): δ ppm 9.39 (s, 1 H), 9.35 (s, 1 H), 8.18 (s, 1 H), 8.14 (d, J = 8.8 Hz, 1 H), 7.23-7.17 (m, 1 H), 6.33-6.00 (m, 1 H), 5.76-5.63 (m, 1 H), 3.22 (s, 2 H), 1.83 (s, 3 H), 1.56-1.51 (m, 6H), 1.28 (s, 6 H). | 3<br>2ⁿᵈ eluting isomer from SFC (column: Daicel Chiralpak IG (250 mm × 50 mm, 10 um); mobile phase: [EtOH with 0.1% NH₄OH] |

TABLE 1-continued

| # | Structure | LCMS (M + 1) | NMR | Synthetic Protocol |
|---|---|---|---|---|
| 166 | 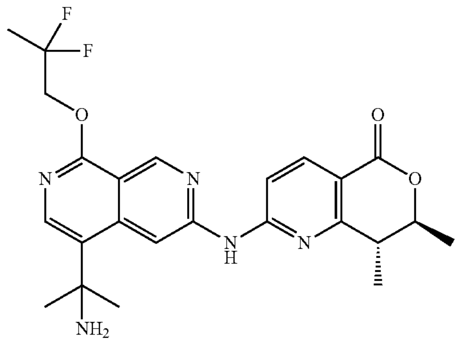 [SMILES: C[C@@H]1OC(=O)c2ccc(Nc3cc4c(C(C)(C)N)cnc(OCC(C)(F)F)c4cn3)nc2[C@H]1C] | 472 | ¹H-NMR (400 MHz, CD₃OD): δ ppm 9.46 (d, J = 6 Hz, 1H), 8.97 (s, 1H), 8.21-8.17 (m, 1H), 7.98 (s, 1H), 7.40 (d, J = 8.8 Hz, 1H), 4.82-4.76 (m, 2H), 4.71-4.65 (m, 1H), 3.04-2.98 (m, 1H), 2.05 (d, J = 10.4 Hz, 6H), 1.90-1.78 (m, 3H), 1.52 (d, J = 7.2 Hz, 3H), 1.47 (d, J = 6.4 Hz, 3H). | 3 Intermediate 17 |
| 167 | | 472 | ¹H-NMR (400 MHz, CD₃OD): δ ppm 9.27 (s, 1H), 8.85 (s, 1H), 8.35 (s, 1H), 8.14 (d, J = 8.4 Hz, 1H), 7.49 (d, J = 8.8 Hz, 1H), 4.67-4.60 (m, 1H), 4.49-4.42 (m, 1H), 1.73-1.54 (m, 6H), 1.37 (d, J = 6.8 Hz, 3H), 1.24-1.14 (m, 2H), 0.93-0.85 (m, 4H), 0.67-0.54 (m, 3H), 0.51-0.42 (m, 1H). | 3 second eluting isomer after Step Example 3B and Intermediate 50 |

TABLE 1-continued
| # | Structure | LCMS (M + 1) | NMR | Synthetic Protocol |
|---|---|---|---|---|
| 168 | 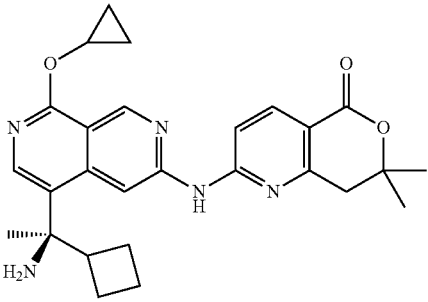 Or 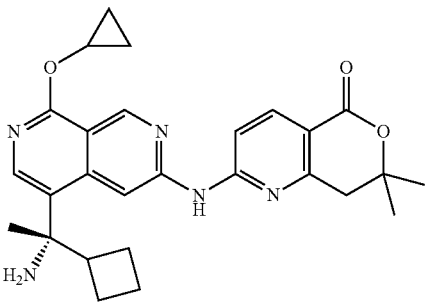 | 474 | ¹H-NMR (400 MHz, CD₃OD): δ ppm 9.33 (s, 1 H), 9.27 (s, 1 H), 8.52 (s, 1 H), 8.15 (d, J = 8.8 Hz, 1 H), 8.06 (s, 1 H), 7.22 (d, J = 8.4 Hz, 1 H), 4.54-4.45 (m, 1 H), 3.70-3.58 (m, 1 H), 3.23 (s, 2 H), 2.24-1.91 (m, 3 H), 1.87 (s, 3 H), 1.84-1.60 (m, 3 H), 1.54 (s, 6 H), 0.95-0.84 (m, 4 H). | 3 Intermediate 63 |
| 169 | 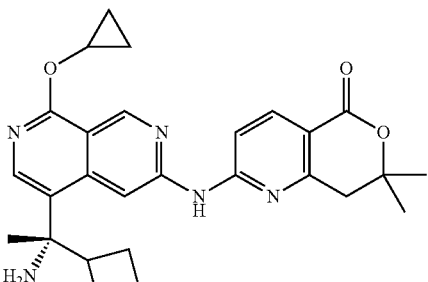 Or 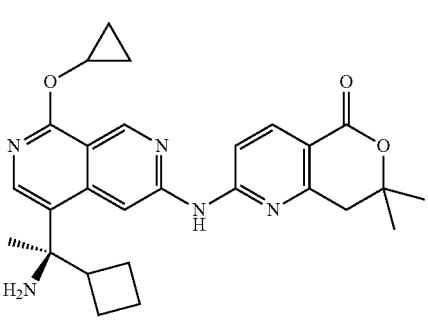 | 474 | ¹H-NMR (400 MHz, CD₃OD): δ ppm 9.35 (s, 1 H), 9.27 (s, 1 H), 8.51 (d, J = 1.2 Hz, 1 H), 8.16 (d, J = 8.8 Hz, 1 H), 8.07 (s, 1 H), 7.22 (d, J = 8.8 Hz, 1 H), 4.54-4.44 (m, 1 H), 3.70-3.59 (m, 1 H), 3.24 (s, 2 H), 2.25-1.90 (m, 3 H), 1.86 (s, 3 H), 1.84-1.60 (m, 3 H), 1.54 (s, 6 H), 0.89 (s, 4 H). | 3 Intermediate 64 |

TABLE 1-continued
| # | Structure | LCMS (M + 1) | NMR | Synthetic Protocol |
|---|---|---|---|---|
| 170 | 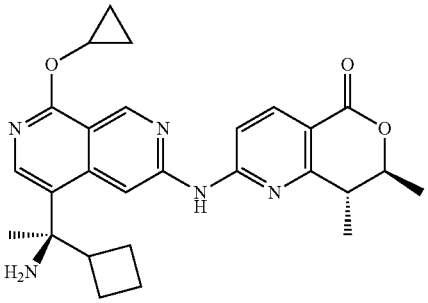 Or 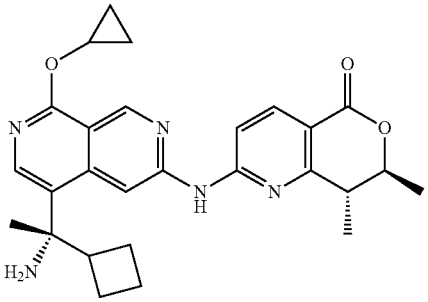 | 474 | ¹H-NMR (400 MHz, CDCl₃): δ ppm 9.31 (d, J = 2.0 Hz, 2H), 8.26 (d, J = 8.4 Hz, 1H), 8.12 (s, 1H), 8.02 (s, 1H), 7.37 (d, J = 8.4 Hz, 1H), 4.63-4.46 (m, 2H), 3.37-3.19 (m, 1H), 3.00 (quin, J = 6.8 Hz, 1H), 2.04-1.93 (m, 4H), 1.77 (d, J = 5.6 Hz, 1H), 1.65 (s, 1H), 1.59 (s, 3H), 1.58-1.53 (m, 6H), 0.95-0.88 (m, 4H). | 3 Intermediate 63 and Intermediate 17 |
| 171 | 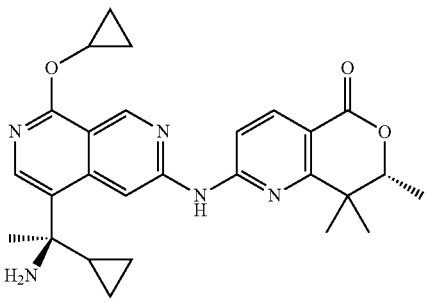 Or 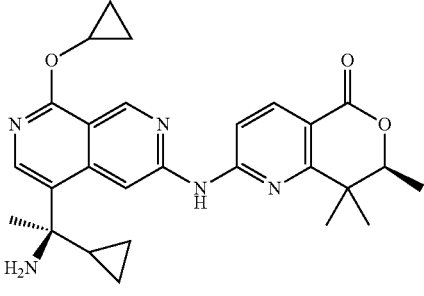 | 474 | ¹H-NMR (400 MHz, 6d-DMSO): δ ppm 10.56 (s, 1H), 9.33 (s, 1H), 9.23 (s, 1H), 8.40 (s, 1H), 8.09 (d, J = 8.4 Hz, 1H), 7.47 (d, J = 8.8 Hz, 1H), 4.60-4.53 (m, 1H), 4.53-4.47 (m, 1H), 1.63-1.57 (m, 1H), 1.51 (d, J = 18.4 Hz, 6H), 1.36 (d, J = 6.4 Hz, 3H), 1.22 (s, 3H), 0.89-0.80 (m, 4H), 0.63-0.53 (m, 1H), 0.52-0.41 (m, 3H) | 3 Intermediate 56 and second eluting isomer after Step 4 Example 3B |

TABLE 1-continued

| # | Structure | LCMS (M + 1) | NMR | Synthetic Protocol |
|---|---|---|---|---|
| 172 | (structure) Or (structure) | 476 | ¹H-NMR (400 MHz, CD$_3$OD): δ ppm 9.45-9.34 (m, 2H), 8.23 (s, 1H), 8.03 (d, J = 8.8 Hz, 1H), 7.31 (d, J = 8.8 Hz, 1H), 5.17-5.10 (m, 2H), 2.27-2.15 (m, 2H), 1.90 (d, J = 6.2 Hz, 6H), 1.75 (s, 3H), 0.81-0.77 (m, 3H) | 3 Intermediate 47 |
| 173 | (structure) Or (structure) | 476 | ¹H-NMR (400 MHz, 6d-DMSO): δ ppm 11.04 (s, 1H), 9.61 (s, 1H), 9.32 (s, 1H), 8.23 (s, 1H), 8.05 (d, J = 8.4 Hz, 1H), 7.37 (d, J = 8.8 Hz, 1H), 5.28-5.16 (m, 2 H), 2.25-2.06 (m, 2H), 1.71-1.64 (m, 9H), 0.61 (t, J = 7.2 Hz, 3H). | 3 1$^{st}$ eluting isomer from SFC (column: Daicel Chiralpak AD-H (250 mm × 30 mm, 5 um); mobile phase: [EtOH with 0.1% NH$_4$OH] |

TABLE 1-continued
| # | Structure | LCMS (M + 1) | NMR | Synthetic Protocol |
|---|---|---|---|---|
| 174 | 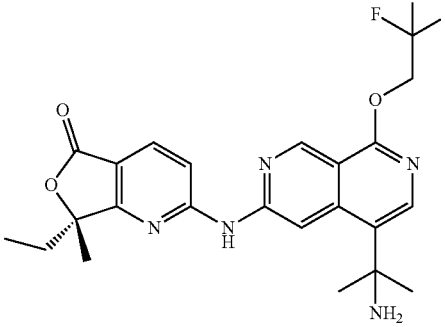 Or 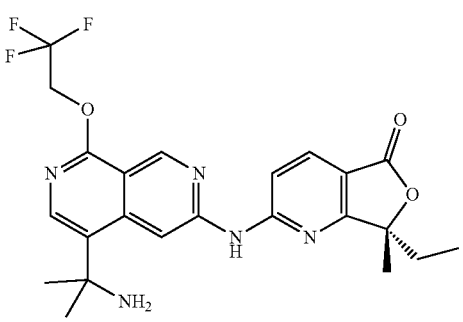 | 476 | ¹H-NMR (400 MHz, CD₃OD): δ ppm 9.45-9.34 (m, 2H), 8.23 (s, 1H), 8.03 (d, J = 8.8 Hz, 1H), 7.31 (d, J = 8.8 Hz, 1H), 5.17-5.10 (m, 2H), 2.27-2.15 (m, 2H), 1.90 (d, J = 6.2 Hz, 6H), 1.75 (s, 3H), 0.81-0.77 (m, 3H) | 3 Intermediate 46 |
| 175 | 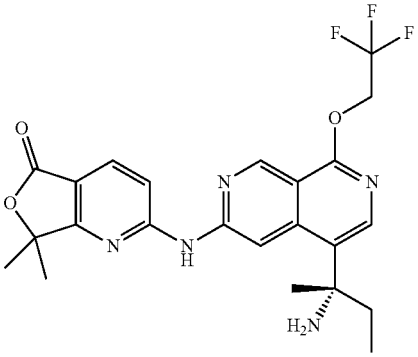 Or 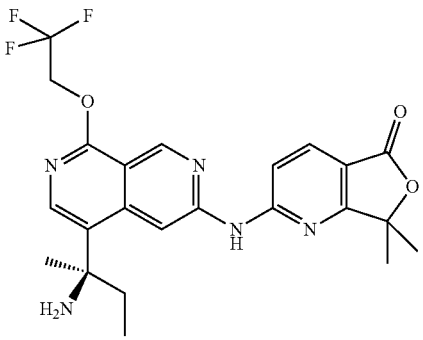 | 476 | ¹H-NMR (400 MHz, 6d-DMSO): δ ppm 11.11 (s, 1H), 9.40 (s, 1H), 9.35 (s, 1H), 8.17 (s, 1H), 8.07 (d, J = 8.4 Hz, 1H), 7.42 (d, J = 8.8 Hz, 1H), 5.30-5.18 (m, 2H), 2.35-2.08 (m, 2H), 1.76 (s, 3H), 1.68 (d, J = 5.6 Hz, 6H), 0.65 (t, J = 7.2 Hz, 3H). | 3 2$^{nd}$ eluting isomer from SFC (column: Daicel Chiralpak AD-H (250 mm × 30 mm, 5 um); mobile phase: [EtOH with 0.1% NH₄OH] |

TABLE 1-continued
| # | Structure | LCMS (M + 1) | NMR | Synthetic Protocol |
|---|-----------|--------------|-----|--------------------|
| 176 | 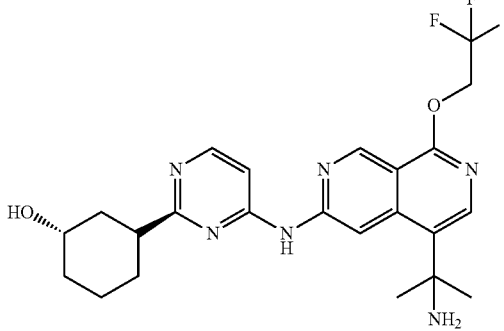Or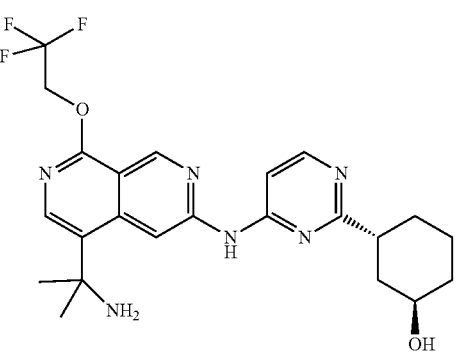 | 477 | ¹H-NMR (400 MHz, CD₃OD): δ ppm 9.38 (s, 1H), 9.28 (s, 1H), 8.33 (d, J = 5.6 Hz, 1H), 7.12 (d, J = 86.0 Hz, 1H), 5.14-5.07 (m, 2H), 4.23 (s, 1H), 3.41-3.35 (m, 1H), 2.05-1.63 (m, 14H). | 3 Intermediate 65 |
| 177 | 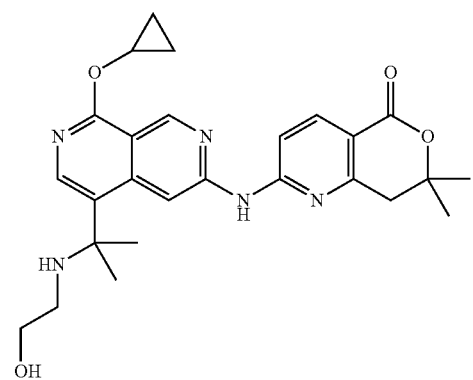 [SMILES: CC1(C)Cc2nc(Nc3cc4c(C(C)(C)NCCO)cnc(OC5CC5)c4cn3)ccc2C(=O)O1] | 478 | ¹H-NMR (400 MHz, CD₃OD): δ ppm 9.91 (s, 1H), 9.23 (s, 1H), 8.18-8.07 (m, 1H), 8.02 (s, 1H), 7.27-7.14 (m, 1H), 4.51-4.36 (m, 1H), 3.55-3.41 (m, 2H), 3.26 (s, 2H), 2.47-2.37 (m, 2H), 1.82-1.66 (m, 6H), 1.54 (s, 6H), 0.89 (s, 4H). | 15 |
| 178 | 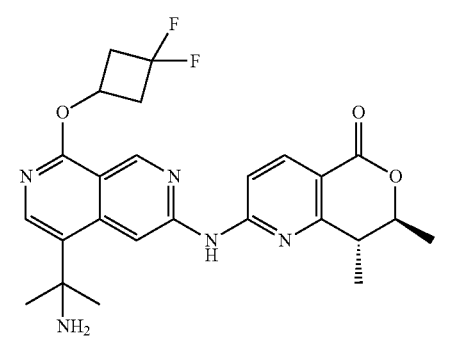 [SMILES: C[C@@H]1OC(=O)c2ccc(Nc3cc4c(C(C)(C)N)cnc(OC5CC(F)(F)C5)c4cn3)nc2[C@H]1C] | 484 | ¹H-NMR (400 MHz, CD₃OD): δ ppm 9.42 (d, J = 0.6 Hz, 1H), 9.15 (s, 1H), 8.20-8.13 (m, 2H), 7.35 (d, J = 8.7 Hz, 1H), 5.44-5.34 (m, 1H), 4.72-4.65 (m, 1H), 3.29-3.19 (m, 2H), 3.08-3.00 (m, 1H), 2.96-2.84 (m, 2H), 1.88 (d, J = 5.5 Hz, 6H), 1.53 (d, J = 7.2 Hz, 3H), 1.48 (d, J = 6.6 Hz, 3H) | 3 Intermediate 17 |

| # | Structure | LCMS (M + 1) | NMR | Synthetic Protocol |
|---|---|---|---|---|
| 179 | | 490 | ¹H-NMR (400 MHz, CD₃OD): δ ppm 9.40 (s, 1H), 9.24 (s, 1H), 8.19 (d, J = 8.8 Hz, 1H), 8.01 (d, J = 1.2 Hz, 1H), 7.26 (d, J = 8.6 Hz, 1H), 6.18-6.10 (m, 1H), 3.22 (s, 2H), 2.07 (s, 6H), 1.63 (d, J = 6.4 Hz, 3H), 1.54 (s, 6H) | 3<br>2$^{nd}$ isomer to elute from SFC Column: Chiralpak IG-3 Mobile Phase: [EtOH + 0.05% Diethylamine] in CO₂ |
| 180 | | 490 | ¹H-NMR (400 MHz, CD₃OD): δ ppm 9.40 (s, 1H), 9.24 (s, 1H), 8.19 (d, J = 8.8 Hz, 1H), 8.01 (d, J = 2.0 Hz, 1H), 7.26 (d, J = 8.4 Hz, 1H), 6.18-6.10 (m, 1H), 3.22 (s, 2H), 2.07 (s, 6H), 1.63 (d, J = 6.4 Hz, 3H), 1.54 (s, 6H) | 3<br>1$^{st}$ isomer to elute from SFC Column: Chiralpak IG-3 Mobile Phase: [EtOH + 0.05% Diethylamine] in CO₂ |

TABLE 1-continued
| # | Structure | LCMS (M + 1) | NMR | Synthetic Protocol |
|---|---|---|---|---|
| 181 | 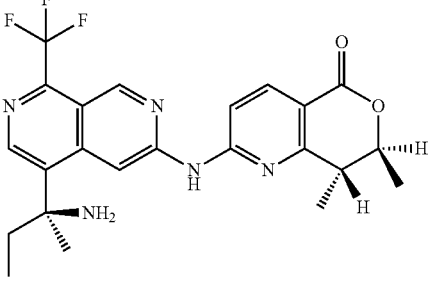 Or 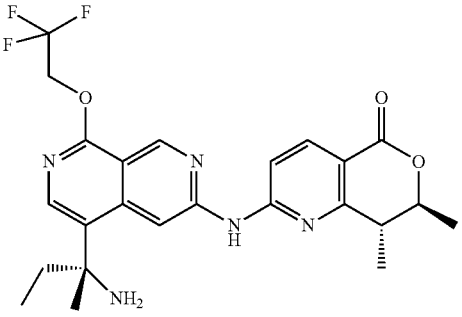 | 490 | | 3 1st isomer to elute from SFC Column: ChiralPak IC-H 21 × 250 mm Mobile Phase: 25% 2-Propanol + 0.5% Diethylamine in CO₂ and Intermediate 17 |
| 182 | 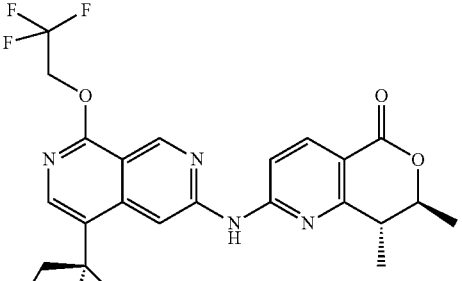 Or 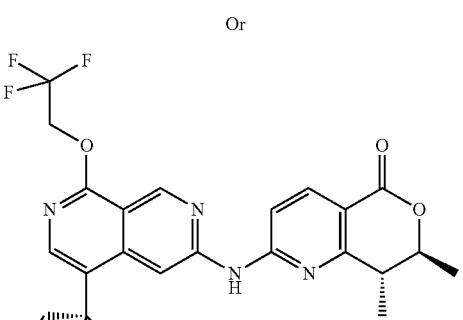 | 490 | | 3 2nd isomer to elute from SFC Column: ChiralPak IC-H 21 × 250 mm Mobile Phase: 25% 2-Propanol + 0.5% Diethylamine in CO₂ and Intermediate 17 |

TABLE 1-continued

| # | Structure | LCMS (M + 1) | NMR | Synthetic Protocol |
|---|---|---|---|---|
| 183 | 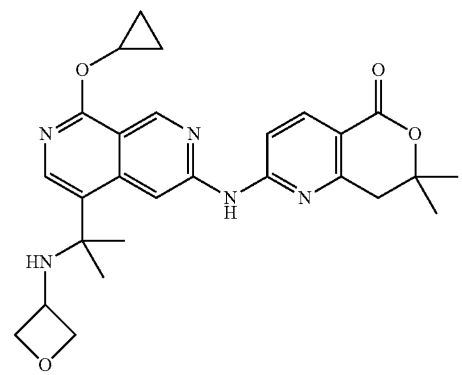 [SMILES: CC1(C)Cc2nc(Nc3cc4c(C(C)(C)NC5COC5)cnc(OC5CC5)c4cn3)ccc2C(=O)O1] | 490 | ¹H-NMR (400 MHz, CD₃OD): δ ppm 9.76 (s, 1H), 9.23 (s, 1H), 8.12 (d, J = 8.8 Hz, 1H), 7.99 (s, 1H), 7.24 (d, J = 8.8 Hz, 1H), 4.57-4.51 (m, 2H), 4.49-4.44 (m, 3H), 3.77-3.69 (m, 1H), 3.26 (s, 2H), 1.65 (s, 6H), 1.55 (s, 6H), 0.91-0.88 (m, 4H). | 14 |
| 184 | Or | 464 | ¹H-NMR (400 MHz, CD₃OD): δ ppm 9.24 (s, 1H), 9.20 (s, 1H), 8.19 (s, 1H), 8.13 (d, J = 8.8 Hz, 1H), 7.29 (d, J = 8.8 Hz, 1H), 4.69-4.63 (m, 1H), 4.45-4.43 (m, 1H), 3.97-3.95 (m, 1H), 3.83-3.81 (m, 1H), 3.35 (s, 3H), 3.06-2.99 (m, 1H), 1.74 (s, 3H), 1.52-1.46 (m, 6H), 0.93-0.87 (m, 4H) | First eluting isomer described in Example 16 and using Intermediate 17 |

TABLE 1-continued
| # | Structure | LCMS (M + 1) | NMR | Synthetic Protocol |
|---|---|---|---|---|
| 185 | 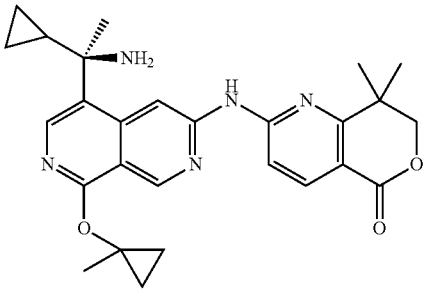 Or 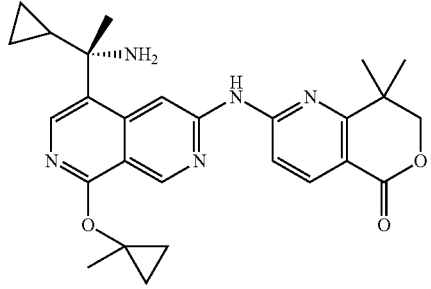 | 474 | ¹H-NMR (400 MHz, CDCl₃): δ ppm 9.33 (s, 1H), 9.18 (s, 1H), 8.52 (s, 1H), 8.23 (d, J = 8.8 Hz, 2H), 7.40 (d, J = 8.8 Hz, 1H), 4.25 (s, 2H), 1.78 (s, 3H), 1.55-1.52 (m, 1H), 1.50 (s, 3H), 1.45 (d, J = 1.6 Hz, 6H), 1.10-1.07 (m, 2H), 0.88-0.83 (m, 2H), 0.71-0.60 (m, 2H), 0.51-0.41 (m, 2H). | 3 Intermediate 39 |
| 186 | 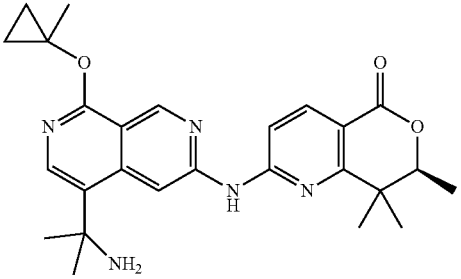 Or 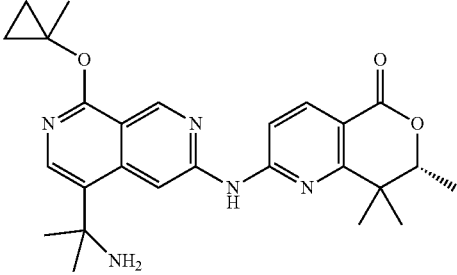 | 462 | ¹H-NMR (400 MHz, CDCl₃): δ ppm 9.25 (s, 1H), 8.94 (s, 1H), 8.17-8.15 (m, 2H), 7.82 (s, 1H), 7.28 (d, J = 8.8 Hz, 1H), 4.45-4.40 (m, 1H), 1.71 (s, 3H), 1.66 (s, 6H), 1.44 (s, 3H), 1.39 (d, J = 6.8 Hz, 3H), 1.22 (s, 3H), 1.03-0.99 (m, 2H), 0.79-0.75 (m, 2H). | 3 Intermediate 56 |

US 11,534,441 B2
147                                                                                 148
TABLE 1-continued
| # | Structure | LCMS (M + 1) | NMR | Synthetic Protocol |
|---|-----------|--------------|-----|--------------------|
| 187 | 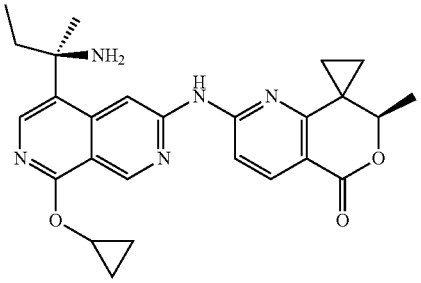 Or 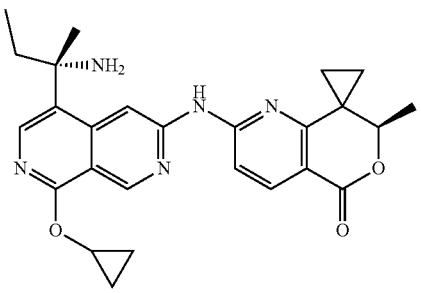 Or 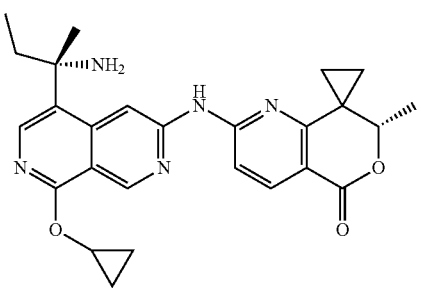 Or 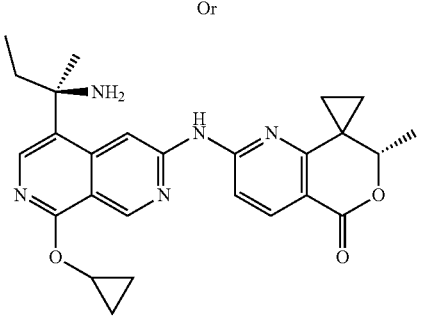 | 460 | ¹H-NMR (400 MHz, CD₃OD): δ ppm 9.25 (s, 1H), 8.47 (s, 1H), 8.15 (s, 1H), 8.13 (d, J = 8.8 Hz, 1H), 7.51 (d, J = 8.8 Hz, 1H), 4.62 (q, J = 6.4 Hz, 1H), 4.49-4.42 (m, 1H), 2.33-2.22 (m, 1H), 2.15-2.05 (m, 1H), 1.72 (s, 3H), 1.67-1.61 (m, 1H), 1.54-1.48 (m, 1H), 1.37 (d, J = 6.8 Hz, 3H), 1.25-1.15 (m, 2H), 0.92-0.86 m, 4H), 0.74 (d, J = 7.6 Hz, 3H) | 3 Intermediate 50 and Intermediate 33 |

TABLE 1-continued
| # | Structure | LCMS (M + 1) | NMR | Synthetic Protocol |
|---|---|---|---|---|
| 188 | 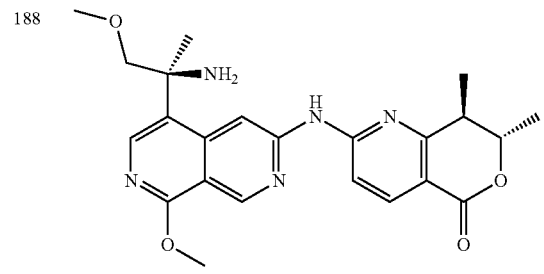<br>Or<br>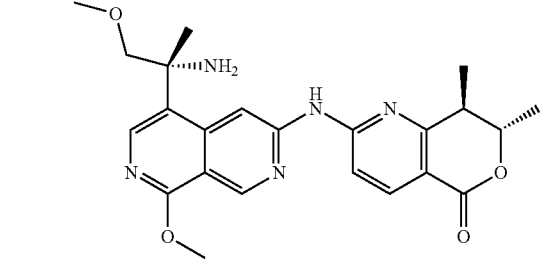 | 438 | ¹H-NMR (400 MHz, CDCl₃): δ ppm 9.38 (s, 1H), 9.27 (s, 1H), 8.24 (d, J = 8.4 Hz, 1H), 8.14 (s, 1H), 8.04 (s, 1H), 7.29 (d, J = 8.4 Hz, 1H), 4.58-4.51 (m, 1H), 4.13 (s, 3H), 3.89 (d, J = 8.8 Hz, 1H), 3.59 (d, J = 8.8 Hz, 1H), 3.43 (s, 3H), 3.02-2.96 (m, 1H), 1.70 (s, 3H), 1.55-1.51 (m, 6H). | 16 Intermediate 67 and Intermediate 17 |
| 189 | 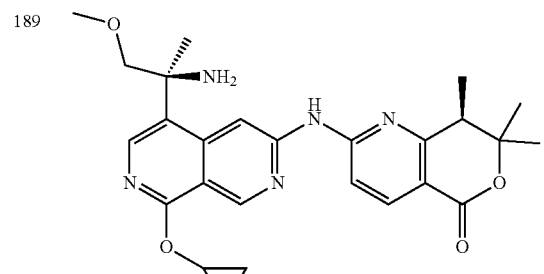<br>Or<br>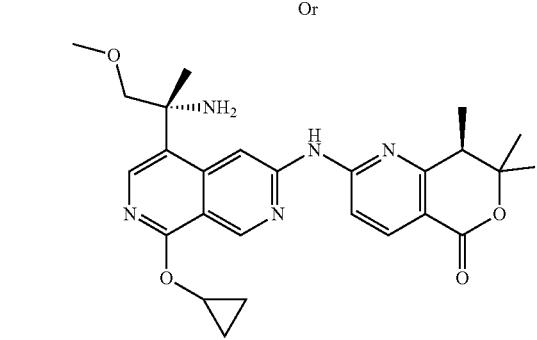 | 478 | ¹H-NMR (400 MHz, CDCl₃): δ ppm 9.40 (s, 1H), 9.30 (s, 1H), 8.24 (t, J = 5.2 Hz, 2H), 8.04 (s, 1H), 7.21 (d, J = 8.8 Hz, 1H), 4.54-4.49 (m, 1H), 3.91 (d, J = 8.8 Hz, 1H), 3.63 (d, J = 9.2 Hz, 1H), 3.44 (s, 3H), 3.04-2.98 (m, 1H), 1.73 (s, 3H), 1.51 (d, J = 8.4 Hz, 6H), 1.45 (d, J = 7.2 Hz, 3H), 0.97-0.89 (m, 4H). | 16 Intermediate 69 and Intermediate 20 |

TABLE 1-continued

| # | Structure | LCMS (M + 1) | NMR | Synthetic Protocol |
|---|---|---|---|---|
| 190 | | 464 | ¹H-NMR (400 MHz, CDCl₃): δ ppm 9.52 (s, 1 H), 9.28 (s, 1 H), 8.25-8.19 (m, 2 H), 7.93-7.89 (m, 1 H), 7.10 (d, J = 8.8 Hz, 1 H), 4.87-4.81 (m, 1 H), 4.55-4.47 (m, 1 H), 3.90 (d, J = 8.8 Hz, 1 H), 3.64 (d, J = 8.8 Hz, 1 H), 3.43 (s, 3 H), 3.03-2.93 (m, 1 H), 1.73 (s, 3 H), 1.52 (d, J = 6.4 Hz, 3 H), 1.36 (d, J = 7.2 Hz, 3 H), 0.96-0.85 (m, 4 H). | 16 Intermediate 69 and Intermediate 41 |

| # | Structure | LCMS (M + 1) | NMR | Synthetic Protocol |
|---|---|---|---|---|
| 191 | 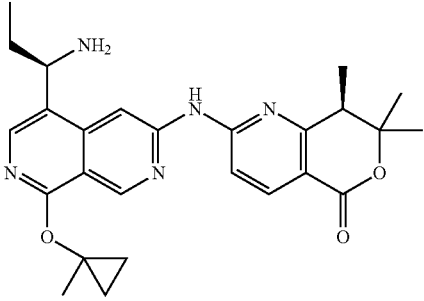<br>Or<br>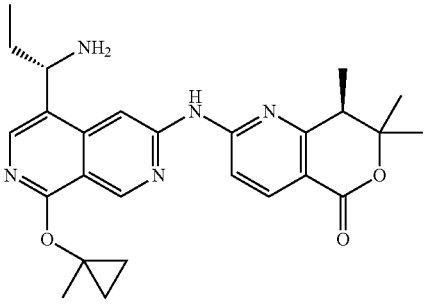 | 462 | ¹H-NMR (400 MHz, CD₃OD): δ ppm 9.27 (d, J = 0.8 Hz, 1 H), 8.84-8.76 (m, 1 H), 8.21 (s, 1 H), 8.14 (d, J = 8.8 Hz, 1 H), 7.28 (d, J = 8.8 Hz, 1 H), 4.60-4.54 (m, 1 H), 3.23-3.14 (m, 1 H), 2.13-2.00 (m, 2 H), 1.76 (s, 3 H), 1.56-1.47 (m, 6 H), 1.44 (s, 3 H), 1.10-1.05 (m, 2 H), 1.05-1.00 (m, 3 H), 0.89-0.82 (m, 2 H). | 17 Intermediate 79 and Intermediate 20 |
| 192 | 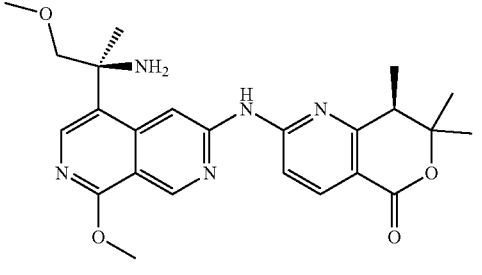<br>Or<br>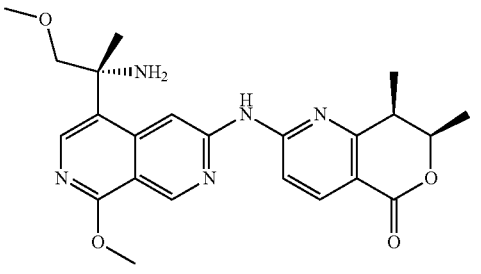<br>Or | 438 | ¹H-NMR (400 MHz, CD₃OD): δ ppm 9.46 (s, 1H), 9.31 (d, J = 0.8 Hz, 1H), 8.20 (s, 1H), 8.12 (d, J = 8.8 Hz, 1H), 7.13 (d, J = 8.8 Hz, 1H), 4.93 (d, J = 3.2, 6.5 Hz, 1H), 4.13 (s, 3H), 3.97-3.88 (m, 2H), 3.38 (s, 3H), 3.04 (d, J = 2.8, 7.2 Hz, 1H), 1.77 (s, 3H), 1.54 (d, J = 6.4 Hz, 3H), 1.34 (d, J = 7.2 Hz, 3H) | 16 Intermediate 67 and Intermediate 41 |

TABLE 1-continued

| # | Structure | LCMS (M + 1) | NMR | Synthetic Protocol |
|---|-----------|--------------|-----|--------------------|

Or

193 | | 490 | ¹H-NMR (400 MHz,CD₃OD): δ ppm 9.40 (s, 1H), 9.01 (s, 1H), 8.16 (d, J = 8.8 Hz, 1H), 8.09 (s, 1H), 7.41 (d, J = 8.8 Hz, 1H), 5.64-5.53 (m, 1H), 4.70-4.55 (m, 2H), 3.06-2.94 (m, 1H), 2.65-2.45 (m, 4H), 1.80 (s, 3H), 1.65-1.56 (m, 1H), 1.51-1.44 (m, 6H), 0.79-0.48 (m, 4H). | Example 18

Or

TABLE 1-continued
| # | Structure | LCMS (M + 1) | NMR | Synthetic Protocol |
|---|-----------|--------------|-----|--------------------|
| 194 | 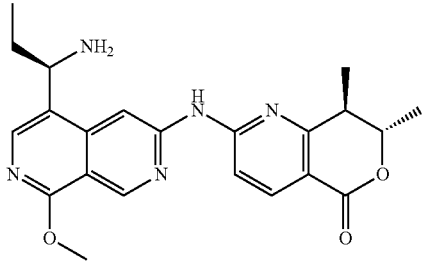  Or  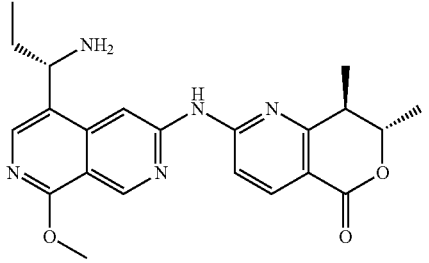 | 407 | ¹H-NMR (400 MHz, CD3OD): δ ppm 9.46 (d, J = 1.6 Hz, 1H), 8.71-8.67 (m, 1H), 8.18-8.15 (m, 1H), 7.82-7.78 (m, 1H), 7.27 (d, J = 8.8 Hz, 1H), 7.04-7.01 (m, 1H), 4.96-4.92 (m, 1H), 4.59-4.52 (m, 1H), 4.04 (s, 3H), 3.14-3.06 (m, 1H), 2.25-2.12 (m, 2H), 1.60 (d, J = 6.8 Hz, 3H), 1.55 (d, J = 6.4 Hz, 3H), 1.01-0.97 (m, 3H). | 17 Intermediate 73 and Intermediate 17 |
| 195 | 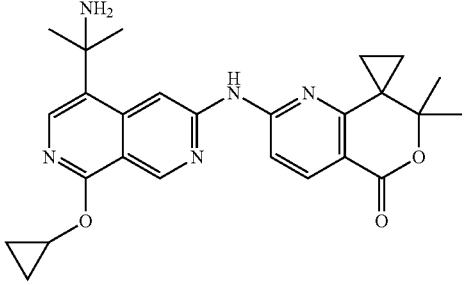 [SMILES: CC(C)(N)c1cnc(OC2CC2)c2cnc(Nc3ccc4c(n3)C3(CC3)C(C)(C)OC4=O)cc12] | 460 | ¹H-NMR (400 MHz, CDCl₃): δ ppm 9.29 (s, 1H), 8.93 (s, 1H), 8.24-8.21 (m, 2H), 8.01 (s, 1H), 7.27-7.25 (m, 1H), 4.51-4.46 (m, 1H), 1.74 (s, 6H), 1.63 (s, 2H), 1.42 (s, 6H), 1.11 (s, 2H), 0.95-0.90 (m, 4H). | 3 |
| 196 | 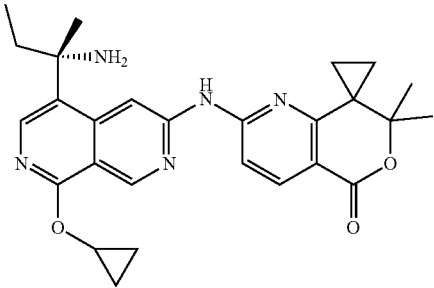  Or  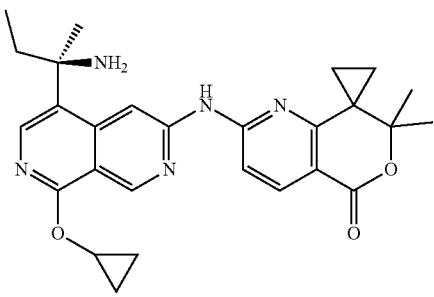 | 474 | | 3 Intermediate 33 |

TABLE 1-continued

| # | Structure | LCMS (M + 1) | NMR | Synthetic Protocol |
|---|---|---|---|---|
| 197 | 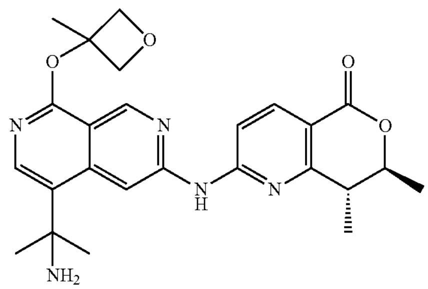 [SMILES: C[C@@H]1OC(=O)c2ccc(Nc3cc4c(C(C)(C)N)cnc(OC5(C)COC5)c4cn3)nc2[C@H]1C] | 464 | ¹H-NMR (400 MHz, CD₃OD): δ ppm 9.37 (s, 1H), 9.22 (s, 1H), 8.18-8.11 (m, 2H), 7.32 (d, J = 8.8 Hz, 1H), 5.03 (d, J = 6.8 Hz, 2H), 4.71 (d, J = 6.8 Hz, 2H), 4.69-4.62 (m, 1H), 3.10-2.98 (m, 1H), 1.94 (s, 3H), 1.79 (d, J = 5.2 Hz, 6H), 1.52-1.45 (m, 6H). | 9 Intermediate 17 |
| 198 | 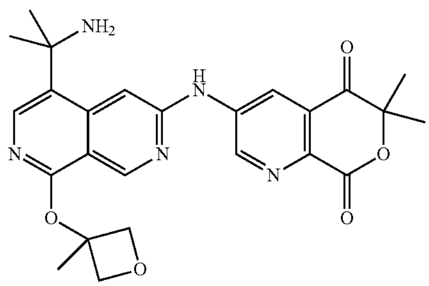 [SMILES: CC1(Oc2ncc(C(C)(C)N)c3cc(Nc4cnc5c(c4)C(=O)C(C)(C)OC5=O)ncc23)COC1] | 478 | ¹H-NMR (400 MHz, CD₃OD): δ ppm 9.40-7.30 (m, 2H), 8.19-8.09 (m, 2H), 7.22 (d, J = 8.8 Hz, 1H), 5.03 (d, J = 7.2 Hz, 2H), 4.71 (d, J = 7.2 Hz, 1H), 1.94 (s, 3H), 1.80 (d, J = 7.2 Hz, 6H), 1.54 (s, 3H), 1.45 (s, 3H), 1.41 (d, J = 7.2 Hz, 3H). | 9 Intermediate 20 |
| 199 | 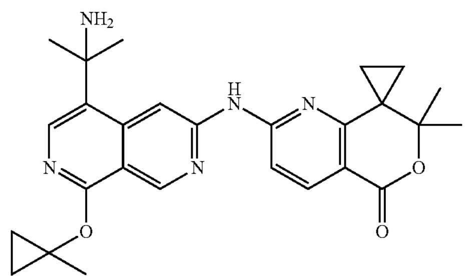 [SMILES: CC1(Oc2ncc(C(C)(C)N)c3cc(Nc4ccc5c(n4)C4(CC4)C(C)(C)OC5=O)ncc23)CC1] | 474 | ¹H-NMR (400 MHz, CDCl₃): δ ppm 9.30 (s, 1H), 8.84 (s, 1H), 8.24-8.22 (m, 2H), 8.04 (s, 1H), 7.30 (s, 1H), 1.77 (s, 9H), 1.60 (s, 1H), 1.41 (s, 6H), 1.08 (s, 2H), 1.06 (s, 2H), 0.89-0.82 (m, 2H). | 3 |
| 200 | Or | 464 | ¹H-NMR (400 MHz, CDCl₃): δ ppm 9.46 (s, 1 H), 9.28 (d, J = 0.8 Hz, 1 H), 8.29-8.17 (m, 2 H), 7.98 (s, 1 H), 7.16 (d, J = 8.4 Hz, 1 H), 4.55-4.47 (m, 1 H), 3.93 (d, J = 9.2 Hz, 1 H), 3.61 (d, J = 8.8 Hz, 1 H), 3.44 (s, 3 H), 3.16 (s, 2 H), 1.72 (s, 3 H), 1.55 (s, 6 H), 0.95-0.87 (m, 4 H). | 16 Intermediate 69 |

161

162

TABLE 1-continued

| # | Structure | LCMS (M + 1) | NMR | Synthetic Protocol |
|---|---|---|---|---|
| 201 | [Structure shown, with "Or" between two stereoisomers] | 452 | $^1$H-NMR (400 MHz, 6d-DMSO): δ ppm 10.88 (s, 1H), 9.37 (s, 1H), 8.96 (s, 1H), 8.90 (s, 2H), 8.13 (d, J = 8.8 Hz, 1H), 7.99 (s, 1H), 7.47 (d, J = 8.8 Hz, 1H), 4.10 (s, 3H), 4.06-4.01 (m, 2H), 3.31 (s, 3H), 2.95-2.90 (m, 1H), 1.87 (s, 3H), 1.45 (s, 3H), 1.39 (s, 3H), 1.29 (d, J = 7.2 Hz, 3H). | 16 Intermediate 67 and Intermediate 20 |
| 202 | [Structure shown, with "Or" between two stereoisomers] | 392 |  | 17 Intermediate 71 and Intermediate |

TABLE 1-continued

| # | Structure | LCMS (M + 1) | NMR | Synthetic Protocol |
|---|---|---|---|---|
| 203 | 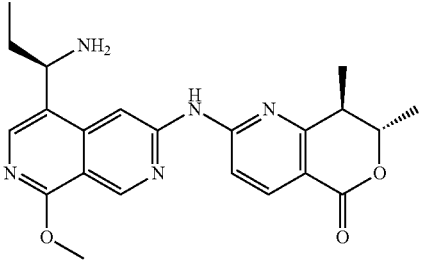 Or | 408 | ¹H NMR (500 MHz, DMSO) δ 10.63 (s, 1H), 9.23 (s, 1H), 8.79 (s, 1H), 8.11 (s, 1H), 8.03 (d, J = 8.7 Hz, 1H), 7.27 (d, J = 8.7 Hz, 1H), 4.51-4.42 (m, 1H), 4.25 (t, J = 6.4 Hz, 1H), 3.99 (s, 3H), 2.99 (p, J = 7.0 Hz, 1H), 2.22 (s, 2H), 1.76 (dq, J = 13.7, 6.9 Hz, 1H), 1.67 (dq, J = 14.0, 7.2 Hz, 1H), 1.43 (d, J = 7.0 Hz, 3H), 1.38 (d, J = 6.3 Hz, 3H), 0.83 (t, J = 7.3 Hz, 3H). | 17 Intermediate 76 and Intermediate 17 |
| 204 | 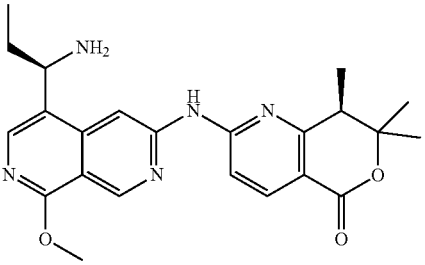 Or | 422 | ¹H NMR (500 MHz, DMSO) δ 10.71 (s, 1H), 9.30 (d, J = 1.9 Hz, 1H), 8.91 (s, 1H), 8.17 (d, J = 1.9 Hz, 1H), 8.08 (dd, J = 8.7, 1.9 Hz, 1H), 7.34 (dd, J = 8.6, 2.0 Hz, 1H), 4.30 (t, J = 6.5 Hz, 1H), 4.06 (d, J = 1.9 Hz, 3H), 3.15 (ddd, J = 13.9, 8.9, 5.1 Hz, 1H), 1.91-1.81 (m, 1H), 1.76 (dq, J = 13.9, 7.5, 7.1 Hz, 1H), 1.45 (d, J = 1.9 Hz, 3H), 1.41 (dd, J = 7.1, 1.9 Hz, 3H), 1.35 (d, J = 1.9 Hz, 3H), 0.91 (td, J = 7.4, 1.9 Hz, 3H). | 17 Intermediate 76 and Intermediate 20 |
| 205 | 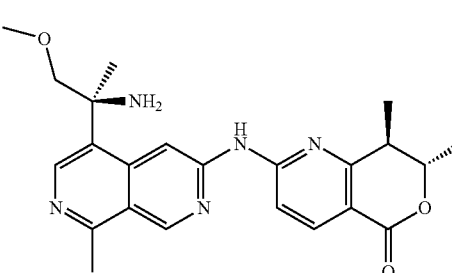 | 422 | ¹H-NMR (400 MHz, 6d-DMSO): δ ppm 10.64 (s, 1H), 9.50 (s, 1H), 9.43 (s, 1H), 8.45 (s, 1H), 8.09 (d, J = 8.7 Hz, 1H), 7.41 (d, J = 8.8 Hz, 1H), 4.67-4.57 (m, 1H), 3.85-3.79 (m, 1H), 3.78-3.72 (m, 1H), 3.25 (s, 3H), 3.05-2.95 (m, 1H), 2.90 (s, 3H), 1.63 (s, 3H), 1.46 (d, J = 7.2 Hz, 3H), 1.39 (d, J = 6.8 Hz, 3H) | 16 Intermediate 17 and Intermediate 70 |

TABLE 1-continued

| # | Structure | LCMS (M + 1) | NMR | Synthetic Protocol |
|---|---|---|---|---|
| 206 | 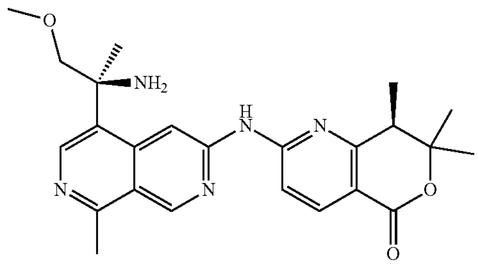 | 436 | ¹H-NMR (400 MHz, 6d-DMSO): δ ppm 10.68 (s, 1H), 9.63 (s, 1H), 9.43 (s, 1H), 8.46 (s, 1H), 8.07 (d, J = 8.8 Hz, 1H), 7.33 (d, J = 8.8 Hz, 1H), 3.81 (s, 2H), 3.26 (s, 3H), 3.07-2.94 (m, 1H), 2.90 (s, 3H), 1.65 (s, 3H), 1.46 (s, 3H), 1.38 (s, 3H), 1.33 (d, J = 7.2 Hz, 3H) | 16 Intermediate 20 and Intermediate 70 |
| 207 | Or | 433 | ¹H-NMR (400 MHz, CD₃OD): δ ppm 9.75-9.52 (m, 1 H), 8.34 (d, J = 8.8 Hz, 1 H), 8.25 (s, 1 H), 8.04 (d, J = 8.4 Hz, 1 H), 7.22 (d, J = 2.0 Hz, 1 H), 7.19 (d, J = 0.8 Hz, 1 H), 5.03-4.94 (m, 1 H), 4.17 (s, 3 H), 2.30-2.09 (m, 2 H), 1.65-1.56 (m, 2 H), 1.55-1.48 (m, 2 H), 1.46 (s, 6 H), 1.04-0.97 (m, 3 H). | 17 Intermediate 73 |
| 208 | Or | 438 | ¹H-NMR (400 MHz, CD₃OD): δ ppm 9.36 (s, 1H), 8.90 (s, 1H), 8.24-8.10 (m, 2H), 7.26 (d, J = 8.8 Hz, 1H), 4.95-4.91 (m, 1H), 4.15 (s, 3H), 3.85-3.80 (m, 1H), 3.66-3.57 (m, 1H), 3.47 (s, 3H), 3.25-3.19 (m, 1H), 1.55-1.43 (m, 9H). | 16 Intermediate 81 and Intermediate 20 |

TABLE 1-continued

| # | Structure | LCMS (M + 1) | NMR | Synthetic Protocol |
|---|---|---|---|---|
| 209 | Or | 425 | ¹H-NMR (400 MHz, CD₃OD): δ ppm 9.37 (s, 1H), 9.00 (s, 1H), 8.08 (d, J = 8.8 Hz, 1H), 7.71 (d, J = 8.0 Hz, 1H), 7.49 (d, J = 8.0 Hz, 1H), 7.18 (d, J = 8.8 Hz, 1H), 4.66-4.59 (m, 1H), 3.13 (q, J = 7.2 Hz, 1H), 2.02-1.83 (m, 2H), 1.52-1.48 (m, 6H), 1.44 (s, 3H), 1.01-0.94 (m, 3H) | 17 Intermediate 77 and Intermediate 20 |
| 210 | Or | 406 | ¹H-NMR (400 MHz, CD₃OD): δ ppm 9.51 (s, 1 1 H), 8.87 (s, 1 H), 8.52 (s, 1 H), 8.47 (s, 1 H), 8.15 (d, J = 8.8 Hz, 1 H), 7.30 (d, J = 8.8 Hz, 1 H), 4.80-4.76 (m, 1 H), 3.23-3.15 (m, 1 H), 3.00 (s, 3 H), 2.19-2.02 (m, 2 H), 1.57-1.48 (m, 6 H), 1.45 (s, 3 H), 1.10-0.96 (m, 3 H), 0.77-0.76 (m, 1 H). | 17 Intermediate 77 and Intermediate 20 |

Included in the present teachings are pharmaceutically acceptable salts of the compounds disclosed herein (including compounds disclosed in Table 1 and Exemplification) as well as the corresponding neutral form.

Another embodiment of the disclosure a deuterated is a compound disclosed herein, including a compound of Formulas I-IV, V(A)-V(C), VI(A)-VI(C), VII-IX, VII(A)-IX(A) and X or a compound in Table 1 and exemplification or a pharmaceutically acceptable salt of any of the foregoing, in which one or more hydrogen atoms is replaced with deuterium. The deuterium enrichment at any one of the sites where hydrogen has been replaced by deuterium is at least 50%, 75%, 85%, 90%, 95%, 98% or 99%. Deuterium enrichment is a mole percent and is obtained by dividing the number of compounds with deuterium enrichment at the site of enrichment with the number of compounds having hydrogen or deuterium at the site of enrichment.

Definitions

As used herein, the term "pharmaceutically acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically acceptable salts are well known in the art. For example, S. M. Berge et al. describes pharmacologically acceptable salts in *J. Pharm. Sci.* (1977) 66:1-19. Compounds of the present teachings with basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as acetic acid, benzenesulfonic, benzoic, methanesulfonic, and p-toluenesulfonic acids). Compounds of the present teachings with acidic groups can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

The term "alkyl" used alone or as part of a larger moiety, such as "alkoxy", "hydroxyalkyl" and the like, means a saturated aliphatic straight-chain or branched monovalent hydrocarbon radical. Unless otherwise specified, an alkyl group typically has 1 to 6 carbon atoms ($C_{1-6}$ alkyl), alternatively, 1 to 3 carbon atoms ($C_{1-3}$ alkyl). "$C_{1-6}$ alkyl" is means a radical having 1 to 6 carbon atoms in a linear or branched arrangement, such as methyl, ethyl, propyl, iso-propyl, butyl, isobutyl, tert-butyl, and the like.

"Alkoxy" means an alkyl radical attached through an oxygen linking atom, represented by —O-alkyl, wherein alkyl is as defined above. For example, "$C_{1-6}$ alkoxy" includes methoxy, ethoxy, propoxy, butoxy, pentoxy, iso-pentoxy, isopropoxy, and hexoxy.

The term "halogen" or "halo" means fluorine or fluoro (F), chlorine or chloro (Cl), bromine or bromo (Br), or iodine or iodo (I).

"Cycloalkyl" means a saturated aliphatic cyclic hydrocarbon ring radical. Unless otherwise specified, a cycloalkyl has 3 to 8 ring carbon atoms ($C_{3-8}$ cycloalkyl) (i.e., 3, 4, 5, 6, 7, or 8), alternatively, 3 to 6 ring carbon atoms ($C_{3-6}$ cycloalkyl) (i.e., 3, 4, 5, or 6), alternatively, 3 to 5 carbon atoms ($C_{3-5}$ cycloalkyl) (i.e., 3, 4, or 5). "$C_{3-6}$ Cycloalkyl" means a radical having from 3 to 6 carbon atoms arranged in a monocyclic ring. A $C_{3-6}$ cycloalkyl includes cyclopropyl, cyclobutyl, cyclopentyl, and cyclohexyl. A $C_{3-5}$ cycloalkyl includes cyclopropyl, cyclobutyl, and cyclopentyl.

The term "heterocycle" refers to a monocyclic non-aromatic ring radical containing unless otherwise specified, 3 to 8 ring atoms (i.e., "3, 4, 5, 6, 7, or 8 membered") selected from carbon atom and 1 or 2 heteroatoms. Each heteroatom is independently selected from nitrogen, quaternary nitrogen, oxidized nitrogen (e.g., NO); oxygen; and sulfur, including sulfoxide and sulfone. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, and the like.

The term "substituted", whether preceded by the term "optionally" or not, refers to the replacement of a hydrogen substituent in a given structure with a non-hydrogen substituent. Thus, for example, a substituted alkyl is an alkyl wherein at least one non-hydrogen substituent is in the place of a hydrogen substituent on the alkyl group. To illustrate, monofluoroalkyl is an alkyl substituted with a fluoro substituent, and difluoroalkyl is an alkyl substituted with two fluoro substituents. It should be recognized that if there is more than one substitution on a substituent, each non-hydrogen substituent can be identical or different (unless otherwise stated).

If a group is described as being "optionally substituted", the group can be either (1) not substituted or (2) substituted. If a group is described as being optionally substituted with up to a particular number of non-hydrogen substituents, that group can be either (1) not substituted; or (2) substituted by up to that particular number of non-hydrogen substituents or by up to the maximum number of substitutable positions on the substituent, whichever is less. Thus, for example, if a group is described as a cycloalkyl optionally substituted with up to 3 non-hydrogen substituents, then any cycloalkyl with less than 3 substitutable positions would be optionally substituted by up to only as many non-hydrogen substituents as the cycloalkyl has substitutable positions.

Compounds having one or more chiral centers can exist in various stereoisomeric forms, i.e., each chiral center can have an R or S configuration or can be a mixture of both. Stereoisomers are compounds that differ only in their spatial arrangement. Stereoisomers include all diastereomeric and enantiomeric forms of a compound. Enantiomers are stereoisomers that are mirror images of each other. Diastereomers are stereoisomers having two or more chiral centers that are not identical and are not mirror images of each other.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9% (except when the designation "rac" or "racemate accompanies the structure or name, as explained in the following two paragraphs). "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When the stereochemical configuration at a chiral center in a compound is depicted by chemical name (e.g., where the configuration is indicated in the name by "R" or "S") or structure (e.g., the configuration is indicated by "wedge" bonds) and the designation "rac" or "racemate" accompanies the structure or is designated in the chemical name, a racemic mixture is intended.

When two or more stereoisomers are depicted by their chemical names or structures, and the names or structures are connected by an "or", one or the other of the two or more stereoisomers is intended, but not both.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with "S" or "R", the name is meant to encompass the compound with the S configuration at that chiral center, the compound with the R configuration at that chiral center or the compound with a mixture of the R and S configuration at that chiral center.

A racemic mixture means a mixture of 50% of one enantiomer and 50% of its corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

"Peak 1" or "first eluting isomer" in the Experimental section refers to an intended reaction product compound obtained from a chromatography separation/purification that elutes earlier than a second intended reaction product compound from the same preceding reaction. The second intended product compound is referred to as "peak 2" or "second eluting isomer".

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that, unless otherwise indicated, one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Use

Compounds of the disclosure are MAP4K1 inhibitors. The use of the word "inhibitor" means that a compound or a pharmaceutically acceptable salt thereof inhibits activity of MAP4K1. By "inhibit" herein is meant to decrease the activity of the target enzyme as compared to the activity of that enzyme in the absence of the inhibitor. In some alternatives, the term "inhibit" means a decrease in MAP4K1 activity of at least 5%, at least 10%, at least 20%, at least 50%, at least 60%, at least 79%, at least 80%, at least 90% or at least 95%. In other alternatives, inhibit means a decrease in MAP4K1 activity of 5% to 25%, 25% to 50%, 50 to 70%, 75 to 100%. In some embodiments, inhibit means a decrease in MAP4K1 activity about 95% to 100%, e.g., a decrease in activity of 95%, 96%, 97%, 98%, 99%, or 100%. Such decreases can be measured using a variety of techniques that would be recognizable by one of skill in the art, including in vitro kinase assays.

Compounds of the disclosure are selective MAP4K1 inhibitors. As used herein, a "selective MAP4K1 inhibitor" refers to a compound or a pharmaceutically acceptable salt thereof that has the ability to selectively inhibit MAP4K1 kinase over other targets. More specifically, a selective MAP4K1 inhibitor has the ability to selectively inhibit MAP4K1 over another kinase. A selective MAP4K1 inhibitor has the ability to selectively reduce target signaling activity relative to off-target signaling activity, via direct or indirect interaction with the target. The ability to selectively target MAP4K1 with a compound or pharmaceutically acceptable salt thereof provides advantages in terms of improved potency, less off-target activity and an increased probability of clinical success in comparison with a nonselective compound or salt. A MAP4K1 inhibitor that selectively inhibits MAP4K1 may have an activity that is at least 2-fold relative to another kinase (e.g., at least 10-fold; at least 15-fold; at least 20-fold; at least 30-fold; at least 40-fold selectivity; at least 50-fold; at least 60-fold; at least 70-fold; at least 80-fold; at least 90-fold; at least 100-fold; at least 125-fold; at least 150-fold; at least 175-fold; or at least 200-fold. In some alternatives, a selective MAP4K1 inhibitor exhibits at least 15-fold selectivity over another kinase, e.g., LCK and MAP4K family members (MAP4K4 (HGK) and MAP4K3 (GLK)). In some alternatives, the selective MAP4K1 inhibitors are selective over EGFR and L858R/T790M EGFR. In some alternatives, the selective MAP4K1 inhibitors of the disclosure are selective over BTK. In some alternatives, the selective MAP4K1 inhibitors of the disclosure are selective over JNK.

The disclosure provides methods of modulating (e.g., inhibiting) MAP4K1 activity in a patient in need thereof, said method comprising administering to the patient a compound provided herein, or a pharmaceutically acceptable salt thereof. In certain embodiments, the compounds of the disclosure, or pharmaceutically acceptable salts thereof, are useful for therapeutic administration to enhance, stimulate and/or increase immunity in patients in need thereof, e.g., in cancer patients or patients with viral infection. In some instances, the compounds of the disclosure, or pharmaceutically acceptable salts thereof reduce, inhibit, or otherwise diminish pSLP76. In some instances, the compounds of the disclosure, or pharmaceutically acceptable salts thereof, are useful for therapeutic administration to enhancing at least one of activation, priming, migration, proliferation, survival and cytolytic activity of T cells relative to prior to administration. In certain aspects, T cell activation is characterized by enhanced levels of IL-2, IFN-gamma, or granzyme B production by T cells relative to prior to administration of the compound or pharmaceutically acceptable salt thereof. In some instances, the compounds of the disclosure, or pharmaceutically acceptable salts thereof, are useful for therapeutic administration to induce a change in cell cycle or cell viability. In some instances, the compounds of the disclosure, or pharmaceutically acceptable salts thereof, are useful for improving function of T effector cells. In some instances, the compounds of the disclosure, or pharmaceutically acceptable salts thereof, are useful for inhibiting the suppressive effects of T regulatory cells or improving the T cell response to immune suppressive factors including adenosine and PGE2. In some instances, the compounds of the disclosure, or pharmaceutically acceptable salts thereof, are useful for increasing the frequency of CD8+ tumor infiltrating lymphocytes (TILS). In some instances, the compounds of the disclosure, or pharmaceutically acceptable salts thereof are useful for enhancing CD8+/Treg ratios. In some instances, the compounds of the disclosure, or pharmaceutically acceptable salts thereof, are useful for enhancing cytokines. In some instances, the compounds of the disclosure, or pharmaceutically acceptable salts thereof, are useful for enhanacing cytokines with no impact on IL-6. In some instances, the compounds of the disclosure, or pharmaceutically acceptable salts there, indirectly inhibit the growth of cancer cells. In some instances, the compounds of the disclosure, or pharmaceutically acceptable salts thereof, are useful for priming of the immune response (i.e., vaccines) to tumors or viruses for boosting or generating anti-viral/anti-tumor immunity. In one instance, the compounds of the disclosure, or pharmaceutically acceptable salts thereof, are useful for enhacing or boosting response to a vaccine (such as a cancer vaccine or a personalized cancer vaccine (PCV)) or a CAR-T cell therapy.

Methods of treating a MAP4K1-dependent disease or disorder can include administering to a patient in need thereof a therapeutically effective amount of a compound provided herein, or a pharmaceutically acceptable salt thereof. For example, the MAP4K1-dependent disease or disorder is a cancer. The term "cancer" encompasses all forms of cancer including, but not limited to, all forms of carcinoma, melanomas, blastomas, sarcomas, lymphomas, leukemias. In some embodiments, cancer includes metastatic forms. Additionally, the disclosure includes refractory or recurrent malignancies whose growth may be inhibited using the compounds of the disclosure or pharmaceutically acceptable salts thereof. For the uses described herein, any of the compounds of the disclosure, or pharmaceutically acceptable salts thereof, may be used alone or in combination with other therapeutic agents.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0× length of the treatment duration.

The treatment methods disclosed herein may result in a partial or complete response. As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the selective MAP4K1 inhibitor. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" (OS) refers to the percentage of subjects in a group who are likely to be alive after a particular duration of time.

In some embodiments, cancers treatable with compounds of the disclosure or pharmaceutically acceptable salts thereof, include colon cancer, pancreatic cancer, breast cancer, prostate cancer, lung cancer, ovarian cancer, cervical cancer, renal cancer, bladder cancer, stomach cancer, liver cancer, gastric cancer, cancer of the head and neck, lymphoma, leukemia, urothelial carcinoma, merkel cell carcinoma, gastroesophageal junction carcinoma, esophageal squamous cell carcinoma, skin squamous cell carcinoma and melanoma.

In some embodiments, cancers treatable with compounds of the disclosure or pharmaceutically acceptable salts thereof, include colon cancer, pancreatic cancer, breast cancer, prostate cancer, lung cancer, ovarian cancer, cervical cancer, renal cancer, bladder cancer, stomach cancer, liver cancer, cancer of the head and neck, lymphoma, leukemia, and melanoma.

In some embodiments, cancers that are treatable using the compounds of the disclosure or pharmaceutically acceptable salts thereof, include, but are not limited to, solid tumors, including prostate cancer, colon cancer, esophageal cancer, endometrial cancer, ovarian cancer, uterine cancer, renal cancer, hepatic cancer, pancreatic cancer, gastric cancer, breast cancer, lung cancer, head and neck cancer, thyroid cancer, brain cancer, and bladder cancer and hematological cancer, including lymphoma, leukemia (chronic and acute forms) such as ALL, AML, CLL, CML, DLBCL, mantle cell lymphoma, Non-Hodgkin's lymphoma (NHL), including relapsed or refractory NHL and recurrent follicular, Hodgkin's lymphoma and multiple myeloma, and myeloproliferative diseases.

In some embodiments, diseases and indications that are treatable using the compounds of the disclosure or pharmaceutically acceptable salts thereof, include, but are not limited to hematological cancer, sarcomas, respiratory cancer, gastrointestinal cancer, genitourinary tract cancer, liver cancer, bone cancer, nervous system cancer, gynecological cancer, and skin cancer.

Exemplary hematological cancer includes, for example, lymphomas and leukemias such as ALL, AML, acute promyelocyte leukemia (APL), CLL, CML, DLBCL, mantle cell lymphoma, Non-Hodgkin lymphoma (NHL), including Primary mediastinal B-cell lymphoma (PMBCL), relapsed or refractory NHL, recurrent follicular, and primary CNS lymphoma, Hodgkin's lymphoma, myeloproliferative diseases, including, primary myelofibrosis (PMF), polycythemia vera (PV), essential thrombocytosis (ET), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma, and Burkitt's lymphoma.

Exemplary sarcoma includes, for example, chondrosarcoma, Ewing's sarcoma, Kaposi's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, sarcoma of the soft tissue, and teratoma.

Exemplary respiratory tract cancer includes, for example, lung cancer such as non-small cell lung cancer (NSCLC), small cell lung cancer, epidermoid cancer, bronchogenic carcinoma, including squamous cell, undifferentiated small cell, undifferentiated large cell, adenocarcinoma, alveolar (bronchiolar) carcinoma, bronchial adenoma, chondromatous hamartoma, mesothelioma, and pleuropulmonary blastoma.

Exemplary gastrointestinal cancer includes, for example, cancers of the esophagus, including squamous cell carcinoma, adenocarcinoma, leiomyosarcoma, and lymphoma; stomach, including carcinoma, lymphoma, and leiomyosarcoma; pancreas, including ductal adenocarcinoma, insulinoma, glucagonoma, gastrinoma, carcinoid tumors, and vipoma; small instestine, including adenocarcinoma, lymphoma, carcinoid tumors, Kaposi's sarcoma, leiomyoma, hemangioma, lipoma, neurofibroma, and fibroma; large intestine, including adenocarcinoma, tubular adenoma, villous adenoma, hamartoma, and leiomyoma; colon; and gall bladder, including adenocarcinoma; and intestinal type and diffuse type gastric adenocarcinoma, rectum carcinoma, familiar adenomatous polyposis carcinoma and hereditary non-polyposis colorectal cancer.

Exemplary genitourinary tract cancer includes, for example, cancers of the kidney, including adenocarcinoma, Wilm's tumor [nephroblastoma], renal cell carcinoma, urothelial carcinoma, juxtaglomerular cell tumor (reninoma), angiomyolipoma, renal oncocytoma, Bellinio duct carcinoma, clear-cell sarcoma of the kidney, and mesoblastic nephroma; adrenal gland; renal pelvis; bladder, including transitional cell carcinoma, squamous cell carcinoma, adenocarcinoma, sarcoma, and small cell carcinoma; urethra, including squamous cell carcinoma, transitional cell carcinoma, and adenocarcinoma; prostate, including adenocarcinoma, sarcoma, and carcinoma; testis, including seminoma, teratoma, embryonal carcinoma, teratocarcinoma, choriocarcinoma, sarcoma, interstitial cell carcinoma, fibroma, fibroadenoma, adenomatoid tumors, and lipoma; penis; and pancreas.

Exemplary liver cancer includes, for example, hepatoma, including hepatocellular carcinoma, cholangiocarcinoma, hepatoblastoma, angiosarcoma, hepatocellular adenoma, biliary tract cancer, and hemangioma.

Exemplary bone cancer includes, for example, osteogenic sarcoma, fibrosarcoma, malignant fibrous histiocytoma, chondrosarcoma, Ewing's sarcoma, malignant lymphoma, including reticulum cell sarcoma, multiple myeloma, malignant giant cell tumor chordoma, osteochronfroma, including osteocartilaginous exostoses, benign chondroma, chondroblastoma, chondromyxofibroma, osteoid osteoma, and giant cell tumors Exemplary nervous system cancer includes, for example, cancer of the skull, including osteoma, hemangioma, granuloma, xanthoma, and osteitis deformans; meninges including, meningioma, meningiosarcoma, and gliomatosis; brain, including astrocytoma, meduoblastoma, glioma, ependymoma, germinoma (pinealoma), neuroectodermal tumor, glioblastoma, glioblastoma multiform, oligodendroglioma, schwannoma, retinoblastoma, congenital tumors, brain stem and hypopthamic glioma; and spinal cord, including neurofibroma, meningioma, glioma, and sarcoma; as well as neuroblastoma and Lhermitte-Duclos disease.

Exemplary gynecological cancer includes, for example, cancer of the uterus, including endometrial carcinoma; cervix, including cervical carcinoma, pre-tumor cervical dysplasia, squamouse cell carcinoma, adenocarcinoma, adenosquamous carcinoma, small cell carcinoma, neuroendocrine tumor, glassy cell carcinoma and villoglandular adenocarcinoma; ovaries, including ovarian carcinoma (serous cystadenocarcinoma, mucinous cystadenocarcinoma, unclassified carcinoma, endometroid tumor), granulosa-thecal cell tumors, Sertoli-Leydig cell tumors, dysgerminoma, malignant teratoma, and arrhenoblastoma; vulva (squamous cell carcinoma, intraepithelial carcinoma, adenocarcinoma, fibrosarcoma, and melanoma; vagina, including clear cell carcinoma, squamous cell carcinoma, and botryoid sarcoma (embryonal rhabdomyosarcoma); labia; and fallopian tubes.

Exemplary skin cancer includes, for example, melanoma, sebaceous gland carcinoma, basal cell carcinoma, squamous cell carcinoma, Kaposi's sarcoma, Merkel cell skin cancer, moles dysplastic nevi, lipoma, angioma, dermatofibroma, and keloids.

Examples of breast cancer include, for example, ER+/HER2− breast cancer, triple-negative breast cancer (TNBC), invasive ductal carcinoma, invasive lobular carcinoma, ductal carcinoma in situ, and lobular carcinoma in situ.

Exemplary head and neck cancer includes, for example, glioblastoma, melanoma, rhabdosarcoma, lymphosarcoma, osteosarcoma, squamous cell carcinomas, adenocarcinomas, oral cancer, throat cancer, including oropharyngeal cancer, laryngeal cancer, nasopharyngeal cancer, nasal and paranasal cancer, salivary gland cancer, mouth cancer, eye cancer, acoustic neuroma, pituitary adenoma, hypopharngx, and thyroid (medullary and papillary) and parathyroid cancer.

Other cancers include, for example, sweat gland cancer, spinal axis tumor, chest cancer, sickle cell anemia, and environmentally induced cancers including those induced by asbestos.

In some instances, the MAP4K1-dependent disease or disorder is a viral infection, such as infection caused by hepatitis B virus (HBV), hepatitis C virus (HCV), human papilloma virus (HPV), cytomegalovirus (CMV), herpes simplex virus (HSV), Epstein-Barr virus (EBV), varicella zoster virus, coxsackie virus, and human immunodeficiency virus (HIV).

Combination Therapies

Compounds of the disclosure or pharmaceutically acceptable salts thereof, can be administered as the sole pharmaceutical agent or in combination with one or more other anti-cancer agents for the treatment of cancer, where the combination causes no unacceptable adverse effects. In some embodiments, the other anti-cancer agents are immune-oncology agent, anticancer agents that are enzyme/protein/receptor inhibitors, radiation or chemotherapy.

Compounds of the disclosure or pharmaceutically acceptable salts thereof, can be co-formulated with an immuno-oncology agent. Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human. In another aspect, the antibody is a bispecific antibody.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNF a, LTR, Lymphotoxin a 1β2, FAS, FASL, RELT, DR6, TROY, NGFR.

In one aspect, T cell responses can be stimulated by a combination of a compound of the disclosure or a pharmaceutically acceptable salt thereof, and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the disclosure or pharmaceutically acceptable salts thereof, for the treatment of cancer include antagonists of inhibitory receptors on NK cells or agonists of activating receptors on NK cells. For example, compounds of the disclosure can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 or FPA-008.

In another aspect, compounds of the disclosure or pharmaceutically acceptable salts thereof, can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In some embodiments, the immuno-oncology agent is a CTLA-4 antagonist, such as an antagonistic CTLA-4 antibody. Suitable CTLA-4 antibodies include, for example, YERVOY (ipilimumab) or tremelimumab. In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, TECENTRIQ (atezolizumab) (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469. In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The compounds of the disclosure or pharmaceutically acceptable salts thereof, can be used in combination with anticancer agents that are enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the disclosure or pharmaceutically acceptable salts thereof, can be used in combination with one or more other enzyme/protein/receptor inhibitors for the treatment of cancer. For example, the compounds of the disclosure or pharmaceutically acceptable salts thereof, can be combined with one or more inhibitors of the following kinases for the treatment of cancer: Akt1, Akt2, Akt3, TGF-βPv, PKA, PKG, PKC, CaM-kinase, phosphorylase kinase, MEKK, ERK, MAPK, mTOR, EGFR, HER2, HER3, HER4, INS-R, IGF-1R, IR-R, PDGFotR, PDGFpR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK, and B-Raf.

In some embodiments, the compounds of the disclosure or pharmaceutically acceptable salts thereof, can be combined with one or more of the following inhibitors for the treatment of cancer. Non-limiting examples of inhibitors that can be combined with the compounds of the present disclosure for treatment of cancers include an FGFR inhibitor (FGFR1, FGFR2, FGFR3 or FGFR4, e.g., fisogatinib, AZD4547, BAY 1187982, ARQ087, BGJ398, BIBF1120, TKI258, lucitanib, dovitinib, TAS-120, J J-42756493, Debio1347, INCB54828, INCB62079, and INCB63904), a JAK inhibitor (JAK1 and/or JAK2, e.g., ruxolitinib, baricitinib, or itacitinib (INCB39110)), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor (eganelisib) or a dual PI3K-delta/gamma selective inhibitor (duvelisib), a CSF1R inhibitor (e.g., PLX3397 and LY3022855), a TAM receptor tyrosine kinases (Tyro-3, Axl, and Mer), an angiogenesis inhibitor (Such as Avastin (bevacizumab)), an interleukin receptor inhibitor, bromo and extra terminal family members inhibitors (for example, bromodomain inhibitors or BET inhibitors such as OTX015, CPI-0610, INCB54329, and INCB57643), and an adenosine receptor antagonist or combinations thereof. Inhibitors of HDAC such as panobinostat and vorinostat can be combined with the compounds of the disclosure. Inhibitors of c-Met such as onartumzumab, tivantnib, and capmatinib (INC-280) be combined with the compounds of the disclosure or pharmaceutically acceptable salts thereof. Inhibitors of BTK such as ibrutinib can be combined with the compounds of the disclosure or pharmaceutically acceptable salts thereof.

Inhibitors of mTOR such as rapamycin, sirolimus, temsirolimus, and everolimus can be combined with the compounds of the disclosure or pharmaceutically acceptable salts thereof. Inhibitors of Raf, such as vemurafenib and dabrafenib can be combined with the compounds of the disclosure or pharmaceutically acceptable salts thereof. Inhibitors of MEK such as trametinib, selumetinib and GDC-0973 can be combined with the compounds of the disclosure or pharmaceutically acceptable salts thereof. Inhibitors of KIT, including avapritinib, imatinib, sunitinib, regorafenib, ripritinib (DCC2618), PLX9486, PLX3397, crenolanib, CDX-0158, CDX-0159. Inhibitors of RET including pralsetinib, selperctinib, alectinib, levatinib, cabozantinib, BOS172738 (DS-5010), SL-1001, TPX-0046, sitravatinib (MGCD516), and RXDX-105. Inhibitors of Hsp90 (e.g., tanespimycin), cyclin dependent kinases (e.g., palbociclib), PARP (e.g., olaparib) and Pim kinases (LGH447, INCB053914, and SGI-1776) can also be combined with compounds of the disclosure or pharmaceutically acceptable salts thereof.

Compounds of the disclosure or pharmaceutically acceptable salts thereof, can be used in combination with one or more agents for the treatment of cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (CYTOXAN), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX).

The compounds of the disclosure or pharmaceutically acceptable salts thereof, can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, anastrozole, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, capecitabine, carmustine, cediranib, cetuximab, chlorambucil, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxifene, dromostanolone propionate, eculizumab, enzalutamide, epidophyllotoxin, epirubicin, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, paclitaxel, pamidronate, panitumumab, pazopanib, pegaspargase, pegfilgrastim, pemetrexed disodium, pentostatin, pilaralisib, pipobroman, plicamycin, cisplatin, carboplatin, oxaliplatin, ponatinib, prednisone, procarbazine, quinacrine, rasburicase, regorafenib, reloxafine, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vinorelbine, vorinostat, and zoledronate.

Other anti-cancer agent(s) include antibody therapeutics such as trastuzumab (Herceptin).

Compounds of the disclosure or pharmaceutically acceptable salts thereof, can be administered as the sole pharmaceutical agent or in combination with one or more anti-viral agents for the treatment of chronic viral infections, where the combination causes no unacceptable adverse effects. Chronic viral infections include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Parasitic infections (e.g., malaria) may also be treated by the above methods wherein compounds known to treat the parasitic conditions are optionally added in place of the antiviral agents.

Suitable antiviral agents contemplated for use in combination with the compounds of the disclosure or pharmaceutically acceptable salts thereof, can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and Iodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrirnidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

When more than one pharmaceutical agent is administered to a patient, they can be administered simultaneously, separately, sequentially, or in combination (e.g., for more than two agents). For examples, when administered together with an additional anti-cancer or antiviral agent, the disclosed compounds or pharmaceutically acceptable salts thereof, can be administered simultaneously in the same pharmaceutical formulation or simultaneously in separate pharmaceutical formulations. Alternatively, when administered together with an additional anti-cancer or antiviral agent, the disclosed compounds or pharmaceutically acceptable salts thereof, can be administered at separate times, depending the dosing requirements of the additional anti-cancer or antiviral agent.

Pharmaceutical compositions are disclosed that include one or more compounds provided herein (such as the compound of Formulas I-IV, V(A)-V(C), VI(A)-VI(C), VII-IX, VII(A)-IX(A) and X) or pharmaceutically acceptable salts thereof, and typically at least one additional substance, such as an excipient, a known therapeutic other than those of the disclosure, and combinations thereof. In some embodiments, the disclosed compounds or pharmaceutically acceptable salts thereof, can be used in combination with other agents known to have beneficial activity targeting diseases or disorders listed above. For example, disclosed compounds or pharmaceutically acceptable salts thereof, can be administered alone or in combination with one or more anti-cancer or antiviral agent, and the pharmaceutically acceptable salts of these compounds.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

A "subject" is a mammal in need of medical treatment, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The precise amount of compound or pharmaceutically acceptable salt thereof, administered to provide an "effective amount" to the subject will depend on the mode of administration, the type, and severity of the disease or condition, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer or antiviral agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the disclosure or pharmaceutically acceptable salt thereof, being used by following, for example, dosages reported in the literature and recommended in the *Physician's Desk Reference* (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years.

The pharmaceutical composition of the disclosure is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

General Synthetic Methods and Intermediates

Compounds of the disclosure, including salts and N-oxides thereof, can be prepared using organic synthesis techniques known to one of ordinary skill in the art and/or by reference to the schemes shown below and the synthetic examples. The below Schemes are synthetic protocols that are meant to provide general guidance in connection with preparing the compounds of the disclosure. One skilled in the art would understand that the preparations shown in the Schemes can be modified or optimized using general knowledge of organic chemistry to prepare various compounds of the disclosure.

The reactions for preparing compounds of the disclosure can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC).

Scheme 1

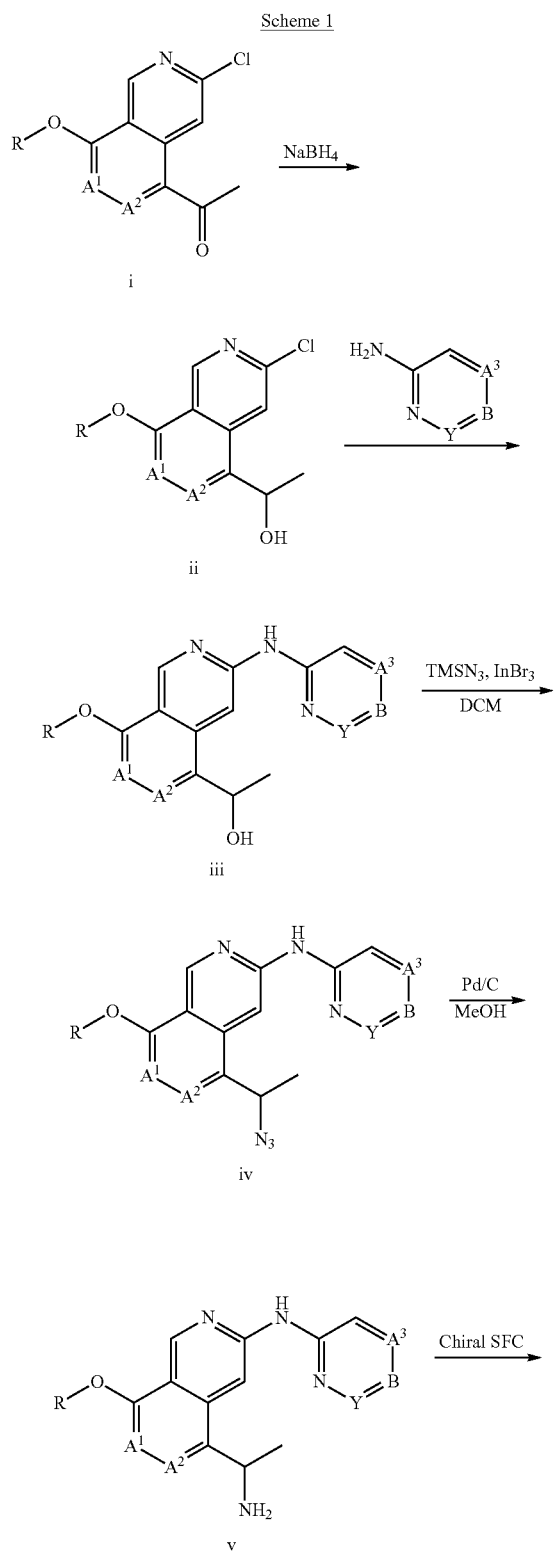

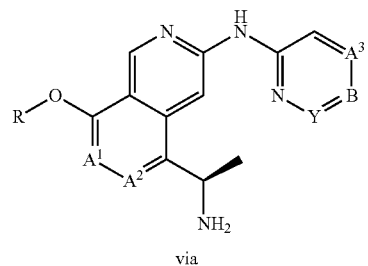

via

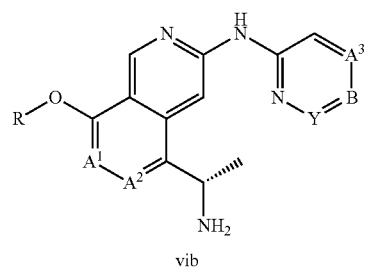

vib

Scheme 1 shows a synthetic protocol for the preparation of compounds of formula via and vib.

In Scheme 1, the definition of R is $R^6$ as described for the embodiments of the disclosure.

The 8-Alkoxy-2,7-Napthyridine methylketone i (see scheme 3 for preparation of i) can be reduced with sodium borohydride in methanol to give ii. The alcohol ii can be coupled to the aniline under Pd-catalyzed coupling conditions to give iii. The benzylic alcohol iii can be treated with TMSN$_3$ and Indium bromide in dichloromethane to yield the corresponding azide intermediate iv. The azide iv can be reduced under typical hydrogenation conditions such as Pd and H$_2$ to give the amine v. Chiral SFC on the racemic amine v can yield the desired isomer via and vib (arbitrarily assigned) which are examples of MAP4K1 inhibitors described herein.

Scheme 2

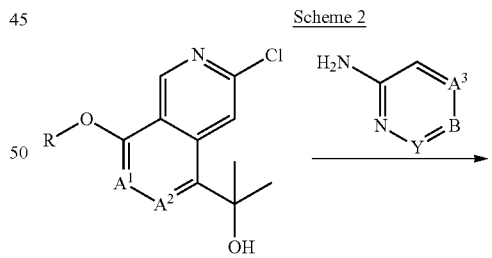

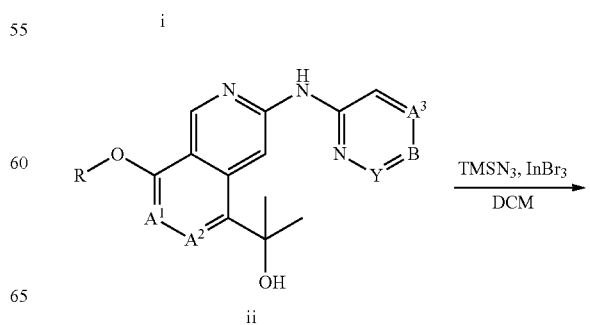

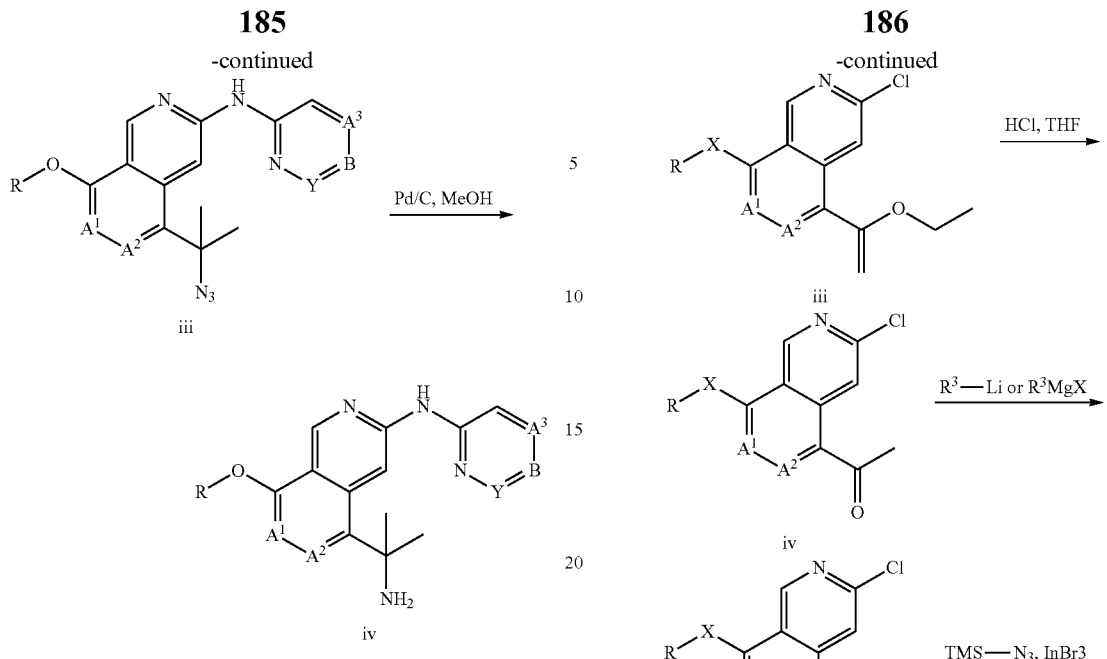

Scheme 2 shows a synthetic protocol for the preparation of compounds of formula iv.

In Scheme 2, the definition of R is $R^6$ or $R^7$ as described for the embodiments of the disclosure. The other variables in Scheme 2 are as described for the embodiments of the disclosure.

8-alkoxy-substituted 2,7-Napthyridine benzylic alcohol intermediate i (see Scheme 3 for preparation of i) can be coupled with an aniline under Pd-catalyzed coupling conditions to give ii. Compound ii can be treated with $TMSN_3$ and Indium bromide in dichloromethane to yield the corresponding azide intermediate iii. The azide iii can be reduced under typical hydrogenation conditions such as Pd and $H_2$ to give the amine iv which are examples of MAP4K1 inhibitors described herein.

Scheme 3 shows a synthetic protocol for the preparation of compounds of formula viii.

In Scheme 3, the definition of R is $R^6$ or $R^7$ as described for the embodiments of the disclosure and X is O or N. The other variables are as described for the embodiments of the disclosure.

Tri-halogen intermediate i (see Intermediate 31 in common intermediates for synthesis of intermediate i) can be treated with an alcohol or an amine to yield intermediate ii.

Intermediate ii can be subjected to Stille coupling with tributyl(1-ethoxyvinyl)stannane to yield iii. Under acidic conditions, iii can be converted to the methyl ketone iv. Subsequent addition of alkyl lithium or alkyl magnesium bromide can yield intermediate v. Compound v can be treated with TMSN$_3$ and Indium bromide in dichloromethane to yield the corresponding azide intermediate vi. The azide vi can be coupled to aryl amines under Pd-catalyzed coupling conditions to yield vii. Compound vii can be reduced under typical hydrogenation conditions such as Pd and H$_2$ to give the amine viii which are examples of MAP4K1 inhibitors described herein. The final amine viii can be separated using chromatography into isomers.

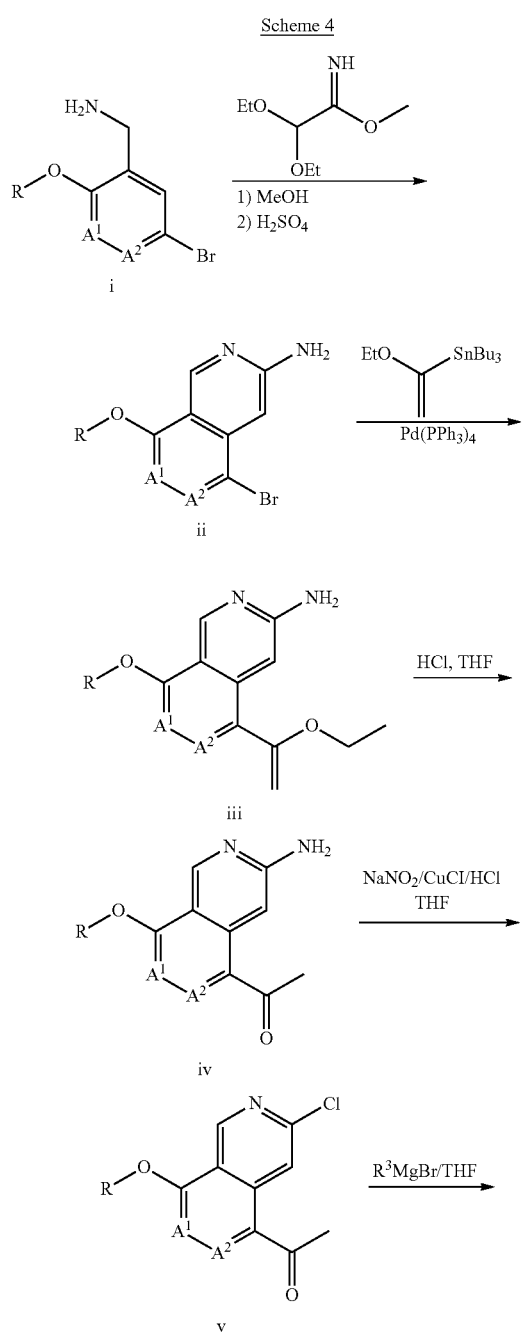

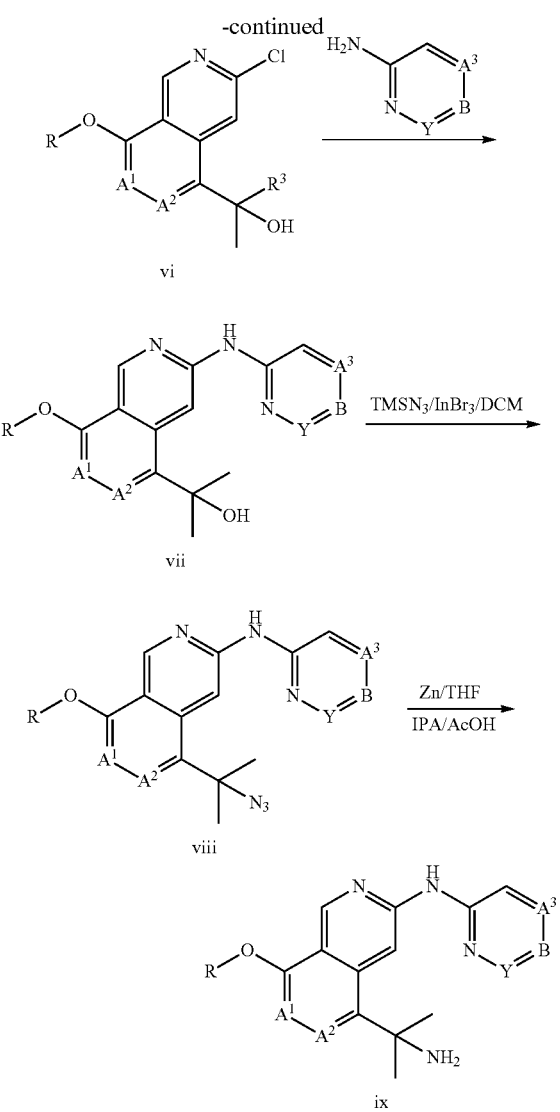

Scheme 4 shows a synthetic protocol for the preparation of compounds of formula ix.

In Scheme 4, the definition of R is R$^6$ as described for the embodiments of the disclosure. The other variables in Scheme 4 are as described for the embodiments of the disclosure.

Benzyl amine i can be condensed with methyl 2,2-diethoxyacetimidate to give the 2-aminoquinoline intermediate ii. Intermediate ii can be subjected to Stille coupling with tributyl(1-ethoxyvinyl)stannane to yield iii. Under acidic conditions, iii can be converted to the methyl ketone iv. The 2-aminoquinoline iv can be diazotized to the 2-Chloroquinoline v using sodium nitrite and cuprous chloride. Subsequent addition of alkyl magnesium bromide can yield intermediate vi. Compound vi can be coupled to aryl amines under Pd-catalyzed coupling conditions to yield vii. Intermediate vii can be treated with TMSN$_3$ and Indium bromide in dichloromethane to yield the corresponding azide intermediate viii. The azide viii can be reduced under typical hydrogenation conditions such as Pd and H$_2$ to give the amine ix which are examples of MAP4K1 inhibitors described herein.

Scheme 5

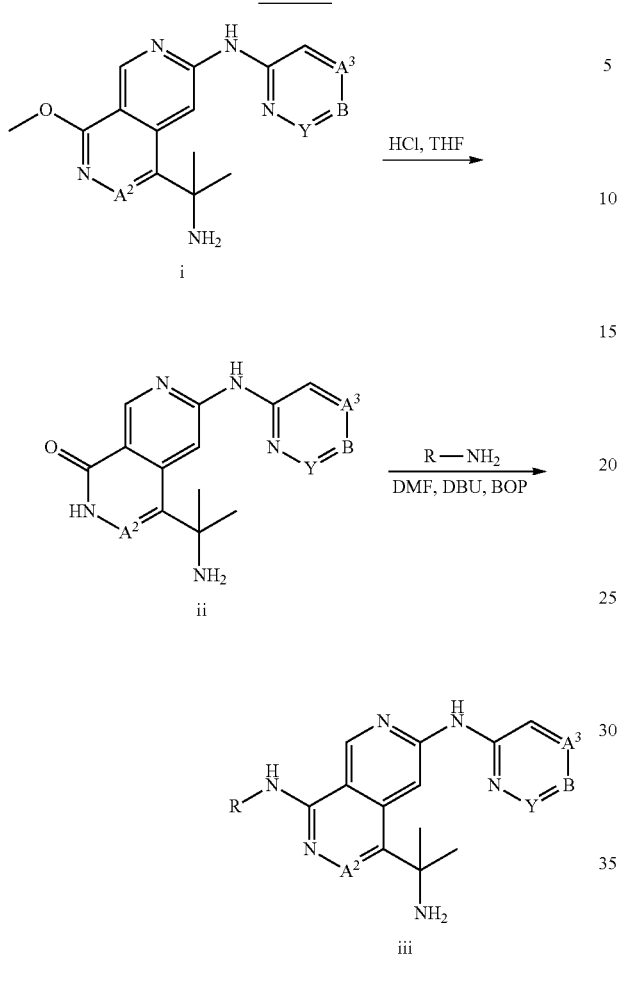

Scheme 5 shows a synthetic protocol for the preparation of compounds of formula iii.

In Scheme 5, the definition of R is $R^7$ as described for the embodiments of the disclosure. The other variables in Scheme 5 are as described for the embodiments of the disclosure.

Intermediate i (see Scheme 3 for preparation of intermediate i) can be converted to the pyridone ii under acidic conditions. Compound ii can be coupled to alkyl amines using a coupling agent such as BOP and DBU in DMF to give the compound iii which are examples of MAP4K1 inhibitors described herein.

Scheme 6

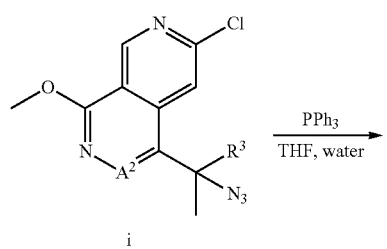

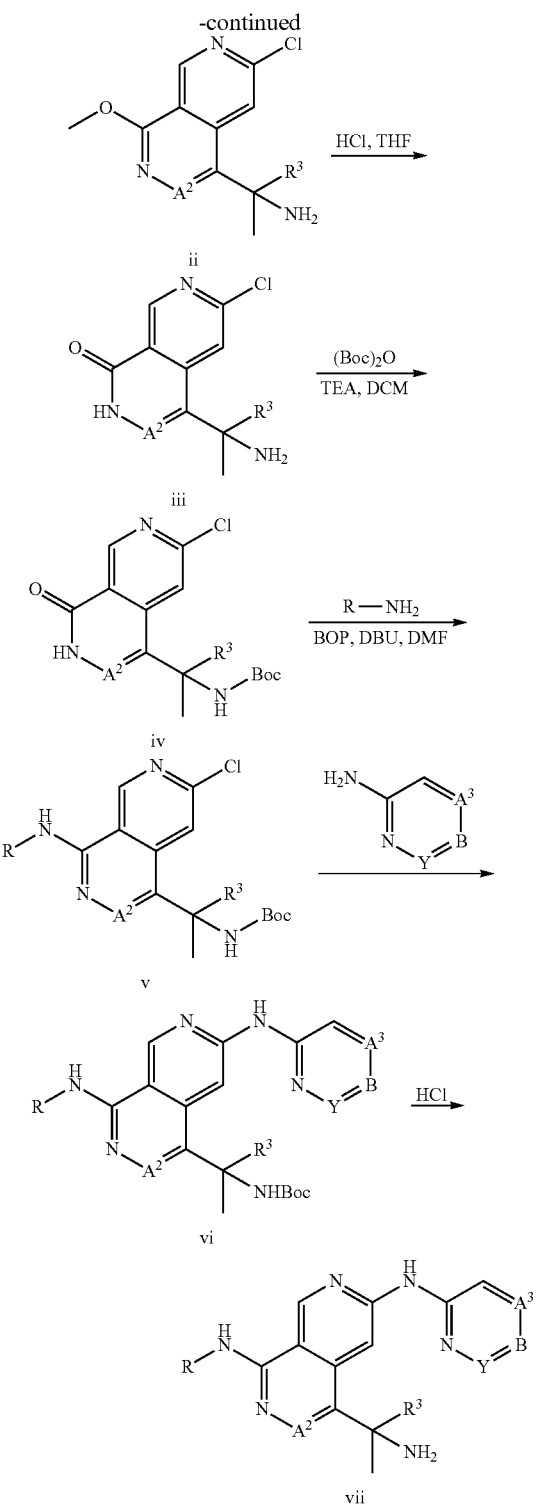

Scheme 6 shows a synthetic protocol for the preparation of compounds of formula vii.

In Scheme 6, the definition of R is $R^7$ as described for the embodiments of the disclosure. The other variables in Scheme 6 are as described for the embodiments of the disclosure.

The intermediate i (see Scheme 3 for preparation of i) can be reduced under Staudinger reaction conditions using triphenylphosphine and water to give amine ii. Conversion to the pyridone iii can be performed under acidic conditions. Subsequent protection of the benzylic amine can be done with Boc-anhydride and TEA to give intermediate iv. Compound iv can be coupled to alkyl amines using the coupling agent BOP in DMF to give v. The compound v can be coupled to the aryl amines under Pd-catalyzed coupling conditions to give vi. The Boc group can be de-protected using HCl or other acidic conditions to give the amine vii which are examples of MAP4K1 inhibitors described herein.

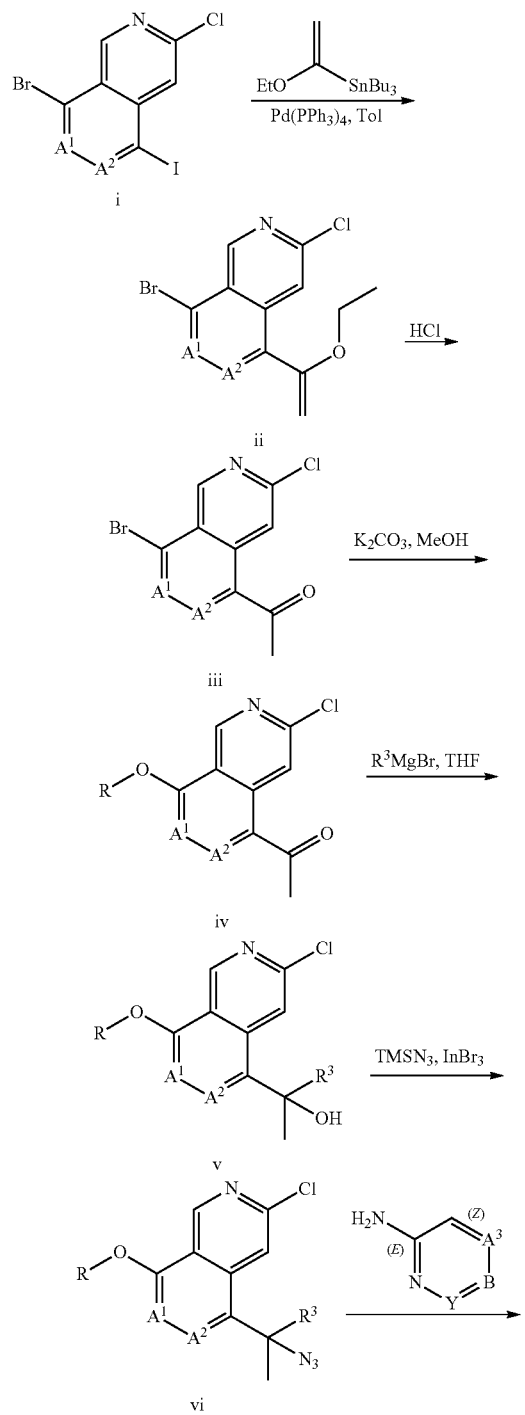

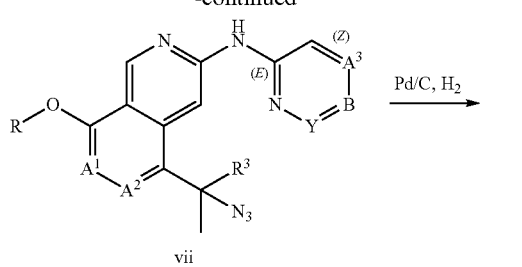

Scheme 7 shows a synthetic protocol for the preparation of compounds of formula viii.

Tri-halogen intermediate i (see Intermediate 32 in common intermediates for synthesis of intermediate i) can be subjected to Stille coupling with tributyl(1-ethoxyvinyl)stannane to yield ii. Under acidic conditions, ii can be converted to the methyl ketone iii. Compound iii can be treated with an alcohol using potassium carbonate in methanol to yield intermediate iv. Subsequent addition of alkyl magnesium bromide can yield intermediate v. Compound v can be treated with TMSN$_3$ and Indium bromide in dichloromethane to yield the corresponding azide intermediate vi. The azide vi can be coupled to aryl amines under Pd-catalyzed coupling conditions to yield vii. Compound vii can be reduced under typical hydrogenation conditions such as Pd and H$_2$ to give the amine viii which are examples of MAP4K1 inhibitors described herein.

193

Scheme 8

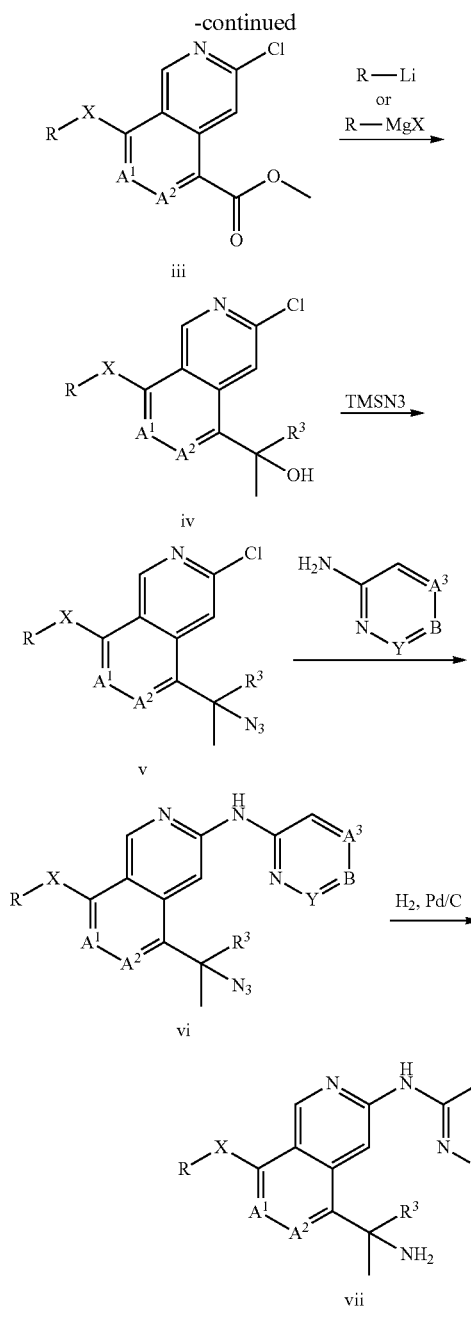

Scheme 8 shows a synthetic protocol for the preparation of compounds of formula vii.

Tri-halogen intermediate i (see Intermediate 31 in common intermediates for synthesis of intermediate i) can be treated with an alcohol or an amine to yield intermediate ii. Intermediate ii can be subjected to Pd-catalyzed carbonylation to yield iii. Subsequent addition of alkyl lithium or alkyl magnesium bromide can yield intermediate iv. Compound iv can be treated with TMSN₃ and Indium bromide in dichloromethane to yield the corresponding azide intermediate v. The azide v can be coupled to aryl amines under Pd-catalyzed coupling conditions to yield vi. Compound vi can be reduced under typical hydrogenation conditions such as Pd and H₂ to give the amine vii which are examples of MAP4K1 inhibitors described herein.

194

Scheme 9

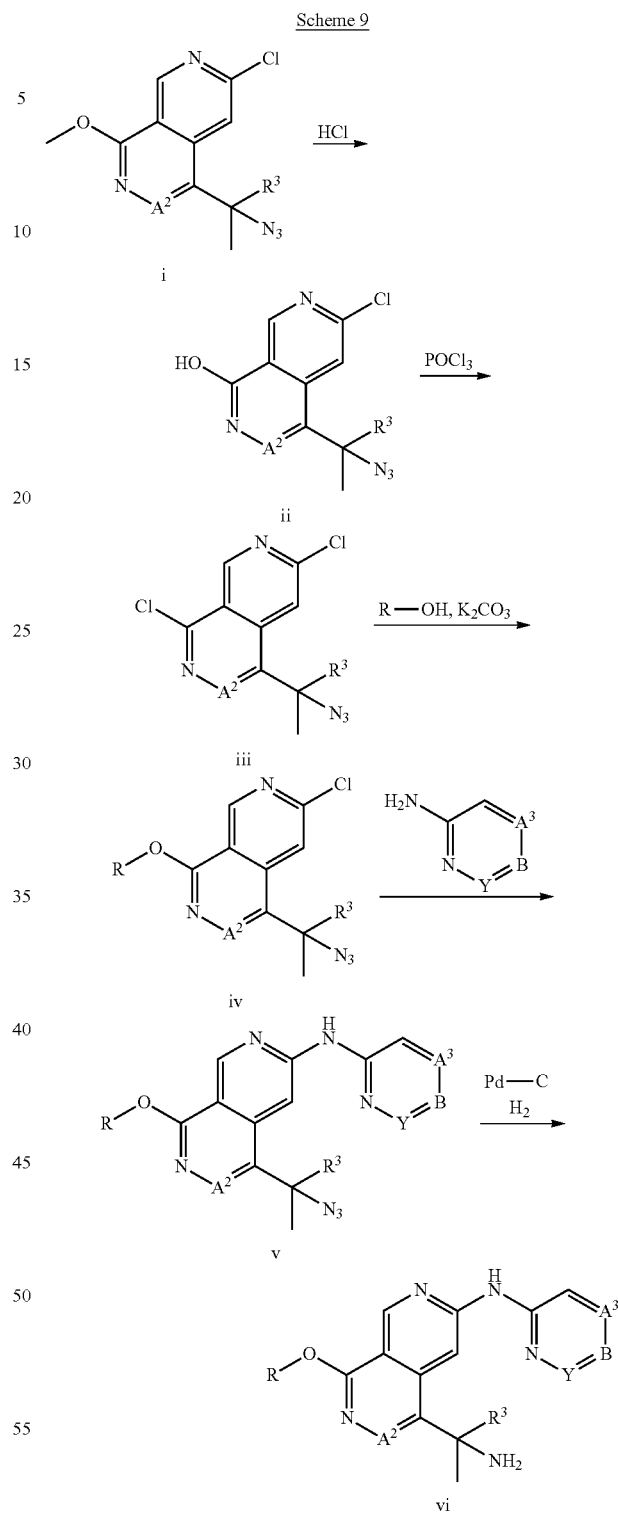

Scheme 9 shows a synthetic protocol for the preparation of compounds of formula vi.

The intermediate i (see scheme 3 for preparation of i) can be to the pyridone ii under acidic conditions. Intermediate ii can be treated with POCl3 to get compound iii which is subsequently reacted with alcohols e.g., oxetan-3-ol, cyclobutanol, methyloxetan-3-ol using potassium carbonate to get the 8-alkoxy intermediate iv. Compound iv can be coupled to the aryl amines under Pd-catalyzed coupling conditions to give v. Compound v can be reduced under typical hydrogenation conditions such as Pd and $H_2$ to give the amine vi which are examples of MAP4K1 inhibitors described herein.

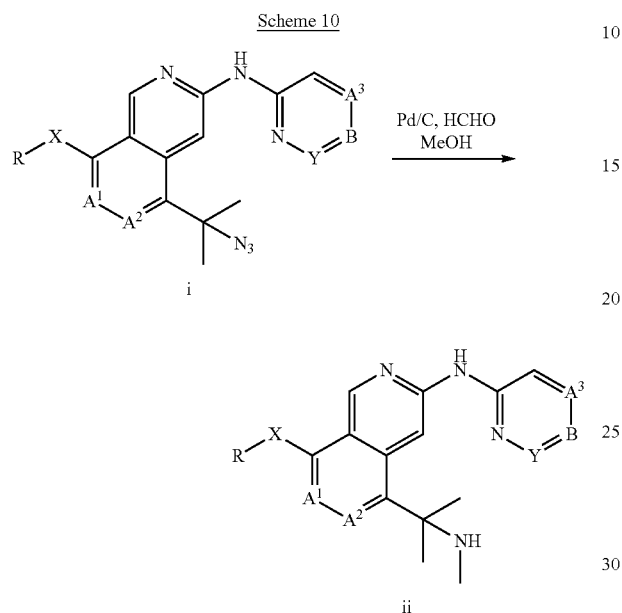

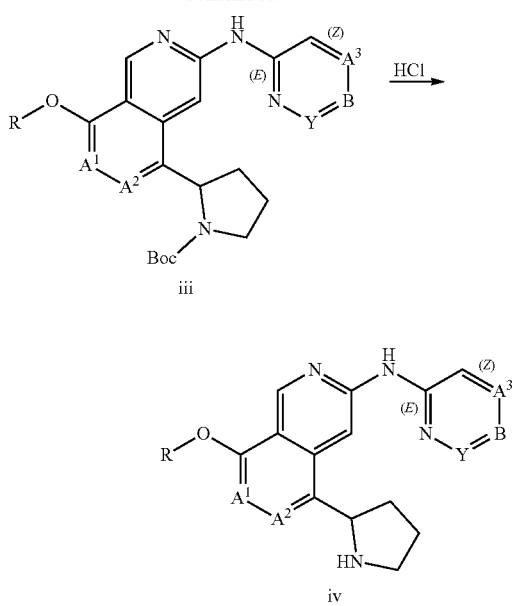

Scheme 10 shows a synthetic protocol for the preparation of compounds of formula ii.

Intermediate i (see scheme 3 for preparation of intermediate i) can be converted to the methyl amine ii under one-pot reduction with Pd/C and H2 followed by reductive amination with formaldehyde in MeOH.

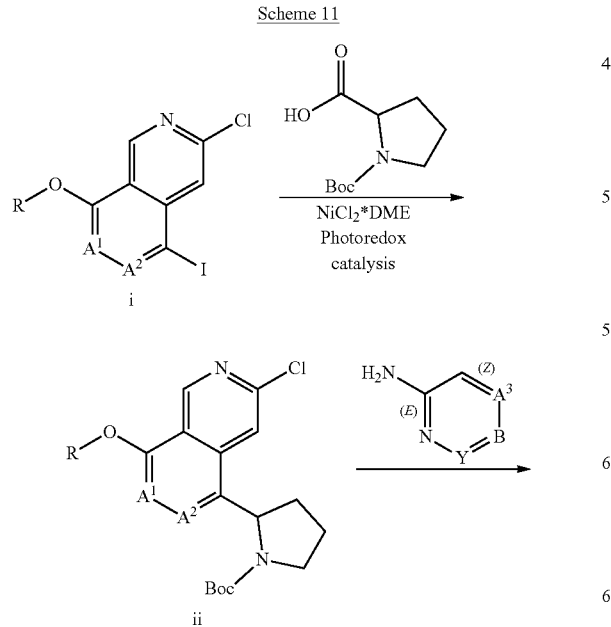

Scheme 11 shows a synthetic protocol for the preparation of compounds of formula iv.

The intermediate i (see scheme 3 for preparation of i) can be coupled to (tert-butoxycarbonyl)proline using photoredox catalysis to give compound ii. Compound ii can be coupled to the aryl amines under Pd-catalyzed coupling conditions to give iii. Compound iii can be de-protected under typical Boc-deprotection conditions such as HCl to give the amine iv which are examples of MAP4K1 inhibitors described herein.

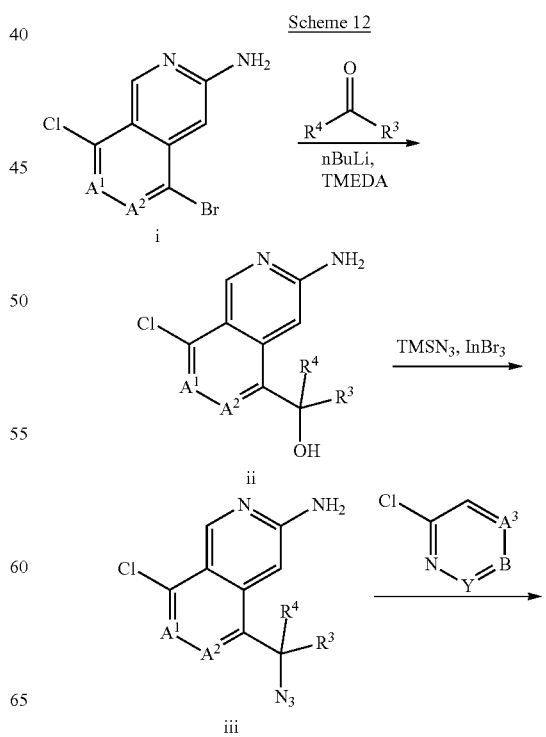

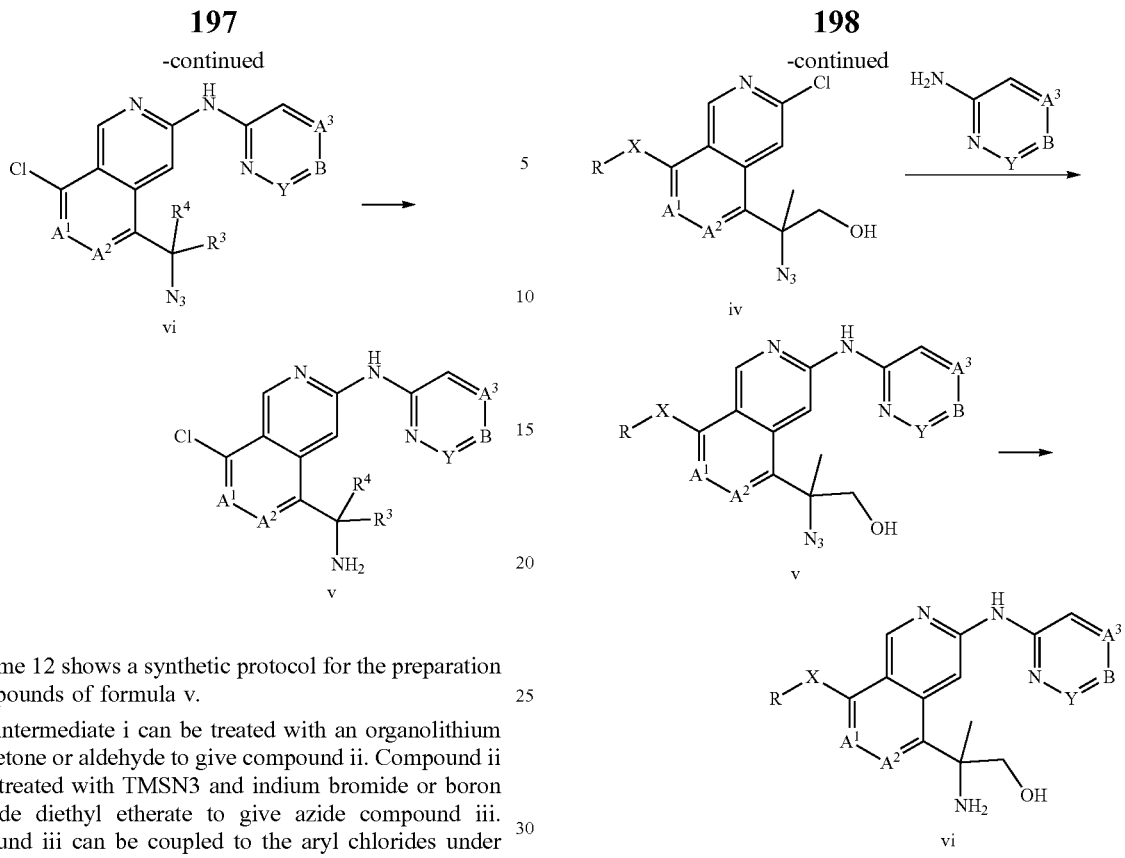

Scheme 12 shows a synthetic protocol for the preparation of compounds of formula v.

The intermediate i can be treated with an organolithium and a ketone or aldehyde to give compound ii. Compound ii can be treated with TMSN3 and indium bromide or boron trifluoride diethyl etherate to give azide compound iii. Compound iii can be coupled to the aryl chlorides under Pd-catalyzed coupling conditions to give iv. Compound iv can be reduced with Zn and acetic acid to give the amine v which are examples of MAP4K1 inhibitors described herein.

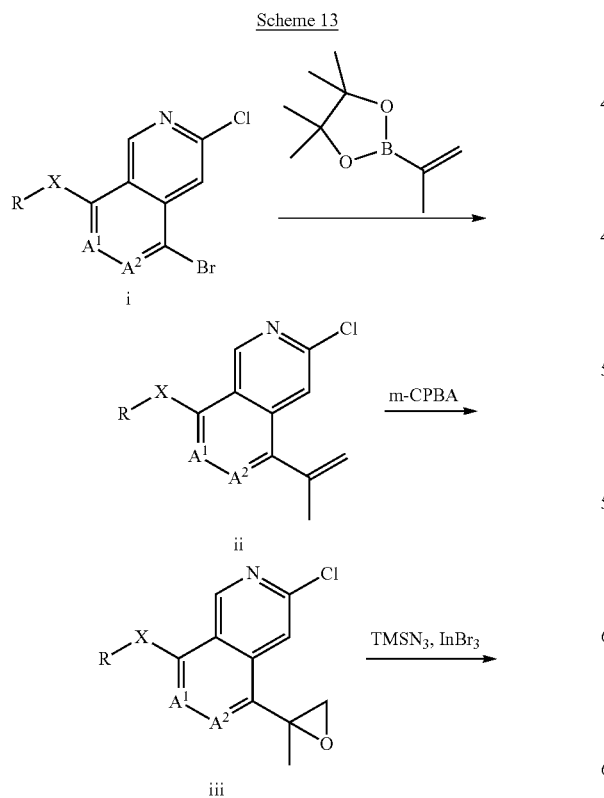

Scheme 13 shows a synthetic protocol for the preparation of compounds of formula vi.

The intermediate i can be coupled to a boronate under Pd catalysis to give compound ii. Compound ii can be treated with an oxidizing reagent such as m-CPBA to give the epoxide compound iii. Compound iii can be treated with TMSN3 and indium bromide or boron trifluoride diethyl etherate to give azide compound iv. Compound iv can be coupled to the aryl amines under Pd-catalyzed coupling conditions to give v. Compound v can be reduced with hydrogen under Pd-catalyzed conditions to give the amine vi which are examples of MAP4K1 inhibitors described herein.

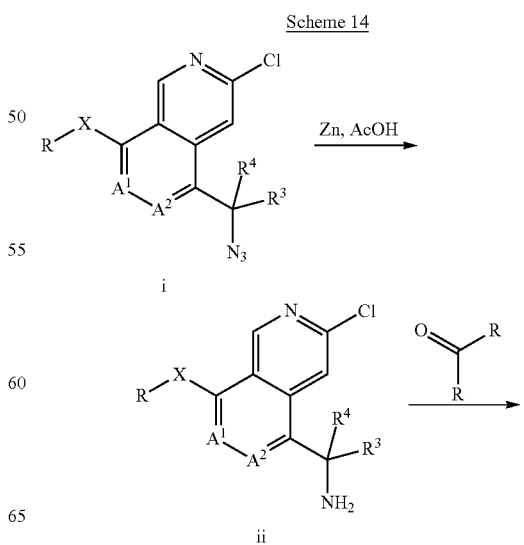

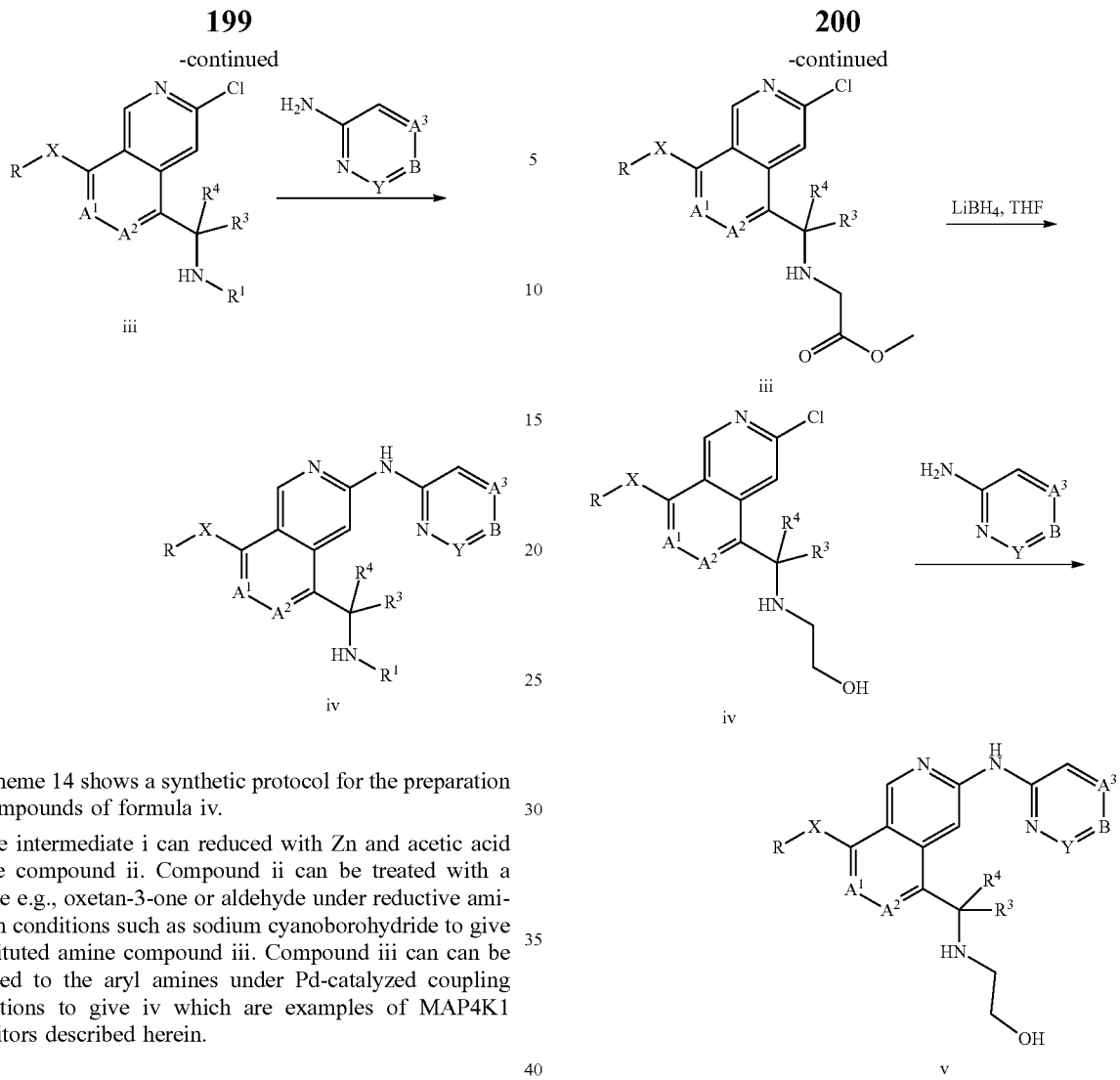

Scheme 14 shows a synthetic protocol for the preparation of compounds of formula iv.

The intermediate i can reduced with Zn and acetic acid amine compound ii. Compound ii can be treated with a ketone e.g., oxetan-3-one or aldehyde under reductive amination conditions such as sodium cyanoborohydride to give substituted amine compound iii. Compound iii can can be coupled to the aryl amines under Pd-catalyzed coupling conditions to give iv which are examples of MAP4K1 inhibitors described herein.

Scheme 15

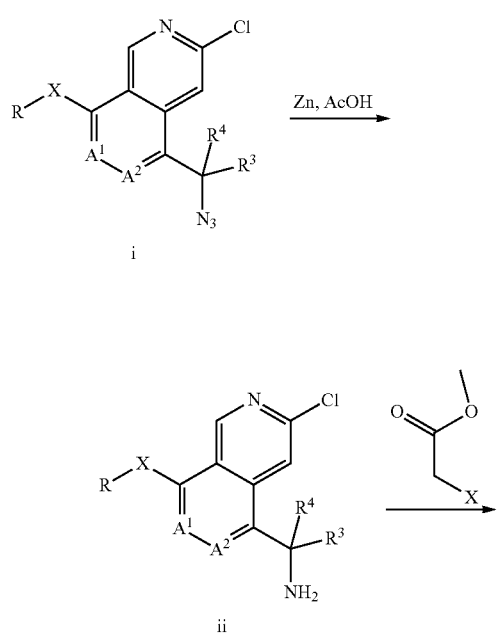

Scheme 15 shows a synthetic protocol for the preparation of compounds of formula v.

The intermediate i can reduced with Zn and acetic acid amine compound ii. Compound ii can be treated with a haloacetate compound such as methyl bromoacetate substituted amine compound iii. Compound iii can be reduced with LiBH₄ to give amino alcohol compound iv. Compound iv can can be coupled to the aryl amines under Pd-catalyzed coupling conditions to give v which are examples of MAP4K1 inhibitors described herein.

Scheme 16

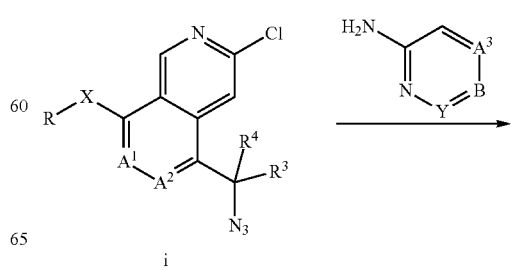

-continued

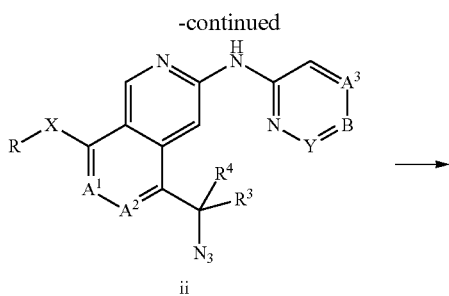
ii

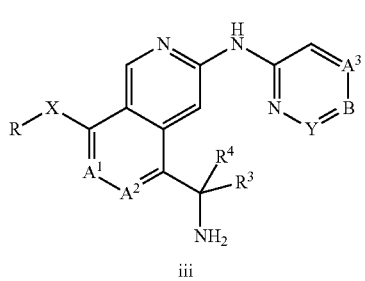
iii

Scheme 16 shows a synthetic protocol for the preparation of compounds of formula iii.

The intermediate i can be coupled to the aryl amines under Pd-catalyzed coupling conditions to give ii. Compound ii can be reduced with hydrogen under Pd-catalyzed conditions to give the amine iii which are examples of MAP4K1 inhibitors described herein.

Scheme 17

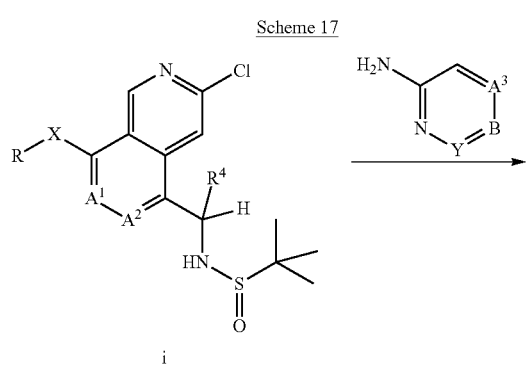
i

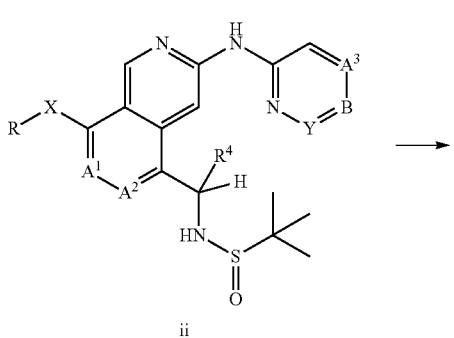
ii

-continued iii

Scheme 17 shows a synthetic protocol for the preparation of compounds of formula vi.

The intermediate i can be coupled to the aryl amines under Pd-catalyzed coupling conditions to give ii. Compound ii can be deprotected under acidic conditions such as HCl to give the amine iii which are examples of MAP4K1 inhibitors described herein.

The following examples are intended to be illustrative and are not meant in any way to be limiting.

EXEMPLIFICATION

Abbreviations

BOP (1H-Benzotriazol-1-yloxy)[tris(dimethylamino)]phosphonium hexafluorophosphate
C Celsius
DAST Diethylaminosulfur trifluoride
DBU 1,8-Diazabicyclo[5.4.0]undec-7-ene
DCE dichloroethane
DCM dichloromethane
DEA diethyl amine
DIPEA diisopropylamine
DMF dimethyl formamide
DMAP 4-Dimethylaminopyridine
DMB 3,3-Dimethyl-1-butanol
DMSO dimethylsulfoxide
EA ethyl acetate
EtOH ethanol
h hour(s)
HPLC high performance liquid chromatography
IC50 inhibitory concentration 50%
IPA isopropyl alcohol
min minutes
MTBE methyl tert-butyl ether
MCCN acetonitrile
MeOH methanol
NMP N-Methyl-2-pyrrolidone
PE petroleum ether
rt room temperature
TEA triethylamine
THF tetrahydrofuran
TFA trifluoroacetic acid LC-MS: Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in MCCN. A constant gradient from 95% aqueous/5% organic to 5% aqueous/95% organic mobile phase over the course of 4 minutes was utilized. The flow rate was constant at 1 mL/min.

Prep LC-MS: Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in MCCN. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Silica gel chromatography: Silica gel chromatography was performed on either a Teledyne Isco CombiFlash® Rf unit or a Biotage® Isolera Four unit.

Proton NMR: Unless otherwise indicated, all $^1$H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d6 solvent as parts-per-million (ppm) with respect to residual DMSO (2.50 ppm).

One of ordinary skill in the art will recognize that modifications of the gradient, column length, and flow rate are possible and that some conditions may be more suitable for compound characterization than others, depending on the chemical species being analyzed.

Synthesis of Intermediates

I. Synthesis of arylamine intermediates

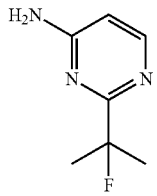

Intermediate 1:
2-(2-Fluoropropan-2-yl)pyrimidin-4-amine

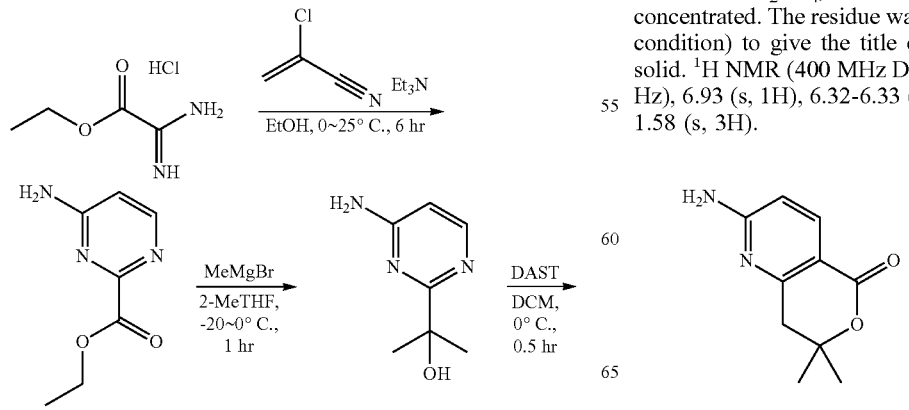

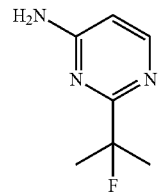

Step 1: Ethyl 4-aminopyrimidine-2-carboxylate

Triethylamine (285 g, 2.81 mol, 2.00 equiv) was added dropwise to a a solution of ethyl 2-amino-2-iminoacetate hydrochloride (215 g, 1.41 mol, 1.00 equiv) and 2-chloro-prop-2-enenitrile (112 mL, 1.41 mol, 1.00 eq) in EtOH (1.8 L) at 0° C. The mixture was allowed to warm to 25° C. and stirred at 25° C. for 6 h. The reaction mixture was concentrated and the residue was partitioned between water (10.0 L) and EA (5.0 L). The layers were separated, and the aqueous layer was extracted with EA (5.0 L×2). The organic layers were combined and dried over Na$_2$SO$_4$. The dried solution was filtered, and the filtrate was concentrated to give the title compound (270 g, crude) as a dark brown solid.

Step 2: 2-(4-Aminopyrimidin-2-yl)propan-2-ol

Methylmagnesium bromide (900 mL, 3.0 M, 5.0 eq) was added to a solution of ethyl 4-aminopyrimidine-2-carboxylate (90.0 g, 538 mmol, 1.00 eq) in 2-Me THE (1.00 L) at −20° C. The reaction mixture was allowed warm to 0° C. and stirred at that temperature for 1 h. The reaction mixture was diluted with saturated aqeuous ammonium chloride solution (10.0 L) and the aqueous layer was extracted with EA (3.0 L×4). The organic layers were combined and dried over Na$_2$SO$_4$, and the dried solution was filtered. The filtrate was concentrated to give the title compound (50 g, crude) as a dark brown solid.

Step 3: 2-(2-Fluoropropan-2-yl)pyrimidin-4-amine

DAST (414 mL, 3.13 mol, 10.0 eq) was added to a solution of 2-(4-aminopyrimidin-2-yl)propan-2-ol (48.0 g, 313 mmol, 1.00 eq) in DCM (1.30 L) at 0° C. The reaction mixture was stirred at 0° C. for 0.5 h, and then was diluted with water (4.50 L). The reaction mixture was adjusted to pH=7-8 with aqueous sodium hydroxide solution (0.50 L) and sodium carbonate solution (200 mL), then was extracted with EA (2.00 L×3). The organic layers were combined and dried over Na$_2$SO$_4$, and the dried solution was filtered and concentrated. The residue was purified by rp-HPLC (neutral condition) to give the title compound (13.0 g) as a white solid. $^1$H NMR (400 MHz DMSO-d6) δ 8.05-8.07 (d, J=5.6 Hz), 6.93 (s, 1H), 6.32-6.33 (d, J=5.6 Hz, 1H), 1.63 (s, 3H), 1.58 (s, 3H).

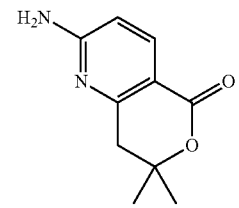

Intermediate 2: 2-Amino-7,7-dimethyl-7,8-dihydro-5H-pyrano[4,3-b]pyridin-5-one

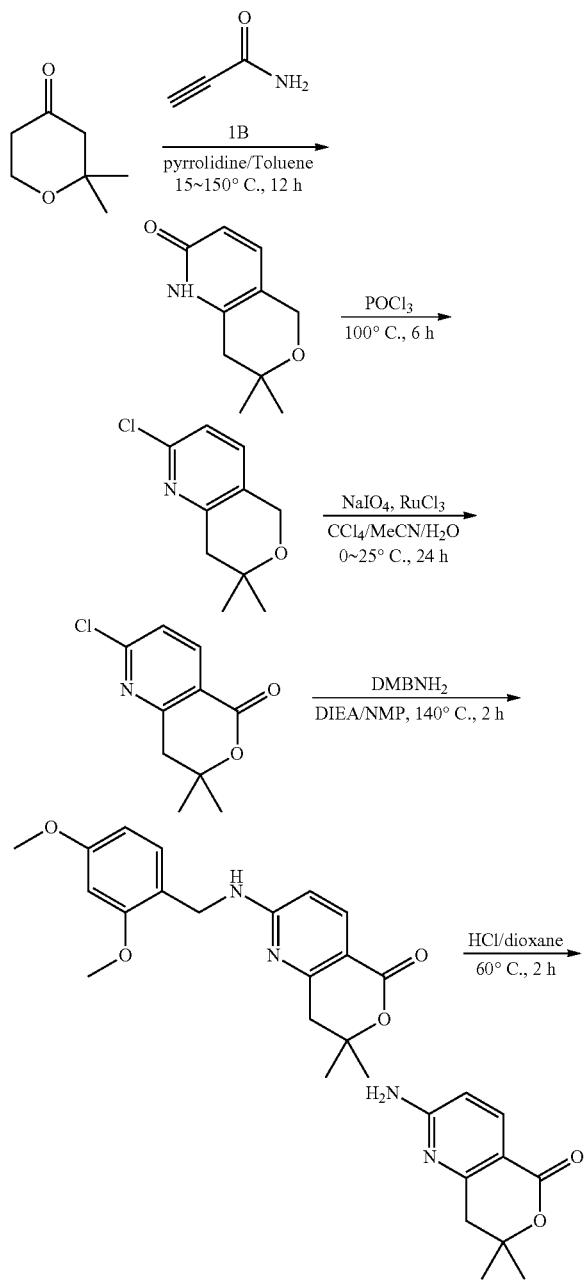

Step 1: 7,7-Dimethyl-1,5,7,8-tetrahydro-2H-pyrano[4,3-b]pyridin-2-one

A mixture of 2,2-dimethyltetrahydro-4H-pyran-4-one (500 g, 3.90 mol, 1.00 eq) and pyrrolidine (391 mL, 4.68 mol, 1.20 eq) in toluene (4.00 L) was heated at 145° C. with a Dean-Stark trap for 2 h. The water layer (~16 mL) was removed from the Dean-Stark trap and the reaction mixture was cooled to 15° C. After cooling, prop-2-ynamide (539 g, 7.80 mol, 2.00 eq) was added and the reaction mixture was heated to 150° C. The reaction mixture was heated at 150° C. for 10 h, then was cooled to ambient temperature. The cooled reaction mixture was filtered and the filtrate was concentrated under reduced pressure to give a residue. The residue was purified by flash-column chromatography on silica gel (10% methanol-dichloromethane) to give the title compound (560 g, 62% yield) as a yellow solid.

Step 2: 2-Chloro-7,7-dimethyl-7,8-dihydro-5H-pyrano[4,3-b]pyridine

A solution of 7,7-dimethyl-1,5,7,8-tetrahydro-2H-pyrano[4,3-b]pyridin-2-one (500 g, 2.23 mol, 1 eq) in POCl$_3$ (350 mL, 3.77 mol, 9.64 eq) was heated to 100° C. for 6 h. The reaction mixture then cooled to ambient temperature and concentrated under vacuum. The residue was poured over ice-water (1.00 L). The mixture was extracted with EA (750 mL×2). The combined organic layers were dried over Na$_2$SO$_4$, filtered and concentrated under vacuum to give the title compound (363 g, 82.2% yield) as a brown oil.

Step 3: 2-Chloro-7,7-dimethyl-7,8-dihydro-5H-pyrano[4,3-b]pyridin-5-one

A solution of NaIO$_4$ (487 g, 2.28 mol, 3.00 eq) in water (1.20 L) as added to a mixture of 2-chloro-7,7-dimethyl-7,8-dihydro-5H-pyrano[4,3-b]pyridine (150 g, 759 mmol, 1.00 eq) in MeCN (50.0 mL) and CCl$_4$ (2.70 L). The mixture was cooled to 0° C., and then RuCl$_3$ (11.0 g, 53.1 mmol, 0.07 eq) was added. The reaction mixture was stirred at 0° C. for 0.5 h, then was warmed to 20° C. for 11.5 h. Saturated aqeuous sodium sulfite solution (1.00 L) was added, and the mixture was filtered. The filtrate was extracted with EA (500 mL×3), and the organic layers were combined. The combined organic layer was washed with brine (1.00 L), dried over Na$_2$SO$_4$, filtered and concentrated to give the title compound (132 g, 624 mmol, 82.1% yield) as a yellow solid.

Step 4: 2-((2,4-Dimethoxybenzyl)amino)-7,7-dimethyl-7,8-dihydro-5H-pyrano[4,3-b]pyridin-5-one (2,4-Dimethoxyphenyl) methanamine (160 g, 957 mmol, 1.50 eq) was added to a solution of 2-chloro-7,7-dimethyl-7,8-dihydro-5H-pyrano[4,3-b]pyridin-5-one (135 g, 638 mmol, 1.00 eq) and DIPEA (222 mL, 1.28 mol, 2.00 eq) in NMP (1.08 L) at ambient temperature. The reaction mixture was heated to 140° C. for 2 h, and then was cooled to ambient temperature. The reaction mixture was partitioned between water (700 mL) and EA. The layers were separated, and the aqueous layer was further extracted with EA (500 mL×3). The organic layers were combined and washed with brine (400 mL×3), dried over anhydrous sodium sulfate, filtered and concentrated to afford the title compound as a yellow solid (160 g). The crude product was used for next step directly.

Step 5: 2-Amino-7,7-dimethyl-7,8-dihydro-5H-pyrano[4,3-b]pyridin-5-one

HCl (4.0 M in dioxane, 1.20 L, 11.0 equiv) was added to: 2-((2,4-dimethoxybenzyl)amino)-7,7-dimethyl-7,8-dihydro-5H-pyrano[4,3-b]pyridin-5-one (150 g, 438 mmol, 1.00 eq) at 20° C. The reaction mixture was heated to 60° C. for 2 h, then was cooled to ambient temperature and concentrated under vacuum. The residue was poured into saturated NaHCO$_3$ aqueous solution (1.00 L) and extracted with EA (500 mL×4). The combined organic layer was washed with brine (500×2), dried over Na$_2$SO$_4$, filtered and concentrated. The residue was dissolved in EA (300 mL) and petroleum ether (150 mL) was added drop wise to get yellow slurry. The solids were filtered and collected to give the title compound (52.0 g, 60.9% yield) as a yellow solid. MS (ES+) $C_{10}H_{12}N_2O_2$ requires: 192, found: 193[M+H]+. 1H NMR (400 MHz, DMSO-d6) δ 7.76 (d, J=8.4 Hz, 1H), 6.98 (s, 2H), 6.39 (d, J=8.8 Hz, 1H), 2.89 (s, 2H), 1.37 (s, 6H).

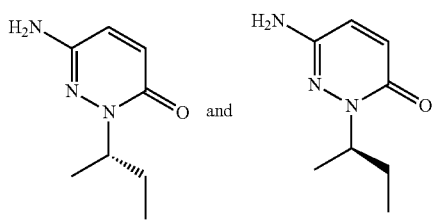

Intermediates 3 and 4: (S)-6-Amino-2-(sec-butyl)pyridazin-3(2H)-one and (R)-6-Amino-2-(sec-butyl)pyridazin-3(2H)-one

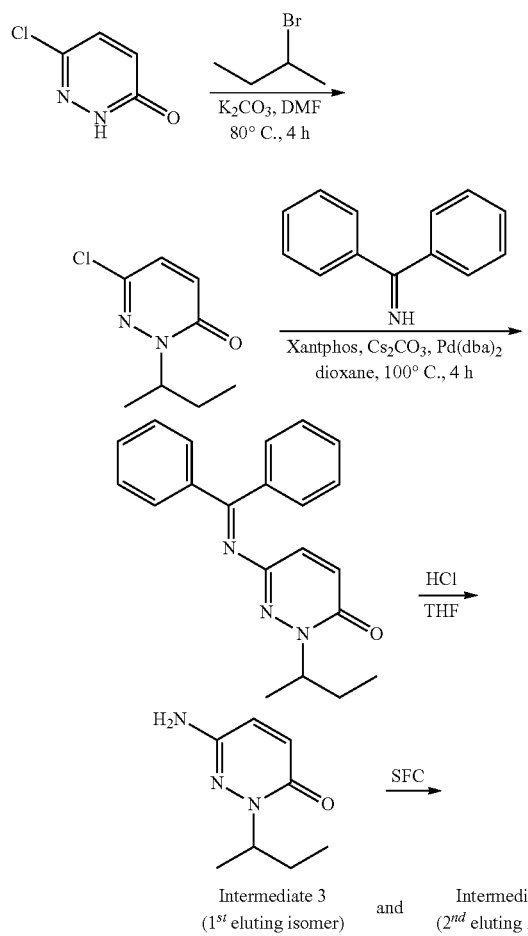

each of which is represented by one of the structures shown below:

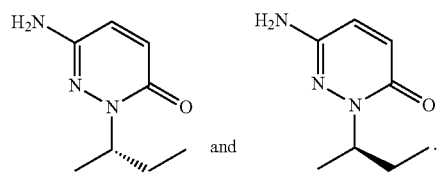

Step 1: 2-(sec-Butyl)-6-chloropyridazin-3(2H)-one

Potassium carbonate (15.6 g, 113 mmol, 3.05 equiv) was added to a solution of 6-chloropyridazin-3(2H)-one (5.00 g, 38.3 mmol, 1.00 equiv) and 2-bromobutane (5.17 g, 37.7 mmol, 0.98 equiv) in DMF (80 mL). The mixture was stirred at 80° C. for 4 h, then was cooled to ambient temperature. The cooled reaction mixture was partitioned between water and dichloromethane, and the layers were separated. The aqueous layer was further extracted with dichlormethane (200 mL×2), and the layers were combined. The combined organic layers were washed with brine and dried over anhydrous sodium sulfate. The dried solution was filtered, and the filtrate was concentrated under reduced pressure to give the title compound (5.90 g, crude) as a yellow oil that was used for next step directly.

Step 2: 2-(sec-Butyl)-6-((diphenylmethylene)amino)pyridazin-3(2H)-one

XantPhos (3.53 g, 6.11 mmol, 0.200 equiv), Pd(dba)$_2$ (1.76 g, 3.05 mmol, 0.100 equiv) and cesium carbonate (24.9 g, 76.4 mmol, 2.50 equiv) were added to a solution of 2-(sec-Butyl)-6-chloropyridazin-3(2H)-one (5.70 g, 30.5 mmol, 1.00 equiv) and diphenylmethanimine (6.09 g, 33.6 mmol, 1.10 equiv) in dioxane (80 mL). The mixture was degassed and purged with N$_2$ three times, and then heated to 100° C. for 4 h. The reaction mixture was cooled to ambient temperature, diluted with water and extracted with EA three times. The combined organic layers were dried over anhydrous sodium sulfate, filtered and concentrated under reduced pressure to give a residue. The residue was purified by flash-column chromatography on silica gel (gradient elution, 0% to 67% EA-petroleum ether) to give the title compound (1.80 g, 18% yield) as a yellow oil.

Step 3: 6-Amino-2-(sec-butyl)pyridazin-3(2H)-one

HCl (aqueous, 6 M, 2.01 mL) was added to a solution of 2-(sec-butyl)-6-((diphenylmethylene)amino)pyridazin-3(2H)-one (0.80 g, 2.4 mmol) in tetrahydrofuran (100 mL) at 25° C. The reaction mixture was stirred at 25° C. for 0.5 h. The reaction mixture was diluted with water (100 mL) and extracted with EA (50 mL×3). The combined organic layers were dried over anhydrous sodium sulfate, filtered and concentrated under reduced pressure to give a residue. The residue was purified by flash-column chromatography on silica gel (gradient elution, 0% to 100% EA-petroleum ether) to give the title compound (190 mg, 47% yield) as a white solid. MS (ES+) $C_8H_{13}N_3O$ requires: 167, found: 168[M+H]+.

Step 4: (S)-6-Amino-2-(sec-butyl)pyridazin-3(2H)-one and (R)-6-Amino-2-(sec-butyl)pyridazin-3(2H)-one 6-Amino-2-(sec-butyl)pyridazin-3(2H)-one (190 mg, 1.14 mmol) was separated by SFC (column: DAICEL CHI- RALPAK IC (250 mm×30 mm, 5 um); mobile phase: [0.5% DEA in MeOH/CO$_2$]; Gradient: 5%-20%. One of (R or S)-6-Amino-2-(sec-butyl)pyridazin-3(2H)-one (1$^{st}$ eluting isomer, Intermediate 3, 60.0 mg, 31%) was obtained as a yellow solid, MS (ES+) C$_8$H$_{13}$N$_3$O requires: 167, found: 168[M+H]$^+$. The remaining one of (R or S)-6-Amino-2-(sec-butyl)pyridazin-3(2H)-one (2$^{nd}$ eluting isomer, Intermediate 4, 70.0 mg, 37% yield) was obtained as a yellow solid, MS (ES+) C$_8$H$_{13}$N$_3$O requires: 167, found: 168[M+H]$^+$.

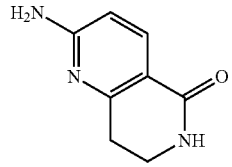

Intermediate 5:
2-Amino-7,8-dihydro-1,6-naphthyridin-5(6H)-one

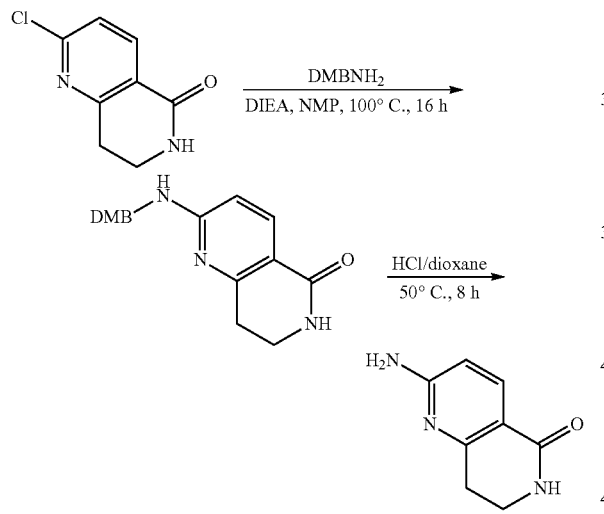

Steps 1 and 2

2-Amino-7,8-dihydro-1,6-naphthyridin-5(6H)-one was prepared from 2-chloro-7,8-dihydro-1,6-naphthyridin-5(6H)-one using the same two-step procedure as described in Steps 4 and 5 in the preparation of Intermediate 2. MS (ES+) C$_8$H$_9$N$_3$O requires: 163, found: 164[M+H]$^+$.

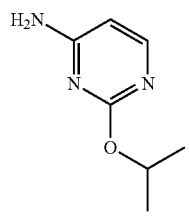

Intermediate 6: 2-Isopropoxypyrimidin-4-amine

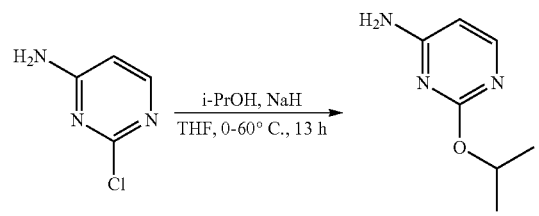

Step 1: 2-Isopropoxypyrimidin-4-amine

Sodium hydride (60% dispersion in oil, 617 mg, 15.4 mmol, 2.00 equiv) was added to a mixture of propan-2-ol (696 mg, 11.6 mmol, 1.50 equiv) in tetrahydrofuran (10 mL) at 0° C. The mixture was stirred at 25° C. for 1 h, 2-chloropyrimidin-4-amine (1.00 g, 7.72 mmol) was added and the mixture was heated to 60° C. After stirring for 12 h, the reaction mixture was cooled to ambient temperature and quenched by addition of water (20 mL). The quenched mixture was extracted with EA (20 mL×3), and the layers were combined. The combined organic layers were dried over anhydrous sodium sulfate, filtered and concentrated under reduced pressure to give a residue. The residue was purified by reverse phase prep-HPLC (column: Xtimate C18 150*25 mm*5 um; mobile phase: [water (0.05% ammonia hydroxide v/v)-MECN]; B %: 0%-30%, 10 min) to give the title compound (140 mg, 12% yield) as a white solid. $^1$H-NMR (400 MHz, DMSO-d6): δ ppm 7.93 (d, J=6.0 Hz, 1H), 7.37 (s, 2H), 6.38 (d, J=6.0 Hz, 1H), 5.08 (td, J=6.4, 12.3 Hz, 1H), 1.22 (d, J=6.0 Hz, 6H).

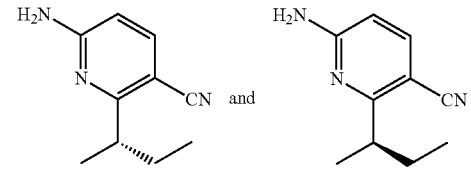

Intermediates 7 and 8: (S)-6-Amino-2-(sec-butyl)nicotinonitrile and (R)-6-Amino-2-(sec-butyl)nicotinonitrile

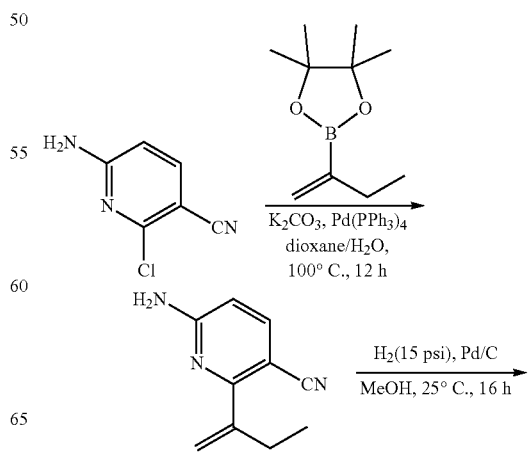

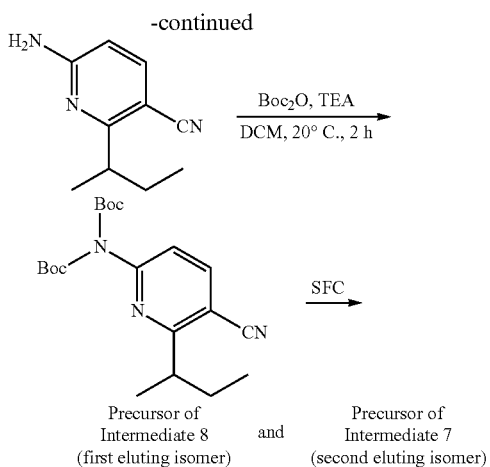

Precursor of Intermediate 8 (first eluting isomer) and Precursor of Intermediate 7 (second eluting isomer)

each of which is represented by one of the structures shown below:

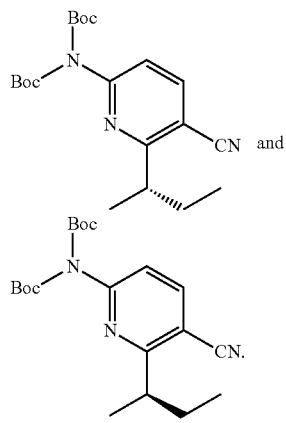

Precursor of Intermediate 8 (first eluting isomer) or Precursor of Intermediate 7 (second eluting isomer)

→ HCl/dioxane, 20° C., 1 h → Intermediate 8 or Intermediate 7 which is represented by one of the structures shown below:

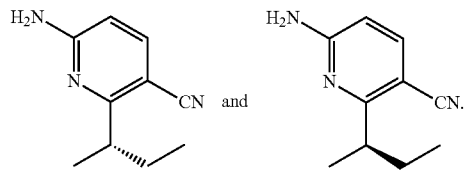

Step 1: 6-Amino-2-(but-1-en-2-yl)nicotinonitrile

Potassium carbonate (3.24 g, 23.4 mmol, 2.00 equiv) and Pd(PPh$_3$)$_4$ (1.35 g, 1.17 mmol, 0.10 eq) were added to a mixture of 6-amino-2-chloronicotinonitrile (1.80 g, 11.7 mmol, 1.00 equiv) and 2-(but-1-en-2-yl)-4,4,5,5-tetramethyl-1,3,2-dioxaborolane (2.30 g, 12.6 mmol, 1.08 equiv) in dioxane (20 mL) and water (4 mL). The mixture was stirred at 100° C. for 12 h under nitrogen. The mixture was then cooled to ambient temperature and partitioned between water (50 mL) and EA (65 mL). The layers were separated, and the aqueous layer was further extracted with EA (65 mL×2). The layers were combined, and the combined layers were dried over anhydrous sodium sulfate, filtered and concentrated to give a residue. The residue was purified by flash-column chromatography on silica gel (gradient elution, 10% to 25% EA-petroleum ether) to give the title compound (1.50 g, 63% yield) as a white solid.

Step 2: 6-Amino-2-(sec-butyl)nicotinonitrile

Palladium on carbon (10 wt %, 300 mg, 0.282 mmol) was added to a mixture of 6-amino-2-(but-1-en-2-yl)nicotinonitrile (1.50 g, 8.66 mmol, 1.00 equiv) in methanol (50 mL). The mixture was stirred at 25° C. for 16 h under hydrogen atmosphere (15 psi), and then was filtered through celite. The filtrate was concentrated under reduced pressure to give a residue. The residue was purified by flash-column chromatography on silica gel (gradient elution, 5% to 10% EA-petroleum ether) to give the title compound (950 mg, 63% yield) as a yellow solid.

Step 3: tert-Butyl N-[6-(butan-2-yl)-5-cyanopyridin-2-yl]-N-[(tert-butoxy)carbonyl]carbamate Di-tert-butyl dicarbonate (2.12 g, 9.70 mmol, 2.00 equiv) and DMAP (59.3 mg, 0.485 mmol, 0.100 equiv) were added to a mixture of 6-amino-2-(sec-butyl)nicotinonitrile (850 mg, 4.85 mmol, 1.00 equiv) and triethylamine (982 mg, 9.70 mmol, 2.00 equiv) in dichloromethane (15 mL). The reaction mixture was stirred at 20° C. for 2 h, and then water (20 mL) was added the resulting mixture was extracted with EA (25 mL×3). The organic layers were combined and dried over anhydrous sodium sulfate. The dried solution was filtered and concentrated to give a residue. The residue was purified by flash-column chromatography on silica gel (gradient elution, 1% to 10% EA-petroleum ether) to give the title compound (1.15 g, 80% yield) as a colorless oil.

Step 4: tert-Butyl N-{6-[(2S)-butan-2-yl]-5-cyanopyridin-2-yl}-N-[(tert-butoxy)carbonyl]carbamate and tert-Butyl N-{6-[(2R)-butan-2-yl]-5-cyanopyridin-2-yl}-N-[(tert-butoxy)carbonyl]carbamate tert-Butyl N-[6-(butan-2-yl)-5-cyanopyridin-2-yl]-N-[(tert-butoxy)carbonyl]carbamate (950 mg, 2.53 mmol) was separated by SFC (column: DAICEL CHIRALPAK IC (250 mm*30 mm, um); mobile phase: [IPA gradient in CO$_2$ with 0.5% DEA]; to give two peaks separately. Absolute stereochemistry of the separated enantiomers was arbitrarily assigned. 1$^{st}$ eluting isomer (340 mg, 34% yield) and second eluting isomer 400 mg, 42% yield) were obtained as colorless oils.

Step 5: one of (R or S)-6-Amino-2-(sec-butyl)nicotinonitrile

HCl (4.0 M in dioxane, 10.0 mL), was added to one of tert-butyl N-{6-[(2R or S)-butan-2-yl]-5-cyanopyridin-2-yl}-N-[(tert-butoxy)carbonyl]carbamate (second eluting isomer, 400 mg, 1.07 mmol) in dioxane (2 mL). The reaction mixture was stirred at 20° C. for 15 h, then was partitioned between saturated aqueous sodium bicarbonate solution (30 mL) and EA (35 mL). The layers were separated, and the aqueous layer was further extracted with EA (35 mL×2). The organic layers were combined and dried over anhydrous sodium sulfate. The dried solution was filtered and concentrated to give a residue. The residue was purified by flash-column chromatography on silica gel (gradient elution, 5% to 25% EA-petroleum ether) to give the title compound ((Intermediate 7, 160 mg, 78% yield) as a yellow oil. MS (ES+) $C_{10}H_{13}N_3$ requires: 175, found: 176[M+H]$^+$. $^1$H-NMR (400 MHz, CDCl$_3$): δ ppm 7.56 (d, J=8.4 Hz, 1H), 6.32 (d, J=8.4 Hz, 1H), 4.87 (s, 2H), 3.17-3.08 (m, 1H), 1.83-1.71 (m, 1H), 1.62-1.54 (m, 1H), 1.24 (d, J=6.4 Hz, 3H), 0.86 (t, J=7.2 Hz, 3H).

Step 6: The remaining one of (R or S)-6-Amino-2-(sec-butyl)nicotinonitrile

The title compound (Intermediate 8) was prepared from the remaining one of tert-butyl N-{6-[(2R or S)-butan-2-yl]-5-cyanopyridin-2-yl}-N-[(tert-butoxy)carbonyl]carbamate (first eluting isomer) using the same procedure as described in Step 5. MS (ES+) $C_{10}H_{13}N_3$ requires: 175, found: 176 [M+H]$^+$. $^1$H-NMR (400 MHz, CDCl$_3$): δ ppm 7.56 (d, J=8.4 Hz, 1H), 6.32 (d, J=8.4 Hz, 1H), 4.87 (s, 2H), 3.17-3.08 (m, 1H), 1.83-1.71 (m, 1H), 1.62-1.54 (m, 1H), 1.24 (d, J=6.4 Hz, 3H), 0.86 (t, J=7.2 Hz, 3H).

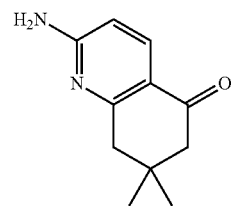

Intermediate 9: 2-Amino-7,7-dimethyl-7,8-dihydroquinolin-5(6H)-one

Steps 1 and 2

2-Amino-7,7-dimethyl-7,8-dihydroquinolin-5(6H)-one was prepared from 2-chloro-7,7-dimethyl-7,8-dihydroquinolin-5(6H)-one using the same two-step procedure as described in Steps 4 and 5 in the preparation of Intermediate 2. MS (ES+) $C_{11}H_{14}N_2O$ requires: 190, found: 191 [M+H]$^+$. $^1$H NMR (400 MHz, DMSO-d6): δ ppm 7.75 (d, J=8.8 Hz, 1H), 6.88 (s, 2H), 6.34 (d, J=8.8 Hz, 1H), 2.66 (s, 2H), 2.33 (s, 2H), 0.99 (s, 6H).

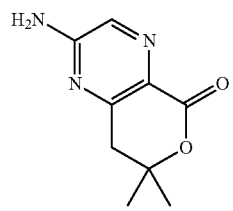

Intermediate 10: 2-Amino-7,7-dimethyl-7,8-dihydro-5H-pyrano[3,4-b]pyrazin-5-one

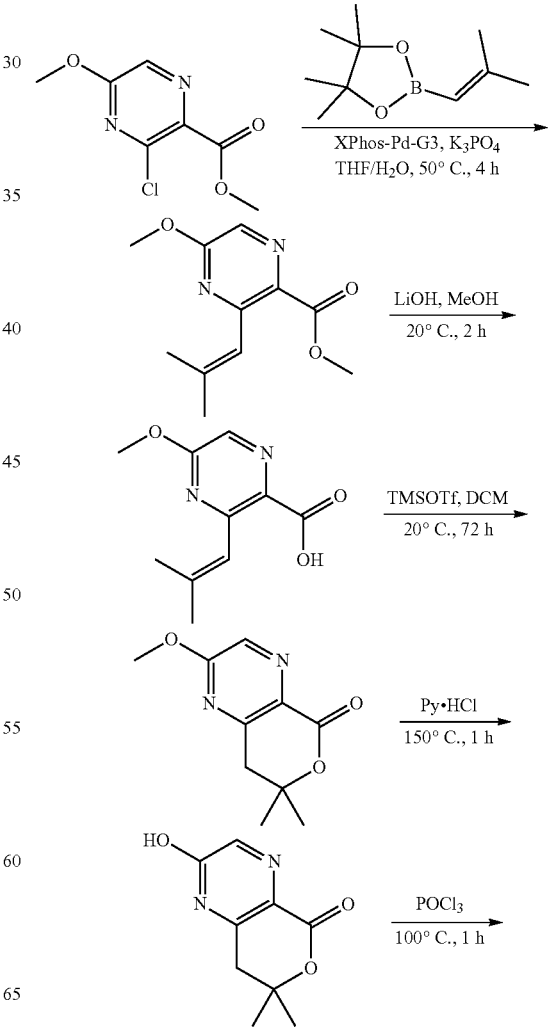

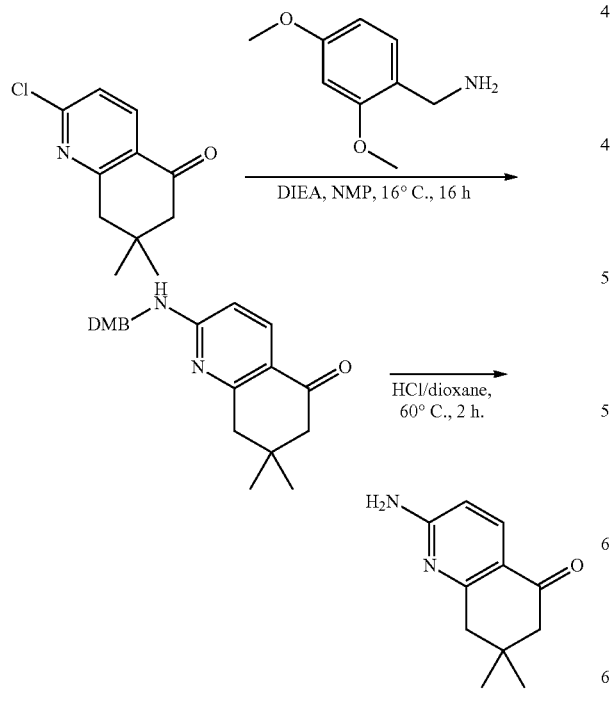

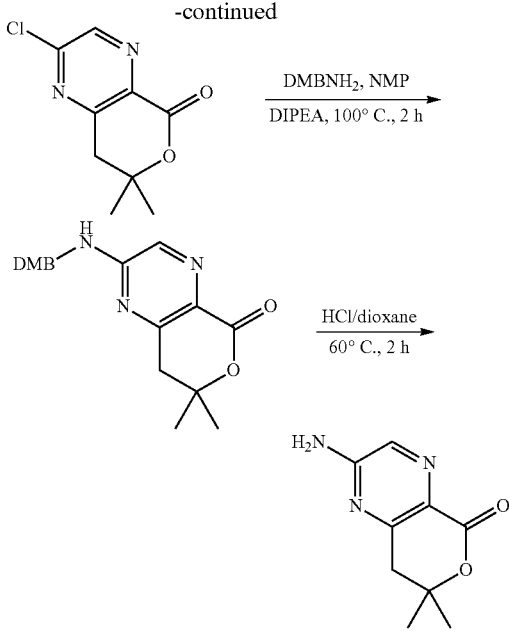

Step 1: Methyl 5-methoxy-3-(2-methylprop-1-en-1-yl)pyrazine-2-carboxylate

Potassium phosphate (7.23 g, 34.1 mmol, 2.99 equiv) and XPhos (G3 precatalyst) (480 mg, 568 μmol, 0.05 equiv) were added to a mixture of methyl 3-chloro-5-methoxypyrazine-2-carboxylate (2.30 g, 11.4 mmol, 1.00 equiv) and 4,4,5,5-tetramethyl-2-(2-methylprop-1-en-1-yl)-1,3,2-dioxaborolane (3.10 g, 17.0 mmol, 1.49 equiv) in tetrahydrofuran (25 mL) and water (3 mL). The reaction mixture was stirred at 50° C. for 4 h under nitrogen. The reaction mixture was then cooled to ambient temperature and concentrated to give a residue. The residue was purified by flash-column chromatography on silica gel (gradient elution, 5% to 50% EA-petroleum ether) to give the title compound (2.00 g, 79% yield) as a white solid.

Step 2: 5-Methoxy-3-(2-methylprop-1-en-1-yl)pyrazine-2-carboxylic acid

LiOH (1.51 g, 63.0 mmol, 5.00 equiv) was added to a mixture of methyl 5-methoxy-3-(2-methylprop-1-en-1-yl)pyrazine-2-carboxylate (2.80 g, 12.6 mmol, 1.00 equiv) in methanol (50 mL). The reaction mixture was stirred at 20° C. for 2 h, and then was diluted with water (100 ml). Aqueous HCl (2 N) was added to the mixture until the pH was 7, and then the mixture was extracted with EA (50 mL×3). The combined organic layers were dried with anhydrous sodium sulfate, filtered and concentrated in vacuo to give the title compound (2.40 g, crude) as a white solid.

Step 3: 2-Methoxy-7,7-dimethyl-7,8-dihydro-5H-pyrano[3,4-b]pyrazin-5-one

Trimethylsilyl trifluoromethanesulfonate (19.1 mL, 106 mmol, 10.0 equiv) was added to a mixture of 5-methoxy-3-(2-methylprop-1-en-1-yl)pyrazine-2-carboxylic acid (2.20 g, 10.6 mmol) in DCM (10 mL). The reaction mixture was stirred at 20° C. for 72 h, then was poured slowly into saturated aqueous sodium bicarbonate solution (80 mL). The mixture was extracted with EA (50 mL×3). The combined organic layers were dried with anhydrous sodium sulfate, filtered and concentrated in vacuo to give a residue. The residue was purified by flash-column chromatography on silica gel (gradient elution, 10% to 30% EA-petroleum ether) to give the title compound (1.00 g, 45% yield) as a yellow solid.

Step 4: 2-Hydroxy-7,7-dimethyl-7,8-dihydro-5H-pyrano[3,4-b]pyrazin-5-one

A mixture of 2-methoxy-7,7-dimethyl-7,8-dihydro-5H-pyrano[3,4-b]pyrazin-5-one (1.00 g, 4.80 mmol, 1.00 equiv) in pyridine hydrochloride (2.78 g, 24.0 mmol, 5.00 equiv) was stirred at 150° C. for 1 h. The reaction mixture was then poured onto water (60 mL) and extracted with EA (50 mL×3). The combined organic layers were dried with anhydrous sodium sulfate, filtered and concentrated in vacuo. The residue was purified by prep-HPLC (column: Xtimate C18 10μ 250 mm*80 mm; mobile phase: [water (0.05% ammonia hydroxide v/v)-MECN]; B %: 0%-7%, 6.5 min) to give the title compound (600 mg, 64% yield) as a white solid.

Step 5: 2-Chloro-7,7-dimethyl-7,8-dihydro-5H-pyrano[3,4-b]pyrazin-5-one

A mixture of 2-hydroxy-7,7-dimethyl-7,8-dihydro-5H-pyrano[3,4-b]pyrazin-5-one (100 mg, 515 μmol) in phosphorus oxychloride (3 mL) was stirred at 100° C. for 1 h. After cooling to ambient temperature, the reaction mixture was poured onto saturated aqueous sodium bicarbonate solution (10 mL), and then extracted with EA (30 mL×3). The combined organic layers were dried with anhydrous sodium sulfate, filtered and concentrated in vacuo. The residue was purified by flash-column chromatography on silica gel (gradient elution, 20% to 50% EA-petroleum ether) to give the title compound (110 mg, crude) as a yellow solid.

Steps 6 and 7: 2-Amino-7,7-dimethyl-7,8-dihydro-5H-pyrano[3,4-b]pyrazin-5-one The title compound was prepared from 2-chloro-7,7-dimethyl-7,8-dihydro-5H-pyrano[3,4-b]pyrazin-5-one using the same two-step procedure as described in Steps 4 and 5 in the preparation of Intermediate 2. $^1$H NMR (400 MHz, CDCl$_3$): δ ppm 7.93 (s, 1H), 7.21 (d, J=8.4 Hz, 1H), 6.48 (d, J=2.0 Hz, 1H), 6.46-6.44 (m, 1H), 6.43 (m, 1H), 4.57 (d, J=5.6 Hz, 2H), 3.82-3.78 (m, 6H), 3.05 (s, 2H), 1.50 (s, 6H).

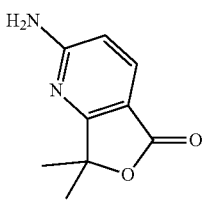

Intermediate 11: 2-Amino-7,7-dimethylfuro[3,4-b]pyridin-5(7H)-one

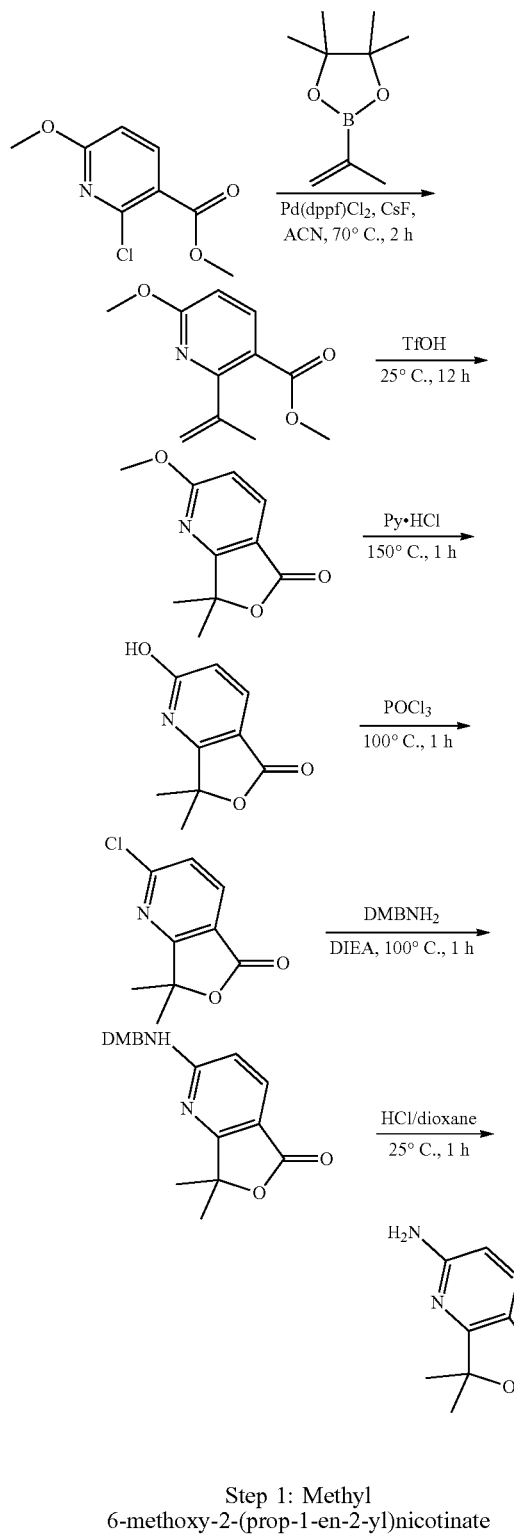

Step 1: Methyl 6-methoxy-2-(prop-1-en-2-yl)nicotinate

Pd(dppf)Cl₂ (544 mg, 744 umol, 0.500 equiv) and cesium fluoride (4.52 g, 29.8 mmol, 2.00 equiv) were added to a mixture of methyl 2-chloro-6-methoxynicotinate (3.00 g, 14.9 mmol) and 4,4,5,5-tetramethyl-2-(prop-1-en-2-yl)-1,3,2-dioxaborolane (3.75 g, 22.3 mmol) in MeCN (50 mL). The mixture was stirred at 70° C. for 2 h under nitrogen atmosphere, then was cooled to ambient temperature. The reaction mixture was then poured onto water (200 mL) and extracted with EA (50 mL×3). The combined organic layers were dried over anhydrous sodium sulfate, filtered and concentrated in vacuo to give a residue. The residue was purified by flash-column chromatography on silica gel (gradient elution, 1% to 2% EA-petroleum ether) to give the title compound (3.0 g, crude) as a colorless oil.

Step 2: 2-Methoxy-7,7-dimethylfuro[3,4-b]pyridin-5(7H)-one

A solution of Methyl 6-methoxy-2-(prop-1-en-2-yl)nicotinate (3.00 g, 14.5 mmol) in TfOH (17.0 g, 113 mmol, 10 mL) was stirred at 25° C. for 12 h. The reaction mixture was then poured over water (50 mL) and saturated aqueous sodium bicarbonate solution was added to adjust the pH to 7. The mixture was extracted with EA (30 mL×3). The combined organic layers were dried over anhydrous sodium sulfate, filtered and concentrated in vacuo to give a residue. The residue was purified by flash-column chromatography on silica gel (gradient elution, 10% to 33% EA-petroleum ether) to give the title compound (2.3 g, 82% yield) as a yellow solid.

Steps 3-6: 2-Amino-7,7-dimethylfuro[3,4-b]pyridin-5(7H)-one

The title compound was prepared from 2-Methoxy-7,7-dimethylfuro[3,4-b]pyridin-5(7H)-one using the two-step procedure described in Steps 4 and 5 for Intermediate 10, followed by the two-step procedure as described in Steps 4 and 5 in the preparation of Intermediate 2. MS (ES+) $C_9H_{10}N_2O_2$ requires: 178, found: 179[M+H]⁺.

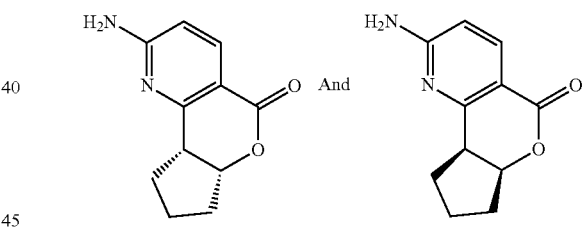

Intermediates 12 and 13: (6aR,9aR)-2-amino-7,8,9,9a-tetrahydrocyclopenta[5,6]pyrano[4,3-b]pyridin-5(6aH)-one and (6aS,9aS)-2-amino-7,8,9,9a-tetrahydrocyclopenta[5,6]pyrano[4,3-b]pyridin-5(6aH)

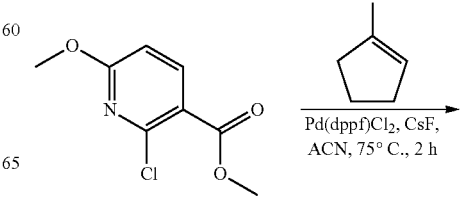

-continued

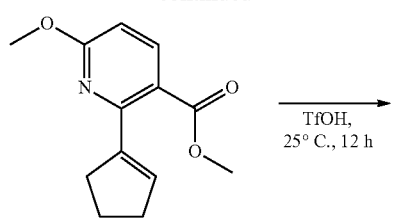

TfOH,
25° C., 12 h

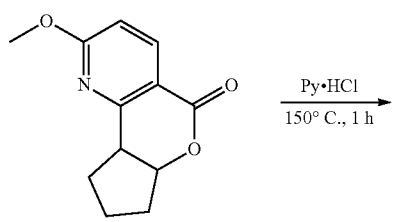

Py·HCl
150° C., 1 h

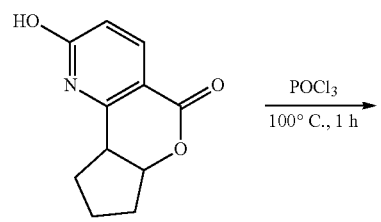

POCl₃
100° C., 1 h

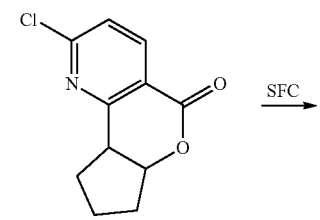

SFC

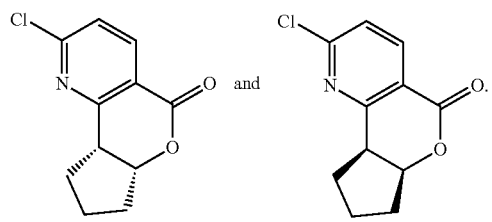 [SMILES: O=C1O[C@@H]2CCC[C@@H]2c2nc(Cl)ccc21 ; O=C1O[C@H]2CCC[C@H]2c2nc(Cl)ccc21]

Precursor I of Intermediate 12 (Cis first eluting isomer) and Precursor I of Intermediate 13 (Cis second eluting isomer)

each of which is represented by one of the structures shown below:

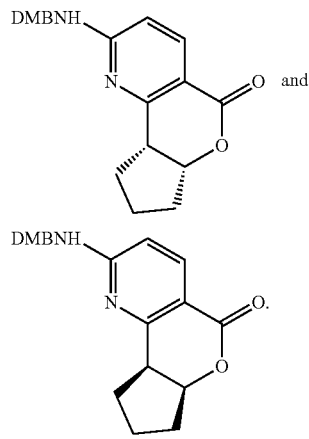

| Precursor I of Intermediate 12 (Cis first eluting isomer) | or | Precursor I of Intermediate 13 (Cis second eluting isomer) | DMBNH₂, NMP 100° C., 2 h |

Precursor II of Intermediate 12 or Precursor II of Intermediate 13 which is represented by one of the structures shown below:

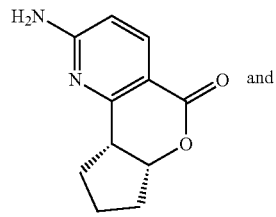 or 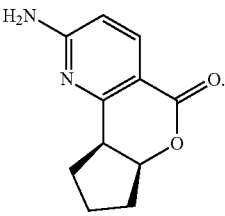

Precursor II of Intermediate 12 or Precursor II of Intermediate 13

HCl/dioxane (4N)
dioxane, 60° C., 2 h

Intermediate 12 or Intermediate 13 which is represented by one of the structures shown below:

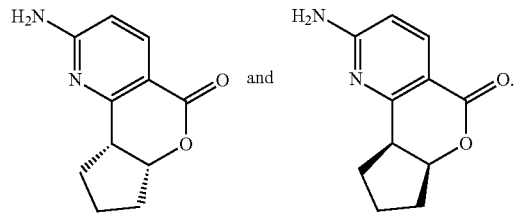 [SMILES: Nc1ccc2c(n1)[C@H]1CCC[C@H]1OC2=O ; Nc1ccc2c(n1)[C@@H]1CCC[C@@H]1OC2=O]

Step 1: Methyl 2-(cyclopent-1-en-1-yl)-6-methoxynicotinate

Cesium fluoride (5.27 g, 34.7 mmol, 1.99 equiv) and Pd(dppf)Cl₂ (1.27 g, 1.74 mmol, 0.100 equiv) were added to a mixture of methyl 2-chloro-6-methoxynicotinate (3.50 g, 17.4 mmol, 1.00 equiv) and 2-(cyclopent-1-en-1-yl)-4,4,5,5-tetramethyl-1,3,2-dioxaborolane (5.05 g, 26.0 mmol, 1.49 equiv) in MCCN (100 mL) and water (5 mL). The reaction mixture was stirred at 75° C. for 2 h, then was cooled to ambient temperature and concentrated to give a residue. The residue was purified by flash-column chromatography on silica gel (gradient elution, 5% to 20% EA-petroleum ether) to give the title compound (3.77 g, 93% yield) as a colorless oil.

Step 2: 2-Methoxy-7,8,9,9a-tetrahydrocyclopenta[5,6]pyrano[4,3-b]pyridin-5(6aH)-one The title compound was prepared from methyl 2-(cyclopent-1-en-1-yl)-6-methoxynicotinate using the same procedure described in Step 2 of Intermediate 11.

Steps 3-4: 2-Chloro-7,8,9,9a-tetrahydrocyclopenta[5,6]pyrano[4,3-b]pyridin-5(6aH)-one The title compound was prepared from 2-Methoxy-7,8,9,9a-tetrahydrocyclopenta[5,6]pyrano[4,3-b]pyridin-5(6aH)-one using the same two-step procedure described in Steps 4 and 5 for Intermediate 10.

Step 5: (6aR,9aR)-2-Chloro-7,8,9,9a-tetrahydrocyclopenta[5,6]pyrano[4,3-b]pyridin-5(6aH)-one and (6aS,9aS)-2-chloro-7,8,9,9a-tetrahydrocyclopenta[5,6]pyrano[4,3-b]pyridin-5(6aH)-one 2-Chloro-7,8,9,9a-tetrahydrocyclopenta[5,6]pyrano[4,3-b]pyridin-5(6aH)-one (1.5 g, 6.71 mmol) was separated by SFC (Chiralpak AD-3, MeOH gradient in $CO_2$ with 0.5% DEA) to give two peaks separately. The first eluting isomer (720 mg, 48% yield) and second eluting isomer 750 mg, 50% yield) were obtained as white solids.

Steps 6 and 7: One of (6aR,9aR)- or (6aS,9aS)-2-Amino-7,8,9,9a-tetrahydrocyclopenta[5,6]pyrano[4,3-b]pyridin-5(6aH)-one The title compound (Intermediate 12) was prepared from one of (6aR,9aR)- or (6aS,9aS)-2-Chloro-7,8,9,9a-tetrahydrocyclopenta[5,6]pyrano[4,3-b]pyridin-5(6aH)-one (first eluting isomer from step 5) using the same two-step procedure as described in Steps 4 and 5 for Intermediate 2. MS (ES+) $C_{11}H_{12}N_2O_2$ requires: 204, found: 205[M+H]$^+$ Steps 8 and 9: The remaining one of (6aR,9aR)- or (6aS,9aS)-22-Amino-7,8,9,9a-tetrahydrocyclopenta[5,6]pyrano[4,3-b]pyridin-5(6aH)-one The title compound (Intermediate 13) was prepared from the remaining one of (6aR,9aR)- or (6aS,9aS)-22-chloro-7,8,9,9a-tetrahydrocyclopenta[5,6]pyrano[4,3-b]pyridin-5(6aH)-one (second eluting isomer from step 5) using the same two-step procedure as described in Steps 4 and 5 for Intermediate 2. MS (ES+) $C_{11}H_{12}N_2O_2$ requires: 204, found: 205[M+H]$^+$

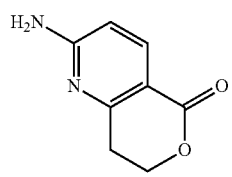

Intermediate 14: 2-Amino-7,8-dihydro-5H-pyrano[4,3-b]pyridin-5-one

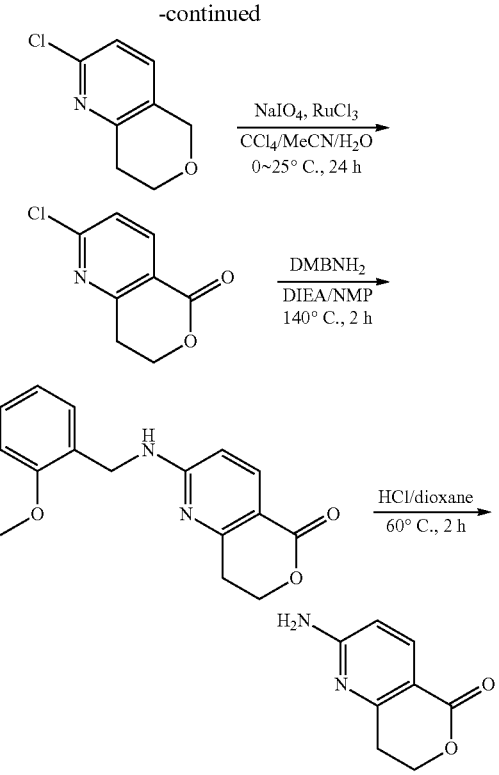

Step 1: 2-Amino-7,8-dihydro-5H-pyrano[4,3-b]pyridin-5-one

The title compound was prepared from tetrahydro-4H-pyran-4-one using the same five-step procedure described in Steps 1-5 for Intermediate 2. MS (ES+) $C_8H_8N_2O_2$ requires: 164, found: 165[M+H]$^+$. $^1$H NMR, 400 MHz, DMSO-d6, δ=7.77 (d, J=8.8 Hz, 1H), 7.01 (s, 2H), 6.41 (d, J=8.8 Hz, 1H), 4.44-4.41 (m, 2H), 2.88-2.85 (m, 2H).

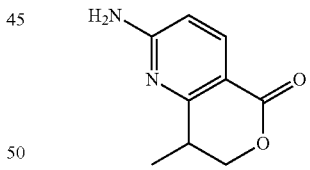

Intermediate 15: 2-Amino-8-methyl-7,8-dihydro-5H-pyrano[4,3-b]pyridin-5-one

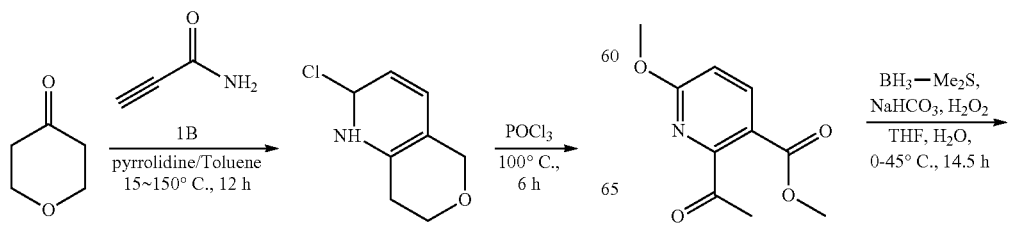

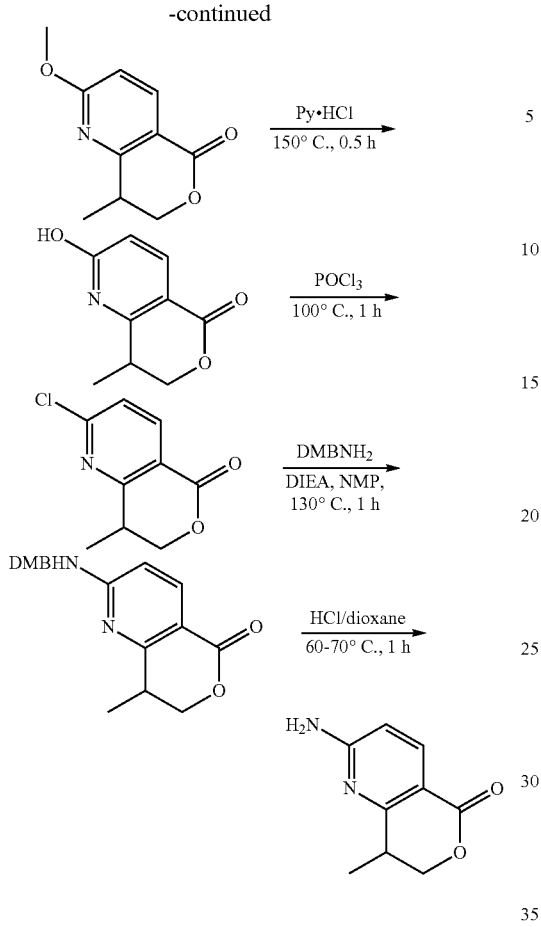

Step 1: 2-Methoxy-8-methyl-7,8-dihydro-5H-pyrano[4,3-b]pyridin-5-one

BH$_3$-Me$_2$S (10 M, 5.31 mL, 53.1 mmol, 1.10 equiv) was added dropwise to a solution of methyl 6-methoxy-2-(prop-1-en-2-yl)nicotinate (10.0 g, 48.3 mmol, 1.00 eq) in THF (100 mL) at 0° C. The mixture was warmed to 20° C. and stirred at that temperature for 2 h. The reaction mixture was then cooled to 0° C. and NaHCO$_3$ (20.3 g, 241 mmol, 5.00 eq) in water (35.0 mL) and H$_2$O$_2$ (30% in water, 69.6 mL, 724 mmol, 15.0 eq) were added dropwise. The reaction mixture was stirred at 20° C. for 30 min and at 30-45° C. for 12 h. The reaction mixture was then poured into saturated aqeuous Na$_2$SO$_3$ solution (200 mL) and extracted with EA (50.0 mL×3). The organic layers were combined and washed with brine (200 mL), dried over Na$_2$SO$_4$, filtered and concentrated. The residue was purified by flash-column chromatography on silica gel (gradient elution, 5% to 15% EA-petroleum ether) to give the title compound (15.0 g, 77.6 mmol, 80.4% yield) as yellow solid.

Steps 2-5: -Amino-8-methyl-7,8-dihydro-5H-pyrano[4,3-b]pyridin-5-one

The title compound was prepared from 2-methoxy-8-methyl-7,8-dihydro-5H-pyrano[4,3-b]pyridin-5-one using the two-step procedure described in Steps 4 and 5 for Intermediate 10, followed by the two-step procedure as described in Steps 4 and 5 in the preparation of Intermediate 2. MS (ES+) C$_9$H$_{10}$N$_2$O$_2$ requires: 178, found: 179[M+H]$^+$.
$^1$H NMR: 400 MHz, DMSO-d6 δ 7.76 (d, J=8.6 Hz, 1H), 7.01 (s, 2H), 6.40 (d, J=8.6 Hz, 1H), 4.44 (dd, J=11.2 Hz, 4.4 Hz, 1H), 4.12 (dd, J=11.0 Hz, 6.8 Hz, 1H), 2.93 (td, J=7.0 Hz, 4.4 Hz, 1H), 1.20 (d, J=7.0 Hz, 3H).

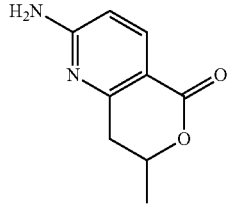

Intermediate 16: 2-Amino-7-methyl-7,8-dihydro-5H-pyrano[4,3-b]pyridin-5-one

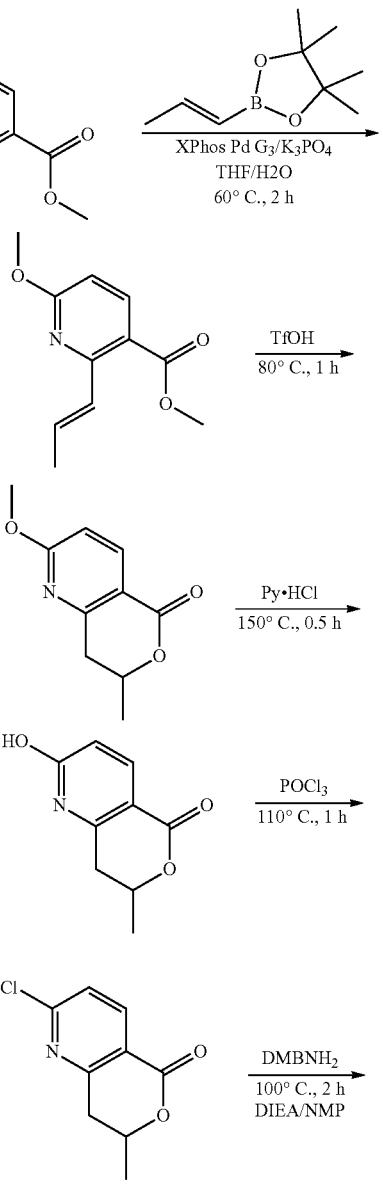

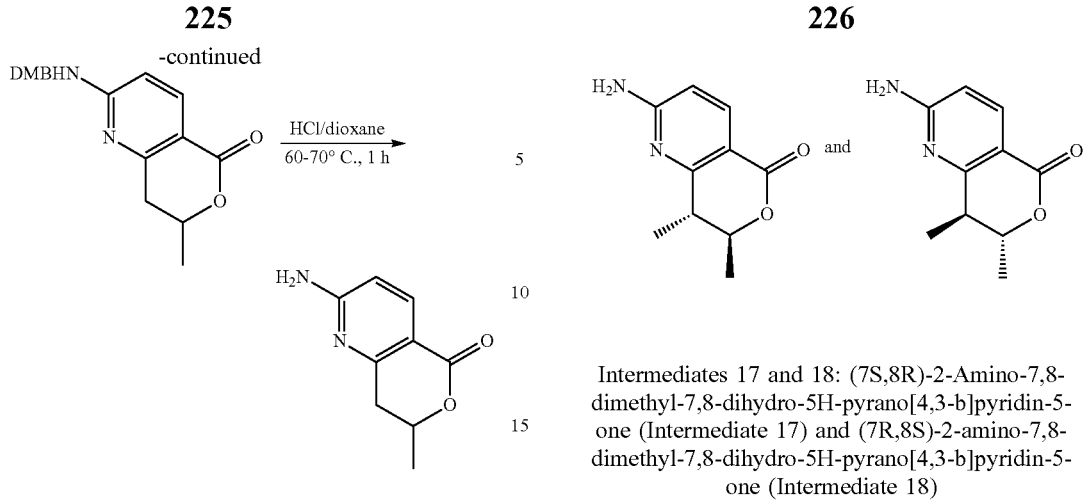

Intermediates 17 and 18: (7S,8R)-2-Amino-7,8-dimethyl-7,8-dihydro-5H-pyrano[4,3-b]pyridin-5-one (Intermediate 17) and (7R,8S)-2-amino-7,8-dimethyl-7,8-dihydro-5H-pyrano[4,3-b]pyridin-5-one (Intermediate 18)

Step 1: Methyl (E)-6-methoxy-2-(prop-1-en-1-yl) nicotinate

A mixture methyl 2-chloro-6-methoxynicotinate (25.0 g, 148 mmol, 1.20 eq), (E)-4,4,5,5-tetramethyl-2-(prop-1-en-1-yl)-1,3,2-dioxaborolane (20.7 g, 123 mmol, 1.00 equiv), XPhos Pd G3 (5.25 g, 6.20 mmol, 0.05 eq) and $K_3PO_4$ (52.6 g, 248 mmol, 2.00 eq) in THF (250 mL) and $H_2O$ (100 mL) was degassed and purged with $N_2$ three times. The mixture was then stirred at 60° C. for 2 h under $N_2$ atmosphere. The reaction mixture was cooled to ambient temperature and partitioned between water (300 mL) and EA (1.20 L). The organic layer was dried over $Na_2SO_4$, filtered and concentrated under reduced pressure to give a residue. The residue was purified by flash-column chromatography on silica gel (gradient elution, 5% to 10% EA-petroleum ether) to give the title compound (25.0 g) as a yellow oil.

Step 2: 2-Methoxy-7-methyl-7,8-dihydro-5H-pyrano[4,3-b]pyridin-5-one

A solution of methyl (E)-6-methoxy-2-(prop-1-en-1-yl) nicotinate (25.0 g, 120 mmol, 1.00 eq) in TfOH (100 mL) was stirred at 80° C. for 1 h. The reaction mixture was then cooled to ambient temperature and and poured into saturated aqueous $NaHCO_3$ solution (1.00 L), then extracted with EA (1.00 L). The organic layer was washed with water (300 mL), dried over $Na_2SO_4$, filtered and concentrated under reduced pressure to give a residue. The residue was purified by flash-column chromatography on silica gel (gradient elution, 2% to 10% EA-petroleum ether) to give the title compound (20.8 g) as a white solid.

Steps 3-6: 2-Amino-7-methyl-7,8-dihydro-5H-pyrano[4,3-b]pyridin-5-one

The title compound was prepared from 2-methoxy-7-methyl-7,8-dihydro-5H-pyrano[4,3-b]pyridin-5-one using the two-step procedure described in Steps 4 and 5 for Intermediate 10, followed by the two-step procedure as described in Steps 4 and 5 in the preparation of Intermediate 2. MS (ES+) $C_9H_{10}N_2O_2$ requires: 178, found: 179$[M+H]^+$. $^1$H NMR, 400 MHz, DMSO-d6 δ 7.75 (d, J=8.8 Hz, 1H), 7.00 (s, 2H), 6.40 (d, J=8.8 Hz, 1H), 4.70-4.45 (m, 2H), 2.90-2.70 (m, 2H), 1.37 (d, J=5.6 Hz, 1H).

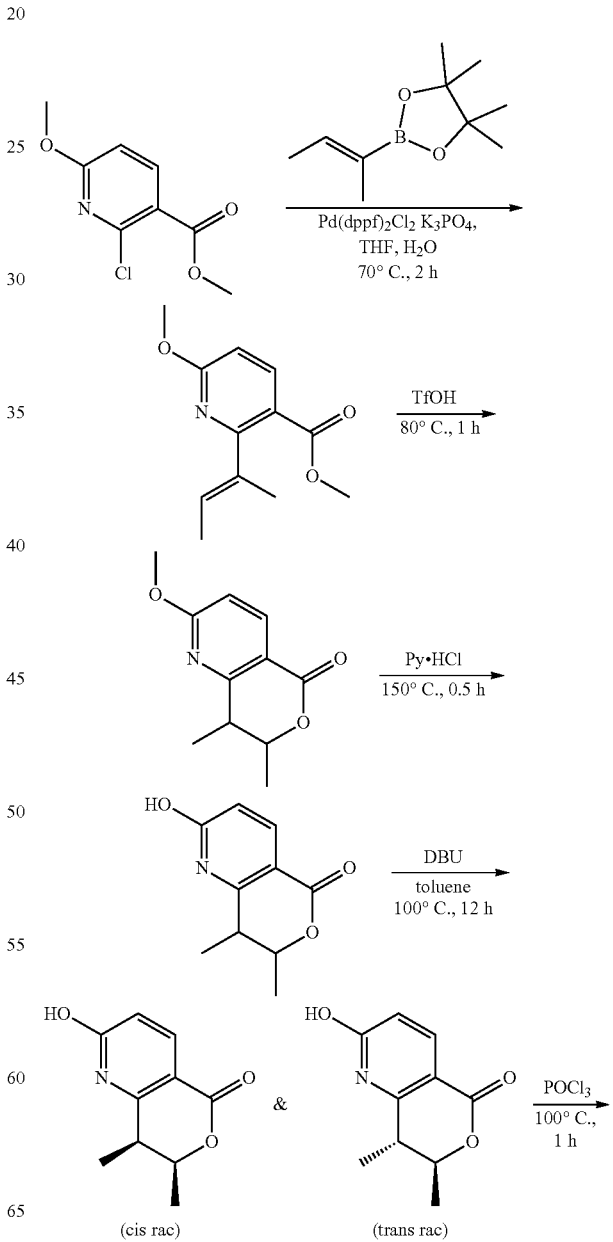

227

-continued

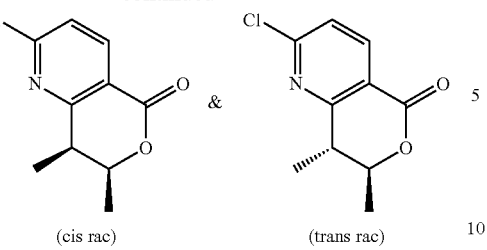

(cis rac)    (trans rac)

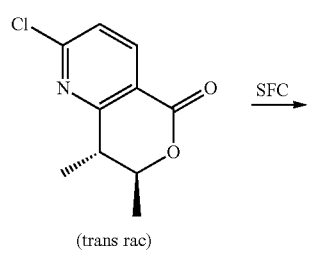

(trans rac)

Precursor I of    Precursor I of
Intermediate 17  and  Intermediate 18
($1^{st}$ eluting isomer)    ($2^{nd}$ eluting isomer)

each of which is represented by one of the structures shown below:

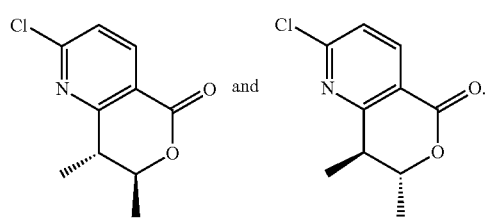

Precursor I of    Precursor I of    DMBNH$_2$
Intermediate 17  or  Intermediate 18  ———————→
($1^{st}$ eluting isomer)    ($2^{nd}$ eluting isomer)    DIEA, NMP
                                                                    100° C., 1 h Precursor II of  or  Precursor II of
Intermediate 17    Intermediate 18 which is represented by one of the structures shown below:

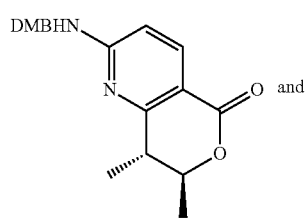

228

-continued

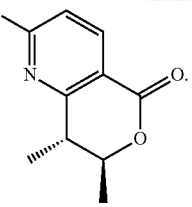

Precursor II of  or  Precursor II of    HCl/dioxane
Intermediate 17    Intermediate 18  ————————→
                                                                    70° C., 1 h Intermediate 17  or  Intermediate 18 which is represented by one of the structures shown below:

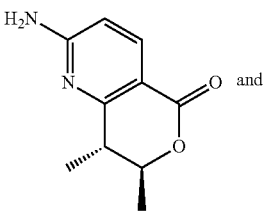
(Intermediate 17) and

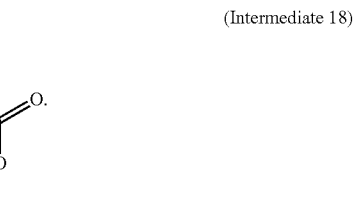
(Intermediate 18)

Step 1: Methyl (E)-2-(but-2-en-2-yl)-6-methoxynicotinate

K$_3$PO$_4$ (120 g, 565 mmol, 3.00 eq) and Pd(dppf)Cl$_2$—CH$_2$Cl$_2$ (7.70 g, 9.42 mmol, 0.05 eq) were added to a solution of methyl 2-chloro-6-methoxynicotinate (38.0 g, 188 mmol, 1.00 eq) and (Z)-2-(but-2-en-2-yl)-4,4,5,5-tetramethyl-1,3,2-dioxaborolane (44.6 g, 245 mmol, 1.30 eq) in THF (320 mL) and H$_2$O (80.0 mL). The reaction mixture was stirred under N$_2$ at 70° C. for 2 h. The reaction mixture was diluted with water (300 mL) and extracted with EA (250 mL×3). The organic layers were combined and dried over sodium sulfate, then filtered and concentrated in vacuo to give the residue. The residue was purified by prep-HPLC (MeCN—H2O gradient with 0.1% TFA additive). The product-containing fractions were adjusted to pH=8-9 with solid sodium carbonate and the mixture was extracted with EA (300 mL×3). The combined organic layers were washed with brine (500 mL), dried over Na$_2$SO$_4$, filtered and concentrated to give the title compound (37.0 g, 167 mmol, 88.7% yield) as a yellow oil.

Steps 2 and 3: 2-Hydroxy-7,8-dimethyl-7,8-dihydro-5H-pyrano[4,3-b]pyridin-5-one

The title compound was prepared from methyl (E)-2-(but-2-en-2-yl)-6-methoxynicotinate using the same procedure as described in Step 2 of Intermediate 16, followed by the same procedure as described in Step 4 for Intermediate 10.

Step 4: rac-(7S,8S)-2-Hydroxy-7,8-dimethyl-7,8-dihydro-5H-pyrano[4,3-b]pyridin-5-one and rac-(7S,8R)-2-hydroxy-7,8-dimethyl-7,8-dihydro-5H-pyrano[4,3-b]pyridin-5-one DBU (60.8 mL, 403 mmol, 3.00 eq) was added to a solution of 2-hydroxy-7,8-dimethyl-7,8-dihydro-5H-pyrano[4,3-b]pyridin-5-one (26.0 g, 134 mmol, 1.00 eq) in toluene (290 mL). The reaction mixture was stirred at 100° C. for 12 h, then was cooled to ambient temperature and concentrated under vacuum. The residue was purified by flash-column chromatography on silica gel (gradient elution, 1% to 10% methanol-dichloromethane) to afford the title compounds as a mixture of isomers that were used in the next step without further purification.

Step 5: rac-(7S,8S)-2-Chloro-7,8-dimethyl-7,8-dihydro-5H-pyrano[4,3-b]pyridin-5-one and rac-(7S,8R)-2-chloro-7,8-dimethyl-7,8-dihydro-5H-pyrano[4,3-b]pyridin-5-one The title compounds were prepared from rac-(7S,8S)-2-hydroxy-7,8-dimethyl-7,8-dihydro-5H-pyrano[4,3-b]pyridin-5-one and rac-(7S,8R)-2-hydroxy-7,8-dimethyl-7,8-dihydro-5H-pyrano[4,3-b]pyridin-5-one using the same procedure as described in Step 5 of Intermediate 10. The cis- and trans-racemic isomers were separated by prep-HPLC (column: Phenomenex luna C18 250*50 mm*10 um; mobile phase: [water(0.1% TFA)-MeCN]; B %: 35% MeCN-55% CAN over 20 min). rac-(7S,8S)-2-Chloro-7,8-dimethyl-7,8-dihydro-5H-pyrano[4,3-b]pyridin-5-one was the first compound to elute and was obtained as a white solid. MS (ES+) $C_{10}H_{13}ClNO_2$ requires: 211, found: 212[M+H]$^+$. $^1$H NMR: 400 MHz, CDCl$_3$ δ 8.29 (d, J=8.2 Hz, 1H), 7.39 (d, J=8.2 Hz, 1H), 4.83 (dq, J=3.2, 6.6 Hz, 1H), 3.09 (dq, J=3.2, 7.2 Hz, 1H), 1.49 (d, J=6.5 Hz, 3H), 1.30 (d, J=7.2 Hz, 3H). rac-(7S,8R)-2-Chloro-7,8-dimethyl-7,8-dihydro-5H-pyrano[4,3-b]pyridin-5-one was the second compound to elute and was obtained as a white solid. MS (ES+) $C_{10}H_{10}ClNO_2$ requires: 211, found: 212[M+H]$^+$. 1H NMR: 400 MHz, CDCl$_3$ δ 8.28 (d, J=8.2 Hz, 1H), 7.38 (d, J=8.2 Hz, 1H), 4.58-4.43 (m, 1H), 3.05 (quin, J=7.2 Hz, 1H), 1.56-1.40 (m, 6H).

Step 6: (7S,8R)-2-Chloro-7,8-dimethyl-7,8-dihydro-5H-pyrano[4,3-b]pyridin-5-one and (7R,8S)-2-chloro-7,8-dimethyl-7,8-dihydro-5H-pyrano[4,3-b]pyridin-5-one rac-(7S,8R)-2-Chloro-7,8-dimethyl-7,8-dihydro-5H-pyrano[4,3-b]pyridin-5-one was separated by SFC (column: DAICEL CHIRALPAK AD (250 mm×50 mm, 10 um); mobile phase: MeOH in CO$_2$) to give the first eluting isomer (peak 1) as a white solid and second eluting isomer (peak 2) as a white solid.

Steps 7 and 8: (7S,8R)-2-Amino-7,8-dimethyl-7,8-dihydro-5H-pyrano[4,3-b]pyridin-5-one The title compound (Intermediate 17) was prepared separately from the first eluting isomer using the same two-step procedure as described in Steps 4 and 5 for Intermediate 2. MS (ES+) $C_{10}H_{12}N_2O_2$ requires: 192, found: 193[M+H]$^+$. $^1$H NMR: 400 MHz, DMSO-d6 δ 7.77 (d, J=8.6 Hz, 1H), 6.97 (s, 2H), 6.40 (d, J=8.6 Hz, 1H), 4.43-4.21 (m, 1H), 2.88-2.65 (m, 1H), 1.35 (d, J=6.4 Hz, 3H), 1.25 (d, J=7.0 Hz, 3H). The absolute stereochemistry of Intermediate 17 was determined by X-ray crystal structure.

Steps 9 and 10: (7R,8S)-2-amino-7,8-dimethyl-7,8-dihydro-5H-pyrano[4,3-b]pyridin-5-one The title compound (Intermediate 18) was prepared separately from the second eluting isomer using the same two-step procedure as described in Steps 4 and 5 for Intermediate 2. MS (ES+) $C_{10}H_{12}N_2O_2$ requires: 192, found: 193[M+H]$^+$. $^1$H NMR: 400 MHz, DMSO-d6 δ 7.77 (d, J=8.6 Hz, 1H), 6.97 (s, 2H), 6.40 (d, J=8.6 Hz, 1H), 4.43-4.21 (m, 1H), 2.88-2.65 (m, 1H), 1.35 (d, J=6.4 Hz, 3H), 1.25 (d, J=7.0 Hz, 3H).

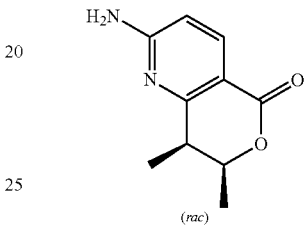

(rac)

Intermediate 19: rac-(7S,8S)-2-Amino-7,8-dimethyl-7,8-dihydro-5H-pyrano[4,3-b]pyridin-5-one

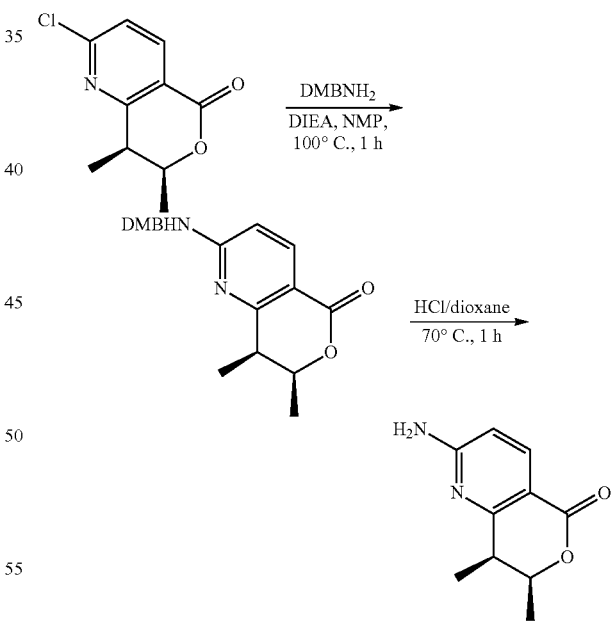

Steps 1 and 2: rac-(7S,8S)-2-Amino-7,8-dimethyl-7,8-dihydro-5H-pyrano[4,3-b]pyridin-5-one The title compound was prepared from rac-(7S,8S)-2-chloro-7,8-dimethyl-7,8-dihydro-5H-pyrano[4,3-b]pyridin-5-one (after step 5, Intermediate 17 and 18 synthesis) using the same two-step procedure as described in Steps 4 and 5 for Intermediate 2. MS (ES+) $C_{10}H_{12}N_2O_2$ requires: 192, found: 193[M+H]$^+$. $^1$H NMR: δ 7.75 (d, J=8.6 Hz, 1H), 7.01 (s, 2H), 6.40 (d, J=8.6 Hz, 1H), 4.69 (d, J=6.6 Hz, 3.2 Hz, 1H), 2.63-2.77 (m, 1H), 1.30 (d, J=6.6 Hz, 3H), 1.07 (d, J=7.2 Hz, 3H).

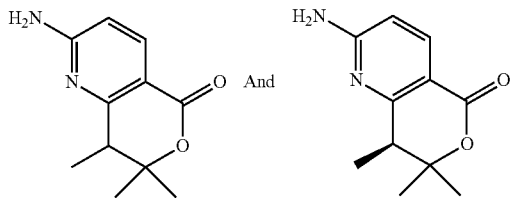

Intermediates 20 and 21: (R)-2-amino-7,7,8-trimethyl-7,8-dihydro-5H-pyrano[4,3-b]pyridin-5-one and (S)-2-amino-7,7,8-trimethyl-7,8-dihydro-5H-pyrano[4,3-b]pyridin-5-one

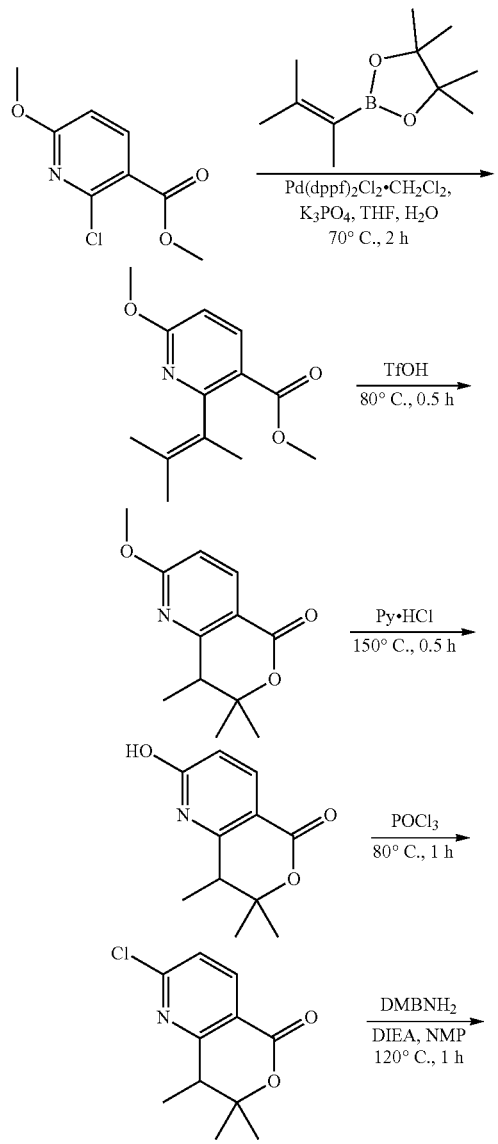

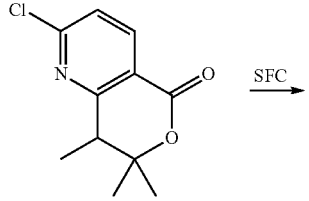

Precursor of Intermediate 20 (1$^{st}$ eluting isomer) and Precursor of Intermediate 21 (2$^{nd}$ eluting isomer)

each of which is represented by one of the structures shown below:

(Precursor Intermediate 20)

(Precursor Intermediate 21)

Precursor of Intermediate 20 (1$^{st}$ eluting isomer) or Precursor of Intermediate 21 (2$^{nd}$ eluting isomer) →[HCl/dioxane, 70° C., 1 h] Intermediate 20 or Intermediate 21 which is represented by one of the structures shown below:

(Intermediate 20)

(Intermediate 21)

Steps 1-5: 2-((2,4-Dimethoxybenzyl)amino)-7,7,8-trimethyl-7,8-dihydro-5H-pyrano[4,3-b]pyridin-5-one The title compound was prepared from methyl 2-chloro-6-methoxynicotinate and 4,4,5,5-tetramethyl-2-(3-methyl-but-2-en-2-yl)-1,3,2-dioxaborolane using similar procedures as described above for Intermediate 17.

Step 6: (R)-2-((2,4-Dimethoxybenzyl)amino)-7,7,8-trimethyl-7,8-dihydro-5H-pyrano[4,3-b]pyridin-5-one and (S)-2-((2,4-Dimethoxybenzyl)amino)-7,7,8-trimethyl-7,8-dihydro-5H-pyrano[4,3-b]pyridin-5-one 2-((2,4-Dimethoxybenzyl)amino)-7,7,8-trimethyl-7,8-dihydro-5H-pyrano[4,3-b]pyridin-5-one was separated by SFC (column: DAICEL CHIRALPAK AS-H (250 mm*30 mm, 5 um); mobile phase: [0.1% NH$_4$OH MeOH in CO$_2$]) to give one of (R or S)-2-((2,4-dimethoxybenzyl)amino)-7,7,8-trimethyl-7,8-dihydro-5H-pyrano[4,3-b]pyridin-5-one (1$^{st}$ eluting isomer, 0.55 g, 79% yield) and the remaining one of (R or S)-2-((2,4-dimethoxybenzyl)amino)-7,7,8-trimethyl-7,8-dihydro-5H-pyrano[4,3-b]pyridin-5-one (2$^{nd}$ eluting isomer, 0.55 g, 79% yield) as yellow oils.

Step 7 and 8: (R)-2-amino-7,7,8-trimethyl-7,8-dihydro-5H-pyrano[4,3-b]pyridin-5-one and (S)-2-amino-7,7,8-trimethyl-7,8-dihydro-5H-pyrano[4,3-b]pyridin-5-one The title compounds (Intermediates 20 and 21) were prepared separately from the 1$^{st}$ and 2$^{nd}$ eluting isomers, i.e., (R)-2-((2,4-dimethoxybenzyl)amino)-7,7,8-trimethyl-7,8-dihydro-5H-pyrano[4,3-b]pyridin-5-one and (S)-2-((2,4-Dimethoxybenzyl)amino)-7,7,8-trimethyl-7,8-dihydro-5H-pyrano[4,3-b]pyridin-5-one, using the same procedure as described in Step 5 of Intermediate 2. Intermediate 20, (R)-2-Amino-7,7,8-trimethyl-7,8-dihydro-5H-pyrano[4,3-b]pyridin-5-one, was obtained as a yellow solid. MS (ES+) C$_{11}$H$_{14}$N$_2$O$_2$ requires: 206, found: 207[M+H]$^+$. $^1$H-NMR (400 MHz, CD$_3$OD): δ ppm 7.89 (d, J=8.8 Hz, 1H), 6.50 (d, J=8.8 Hz, 1H), 2.85-2.80 (m, 1H), 1.41 (s, 6H), 1.27 (d, J=7.2 Hz, 3H). Intermediate 21, (S)-2-Amino-7,7,8-trimethyl-7,8-dihydro-5H-pyrano[4,3-b]pyridin-5-one, was obtained as a yellow solid. MS (ES+) C$_{11}$H$_{14}$N$_2$O$_2$ requires: 206, found: 207[M+H]$^+$. $^1$H-NMR (400 MHz, CD$_3$OD): δ ppm 7.89 (d, J=8.8 Hz, 1H), 6.50 (d, J=8.8 Hz, 1H), 2.85-2.80 (m, 1H), 1.41 (s, 6H), 1.27 (d, J=7.2 Hz, 3H). The stereochemistry of Intermediate 20 was determined in the context of another compound using an X-ray crystal structure.

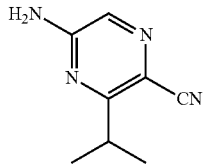

Intermediate 22: 5-Amino-3-isopropylpyrazine-2-carbonitrile

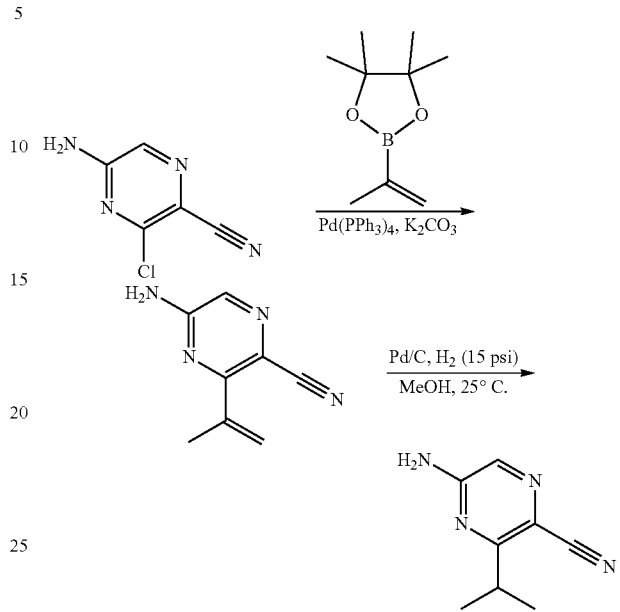

Step 1: 5-Amino-3-(prop-1-en-2-yl)pyrazine-2-carbonitrile

A mixture of 5-amino-3-chloropyrazine-2-carbonitrile (50.0 g, 324 mmol, 1.00 eq), 4,4,5,5-tetramethyl-2-(prop-1-en-2-yl)-1,3,2-dioxaborolane (81.54 g, 485.3 mmol, 1.50 eq), K$_2$CO$_3$ (89.42 g, 647.0 mmol, 2.00 eq), and Pd(PPh$_3$)$_4$ (18.69 g, 16.18 mmol, 0.05 eq) in dioxane (250 mL) and H$_2$O (50 mL) was stirred at 100° C. for 20 h under N$_2$. The reaction mixture was then cooled to ambient temperature and diluted with EA (800 mL) and H$_2$O (300 mL). The biphasic mixture was then filtered through celite, then partitioned. The organic layer was washed with brine (500 mL×4), and then the organic layer was dried over Na$_2$SO$_4$, filtered and concentrated under vacuum. The residue was purified by flash-column chromatography on silica gel (gradient elution, 10% to 33% EA-petroleum ether) to give the title compound (41.0 g, 39.0% yield) as a light yellow solid.

Step 2: 5-Amino-3-isopropylpyrazine-2-carbonitrile

Pd/C (10 wt %, 10.0 g) was added to a solution of 5-amino-3-(prop-1-en-2-yl)pyrazine-2-carbonitrile (45.0 g, 281 mmol, 1.00 eq) in MeOH (800 mL). The suspension was degassed under vacuum and purged with H$_2$ three times. The reaction mixture was stirred under H$_2$ (15 psi) at 25° C. for 16 h. The mixture was filtered through celite and the filtrate was concentrated under vacuum. The residue was treated with petroleum ether/EA (110 mL, 10:1) and stirred at 25° C. for 10 min, then filtered. The filter cake was dried under vacuum to give the title compound (39.5 g, 85.6% yield) as a light yellow solid. MS (ES+) C$_8$H$_{10}$N$_4$ requires: 162, found: 163[M+H]$^+$. $^1$H NMR: 400 MHz CDCl$_3$ δ: 7.83 (s, 1H), 5.07 (br s, 2H), 3.43-3.33 (m, 1H), 1.28 (s, 3H), 1.26 (s, 3H).

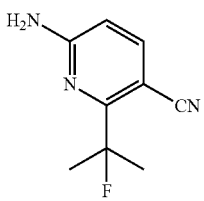

Intermediate 23:
6-Amino-2-(2-fluoropropan-2-yl)nicotinonitrile

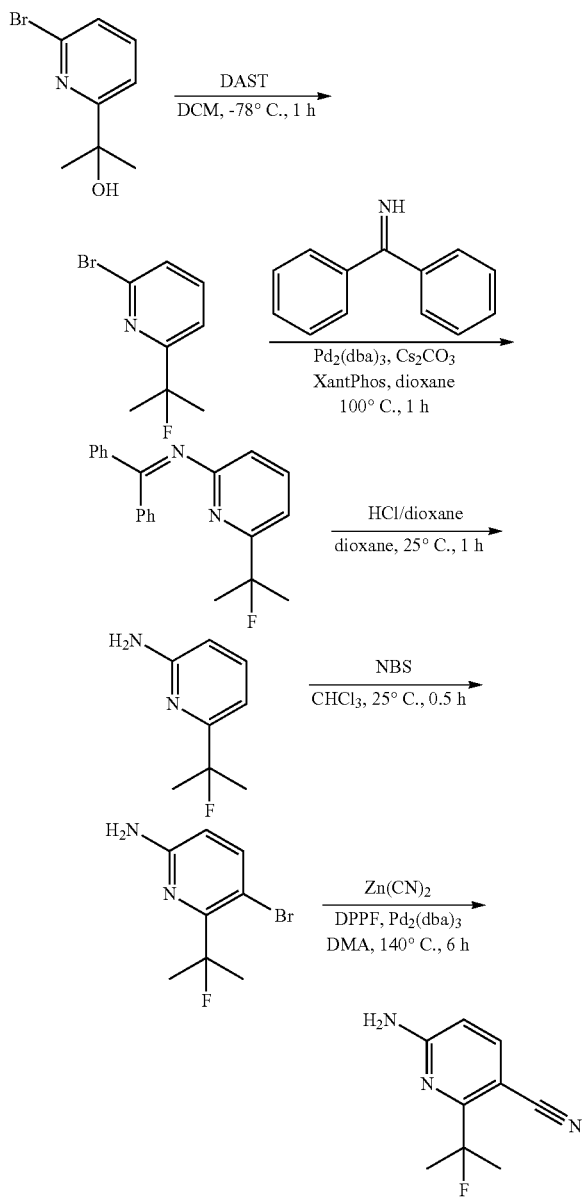

Step 1: 2-Bromo-6-(2-fluoropropan-2-yl)pyridine

DAST (10.3 g, 63.9 mmol, 3.00 equiv) was added to a solution of 2-(6-bromopyridin-2-yl)propan-2-ol (4.60 g, 21.3 mmol, 1.00 equiv) in dichloromethane (80 mL) at −78° C. under nitrogen atmosphere. The reaction mixture was stirred for 1 h, and then water (20 mL) was added. The reaction mixture was further diluted with water (150 mL) and extracted with EA (150 mL×3). The combined organic layers were dried over anhydrous sodium sulfate, filtered and concentrated under reduced pressure to give the title compound (4.50 g, 97% yield) as a yellow oil which was used in the next step without further purification.

Step 2: N-(6-(2-Fluoropropan-2-yl)pyridin-2-yl)-1,1-diphenylmethanimine

A mixture of 2-bromo-6-(2-fluoropropan-2-yl)pyridine (3.99 g, 22.0 mmol, 1.20 equiv), diphenylmethanimine (4.00 g, 18.3 mmol, 1.00 equiv), Pd$_2$(dba)$_3$ (1.68 g, 1.83 mmol, 0.10 equiv), XantPhos (2.12 g, 3.67 mmol, 0.20 equiv) and cesium carbonate (17.9 g, 55.0 mmol, 3.00 equiv) in dioxane (40 mL) was degassed and purged with nitrogen three times. The reaction mixture was stirred at 100° C. for 1 hour under nitrogen atmosphere, then was filtered and concentrated under reduced pressure to give a residue. The residue was purified by flash-column chromatography on silica gel (gradient elution, 0% to 25% EA-petroleum ether) to give the title compound (5.00 g, 86% yield) as yellow oil.

Step 3: 6-(2-Fluoropropan-2-yl)pyridin-2-amine

HCl (4.0 M in dioxane, 10 mL) was added to a solution of N-(6-(2-fluoropropan-2-yl)pyridin-2-yl)-1,1-diphenylmethanimine (5.30 g, 16.7 mmol) in dioxane (20 mL) at 25° C. The reaction mixture was stirred at 25° C. for 1 h, then was treated with dropwise addition of saturated sodium bicarbonate aqueous (20 mL). The crude mixture was diluted with water (50 mL) and extracted with EA (60 mL×3). The combined organic layers were dried over anhydrous sodium sulfate, filtered and concentrated. The residue was purified by flash-column chromatography on silica gel (gradient elution, 0% to 20% EA-petroleum ether) to give the title compound (1.20 g, 47% yield) as a yellow solid.

Step 4: 5-Bromo-6-(2-fluoropropan-2-yl)pyridin-2-amine

N-bromosuccinimide (1.25 g, 7.00 mmol, 0.900 equiv) was added to a solution of 6-(2-fluoropropan-2-yl)pyridin-2-amine (1.20 g, 7.78 mmol, 1.00 equiv) in chloroform (30 mL). The reaction mixture was stirred at 25° C. for 0.5 h, then sas diluted with water (30 mL) and extracted with EA (30 mL×3). The combined organic layers were dried over anhydrous sodium sulfate, filtered and concentrated under reduced pressure to give a residue. The residue was purified by flash-column chromatography on silica gel (gradient elution, 0% to 25% EA-petroleum ether) to give the title compound (480 mg, 25% yield) as a yellow oil. $^1$H NMR (400 MHz, CDCl$_3$): δ ppm 7.59 (d, J=8.4 Hz, 1H), 6.32 (d, J=8.4 Hz, 1H), 4.42 (s, 2H), 1.81 (s, 3H), 1.76 (s, 3H).

Step 5: 6-Amino-2-(2-fluoropropan-2-yl)nicotinonitrile

A mixture of 5-bromo-6-(2-fluoropropan-2-yl)pyridin-2-amine (200 mg, 858 µmol, 1.00 equiv), zinc cyanide (302 mg, 2.57 mmol, 3.00 equiv), DPPF (95.0 mg, 172 µmol, 0.200 equiv) and Pd$_2$(dba)$_3$ (79.0 mg, 85.8 µmol, 0.100 equiv) in N,N-dimethylacetamide (2 mL) was degassed and purged with nitrogen three times. The reaction mixture was then stirred at 140° C. for 6 h under nitrogen. The reaction mixture was then diluted with water (20 mL) and extracted with EA (20 mL×3). The combined organic layers were dried over anhydrous sodium sulfate, filtered and concentrated under reduced pressure to give a residue. The residue was purified flash-column chromatography on silica gel (gradient elution, 0% to 25% EA-petroleum ether) to give the title compound (140 mg, 91% yield) as a brown solid. $^1$H NMR (400 MHz, CDCl$_3$): δ ppm 7.68 (d, J=8.4 Hz, 1H), 6.42 (d, J=8.8 Hz, 1H), 4.91 (s, 2H), 1.76 (s, 3H), 1.71 (s, 3H).

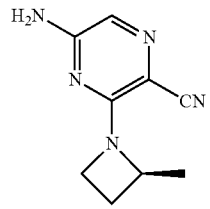

Intermediate 25: (S)-5-Amino-3-(2-methylazetidin-1-yl)pyrazine-2-carbonitrile

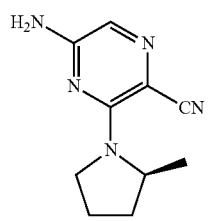

Intermediate 24: (S)-5-Amino-3-(2-methylpyrrolidin-1-yl)pyrazine-2-carbonitrile

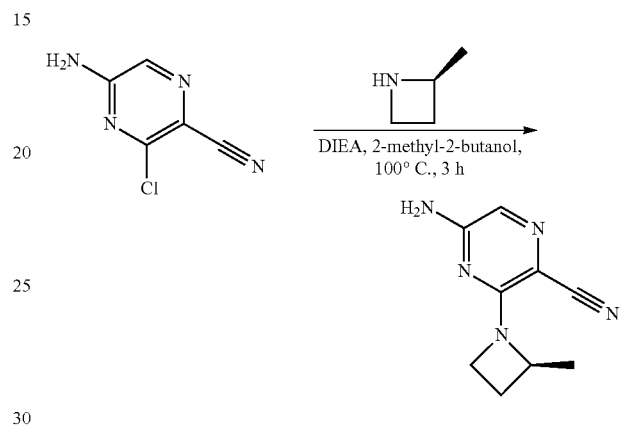

Step 1: (S)-5-Amino-3-(2-methylazetidin-1-yl)pyrazine-2-carbonitrile

The title compound was prepared from 5-amino-3-chloropyrazine-2-carbonitrile and (S)-2-methylazetidine CSA salt using the same procedure as described in Step 1 of Intermediate 24. MS (ES+) C$_9$H$_{11}$N$_5$ requires: 189, found: 190[M+H]$^+$.

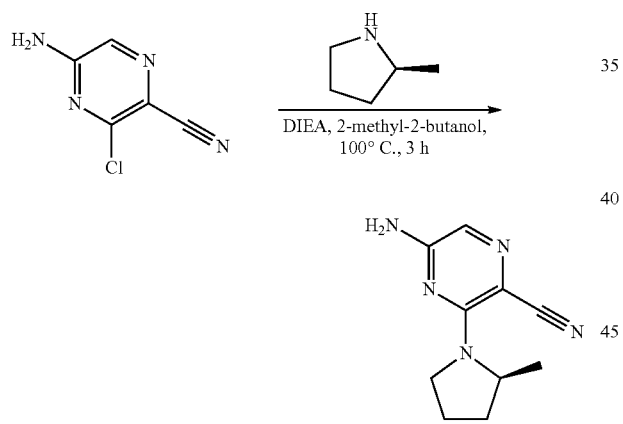

Step 1: (S)-5-Amino-3-(2-methylpyrrolidin-1-yl)pyrazine-2-carbonitrile

N,N-Diisopropylethylamine (0.237 mL, 1.36 mmol, 3.00 equiv) was added to a mixture of 5-amino-3-chloropyrazine-2-carbonitrile (70.0 mg, 453 umol, 1.00 equiv) and (S)-2-methylpyrrolidine (HCl salt, 71.6 mg, 589 umol, 1.30 equiv) in 2-methyl-2-butanol (2 mL). The reaction mixture was stirred at 100° C. for 3 h, then was poured into 20 mL of water and extracted with EA (15 mL×3). The organic layers were dried by anhydrous sodium sulfate, filtered and concentrated under reduced pressure to give the title compound (90.0 mg, crude) as a yellow solid that was used without further purification. MS (ES+) C$_{10}$H$_{13}$N$_5$ requires: 203, found: 204[M+H]$^+$.

Intermediate 26: 6-Amino-2-(1-fluoropropyl)nicotinonitrile

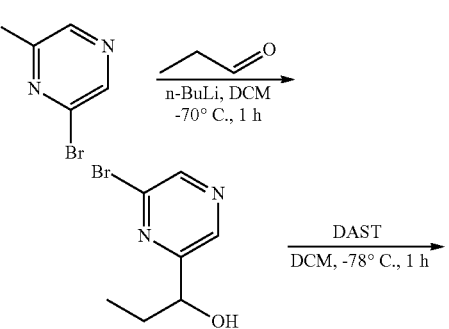

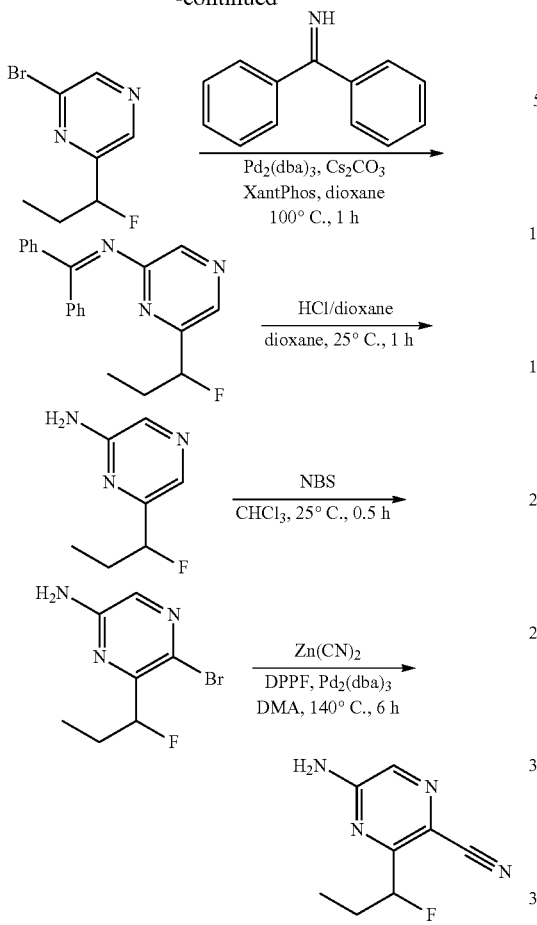

Step 1: 1-(6-Bromopyrazin-2-yl)propan-1-ol n-BuLi (2.5 M, 6.73 mL, 16.8 mmol, 2.00 equiv) was added dropwise to a mixture of 2,6-dibromopyrazine (2.00 g, 8.41 mmol, 1.00 equiv) in dichloromethane (20 mL) at −70° C., then propionaldehyde (1.60 g, 27.5 mmol, 3.27 equiv) in dichloromethane (3 mL) was added into the mixture at −70° C. The reaction mixture was stirred at −70° C. for 1 h under nitrogen, and then saturated aqueous ammonium chloride solution (60 mL) was added. The reaction mixture was extracted with EA (60 mL×3), and the organic layers were combined. The combined organic layers were dried over anhydrous sodium sulfate, filtered, and concentrated to give a residue. The residue was purified by flash-column chromatography on silica gel (gradient elution, 5% to 10% EA-petroleum ether) to give the title compound (1.40 g, 74% yield) as yellow oil.

Steps 2-6:
5-Amino-3-(1-fluoropropyl)pyrazine-2-carbonitrile

The title compound was prepared from 1-(6-bromopyrazin-2-yl)propan-1-ol using the same five-step procedure as described in Steps 1-5 of Intermediate 23. $^1$H-NMR (400 MHz, CD$_3$OD): δ ppm 7.98 (s, 1H), 5.67-5.50 (m, 1H), 5.34 (s, 2H), 2.18-1.90 (m, 2H), 1.07 (t, J=7.2 Hz, 3H).

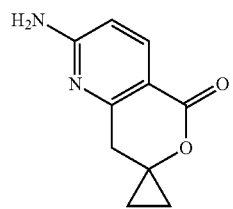 [SMILES: Nc1ccc2c(n1)CC1(CC1)OC2=O]

Intermediate 27: 2'-Aminospiro[cyclopropane-1,7'-pyrano[4,3-b]pyridin]-5'(8'H)-one

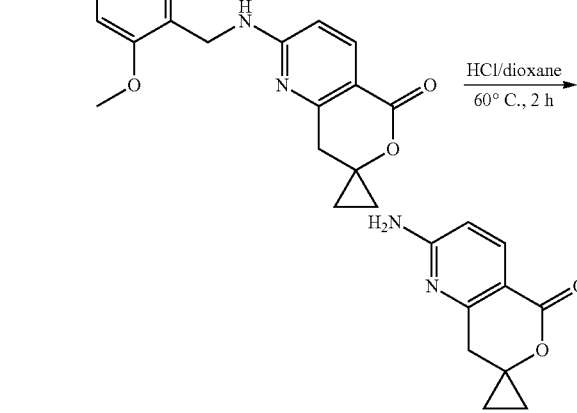

Steps 1-5: 2'-Aminospiro[cyclopropane-1,7'-pyrano[4,3-b]pyridin]-5'(8'1)-one The title compound was prepared from 4-oxaspiro[2.5]octan-7-one using the same five-step procedure described in Steps 1-5 for Intermediate 2. MS (ES+) $C_{10}H_{10}N_2O_2$ requires: 190, found: 191 $[M+H]^+$.

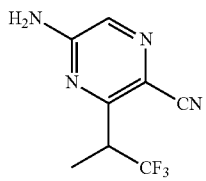

Intermediate 28: 5-Amino-3-(1,1,1-trifluoropropan-2-yl)pyrazine-2-carbonitrile Compound 63

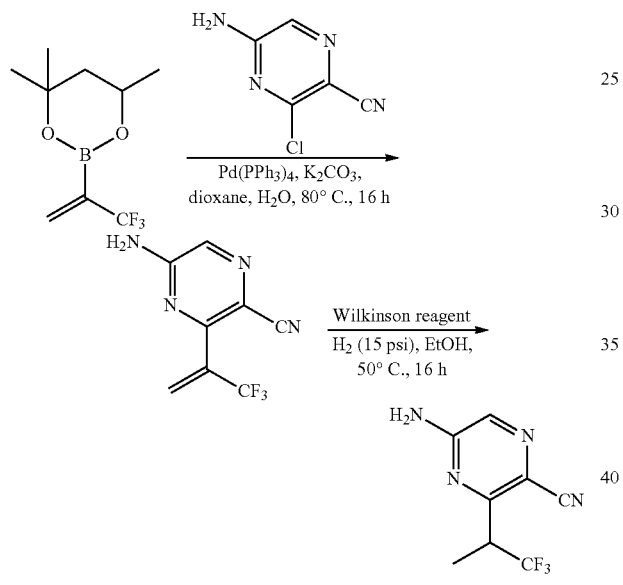

Step 1: 5-Amino-3-(3,3,3-trifluoroprop-1-en-2-yl)pyrazine-2-carbonitrile

Pd(PPh$_4$)$_3$ (657 mg, 776 umol, 0.200 equiv) and potassium carbonate (1.07 g, 7.76 mmol, 2.00 equiv) were added to a solution of 5-amino-3-chloropyrazine-2-carbonitrile (600 mg, 3.88 mmol, 1.00 equiv) and 4,4,6-trimethyl-2-(3,3,3-trifluoroprop-1-en-2-yl)-1,3,2-dioxaborinane (1.03 g, 4.66 mmol, 1.20 equiv) in dioxane (5 mL) and water (0.5 mL). The mixture was stirred at 80° C. for 16 h under nitrogen. The reaction mixture was then cooled to ambient temperature, filtered, and concentrated under reduced pressure to give a residue. The residue was purified by prep-HPLC (column: Phenomenex Synergi Max-RP 250*50 mm*10 um; mobile phase: [water(0.1% TFA)-MeCN]; B %: 22MeCN %-52MeCN %) to give the title compound (200 mg, 24% yield) as white solid.

Step 2: 5-Amino-3-(1,1,1-trifluoropropan-2-yl)pyrazine-2-carbonitrile

Chlororhodium triphenylphosphine (432 mg, 467 umol, 0.50 equiv) was added to a solution of 5-amino-3-(3,3,3-trifluoroprop-1-en-2-yl)pyrazine-2-carbonitrile (200 mg, 934 umol, 1.00 equiv) in ethanol (10 mL). The reaction mixture was stirred at 50° C. for 16 h under H$_2$ (15 psi), then was filtered and concentrated under reduced pressure to give a residue. The residue was purified by prep-HPLC (column: Phenomenex luna C18 250*50 mm*10 um; mobile phase: [water(0.1% TFA)-MeCN]; B %: 32%-62%) to give the title compound (20 mg, 9.9% yield) as white solid. $^1$H-NMR (400 MHz, CD$_3$OD): δ ppm 7.90 (s, 1H), 3.99-3.90 (m, 1H), 1.54 (d, J=6.8, 3H).

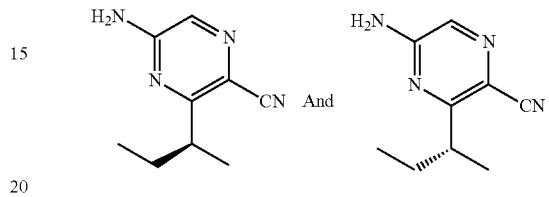

Intermediates 29 and 30: (S)-5-Amino-3-(sec-butyl)pyrazine-2-carbonitrile and (R)-5-amino-3-(sec-butyl)pyrazine-2-carbonitrile

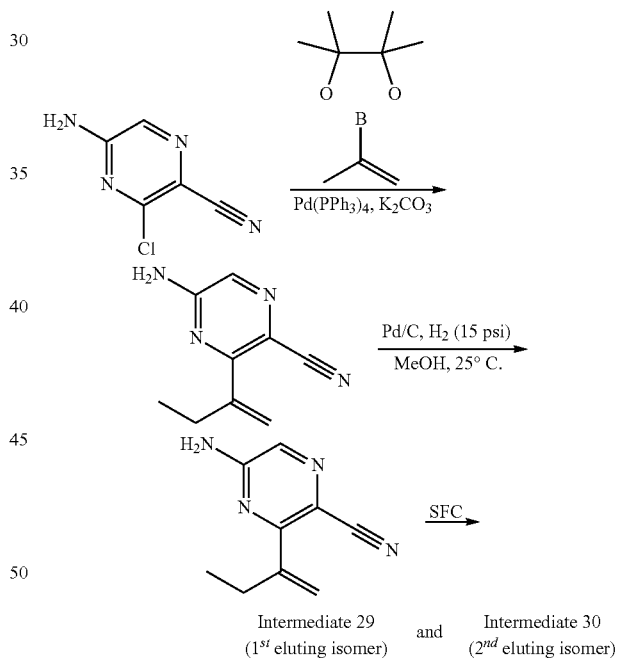

Intermediate 29 and Intermediate 30
(1$^{st}$ eluting isomer) (2$^{nd}$ eluting isomer)

each of which is represented by one of the structures shown below:

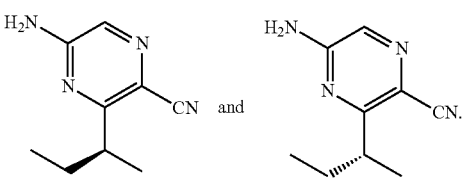

Steps 1 and 2: 5-Amino-3-(sec-butyl)pyrazine-2-carbonitrile

The title compound was prepared using the same procedure as described in Steps 1 and 2 of Intermediate 22.

Step 3: (S)-5-Amino-3-(sec-butyl)pyrazine-2-carbonitrile and (R)-5-amino-3-(sec-butyl)pyrazine-2-carbonitrile 5-Amino-3-(sec-butyl)pyrazine-2-carbonitrile (320 mg, 1.82 mmol) was separated by SFC (column: DAICEL CHIRALPAK AD-H (250 mm*30 mm, 5 um); mobile phase: EtOH with 0.1% NH$_4$OH gradient in CO$_2$) to give one of (R or S)-5-Amino-3-(sec-butyl)pyrazine-2-carbonitrile (1$^{st}$ eluting isomer, 95 mg, 30% yield) as an off-white solid and the remaining one of (R or S)-5-Amino-3-(sec-butyl)pyrazine-2-carbonitrile (2$^{nd}$ eluting isomer, 128 mg, 39.7% yield) as a white solid. Peak 1: MS (ES+) C$_9$H$_{12}$N$_4$ requires: 176, found: 177[M+H]$^+$. $^1$H-NMR (400 MHz, CDCl$_3$) δ=7.83 (s, 1H), 5.07 (br s, 2H), 3.23-3.03 (m, 1H), 1.81-1.62 (m, 2H), 1.25 (d, J=6.8 Hz, 3H), 0.87 (t, J=7.6 Hz, 3H). Peak 2: MS (ES+) C$_9$H$_{12}$N$_4$ requires: 176, found: 177[M+H]$^+$. $^1$H-NMR (400 MHz, CDCl$_3$) δ=7.83 (s, 1H), 5.08 (br s, 2H), 3.20-3.02 (m, 1H), 1.85-1.64 (m, 2H), 1.25 (d, J=6.8 Hz, 3H), 0.87 (t, J=7.6 Hz, 3H).

II. Synthesis of Arylchloride Intermediates

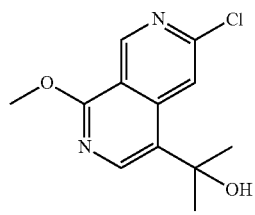 [SMILES: COc1ncc(C(C)(C)O)c2cc(Cl)ncc12]

Intermediate 31: 2-(6-Chloro-1-methoxy-2,7-naphthyridin-4-yl)propan-2-ol

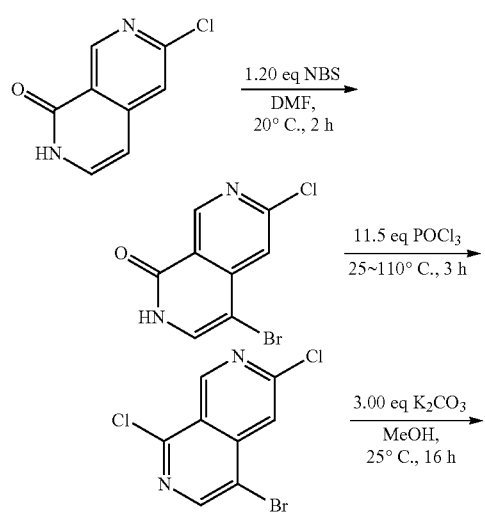

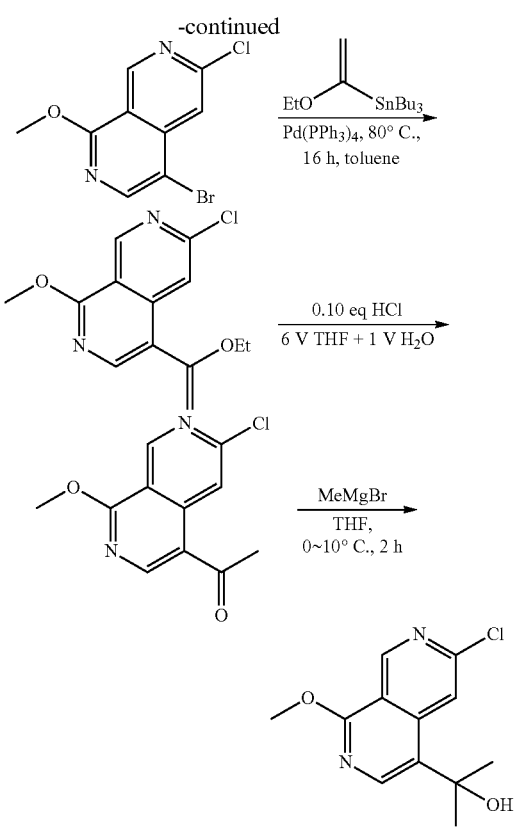

Step 1: 4-Bromo-6-chloro-2,7-naphthyridin-1(2H)-one

NBS (70.9 g, 398 mmol, 1.20 eq) was added to a solution of 6-chloro-2,7-naphthyridin-1(2H)-one (60.0 g, 332 mmol, 1.00 eq) in DMF (600 mL). The reaction mixture was stirred at 20° C. for 2 h, then was poured into water (1 L) and filtered. The filter cake was dried under vacuum to give compound 2 (90.8 g, crude) as a brown solid. MS (ES+) C$_8$H$_4$BrClN$_2$O requires: 260, found: 261 [M+H]$^+$.

Step 2: 4-Bromo-1,6-dichloro-2,7-naphthyridine

4-Bromo-6-chloro-2,7-naphthyridin-1(2H)-one (70.8 g, 272 mmol, 1.00 eq) was added in portions to POCl$_3$ (484 g, 3.16 mol, 293 mL, 11.5 eq) at 25° C. The reaction mixture was then stirred at 110° C. for 3 h. The reaction mixture was then concentrated under vacuum, and the residue was adjusted to pH=8 with saturated aqueous Na$_2$CO$_3$ at 25° C. The mixture was extracted with DCM (500 mL×3), washed with brine (500 mL), dried over Na$_2$SO$_4$, filtered and concentrated under vacuum to give the title compound (75.0 g, 269 mmol, 98.9% yield) as a yellow solid. MS (ES+) C5H$_3$BrCl$_2$N$_2$ requires: 278, found: 279[M+H]$^+$.

Step 3: 4-Bromo-6-chloro-1-methoxy-2,7-naphthyridine

A suspension of 4-bromo-1,6-dichloro-2,7-naphthyridine (75.0 g, 269 mmol, 1.00 eq), K$_2$CO$_3$ (111 g, 809 mmol, 3.00 eq) in MeOH (3 L) was stirred at 25° C. for 16 h. The reaction mixture was then concentrated under vacuum, and the residue was dissolved in H$_2$O (300 mL) and extracted with DCM (100 mL×2). The combined organic layers were concentrated under vacuum to give a residue. The residue was triturated in petroleum ether/EA (40 mL 20:1) and filtered. The filter cake was dried under vacuum to give the title compound (47.0 g, 171 mmol, 63.6% yield) as a yellow solid.

Step 4: 6-Chloro-4-(1-ethoxyvinyl)-1-methoxy-2,7-naphthyridine

A solution of 4-bromo-6-chloro-1-methoxy-2,7-naphthyridine (47.0 g, 171 mmol, 1.00 eq), tributyl(1-ethoxyvinyl)stannane (74.4 g, 206 mmol, 69.6 mL, 1.20 eq) and Pd(PPh$_3$)$_4$ (19.8 g, 17.1 mmol, 0.10 eq) in toluene (500 mL) was stirred at 80° C. for 16 h under N$_2$. The reaction mixture was then cooled to 20° C. and poured into saturated aqueous KF solution (500 mL) and stirred for 1 h. The aqueous mixture was extracted with EA (300 mL×3), and the organic layers were combined. The combined organic layer was concentrated under vacuum to give the title compound (64.0 g, crude) as a yellow oil. MS (ES+) C$_{13}$H$_{13}$ClN$_2$O$_2$ requires: 264, found: 265 [M+H]$^+$.

Step 5: 1-(6-Chloro-1-methoxy-2,7-naphthyridin-4-yl)ethan-1-one

Aqueous HCl (1.50 M, 20.1 mL, 0.10 eq) was added to a solution of 6-chloro-4-(1-ethoxyvinyl)-1-methoxy-2,7-naphthyridine (80.0 g, 302 mmol, 1.00 eq) in THF (480 mL) and H$_2$O (80 mL). The reaction mixture was stirred at 25° C. for 1 h. The reaction mixture was then poured into saturated aqueous NaHCO$_3$ solution (500 mL) and extracted with EA (300 mL×2). The organic layers were combined and concentrated under vacuum. The residue was purified by flash-column chromatography on silica gel (gradient elution, 5% to 50% EA-petroleum ether) to give the title compound (28.0 g, 118 mmol, 39.1% yield) as a white solid. MS (ES+) C$_{11}$H$_9$ClN$_2$O$_2$ requires: 236, found: 237[M+H]$^+$.

Step 6: 2-(6-Chloro-1-methoxy-2,7-naphthyridin-4-yl)propan-2-ol

MeMgBr (3.0 M in diethyl ether, 118 mL, 3.00 eq) was added to a solution of 1-(6-chloro-1-methoxy-2,7-naphthyridin-4-yl)ethan-1-one (28.0 g, 118 mmol, 1.00 eq) in THF (300 mL) at 0~10° C. The mixture was stirred at 0~10° C. for 2 h, and then was poured into saturated aqueous NH$_4$Cl solution (300 mL) and extracted with EA (200 mL×2). The organic layers were combined and concentrated under vacuum to give the title compound (33 g, crude) as a yellow oil. MS (ES+) C$_{12}$H$_{13}$ClN$_2$O$_2$ requires: 252, found: 253[M+H]$^+$.

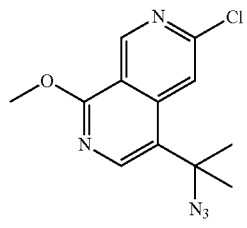 [SMILES: COc1ncc(C(C)(C)N=[N+]=[N-])c2cc(Cl)ncc12]

Intermediate 31a 4-(2-azidopropan-2-yl)-6-chloro-1-methoxy-2,7-naphthyridine can be obtained from 2-(6-Chloro-1-methoxy-2,7-naphthyridin-4-yl)propan-2-ol upon treatment with TMSN$_3$, InBr$_3$ and DCM.

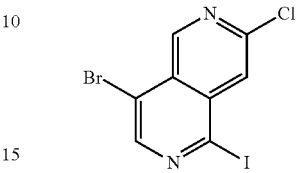

Intermediate 32: 4-bromo-7-chloro-1-iodo-2,6-naphthyridine

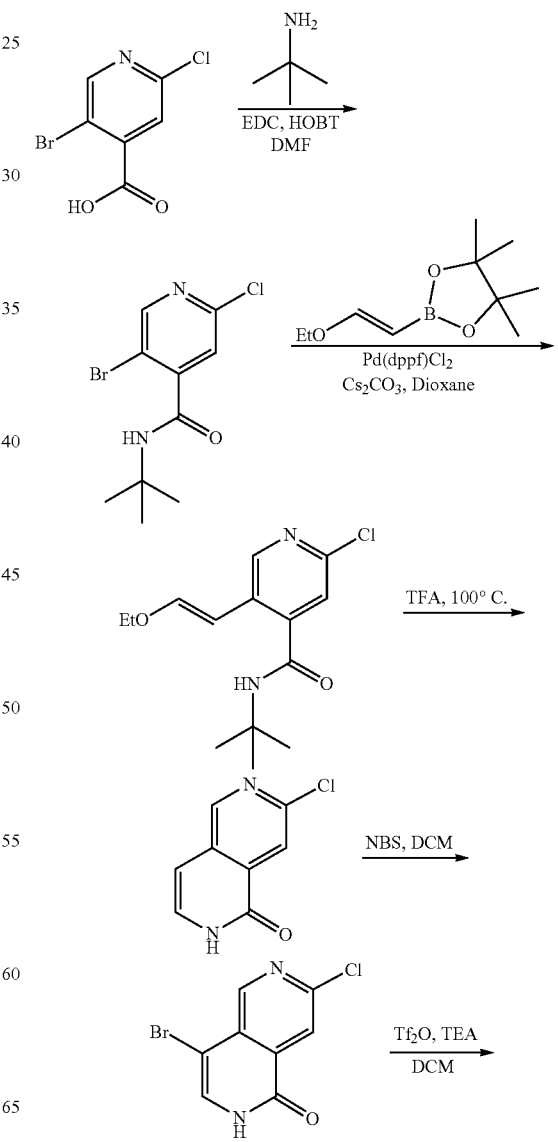

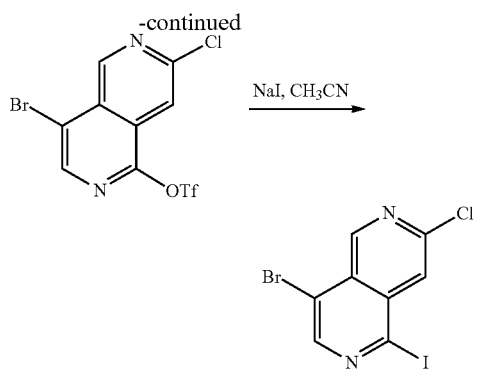

Step 1: 5-bromo-N-tert-butyl-2-chloroisonicotinamide 2-methylpropan-2-amine (1.47 g, 20.2 mmol), EDC HCl (4.85 g, 25.3 mmol) and HOBT (3.41 g, 25.3 mmol) were added to a solution of 5-bromo-2-chloropyridine-4-carboxylic acid (4 g, 16.9 mmol) in DMF (30 mL) under an atmosphere of nitrogen and the reaction mixture was stirred overnight at rt. The resulting solution was added water and suspension was extracted with EA, and then the organic layers were combined, dried over anhydrous sodium sulfate and concentrated under vacuum. The residue was purified by flash-column chromatography-column chromatography to give 3 g (60.9%) of the title compound as a white solid. MS (ES+) $C_{10}H_{12}BrClN_2O$ requires 290, found 291 [M+H]$^+$. $^1$H NMR (300 MHz, DMSO-d$_6$) δ 8.64 (s, 1H), 8.30 (s, 1H), 7.58 (s, 1H), 1.36 (s, 9H).

Step 2: (E)-N-tert-butyl-2-chloro-5-(2-ethoxyvinyl)isonicotinamide

2-[(E)-2-ethoxyethenyl]-4,4,5,5-tetramethyl-1,3,2-dioxaborolane (1.49 g, 7.53 mmol), Cs$_2$CO$_3$ (4.46 g, 13.7 mmol) and Pd(dppf)Cl$_2$ (501 mg, 685 μmol) were added to a solution of 5-bromo-N-tert-butyl-2-chloropyridine-4-carboxamide (2 g, 6.85 mmol) in dioxane (30 mL) and H$_2$O (6 mL) under an atmosphere of nitrogen and the reaction mixture was stirred for 2 h at 80° C. The resulting solution was diluted with water and extracted with EA, and then the organic layers combined, dried over anhydrous sodium sulfate and concentrated under vacuum. The residue was purified by flash-column chromatography to give 1.2 g (62.1%) of the title compound as a yellow solid. MS (ES+) $C_{14}H_{19}ClN_2O_2$ requires 282, found 283 [M+H]$^+$. $^1$H NMR (300 MHz, DMSO-d$_6$) δ 8.55 (s, 1H), 8.20 (s, 1H), 7.35 (d, 114, J=13.0 Hz), 7.28 (s, 1H), 5.79 (d, 114, J=13.0 Hz), 3.90 (q, 211, J=7.0 Hz), 1.35 (s, 9H), 1.26 (t, 311, J=7.0 Hz).

Step 3: 7-chloro-2,6-naphthyridin-1(2H)-one

TFA (20 mL) was added to N-tert-butyl-2-chloro-5-[(E)-2-ethoxyethenyl]pyridine-4-carboxamide (1.2 g, 4.24 mmol) and the reaction mixture was stirred overnight at 100° C. The resulting mixture was concentrated under vacuum to give 600 mg (91.5%) of the title compound as a red solid. The crude product was used directly for next step without any further purification. MS (ES+) $C_8H_5ClN_2O$ requires 180, found 181 [M+H]$^+$.

Step 4: 4-bromo-7-chloro-2,6-naphthyridin-1(2H)-one

NBS (3.54 g, 19.9 mmol) was added to a solution of 7-chloro-1,2-dihydro-2,6-naphthyridin-1-one (3 g, 16.6 mmol) in DCM (40 mL) and the reaction mixture was stirred for 1 h at rt. The solid was collected by filtration to give 3 g (69.7%) of the title compound as a white solid. MS (ES+) $C_8H_4BrClN_2O$ requires 258, found 259 [M+H]$^+$. $^1$H NMR (300 MHz, DMSO-d$_6$) δ 12.09 (s, 1H), 8.93 (s, 1H), 8.04 (s, 1H), 7.70 (d, 114, J=6.0 Hz).

Step 5: 4-bromo-7-chloro-2,6-naphthyridin-1-yl trifluoromethanesulfonate

Tf$_2$O (4.34 g, 15.4 mmol) was added drop wise over 10 min to a solution of 4-bromo-7-chloro-1,2-dihydro-2,6-naphthyridin-1-one (1 g, 3.85 mmol) in DCM (15 mL) and TEA (777 mg, 7.70 mmol) at −78° C. and the resulting solution was stirred for 0.5 h at −78° C. The mixture was warmed to room temperature and stirred at this temperature for another 0.5 h. The reaction was then quenched by the addition of 2 mL of water/ice, extracted with DCM, and then the organic layers combined, dried over anhydrous sodium sulfate and concentrated under vacuum. The residue was purified using flash-column chromatography to give 1 g (66.6%) of the title compound as a white solid. MS (ES+) $C_9H_3BrClF_3N_2O_3S$ requires 390, found 391 [M+H]$^+$. $^1$H NMR (300 MHz, DMSO-d$_6$) δ 9.47 (s, 1H), 8.78 (s, 1H), 8.14 (d, 1H, J=0.9 Hz).

Step 6: 4-bromo-7-chloro-1-iodo-2,6-naphthyridine

NaI (952 mg, 6.35 mmol) was added to a solution of 4-bromo-7-chloro-2,6-naphthyridin-1-yl trifluoromethanesulfonate (500 mg, 1.27 mmol) in MCCN (9 mL) and the resulting mixture was cooled to 0° C. followed by addition of trifluoromethanesulfonic acid (381 mg, 2.54 mmol) in MCCN (1 mL) drop wise over 10 min. The mixture was then stirred at rt for 1.5 h. The resulting solution was extracted with EA, and then the organic layers combined, washed with brine, dried over anhydrous sodium sulfate and concentrated under vacuum to give 500 mg of title compound as a black solid which was used directly for next without further purification. MS (ES+) $C_9H_3BrClF_3N_2O_3S$ requires 368, found 369 [M+H]$^+$.

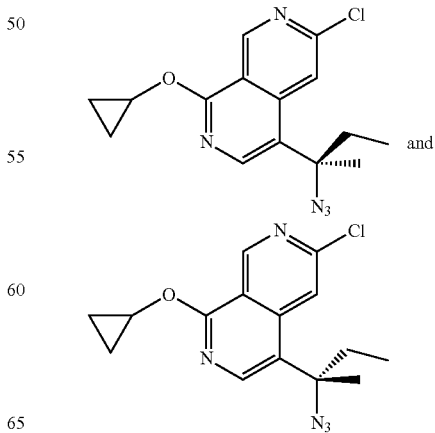

Intermediates 33 and 34: (R)-2-(6-Chloro-1-cyclopropoxy-2,7-naphthyridin-4-yl)butan-2-amine and (S)-2-(6-chloro-1-cyclopropoxy-2,7-naphthyridin-4-yl)butan-2-amine

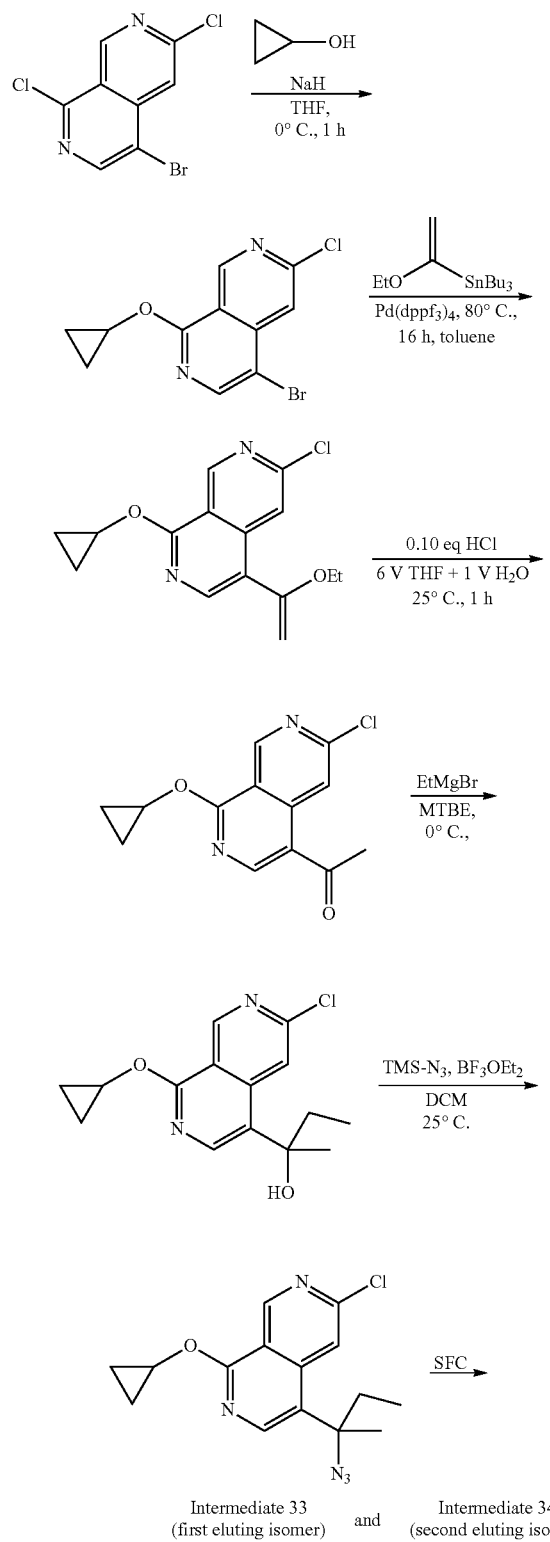

Each of which is represented by one of the structures below:

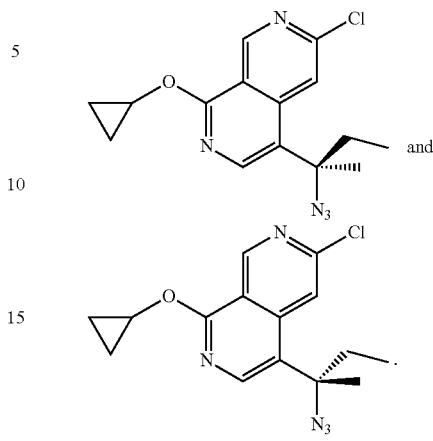

Step 1: 4-Bromo-6-chloro-1-cyclopropoxy-2,7-naphthyridine

To a solution of cyclopropanol (5.75 g, 98.9 mmol) in THF (250 mL) was added sodium hydride (4.32 g, 108 mmol, 60% purity) at 0° C. The reaction mixture was stirred at 0° C. for 20 min, and then 4-bromo-1,6-dichloro-2,7-naphthyridine (25.0 g, 90.0 mmol) was added to reaction mixture. The reaction mixture was warmed to 25° C. for 40 min, then was poured into water (1 L) and extracted with ethyl acetate (500 mL×3). The combined organic layers were dried over anhydrous sodium sulfate, filtered and concentrated under reduced pressure to give a residue. The crude product was purified by tritaration in petroleum ether/EA (240 mL/20 mL) at 25° C. to give the title compound (45.0 g, 84% yield) as a yellow solid. $^1$H NMR (400 MHz, CDCl$_3$): δ ppm 9.27 (s, 1H), 8.40 (s, 1H), 7.88 (s, 1H), 4.57-4.50 (m, 1H), 0.95-0.92 (m, 4H).

Steps 2-3: 1-(6-Chloro-1-cyclopropoxy-2,7-naphthyridin-4-yl)ethan-1-one

The title compound was prepared from 4-bromo-6-chloro-1-cyclopropoxy-2,7-naphthyridine using the same two-step sequence as described in Steps 4 and 5 of Intermediate 31.

Step 4: 2-(6-Chloro-1-cyclopropoxy-2,7-naphthyridin-4-yl)butan-2-ol

To a solution of 1-(6-chloro-1-cyclopropoxy-2,7-naphthyridin-4-yl)ethan-1-one (27.0 g, 103 mmol) in MTBE (540 mL) was added ethylmagnesium bromide (3.0 M, 103 mL) at 0° C. under nitrogen atmosphere. The reaction mixture was stirred at 0° C. for 15 min, then was quenched by addition water (1000 mL) and extracted with EA (800 mL×3). The combined organic layers were dried over anhydrous sodium sulfate, filtered and concentrated under reduced pressure to give the title compound (34 g, crude) as a yellow oil which was used in the next step directly.

Step 5: (R)-2-(6-Chloro-1-cyclopropoxy-2,7-naphthyridin-4-yl)butan-2-amine or (S)-2-(6-chloro-1-cyclopropoxy-2,7-naphthyridin-4-yl)butan-2-amine To a solution of 2-(6-chloro-1-cyclopropoxy-2,7-naphthyridin-4-yl)butan-2-ol (34.0 g, 116 mmol) in dichloromethane (340 mL) was added trimethylsilyl azide (35.0 g, 304 mmol, 40 mL) and boron trifluoride diethyl etherate (34.5 g, 243 mmol, 30 mL) under nitrogen atmosphere. The reaction mixture was stirred at 25° C. for 2 h, then was diluted with water (1000 mL) and extracted with DCM (800 mL×3). The combined organic layers were dried over anhydrous sodium sulfate, filtered and concentrated under reduced pressure to give a residue. The residue was purified by silica gel column chromatography (petroleum ether:ethyl acetate=1:0 to 3:1) to give rac-2-(6-chloro-1-cyclopropoxy-2,7-naphthyridin-4-yl)butan-2-amine (15.0 g, 45% yield for two steps) as a yellow solid. This racemic compound was separated by SFC (column: Phenomenex-Cellulose-2 (250 mm×30 mm, 10 um); mobile phase: [0.1% MeOH (with 0.1% NH$_4$OH) in CO$_2$] to give (R)-2-(6-chloro-1-cyclopropoxy-2,7-naphthyridin-4-yl)butan-2-amine or (S)-2-(6-chloro-1-cyclopropoxy-2,7-naphthyridin-4-yl)butan-2-amine (Intermediate 33, first eluting isomer, 2.90 g, 19% yield) as a yellow solid and a second eluting isomer (Intermediate 34, 4.80 g, 32% yield) as a white solid. Intermediate 33: $^1$H NMR (400 MHz, CDCl$_3$): δ ppm 9.36 (s, 1H), 8.36 (s, 1H), 8.23 (s, 1H), 4.58-4.51 (m, 1H), 2.10-2.04 (m, 2H), 1.84 (s, 3H), 0.96-0.92 (m, 4H), 0.87 (t, J=7.2 Hz, 3H).

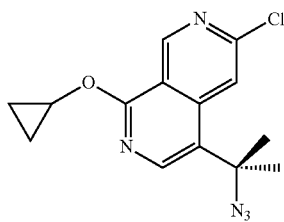

Intermediate 35: 4-(2-azidopropan-2-yl)-6-chloro-1-cyclopropoxy-2,7-naphthyridine Intermediate 35 was made using a similar procedure as described for Intermediates 33 and 34, except in step 4, methylmagnesium Grignard was used and no chiral separation was needed.

Intermediates 36a-36o

Intermediates were made using a similar procedure as described for Intermediate 35, except that a different reagent was used as noted below in Step 1.

| Intermediates | Structure | Reagent used in Step 1 of prep for Intermediate 35 |
|---|---|---|
| 36a | 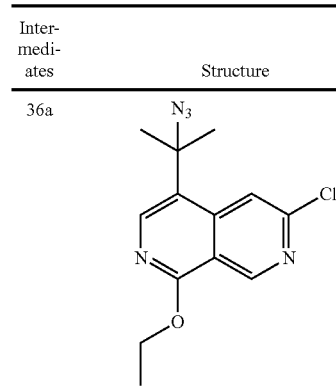 | EtOH |
| 36b | 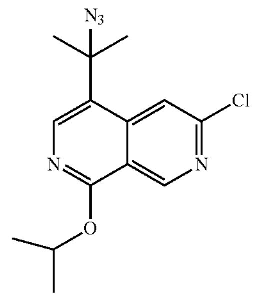 [SMILES: CC(C)Oc1ncc(C(C)(C)N=[N+]=[N-])c2cc(Cl)ncc12] | iPrOH |
| 36c | 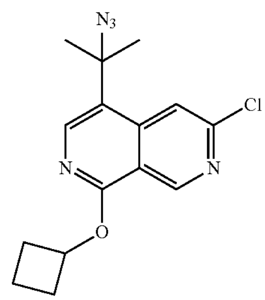 [SMILES: CC(C)(N=[N+]=[N-])c1cnc(OC2CCC2)c2cnc(Cl)cc12] | cyclobutanol |
| 36d | 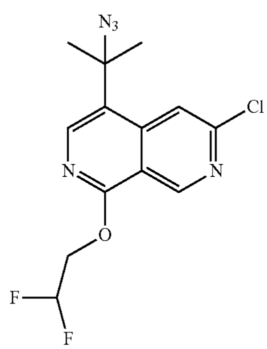 [SMILES: CC(C)(N=[N+]=[N-])c1cnc(OCC(F)F)c2cnc(Cl)cc12] | OH with F, F on CH |
| 36e | 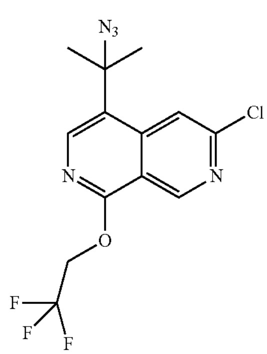 [SMILES: CC(C)(N=[N+]=[N-])c1cnc(OCC(F)(F)F)c2cnc(Cl)cc12] | OH with F, F, F |

| Intermediates | Structure | Reagent used in Step 1 of prep for Intermediate 35 |
|---|---|---|
| 36f | 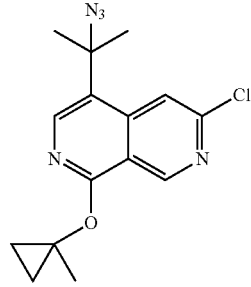 [SMILES: CC1(Oc2ncc(C(C)(C)N=[N+]=[N-])c3cc(Cl)ncc23)CC1] |  |
| 36g | 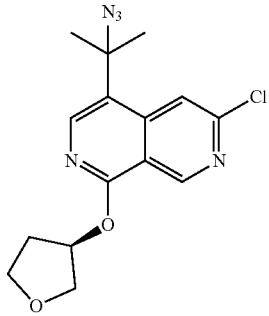 [SMILES: CC(C)(N=[N+]=[N-])c1cnc(O[C@@H]2CCOC2)c2cnc(Cl)cc12] | 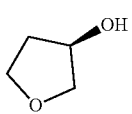 |
| 36h | 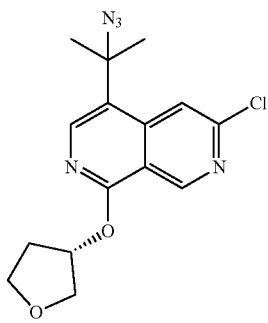 [SMILES: CC(C)(N=[N+]=[N-])c1cnc(O[C@H]2CCOC2)c2cnc(Cl)cc12] | 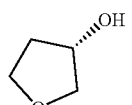 |
| 36i | 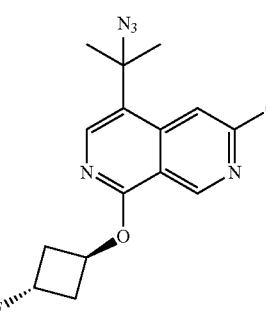 | 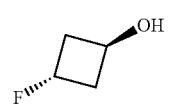 |
| 36j | 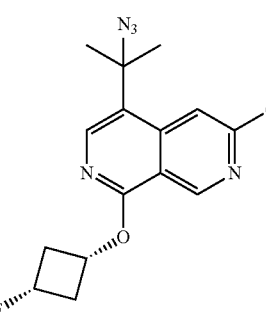 | 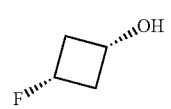 |
| Intermediates | Structure | Reagent used in Step 1 of prep for Intermediate 35 |
|---|---|---|
| 36k | 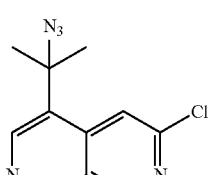 | 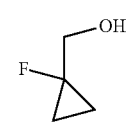 |
| 36l | 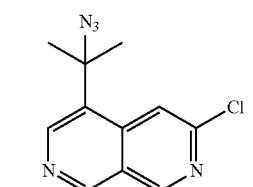 | 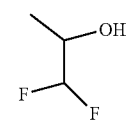 |
| 36m | 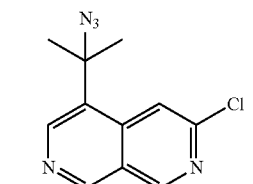 | 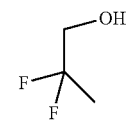 |
| 36n | 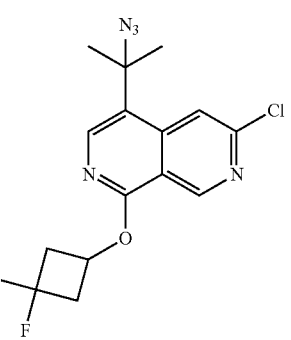 | 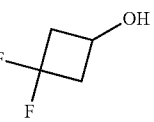 |

| Intermediates | Structure | Reagent used in Step 1 of prep for Intermediate 35 |
|---|---|---|
| 36o | 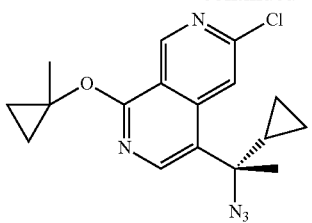 | 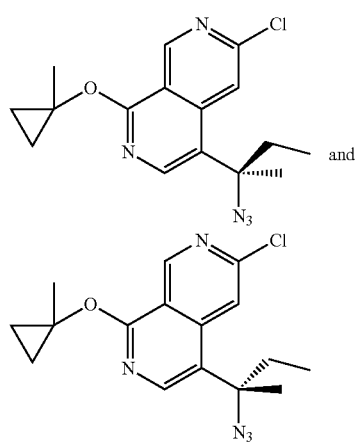 |

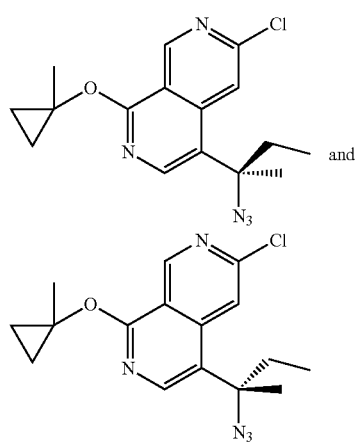

Intermediate 37 and 38: (R)-4-(2-Azidobutan-2-yl)-6-chloro-1-(1-methylcyclopropoxy)-2,7-naphthyridine and (S)-4-(2-azidobutan-2-yl)-6-chloro-1-(1-methylcyclopropoxy)-2,7-naphthyridine Intermediates 37 and 38 were made using a similar procedure as described for Intermediates 33 and 34, except in step 1, 1-methylcyclopropane-1-ol was used. The racemic title compound was separated by SFC (column: Daicel Chiralpak AD-H (250 mm×30 mm, 5 um); mobile phase: [IPA (with 0.1% NH$_4$OH) in CO$_2$]) to give (R)-4-(2-azidobutan-2-yl)-6-chloro-1-(1-methylcyclopropoxy)-2,7-naphthyridine or (S)-4-(2-azidobutan-2-yl)-6-chloro-1-(1-methylcyclopropoxy)-2,7-naphthyridine (Intermediate 37, first eluting isomer, 200 mg, 29% yield) as a white oil and a second eluting isomer (Intermediate 38, 290 mg, 42% yield) as a white oil. Intermediate 37 and 38: MS (ES+) C$_{16}$H$_{18}$ClN$_5$O requires 331, found 332 [M+H]$^+$.

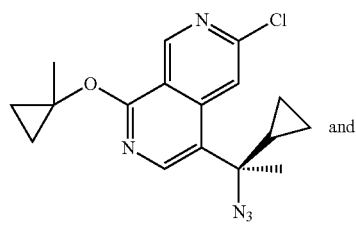

Intermediate 39 and 40: (R)-4-(1-Azido-1-cyclopropylethyl)-6-chloro-1-(1-methylcyclopropoxy)-2,7-naphthyridine and (S)-4-(1-azido-1-cyclopropylethyl)-6-chloro-1-(1-methylcyclopropoxy)-2,7-naphthyridine Intermediates 39 and 40 were made using a similar procedure as described for Intermediates 33 and 34, except in step 4, cyclopropylmagnesium bromide was used and the reaction was stirred at 60° C. for 30 min. The racemic title compound was separated by SFC(column: Daicel Chiralpak AD-H (250 mm×30 mm, 5 um); mobile phase: [IPA (with 0.1% NH$_4$OH) in CO$_2$]) to give: (R)-4-(1-Azido-1-cyclopropylethyl)-6-chloro-1-(1-methylcyclopropoxy)-2,7-naphthyridine or (S)-4-(1-azido-1-cyclopropylethyl)-6-chloro-1-(1-methylcyclopropoxy)-2,7-naphthyridine (Intermediate 39, first eluting isomer, 130 mg, 28% yield) as a yellow solid and a second eluting isomer (Intermediate 40, 150 mg, 32% yield) as a yellow solid.

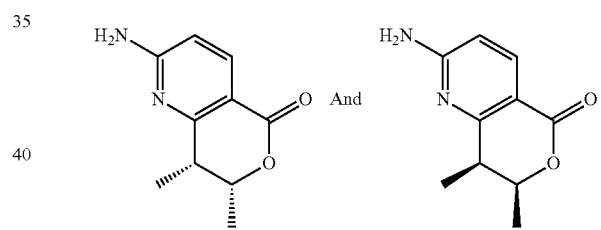

Intermediates 41 and 42: (7R,8R)-2-Amino-7,8-dimethyl-7,8-dihydro-5H-pyrano[4,3-b]pyridin-5-one and (7S,8S)-2-amino-7,8-dimethyl-7,8-dihydro-5H-pyrano[4,3-b]pyridin-5-one

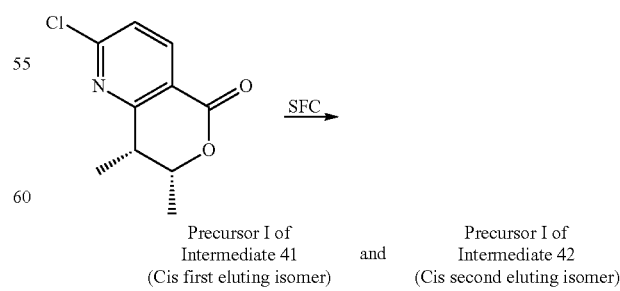

Precursor I of Intermediate 41 (Cis first eluting isomer) and Precursor I of Intermediate 42 (Cis second eluting isomer)

each of which is represented by one of the structures shown below:

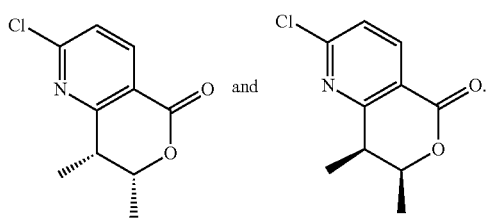

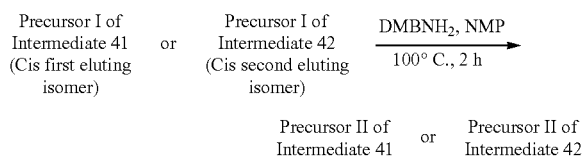

which is represented by one of the structures shown below:

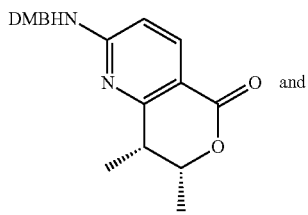

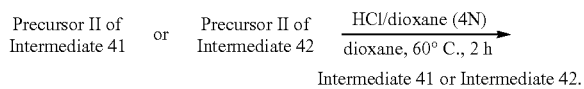

which is represented by one of the structures shown below:

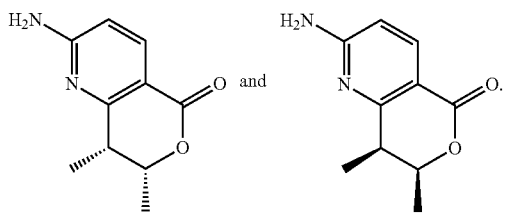

Step 1: (7R,8R)-2-Chloro-7,8-dimethyl-7,8-dihydro-5H-pyrano[4,3-b]pyridin-5-one and (7S,8S)-2-chloro-7,8-dimethyl-7,8-dihydro-5H-pyrano[4,3-b]pyridin-5-one rac-(7R,8R)-2-Chloro-7,8-dimethyl-7,8-dihydro-5H-pyrano[4,3-b]pyridin-5-one (6.0 g, 28.3 mmol) was separated by SFC (Daicel Chiralpak AD, MeOH gradient in $CO_2$ with 0.1% $NH_4OH$) to give two peaks separately. The first eluting isomer (3 g, 50% yield) and second eluting isomer (2.8 g, 46% yield) were obtained as yellow solids.

Steps 2 and 3: One of (7R,8R)- or (7S,8S)-2-Amino-7,8-dimethyl-7,8-dihydro-5H-pyrano[4,3-b]pyridin-5-one The title compound (Intermediate 41) was prepared from one of (7R,8R)- or (7S,8S)-2-chloro-7,8-dimethyl-7,8-dihydro-5H-pyrano[4,3-b]pyridin-5-one (first eluting isomer from step 1) using the same two-step procedure as described in Steps 4 and 5 for Intermediate 2. $^1$H-NMR (400 MHz, 6d-DMSO): δ ppm 7.76 (d, J=8.8 Hz, 1H), 7.02 (s, 2H), 6.41 (d, J=8.8 Hz, 1H), 4.70 (d, J=3.2, 6.4 Hz, 1H), 2.77-2.66 (m, 1H), 1.31 (d, J=6.8 Hz, 3H), 1.08 (d, J=7.2 Hz, 3H). MS (ES+) $C_{10}H_{12}N_2O_2$ requires: 192, found: 193[M+H]$^+$.

Steps 4 and 5: The remaining one of (7R,8R)- or (7S,8S)-2-Amino-7,8-dimethyl-7,8-dihydro-5H-pyrano[4,3-b]pyridin-5-one The title compound (Intermediate 42) was prepared from the remaining one of (7R,8R)- or (7S,8S)-2-chloro-7,8-dimethyl-7,8-dihydro-5H-pyrano[4,3-b]pyridin-5-one (second eluting isomer from step 1) using the same two-step procedure as described in Steps 4 and 5 for Intermediate 2. MS (ES+) $C_{10}H_{12}N_2O_2$ requires: 192, found: 193[M+H]$^+$.

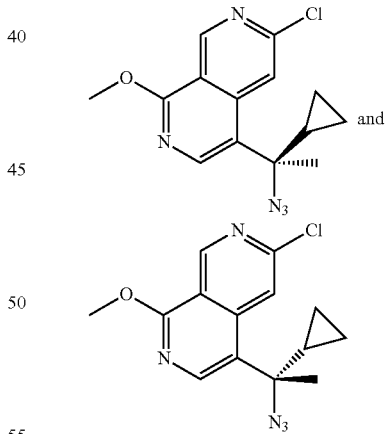

Intermediate 43 and 44: (R)-4-(1-Azido-1-cyclopropylethyl)-6-chloro-1-methoxy-2,7-naphthyridine or (S)-4-(1-azido-1-cyclopropylethyl)-6-chloro-1-methoxy-2,7-naphthyridine Intermediates 43 and 44 were made using a similar procedure as described for Intermediates 33 and 34, except in step 1, methanol was used and in step 4, cyclopropylmagnesium bromide was used and the reaction was stirred at 60° C. for 30 min. The racemic title compound (1.20 g, 3.95 mmol) was separated by SFC (column: Daicel Chiralpak IG (250 mm×30 mm, 10 um); mobile phase: [MeOH (with 0.1% NH₄OH) in CO₂]) to give: (R)-4-(1-azido-1-cyclopropylethyl)-6-chloro-1-methoxy-2,7-naphthyridine or (S)-4-(1-azido-1-cyclopropylethyl)-6-chloro-1-methoxy-2,7-naphthyridine (Intermediate 43, first eluting isomer, 490 mg, 40% yield) as a yellow oil and a second eluting isomer (Intermediate 44, 430 mg, 34% yield) as a yellow oil.

Intermediate 45: 2'-Amino-5'H,7'H-spiro[cyclopropane-1,8'-pyrano[4,3-b]pyridin]-5'-one

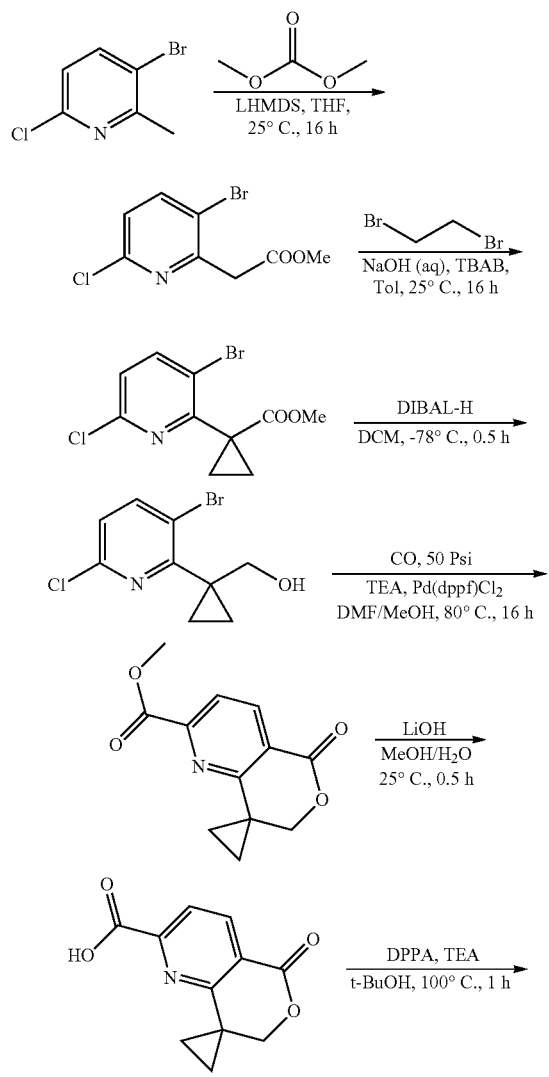

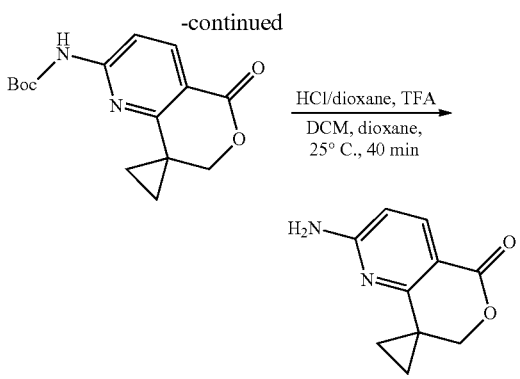

Step 1: Methyl 2-(3-bromo-6-chloropyridin-2-yl)acetate

LiHMDS (1 M, 388 mL) was added to a solution of 3-bromo-6-chloro-2-methylpyridine (20.0 g, 96.9 mmol) in THF (300 mL) at 25° C. under nitrogen. After 2.5 h, dimethyl carbonate (14.0 g, 155 mmol) was added to the mixture and stirred at 25° C. for 13.5 h. The reaction mixture was then was added to saturated aqueous NH₄Cl (1000 mL) and extracted with EA (60 mL×3). The combined organic layers were dried over anhydrous sodium sulfate, filtered and concentrated to give a residue. The residue was purified by flash-column chromatography on silica gel (gradient elution, 0% to 10% EA-petroleum ether) to give the title compound (18.0 g, 70% yield) as a yellow oil. ¹H NMR (400 MHz, CDCl₃): δ ppm 7.81 (d, J=8.4 Hz, 1H), 7.16 (d, J=8.0 Hz, 1H), 4.03 9s, 2H), 3.74 (s, 3H).

Step 2: Methyl 1-(3-bromo-6-chloropyridin-2-yl)cyclopropane-1-carboxylate

Tetrabutylammonium bromide (2.44 g, 7.56 mmol) and NaOH (50 mL, 50 wt % in water) were added to a solution of 1,2-dibromoethane (10.7 g, 56.7 mmol) and methyl 2-(3-bromo-6-chloropyridin-2-yl)acetate (10.0 g, 37.8 mmol) in toluene (50 mL) at 25° C. The reaction mixture was stirred at 25° C. for 16 h, then was diluted with water (300 mL) and extracted with EA (200 mL×3). The combined organic layers were dried over anhydrous sodium sulfate, filtered and concentrated to give a residue. The residue was purified by flash-column chromatography on silica gel (gradient elution, 0% to 10% EA-petroleum ether) to give the title compound (6.10 g, 56% yield) as a yellow solid. ¹H NMR (400 MHz, CDCl₃): δ ppm 7.81 (d, J=8.4 Hz, 1H), 7.15 (d, J=8.0 Hz, 1H), 3.66 (s, 3H), 1.81-1.75 (m, 2H), 1.46-1.41 (m, 2H).

Step 3: (1-(3-Bromo-6-chloropyridin-2-yl)cyclopropyl)methanol

Diisobutylaluminium hydride (1 M, 56 mL) was added to a solution of methyl 1-(3-bromo-6-chloropyridin-2-yl)cyclopropane-1-carboxylate (5.40 g, 18.6 mmol) in DCM (80 mL) at −78° C. under nitrogen. The reaction mixture was stirred at −78° C. for 0.5 h, then was quenched by addition of aqueous saturated NH₄Cl solution (50 mL), diluted with water (200 mL) and extracted with EA (200 mL×3). The combined organic layers were dried over anhydrous sodium sulfate, filtered and concentrated to give the crude title compound (5.00 g, crude) as a yellow solid which was used in the next step without further purification.

Step 4: Methyl 5'-oxo-5'H,7'H-spiro[cyclopropane-1,8'-pyrano[4,3-b]pyridine]-2'-carboxylate Triethylamine (2.31 g, 22.9 mmol) and Pd(dppf)Cl$_2$ (557 mg, 762 μmol) were added to a solution of (1-(3-Bromo-6-chloropyridin-2-yl)cyclopropyl)methanol in MeOH (25 mL) and DMF (25 mL) under nitrogen atmosphere. The suspension was degassed under vacuum and purged with carbon monoxide several times. The mixture was stirred under carbon monoxide (50 psi) at 80° C. for 16 h. The reaction mixture was then concentrated to remove methanol, diluted with water (100 mL) and extracted with EA (60 mL×3). The combined organic layers were washed with brine (100 mL×3), dried over anhydrous sodium sulfate, filtered and concentrated to give a residue. The title compound (1.8 g, crude) was obtained as a yellow solid and used in the next step without further purification. MS (ES+) C$_{10}$H$_{10}$N$_2$O$_2$ requires: 233, found: 234[M+H]$^+$.

Step 5: 5'-Oxo-5'H,7'H-spiro[cyclopropane-1,8'-pyrano[4,3-b]pyridine]-2'-carboxylic acid Lithium hydroxide (555 mg, 23.2 mmol) was added to a solution of methyl 5'-oxo-5'H,7'H-spiro[cyclopropane-1,8'-pyrano[4,3-b]pyridine]-2'-carboxylate (1.80 g, 7.72 mmol) in methanol (30 mL) and water (10 mL). The reaction mixture was stirred at 25° C. for 0.5 h, then was concentrated to remove the methanol. The mixture was diluted with water (60 mL) and extracted with EA (50 mL×3). The aqueous layer was acidified by addition aqueous hydrochloric acid solution (6 M, 5 mL), then the mixture was extracted with EA (50 mL×3). The combined organic layers were dried over anhydrous sodium sulfate, filtered and concentrated to give the title compound (1.20 g, 71% yield) as a brown solid that was used without further purification.

Step 6: tert-Butyl (5'-oxo-5'H,7'H-spiro[cyclopropane-1,8'-pyrano[4,3-b]pyridin]-2'-yl)carbamate Triethylamine (831 mg, 8.21 mmol) and diphenyl phosphoryl azide (2.26 g, 8.21 mmol) were added to a solution of 5'-oxo-5'H,7'H-spiro[cyclopropane-1,8'-pyrano[4,3-b]pyridine]-2'-carboxylic acid (1.20 g, 5.47 mmol) in tert-butanol (20 mL). The reaction mixture was stirred at 100° C. for 1 h, then was cooled to ambient temperature, diluted with water (60 mL), and extracted with EA (50 mL×3). The combined organic layers were dried over anhydrous sodium sulfate, filtered and concentrated to give a residue. The residue was purified by flash-column chromatography on silica gel (gradient elution, 0% to 50% EA-petroleum ether) to give the title compound (330 mg, 19% yield) as a yellow solid and 2'-amino-5'H,7'H-spiro[cyclopropane-1,8'-pyrano[4,3-b]pyridin]-5'-one (420 mg, 28% yield) as a yellow oil.

Step 7: 2'-Amino-5'H,7'H-spiro[cyclopropane-1,8'-pyrano[4,3-b]pyridin]-5'-one HCl in dioxane (4.0 M, 0.5 mL) was added to a solution of tert-butyl (5'-oxo-5'H,7'H-spiro[cyclopropane-1,8'-pyrano[4,3-b]pyridin]-2'-yl)carbamate (100 mg, 344 μmol) in dioxane (1.5 mL) at 25° C. The reaction mixture was stirred for 10 min, then was concentrated. DCM (2 mL) and TFA (1 mL, 13.5 mmol) were added to the residue, and the reaction mixture was stirred at 25° C. for 30 min. The reaction mixture was then concentrated and EA (5 mL) was added to the residue. The mixture was neutralized by addition of saturated aqueous NaHCO$_3$ (20 mL) and extracted with EA (15 mL×3). The combined organic layers were dried over anhydrous sodium sulfate, filtered and concentrated under to give the title compound (60.0 mg, 92% yield) as a yellow oil that was used in the next step without further purification. MS (ES+) C$_{12}$H$_{11}$NO$_4$ requires: 190, found: 191 [M+H]$^+$.

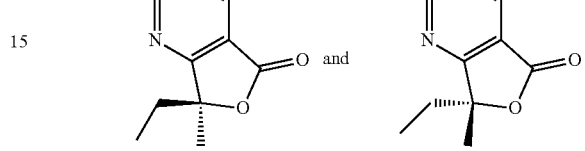

Intermediates 46 and 47: (S)-2-Amino-7-ethyl-7-methylfuro[3,4-b]pyridin-5(7H)-one and (R)-2-amino-7-ethyl-7-methylfuro[3,4-b]pyridin-5(7H)-one

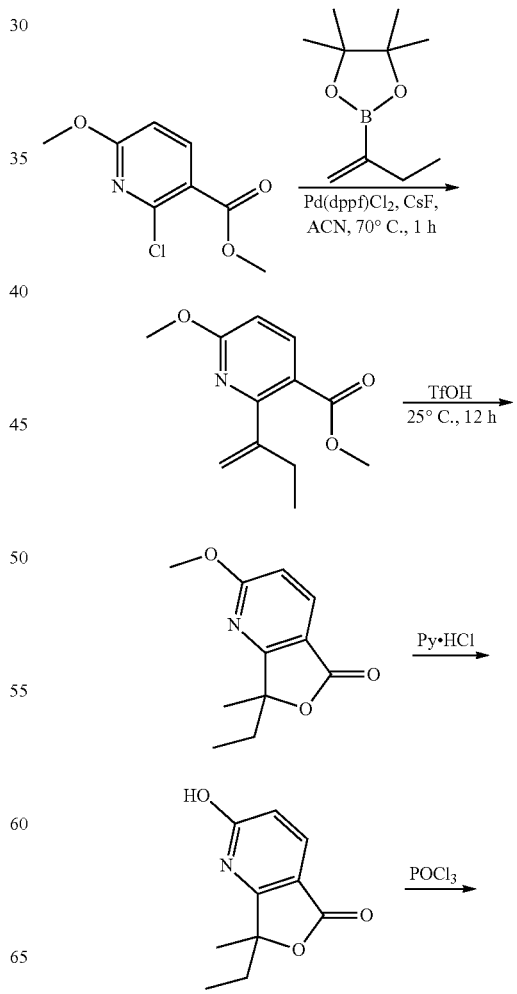

-continued

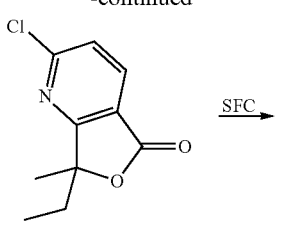

Precursor of Intermediate 46 (1st eluting isomer) and Precursor of Intermediate 47 (2nd eluting isomer)

each of which is represented by one of the structures shown below:

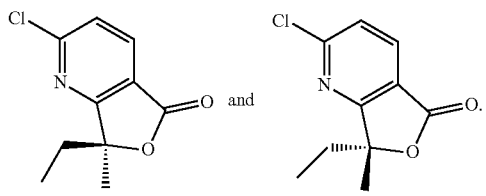

Precursor I of Intermediate 46 or Precursor I of Intermediate 47 →(DMBNH₂, NMP / 100° C., 2 h) Precursor II of Intermediate 46 or Precursor II of Intermediate 47 which is represented by one of the structures shown below:

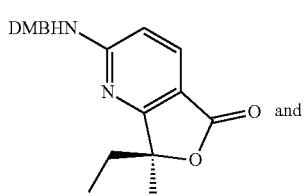

Precursor II of Intermediate 46 or Precursor II of Intermediate 47 →(HCl/dioxane (4N) / dioxane, 60° C., 2 h) Intermediate 46 or Intermediate 47 which is represented by one of the structures shown below:

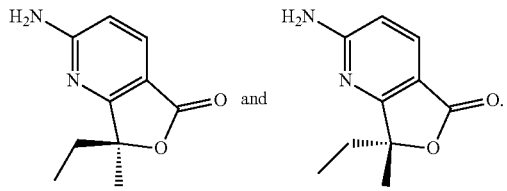

Steps 1-4: 2-Chloro-7-ethyl-7-methylfuro[3,4-b]pyridin-5(7H)-one

The title compound was prepared from methyl 2-chloro-6-methoxynicotinate and 2-(but-1-en-2-yl)-4,4,5,5-tetramethyl-1,3,2-dioxaborolane using similar procedures as described above for Intermediate 17 (Steps 1-3, 5), except CsF was used as a base in Step 1 and Step 2 was conducted at 25° C. for 1 h.

Step 5: (S)-2-Chloro-7-ethyl-7-methylfuro[3,4-b]pyridin-5(7H)-one and (R)-2-chloro-7-ethyl-7-methylfuro[3,4-b]pyridin-5(7H)-one 2-Chloro-7-ethyl-7-methylfuro[3,4-b]pyridin-5(7H)-one (1.9 g, 8.98 mmol) was separated by SFC (column: DAICEL CHIRALPAK AS-H (250 mm*30 mm, 5 um); mobile phase: [0.1% NH₄OH EtOH in CO₂]) to give one of (R or S)-2-chloro-7-ethyl-7-methylfuro[3,4-b]pyridin-5(7H)-one (1a eluting isomer, 0.70 g, 37% yield) and the remaining one of (R or S)-2-Chloro-7-ethyl-7-methylfuro[3,4-b]pyridin-5(7H)-one (2$^{nd}$ eluting isomer, 0.90 g, 47% yield) as yellow oils.

Steps 6 and 7: One of (R or S)-2-amino-7-ethyl-7-methylfuro[3,4-b]pyridin-5(7H)-one The title compound (Intermediate 46) was prepared from one of (R or S)-2-chloro-7-ethyl-7-methylfuro[3,4-b]pyridin-5(7H)-one (first eluting isomer from step 5) using the same two-step procedure as described in Steps 4 and 5 for Intermediate 2. ¹H-NMR (400 MHz, 6d-DMSO): δ ppm 7.67 (d, J=8.4 Hz, 1H), 7.29 (s, 2H), 6.52-6.46 (m, 1H), 1.93-1.78 (m, 2H), 1.47 (s, 3H), 0.63 (d, J=7.2 Hz, 3H). MS (ES+) C₁₀H₁₂N₂O₂ requires: 192, found: 193 [M+H]⁺.

Steps 8 and 9: The remaining one of (R or S)-2-amino-7-ethyl-7-methylfuro[3,4-b]pyridin-5(7H)-one The title compound (Intermediate 47) was prepared from the remaining one of (R or S)-2-chloro-7-ethyl-7-methylfuro[3,4-b]pyridin-5(7H)-one (second eluting isomer from step 5) using the same two-step procedure as described in Steps 4 and 5 for Intermediate 2. ¹H-NMR (400 MHz, 6d-DMSO): δ ppm 7.68 (d, J=8.8 Hz, 1H), 7.30 (s, 2H), 6.49 (d, J=8.8 Hz, 1H), 1.95-1.79 (m, 2H), 1.48 (s, 3H), 0.64 (d, J=7.4 Hz, 3H). MS (ES+) C₁₀H₁₂N₂O₂ requires: 192, found: 193 [M+H]⁺.

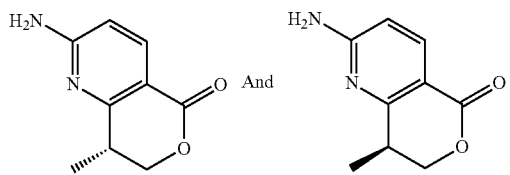

Intermediates 48 and 49: (R)-2-Amino-8-methyl-7,8-dihydro-5H-pyrano[4,3-b]pyridin-5-one and (S)-2-amino-8-methyl-7,8-dihydro-5H-pyrano[4,3-b]pyridin-5-one

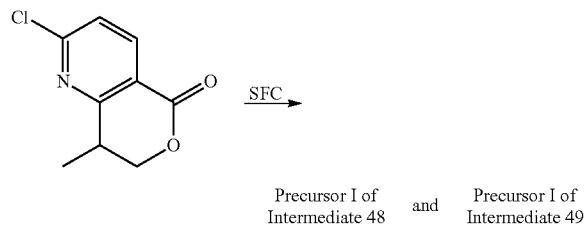

each of which is represented by one of the structures shown below:

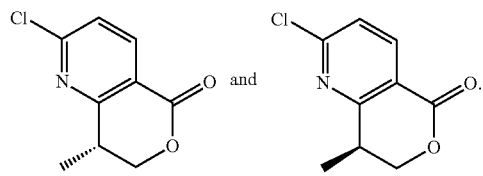

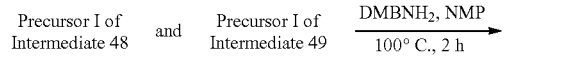

which is represented by one of the structures shown below:

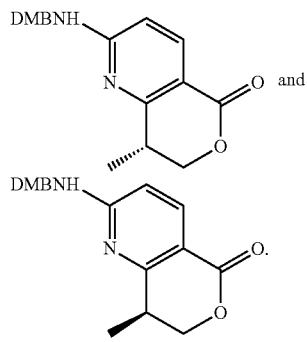

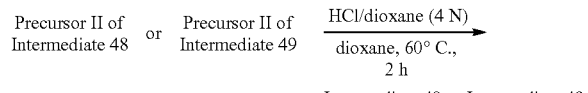

which is represented by one of the structures below:

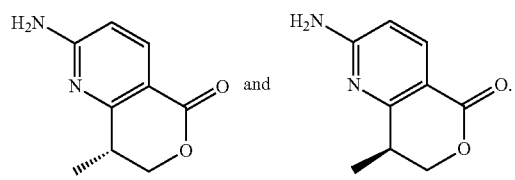

Step 1: (R)-2-chloro-8-methyl-7,8-dihydro-5H-pyrano[4,3-b]pyridin-5-one and (S)-2-chloro-8-methyl-7,8-dihydro-5H-pyrano[4,3-b]pyridin-5-one rac-2-Chloro-8-methyl-7,8-dihydro-5H-pyrano[4,3-b]pyridin-5-one (700 mg, 3.54 mmol) was separated by SFC (Daicel Chiralpak IG, MeOH gradient in $CO_2$ with 0.1% $NH_4OH$) to give two peaks separately. The first eluting isomer (330 mg, 47% yield) and second eluting isomer (330 mg, 47% yield) were obtained as yellow solids.

Steps 2 and 3: One of (R or S)-2-amino-8-methyl-7,8-dihydro-5H-pyrano[4,3-b]pyridin-5-one The title compound (Intermediate 48) was prepared from one of (R or S)-2-chloro-8-methyl-7,8-dihydro-5H-pyrano[4,3-b]pyridin-5-one (first eluting isomer from step 1) using the same two-step procedure as described in Steps 4 and 5 for Intermediate 2. MS (ES+) $C_9H_{10}N_2O_2$ requires: 178, found: 179$[M+H]^+$.

Steps 3 and 4: The remaining one of (R or S)-2-amino-8-methyl-7,8-dihydro-5H-pyrano[4,3-b]pyridin-5-one The title compound (Intermediate 49) was prepared from the remaining one of (R or S)-2-chloro-8-methyl-7,8-dihydro-5H-pyrano[4,3-b]pyridin-5-one (second eluting isomer from step 1) using the same two-step procedure as described in Steps 4 and 5 for Intermediate 2. MS (ES+) $C_9H_{10}N_2O_2$ requires: 178, found: 179$[M+H]^+$.

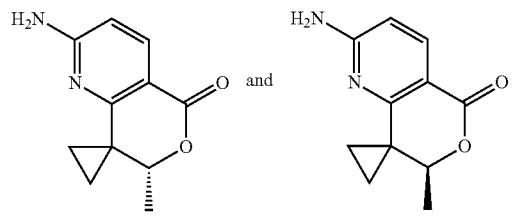

Intermediates 50 and 51: (R)-2'-Amino-7'-methyl-5'H,7'H-spiro[cyclopropane-1,8'-pyrano[4,3-b]pyridin]-5'-one and (S)-2'-Amino-7'-methyl-5'H,7'H-spiro[cyclopropane-1,8'-pyrano[4,3-b]pyridin]-5'-one

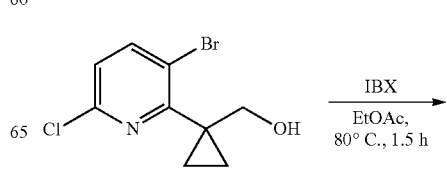

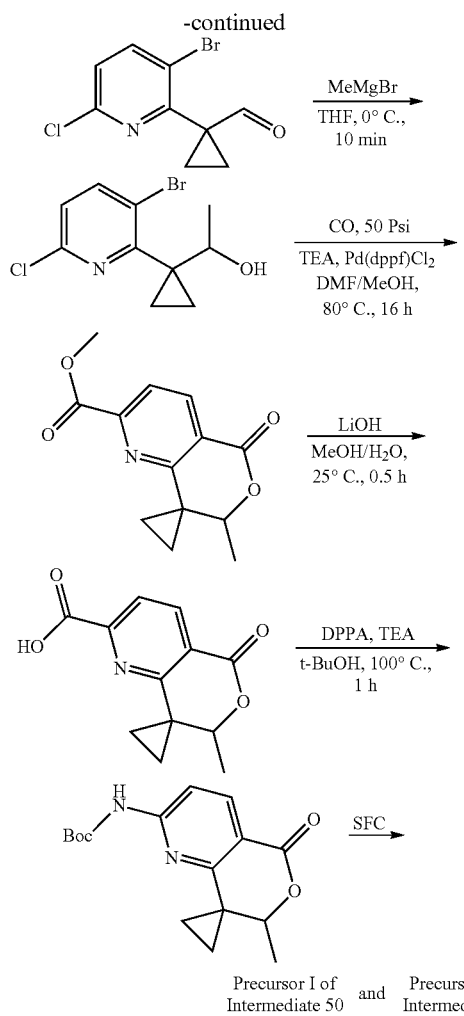

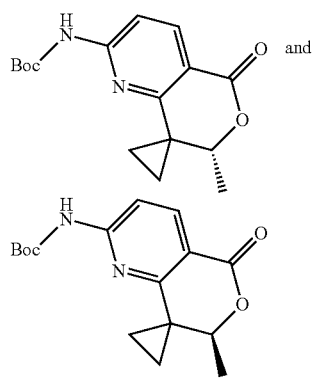

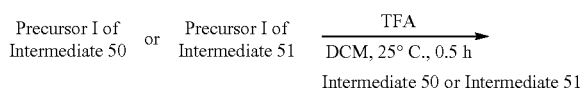

each of which is represented by one of the structures shown below:

which is represented by one of the structures shown below:

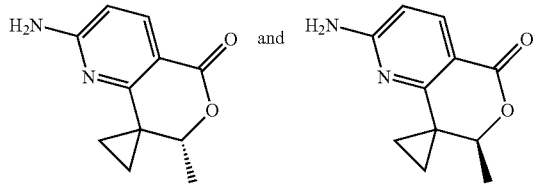

Step 1: 1-(3-Bromo-6-chloropyridin-2-yl)cyclopropane-1-carbaldehyde

IBX (6.50 g, 10.7 mmol, 46% purity) was added to a solution of (1-(3-bromo-6-chloropyridin-2-yl)cyclopropyl)methanol (2.65 g, 10.1 mmol) in EA (80 mL). The reaction mixture was stirred at 80° C. for 1 h, then additional IBX (2.00 g, 3.29 mmol, 46% purity) was added. The reaction mixture was stirred at 80° C. for 0.5 h, then was filtered and concentrated to give the title compound (2.60 g, crude) as a yellow solid that was used without further purification. MS (ES+) $C_9H_7BrClNO$ requires: 261, found: 262 $[M+H]^+$.

Step 2: 1-(1-(3-Bromo-6-chloropyridin-2-yl)cyclopropyl)ethan-1-ol

Methylmagnesium bromide (3 M, 17 mL) was added to a solution of 1-(3-bromo-6-chloropyridin-2-yl)cyclopropane-1-carbaldehyde (2.60 g, 9.98 mmol) in THF (80 mL) at 0° C. The reaction mixture was stirred for 10 min, then was quenched by addition of aqueous saturated $NH_4Cl$ solution (80 mL), diluted with water (40 mL) and extracted with EA (80 mL×3). The combined organic layers were dried over anhydrous sodium sulfate, filtered and concentrated to give the title compound (2.70 g, crude) as a yellow oil that was used without further purification. MS (ES+) $C_{10}H_{11}N_2O_2$ requires: 277, found: 278 $[M+H]^+$.

Steps 3-5: tert-Butyl (7'-methyl-5'-oxo-5'H,7'H-spiro[cyclopropane-1,8'-pyrano[4,3-b]pyridin]-2'-yl)carbamate The title compound was prepared from 1-(1-(3-bromo-6-chloropyridin-2-yl)cyclopropyl)ethan-1-ol using a similar procedure as described in Steps 4-6 for Intermediate 45 above. $^1$H NMR (400 MHz, $CDCl_3$): δ ppm 8.29 (d, J=8.8 Hz, 1H), 7.90 (d, J=8.8 Hz, 1H), 7.31 (s, 1H), 4.63-4.53 (m, 1H), 1.61 (s, 3H), 1.53 (s, 9H), 1.38-1.35 (m, 1H), 1.09-1.00 (m, 2H).

Step 6: tert-Butyl (R)-(7'-methyl-5'-oxo-5'H,7'H-spiro[cyclopropane-1,8'-pyrano[4,3-b]pyridin]-2'-yl)carbamate and tert-butyl (S)-(7'-methyl-5'-oxo-5'H,7'H-spiro[cyclopropane-1,8'-pyrano[4,3-b]pyridin]-2'-yl)carbamate tert-Butyl (7'-methyl-5'-oxo-5'H,7'H-spiro[cyclopropane-1,8'-pyrano[4,3-b]pyridin]-2'-yl)carbamate (400 mg) was separated by SFC (column: REGIS (s,s) WHELK-O1 (250 mm×50 mm, 10 um), EtOH gradient in $CO_2$ with 0.1% $NH_4OH$) to give two separate peaks. The first eluting isomer (100 mg, 24% yield) and second eluting isomer (140 mg, 34% yield) were obtained as yellow solids.

Step 7: One of (R or S)-2'-amino-7'-methyl-5'H, 7'H-spiro[cyclopropane-1,8'-pyrano[4,3-b]pyridin]-5'-one TFA (2.31 g, 20.3 mmol) was added to a solution of one of tert-butyl (R or S)-(7'-methyl-5'-oxo-5H',7'H-spiro[cyclopropane-1,8'-pyrano[4,3-b]pyridin]-2'-yl)carbamate (first eluting isomer from Step 6, 100 mg) in DCM (6 mL). The reaction mixture was stirred at 25° C. for 30 min, then was quenched with saturated aqueous NaHCO$_3$ solution (30 mL) and extracted with DCM (20 mL×3). The combined organic layers were dried over anhydrous sodium sulfate, filtered and concentrated to give the title compound (Intermediate 50, 70 mg, crude) as a yellow oil that was used without further purification. MS (ES+) C$_{11}$H$_{12}$N$_2$O$_2$ requires: 204, found: 205 [M+H]$^+$.

Step 8: The remaining one of (R or S)-2'-amino-7-methyl-5'H,7'H-spiro[cyclopropane-1,8'-pyrano[4,3-b]pyridin]-5'-one The title compound (Intermediate 51) was prepared from one of tert-butyl (R or S)-(7'-methyl-5'-oxo-5'H, 7'H-spiro[cyclopropane-1,8'-pyrano[4,3-b]pyridin]-2'-yl)carbamate (second eluting isomer from Step 6) using the same procedure as described in Step 7 for Intermediate 50. MS (ES+) C$_{11}$H12N$_2$O$_2$ requires: 204, found: 205[M+H]$^+$.

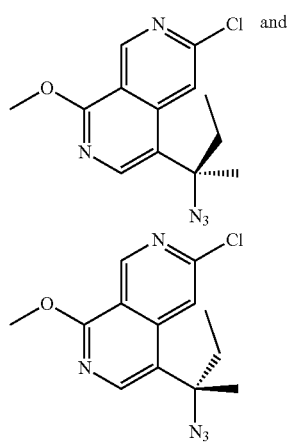

Intermediate 52 and 53: (R)-4-(2-Azidobutan-2-yl)-6-chloro-1-methoxy-2,7-naphthyridine and (S)-4-(2-azidobutan-2-yl)-6-chloro-1-methoxy-2,7-naphthyridine Intermediates 52 and 53 were made using a similar procedure as described for Intermediates 33 and 34, except in step 1, methanol was used. The racemic title compound (0.84 g, 2.87 mmol) was separated by SFC (column: Daicel Chiralpak IG (250 mm×30 mm, 10 um); mobile phase: [MeOH (with 0.1% NH$_4$OH) in CO$_2$]) to give: (R)-4-(2-azidobutan-2-yl)-6-chloro-1-methoxy-2,7-naphthyridine or (S)-4-(2-azidobutan-2-yl)-6-chloro-1-methoxy-2,7-naphthyridine (Intermediate 52, first eluting isomer, 350 mg, 42% yield) as a yellow oil and a second eluting isomer (Intermediate 53, 360 mg, 43% yield) as a yellow solid.

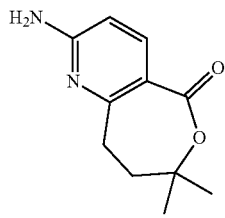

Intermediate 54: 2-Amino-7,7-dimethyl-8,9-dihydrooxepino[4,3-b]pyridin-5(7H)-one

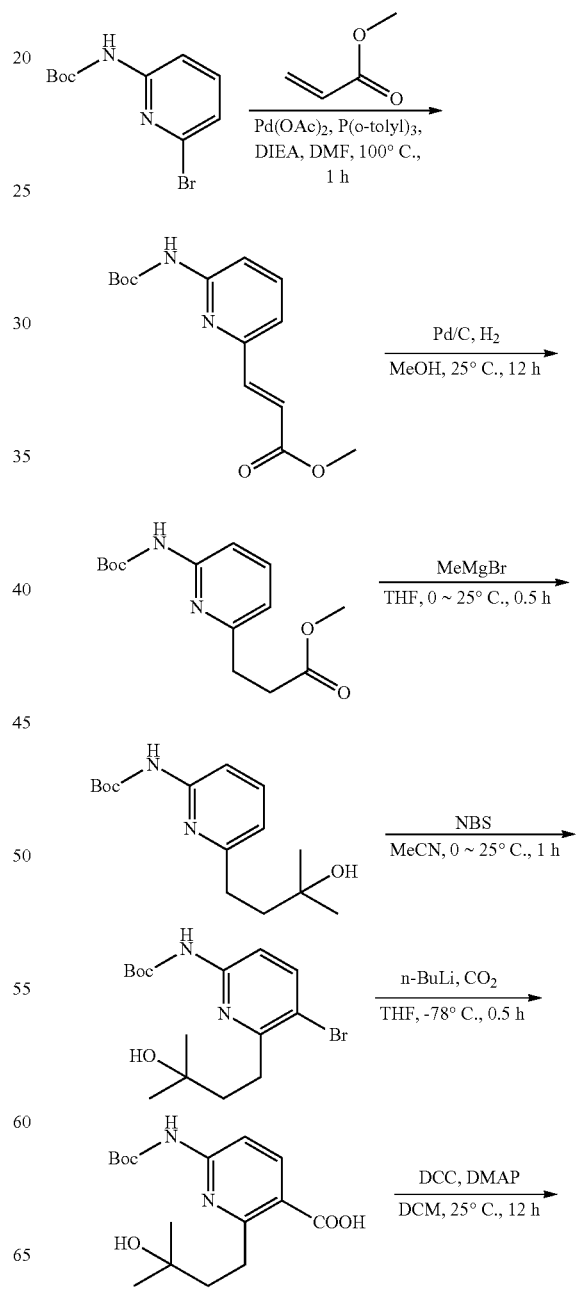

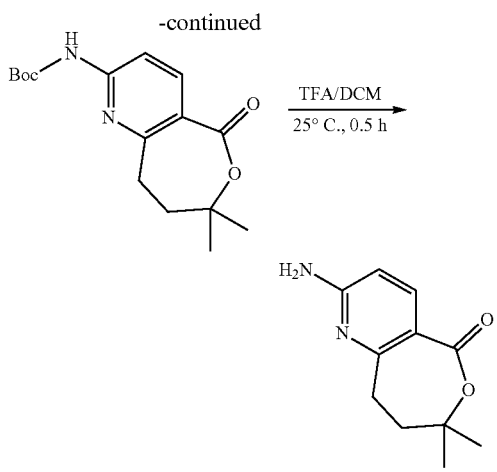

Step 1: Methyl (E)-3-(6-((tert-butoxycarbonyl)amino)pyridin-2-yl)acrylate

Pd(OAc)$_2$ (1.23 g, 5.49 mmol), P(o-tolyl)$_3$ (2.51 g, 8.24 mmol) and diisopropylethylamine (71.0 g, 549 mmol, 95.7 mL) were added to a solution of tert-butyl (6-bromopyridin-2-yl)carbamate (15.0 g, 54.9 mmol) and methyl acrylate (18.9 g, 220 mmol, 19.8 mL) in DMF (150 mL). The reaction mixture was stirred at 100° C. for 1 h, then was diluted EA (200 mL) and washed with brine (200 mL×3). The organic layers were dried over sodium sulfate, filtered and concentrated to give a residue. The residue was purified by flash-column chromatography on silica gel (gradient elution, 10% to 33% EA-petroleum ether) to give the title compound (7.00 g, 39% yield) as a yellow solid.

Step 2: Methyl 3-(6-((tert-butoxycarbonyl)amino)pyridin-2-yl)propanoate

Pd/C (100 mg, 10% purity) was added to a solution of methyl (E)-3-(6-((tert-butoxycarbonyl)amino)pyridin-2-yl)acrylate (7.00 g, 25.2 mmol) in MeOH (100 mL). The mixture was stirred at 25° C. for 12 h under hydrogen, then was filtered and concentrated to give a residue. The residue was purified by flash-column chromatography on silica gel (gradient elution, 10% to 33% EA-petroleum ether) to give the title compound (6.00 g, 18.6 mmol, 74% yield) as a yellow solid.

Step 3: tert-Butyl (6-(3-hydroxy-3-methylbutyl)pyridin-2-yl)carbamate

Methyl magnesium bromide (3 M, 35.7 mL) was added to a solution of methyl 3-(6-Wert-butoxycarbonyl)amino)pyridin-2-yl)propanoate (6.00 g, 21.4 mmol) in THF (100 mL) at 0° C. The reaction mixture was stirred at 25° C. for 0.5 h, then was poured into water (200 mL) and extracted with EA (50 mL×3). The combined organic layers were dried over sodium sulfate, filtered, and concentrated to give a residue. The residue was purified by flash-column chromatography on silica gel (gradient elution, 15% to 50% EA-PE) to give the title compound (5.00 g, 15.9 mmol, 74% yield) as a yellow solid.

Step 4: tert-Butyl (5-bromo-6-(3-hydroxy-3-methylbutyl)pyridin-2-yl)carbamate N-Bromosuccinimide (3.17 g, 17.8 mmol) in ACN (50 mL) was added to a solution of tert-butyl (6-(3-hydroxy-3-methylbutyl)pyridin-2-yl)carbamate (5.00 g, 17.8 mmol) in ACN (50 mL) at 0° C. The reaction mixture was stirred at 25° C. for 1 h, then was poured into water (200 mL) and extracted with EA (50 mL×3). The combined organic layers were dried over sodium sulfate, filtered, and concentrated to give a residue. The residue was purified by flash-column chromatography on silica gel (gradient elution, 10% to 33% EA-petroleum ether) to give the title compound (4.00 g, 62% yield) as a yellow solid. $^1$H-NMR (400 MHz, CDCl$_3$): δ ppm 7.72 (d, J=8.4 Hz, 1H), 7.65 (d, J=8.8 Hz, 1H), 7.39 (S, 1H), 2.99-2.93 (m, 2H), 1.87-1.78 (m, 2H), 1.49 (s, 9H), 1.27 (s, 6H).

Step 5: 6-((tert-Butoxycarbonyl)amino)-2-(3-hydroxy-3-methylbutyl)nicotinic acid n-Butyllithium (2.5 M, 11.1 mL) was added to a solution of tert-butyl (5-bromo-6-(3-hydroxy-3-methylbutyl)pyridin-2-yl)carbamate (2.00 g, 5.57 mmol) in THF (50 mL) at −78° C. The reaction mixture was stirred at −78° C. for 10 min, then carbon dioxide was added and the mixture was stirred at −78° C. for 20 min. The reaction mixture was then poured into water (100 mL) and extracted with EA (30 mL×3). The organic layers were discarded and aqueous ammonium chloride solution was added to the aqueous layer to adjust pH<7. The mixture was extracted with EA (30 mL×5), and the combined organic layers was dried over sodium sulfate, filtered and concentrated to give the title compound (200 mg, crude) as a yellow solid.

Step 6: tert-Butyl (7,7-dimethyl-5-oxo-5,7,8,9-tetrahydrooxepino[4,3-b]pyridin-2-yl)carbamate Dicyclohexylcarbodiimide (229 mg, 1.11 mmol, 225 μL) was added to a solution of 6-((tert-butoxycarbonyl)amino)-2-(3-hydroxy-3-methylbutyl)nicotinic acid (180 mg, crude) and 4-N,N-dimethylaminopyridine (33.9 mg, 277 μmol) in DCM (20 mL). The reaction mixture was stirred at 25° C. for 12 h, then was concentrated to give the residue. The residue purified by prep-TLC on silica gel (33% EA-petroleum ether) to give the title compound (30.0 mg, crude) as a yellow solid.

Step 7: 2-Amino-7,7-dimethyl-8,9-dihydrooxepino[4,3-b]pyridin-5(7H)-one

The title compound was prepared from tert-butyl (7,7-dimethyl-5-oxo-5,7,8,9-tetrahydrooxepino[4,3-b]pyridin-2-yl)carbamate using a similar procedure as describe in Step 7 of Intermediate 50. $^1$H-NMR (400 MHz, CDCl$_3$): δ ppm 7.92 (d, J=8.8 Hz, 1H), 6.36 (d, J=8.8 Hz, 1H), 5.17 (s, 2H), 2.96-2.92 (m, 2H), 2.11-2.09 (m, 2H), 1.33 (s, 6H).

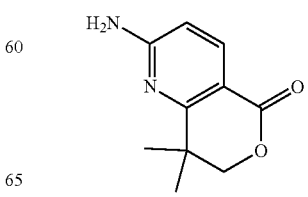

Intermediate 55: 2-Amino-8,8-dimethyl-7,8-dihydro-5H-pyrano[4,3-b]pyridin-5-one

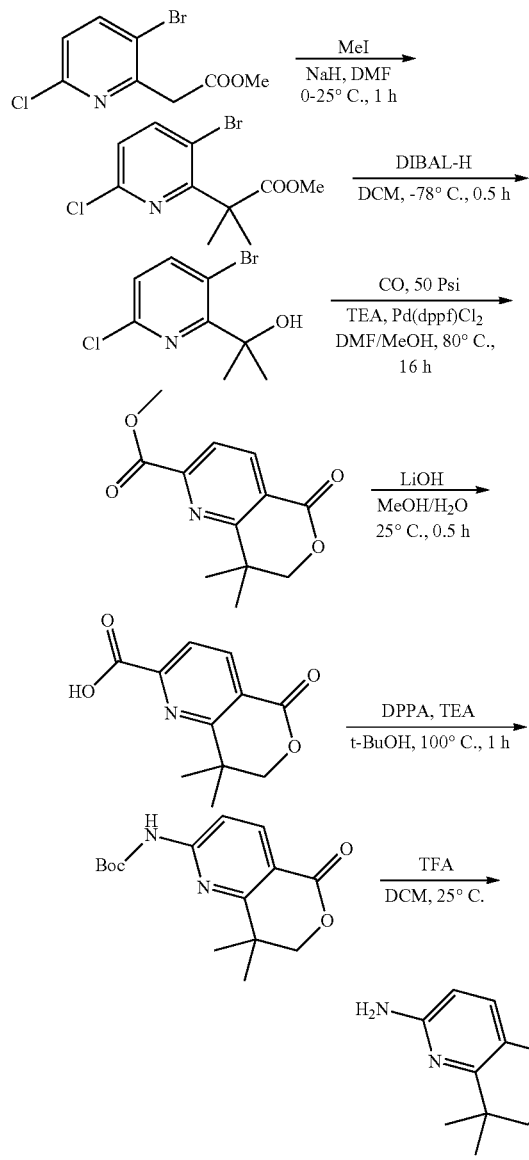

Step 1: Methyl 2-(3-bromo-6-chloropyridin-2-yl)-2-methylpropanoate

Sodium hydride (2.91 g, 72.8 mmol, 60% purity) was added to a solution of methyl 2-(3-bromo-6-chloropyridin-2-yl)acetate (5.50 g, 20.8 mmol) in THF (20 mL) at 0° C. The reaction mixture was stirred for 15 minutes at 0° C., then iodomethane (7.38 g, 51.9 mmol) was added. The reaction mixture was warmed to 25° C. and stirred for 45 min, then was quenched with water (30 mL) and extracted with EA (30 mL×2). The combined organic layers were concentrated to give a residue. The residue was purified by flash-column chromatography on silica gel (gradient elution, 0% to 10% EA-petroleum ether) to give the title compound (5.5 g, 90% yield) as a yellow oil. $^1$H NMR (400 MHz, CD$_3$OD): δ ppm 7.97 (d, J=8.4 Hz, 1H), 7.20 (d, J=8.4 Hz, 1H), 3.95 (s, 2H), 1.50 (s, 6H)

Steps 2-6: 2-Amino-8,8-dimethyl-7,8-dihydro-5H-pyrano[4,3-b]pyridin-5-one

The title compound was prepared using similar procedures as described in Steps 3-6 of Intermediate 45 and Step 7 of Intermediate 50. MS (ES+) C$_{10}$H$_{12}$N$_2$O$_2$ requires: 192, found: 193 [M+H]$^+$. $^1$H NMR (400 MHz, 6d-DMSO): δ ppm 7.77 (d, J=8.8 Hz, 1H), 7.01 (s, 2H), 6.40 (d, J=8.8 Hz, 1H), 4.15 (s, 2H), 1.21 (s, 6H).

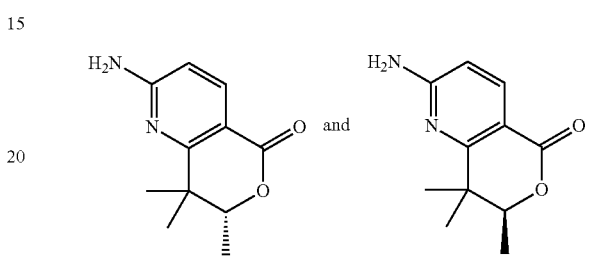

Intermediates 56 and 57: (R)-2-Amino-7,8,8-trimethyl-7,8-dihydro-5H-pyrano[4,3-b]pyridin-5-one and (S)-2-amino-7,8,8-trimethyl-7,8-dihydro-5H-pyrano[4,3-b]pyridin-5-one

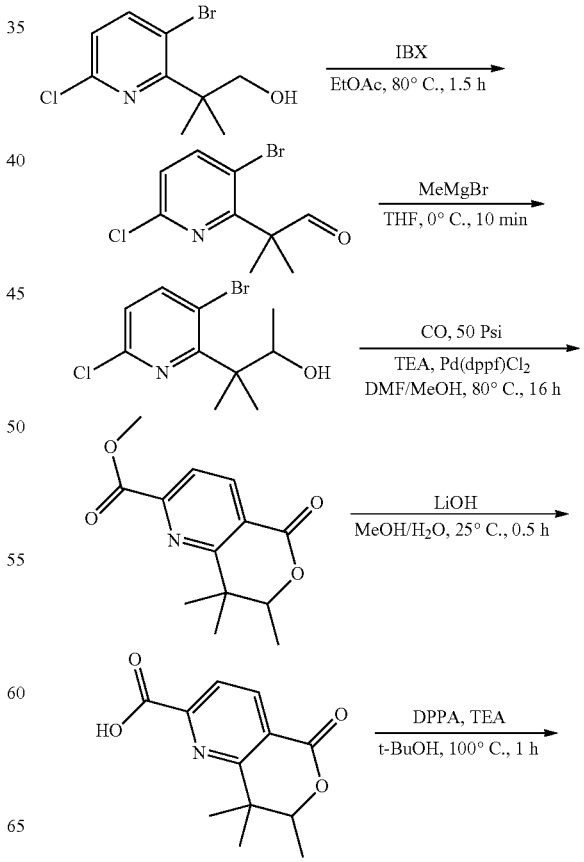

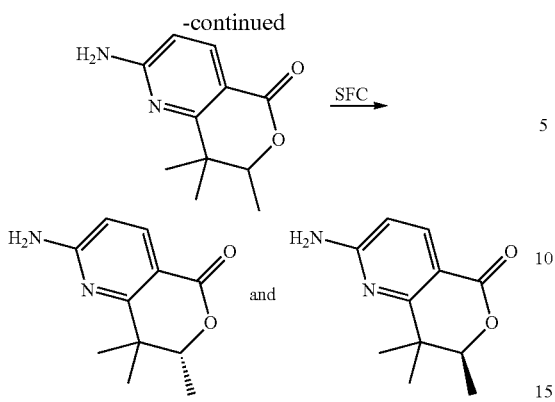

Steps 1-5: (rac)-2-Amino-7,8,8-trimethyl-7,8-di-hydro-5H-pyrano[4,3-b]pyridin-5-one The title compound was prepared from 2-(3-bromo-6-chloropyridin-2-yl)-2-methylpropan-1-ol using a similar procedure as described in Steps 1-5 of Intermediate 50. $C_{11}H_{14}N_2O_2$ requires: 206, found: 207 [M+H]$^+$.

Step 6: (R)-2-Amino-7,8,8-trimethyl-7,8-dihydro-5H-pyrano[4,3-b]pyridin-5-one and (S)-2-amino-7,8,8-trimethyl-7,8-dihydro-5H-pyrano[4,3-b]pyridin-5-one (rac)-2-Amino-7,8,8-trimethyl-7,8-dihydro-5H-pyrano[4,3-b]pyridin-5-one (120 mg) was separated by SFC (column: REGIS (s,s) WHELK-O1 (250 mm×50 mm, 10 um), MeOH gradient in $CO_2$ with 0.1% $NH_4OH$) to give two peaks separately. The first eluting isomer, one of (R or S)-2-Amino-7,8,8-trimethyl-7,8-dihydro-5H-pyrano[4,3-b]pyridin-5-one (Intermediate 56, 60 mg, 50% yield) and second eluting isomer, one of (R or S)-2-Amino-7,8,8-trimethyl-7,8-dihydro-5H-pyrano[4,3-b]pyridin-5-one (Intermediate 5760 mg, 50% yield) were obtained as yellow solids.

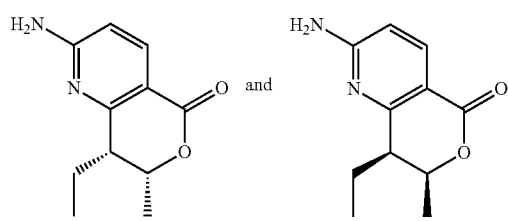

Intermediates 58 and 59: (7R,8R)-2-Amino-8-ethyl-7-methyl-7,8-dihydro-5H-pyrano[4,3-b]pyridin-5-one and (7S,8S)-2-amino-8-ethyl-7-methyl-7,8-dihydro-5H-pyrano[4,3-b]pyridin-5-one

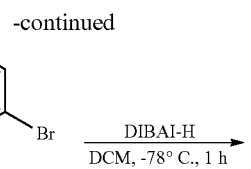

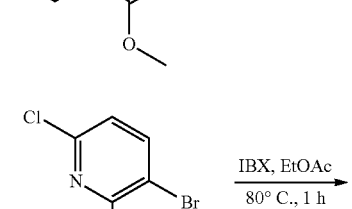

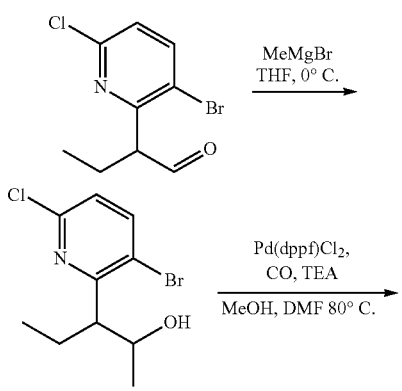

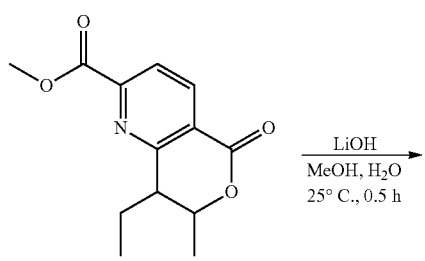

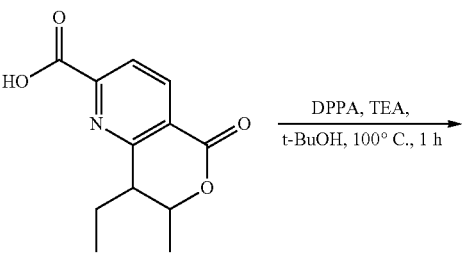

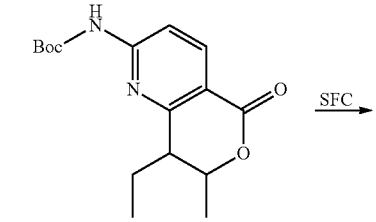

Precursor I of Intermediate 58 and Precursor I of Intermediate 59 each of which is represented by one of the structures shown below:

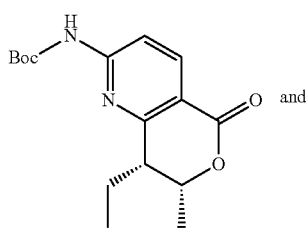

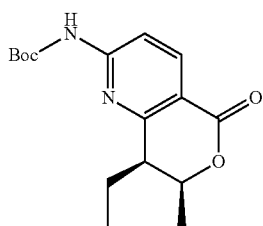

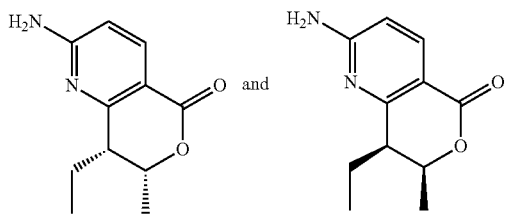

which is represented by one of the structures shown below:

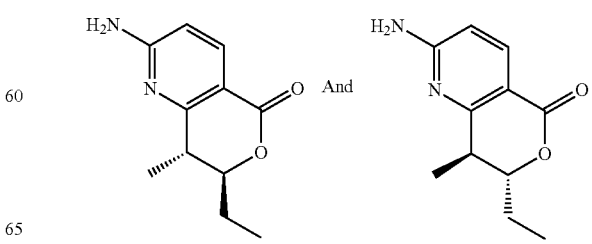

Step 1: Methyl 2-(3-bromo-6-chloropyridin-2-yl)butanoate

NaH (1.69 g, 42.2 mmol, 60 wt%) was added to a solution of methyl 2-(3-bromo-6-chloropyridin-2-yl)acetate (9.3 g, 35.2 mmol) in THF (100 mL) at 0° C. The reaction mixture was stirred at 0° C. for 0.5 h, iodoethane (6.03 g, 38.9 mmol) was added to the reaction mixture. The reaction mixture was stirred for 30 min, then was quenched by addition of aqeuous $NH_4Cl$ solution (20 mL) and extracted with EA (20 mL×3). The combined organic layers were concentrated under reduced pressure to give a residue. The aqueous layer was also concentrated to give a residue. That residue was dissolved in EA (500 mL), filtered and concentrated to give a residue. The residues were purified by flash-column chromatography on silica gel (gradient elution, 0% to 20% EA-PE) to give the title compound (6.5 g, 63% yield) as a colorless oil. $^1$H NMR (400 MHz, $CDCl_3$): δ ppm 7.71 (d, J=8.4 Hz, 1H), 7.04-7.01 (m, 1H), 4.12-4.03 (m, 1H), 3.62 (s, 3H), 2.14-2.09 (m, 1H), 2.02-1.96 (m, 1H), 0.89-0.84 (m, 3H).

Steps 2-7: tert-Butyl (8-ethyl-7-methyl-5-oxo-7,8-dihydro-5H-pyrano[4,3-b]pyridin-2-yl)carbamate The title compound was prepared from methyl 2-(3-bromo-6-chloropyridin-2-yl)butanoate using a similar procedure as described in Step 3 of Intermediate 45 and Steps 1-5 of Intermediate 50.

Step 8: tert-Butyl ((7R,8R)-8-ethyl-7-methyl-5-oxo-7,8-dihydro-5H-pyrano[4,3-b]pyridin-2-yl)carbamate and tert-butyl ((7S,8S)-8-ethyl-7-methyl-5-oxo-7,8-dihydro-5H-pyrano[4,3-b]pyridin-2-yl)carbamate tert-Butyl (8-ethyl-7-methyl-5-oxo-7,8-dihydro-5H-pyrano[4,3-b]pyridin-2-yl)carbamate (200 mg) was separated by SFC (column: Daicel Chiralpak AD-H (250 mm×30 mm, 5 um), IPA gradient in $CO_2$ with 0.1% $NH_4OH$) to give two peaks separately. The first eluting isomer (80 mg, 40% yield) and second eluting isomer (70 mg, 35% yield) were obtained as colorless oils

Step 9: One of (7R,8R or 7S,8S)-2-amino-8-ethyl-7-methyl-7,8-dihydro-5H-pyrano[4,3-b]pyridin-5-one The title compound (Intermediate 58) was prepared from one of tert-butyl ((7R,8R or 7S,8S)-8-ethyl-7-methyl-5-oxo-7,8-dihydro-5H-pyrano[4,3-b]pyridin-2-yl)carbamate (first eluting isomer from Step 8) using the same procedure as described in Step 7 for Intermediate 50. MS (ES+) $C_{11}H_{14}N_2O_2$ requires: 206, found: 207[M+H]$^+$.

Step 10: The remaining one of (7R,8R or 7S,8S)-2-amino-8-ethyl-7-methyl-7,8-dihydro-5H-pyrano[4,3-b]pyridin-5-one The title compound (Intermediate 59) was prepared from one tert-butyl ((7R,8R or 7S,8S)-8-ethyl-7-methyl-5-oxo-7,8-dihydro-5H-pyrano[4,3-b]pyridin-2-yl)carbamate (second eluting isomer from Step 8) using the same procedure as described in Step 7 for Intermediate 50. MS (ES+) $C_{11}H_{14}N_2O_2$ requires: 206, found: 207[M+H]$^+$.

Intermediates 60 and 61: (7S,8R)-2-Amino-7-ethyl-8-methyl-7,8-dihydro-5H-pyrano[4,3-b]pyridin-5-one and (7R,8S)-2-amino-7-ethyl-8-methyl-7,8-dihydro-5H-pyrano[4,3-b]pyridin-5-one

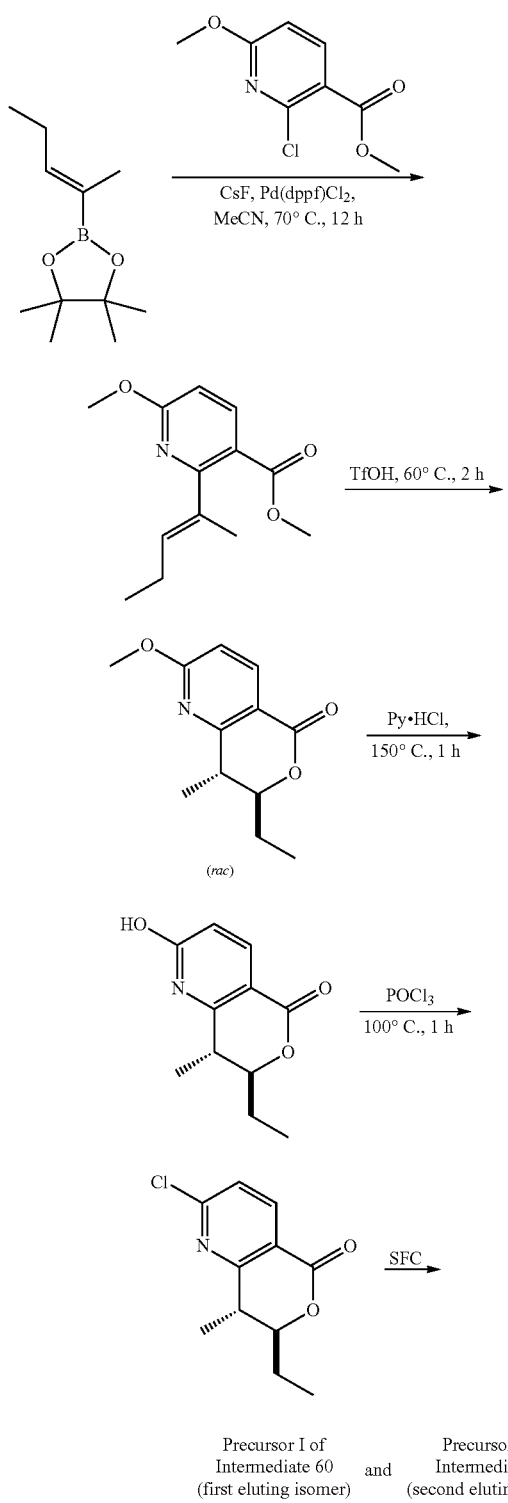

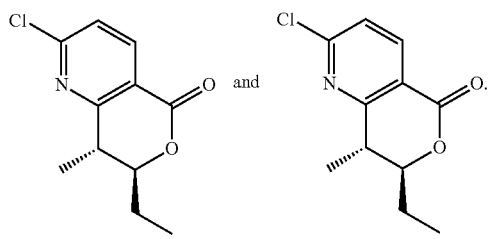

Precursor I of Intermediate 60 or Precursor I of Intermediate 61 $\xrightarrow{\text{DMBNH}_2,\ \text{NMP}}{100°\ \text{C.},\ 2\ \text{h}}$ Precursor II of Intermediate 60 or Precursor II of Intermediate 61 which is represented by one of the structures shown below:

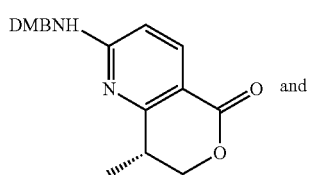

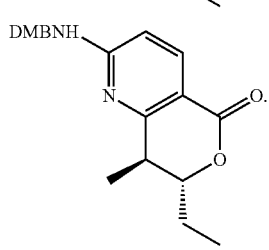

Precursor II of Intermediate 60 or Precursor II of Intermediate 61 $\xrightarrow{\text{HCl/dioxane (4 N)}}{\text{dioxane},\ 60°\ \text{C.},\ 2\ \text{h}}$ Intermediate 60 or Intermediate 61 which is represented by one of the structures shown below:

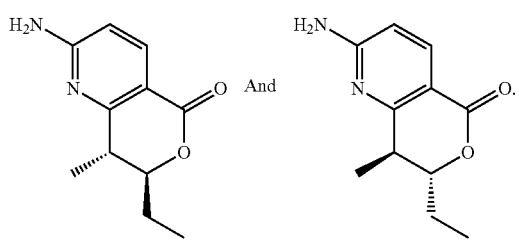

each of which is represented by one of the structures shown below:

Steps 1-2: (7S,8R and 7R,8S)-7-Ethyl-2-methoxy-8-methyl-7,8-dihydro-5H-pyrano[4,3-b]pyridin-5-one The title compound was prepared from (Z)-4,4,5,5-tetramethyl-2-(pent-2-en-2-yl)-1,3,2-dioxaborolane and methyl 2-chloro-6-methoxynicotinate using a similar procedure as described above of Intermediate 17, except CsF was used as a base in Step 1 and Step 2 was conducted at 60° C. for 2 h. The product mixture (4 compounds, cis and trans racemates) was purified by prep-HPLC [column: Phenomenex luna C18 250*80 mm*10 um; mobile phase: [water (0.225% FA)-ACN]; B %: 45%-75%, 25 min] to give the title compound (trans, racemic, 2 g, 27% yield) as a white solid. $^1$H NMR (400 MHz, CDCl$_3$): δ ppm 8.19 (d, J=8.4 Hz, 1H), 6.71 (d, J=8.4 Hz, 1H), 4.27-4.22 (m, 1H), 4.01 (m, 3H), 3.10-2.97 (m, 1H), 1.91-1.85 (m, 1H), 1.84-1.78 (m, 1H), 1.42 (d, J=7.2 Hz, 3H), 1.13-1.08 (m, 3H)

Steps 3-4: (7S,8R and 7R,8S)-2-Chloro-7-ethyl-8-methyl-7,8-dihydro-5H-pyrano[4,3-b]pyridin-5-one The title compound was prepared from (7S,8R and 7R,8S)-7-ethyl-2-methoxy-8-methyl-7,8-dihydro-5H-pyrano[4,3-b]pyridin-5-one using the same procedure as described in Steps 4 and 5 for Intermediate 10.

Step 5: (7S,8R)-2-Chloro-7-ethyl-8-methyl-7,8-dihydro-5H-pyrano[4,3-b]pyridin-5-one and (7R,8S)-2-chloro-7-ethyl-8-methyl-7,8-dihydro-5H-pyrano[4,3-b]pyridin-5-one (7S,8R and 7R,8S)-2-Chloro-7-ethyl-8-methyl-7,8-dihydro-5H-pyrano[4,3-b]pyridin-5-one (255 mg, 1.13 mmol) was separated by SFC (Daicel Chiralpak AD, MeOH gradient in CO$_2$ with 0.1% NH$_4$OH) to give two peaks separately. The first eluting isomer (100 mg, 39% yield) and second eluting isomer (120 mg, 47% yield) were obtained as yellow solids. $^1$H NMR (400 MHz, CDCl$_3$): δ ppm 8.29 (d, J=8.4 Hz, 1H), 7.39 (d, J=8.4 Hz, 1H), 4.36-4.31 (m, 1H), 3.19-3.12 (m, 1H), 1.87-1.75 (m, 2H), 1.46 (d, J=7.2 Hz, 3H), 1.11-1.08 (m, 3H).

Steps 6 and 7: One of (7S,8R)- or (7R,8S)-2-amino-7-ethyl-8-methyl-7,8-dihydro-5H-pyrano[4,3-b]pyridin-5-one The title compound (Intermediate 60) was prepared from one of (7S,8R)- or (7R,8S)-2-chloro-7-ethyl-8-methyl-7,8-dihydro-5H-pyrano[4,3-b]pyridin-5-one (first eluting isomer from step 5) using the same two-step procedure as described in Steps 4 and 5 for Intermediate 2. MS (ES+) C$_{11}$H$_{14}$N$_2$O$_2$ requires: 206, found: 207[M+H]$^+$.

Steps 8 and 9: The remaining one of (7S,8R)- or (7R,8S)-2-amino-7-ethyl-8-methyl-7,8-dihydro-5H-pyrano[4,3-b]pyridin-5-one The title compound (Intermediate 60) was prepared from one of (7S,8R)- or (7R,8S)-2-chloro-7-ethyl-8-methyl-7,8-dihydro-5H-pyrano[4,3-b]pyridin-5-one (second eluting isomer from step 5) using the same two-step procedure as described in Steps 4 and 5 for Intermediate 2. MS (ES+) C$_{11}$H$_{14}$N$_2$O$_2$ requires: 206, found: 207[M+H]$^+$.

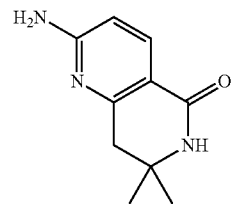

Intermediate 62: 2-Amino-7,7-dimethyl-7,8-dihydro-1,6-naphthyridin-5(6H)-one

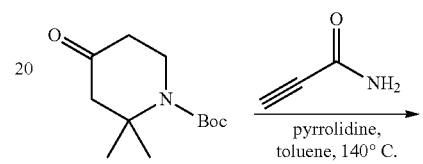

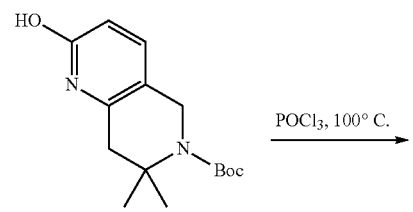

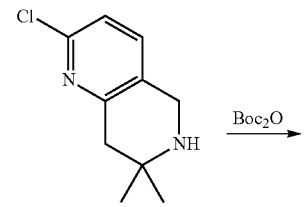

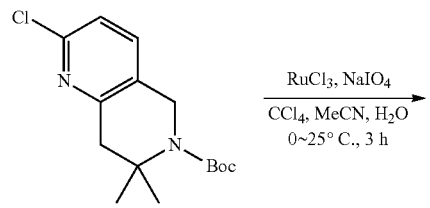

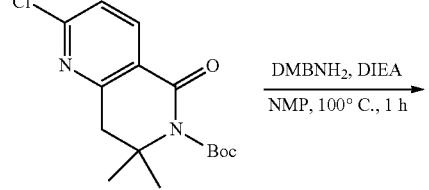

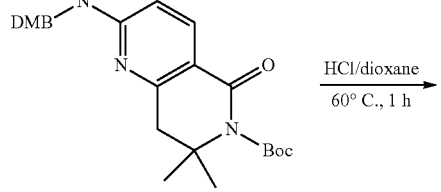

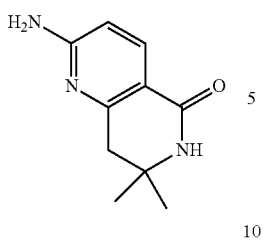

Step 1: tert-Butyl 2-hydroxy-7,7-dimethyl-7,8-dihydro-1,6-naphthyridine-6(5H)-carboxylate A mixture of tert-butyl 2,2-dimethyl-4-oxopiperidine-1-carboxylate (4.00 g, 17.6 mmol) and pyrrolidine (1.25 g, 17.6 mmol) were dissolved in toluene (60 mL), and the solution was heated to 140° C. in a vessel capped with a Dean-Stark trap for 5 h. The mixture was concentrated, then the residue was dissolved in toluene (60 mL) and prop-2-ynamide (1.82 g, 26.4 mmol) was added. The reaction mixture was heated to 140° C. for 16 h, then was concentrated to give a residue. The residue was purified by prep-HPLC: reverse phase [ACN/(0.1% TFA in water), 0% to 50%] to give the title compound (500 mg, 9.5% yield, 93% purity) as brown oil. $^1$H-NMR (400 MHz, CD$_3$OD): δ ppm 7.45 (d, J=9.6 Hz, 1H), 6.54-6.47 (m, 1H), 4.20 (s, 2H), 2.85 (s, 2H), 1.52-1.48 (m, 9H).

Step 2: 2-Chloro-7,7-dimethyl-5,6,7,8-tetrahydro-1,6-naphthyridine

The title compound was prepared from tert-butyl 2-hydroxy-7,7-dimethyl-7,8-dihydro-1,6-naphthyridine-6(5H)-carboxylate using a similar procedure as described in Step 2 of Intermediate 2.

Step 3: tert-Butyl 2-chloro-7,7-dimethyl-7,8-dihydro-1,6-naphthyridine-6(5H)-carboxylate A mixture of 2-chloro-7,7-dimethyl-5,6,7,8-tetrahydro-1,6-naphthyridine (300 mg, 1.53 mmol), sodium hydroxide (305 mg, 7.63 mmol), and Boc$_2$O (665 mg, 3.05 mmol) in water (50 mL) and EtOH (5.0 mL) was stirred at 20° C. for 0.5 h. The reaction mixture was extracted with EA (30 mL×3), and the combined organic layers were washed with water, brine, dried over anhydrous sodium sulfate and concentrated to give a residue. The residue was purified by flash-column chromatography on silica gel (gradient elution, 1% to 25% EA-petroleum ether) to give the title compound (250 mg, 798 umol) as yellow oil.

Steps 4-6: 2-Amino-7,7-dimethyl-7,8-dihydro-1,6-naphthyridin-5(6H)-one

The title compound was prepared from tert-butyl 2-chloro-7,7-dimethyl-7,8-dihydro-1,6-naphthyridine-6 (5H)-carboxylate using a similar procedure as described in Steps 3-5 of Intermediate 2. $^1$H NMR (400 MHz, CDCl$_3$): δ ppm 8.06 (d, J=8.4 Hz, 1H), 6.44 (d, J=8.4 Hz, 1H), 5.48 (s, 1H), 4.80 (s, 2H), 2.89 (s, 2H), 1.34 (s, 6H).

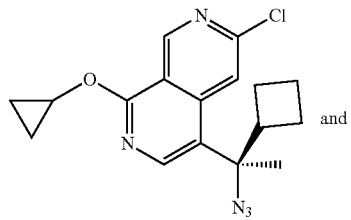

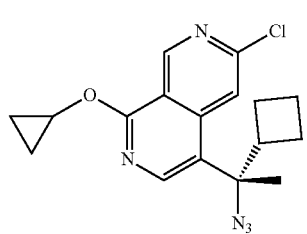

Intermediates 63 and 64: (R)-4-(1-Azido-1-cyclobutylethyl)-6-chloro-1-cyclopropoxy-2,7-naphthyridine and (S)-4-(1-azido-1-cyclobutylethyl)-6-chloro-1-cyclopropoxy-2,7-naphthyridine Intermediates 63 and 64 were made using a similar procedure as described for Intermediates 33 and 34, except in step 4, cyclobutylmagnesium bromide was used and the reaction was stirred at 60° C. for 1 h. The racemic title compound was separated by SFC(column: Daicel Chiralpak AY (250 mm×50 mm, 10 um); mobile phase: [EtOH (with 0.1% NH$_4$OH) in CO$_2$]) to give (R)-4-(1-azido-1-cyclobutylethyl)-6-chloro-1-cyclopropoxy-2,7-naphthyridine or (S)-4-(1-azido-1-cyclobutylethyl)-6-chloro-1-cyclopropoxy-2,7-naphthyridine (Intermediate 63, first eluting isomer, 27 mg, 18% yield) as a white solid and a second eluting isomer (R)-4-(1-azido-1-cyclobutylethyl)-6-chloro-1-cyclopropoxy-2,7-naphthyridine or (S)-4-(1-azido-1-cyclobutylethyl)-6-chloro-1-cyclopropoxy-2,7-naphthyrid (Intermediate 64, 67 mg, 45% yield) as a white solid.

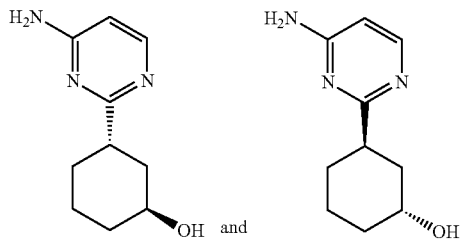 [SMILES: Nc1ccnc([C@H]2CCC[C@H](O)C2)n1 ; Nc1ccnc([C@@H]2CCC[C@@H](O)C2)n1]

Intermediates 65 and 66: (1S,3S)-3-(4-Aminopyrimidin-2-yl)cyclohexan-1-ol or (1R,3R)-3-(4-aminopyrimidin-2-yl)cyclohexan-1-ol

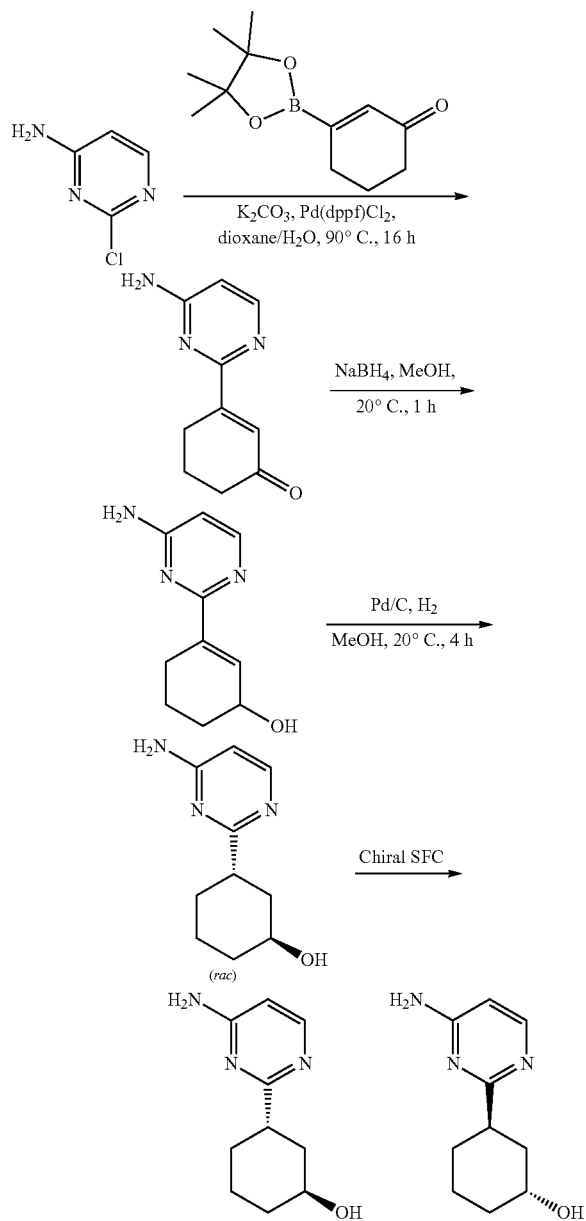

Step 1: 3-(4-Aminopyrimidin-2-yl)cyclohex-2-en-1-one

Potassium carbonate (600 mg, 4.34 mmol) and Pd(dppf)Cl₂ (160 mg, 218 umol) were added to a mixture of 2-chloropyrimidin-4-amine (280 mg, 2.16 mmol) and 3-(4,4,5,5-tetramethyl-1,3,2-dioxaborolan-2-yl)cyclohex-2-en-1-one (500 mg, 2.25 mmol) in dioxane (10 mL) and water (3 mL). The reaction mixture was stirred at 90° C. for 16 h, then was poured into water (30 mL) and extracted with EA (50 mL×3). The organic layers were combined, dried over anhydrous sodium sulfate, filtered, and concentrated under reduced pressure to give a residue. The residue was purified by column chromatography [SiO₂, Petroleum ether/Ethyl acetate=2/1 to 1:2] to give the title compound (300 mg, 73.4% yield) as a yellow solid.

Step 2: 3-(4-Aminopyrimidin-2-yl)cyclohex-2-en-1-ol

NaBH₄ (120 mg, 3.17 mmol) was added to a mixture of 3-(4-aminopyrimidin-2-yl)cyclohex-2-en-1-one (300 mg, 1.59 mmol) in MeOH (2 mL). The reaction mixture was stirred at 20° C. for 1 h, then was quenched with water (10 mL) and concentrated to give a residue. The residue was washed with DCM (10 mL) and filtered, and the filtrate was concentrated to give the title compound (290 mg, crude) as a yellow solid.

Step 3: rac-(1S,3S)-3-(4-Aminopyrimidin-2-yl)cyclohexan-1-ol

Pd/C (20 mg, 0.304 mmol) was added to a solution of 3-(4-aminopyrimidin-2-yl)cyclohex-2-en-1-ol (290 mg, 1.52 mmol) in MeOH (10 mL) and the reaction mixture was stirred at 20° C. for 4 h under hydrogen (50 psi). The reaction mixture was then filtered and concentrated to give a residue. The residue contained a mixture of cis and trans products which were separated by prep-HPLC (column: Welch Ultimate AQ-C18 150*30 mm*5 um; mobile phase: [water(0.1% TFA)-ACN]; B %: 2%-22%, 13 min). WH103959-6 (350.0 mg, 1.81 mmol, 58% yield) to give the title compound as a TFA salt. The TFA salt of the title compound (7.50 g, 24.41 mmol, from several batches) in MeOH (150 mL) was treated with basic resin (Ambersep 900) (100 g) and stirred for 12 h at 25° C. The mixture was filtered and the filtrate was concentrated to give the title compound (5.40 g, crude) as a white solid.

Step 4: (1S,3S)-3-(4-Aminopyrimidin-2-yl)cyclohexan-1-ol and (1R,3R)-3-(4-aminopyrimidin-2-yl)cyclohexan-1-ol rac-(1S,3S)-3-(4-Aminopyrimidin-2-yl)cyclohexan-1-ol (700 mg) was separated by SFC (column: ChiralPak IC (250 mm*30 mm, 10 um); mobile phase: [0.1% NH₃H₂O IPA]; B %). To give (1S,3S)-3-(4-aminopyrimidin-2-yl)cyclohexan-1-ol or (1R,3R)-3-(4-aminopyrimidin-2-yl)cyclohexan-1-ol (Intermediate 65, first eluting isomer, 315 mg, 45% yield) as a white solid and (1S,3S)-3-(4-aminopyrimidin-2-yl)cyclohexan-1-ol or (1R,3R)-3-(4-aminopyrimidin-2-yl)cyclohexan-1-ol (Intermediate 66, second eluting isomer, 320 mg, 45% yield) as a white solid. MS (ES+) $C_{10}H_{15}N_3O$ requires: 193, found: 194[M+H]⁺.

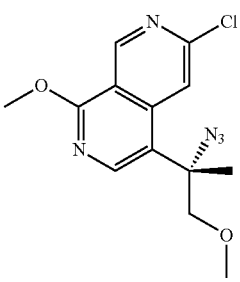 [SMILES: COC[C@@](C)(N=[N+]=[N-])c1cnc(OC)c2cnc(Cl)cc12]

Intermediate 67: (S)-4-(2-azido-1-methoxypropan-2-yl)-6-chloro-1-methoxy-2,7-naphthyridine

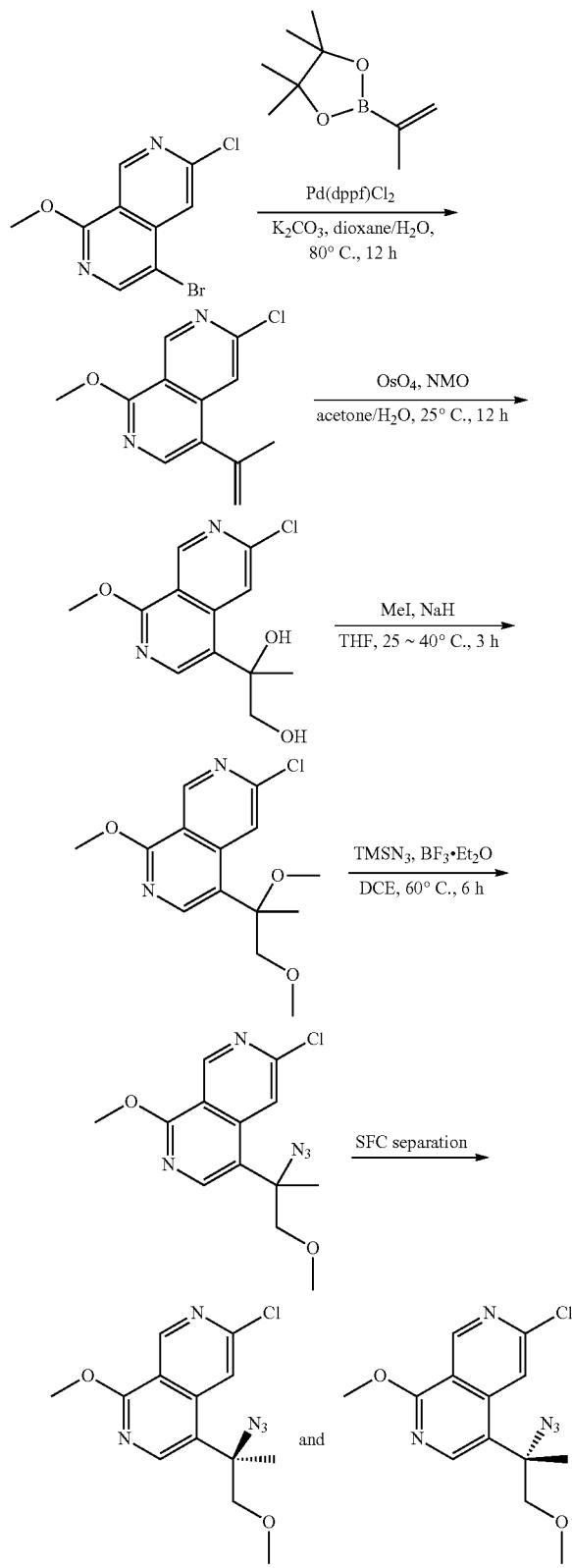

Step 1: 6-Chloro-1-methoxy-4-(prop-1-en-2-yl)-2,7-naphthyridine

The title compound was prepared from 4-bromo-6-chloro-1-methoxy-2,7-naphthyridine and 2-isopropenyl-4,4,5,5-tetramethyl-1,3,2-dioxaborolane using the same procedure described in Step 1 of Example 13.

Step 2: 2-(6-Chloro-1-methoxy-2,7-naphthyridin-4-yl)propane-1,2-diol

OsO4 (1.02 g, 4.01 mmol) was added to a mixture of 6-chloro-1-methoxy-4-(prop-1-en-2-yl)-2,7-naphthyridine (9.4 g, 40.0 mmol) and NMO (9.38 g, 80.1 mmol) in acetone (160 mL) and H$_2$O (40 mL). The reaction mixture was stirred at 25° C. for 12 h, then was quenched saturated aqueous KF solution (150 mL) and filtered. The solution was extracted with EA (2×300 mL). The organic phase was dried over Na$_2$SO$_4$, filtered and concentrated to give the title compound (9.3 g, 86% yield) as yellow oil which was used in the next step without further purification.

Step 3: 6-Chloro-4-(1,2-dimethoxypropan-2-yl)-1-methoxy-2,7-naphthyridine

NaH (4.85 g, 121 mmol, 60% purity) was added to a solution of 2-(6-chloro-1-methoxy-2,7-naphthyridin-4-yl)propane-1,2-diol (9.3 g, 34.6 mmol) in THF (150 mL). The reaction mixture was stirred at 25° C. for 0.5 h, then MeI (12.3 g, 86.5 mmol) was added. The reaction mixture was stirred at 25° C. for 0.5 h, and then stirred at 40° C. for 2 h. The reaction mixture was then added into a stirring solution of the saturated aqueous NH$_4$Cl (50 mL) and extracted with EA (300 mL). The organic layer was washed with saturated aqueous NH$_4$Cl (100 mL×3), dried over Na$_2$SO$_4$, filtered and concentrated to give the title compound (10 g, 85% yield) as a yellow oil which was used in the next step without further purification.

Step 4: 4-(2-Azido-1-methoxypropan-2-yl)-6-chloro-1-methoxy-2,7-naphthyridine

BF$_3$.Et$_2$O (8.80 g, 62.0 mmol) was added to a mixture of 6-chloro-4-(1,2-dimethoxypropan-2-yl)-1-methoxy-2,7-naphthyridine (9.2 g, 31.0 mmol), TMSN$_3$ (17.9 g, 155 mmol) in DCE (150 mL) at 25° C. The reaction mixture heated to 60° C. for 6 h under N$_2$. The reaction mixture was then added into a stirring solution of aqueous saturated NaHCO$_3$ (300 mL) and extracted with EA (300 mL). The organic layer was dried over Na$_2$SO$_4$, filtered and concentrated to give a residue. The residue was purified by flash-column chromatography on silica gel (20% EA-PE) to give the title compound (8 g, 73% yield) as a colorless oil.

Step 4: (R)-4-(2-Azido-1-methoxypropan-2-yl)-6-chloro-1-methoxy-2,7-naphthyridine and (S)-4-(2-azido-1-methoxypropan-2-yl)-6-chloro-1-methoxy-2,7-naphthyridine The title compound was prepared by chiral SFC separation of 4-(2-azido-1-methoxypropan-2-yl)-6-chloro-1-methoxy-2,7-naphthyridine (column: Daicel ChiralPak IG (250*30 mm, 10 um); mobile phase: [15% (IPA with 0.1% NH$_4$OH)] to give two isomers. The first isomer to elute was (R)-4-(2-Azido-1-methoxypropan-2-yl)-6-chloro-1-methoxy-2,7-naphthyridine and the second isomer to elute was the title compound, (S)-4-(2-azido-1-methoxypropan- 2-yl)-6-chloro-1-methoxy-2,7-naphthyridine. The isomers were determined by X-ray crystal structure of a compound which was derived from the second isomer.

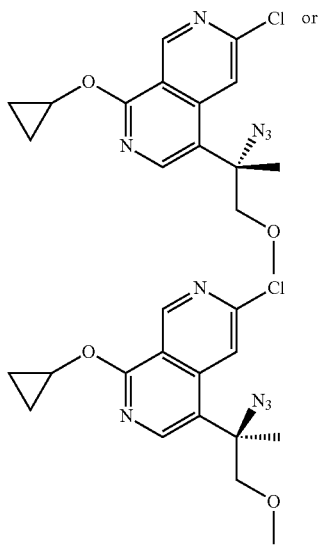

Intermediate 68 and 69: (S)-4-(2-Azido-1-methoxypropan-2-yl)-6-chloro-1-cyclopropoxy-2,7-naphthyridine and (R)-4-(2-azido-1-methoxypropan-2-yl)-6-chloro-1-cyclopropoxy-2,7-naphthyridine

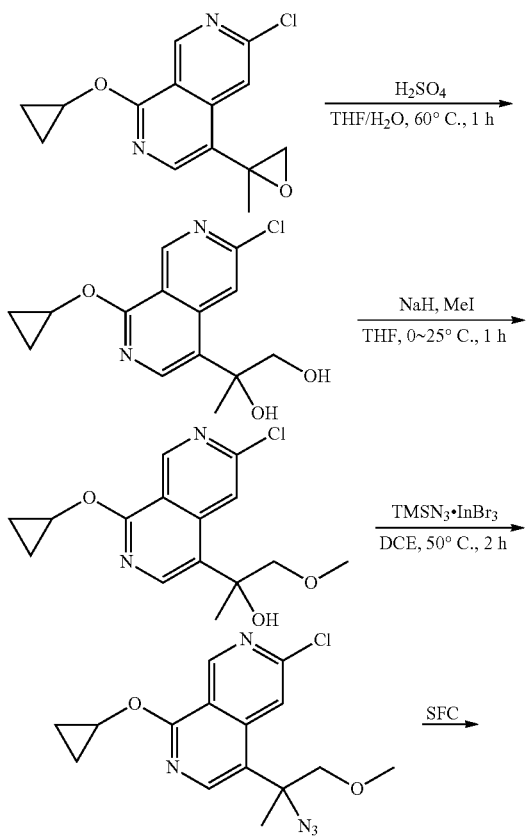

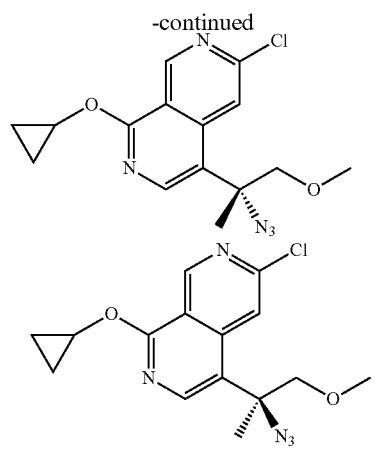

Step 1: rac-2-(6-Chloro-1-cyclopropoxy-2,7-naphthyridin-4-yl)propane-1,2-diol Sulfuric acid (106 mg, 1.08 mmol, 57.8 uL) was added to a solution of 6-chloro-1-cyclopropoxy-4-(2-methyloxiran-2-yl)-2,7-naphthyridine (prepared as described in Step 2 of Example 13, 300 mg, 1.08 mmol) in THF (2 mL) and water (0.5 mL). The reaction mixture was stirred at 60° C. for 1 h, then was poured into water (100 mL) and extracted with EA (30 mL×3). The organic layers were dried over sodium sulfate, filtered and concentrated to give a residue. The residue was purified by column chromatography (SiO$_2$, PE:EA=5:1 to 1:1) to give the title compound (250 mg, 78% yield) as a white solid.

Step 2: rac-2-(6-Chloro-1-cyclopropoxy-2,7-naphthyridin-4-yl)-1-methoxypropan-2-ol NaH (40.7 mg, 1.02 mmol, 60% purity) was added to a solution of 2-(6-chloro-1-cyclopropoxy-2,7-naphthyridin-4-yl)propane-1,2-diol (200 mg, 679 μmol) in THF (5 mL) at 0° C. The reaction mixture was stirred at 0° C. for 0.5 h, then methyl iodide (289 mg, 2.04 mmol, 127 uL) was added. The cooling bath was removed and the reaction mixture was stirred at 25° C. for 0.5 h, then was poured into water (100 mL) and extracted with EA (30 mL×3). The organic layers were dried over sodium sulfate, filtered and concentrated to give a residue. The residue was purified by column chromatography (SiO$_2$, PE:EA=5:1 to 1:1) to give the title compound (70.0 mg, 33% yield) as a yellow solid.

Step 3: rac-4-(2-Azido-1-methoxypropan-2-yl)-6-chloro-1-cyclopropoxy-2,7-naphthyridine TMSN$_3$ (93.3 mg, 106 uL) and InBr$_3$ (287.06 mg, 810 μmol) were added to a solution of 2-(6-chloro-1-cyclopropoxy-2,7-naphthyridin-4-yl)-1-methoxypropan-2-ol (50.0 mg, 162 μmol) in DCE (2 mL). The reaction mixture was stirred at 50° C. for 2 h, then was poured into water (100 mL) and saturated aqueous sodium bicarbonate solution was added to adjust to pH>7. The mixture was extracted with EA (20 mL×3), the organic layers were dried over sodium sulfate, filtered and concentrated to give a residue. The residue purified by prep-TLC (PE:EA=2:1) to obtain give the title compound (40.0 mg, crude) as a yellow solid.

Step 4: (S)-4-(2-Azido-1-methoxypropan-2-yl)-6-chloro-1-cyclopropoxy-2,7-naphthyridine and (R)-4-(2-azido-1-methoxypropan-2-yl)-6-chloro-1-cyclopropoxy-2,7-naphthyridine Rac-4-(2-Azido-1-methoxypropan-2-yl)-6-chloro-1-cyclopropoxy-2,7-naphthyridine (0.35 g, 1.05 mmol) was separated by SFC (column: Daicel Chiralpak IG (250 mm*30 mm, 10 um); mobile phase: [0.1% NH$_3$H$_2$O in MeOH]) to give (S)-4-(2-azido-1-methoxypropan-2-yl)-6-chloro-1-cyclopropoxy-2,7-naphthyridine or (R)-4-(2-azido-1-methoxypropan-2-yl)-6-chloro-1-cyclopropoxy-2,7-naphthyridine (Intermediate 68, first eluting isomer, 150 mg, 446 umol, 43% yield) as white solid and (S)-4-(2-azido-1-methoxypropan-2-yl)-6-chloro-1-cyclopropoxy-2,7-naphthyridine or (R)-4-(2-azido-1-methoxypropan-2-yl)-6-chloro-1-cyclopropoxy-2,7-naphthyridine (Intermediate 69, second eluting isomer, 140 mg, 417 umol, 40% yield) as a white solid. MS (ES+) C$_{15}$H$_{16}$ClN$_5$O$_2$ requires: 333, found: 334[M+H]$^+$.

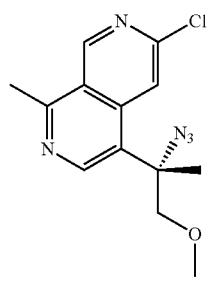 [SMILES: COC[C@@](C)(N=[N+]=[N-])c1cnc(C)c2cnc(Cl)cc12]

Intermediate 70: (S)-4-(2-Azido-1-methoxypropan-2-yl)-6-chloro-1-methyl-2,7-naphthyridine

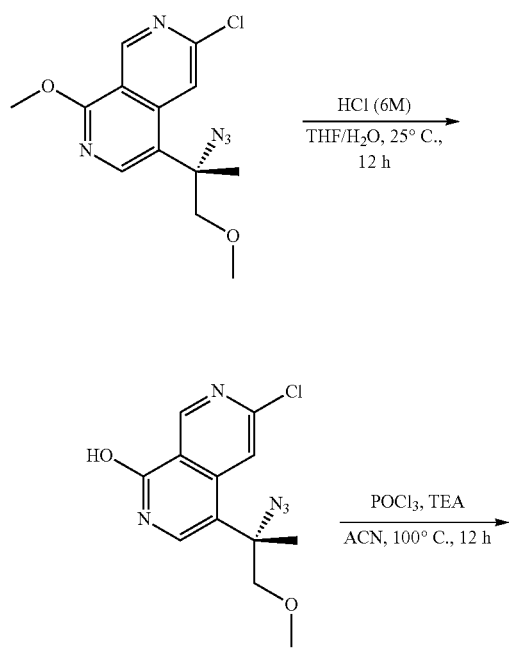

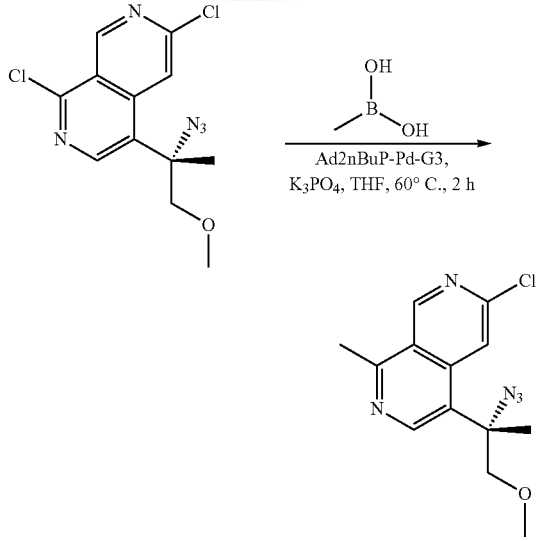

Step 1: (S)-4-(2-Azido-1-methoxypropan-2-yl)-6-chloro-2,7-naphthyridin-1-ol

Aqueous HCl (6 M, 5.41 mL) was added to a solution of (S)-4-(2-azido-1-methoxypropan-2-yl)-6-chloro-1-methoxy-2,7-naphthyridine (Intermediate 67) (3 g, 9.75 mmol) in THF (240 mL). The mixture was stirred at 25° C. for 12 h, then was adjusted to pH ~8 with addition of solid NaHCO$_3$. The mixture was extracted with EA (2×150 mL) and the organic layer was dried over Na$_2$SO$_4$, filtered and concentrated to give the title compound (2.7 g, 83% yield, 88% purity) as a white solid which was used in the next step without further purification.

Step 2: (S)-4-(2-Azido-1-methoxypropan-2-yl)-1,6-dichloro-2,7-naphthyridine

POCl$_3$ (3.34 g, 21.8 mmol) was added to a mixture of (S)-4-(2-azido-1-methoxypropan-2-yl)-6-chloro-2,7-naphthyridin-1-ol (1.28 g, 4.36 mmol) and TEA (1.16 g, 11.5 mmol) in MCCN (20 mL). The mixture was heated to 100° C. for 12 h. The reaction mixture was then added to saturated aqueous NH$_4$Cl (50 mL) and extracted with EA (100 mL×3). The organic layers were combined and dried over Na$_2$SO$_4$, filtered, and concentrated to give a residue. The residue was purified by flash-column chromatography on silica gel (25% EA-PE) to give the title compound (1.2 g, 88% yield) as a yellow oil. $^1$H NMR (400 MHz, CDCl$_3$): δ ppm 9.61 (s, 1H), 8.57 (s, 1H), 8.48 (s, 1H), 3.98 (d, J=9.6 Hz, 1H), 3.78 (d, J=9.6 Hz, 1H), 3.41 (s, 3H), 1.80 (s, 3H).

Step 3: (S)-4-(2-Azido-1-methoxypropan-2-yl)-6-chloro-1-methyl-2,7-naphthyridine Ad$_2$nBuP Pd G3 (cataCXium® A Pd G3) (81.6 mg, 112 μmol) and potassium phosphate (714 mg, 3.36 mmol) were added to a mixture of (S)-4-(2-azido-1-methoxypropan-2-yl)-1,6-dichloro-2,7-naphthyridine (350 mg, 1.12 mmol) and methylboronic acid (73.8 mg, 1.23 mmol) in THF (5 mL). The reaction mixture was stirred at 60° C. for 2 h, then was diluted with water (40 mL) and extracted with EA (40 mL×3). The combined organic layers were dried over anhydrous sodium sulfate, filtered and concentrated to give a residue. The residue was purified by flash-column column chromatography on silica gel (PE/EA=10/1 to 1/1) to give the title compound (220 mg, 67% yield) as a white solid. MS (ES+) $C_{13}H_{14}ClN_5O$ requires: 291, found: 292[M+H]⁺.

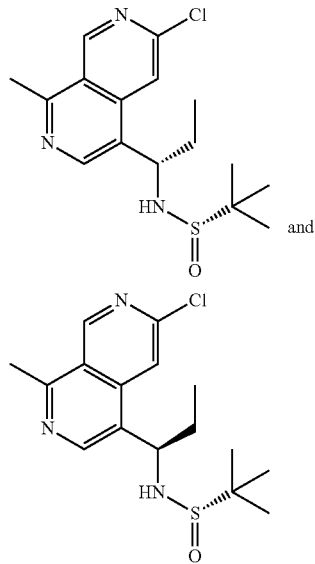

Intermediates 71 and 72: (S)—N—((S)-1-(6-Chloro-1-methyl-2,7-naphthyridin-4-yl)propyl)-2-methylpropane-2-sulfinamide and (S)—N—((R)-1-(6-chloro-1-methyl-2,7-naphthyridin-4-yl)propyl)-2-methylpropane-2-sulfinamide

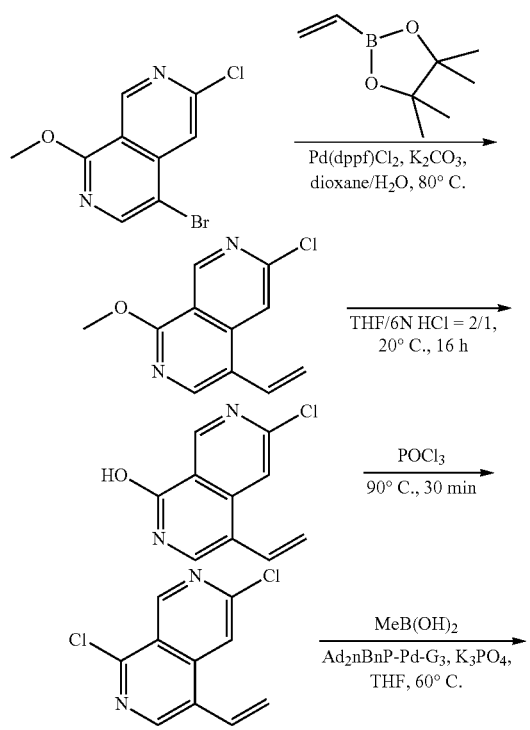

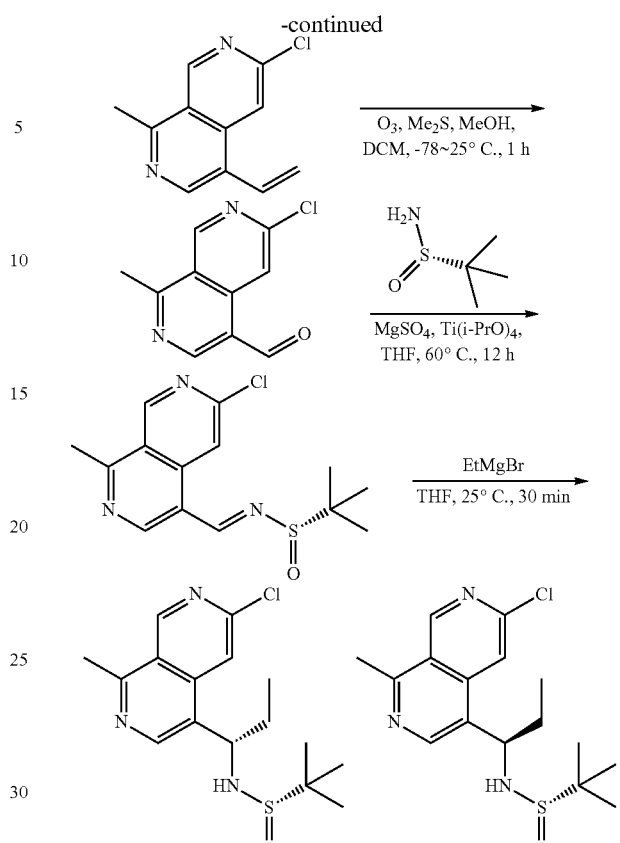

Step 1: 6-Chloro-1-methoxy-4-vinyl-2,7-naphthyridine

The title compound was prepared from 4-bromo-6-chloro-1-methoxy-2,7-naphthyridine and 4,4,5,5-tetramethyl-2-vinyl-1,3,2-dioxaborolane using a similar procedure as described in Step 1 of Example 13. MS (ES+) $C_{11}H_9ClN_2O$ requires: 220, found: 221 [M+H]⁺.

Steps 2-4: 6-Chloro-1-methyl-4-vinyl-2,7-naphthyridine

The title compound was prepared from 6-chloro-1-methoxy-4-vinyl-2,7-naphthyridine using a similar procedure as described in Steps 1-3 of Intermediate 70. MS (ES+) $C_{11}H_9ClN_2$ requires: 204, found: 205 [M+H]⁺.

Step 5: 6-Chloro-1-methyl-2,7-naphthyridine-4-carbaldehyde

A solution of 6-chloro-1-methyl-4-vinyl-2,7-naphthyridine (400 mg, 1.95 mmol) in MeOH (3 mL) and DCM (30 mL) was cooled to −78° C. Ozone was bubbled into the reaction mixture, and after 10 min nitrogen gas was bubbled through the reaction mixture. Me₂S (364 mg, 5.86 mmol) was added to the reaction mixture, and the mixture was stirred at 25° C. for 50 min. The reaction mixture was then concentrated to give a residue, and the residue was purified by column chromatography (SiO₂, PE:EA=1/0 to 0/1) to give the title compound (330 mg, 78% yield) as a yellow solid. MS (ES+) $C_{10}H_7ClN_2O$ requires: 206, found: 207[M+

H]+. 1H NMR (400 MHz, CD3OD): δ ppm 10.29 (s, 1H), 9.50 (s, 1H), 9.12 (s, 1H), 8.99 (s, 1H), 3.15 (s, 3H).

Step 6: (S)—N-((6-Chloro-1-methyl-2,7-naphthyridin-4-yl)methylene)-2-methylpropane-2-sulfinamide MgSO4 (576 mg, 4.79 mmol) and Ti(i-PrO)4 (2.72 g, 9.58 mmol, 2.83 mL) were added to a solution of 6-chloro-1-methyl-2,7-naphthyridine-4-carbaldehyde (330 mg, 1.60 mmol) and (S)-2-methylpropane-2-sulfinamide (580 mg, 4.79 mmol) in THF (10 mL). The reaction mixture was stirred at 60° C. for 12 h, then was diluted with water (70 ml) and EA (150 ml), stirred at 25° C. for 10 min, then filtered. The filtrate was extracted with EA (70 ml×3), and the combined organic layers were dried over anhydrous sodium sulfate, filtered and concentrated give a residue. The residue was purified by flash-column chromatography on silica gel (gradient elution, 0-60% EA/PE) to give the title compound (300 mg, 58% yield) as a yellow solid. MS (ES+) C14H16ClN3OS requires: 309, found: 310[M+H]+.

Step 7: (S)—N—((S)-1-(6-Chloro-1-methyl-2,7-naphthyridin-4-yl)propyl)-2-methylpropane-2-sulfinamide and (S)—N—((R)-1-(6-chloro-1-methyl-2,7-naphthyridin-4-yl)propyl)-2-methylpropane-2-sulfinamide EtMgBr (3 M, 915 uL) was added to a solution of (S)—N-((6-chloro-1-methyl-2,7-naphthyridin-4-yl)methylene)-2-methylpropane-2-sulfinamide (170 mg, 549 umol) in THF (20 mL) at 25° C. The reaction mixture was stirred at 25° C. for 30 min, then was quenched by addition of saturated aqueous NH4Cl solution (40 mL) and extracted with EA (40 mL×3). The combined organic layers were dried over anhydrous sodium sulfate, filtered and concentrated to give a residue. The residue was purified by prep-HPLC (column: Phenomenex Gemini-NX C18 75×30 mm×3 um; mobile phase: [water (0.05% ammonia hydroxide v/v)-ACN]; B %: 18%-48%, 11.5 min) to give the title compounds separately. The stereochemistry at the ethyl amine stereocenter was arbitrarily assigned.

Peak 1 (Intermediate 71): (S)—N—((S)-1-(6-Chloro-1-methyl-2,7-naphthyridin-4-yl)propyl)-2-methylpropane-2-sulfinamide or (S)—N—((R)-1-(6-chloro-1-methyl-2,7-naphthyridin-4-yl)propyl)-2-methylpropane-2-sulfinamide (55 mg, 22% yield) as a yellow oil. MS (ES+) C16H22ClN3OS requires: 339, found: 340[M+H]+. 1H NMR (400 MHz, CD3OD): δ ppm 9.43 (d, J=0.8 Hz, 1H), 8.59 (s, 1H), 8.07 (s, 1H), 4.91-4.73 (m, 1H), 4.17-4.08 (m, 1H), 3.60-3.50 (m, 1H), 3.05 (s, 3H), 2.13-2.07 (m, 1H), 2.03 (s, 1H), 1.20 (s, 9H), 0.96-0.89 (m, 3H).

Peak 2 (Intermediate 72): (S)—N—((S)-1-(6-Chloro-1-methyl-2,7-naphthyridin-4-yl)propyl)-2-methylpropane-2-sulfinamide or (S)—N—((R)-1-(6-chloro-1-methyl-2,7-naphthyridin-4-yl)propyl)-2-methylpropane-2-sulfinamide (55 mg, 26% yield) as a yellow oil. MS (ES+) C16H22ClN3OS requires: 339, found: 340[M+H]+. 1H NMR (400 MHz, CD3OD): δ ppm 9.43 (d, J=0.4 Hz, 1H), 8.61 (s, 1H), 8.06 (s, 1H), 4.88-4.81 (m, 1H), 4.18-4.05 (m, 1H), 3.79-3.68 (m, 2H), 3.58-3.53 (d, J=3.18 Hz, 1H), 3.05 (s, 3H), 2.28-2.18 (m, 1H), 2.14-2.01 (m, 1H), 1.24 (s, 9H), 0.90-0.86 (m, 3H).

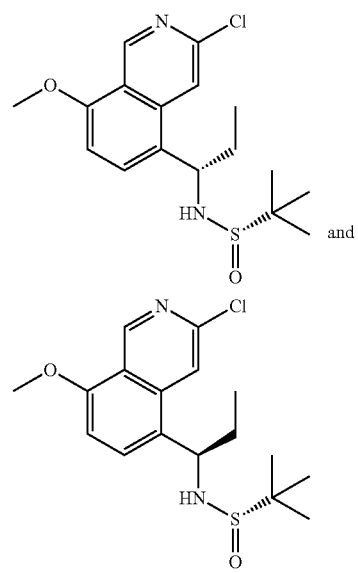

Intermediates 73 and 74: (S)—N—((S)-1-(3-Chloro-8-methoxyisoquinolin-5-yl)propyl)-2-methylpropane-2-sulfinamide and (S)—N—((R)-1-(3-chloro-8-methoxyisoquinolin-5-yl)propyl)-2-methylpropane-2-sulfinamide

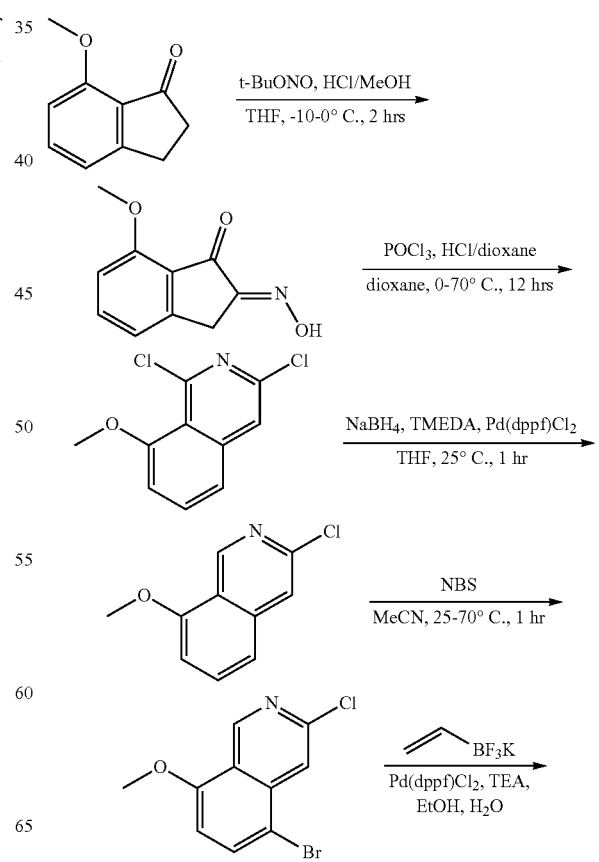

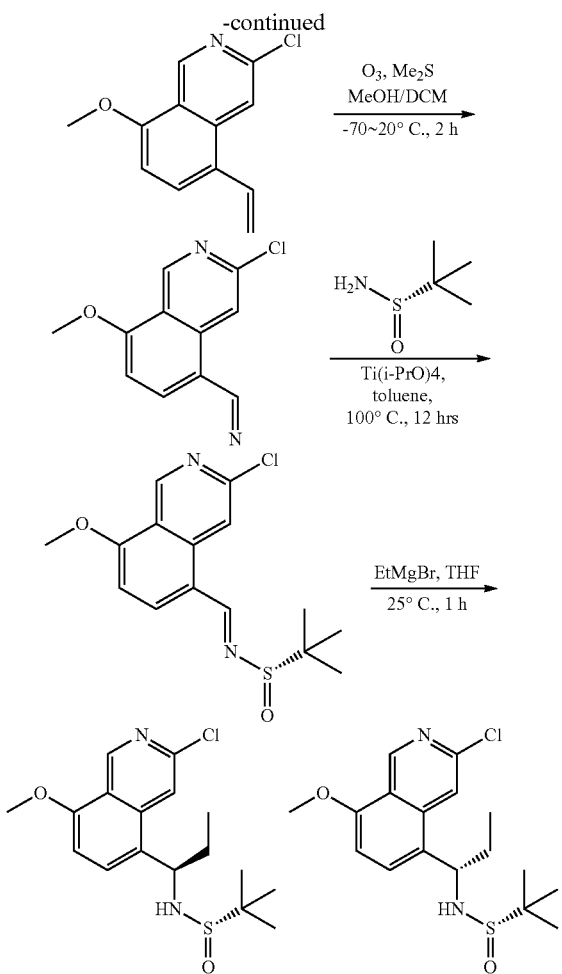

Step 1: (E)-2-(Hydroxyimino)-7-methoxy-2,3-dihydro-1H-inden-1-one t-BuONO (67.9 g, 659 mmol, 78.4 mL, 1.10 eq) was added to a solution of 7-methoxy-2,3-dihydro-1H-inden-1-one (99.0 g, 599 mmol, 1.00 eq) in THF (500 mL) at −10-0° C., followed by dropwise addition of HCl (4 M in MeOH, 15.0 mL, 0.10 eq) to the mixture at −10-0° C. The reaction mixture was stirred at 0° C. for 2 h, then was concentrated to give a residue. The residue was slurried in PE/EA=20:1 (200 mL) and filtered to give the title compound (107 g, 87% yield) as yellow solid. MS (ES+) $C_{10}H_9NO_3$ requires: 191, found: 192[M+H]$^+$.

Step 2: 1,3-Dichloro-8-methoxyisoquinoline

To a solution of (E)-2-(hydroxyimino)-7-methoxy-2,3-dihydro-1H-inden-1-one (107 g, 522 mmol, 1.00 eq) in dioxane (500 mL) was added POCl$_3$ (126 g, 827 mmol, 76.9 mL, 1.59 eq) and HCl (4 M in dioxane, 1.31 mL, 0.01 eq) at 0-10° C. The reaction mixture was stirred at 70° C. for 12 h, then was cooled to 25° C. and quenched with water (2.00 L). The quenched mixture was extracted with DCM (500 mL×4) and the organic layers were washed with brine (500 mL×2), dried over Na$_2$SO$_4$, filtered and concentrated to give a residue. The residue was purified by column chromatography (SiO$_2$, PE/EA=20/1 to 10/1) to give the title compound (48.8 g, 40.9% yield) as light yellow solid. MS (ES+) $C_{10}H_7C_{12}NO$ requires: 227, found: 228[M+H]$^+$.

Step 3: 3-Chloro-8-methoxyisoquinoline

To a solution of 1,3-dichloro-8-methoxyisoquinoline (48.8 g, 213 mmol, 1.00 eq) in THF (250 mL) was added TMEDA (37.3 g, 320 mmol, 48.4 mL, 1.50 eq) and Pd(dppf)Cl$_2$ (1.57 g, 2.14 mmol, 0.01 eq) at 25° C. Then NaBH$_4$ (17.2 g, 456 mmol, 2.13 eq) was slowly added to the reaction mixture and the reaction mixture was stirred at 25° C. for 1 h. The reaction mixture was poured into 1N HCl (1.00 L), extracted with EA (200 mL×3). The combined organic layers were filtered through Celite® and the filtrate was washed with brine (500 mL), dried over Na$_2$SO$_4$, filtered and concentrated to give a residue. The residue was purified by column chromatography (SiO$_2$, PE/EA=20/1 to 5/1) to give the title compound (26.7 g, 64.3% yield) as a light yellow solid. MS (ES+) $C_{10}H_8ClNO$ requires: 193, found: 194[M+H]$^+$.

Step 4: 5-Bromo-3-chloro-8-methoxyisoquinoline

To a solution of 3-chloro-8-methoxyisoquinoline (26.7 g, 137 mmol, 1.00 eq) in MeCN (300 mL) was added NBS (29.3 g, 165 mmol, 1.20 eq) at 25° C. The reaction mixture was stirred at 70° C. for 1 h, then was cooled to 25° C. The mixture was filtered and the filter cake was washed with MeCN (100 mL). The filter cake was collected and dried under vacuum. The filtrate was purified by column chromatography (SiO$_2$, PE/EA=1:0 to 1:1, Rf=0.45) to give the title compound (26.17 g, 69.6% yield) as an off-white solid. MS (ES+) $C_{10}H_7BrClNO$ requires: 273, found: 274[M+H]$^+$.

Step 5: 3-Chloro-8-methoxy-5-vinylisoquinoline

To a mixture of 5-bromo-3-chloro-8-methoxyisoquinoline (1.00 g, 3.67 mmol), potassium vinyltrifluoroborate (688 mg, 5.14 mmol) in EtOH (20.0 mL) and water (2.00 mL) was added TEA (743 mg, 7.34 mmol, 1.02 mL) and Pd(dppf)Cl$_2$.CH$_2$Cl$_2$ (300 mg, 367 µmol), then the mixture was stirred at 80° C. for 1 h. The reaction mixture was then concentrated to give a residue. The residue was diluted with water (30.mL) and extracted with EA (20 ml×3). The combined organic layers were dried over anhydrous sodium sulfate, filtered and concentrated to give a residue. The residue was purified by column chromatography (SiO$_2$, PE/EA=1/0 to 10/1) to give the title compound (620 mg, 2.82 mmol, 77% yield) as a yellow solid. MS (ES+) $C_{12}H_{10}ClNO$ requires: 219, found: 220[M+H]$^+$.

Steps 6-8: (S)—N—((S)-1-(3-Chloro-8-methoxyisoquinolin-5-yl)propyl)-2-methylpropane-2-sulfinamide and (S)—N—((R)-1-(3-chloro-8-methoxyisoquinolin-5-yl)propyl)-2-methylpropane-2-sulfinamide The title compounds were prepared from 3-chloro-8-methoxy-5-vinylisoquinoline using a similar procedure as described in Steps 5-7 for Intermediates 71 and 72. The mixture of diastereomers was separated by prep-HPLC (column: Welch Xtimate C18 150*30 mm*5 um; mobile phase: [water (0.05% ammonia hydroxide v/v)-ACN]; B %: 32%-62%, 11.5 min) to give the title compounds separately. The stereochemistry at the ethyl amine stereocenter was arbitrarily assigned.

Peak 1 (Intermediate 73): (S)—N—((S)-1-(3-Chloro-8-methoxyisoquinolin-5-yl)propyl)-2-methylpropane-2-sulfinamide or (S)—N—((R)-1-(3-chloro-8-methoxyisoquinolin-5-yl)propyl)-2-methylpropane-2-sulfinamide (15.0 mg, 17% yield) as a yellow oil. MS (ES+) $C_{17}H_{23}ClN_2O_2S$ requires: 354, found: 355[M+H]+.

Peak 2 (Intermediate 74): (S)—N—((S)-1-(3-Chloro-8-methoxyisoquinolin-5-yl)propyl)-2-methylpropane-2-sulfinamide or (S)—N—((R)-1-(3-chloro-8-methoxyisoquinolin-5-yl)propyl)-2-methylpropane-2-sulfinamide (15.0 mg, 17% yield) as a yellow oil. MS (ES+) $C_{17}H_{23}ClN_2O_2S$ requires: 354, found: 355[M+H]+.

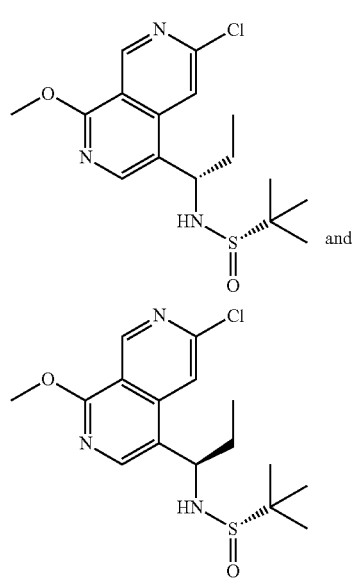

Intermediates 75 and 76: (S)—N—((S)-1-(6-Chloro-1-methoxy-2,7-naphthyridin-4-yl)propyl)-2-methylpropane-2-sulfinamide and (S)—N—((R)-1-(6-chloro-1-methoxy-2,7-naphthyridin-4-yl)propyl)-2-methylpropane-2-sulfinamide

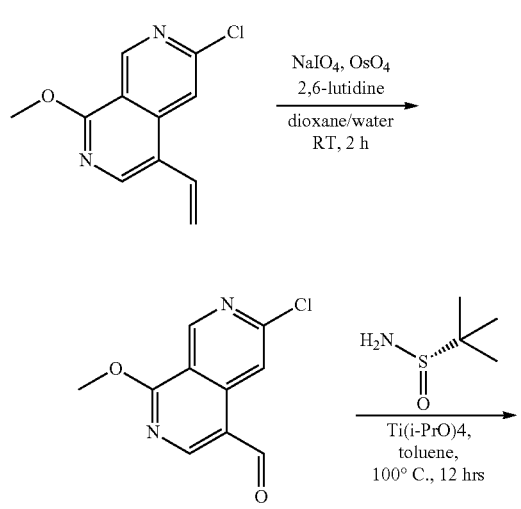

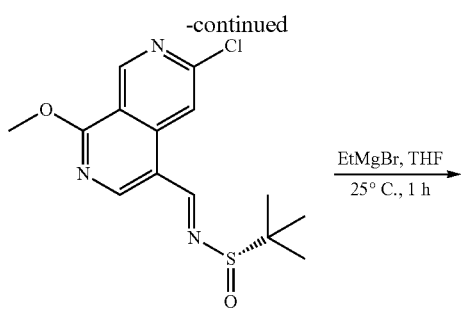

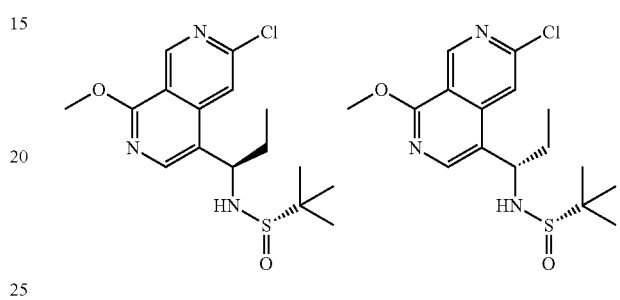

Step 1: 6-Chloro-1-methoxy-2,7-naphthyridine-4-carbaldehyde OsO$_4$ (4% in water, 0.576 mL, 0.113 mmol) was added to a mixture of 6-chloro-1-methoxy-4-vinyl-2,7-naphthyridine (Step 1, Intermediate 71) (1 g, 4.54 mmol), 2,6-lutidine (0.528 mL, 4.53 mmol), NaIO$_4$ (0.969 g, 4.53 mmol) in dioxane (34 mL) and water (11 mL). The reaction mixture was stirred at 25° C. for 2 h, then was partitioned between DCM and water. The organic layer was dried over sodium sulfate, filtered, and concentrated to give a residue. The residue was purified by column chromatography (SiO$_2$, PE:EA=1/0 to 0/1) to give the title compound (360 mg) as a yellow solid.

Steps 2-3: (S)—N—((S)-1-(6-Chloro-1-methoxy-2,7-naphthyridin-4-yl)propyl)-2-methylpropane-2-sulfinamide and (S)—N—((R)-1-(6-chloro-1-methoxy-2,7-naphthyridin-4-yl)propyl)-2-methylpropane-2-sulfinamide The title compounds were prepared from 6-chloro-1-methoxy-2,7-naphthyridine-4-carbaldehyde using a similar procedure as described in Steps 6-7 of Intermediate 71. The mixture of diastereomers was separated by SFC (column: Chiralpak IC-H 21×250 mm; mobile phase: MeOH in CO$_2$) to give the title compounds separately. The stereochemistry at the ethyl amine stereocenter was arbitrarily assigned.

Peak 1 (Intermediate 75): (S)—N—((S)-1-(6-Chloro-1-methoxy-2,7-naphthyridin-4-yl)propyl)-2-methylpropane-2-sulfinamide or (S)—N—((R)-1-(6-chloro-1-methoxy-2,7-naphthyridin-4-yl)propyl)-2-methylpropane-2-sulfinamide (70 mg) as a yellow oil. MS (ES+) $C_{16}H_{22}ClN_3O_2S$ requires: 355, found: 356[M+H]+.

Peak 2 (Intermediate 76): (S)—N—((S)-1-(6-Chloro-1-methoxy-2,7-naphthyridin-4-yl)propyl)-2-methylpropane-2-sulfinamide or (S)—N—((R)-1-(6-chloro-1-methoxy-2,7-naphthyridin-4-yl)propyl)-2-methylpropane-2-sulfinamide (73 mg) as a yellow oil. MS (ES+) $C_{16}H_{22}ClN_3O_2S$ requires: 355, found: 356[M+H]+.

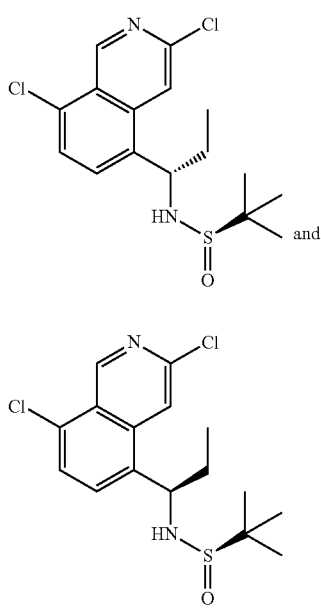

Intermediates 77 and 78: (R)—N—((S)-1-(3,8-Dichloroisoquinolin-5-yl)propyl)-2-methylpropane-2-sulfinamide and (R)—N—((R)-1-(3,8-dichloroisoquinolin-5-yl)propyl)-2-methylpropane-2-sulfinamide

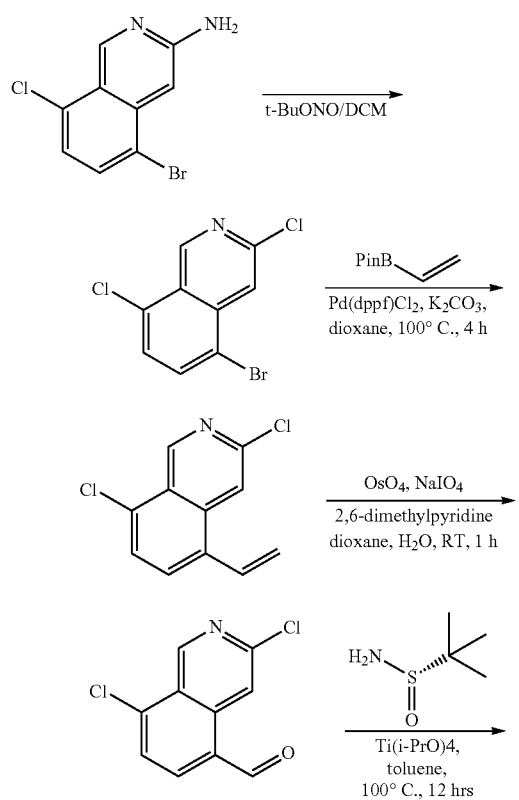

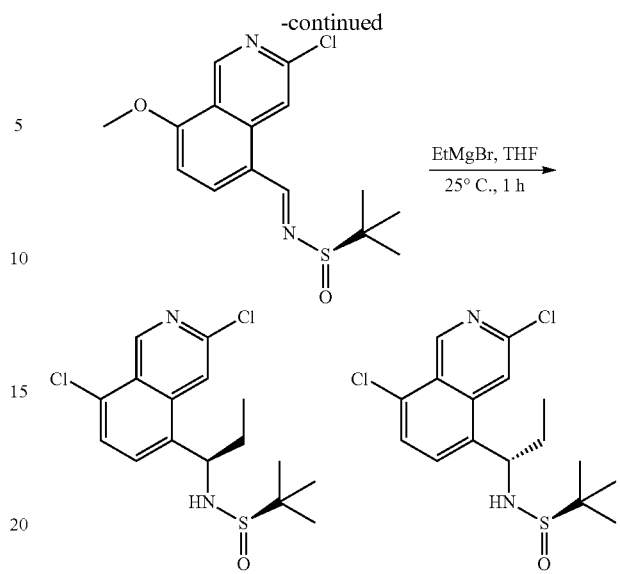

Step 1: 5-Bromo-3,8-dichloroisoquinoline

To a solution of 5-bromo-8-chloro-isoquinolin-3-amine (2 g, 7.77 mmol, 1 eq) and benzyl(triethyl)ammonium chloride (3.54 g, 15.53 mmol, 2 eq) in DCM (20 mL) was added 1-BuONO (3.20 g, 31.07 mmol, 3.69 mL, 4 eq) at 0° C. The mixture was stirred at 30° C. for 12 h, then was poured into saturated aqueous NaHCO₃ solution (100 mL) and extracted with EA (50 mL×3). The combined organic layers were dried over Na₂SO₄, filtered and concentrated to give a residue. The residue was purified by column chromatography (SiO₂, PE/EA=50/1 to 5/1) to give the title compound (1.1 g, 3.97 mmol, 51.14% yield) as a yellow solid.

Steps 2-5: (R)—N—((S)-1-(3,8-Dichloroisoquinolin-5-yl)propyl)-2-methylpropane-2-sulfinamide and (R)—N—((R)-1-(3,8-dichloroisoquinolin-5-yl)propyl)-2-methylpropane-2-sulfinamide The title compounds were prepared from 5-bromo-3,8-dichloroisoquinoline using a similar procedure as described in Step 1 of Example 13, Step 1 of Intermediate 75, and Steps 6-7 of Intermediate 71. The mixture of diastereomers was separated by column chromatography (SiO₂, Petroleum ether/Ethyl acetate=10/1 to 1/2) followed by prep-TLC (SiO₂, Petroleum ether/Ethyl acetate=1/2) to give the title compounds separately. The stereochemistry at the ethyl amine stereocenter was arbitrarily assigned.

Peak 1 (Intermediate 77): (R)—N—((S)-1-(3,8-Dichloroisoquinolin-5-yl)propyl)-2-methylpropane-2-sulfinamide and (R)—N—((R)-1-(3,8-dichloroisoquinolin-5-yl)propyl)-2-methylpropane-2-sulfinamide (35 mg, 21% yield) as a yellow solid. MS (ES+) $C_{16}H_{20}Cl_2N_2OS$ requires: 358, found: 359[M+H]⁺.

Peak 2 (Intermediate 78): (R)—N—((S)-1-(3,8-Dichloroisoquinolin-5-yl)propyl)-2-methylpropane-2-sulfinamide and (R)—N—((R)-1-(3,8-dichloroisoquinolin-5-yl)propyl)-2-methylpropane-2-sulfinamide (35 mg, 19% yield) as a yellow solid. MS (ES+) $C_{16}H_{20}Cl_2N_2OS$ requires: 358, found: 359[M+H]⁺.

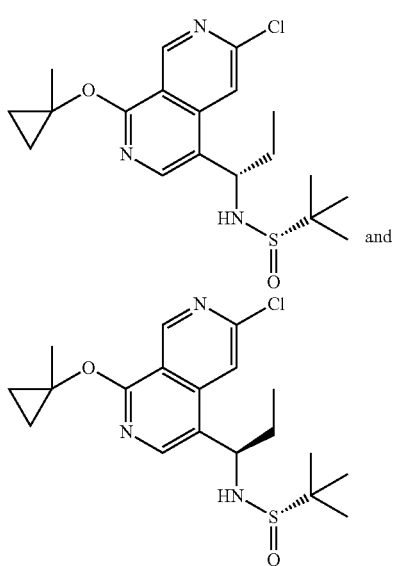

Intermediates 79 and 80: (S)—N—((S)-1-(6-Chloro-1-(1-methylcyclopropoxy)-2,7-naphthyridin-4-yl)propyl)-2-methylpropane-2-sulfinamide and (S)—N—((R)-1-(6-chloro-1-(1-methylcyclopropoxy)-2,7-naphthyridin-4-yl)propyl)-2-methyl-propane-2-sulfinamide

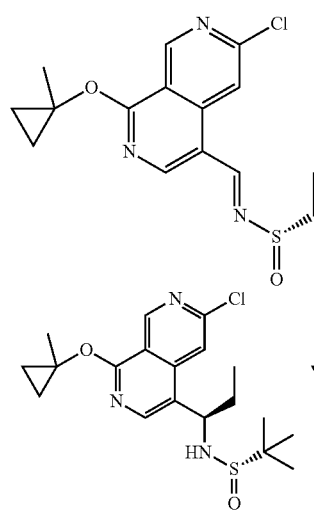

The title compounds were prepared from (S,E)-N-((6-chloro-1-(1-methylcyclopropoxy)-2,7-naphthyridin-4-yl)methylene)-2-methylpropane-2-sulfinamide (which was prepared from 4-bromo-1,6-dichloro-2,7-naphthyridine (Intermediates 33 and 34) using similar procedures as described above for Intermediate 75) using a similar procedure as described in Step 7 of Intermediate 71. The mixture of diastereomers was separated by prep-TLC (petroleum ether: ethyl acetate=1:1) to give the title compounds separately. The stereochemistry at the ethyl amine stereocenter was arbitrarily assigned.

Peak 1 (Intermediate 79): (S)—N—((S)-1-(6-Chloro-1-(1-methylcyclopropoxy)-2,7-naphthyridin-4-yl)propyl)-2-methylpropane-2-sulfinamide or (S)—N—((R)-1-(6-chloro-1-(1-methylcyclopropoxy)-2,7-naphthyridin-4-yl)propyl)-2-methylpropane-2-sulfinamide (20 mg, 36% yield) as a yellow solid. MS (ES+) $C_{19}H_{26}ClN_3O_2S$ requires: 395, found: 396[M+H]+.

Peak 2 (Intermediate 80): (S)—N—((S)-1-(6-Chloro-1-(1-methylcyclopropoxy)-2,7-naphthyridin-4-yl)propyl)-2-methylpropane-2-sulfinamide or (S)—N—((R)-1-(6-chloro-1-(1-methylcyclopropoxy)-2,7-naphthyridin-4-yl)propyl)-2-methylpropane-2-sulfinamide (20 mg, 41% yield) as a white solid. MS (ES+) $C_{19}H_{26}ClN_3O_2S$ requires: 395, found 396[M+H]+.

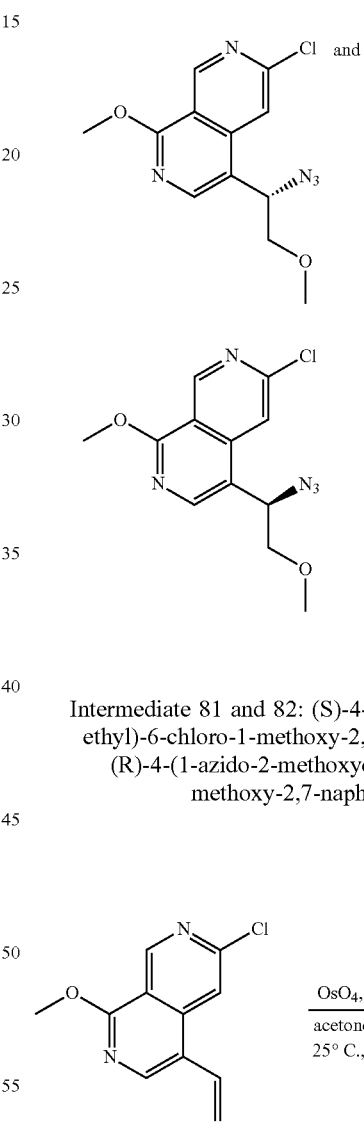

Intermediate 81 and 82: (S)-4-(1-Azido-2-methoxyethyl)-6-chloro-1-methoxy-2,7-naphthyridine and (R)-4-(1-azido-2-methoxyethyl)-6-chloro-1-methoxy-2,7-naphthyridine -continued

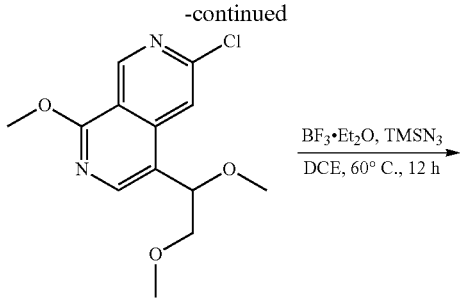

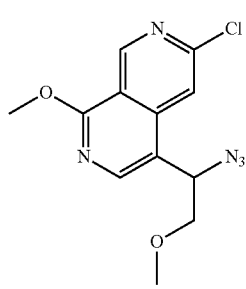

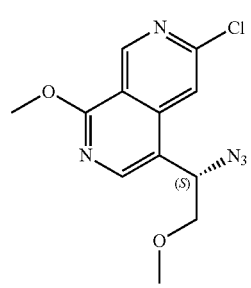 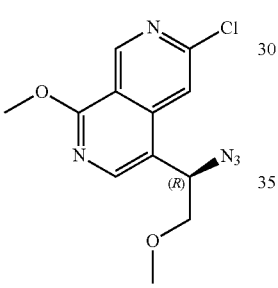

Steps 1-3: (S)-4-(1-Azido-2-methoxyethyl)-6-chloro-1-methoxy-2,7-naphthyridine or (R)-4-(1-azido-2-methoxyethyl)-6-chloro-1-methoxy-2,7-naphthyridine The title compound was prepared from 6-chloro-1-methoxy-4-vinyl-2,7-naphthyridine (Step 1, Intermediate 71) using a similar procedure as described in Steps 2-4 of Intermediate 67, except that after Step 2 the dimethoxy intermediate was isolated and used in Step 3. The racemic mixture (6.5 g, 22.1 mmol) was separated by chiral-SFC (column: Daicel Chiralpak AD (250 mm×50 mm, 10 um); mobile phase: [0.1% NH$_3$H$_2$O-MeOH]) to give (S)-4-(1-azido-2-methoxyethyl)-6-chloro-1-methoxy-2,7-naphthyridine or (R)-4-(1-azido-2-methoxyethyl)-6-chloro-1-methoxy-2,7-naphthyridine (Intermediate 81, first eluting isomer, 3.2 g, 45% yield) as white solid and (S)-4-(1-azido-2-methoxyethyl)-6-chloro-1-methoxy-2,7-naphthyridine or (R)-4-(1-azido-2-methoxyethyl)-6-chloro-1-methoxy-2,7-naphthyridine (Intermediate 82, second eluting isomer, 3 g, 46% yield) as a white solid. $^1$H NMR (400 MHz, CDCl$_3$): δ ppm 9.43 (s, 1H), 8.25 (s, 1H), 7.86 (s, 1H), 5.03-4.99 (m, 1H), 4.18 (s, 3H), 3.84-3.79 (m, 1H), 3.78-3.74 (m, 1H), 3.45 (s, 3H).

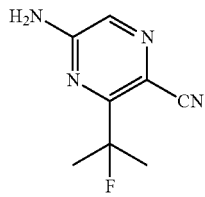

Intermediate 83: 5-Amino-3-(2-fluoropropan-2-yl)pyrazine-2-carbonitrile

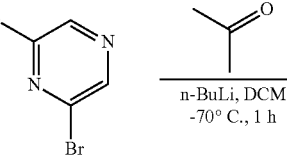

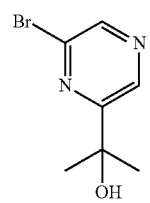

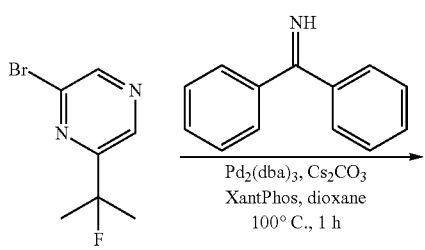

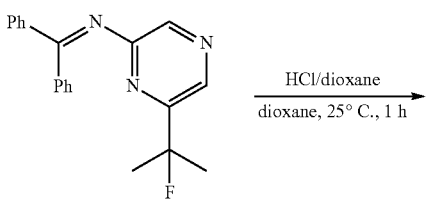

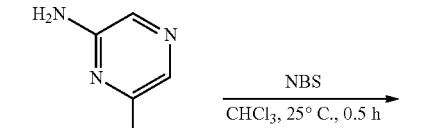

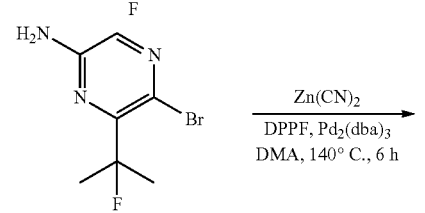

-continued

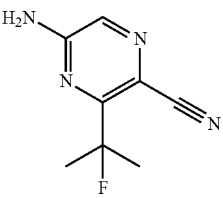

Steps 1-6: 5-Amino-3-(2-fluoropropan-2-yl)pyrazine-2-carbonitrile

The title compound was prepared from 2,6-dibromopyrazine using the same six-step procedure as described in Step 1 of Intermediate 26 (substituting acetone instead of propionaldehyde) and Steps 1-5 of Intermediate 23. MS (ES+) $C_8H_9FN_4$ requires: 180, found: 181 [M+H]$^+$.

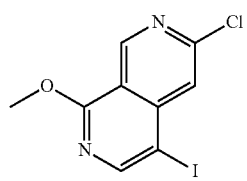

Intermediate 84: 6-Chloro-4-iodo-1-methoxy-2,7-naphthyridine for 60 h, then the acetic acid was removed in vacuo. The residue was treated with saturated aqueous NaHCO$_3$ solution, stirred for 1 h, then filtered. The filter cake was washed with water and dried under vacuum to give the title compound (1.52 g, 90%) as an off-white solid. MS (ES+) $C_9H_4ClIN_2O$ requires: 306, found: 307[M+H]$^+$.

Steps 2-3: 6-Chloro-4-iodo-1-methoxy-2,7-naphthyridine

The title compound was prepared from 6-chloro-4-iodo-2,7-naphthyridin-1(2H)-one using the same two-step procedure described in Steps 2-3 of Intermediate 31. MS (ES+) $C_9H_6ClIN_2O$ requires: 320, found: 321 [M+H]$^+$.

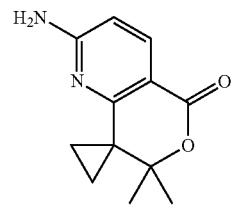 [SMILES: CC1(C)OC(=O)c2ccc(N)nc2C12CC2]

Intermediate 85: 2'-Amino-7',7'-dimethyl-5'H,7'H-spiro[cyclopropane-1,8'-pyrano[4,3-b]pyridin]-5'-one

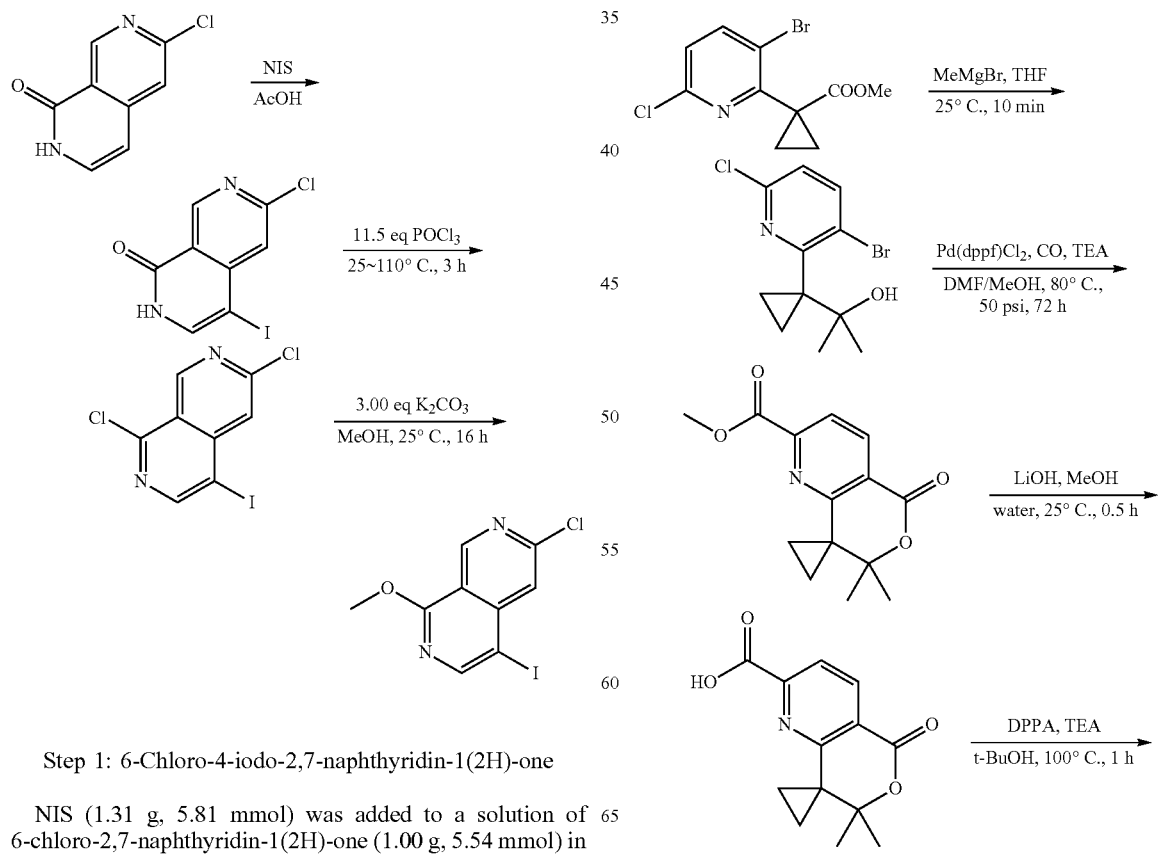

Step 1: 6-Chloro-4-iodo-2,7-naphthyridin-1(2H)-one

NIS (1.31 g, 5.81 mmol) was added to a solution of 6-chloro-2,7-naphthyridin-1(2H)-one (1.00 g, 5.54 mmol) in AcOH (20 mL). The reaction mixture was stirred at 23° C.

309
-continued

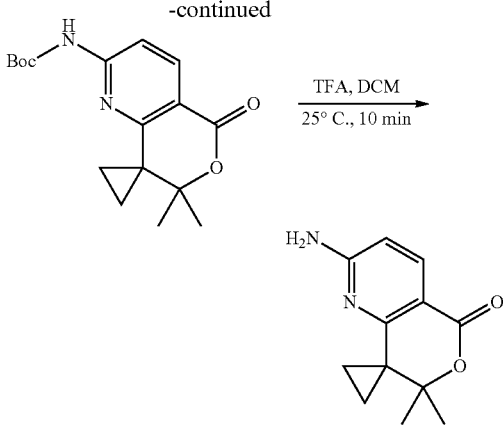

Step 1: 2-(1-(3-Bromo-6-chloropyridin-2-yl)cyclopropyl)propan-2-ol

To a solution of methyl 1-(3-bromo-6-chloropyridin-2-yl)cyclopropane-1-carboxylate (1.3 g, 4.47 mmol) in THF (10 mL) was added MeMgBr (3 M, 14.9 mL) at 25° C. The reaction mixture was stirred at 25° C. for 10 min, then was poured into water (20 mL) and extracted with EA (50 mL×3). The organic layers were combined and dried over sodium sulfate, filtered, and concentrated to give a residue. The residue was purified by column chromatography (SiO$_2$, PE/EA=1/0 to 50/1) to give the title compound (500 mg, 38% yield) as colorless oil.

310

Steps 2-5: 2'-Amino-7',7'-dimethyl-5'H,7'H-spiro[cyclopropane-1,8'-pyrano[4,3-b]pyridin]-5'-one The title compound was prepared from 2-(1-(3-Bromo-6-chloropyridin-2-yl)cyclopropyl)propan-2-ol using a similar procedure as described in Steps 4-6 for Intermediate 45 and Step 7 of Intermediate 50 above. $^1$H NMR (400 MHz, CDCl$_3$): δ ppm 8.05 (d, J=8.4 Hz, 1H), 6.36 (d, J=8.8 Hz, 1H), 4.85 (s, 2H), 1.42-1.32 (m, 8H), 1.06-1.03 (m, 2H).

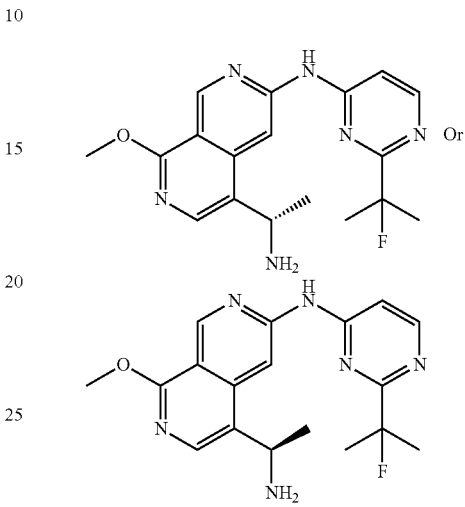

Example 1: 5-(1-Aminoethyl)-N-(2-(2-fluoropropan-2-yl)pyrimidin-4-yl)-8-methoxy-2,7-naphthyridin-3-amine (1)

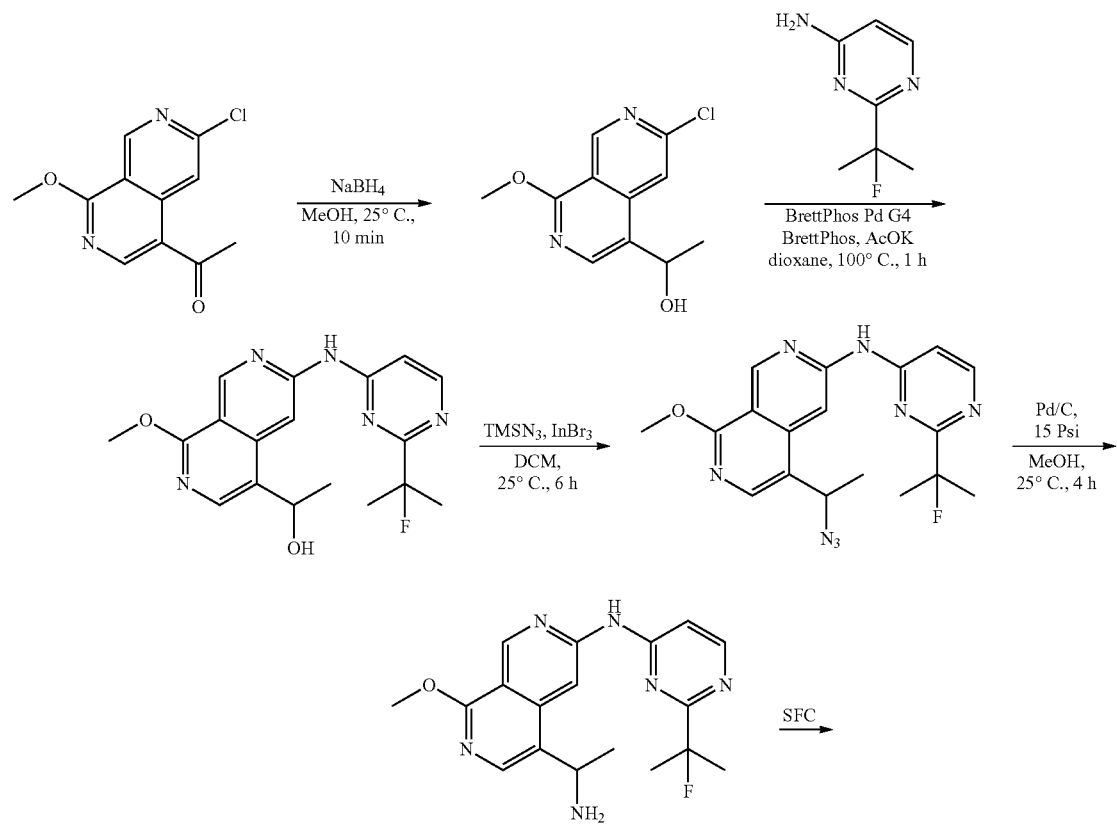

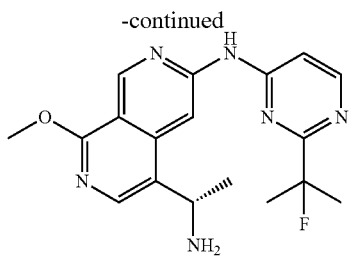 and 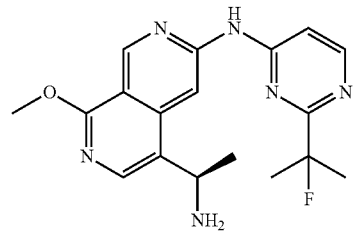

Step 1: 1-(6-Chloro-1-methoxy-2,7-naphthyridin-4-yl)ethan-1-ol

Sodium borohydride (120 mg, 3.17 mmol) was added to a solution of 1-(6-chloro-1-methoxy-2,7-naphthyridin-4-yl)ethan-1-one (500 mg, 2.11 mmol) in methanol (10 mL) and the mixture was stirred at 25° C. for 10 minutes. The reaction was quenched by addition of water (5 mL) and extracted with EA (5 mL×3). The combined organic layers were concentrated under reduced pressure to give a residue. The residue was purified by flash-column chromatography to give the title compound (400 mg, 79% yield) as an off-white solid.

Step 2: 1-(6-((2-(2-Fluoropropan-2-yl)pyrimidin-4-yl)amino)-1-methoxy-2,7-naphthyridin-4-yl)ethan-1-ol 2-(Dicyclohexylphosphino)-3,6-dimethoxy-2',4',6'-triisopropyl-1,1'-biphenyl (BrettPhos) (90.0 mg, 168 umol) and BrettPhos Pd G4 (154.28 mg, 167.60 umol) were added to a mixture of 1-(6-chloro-1-methoxy-2,7-naphthyridin-4-yl)ethan-1-ol (400 mg, 1.68 mmol), 2-(2-fluoropropan-2-yl)pyrimidin-4-amine (Intermediate 1, 312 mg, 2.01 mmol) and potassium acetate (822 mg, 8.38 mmol) in dioxane (20 mL). The solution was degassed and purged with $N_2$ for 3 times, and the mixture was stirred at 100° C. for 1 h under $N_2$ atmosphere. The reaction mixture was quenched by addition of water (30 mL) and extracted with EA (30 mL×3). The combined organic layers were washed with water (60 mL×3) and concentrated under reduced pressure to give a residue. The residue was purified by flash-column chromatography and reverse phase prep-HPLC to give the title compound (280 mg, 45% yield) as a white solid. MS (ES+) $C_{14}H_{20}FN_5O_2$ requires 357, found 358 [M+H]$^+$. $^1$H NMR (400 MHz, DMSO-$d_6$): δ ppm 10.70 (s, 1H), 9.31 (s, 1H), 8.94-8.76 (m, 1H), 8.48 (d, J=5.6 Hz, 1H), 8.17 (s, 1H), 8.07 (d, J=5.6 Hz, 1H), 7.25 (d, J=5.6 Hz, 1H), 5.28-5.18 (m, 1H), 4.11-4.03 (m, 3H), 1.82 (d, J=2.4 Hz, 3H), 1.76 (d, J=2.4 Hz, 3H), 1.50 (d, J=6.4 Hz, 3H).

Step 3: 5-(1-Azidoethyl)-N-(2-(2-fluoropropan-2-yl)pyrimidin-4-yl)-8-methoxy-2,7-naphthyridin-3-amine Trimethylsilylazide (116 mg, 1.01 mmol) and indium bromide (238 mg, 672 umol) were added under an atmosphere of nitrogen to a solution of 1-(6-((2-(2-fluoropropan-2-yl)pyrimidin-4-yl)amino)-1-methoxy-2,7-naphthyridin-4-yl)ethan-1-ol (120 mg, 336 umol) in dichloromethane (10 mL). The mixture was stirred at 25° C. for 6 h. TLC showed starting material was consumed and a new spot was detected. The reaction mixture was poured into water (20 mL), and extracted with EA (20 mL×3). The combined organic layers were concentrated under reduced pressure to give a residue. The residue was purified by prep-TLC [petroleum ether:EA=1:1] to give the title compound (80 mg, 61% yield) as a white solid. MS (ES+) $C_{18}H_{19}FN_8O$ requires 382, found 383 [M+H]$^+$

Step 4: 5-(1-Aminoethyl)-N-(2-(2-fluoropropan-2-yl)pyrimidin-4-yl)-8-methoxy-2,7-naphthyridin-3-amine Pd/C (10.0 mg, 78.5 umol, 10% purity) was added under $N_2$. to a solution of 5-(1-Azidoethyl)-N-(2-(2-fluoropropan-2-yl)pyrimidin-4-yl)-8-methoxy-2,7-naphthyridin-3-amine (50 mg, 131 umol) in methanol (10 mL). The suspension was degassed under vacuum and purged with $H_2$ several times. The mixture was stirred under $H_2$ (15 psi) at 25° C. for 4 h. The reaction mixture was filtered and concentrated under reduced pressure to remove solvent. The residue was diluted with EA (10 mL) and extracted with water (10 mL×3). The combined organic layers were washed with EA (5 mL×3) and concentrated under reduced pressure to give a residue. The residue was combined with a previous batch (20 mg). The combined residue was purified by reverse phase prep-HPLC (column: Phenomenex Gemini 150×25 mm×10 um; mobile phase: [water (10 mM NHsHCO$_3$)-MECN]; B %: 30%-51%, 7 min) to give the title compound (45 mg, 60% yield) as a white solid. MS (ES+) $C_{18}H_{21}FN_6O$ requires 356, found 357 [M+H]$^+$. $^1$H NMR (400 MHz, DMSO-$d_6$): δ ppm 9.59-9.46 (m, 1H), 8.86 (s, 1H), 8.04 (s, 1H).

Step 5: (R or S)-5-(1-Aminoethyl)-N-(2-(2-fluoropropan-2-yl)pyrimidin-4-yl)-8-methoxy-2,7-naphthyridin-3-amine 5-(1-aminoethyl)-N-(2-(2-fluoropropan-2-yl)pyrimidin-4-yl)-8-methoxy-2,7-naphthyridin-3-amine (60 mg, 168 umol) was separated by SFC (column: DAICEL CHIRALPAK AS (250 mm×30 mm, 10 um); mobile phase: [0.1% NH$_3$H$_2$O MeOH]; B %: 30MeOH (NH$_4$OH) %-30MeOH (NH$_4$OH) %, 5.0 min; 65 min) to give the 2 isomers (first eluting isomer (12.9 mg, 26% yield) and second eluting isomer (13.7 mg, 29% yield)) as brown solids (stereochemistry arbritrarily assigned). Spectra analysis of isomer 1: MS (ES+) $C_{18}H_{21}FN_6O$ requires 356, found 357 [M+H]$^+$. $^1$H NMR (400 MHz, CD$_3$OD): δ ppm 9.33 (s, 1H), 8.83 (s, 1H), 8.41 (d, J=6.0 Hz, 1H), 8.20 (s, 1H), 7.20 (d, J=6.0 Hz, 1H), 4.70 (q, J=6.8 Hz, 1H), 4.13 (s, 3H), 1.87 (d, J=2.0 Hz, 3H), 1.81 (d, J=2.0 Hz, 3H), 1.59 (d, J=6.8 Hz, 3H). Spectra analysis of isomer 2: MS (ES+) $C_{18}H_{21}FN_6O$ requires 356, found 357 [M+H]$^+$. $^1$H NMR (400 MHz, CD$_3$OD): δ ppm 9.23 (s, 1H), 8.74 (s, 1H), 8.30 (br s, 1H), 8.09 (d, J=3.2 Hz, 1H), 7.08 (s, 1H), 4.60 (s, 1H), 4.02 (d, J=4.0 Hz, 3H), 1.84-1.61 (m, 6H), 1.49 (s, 3H), 1.19 (s, 1H).

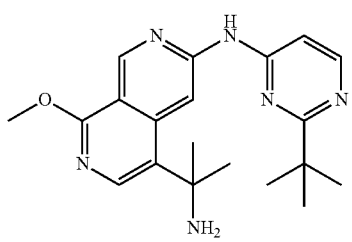 [SMILES: COc1ncc(C(C)(C)N)c2cc(Nc3ccnc(C(C)(C)C)n3)ncc12]

Example 2: 5-(2-Aminopropan-2-yl)-N-(2-(tert-butyl)pyrimidin-4-yl)-8-methoxy-2,7-naphthyridin-3-amine (3)

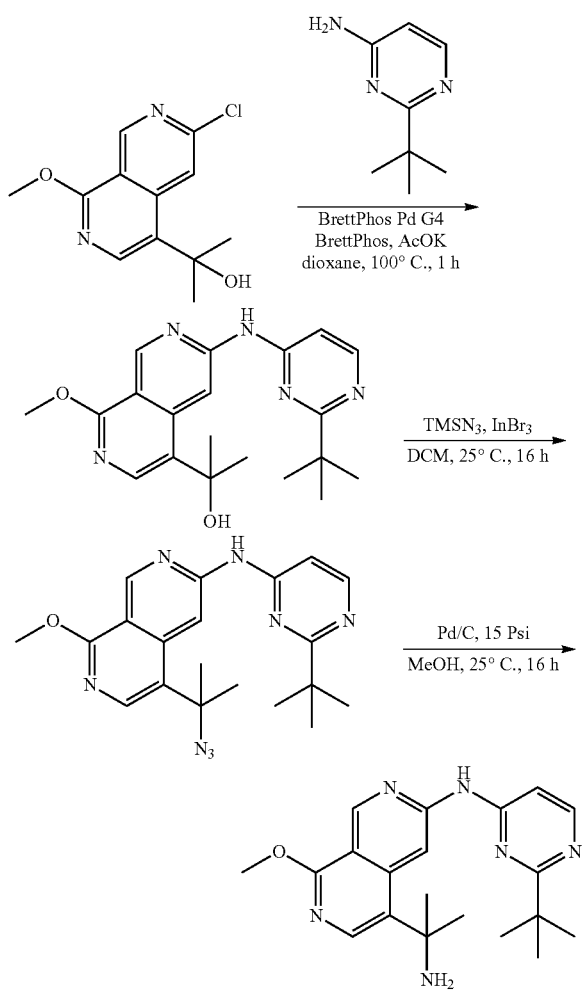

Step 1: 2-(6-((2-(Tert-butyl)pyrimidin-4-yl)amino)-1-methoxy-2,7-naphthyridin-4-yl)propan-2-ol 2-(Dicyclohexylphosphino)-3,6-dimethoxy-2',4',6'-triisopropyl-1,1'-biphenyl (BrettPhos) (40.0 mg, 75.2 umol) and BrettPhos Pd G4 (69.0 mg, 75.2 umol) were added to a mixture of 2-(6-chloro-1-methoxy-2,7-naphthyridin-4-yl)propan-2-ol (Intermediate 31, 190 mg, 752 umol), 2-(tert-butyl)pyrimidin-4-amine (125 mg, 827 umol) and potassium acetate (221 mg, 2.26 mmol) in dioxane (3 mL). The solution was degassed and purged with $N_2$ for 3 times, and then the mixture was stirred at 100° C. for 1 hour under $N_2$ atmosphere. LCMS showed desired mass was detected and starting material was consumed. The reaction mixture was concentrated and the residue was purified by reverse phase prep-HPLC (column: Phenomenex Gemini 150×25 mm×10 um; mobile phase: [water (10 mM $NH_4HCO_3$)-MeCN]; B %: 50%-71%, 7 min) to give the title compound (106.9 mg, 39% yield) as a white solid. MS (ES+) $C_{20}H_{25}N_5O_2$ requires 367, found 368 [M+H]$^+$. $^1$H NMR (400 MHz, $CD_3OD$): δ ppm 9.36 (s, 1H), 8.76 (s, 1H), 8.31 (d, J=6.0 Hz, 1H), 8.14 (s, 1H), 7.40 (d, J=6.0 Hz, 1H), 4.12 (s, 3H), 1.79 (s, 6H), 1.45 (s, 9H).

Step 2: 5-(2-Azidopropan-2-yl)-N-(2-(tert-butyl)pyrimidin-4-yl)-8-methoxy-2,7-naphthyridin-3-amine Indium bromide (183 mg, 517 umol) and trimethylsilylazide (33.0 mg, 284 umol, 37 uL) were added to a solution of 2-(6-((2-(tert-butyl)pyrimidin-4-yl)amino)-1-methoxy-2,7-naphthyridin-4-yl)propan-2-ol (95.0 mg, 259 umol) in dichloromethane (8 mL) under $N_2$. The mixture was stirred at 25° C. for 16 h. LCMS showed desired mass was detected and starting material was consumed. The reaction mixture was diluted with water (15 mL) and extracted with dichloromethane (15 mL×3). The combined organic layers were dried over anhydrous sodium sulfate, filtered and concentrated under reduced pressure to give the title compound (100 mg, 99% yield) as a yellow solid which was used for next step without further purification. MS (ES+) $C_{20}H_{24}N_8O$ requires 392, found 393 [M+H]$^+$. $^1$H NMR (400 MHz, $CDCl_3$): δ ppm 9.43 (s, 1H), 8.67 (s, 1H), 8.48 (d, J=5.6 Hz, 1H), 8.14 (s, 1H), 7.21-7.12 (m, 1H), 4.16 (s, 3H), 1.84 (s, 6H), 1.50 (s, 9H).

Step 3: 5-(2-Aminopropan-2-yl)-N-(2-(tert-butyl)pyrimidin-4-yl)-8-methoxy-2,7-naphthyridin-3-amine Pd/C (40.0 mg, 10% purity) was added to a solution of 5-(2-Azidopropan-2-yl)-N-(2-(tert-butyl)pyrimidin-4-yl)-8-methoxy-2,7-naphthyridin-3-amine (80.0 mg, 204 umol) in methanol (8 mL) under $N_2$. The suspension was degassed under vacuum and purged with $H_2$ several times. The mixture was stirred under $H_2$ (15 psi) at 25° C. for 16 h. LCMS showed desired mass was detected and starting material was consumed. The reaction mixture was filtered and concentrated. The residue was purified by reverse phase prep-HPLC (column: Phenomenex Gemini 150×25 mm×10 um; mobile phase: [water (10 mM $NH_4OAc$)-MECN]; B %: 20%-71%, 7 min) followed by prep-TLC to give the title compound (31.5 mg, 42% yield) as a white solid. MS (ES+) $C_{20}H_{26}N_6O$ requires 366, found 367 [M+H]$^+$. $^1$H NMR (400 MHz, $CD_3OD$): δ ppm 9.39 (s, 1H), 8.58 (s, 1H), 8.34 (d, J=5.6 Hz, 1H), 8.19 (s, 1H), 7.47 (d, J=6.0 Hz, 1H), 4.12 (s, 3H), 1.76 (s, 6H), 1.45 (s, 9H).

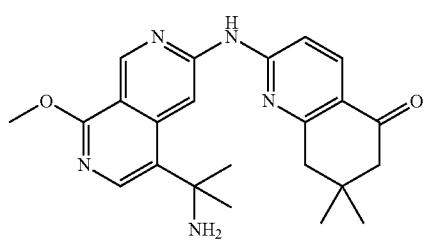 [SMILES: COc1ncc(C(C)(C)N)c2cc(Nc3ccc4c(n3)CC(C)(C)CC4=O)ncc12]

Example 3a: 5-(2-Aminopropan-2-yl)-N-(2-(tert-butyl)pyrimidin-4-yl)-8-methoxy-2,7-naphthyridin-3-amine (34)

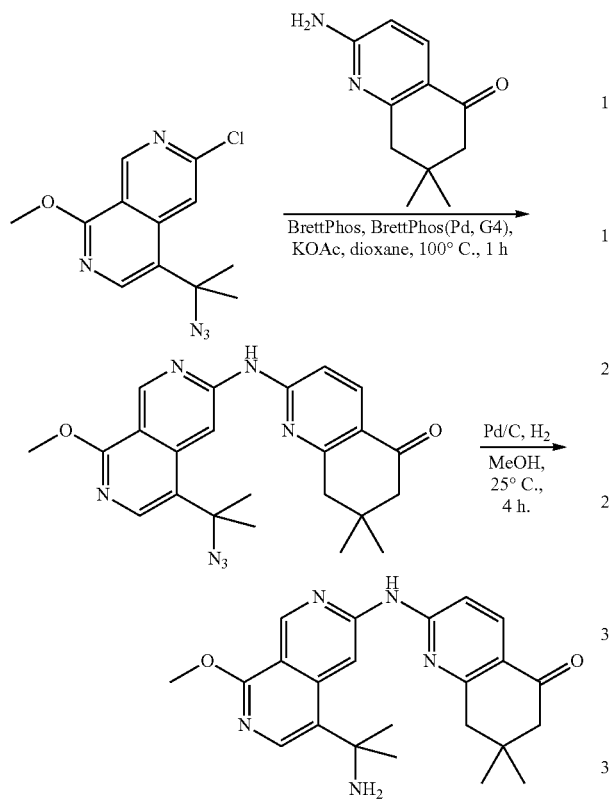

Step 1: 2-((5-(2-Azidopropan-2-yl)-8-methoxy-2,7-naphthyridin-3-yl)amino)-7,7-dimethyl-7,8-dihydroquinolin-5 (6H)-one 2-(Dicyclohexylphosphino)-3,6-dimethoxy-2',4',6'-triisopropyl-1,1'-biphenyl (BrettPhos) (30.9 mg, 57.6 µmol) and BrettPhos Pd G4 (26.5 mg, 28.8 µmol) were added to a mixture of 2-amino-7,7-dimethyl-7,8-dihydroquinolin-5 (6H)-one (Intermediate 9, 80.0 mg, 288 µmol), 4-(2-azidopropan-2-yl)-6-chloro-1-methoxy-2,7-naphthyridine (Intermediate 31a, 56.0 mg, 294 µmol) and potassium acetate (84.8 mg, 864 µmol) in dioxane (2 mL). The solution was degassed and purged with nitrogen atmosphere for 3 times, and then the mixture was stirred at 100° C. for 1 hour under nitrogen atmosphere. LCMS showed desired mass was detected and starting material was consumed. The reaction mixture was concentrated under reduced pressure to give a residue. The residue was purified by flash-column chromatography to give the title compound (120 mg, 78% yield) as a white solid. MS (ES+) $C_{23}H_{25}N_7O_2$ requires 431, found 432 $[M+H]^+$.

Step 2: 2-((5-(2-Aminopropan-2-yl)-8-methoxy-2,7-naphthyridin-3-yl)amino)-7,7-dimethyl-7,8-dihydroquinolin-5 (6H)-one Pd/C (232 µmol, 10% purity) was added to a solution of 2-((5-(2-azidopropan-2-yl)-8-methoxy-2,7-naphthyridin-3-yl)amino)-7,7-dimethyl-7,8-dihydroquinolin-5(6H)-one (100 mg, 232 µmol) in methanol (2 mL) under $H_2$. The suspension was degassed under vacuum and purged with $H_2$ several times. The mixture was stirred under $H_2$ (15 psi) at 25° C. for 1 hour. The reaction mixture was filtered and concentrated under reduced pressure to give a residue. The residue was purified by reverse phase prep-HPLC (column: Phenomenex luna C18 150×25 mm×10 um; mobile phase: [water (10 mM $NH_4HCO_3$)-MeCN]; B %: 30%-60%, 10 min) to give the title compound (4.80 mg, 4.9% yield) as a white solid. MS (ES+) $C_{23}H_{27}N_5O_2$ requires 405, found 406 $[M+H]^+$. $^1$H NMR (400 MHz, $CD_3OD$): δ ppm 9.47 (s, 1H), 9.33 (s, 1H), 8.19 (s, 1H), 8.11 (d, J=8.8 Hz, 1H), 7.09 (d, J=8.8 Hz, 1H), 4.12 (s, 3H), 3.04 (s, 2H), 2.53 (s, 2H), 1.84 (s, 6H), 1.14 (s, 6H).

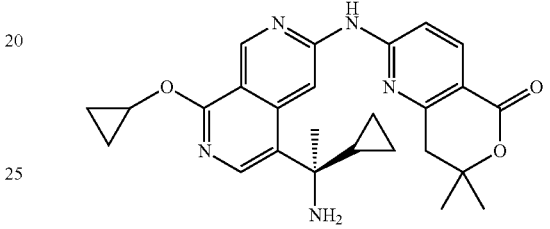

Example 3b: R-2-((5-(1-amino-1-cyclopropylethyl)-8-cyclopropoxy-2,7-naphthyridin-3-yl)amino)-7,7-dimethyl-7,8-dihydro-5H-pyrano[4,3-b]pyridin-5-one (74)

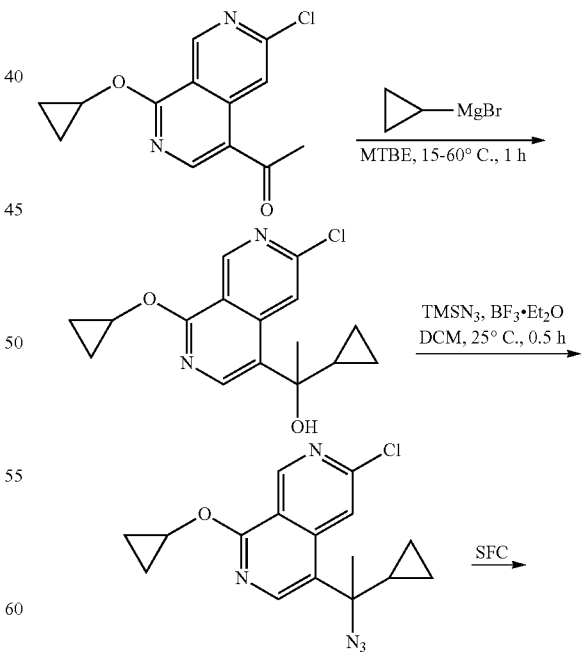

First eluting isomer and Second eluting isomer each of which is represented by one of the structures shown below:

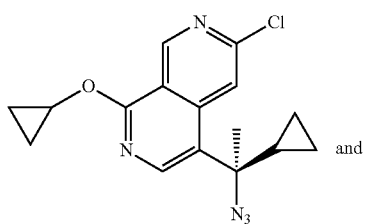

(second eluting isomer)

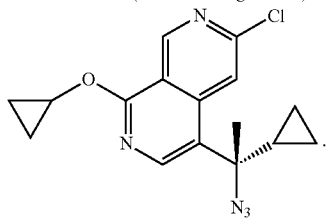

(first eluting isomer)

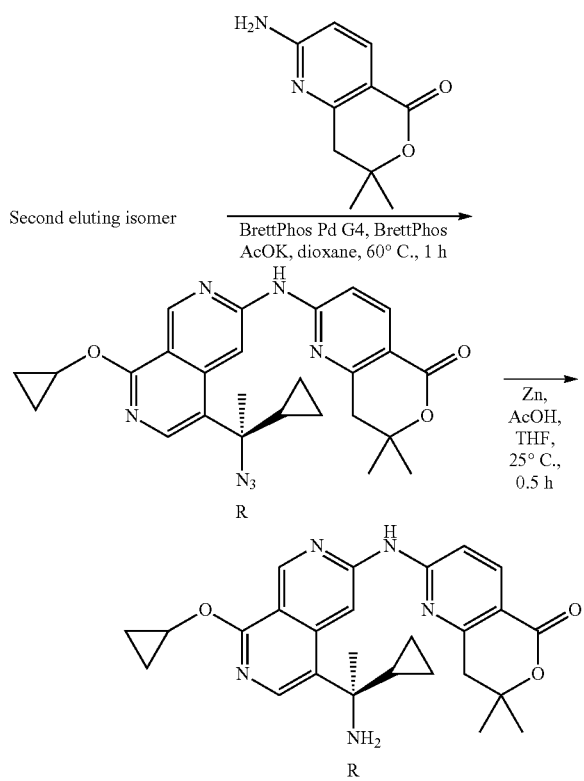

Step 1: 1-(6-Chloro-1-cyclopropoxy-2,7-naphthyridin-4-yl)-1-cyclopropylethan-1-ol Cyclopropylmagnesium bromide (3 M, 3.17 mL) was added to a solution of 1-(6-chloro-1-cyclopropoxy-2,7-naphthyridin-4-yl)ethan-1-one (500 mg, 1.90 mmol) in methyl tert butyl ether (8 mL) at 15° C. under nitrogen atmosphere. The mixture was stirred for 1 h at 60° C. LCMS showed desired mass was detected and starting material was consumed. The reaction mixture was quenched by the addition of saturated aqueous ammonium chloride (20 mL), followed by addition of water (20 mL) and extracted with EA (30 mL×3). The combined organic layers were dried over anhydrous sodium sulfate, filtered and concentrated under reduced pressure to give a residue. The residue was purified by flash-column chromatography to give the title compound (460 mg, 72% yield) as a white solid. MS (ES+) $C_{16}H_{17}ClN_2O_2$ requires 304, found 305 [M+H]$^+$. $^1$H NMR (400 MHz, CDCl$_3$): δ ppm 9.32-9.28 (m, 1H), 8.59 (d, J=0.8 Hz, 1H), 8.54-8.50 (m, 1H), 4.56-4.48 (m, 1H), 2.43-2.21 (m, 1H), 1.58 (d, J=0.8 Hz, 1H), 1.57-1.48 (m, 2H), 0.73-0.50 (m, 6H).

Step 2: 4-(1-Azido-1-cyclopropylethyl)-6-chloro-1-cyclopropoxy-2,7-naphthyridine BF$_3$.Et$_2$O (382 mg, 2.69 mmol) was added to a solution of 1-(6-chloro-1-cyclopropoxy-2,7-naphthyridin-4-yl)-1-cyclopropylethan-1-ol (410 mg, 1.35 mmol) and TMSN$_3$ (155 mg, 1.35 mmol) in dichloromethane (8 mL) under nitrogen atmosphere. The reaction mixture was stirred at 25° C. for 0.5 h. LCMS showed desired mass was detected and starting material was consumed. The reaction mixture was diluted with water (30 mL) and was extracted with EA (30 mL×3). The combined organic layers were dried over anhydrous sodium sulfate, filtered and concentrated under reduced pressure to give a residue. The residue was purified by flash-column chromatography to give the title compound (225 mg, 48% yield) as a colorless oil. MS (ES+) $C_{16}H_{16}ClN_5O$ requires 329, found 330 [M+H]$^+$.

Step 3: (R)-4-(1-azido-1-cyclopropylethyl)-6-chloro-1-cyclopropoxy-2,7-naphthyridine and (S)-4-(1-azido-1-cyclopropylethyl)-6-chloro-1-cyclopropoxy-2,7-naphthyridine 4-(1-Azido-1-cyclopropylethyl)-6-chloro-1-cyclopropoxy-2,7-naphthyridine (225 mg) was separated by SFC (column: DAICEL CHIRALPAK AD-H (250 mm×30 mm, 5 μm); mobile phase: [0.1% NH$_3$H$_2$O EtOH]; B %: 25%-25%, 4 min; 180 min). The title compounds (35 mg, 16% yield; first eluting isomer ((S)-4-(1-azido-1-cyclopropylethyl)-6-chloro-1-cyclopropoxy-2,7-naphthyridine)) and (50 mg, 22% yield; second eluting isomer ((R)-4-(1-azido-1-cyclopropylethyl)-6-chloro-1-cyclopropoxy-2,7-naphthyridine)) were obtained as white solids. The stereochemistry of the isomers were assigned based on an X-ray crystal structure of compound 75. MS (ES+) $C_{16}H_{16}ClN_5O$ requires 329, found 330 [M+H]$^+$.

Step 4: R-2-((5-(1-azido-1-cyclopropylethyl)-8-cyclopropoxy-2,7-naphthyridin-3-yl)amino)-7,7-dimethyl-7,8-dihydro-5H-pyrano[4,3-b]pyridin-5-one 2-(Dicyclohexylphosphino)-3,6-dimethoxy-2',4',6'-triisopropyl-1,1'-biphenyl (BrettPhos) (11.4 mg, 21.2 umol) and BrettPhos Pd G4 (9.77 mg, 10.6 umol) were added to a mixture of 2-amino-7,7-dimethyl-7,8-dihydro-5H-pyrano[4,3-b]pyridin-5-one (Intermediate 2, 22.4 mg, 117 umol), R-4-(1-azido-1-cyclopropylethyl)-6-chloro-1-cyclopropoxy-2,7-naphthyridine (second eluting isomer from step 3, 35 mg, 106 umol) and potassium acetate (31.3 mg, 318 umol) in dioxane (4 mL). The mixture was degassed and purged with nitrogen atmosphere for 3 times, and then stirred at 60° C. for 1 h under nitrogen atmosphere. LCMS showed desired mass was detected and starting material was consumed. The reaction mixture was filtered and concentrated under reduced pressure to give a residue. The residue was purified by prep-TLC to give the title compound (50 mg, 93% yield) as a yellow solid. MS (ES+) $C_{26}H_{27}N_7O_3$ requires 485, found 486 $[M+H]^+$.

Step 5: R-2-((5-(1-amino-1-cyclopropylethyl)-8-cyclopropoxy-2,7-naphthyridin-3-yl)amino)-7,7-dimethyl-7,8-dihydro-5H-pyrano[4,3-b]pyridin-5-one Zn (23.6 mg, 360 umol) and acetic acid (43.3 mg, 721 umol) were added to a solution of R-2-((5-(1-azido-1-cyclopropylethyl)-8-cyclopropoxy-2,7-naphthyridin-3-yl)amino)-7,7-dimethyl-7,8-dihydro-5H-pyrano[4,3-b]pyridin-5-one (35 mg, 72.1 umol) from Step 4 in tetrahydrofuran (6 mL) and the mixture was stirred at 25° C. for 0.5 h. LCMS showed desired mass was detected and starting material was consumed. The reaction mixture was filtered, concentrated in vacuo to give the residue. The residue was purified by reverse phase prep-HPLC to give the title compound (13.4 mg, 39% yield) as a yellow solid. MS (ES+) $C_{26}H_{29}N_5O_3$ requires 459, found 460 $[M+H]^+$. $^1$H NMR (400 MHz, $CD_3OD$): δ ppm 9.27 (s, 1H), 9.19 (s, 1H), 8.52 (s, 1H), 8.15-8.11 (m, 2H), 7.24 (d, J=8.8 Hz, 1H), 4.54-4.46 (m, 1H), 3.18 (d, J=0.8 Hz, 2H), 1.84 (s, 3H), 1.65-1.56 (m, 1H), 1.52 (d, J=7.6 Hz, 6H), 0.94-0.86 (m, 4H), 0.84-0.67 (m, 3H), 0.65-0.54 (m, 1H).

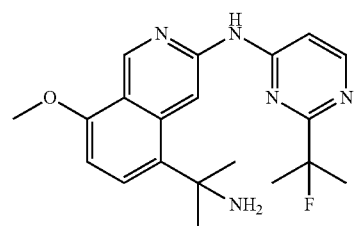 [SMILES: COc1ccc(C(C)(C)N)c2cc(Nc3ccnc(C(C)(C)F)n3)ncc12]

Example 4: 5-(2-Aminopropan-2-yl)-N-(2-(2-fluoropropan-2-yl)pyrimidin-4-yl)-8-methoxyisoquinolin-3-amine (5)

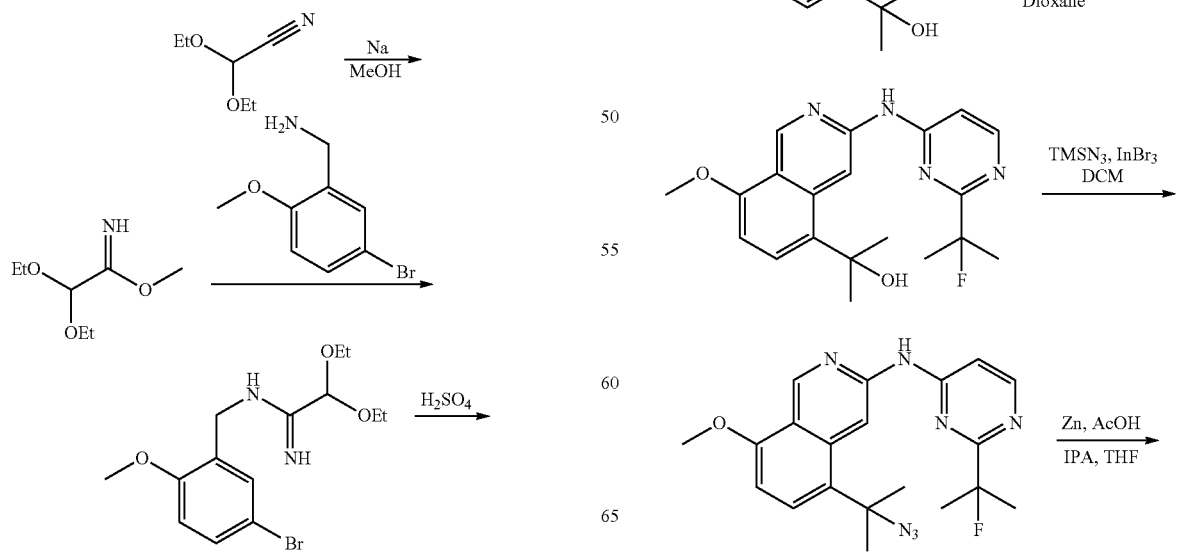

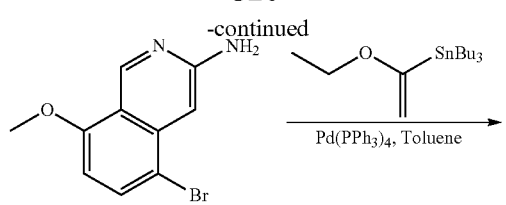

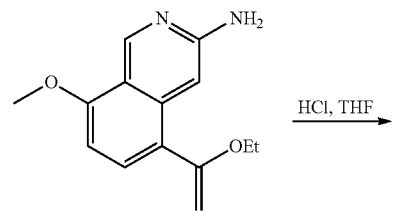

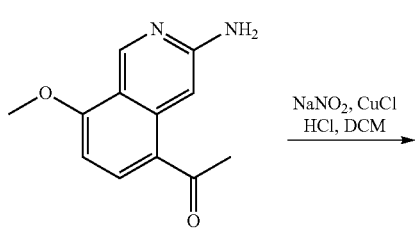

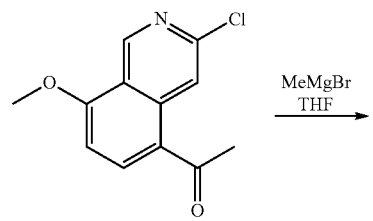

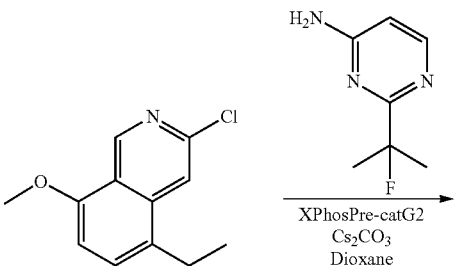

-continued

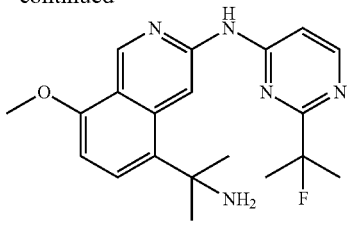

Step 1: Methyl 2,2-diethoxyacetimidate 2,2-diethoxyMeCN (8.4 g, 65 mmol, 9 mL) was added to a solution of Na (149.5 mg, 6.5 mmol, 154.1 uL) in MeOH (70 mL). The mixture was stirred at 25° C. for 12 h. The reaction mixture was filtered and concentrated under reduced pressure to give a residue. The residue was filtered, washed with Petroleum ether:MeOH (2:1; 3 times), and then the filtrate was concentrated under reduced pressure to give the title compound (10 g, crude) as a white oil.

Step 2: N-(5-bromo-2-methoxybenzyl)-2,2-diethoxyacetimidamide

Methyl 2,2-diethoxyethanimidate (8.9 g, 55.5 mmol) was added to a solution of (5-bromo-2-methoxy-phenyl)methanamine (10 g, 46.3 mmol) in MeOH (100 mL) under an atmosphere of $N_2$. The mixture was stirred at 25° C. for 12 h. LCMS showed desired MS was detected. The reaction mixture was filtered and concentrated under reduced pressure to give a residue. The residue was diluted with $H_2O$ (50 mL) and extracted with DCM 200 mL (50 mL×4). The combined organic layers were washed with saturated aqueous NaCl solution (50 mL), dried over $Na_2SO_4$, filtered and concentrated under reduced pressure to give the title compound (12 g, crude) as a white solid which was used in the next step without further purification.

Step 3: 5-Bromo-8-methoxyisoquinolin-3-amine

N-(5-bromo-2-methoxybenzyl)-2,2-diethoxyacetimidamide (11 g, 31.9 mmol) was added to $H_2SO_4$ (111.61 g, 1.1 mol, 60.6 mL, 98% purity) at 0° C., and then the mixture was stirred at 25° C. for 3 h under an atmosphere of $N_2$. The reaction mixture was quenched by addition of NaOH (120 g) in $H_2O$ (5 L) at 0° C., and extracted with 2-MeTHF (1 L×2). The combined organic layers were washed with saturated aqueous NaCl solution (1 L), dried over $Na_2SO_4$, filtered and concentrated under reduced pressure to give a residue. The residue was purified by reverse phase prep-HPLC to give the title compound (3 g, 11.8 mmol, 37% yield) as a yellow solid.

Step 4: 5-(1-Ethoxyvinyl)-8-methoxyisoquinolin-3-amine $Pd(PPh_3)_4$ (1.02 g, 884.8 μmol) and tributyl(1-ethoxyvinyl)stannane (6.79 g, 18.8 mmol, 6.3 mL) were added to a solution of 5-bromo-8-methoxyisoquinolin-3-amine (2.8 g, 11.1 mmol) in toluene (30 mL) under $N_2$ atmosphere. The mixture was stirred at 100° C. for 4 hs under $N_2$ atmosphere. The reaction mixture was quenched by addition of aqueous CsF solution (60 mL) at 0° C. and extracted with EA (40 mL×3). The combined organic layers were washed with saturated aqueous NaCl solution (50 mL), dried over $Na_2SO_4$, filtered and concentrated under reduced pressure to give the title compound (2.7 g, crude) as a brown oil which was used in the next step without further purification.

Step 5: 1-(3-Amino-8-methoxyisoquinolin-5-yl)ethan-1-one

A mixture of 5-(1-ethoxyvinyl)-8-methoxyisoquinolin-3-amine (2.7 g, 11.1 mmol) in THF (20 mL) and HCl (1M, 11 mL) was stirred at 25° C. for 30 min under $N_2$ atmosphere. The reaction mixture was filtered to give the title compound (1.1 g, crude) as a yellow solid which was used in the next step without further purification.

Step 6: 1-(3-Chloro-8-methoxyisoquinolin-5-yl)ethan-1-one

Pyridine hydrochloride (1.03 g, 8.9 mmol), CuCl (25.2 mg, 254.3 umol, 6.08 uL) and $NaNO_2$ (614.2 mg, 8.9 mmol) were added to a solution of 1-(3-amino-8-methoxyisoquinolin-5-yl)ethan-1-one (550 mg, 2.5 mmol) in DCM (5 mL) under $N_2$ atmosphere. HCl (37.6 mg, 381.5 umol, 36.9 uL, 37% purity) was then added to the reaction mixture at −10° C., and the mixture was stirred at 0° C. for 30 min. The mixture was stirred at 25° C. for 1 h under $N_2$ atmosphere. The reaction mixture was filtered and concentrated under reduced pressure to give a residue. The residue was purified by flash-column chromatography to give the title compound (530 mg, 44% yield) as a white solid.

Step 7: 2-(3-Chloro-8-methoxyisoquinolin-5-yl)propan-2-ol

MeMgBr (3M in THF, 1.41 mL) was added to a solution of 1-(3-Chloro-8-methoxyisoquinolin-5-yl)ethan-1-one (200 mg, 848.7 umol) in THF (2 mL) under $N_2$ atmosphere, and the reaction mixture was stirred at 25° C. for 1 h under $N_2$ atmosphere. The reaction mixture was quenched by the addition of $H_2O$ (10 mL) at 0° C. The reaction mixture was filtered and concentrated under reduced pressure to give a residue. The residue was purified by flash-column chromatography to give the title compound (580 mg, 90.5% yield) as a yellow solid.

Step 8: 2-(3-((2-(2-Fluoropropan-2-yl)pyrimidin-4-yl)amino)-8-methoxyisoquinolin-5-yl)propan-2-ol

[2-(2-aminophenyl)phenyl]-chloro-palladium; dicyclohexyl-[3-(2,4,6-triisopropylphenyl)phenyl]phosphane (62.5 mg, 79.5 umol) was added to a solution of 2-(3-chloro-8-methoxyisoquinolin-5-yl)propan-2-ol (200 mg, 794.6 umol), $Cs_2CO_3$ (517.7 mg, 1.59 mmol) and 2-(2-fluoropropan-2-yl)pyrimidin-4-amine (Intermediate 1, 135.6 mg, 874 umol) in dioxane (2 mL) under $N_2$ atmosphere. The mixture was stirred at 120° C. for 12 h under $N_2$ atmosphere. The reaction mixture was filtered and concentrated under reduced pressure to give a residue. The residue was purified by flash-column chromatography to give the title compound (250 mg, 84% yield) as a yellow solid. $^1$H-NMR (400 MHz, $CD_3OD$) δ ppm 9.41 (s, 1H), 9.02 (s, 1H), 8.34 (d, 1H, J=6.0 Hz), 7.76 (d, 1H, J=8.0 Hz), 7.33 (d, 1H, J=6.0 Hz), 6.84 (d, 1H, J=8.4 Hz), 4.05 (s, 3H), 1.84 (t, 12H, J=9.2 Hz). MS (ES+) $C_{20}H_{23}FN_4O_2$ requires 370, found 371 [M+H]$^+$.

Step 9: 5-(2-Azidopropan-2-yl)-N-(2-(2-fluoropropan-2-yl)-pyrimidin-4-yl)-8-methoxyisoquinolin-3-amine Indium tribromide (248.8 mg, 701.9 umol) and trimethylsilylazide (60.6 mg, 526.4 umol, 69.2 uL) were added to a solution of 2-(3-((2-(2-fluoropropan-2-yl)pyrimidin-4-yl)amino)-8-methoxyisoquinolin-5-yl)propan-2-ol (130 mg, 350.9 umol) under N$_2$ atmosphere in dichloromethane (2 mL). The mixture was stirred at 25° C. for 16 h. The reaction mixture was concentrated under reduced pressure and the residue was diluted with H$_2$O (5 mL) and extracted with EA (5 mL×3). The combined organic layers were washed with saturated aqueous sodium chloride solution (5 mL), dried over Na$_2$SO$_4$, filtered and concentrated under reduced pressure to give the title compound (138 mg, crude) as a brown oil which was used in the next without further purification.

Step 10: 5-(2-aminopropan-2-yl)-N-(2-(2-fluoropropan-2-yl)pyrimidin-4-yl)-8-methoxyisoquinolin-3-amine Zn (228.2 mg, 3.5 mmol) and AcOH (0.2 mL) were added to a solution of 5-(2-azidopropan-2-yl)-N-(2-(2-fluoropropan-2-yl)pyrimidin-4-yl)-8-methoxyisoquinolin-3-amine (138 mg, 349 umol) in THF (2 mL) and IPA (0.4 mL). The mixture was stirred at 25° C. for 3 h. The reaction mixture was filtered and concentrated under reduced pressure to give a residue. The residue was purified by reverse phase prep-HPLC (column: Kromasil 150×25 mm×10 um; mobile phase: [water(0.04% NH$_3$H$_2$O+10 mM NH$_4$HCO$_3$)-MECN]; B %: 15%-45%, 10 min) to give the title compound (64 mg, 49% yield) as a white solid. $^1$H-NMR (400 MHz, CD$_3$OD) δ ppm 9.42 (s, 1H), 9.03 (s, 1H), 8.35 (d, 1H, J=6.0 Hz), 7.76 (d, 1H, J=8.4 Hz), 7.28 (d, 1H, J=5.6 Hz), 6.85 (d, 1H, J=8.4 Hz), 4.05 (s, 3H), 1.80 (t, 13H, J=10.8 Hz). MS (ES+) C$_{20}$H$_{24}$FN$_5$O requires 369, found 370 [M+H]$^+$.

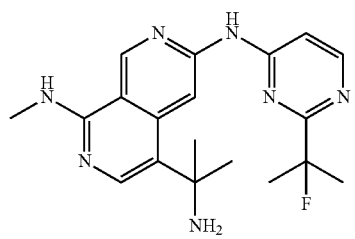

Example 5: 4-(2-Aminopropan-2-yl)-N6-(2-(2-fluoropropan-2-yl)pyrimidin-4-yl)-N1-methyl-2,7-naphthyridine-1,6-diamine (6)

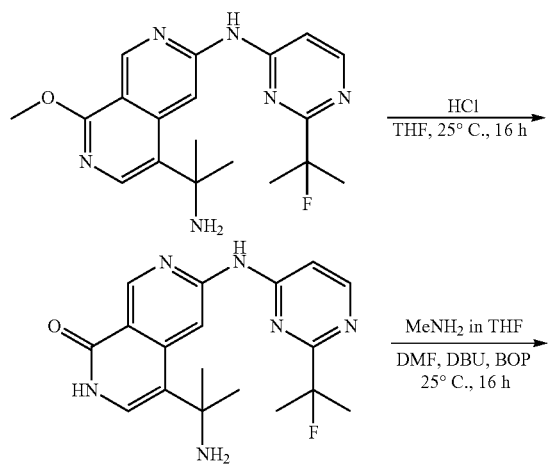

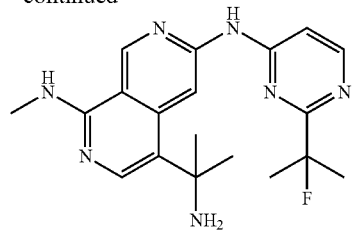

Step 1: 4-(2-Aminopropan-2-yl)-6-((2-(2-fluoropropan-2-yl)pyrimidin-4-yl)amino)-2,7-naphthyridin-1(2H)-one HCl (1.5 M, 0.18 mL) was added to a solution of 5-(2-aminopropan-2-yl)-N-(2-(2-fluoropropan-2-yl)pyrimidin-4-yl)-8-methoxy-2,7-naphthyridin-3-amine (prepared similar to Example 3a, 20.0 mg, 54 umol) in tetrahydrofuran (2 mL) and the solution was stirred at 25° C. for 16 h. The reaction mixture was basified by the addition of aqueous saturated sodium bicarbonate solution (5 mL) followed by addition of water (15 mL) and the mixture was extracted with EA (15 mL×3). The combined organic layers were dried over anhydrous sodium sulfate, filtered and concentrated to give the title compound (19.0 mg, 99% yield) as a yellow solid which was used for next step without further purification. MS (ES+) C$_{18}$H$_{21}$FN$_6$O requires 356, found 357 [M+H]$^+$. $^1$H NMR (400 MHz, CD$_3$OD): δ ppm 9.30 (s, 1H), 8.84 (s, 1H), 8.42 (d, J=6.0 Hz, 1H), 7.42 (d, J=6.0 Hz, 1H), 7.38 (s, 1H), 1.81 (s, 3H), 1.75 (s, 3H), 1.70 (s, 6H).

Step 2: 4-(2-Aminopropan-2-yl)-N6-(2-(2-fluoropropan-2-yl)pyrimidin-4-yl)-N1-methyl-2,7-naphthyridine-1,6-diamine DBU (6.0 mg, 42.1 umol, 6.3 uL) and BOP (19 mg, 42.1 umol) were added to a solution of methylamine (2 M in THF, 1 mL) in DMF (1 mL) followed by addition of 4-(2-aminopropan-2-yl)-6-((2-(2-fluoropropan-2-yl)pyrimidin-4-yl)amino)-2,7-naphthyridin-1(2H)-one (10.0 mg, 28.1 umol). The mixture was stirred at 25° C. for 16 h. The reaction mixture was diluted with water (15 mL) and extracted with EA (15 mL×3). The combined organic layers were dried over anhydrous sodium sulfate, filtered and concentrated. The residue was purified by reverse phase prep-HPLC to give the title compound (3.4 mg, 32% yield) as a yellow solid. MS (ES+) C$_{19}$H$_{24}$FN$_7$ requires 369, found 370 [M+H]$^+$. $^1$H NMR (400 MHz, CD$_3$OD): δ ppm 9.22 (s, 1H), 8.89 (s, 1H), 8.37 (d, J=6.0 Hz, 1H), 8.04 (s, 1H), 7.32 (d, J=6.0 Hz, 1H), 3.05 (s, 3H), 1.81 (s, 3H), 1.76 (s, 3H), 1.74 (s, 6H).

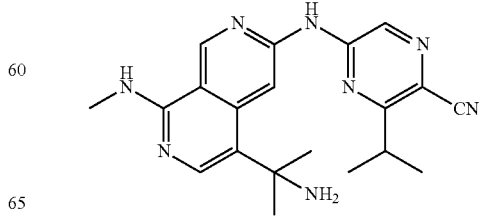

Example 6: 5-((5-(2-Aminopropan-2-yl)-8-(methylamino)-2,7-naphthyridin-3-yl)amino)-3-isopropylpyrazine-2-carbonitrile (8)

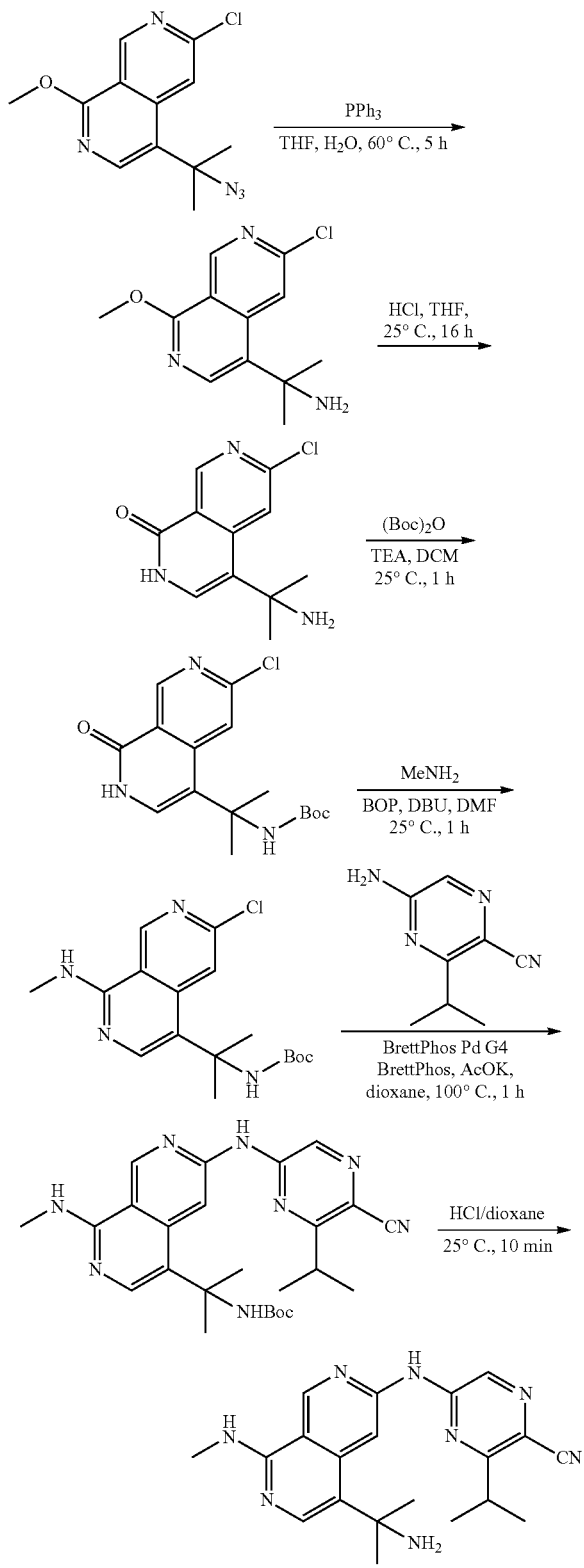

Step 1: 2-(6-Chloro-1-methoxy-2,7-naphthyridin-4-yl)propan-2-amine

Triphenyl phosphine (2.05 g, 7.83 mmol) was added to a solution of 4-(2-azidopropan-2-yl)-6-chloro-1-methoxy-2,7-naphthyridine (Intermediate 31a, 870 mg, 3.13 mmol) in tetrahydrofuran (20 mL) and water (5 mL) and then the mixture was stirred at 60° C. for 5 h. The reaction mixture was diluted with water (15 mL) and extracted with EA (15 mL×3). The combined organic layers were dried over anhydrous sodium sulfate, filtered and concentrated. The residue was purified by flash-column chromatography to give the title compound (1.7 g, crude) as a white solid.
$^1$H NMR (400 MHz, CDCl$_3$): δ ppm 9.24 (s, 1H), 9.07 (s, 1H), 7.75 (s, 1H), 4.03 (s, 3H), 1.81 (s, 6H).

Step 2: 4-(2-Aminopropan-2-yl)-6-chloro-2,7-naphthyridin-1(2H)-one

HCl (3 M, 11 mL) was added to a solution of 2-(6-chloro-1-methoxy-2,7-naphthyridin-4-yl)propan-2-amine (1.70 g, 6.75 mmol) in tetrahydrofuran (15 mL) and the mixture was stirred at 25° C. for 16 h. The reaction mixture was diluted with water (15 mL) and extracted with EA (15 mL×3). The aqueous phase was basified by the addition of saturated aqueous sodium bicarbonate solution (5 mL) and extracted with EA (15 mL×3). The combined organic layers were dried over anhydrous sodium sulfate, filtered and concentrated to give the title compound (430 mg, 27% yield) as a yellow solid which was used for next step without further purification. $^1$H NMR (400 MHz, CDCl$_3$): δ ppm 9.42 (s, 1H), 9.12 (s, 1H), 8.7 (s, 1H), 1.72 (s, 6H).

Step 3: Tert-butyl (2-(6-chloro-1-oxo-1,2-dihydro-2,7-naphthyridin-4-yl)propan-2-yl)carbamate Triethylamine (128 mg, 1.26 mmol, 176 uL) was added to a solution of 4-(2-aminopropan-2-yl)-6-chloro-2,7-naphthyridin-1(2H)-one (100 mg, 421 umol) and (Boc)$_2$O (459 mg, 2.1 mmol, 483 uL) in dichloromethane (2 mL) and the mixture was stirred at 25° C. for 1 hour. The reaction mixture was diluted with water (15 mL) and extracted with dichloromethane (15 mL×3). The combined organic layers were dried over anhydrous sodium sulfate, filtered and concentrated. The residue was purified by prep-TLC (silica, petroleum ether:EA=5:1) to give the title compound (20.0 mg, 14% yield) as a yellow solid.
$^1$H NMR (400 MHz, CDCl$_3$): δ ppm 9.40 (s, 1H), 8.03 (s, 1H), 7.78 (s, 1H), 4.98 (s, 1H), 1.70 (s, 6H), 1.65 (s, 9H).

Step 4: Tert-butyl (2-(6-chloro-1-(methylamino)-2,7-naphthyridin-4-yl)propan-2-yl)carbamate DBU (14 mg, 88.8 umol, 13.4 uL) and BOP (39 mg, 88.8 umol) followed by methylamine (2 M in THF, 22 mL) were added to a solution of tert-butyl (2-(6-chloro-1-oxo-1,2-dihydro-2,7-naphthyridin-4-yl)propan-2-yl)carbamate (20.0 mg, 59.2 umol) in DMF (1 mL) and the mixture was stirred at 25° C. for 1 hour. The reaction mixture was diluted with water (15 mL) and extracted with EA (15 mL×3). The combined organic layers were washed with brine (15 mL×3), dried over anhydrous sodium sulfate, filtered and concentrated to give the title compound (20.0 mg, 96% yield) as a white solid which was used for the next step without further purification. MS (ES+) C$_{17}$H$_{23}$ClN$_4$O$_2$ requires 350, found 351 [M+H]$^+$.

Step 5: Tert-butyl (2-(6-((5-cyano-6-isopropylpyrazin-2-yl)amino)-1-(methylamino)-2,7-naphthyridin-4-yl)propan-2-yl)carbamate 2-(Dicyclohexylphosphino)-3,6-dimethoxy-2',4',6'-triisopropyl-1,1'-biphenyl (BrettPhos) (6 mg, 11.4 umol) and BrettPhos Pd G4 (10 mg, 11.4 umol) were added to a mixture of tert-butyl (2-(6-chloro-1-(methylamino)-2,7-naphthyridin-4-yl)propan-2-yl)carbamate (40 mg, 114 umol), 5-amino-3-isopropylpyrazine-2-carbonitrile (20 mg, 123 umol) and potassium acetate (34 mg, 342 umol) in dioxane (2 mL). The solution was degassed and purged with $N_2$ for 3 times, and then the mixture was stirred at 100° C. for 1 hour under an atmosphere of $N_2$. The reaction mixture was diluted with water (15 mL) and extracted with EA (15 mL×3). The combined organic layers were dried over anhydrous sodium sulfate, filtered and concentrated. The residue was purified by prep-TLC (silica, petroleum ether:EA=1:1) to give the title compound (30 mg, 55% yield) as a yellow solid. MS (ES+) $C_{25}H_{32}N_8O_2$ requires 476, found 477 $[M+H]^+$

Step 6: 5-((5-(2-Aminopropan-2-yl)-8-(methylamino)-2,7-naphthyridin-3-yl)amino)-3-isopropylpyrazine-2-carbonitrile Hydrochloric acid in dioxane (4M, 1 mL) was added to a solution of tert-butyl (2-(6-((5-cyano-6-isopropylpyrazine-2-yl)amino)-1-(methylamino)-2,7-naphthyridin-4-yl)propan-2-yl)carbamate (25 mg, 52.5 umol) in dioxane (1 mL) and the solution was stirred at 25° C. for 10 minutes. The reaction mixture was concentrated and the residue was purified by reverse phase prep-HPLC (column: Luna C18 150*25 5 u; mobile phase: [water(0.075% TFA)-MeCN]; B %: 5%-35%, 9 min) to give the title compound (14.9 mg, 74% yield) as a yellow solid. MS (ES+) $C_{20}H_{24}N_8$ requires 376, found 377 $[M+H]^+$. $^1H$ NMR (400 MHz, $CD_3OD$): δ ppm 9.49 (s, 1H), 9.08 (s, 1H), 8.28 (s, 1H), 7.56 (s, 1H), 3.55-3.46 (m, 1H), 3.24 (s, 3H), 2.00 (s, 6H), 1.42 (d, J=7.2 Hz, 6H).

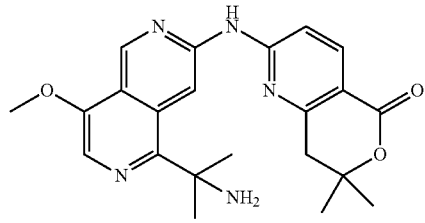 [SMILES: COc1cnc(C(C)(C)N)c2cc(Nc3ccc4c(n3)CC(C)(C)OC4=O)ncc12]

Example 7: 2-((5-(2-Aminopropan-2-yl)-8-methoxy-2,6-naphthyridin-3-yl)amino)-7,7-dimethyl-7,8-dihydro-5H-pyrano[4,3-b]pyridin-5-one (46)

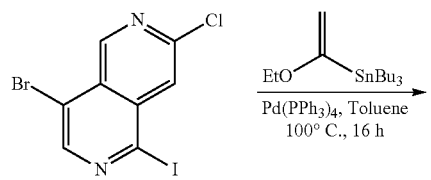

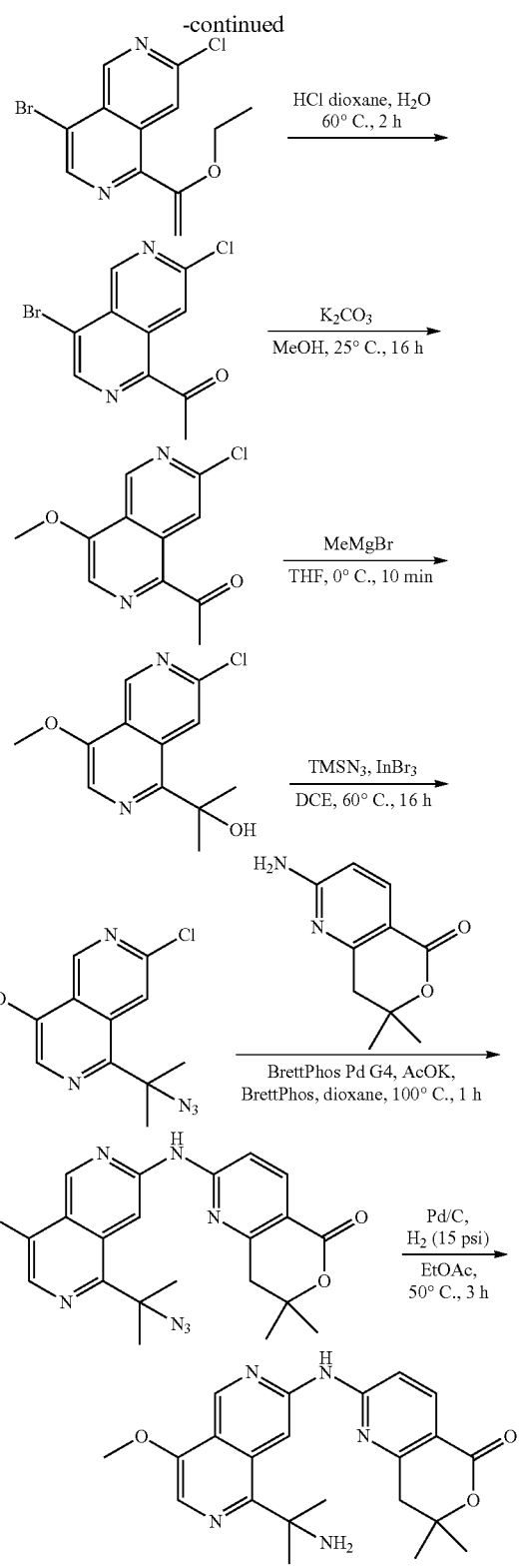

Step 1: 4-bromo-7-chloro-1-(1-ethoxyvinyl)-2,6-naphthyridine $Pd(PPh_3)_4$ (313 mg, 271 umol) was added to a mixture of 4-bromo-7-chloro-1-iodo-2,6-naphthyridine (Intermediate 32, 1.0 g, 2.71 mmol) and tributyl(1-ethoxyvinyl)stannane (1.0 g, 2.77 mmol, 935 uL) in toluene (20 mL). The solution was degassed and purged with nitrogen for 3 times, and then the mixture was stirred at 100° C. for 16 h under an atmosphere of nitrogen. The reaction mixture was quenched by addition of saturated potassium fluoride solution (50 mL), and then diluted with water (20 mL) and extracted with EA (50 mL×3). The combined organic layers were dried over anhydrous sodium sulfate, filtered and concentrated under reduced pressure to give a residue. The residue was purified by flash-column chromatography (petroleum ether:EA=1:0 to 10:1) to give the title compound (640 mg, 75% yield) as a yellow solid. $^1$H NMR (400 MHz, CDCl$_3$): δ ppm 9.43 (s, 1H), 8.79 (s, 1H), 8.30 (d, J=0.8 Hz, 1H), 4.88-4.85 (m, 1H), 4.72-4.69 (m, 1H), 4.15-4.08 (m, 2H), 1.49 (t, J=6.8 Hz, 3H).

Step 2: 1-(4-Bromo-7-chloro-2,6-naphthyridin-1-yl)ethan-1-one

HCl in dioxane (4 M, 6 mL) and water (1 mL) were added to 4-bromo-7-chloro-1-(1-ethoxyvinyl)-2,6-naphthyridine (640 mg, 2.04 mmol) and the solution was stirred at 60° C. for 2 h. The reaction mixture was basified by the addition of saturated aqueous sodium bicarbonate solution (10 mL) followed by addition of water (20 mL). The aqueous layer was extracted with EA (20 mL×3). The combined organic layers were dried over anhydrous sodium sulfate, filtered and concentrated. The residue was purified by flash-column chromatography (petroleum ether:EA=1:0 to 10:1) to give the title compound (550 mg, 94% yield) as a yellow solid.

Step 3: 1-(7-Chloro-4-methoxy-2,6-naphthyridin-1-yl)ethan-1-one

Potassium carbonate (799 mg, 5.78 mmol) was added to a solution of 1-(4-bromo-7-chloro-2,6-naphthyridin-1-yl)ethan-1-one (550 mg, 1.93 mmol) in methanol (15 mL) and the solution was stirred at 25° C. for 16 h. The reaction mixture was concentrated, diluted with water (30 mL) and extracted with EA (30 mL×3). The combined organic layers were dried over anhydrous sodium sulfate, filtered and concentrated under reduced pressure to give the title compound (410 mg, 90% yield) as a yellow solid which was used for next step without further purification. $^1$H NMR (400 MHz, CDCl$_3$): δ ppm 9.51 (s, 1H), 9.10 (d, J=1.2 Hz, 1H), 8.28 (s, 1H), 4.23 (s, 3H), 2.80 (s, 3H).

Step 4: 2-(7-Chloro-4-methoxy-2,6-naphthyridin-1-yl)propan-2-ol

Methylmagnesium bromide (3 M in THF, 2 mL) was added to a solution of 1-(7-chloro-4-methoxy-2,6-naphthyridin-1-yl)ethan-1-one (410 mg, 1.73 mmol) in tetrohydrofuran (15 mL) at 0° C. under an atmosphere of nitrogen. The solution was stirred at 0° C. for 10 minutes. The reaction mixture was quenched by addition of water (25 mL) and extracted with EA (25 mL×3). The combined organic layers were dried over anhydrous sodium sulfate, filtered and concentrated under reduced pressure to give a residue. The residue was purified by flash-column chromatography (petroleum ether:EA=1:0 to 3:1) to give the title compound (110 mg, 22% yield) as a yellow solid. $^1$H NMR (400 MHz, CDCl$_3$): δ ppm 9.53 (d, J=0.8 Hz, 1H), 8.21 (s, 1H), 8.09 (s, 1H), 5.38 (s, 1H), 4.13 (s, 3H), 1.78 (s, 6H).

Step 5: 1-(2-Azidopropan-2-yl)-7-chloro-4-methoxy-2,6-naphthyridine

Indium bromide (224 mg, 633 umol) and trimethylsilyl azide (91.0 mg, 791 umol) were added to a solution of 2-(7-chloro-4-methoxy-2,6-naphthyridin-1-yl)propan-2-ol (80.0 mg, 317 umol) in 1, 2-dichloroethane (3 mL) under an atmosphere of nitrogen. The mixture was stirred at 60° C. for 16 h. The reaction mixture was diluted with water (15 mL) and extracted with dichloromethane (15 mL×3). The combined organic layers were dried over anhydrous sodium sulfate, filtered and concentrated under reduced pressure to give a residue. The residue was purified by prep-TLC (petroleum ether:EA=3:1) to give the title compound (30.0 mg, 32% yield) as a yellow solid. MS (ES+) C$_{12}$H$_{12}$ClN$_5$O requires 277, found 278 [M+H]$^+$ Step 6: 2-((5-(2-Azidopropan-2-yl)-8-methoxy-2,6-naphthyridin-3-yl)amino)-7,7-dimethyl-7,8-dihydro-5H-pyrano[4,3-b]pyridin-5-one 2-(Dicyclohexylphosphino)-3,6-dimethoxy-2',4',6'-triisopropyl-1,1'-biphenyl (BrettPhos) (12 mg, 21.6 umol) and BrettPhos Pd G4 (10 mg, 10.8 umol) were added to a mixture of 1-(2-azidopropan-2-yl)-7-chloro-4-methoxy-2,6-naphthyridine (30 mg, 108 umol), 2-amino-7,7-dimethyl-7,8-dihydro-5H-pyrano[4,3-b]pyridin-5-one (Intermediate 2, 22.0 mg, 113 umol) and potassium acetate (32.0 mg, 324 umol) in dioxane (2 mL). The solution was degassed and purged with nitrogen 3 times, and then the mixture was stirred at 100° C. for 1 hour under an atmosphere of nitrogen. The reaction mixture was concentrated and the residue was purified by prep-TLC (petroleum ether:EA=1:1) to give the title compound (20.0 mg, 43% yield) as a yellow solid. MS (ES+) C$_{22}$H$_{23}$N$_7$O$_3$ requires 433, found 434 [M+H]$^+$.

Step 7: 2-((5-(2-Aminopropan-2-yl)-8-methoxy-2,6-naphthyridin-3-yl)amino)-7,7-dimethyl-7,8-dihydro-5H-pyrano[4,3-b]pyridin-5-one Pd/C (20 mg, 10% purity) was added to a solution of 2-((5-(2-azidopropan-2-yl)-8-methoxy-2,6-naphthyridin-3-yl)amino)-7,7-dimethyl-7,8-dihydro-5H-pyrano[4,3-b]pyridin-5-one (20 mg, 46.1 umol) in EA (6 mL) under an atmosphere of nitrogen. The suspension was degassed under vacuum and purged with hydrogen several times. The mixture was stirred under hydrogen (15 psi) at 50° C. for 3 h. The reaction mixture was filtered and concentrated. The residue was purified by prep-TLC (methanol:EA=1:10) to give the title compound (5.8 mg, 28% yield) as a yellow solid. MS (ES+) C$_{22}$H$_{25}$N$_5$O$_3$ requires 407, found 408 [M+H]$^+$. $^1$H NMR (400 MHz, CD$_3$OD): δ ppm 9.43 (s, 1H), 8.14 (d, J=8.8 Hz, 1H), 8.06 (s, 1H), 7.17 (d, J=8.4 Hz, 1H), 4.13 (s, 3H), 3.22 (s, 2H), 1.92 (s, 6H), 1.54 (s, 6H).

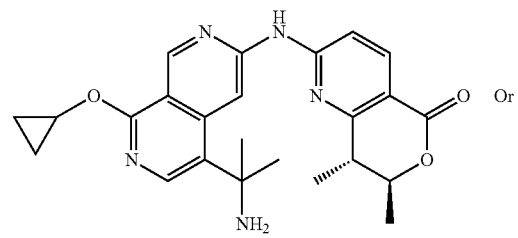

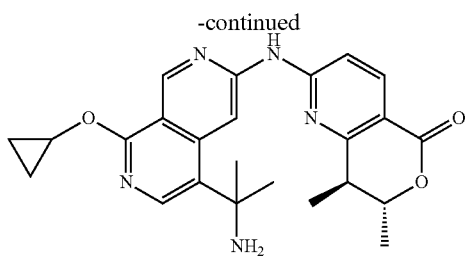

Example 8: (7S, 8R)-2-((5-(2-aminopropan-2-yl)-8-cyclopropoxy-2,7-naphthyridin-3-yl)amino)-7,8-dimethyl-7,8-dihydro-5H-pyrano[4,3-b]pyridin-5-one (66)

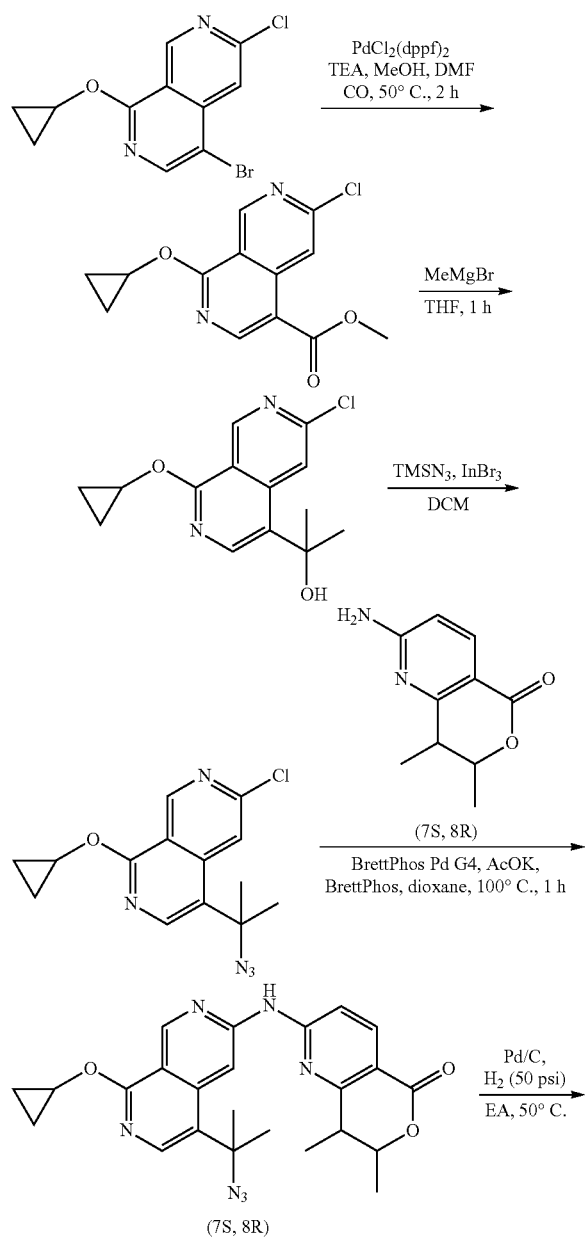

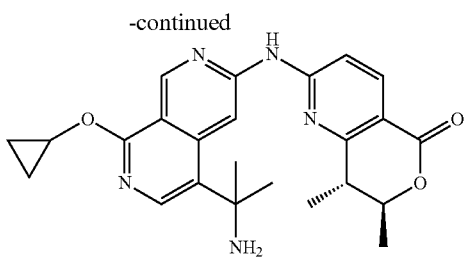

Step 1: Methyl 6-chloro-1-cyclopropoxy-2,7-naphthyridine-4-carboxylate

[1,1'-bis(diphenylphosphino)ferrocene]dichloropalladium(II) dichloromethane complex (1.09 g, 1.335 mmol) was added to a mixture of 4-bromo-6-chloro-1-cyclopropoxy-2,7-naphthyridine (4 g, 13.35 mmol) and triethylamine (2.233 ml, 16.02 mmol) in MeOH (30 ml) and DMF (15 ml). The reaction vessel was capped under CO (50 psi) and allowed to stir at 50° C. After 2 h, the reaction mixture was evaporated to dryness and the residue was purified using flash-column chromatography (0-15% EA/hexanes) to give the title compound (2.31 g, 62% yield) as a white solid. MS (ES+) $C_{13}H_{11}ClN_2O_3$ requires 278, found 279 [M+H]$^+$ Step 2: 2-(6-Chloro-1-cyclopropoxy-2,7-naphthyridin-4-yl)propan-2-ol Methylmagnesium bromide (3.47 ml, 10.41 mmol) was added to a solution of methyl 6-chloro-1-cyclopropoxy-2,7-naphthyridine-4-carboxylate (580 mg, 2.08 mmol) in THF (20 ml). After 1 h, the reaction mixture was diluted with saturated aqueous NH$_4$Cl solution and extracted with EA. The organic layers were dried, filtered, and evaporated. The residue was purified using flash-column chromatography (0-40% EA/hexanes) to give the title compound (393 mg, 67.7% yield). MS (ES+) $C_{14}H_{15}ClN_2O_2$ requires 278, found 279 [M+H]$^+$ Step 3: 4-(2-Azidopropan-2-yl)-6-chloro-1-cyclopropoxy-2,7-naphthyridine Indium(III) bromide (6.36 g, 17.94 mmol) and azidotrimethylsilane (4.72 ml, 35.9 mmol) were added to a solution of 2-(6-chloro-1-cyclopropoxy-2,7-naphthyridin-4-yl)propan-2-ol (2.5 g, 8.97 mmol) in CH$_2$Cl$_2$ (80 ml) at 0° C. and the reaction mixture was allowed to stir overnight. An additional 1 equivalent each of Indium(III) bromide and azidotrimethylsilane were added and the reaction mixture was heated to 40° C. for 48 h. The reaction was filtered through celite and evaporated. The residue was purified using flash-column chromatography (0-20% EA/hexanes) to give the title compound (1.9 g, 69.7% yield). MS (ES+) $C_{14}H_{14}ClN_5O$ requires 303, found 304 [M+H]$^+$ Step 4: (7S, 8R)-2-((5-(2-azidopropan-2-yl)-8-cyclopropoxy-2,7-naphthyridin-3-yl)amino)-7,8-dimethyl-7,8-dihydro-5H-pyrano[4,3-b]pyridin-5-one Chloro{[brettphos][2-(2-aminoethylphenyl)palladium(II)]}/[brettphos] (0.57 g, 0.63 mmol) was added to a mixture of (7S, 8R)-2-amino-7,8-dimethyl-7,8-dihydro-5H-pyrano[4,3-b]pyridin-5-one (Intermediate 17, 1.323 g, 6.88 mmol), 4-(2-azidopropan-2-yl)-6-chloro-1-cyclopropoxy-2,7-naphthyridine (1.9 g, 6.26 mmol) and potassium acetate (3.07 g, 31.3 mmol) in dioxane (60 ml). The reaction vessel was capped under N₂ and heated at 100° C. After 30 min the reaction was filtered and evaporated. The residue was then purified using flash-column chromatography (0-80% EA/hexanes) to give the title compound (1.74 g, 60% yield). ¹H NMR (400 MHz, DMSO-$d_6$) δ 10.76 (s, 1H), 9.25 (s, 1H), 9.18 (s, 1H), 8.21 (s, 1H), 8.09 (d, J=8.7 Hz, 1H), 7.37 (d, J=8.7 Hz, 1H), 4.59 (p, J=6.3 Hz, 1H), 4.51 (dq, J=6.3, 4.1, 3.3 Hz, 1H), 3.05-2.93 (m, 1H), 1.82 (d, J=2.0 Hz, 5H), 1.44 (d, J=7.1 Hz, 3H), 1.37 (d, J=6.5 Hz, 3H), 0.89-0.78 (m, 4H). MS (ES+) $C_{24}H_{25}N_7O_3$ requires 459, found 460 [M+H]⁺.

Step 5: (7S, 8R)-2-((5-(2-aminopropan-2-yl)-8-cyclopropoxy-2,7-naphthyridin-3-yl)amino)-7,8-dimethyl-7,8-dihydro-5H-pyrano[4,3-b]pyridin-5-one Pd/C (3 g, 10%) was added to a solution of (7S, 8R)-2-((5-(2-azidopropan-2-yl)-8-cyclopropoxy-2,7-naphthyridin-3-yl)amino)-7,8-dimethyl-7,8-dihydro-5H-pyrano[4,3-b]pyridin-5-one (10.76 g, 23.42 mmol) in 100 ml of EA under an atmosphere of nitrogen. The suspension was degassed under vacuum and purged with hydrogen several times. The reaction mixture was stirred under hydrogen at room temperature overnight. The reaction mixture was then transferred to a pressure flask and heated at 50 psi and 50° C. with an additional 1.8 g of Pd/C until starting material was consumed. The reaction mixture was cooled to room temperature, filtered, and evaporated. The residue was purified via flash-column chromatography (0-10% MeOH/DCM) to give the title compound (3.7 g, 36.4% yield). MS (ES+) $C_{24}H_{27}N_5O_3$ requires 433, found 434 [M+H]⁺. ¹H NMR (400 MHz, DMSO-$d_6$) δ 10.61 (s, 1H), 9.38 (s, 1H), 9.19 (d, J=0.7 Hz, 1H), 8.20 (s, 1H), 8.06 (d, J=8.7 Hz, 1H), 7.36 (d, J=8.7 Hz, 1H), 5.73 (s, 1H), 4.63-4.52 (m, 1H), 4.52-4.43 (m, 1H), 3.03-2.92 (m, 1H), 1.64 (d, J=2.0 Hz, 6H), 1.39 (dd, J=24.8, 6.8 Hz, 6H), 0.85-0.78 (m, 4H).

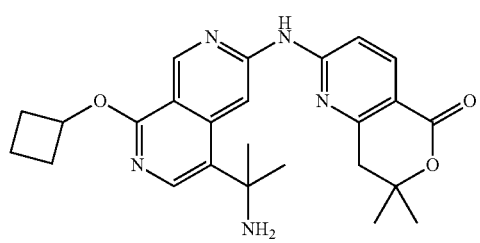 [SMILES: CC1(C)Cc2nc(Nc3cc4c(C(C)(C)N)cnc(OC5CCC5)c4cn3)ccc2C(=O)O1]

Example 9: 2-((5-(2-Aminopropan-2-yl)-8-cyclobutoxy-2,7-naphthyridin-3-yl)amino)-7,7-dimethyl-7,8-dihydro-5H-pyrano[4,3-b]pyridin-5-one (72)

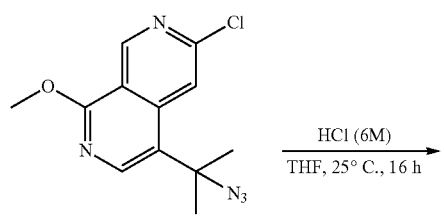

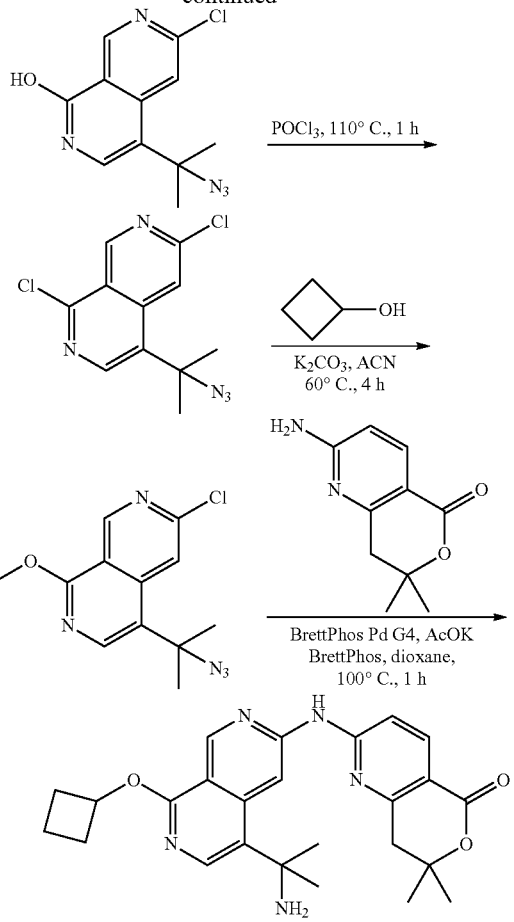

Step 1: 4-(2-Azidopropan-2-yl)-6-chloro-2,7-naphthyridin-1-ol

Hydrochloric (6 M, 240 uL) was added to a solution of 4-(2-azidopropan-2-yl)-6-chloro-1-methoxy-2,7-naphthyridine (Intermediate 31a, 200 mg, 720 umol) in tetrahydrofuran (1 mL) and the solution was stirred at 25° C. for 16 h. The reaction mixture was diluted with water (20 mL) and extracted with EA (20 mL×3). The combined organic layers were dried over anhydrous sodium sulfate, filtered and concentrated under reduced pressure to give a residue. The residue was purified by flash-column chromatography to give the title compound (130 mg, 68% yield) as a white solid. ¹H NMR (400 MHz, DMSO-$d_6$): δ ppm 11.90 (s, 1H), 9.20 (s, 1H), 8.02 (s, 1H), 7.43 (d, J=3.2 Hz, 1H), 1.67 (s, 6H).

Step 2: 4-(2-azidopropan-2-yl)-1,6-dichloro-2,7-naphthyridine

Phosphorus oxychloride (2.86 g, 18.7 mmol, 1.7 mL) was added to 4-(2-azidopropan-2-yl)-6-chloro-2,7-naphthyridin-1-ol (130 mg, 493 umol) and the solution was stirred at 110° C. for 1 hour. The reaction mixture was concentrated and the residue was dissolved in EA (10 mL). The mixture was diluted with saturated aqueous sodium bicarbonate solution (20 mL) and extracted with EA (10 mL×3). The combined organic layers were dried over anhydrous sodium sulfate, filtered and concentrated to give the title compound (110 mg, 79% yield) as a yellow solid which was used for next step without further purification. ¹H NMR (400 MHz, DMSO-d₆): δ ppm 9.61 (d, J=0.8 Hz, 1H), 8.63 (s, 1H), 8.47 (s, 1H), 1.84 (s, 6H).

Step 3: 4-(2-Azidopropan-2-yl)-6-chloro-1-cyclobutoxy-2,7-naphthyridine

Potassium carbonate (132 mg, 957 umol) was added to a solution of 4-(2-azidopropan-2-yl)-1,6-dichloro-2,7-naphthyridine (90.0 mg, 319 umol) and cyclobutanol (69.0 mg, 957 umol) in MCCN (5 mL) and stirred at 60° C. for 4 h. The reaction mixture was concentrated; diluted with water (20 mL) and extracted with EA (20 mL×3). The combined organic layers were dried over anhydrous sodium sulfate, filtered and concentrated under reduced pressure to give a residue. The residue was purified by prep-TLC to give the title compound (50.0 mg, 49% yield) as yellow oil. ¹H NMR (400 MHz, CDCl₃): δ ppm 9.45 (s, 1H), 8.32 (s, 1H), 8.17 (s, 1H), 5.48-5.37 (m, 1H), 2.62-2.52 (m, 2H), 2.36-2.23 (m, 2H), 1.98-1.87 (m, 1H), 1.79 (s, 6H), 1.77-1.71 (m, 1H).

Step 4: 4-(2-Azidopropan-2-yl)-6-chloro-1-cyclobutoxy-2,7-naphthyridine 2-(Dicyclohexylphosphino)-3,6-dimethoxy-2',4',6'-triisopropyl-1,1'-biphenyl (BrettPhos) (10 mg, 18.9 umol) and BrettPhos Pd G4 (9 mg, 9.44 umol) were added to a mixture of 2-amino-7,7-dimethyl-7,8-dihydro-5H-pyrano[4,3-b]pyridin-5-one (Intermediate 2, 20 mg, 104 umol), 4-(2-azidopropan-2-yl)-6-chloro-1-cyclobutoxy-2,7-naphthyridine (30 mg, 94.4 umol) and potassium acetate (28 mg, 283 umol) in dioxane (2 mL). The solution was degassed and purged with nitrogen for 3 times, and then the mixture was stirred at 100° C. for 1 hour under nitrogen atmosphere. The reaction mixture was concentrated and the residue was purified by prep-TLC to give the title compound (26.3 mg, 60% yield) as a yellow solid. MS (ES+) C₂₅H₂₉N₅O₃ requires 447, found 448 [M+H]⁺. ¹H NMR (400 MHz, CD₃OD): δ ppm 9.37 (s, 1H), 9.32 (s, 1H), 8.15 (d, J=8.8 Hz, 1H), 8.10 (s, 1H), 7.21 (d, J=8.8 Hz, 1H), 5.48-5.35 (m, 1H), 3.22 (s, 2H), 2.62-2.51 (m, 2H), 2.34-2.22 (m, 2H), 1.96-1.91 (m, 1H), 1.85 (s, 6H), 1.82-1.74 (m, 1H), 1.53 (s, 6H).

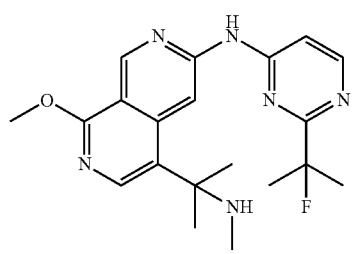 [SMILES: CNC(C)(C)c1cnc(OC)c2cnc(Nc3ccnc(C(C)(C)F)n3)cc12]

Example 10: N-(2-(2-Fluoropropan-2-yl)pyrimidin-4-yl)-8-methoxy-5-(2-(methylamino)propan-2-yl)-2,7-naphthyridin-3-amine (17)

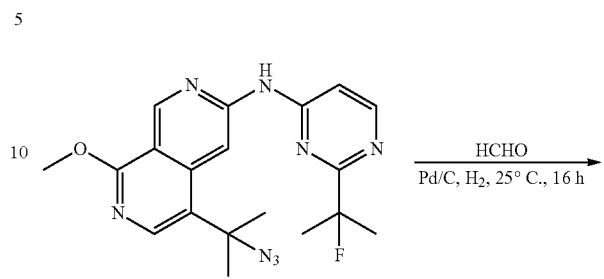

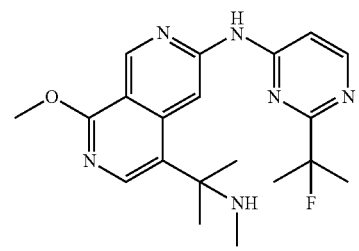

Step 1: N-(2-(2-Fluoropropan-2-yl)pyrimidin-4-yl)-8-methoxy-5-(2-(methylamino)propan-2-yl)-2,7-naphthyridin-3-amine Pd/C (10 mg, 10% purity) and formaldehyde (16.4 mg, 202 umol) were added under nitrogen to a solution of 5-(2-azidopropan-2-yl)-N-(2-(2-fluoropropan-2-yl)pyrimidin-4-yl)-8-methoxy-2,7-naphthyridin-3-amine (100 mg, 252 umol) in methanol (20 mL). The suspension was degassed under vacuum and purged with hydrogen several times. The mixture was stirred under hydrogen (15 psi) at 25° C. for 16 h. The reaction mixture was filtered and concentrated under reduce pressure to give a residue. The residue was purified by reverse phase prep-HPLC to give the title compound (16.0 mg, 16% yield) as a white solid. MS (ES+) C₂₀H₂₅FN₆O requires 384, found 385 [M+H]⁺. ¹H NMR (400 MHz, CD₃OD): δ ppm 9.37 (s, 1H), 9.31 (s, 1H), 8.39 (d, J=6.0 Hz, 1H), 8.03 (s, 1H), 7.29 (d, J=56.0 Hz, 1H), 4.13 (s, 3H), 2.07 (s, 3H), 1.83 (s, 3H) 1.78 (s, 3H), 1.69 (s, 6H)

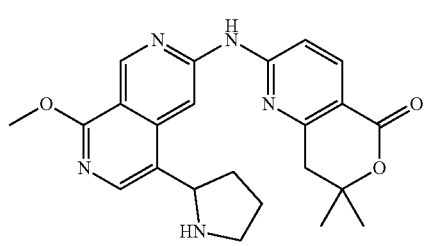 [SMILES: COc1ncc(C2CCCN2)c2cc(Nc3ccc4c(n3)CC(C)(C)OC4=O)ncc12]

Example 11: 2-((8-Methoxy-5-(pyrrolidin-2-yl)-2,7-naphthyridin-3-yl)amino)-7,7-dimethyl-7,8-dihydro-5H-pyrano[4,3-b]pyridin-5-one (50)

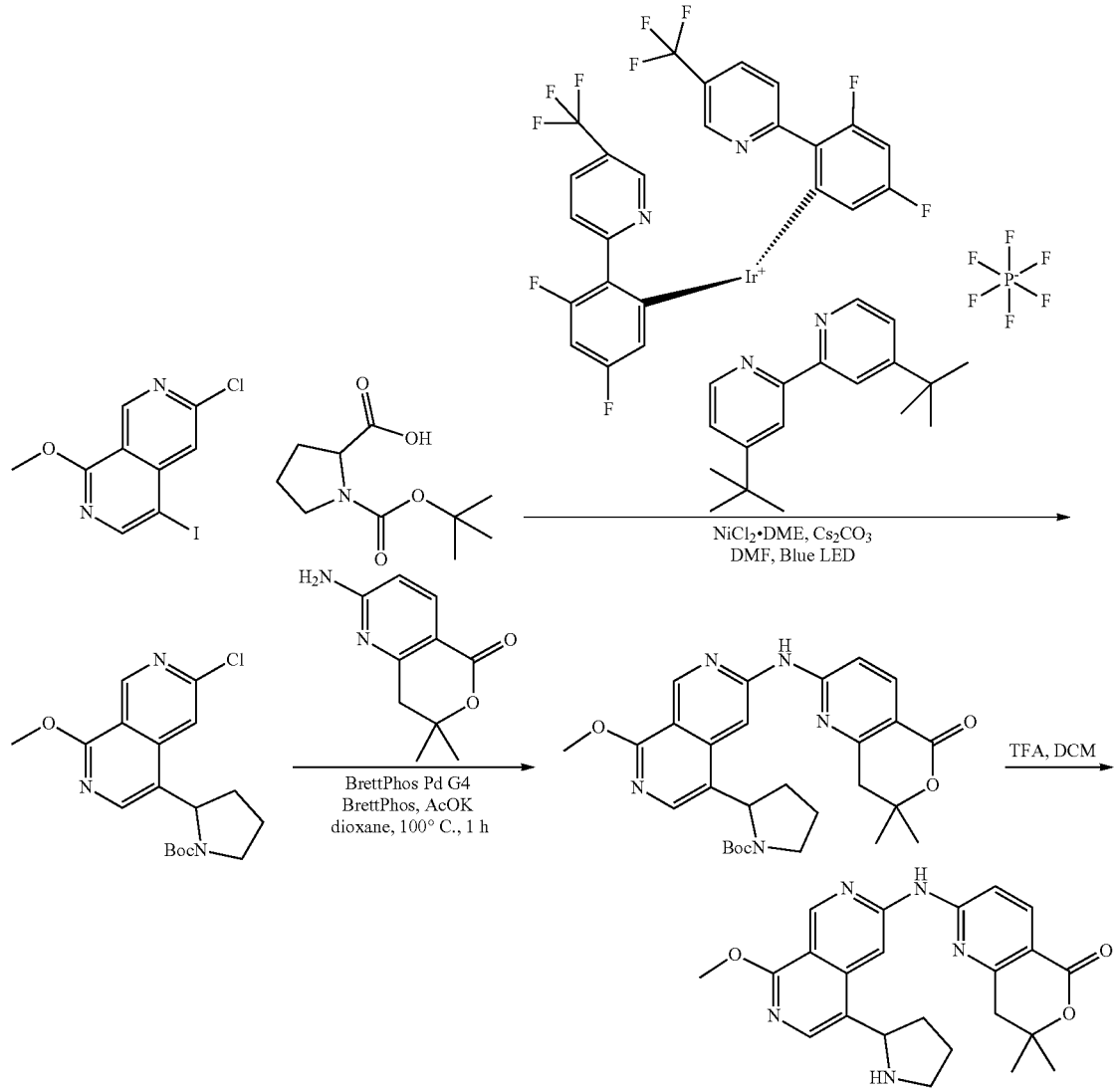

EA:Hexanes). Desired fractions were identified, combined, and concentrated in vacuo to afford the title compound. MS (ES+) $C_{18}H_{22}ClN_3O_3$ requires 363, found 364 $[M+H]^+$.

Step 1: Tert-butyl 2-(6-chloro-1-methoxy-2,7-naphthyridin-4-yl)pyrrolidine-1-carboxylate 6-Chloro-4-iodo-1-methoxy-2,7-naphthyridine (0.4 g, 1.248 mmol), Nickel(II) chloride dimethoxyethane adduct (0.016 g, 0.075 mmol), 1-[(tert-Butoxy)carbonyl]pyrrolidine-2-carboxylic acid (0.537 g, 2.496 mmol), (4,4'-Di-t-butyl-2,2' bipyridine)bis[3,5-difluoro-2-(5-trifluoromethyl-2-pyridinyl-kN)phenyl-kC]iridium(III) hexafluorophosphate (0.014 g, 0.012 mmol), and cesium carbonate (1.220 g, 3.74 mmol) were combined in a 40 mL vial. DMF (24.96 ml) was added and the reaction mixture was surrounded by Blue LED light and stirred at ambient temperature for 16 h. The reaction mixture was diluted with EA and washed with water, saturated brine solution, dried over anhydrous sodium sulfate, filtered and concentrated in vacuo. The residue was purified by flash-column chromatography (20-100% EA:Hexanes). Desired fractions were identified, combined, Step 2: Tert-butyl 2-(6-(((7,7-dimethyl-5-oxo-7,8-dihydro-5H-pyrano[4,3-b]pyridin-2-yl)amino)-1-methoxy-2,7-naphthyridin-4-yl)pyrrolidine-1-carboxylate Tert-butyl 2-(6-chloro-1-methoxy-2,7-naphthyridin-4-yl) pyrrolidine-1-carboxylate (104 mg, 0.286 mmol), 2-amino-7,7-dimethyl-7,8-dihydro-5H-pyrano[4,3-b]pyridin-5-one (Intermediate 2, 50 mg, 0.26 mmol), potassium acetate (77 mg, 0.780 mmol), and 1:1 mix of BrettPhos Pd G4 admixture and 2-(Dicyclohexylphosphino)3,6-dimethoxy-2',4',6'-triisopropyl-1,1'-biphenyl (38 mg, 0.026 mmol) were combined in a vial and capped under $N_2$. Dioxane (1.3 ml) as added and the mixture was heated to 100° C. After 4 h, another 38 mg of 1:1 catalyst mix was added and heating continued for another 12 h. The mixture was then cooled to ambient temperature and concentrated in vacuo. The residue was purified by flash-column chromatography (20-100% EA:Hexanes). Desired fractions were identified, combined, and concentrated in vacuo to afford the title compound. MS (ES+) $C_{28}H_{33}N_5O_5$ requires 519, found 520 $[M+H]^+$.

Step 3: 2-((8-Methoxy-5-(pyrrolidin-2-yl)-2,7-naphthyridin-3-yl)amino)-7,7-dimethyl-7,8-dihydro-5H-pyrano[4,3-b]pyridin-5-one Tert-butyl 2-(6-((7,7-dimethyl-5-oxo-7,8-dihydro-5H-pyrano[4,3-b]pyridin-2-yl)amino)-1-methoxy-2,7-naphthyridin-4-yl)pyrrolidine-1-carboxylate (20 mg, 0.038 mmol) was stirred in 5:1 DCM:TFA for 2 h. The reaction mixture was diluted with EA and carefully washed with saturated aqueous sodium bicarbonate, saturated aqueous brine solution, dried over anhydrous sodium sulfate, filtered and concentrated in vacuo. The residue was purified by flash-column chromatography. Desired fractions were identified, combined, and concentrated in vacuo to afford the title compound. MS (ES+) $C_{23}H_{25}N_5O_3$ requires 419, found 420 $[M+H]^+$. $^1$H NMR (400 MHz, DMSO-$d_6$) δ 10.64 (s, 1H), 9.18 (d, J=0.8 Hz, 1H), 8.49 (s, 1H), 8.05 (d, J=8.7 Hz, 1H), 7.38-7.31 (m, 2H), 4.22 (t, J=6.7 Hz, 1H), 4.06 (s, 3H), 3.21 (s, 2H), 3.15 (s, 1H), 3.09 (dt, J=10.4, 6.4 Hz, 1H), 2.98 (dt, J=10.1, 6.7 Hz, 1H), 2.24-2.09 (m, 1H), 1.84-1.70 (m, 3H), 1.43 (s, 6H).

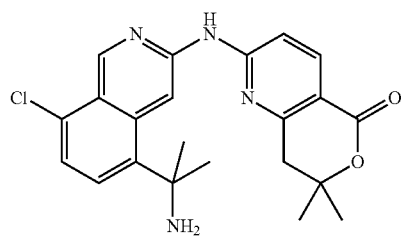 [SMILES: CC1(C)Cc2nc(Nc3cc4c(C(C)(C)N)ccc(Cl)c4cn3)ccc2C(=O)O1]

Example 12: 2-((5-(2-Aminopropan-2-yl)-8-chloroisoquinolin-3-yl)amino)-7,7-dimethyl-7,8-dihydro-5H-pyrano[4,3-b]pyridin-5-one (104)

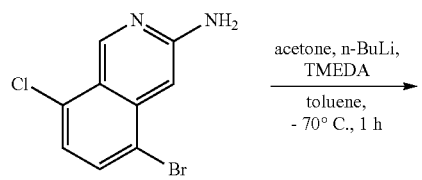

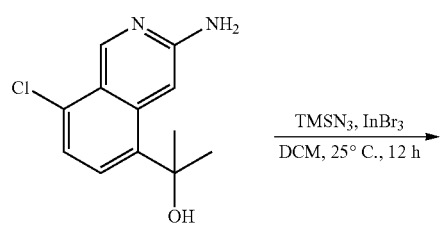

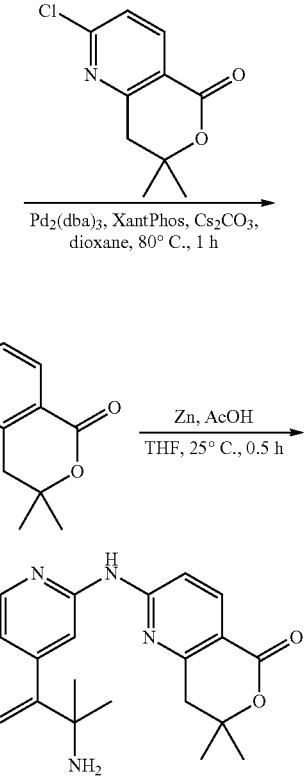

Step 1:
2-(3-Amino-8-chloroisoquinolin-5-yl)propan-2-ol n-Butyllithium (2.5 mol/L in n-hexane, 6.21 mL) was added to a solution of 5-bromo-8-chloroisoquinolin-3-amine (Journal of Medicinal Chemistry, 60(9), 3755-3775; 2017) (800 mg, 3.11 mmol) and TMEDA (1.81 g, 15.5 mmol) in toluene (10 mL) at –70° C. The reaction mixture was stirred for 0.5 h at –70° C., then acetone (1.80 g, 31.1 mmol) was added to the reaction mixture. The reaction mixture was stirred for 0.5 h at –70° C., then was quenched by addition of aqueous saturated NH$_4$Cl solution (30 mL) at –70° C. After warming to ambient temperature, the reaction mixture was extracted with EA 80 mL (40 mL×2), washed with brine 40 mL (20 mL×2), dried over sodium sulfate, filtered and concentrated to give a residue. The residue was purified by flash-column chromatography on silica gel (gradient elution, 10% to 50% ethyl acetate-petroleum ether) to give the title compound (200 mg, 25% yield) as a yellow solid. MS (ES+) $C_{12}H_{13}ClN_2O$ requires 236, found 237 $[M+H]^+$.

Step 2:
5-(2-Azidopropan-2-yl)-8-chloroisoquinolin-3-amine

TMSN$_3$ (107 mg, 929 umol) was added to a solution of 2-(3-Amino-8-chloroisoquinolin-5-yl)propan-2-ol (200 mg, 845 umol) and indium bromide (599 mg, 1.69 mmol) in DCM (8 mL). The reaction mixture was stirred at 25° C. for 16 h, then was diluted with water (20 mL) and extracted with DCM (20 mL×3). The combined organic layers were dried over anhydrous sodium sulfate, filtered and concentrated to give the title compound (210 mg, crude) as a yellow solid. MS (ES+) $C_{12}H_{12}ClN_5$ requires 261, found 262 $[M+H]^+$.

Step 3: 2-((5-(2-Azidopropan-2-yl)-8-chloroisoquinolin-3-yl)amino)-7,7-dimethyl-7,8-dihydro-5H-pyrano[4,3-b]pyridin-5-one Pd$_2$(dba)$_3$ (70.0 mg, 76.4 umol), XantPhos (88.4 mg, 153 umol) and cesium carbonate (747 mg, 2.29 mmol) were added to a solution of 5-(2-azidopropan-2-yl)-8-chloroisoquinolin-3-amine (200 mg, 764 umol) and 2-chloro-7,7-dimethyl-7,8-dihydro-5H-pyrano[4,3-b]pyridin-5-one (Steps 1-3, Intermediate 2) (162 mg, 764 umol) in dioxane (5 mL). The reaction mixture was stirred at 80° C. for 1 h, then was cooled to ambient temperature, filtered, and concentrated to give a residue. The residue was purified by column chromatography (SiO2, PE/EA=10/1 to 1/1) to give the title compound (210 mg, 60% yield) as a yellow solid. MS (ES+) C$_{22}$H$_{21}$ClN$_6$O$_2$ requires 436, found 437 [M+H]$^+$.

Step 4: 2-((5-(2-Aminopropan-2-yl)-8-chloroisoquinolin-3-yl)amino)-7,7-dimethyl-7,8-dihydro-5H-pyrano[4,3-b]pyridin-5-one Zinc (67.4 mg, 1.03 mmol) and acetic acid (124 mg, 2.06 mmol) were added to a solution of 2-((5-(2-azidopropan-2-yl)-8-chloroisoquinolin-3-yl)amino)-7,7-dimethyl-7,8-dihydro-5H-pyrano[4,3-b]pyridin-5-one (90 mg, 206 umol) in THF (5 mL). The reaction mixture was stirred at 15° C. for 0.5 h, then was filtered and concentrated to give a residue. The residue was purified by prep-HPLC (column: Waters Xbridge 150*25 mm*5 um; mobile phase: [water (10 mM NH$_4$HCO$_3$)-ACN]; B %: 38%-68%, 10 min) to give the title compound (25 mg, 30% yield) as a yellow solid. MS (ES+) C$_{22}$H$_{23}$ClN$_4$O$_2$ requires 410, found 411 [M+H]$^+$. $^1$H-NMR (400 MHz, CD$_3$OD): δ ppm 9.61 (s, 1H), 9.42 (s, 1H), 8.12 (d, J=8.8 Hz, 1H), 7.79 (d, J=8.0 Hz, 1H), 7.48 (d, J=8.0 Hz, 1H), 7.14 (d, J=8.8 Hz, 1H), 3.24 (s, 2H), 1.87 (s, 6H), 1.55 (s, 6H).

Example 13: (7S,8R)-2-((5-((R)-2-Amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one and (7S,8R)-2-((5-((S)-2-amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one (139 and 140)

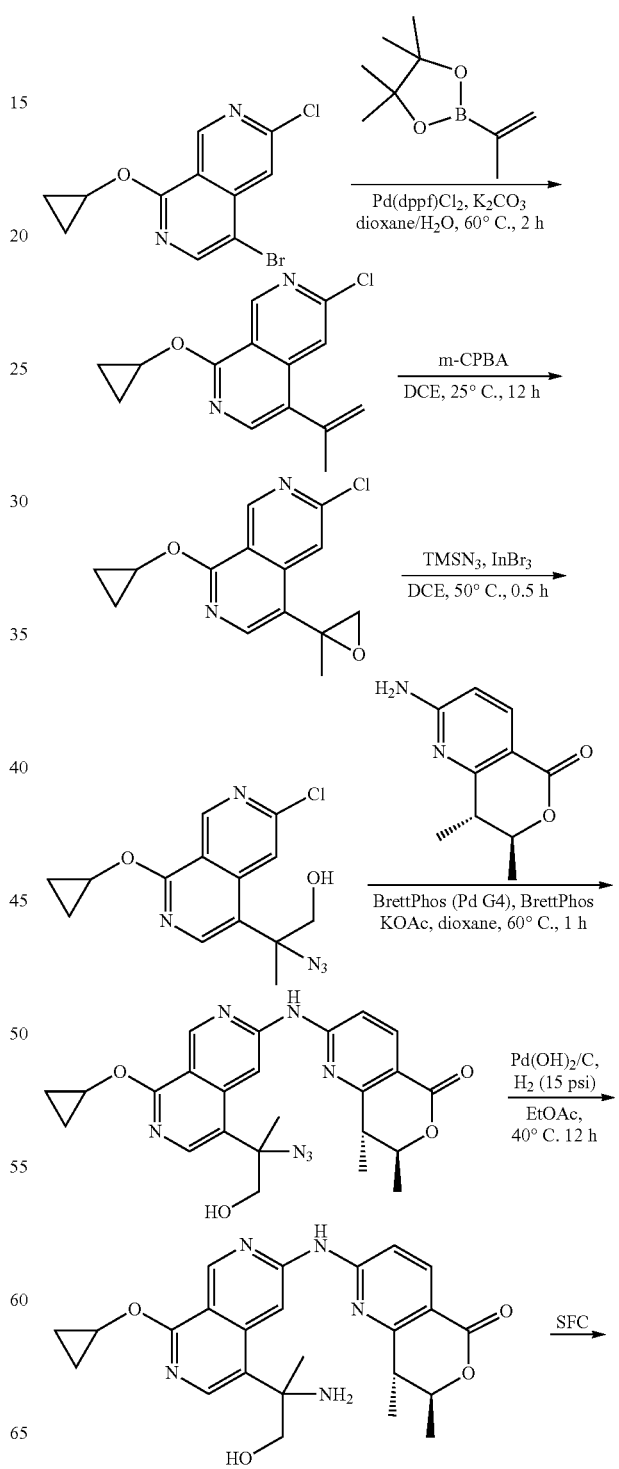

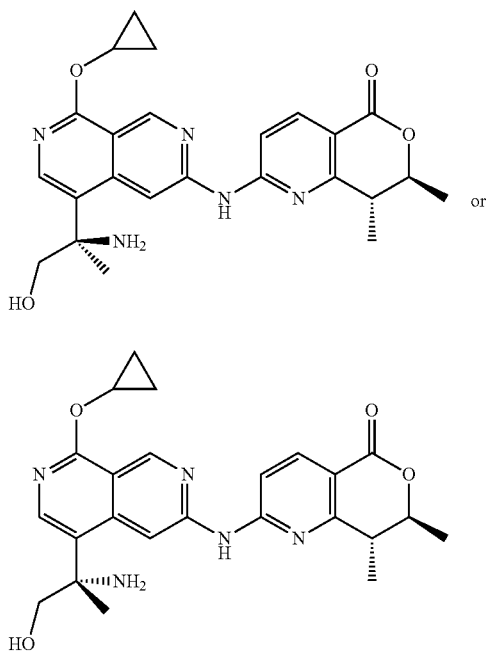

-continued

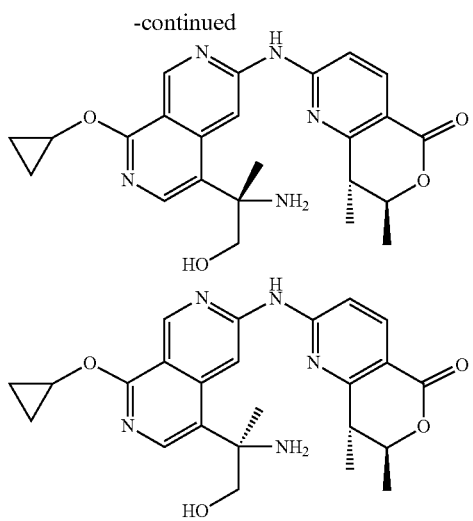

Step 1: 6-Chloro-1-cyclopropoxy-4-(prop-1-en-2-yl)-2,7-naphthyridine

A mixture of 4-bromo-6-chloro-1-cyclopropoxy-2,7-naphthyridine (Intermediate 33 and 34, step 1)(5.00 g, 16.7 mmol), 2-isopropenyl-4,4,5,5-tetramethyl-1,3,2-dioxaborolane (3.09 g, 18.4 mmol), Pd(dppf)Cl$_2$ (1.22 g, 1.67 mmol), and potassium carbonate (4.61 g, 33.4 mmol) in dioxane (30 mL) and water (6 mL) was degassed and purged with nitrogen 3 times. The reaction mixture was stirred at 60° C. for 2 h, then was concentrated to give a residue. The residue was purified by column chromatography (SiO$_2$, PE/EA=10/1) to give the title compound (2.50 g, 9.59 mmol, 57% yield) as a white solid.

Step 2: 6-Chloro-1-cyclopropoxy-4-(2-methyloxiran-2-yl)-2,7-naphthyridine m-CPBA (4.48 g, 22.1 mmol, 85% purity) was added to a solution of 6-chloro-1-cyclopropoxy-4-(prop-1-en-2-yl)-2,7-naphthyridine (2.30 g, 8.82 mmol) in DCM (100 mL). The reaction mixture was stirred at 25° C. for 12 h, then was quenched by addition of aqueous saturated sodium sulfite solution (50 mL) and extracted with DCM (50 mL). The organic layer was dried over sodium sulfate, filtered and concentrated to give a residue. The residue was purified by column chromatography (SiO$_2$, PE/EA=5/1) to give the title compound (750 mg, 2.71 mmol, 31% yield) as a white solid.

Step 3: 2-Azido-2-(6-chloro-1-cyclopropoxy-2,7-naphthyridin-4-yl)propan-1-ol TMSN$_3$ (625 mg, 5.42 mmol, 713 uL) and InBr$_3$ (1.92 g, 5.42 mmol) were added to a solution of 6-chloro-1-cyclopropoxy-4-(2-methyloxiran-2-yl)-2,7-naphthyridine (300 mg, 1.08 mmol) in 1,2-dichloroethane (10 mL). The reaction mixture was stirred at 50° C. for 0.5 h, then was poured into water (100 mL) and extracted with EA (30 mL×3). The organic layers were dried over sodium sulfate, filtered and concentrated to give a residue. The residue was purified by column chromatography (SiO2, PE:EA=5:1 to 1:1) to give the title compound (60.0 mg) as a yellow solid.

Step 4: (7S,8R)-2-((5-(2-Azido-1-hydroxypropan-2-yl)-8-cyclopropoxy-2,7-naphthyridin-3-yl)amino)-7,8-dimethyl-7,8-dihydro-5H-pyrano[4,3-b]pyridin-5-one BrettPhos (Pd, G4) (10 mg, 10.9 µmol), BrettPhos (8.39 mg, 15.6 µmol) and potassium acetate (46.0 mg, 469 µmol) were added to a solution of 2-azido-2-(6-chloro-1-cyclopropoxy-2,7-naphthyridin-4-yl)propan-1-ol (50.0 mg) and (7S,8R)-2-amino-7,8-dimethyl-7,8-dihydro-5H-pyrano[4,3-b]pyridin-5-one (Intermediate 17×36.1 mg, 188 µmol) in dioxane (2 mL). The reaction mixture was stirred at 60° C. for 1 h, then was concentrated to give a residue. The residue purified by prep-TLC (ethyl acetate) to give the title compound (40.0 mg, crude) as a yellow solid.

Step 5: (7S,8R)-2-((5-(2-Amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one Pd(OH)$_2$/C (10.0 mg, 20% purity) was added to a solution of (7S,8R)-2-((5-(2-azido-1-hydroxypropan-2-yl)-8-cyclopropoxy-2,7-naphthyridin-3-yl)amino)-7,8-dimethyl-7,8-dihydro-5H-pyrano[4,3-b]pyridin-5-one (40.0 mg, crude) in EA (2 mL). The reaction mixture was stirred at 40° C. under hydrogen (15 psi) for 12 h, then was filtered and concentrated to give a residue. The residue purified by prep-TLC (EA:MeOH=10:1) to give the title compound (25.0 mg, 50.7 µmol, 60% yield) as a yellow solid.

Step 6: (7S,8R)-2-((5-((R)-2-Amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one and (7S,8R)-2-((5-((S)-2-amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one (7S,8R)-2-((5-(2-Amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one (20.0 mg, 44.5 µmol) was separated by SFC (column: Daicel Chiralpak IC (250 mm*30 mm, 10 um); mobile phase: [0.1% NH$_4$OH in EtOH]) to give (7S,8R)-2-((5-((R)-2-Amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one or (7S,8R)-2-((5-((S)-2-amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one (first eluting isomer, 3.00 mg, 11% yield) as a yellow solid and (7S,8R)-2-((5-((R)-2-Amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one or (7S,8R)-2-((5-((S)-2-amino-1-hydroxypropan-2-yl)-8-cyclopropoxy-2,7-naphthyridin-3-yl)amino)-7,8-dimethyl-7,8-dihydro-5H-pyrano[4,3-b]pyridin-5-one (second eluting isomer 3.00 mg, 10% yield) as a yellow solid. First eluting isomer: MS (ES+) $C_{24}H_{27}N_5O_4$ requires 449, found 450 [M+H]$^+$. $^1$H-NMR (400 MHz, CD$_3$OD): δ ppm 9.33 (s, 1H), 8.92 (s, 1H), 8.18 (d, J=8.8 Hz, 1H), 8.01 (s, 1H), 7.35 (d, J=8.4 Hz, 1H), 4.68-4.65 (m, 1H), 4.54 (m, 1H), 4.42-4.38 (m, 1H), 4.11-4.08 (m, 1H), 3.03-3.01 (m, 1H), 1.99 (s, 3H), 1.53-1.45 (m, 6H), 0.91 (m, 4H). Second eluting isomer: MS (ES+) $C_{24}H_{27}N_5O_4$ requires 449, found 450 [M+H]$^+$. $^1$H-NMR (400 MHz, CD$_3$OD): δ ppm 9.33 (s, 1H), 8.94 (s, 1H), 8.18 (d, J=8.8 Hz, 1H), 8.01 (s, 1H), 7.34 (d, J=8.4 Hz, 1H), 4.69-4.67 (m, 1H), 4.55-4.50 (m, 1H), 4.39-4.36 (m, 1H), 4.16-4.13 (m, 1H), 3.06-3.03 (m, 1H), 1.99 (s, 3H), 1.51-1.46 (m, 6H), 0.91 (m, 4H).

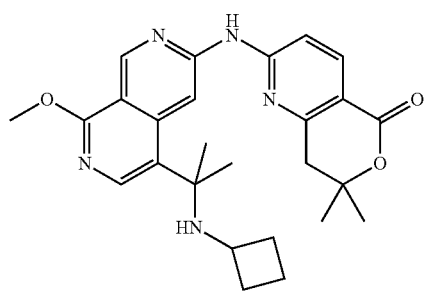 [SMILES: COc1ncc(C(C)(C)NC2CCC2)c2cc(Nc3ccc4c(n3)CC(C)(C)OC4=O)ncc12]

Example 14: 2-((5-(2-(Cyclobutylamino)propan-2-yl)-8-methoxy-2,7-naphthyridin-3-yl)amino)-7,7-dimethyl-7,8-dihydro-5H-pyrano[4,3-b]pyridin-5-one (158)

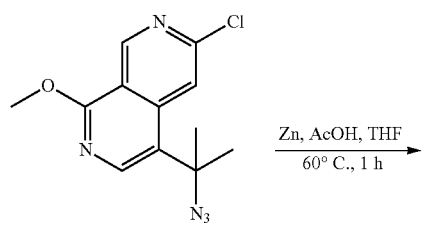

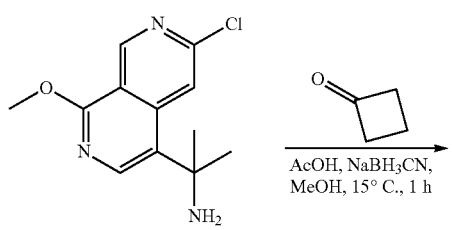

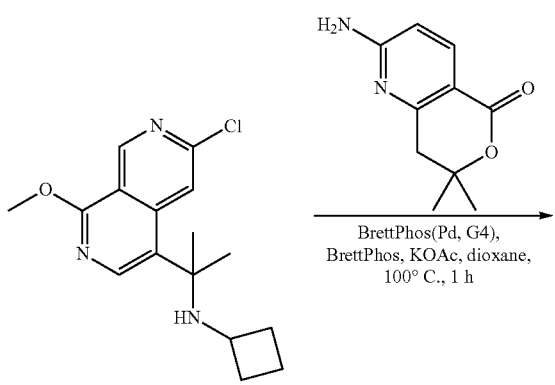

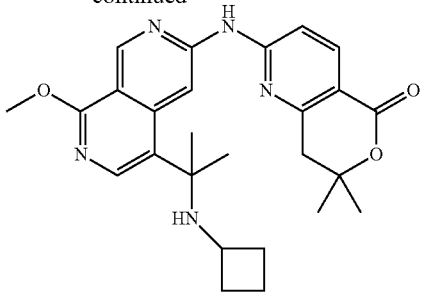

Step 1: 2-(6-Chloro-1-methoxy-2,7-naphthyridin-4-yl)propan-2-amine

Zinc (589 mg, 9.00 mmol) and acetic acid (1.08 g, 18.0 mmol, 1.03 mL) were added to a solution of 4-(2-azidopropan-2-yl)-6-chloro-1-methoxy-2,7-naphthyridine (Intermediate 31a) (500 mg, 1.80 mmol) in THF (5.00 mL). The reaction mixture was stirred at 60° C. for 1 h, then was cooled to ambient temperature and treated with saturated aqueous ammonium hydroxide solution to adjust to pH-7. The reaction mixture was filtered and concentrated to give a residue. The residue was purified by column chromatography (SiO$_2$, PE/EA=1:0 to 3:2) to give the title compound (272 mg, 1.08 mmol, 60% yield) was obtained as a white solid.

Step 2: N-(2-(6-Chloro-1-methoxy-2,7-naphthyridin-4-yl)propan-2-yl)cyclobutanamine A solution of 2-(6-chloro-1-methoxy-2,7-naphthyridin-4-yl)propan-2-amine (50.0 mg, 199 μmol), cyclobutanone (55.7 mg, 795 μmol, 59.4 μL) and acetic acid (11.9 mg, 199 μmol, 11.4 μL) in MeOH (2.00 mL) was stirred at 15° C. for 0.5 h, then sodium cyanoborohydride (37.5 mg, 596 μmol) was added. The reaction mixture was stirred at 15° C. for 0.5 h., then was concentrated to give a residue. The residue was purified by prep-TLC (PE:EA=5:1) to give the title compound (60.0 mg, 196 μmol, 99% yield) as white oil. MS (ES+) $C_{16}H_{20}ClN_3O$ requires 305, found 306 [M+H]$^+$. $^1$H NMR (400 MHz, CDCl$_3$): δ ppm 9.38 (s, 1H), 9.16 (d, J 3.8 Hz, 1H), 8.08 (s, 1H), 4.13 (s, 3H), 2.87-2.79 (m, 1H), 2.03-1.96 (m, 2H), 1.68-1.59 (m, 2H), 1.55 (s, 6H), 1.52-1.45 (m, 2H), 0.08-0.06 (m, 1H).

Step 3: 2-((5-(2-(Cyclobutylamino)propan-2-yl)-8-methoxy-2,7-naphthyridin-3-yl)amino)-7,7-dimethyl-7,8-dihydro-5H-pyrano[4,3-b]pyridin-5-one A mixture of N-(2-(6-chloro-1-methoxy-2,7-naphthyridin-4-yl)propan-2-yl)cyclobutanamine (40.0 mg, 131 μmol), Intermediate 2 (25.1 mg, 131 μmol), BrettPhos (Pd, G4) (12.0 mg, 13.1 μmol), BrettPhos (7.02 mg, 13.1 μmol) and potassium acetate (64.2 mg, 654 μmol) in dioxane (1.00 mL) was stirred at 100° C. for 1 h. The reaction mixture was then concentrated to give a residue. The residue was purified by prep-HPLC (column: Phenomenex Gemini-NX C18 75*30 mm*3 um; mobile phase: [water(0.1% TFA)-ACN]; B %: 25%-35%, 7 min) to give the title compound (27.9 mg, 45% yield) as a yellow solid. MS (ES+) $C_{26}H_{31}N_5O_3$ requires 461, found 462 [M+H]$^+$. $^1$H NMR (400 MHz, 6d-DMSO): δ ppm 10.80 (s, 1H), 9.38 (s, 1H), 9.14 (s, 2H), 8.83 (s, 1H), 8.17-8.13 (m, 2H), 7.41-7.39 (m, 1H), 4.11 (s, 3H), 3.09 (s, 2H), 2.52 (s, 1H), 2.12-2.05 (m, 2H), 1.99 (s, 5H), 1.92-1.87 (m, 2H), 1.69-1.58 (m, 2H), 1.45 (s, 6H)

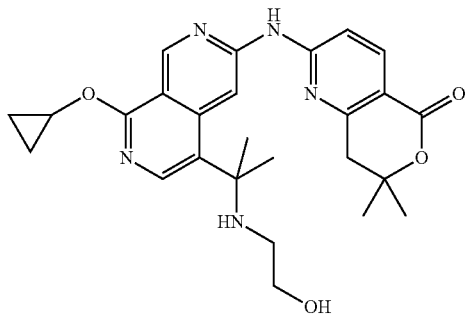 [SMILES: CC1(C)Cc2nc(Nc3cc4c(C(C)(C)NCCO)cnc(OC5CC5)c4cn3)ccc2C(=O)O1]

Example 15: 2-((8-Cyclopropoxy-5-(2-((2-hydroxyethyl)amino)propan-2-yl)-2,7-naphthyridin-3-yl)amino)-7,7-dimethyl-7,8-dihydro-5H-pyrano[4,3-b]pyridin-5-one (177)

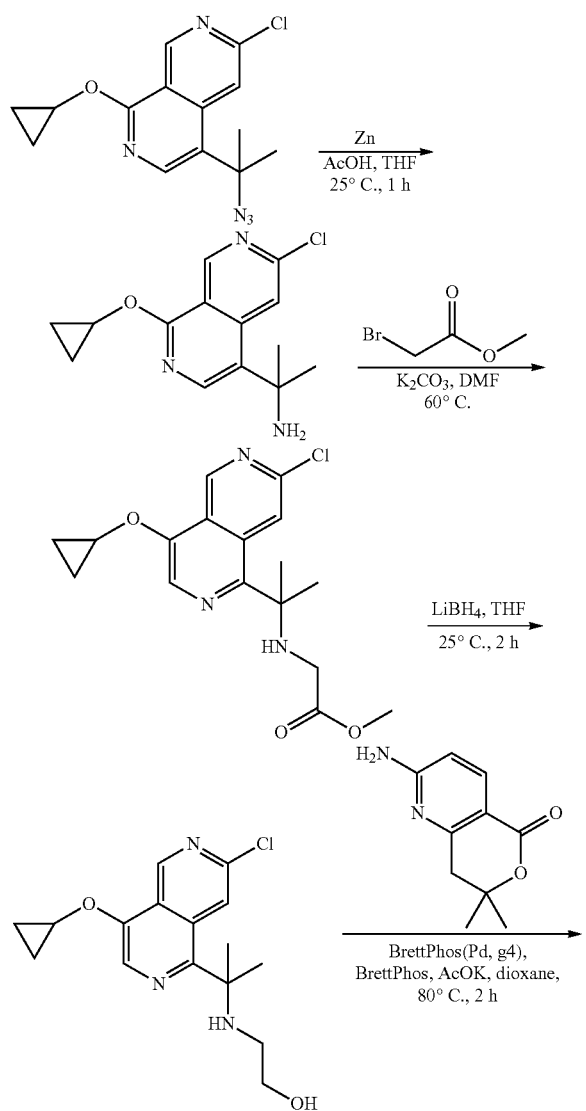

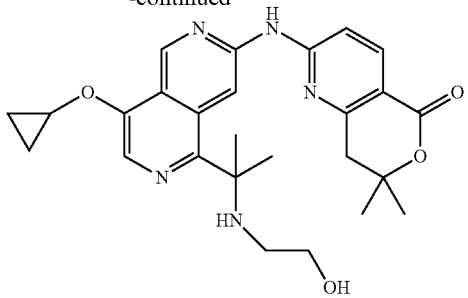

Step 1: 2-(6-Chloro-1-cyclopropoxy-2,7-naphthyridin-4-yl)propan-2-amine

Zinc (323 mg, 4.94 mmol) was added to a solution of 4-(2-azidopropan-2-yl)-6-chloro-1-cyclopropoxy-2,7-naphthyridine (Example 8, Steps 1-3)(300 mg, 988 μmol) and acetic acid (5297 mg, 4.94 mmol) in THF (8 mL). The reaction mixture was stirred at 25° C. for 10 min, then was filtered and concentrated. The residue was purified flash-column MeOH=3:1) to give the title compound (200 mg, 73% yield) as a yellow solid. MS (ES+) $C_{14}H_{16}ClN_3O$ requires 277, found 278 [M+H]$^+$.

Step 2: Methyl (2-(6-chloro-1-cyclopropoxy-2,7-naphthyridin-4-yl)propan-2-yl)glycinate Potassium carbonate (179 mg, 1.30 mmol) was added to a mixture of 2-(6-Chloro-1-cyclopropoxy-2,7-naphthyridin-4-yl)propan-2-amine (180 mg, 648 μmol) and methyl 2-bromoacetate (297 mg, 1.94 mmol) in N,N-dimethylformamide (4 mL). The reaction mixture was stirred at 60° C. for 2 h. then was diluted with water (20 mL) and extracted with EA (20 mL×3). The combined organic layers were dried over anhydrous sodium sulfate, filtered and concentrated to give a residue. The residue was purified by flash-column chromatography on silica gel (PE:EA=1:0 to 3:1) to give the title compound (170 mg, 75% yield) as a white solid.

Step 3: 2-((2-(6-Chloro-1-cyclopropoxy-2,7-naphthyridin-4-yl)propan-2-yl)amino)ethan-1-ol Lithium borohydride (24.9 mg, 1.14 mmol) was added to a solution of methyl (2-(6-chloro-1-cyclopropoxy-2,7-naphthyridin-4-yl)propan-2-yl)glycinate (80.0 mg, 229 μmol) in THF (4 mL). The reaction mixture was stirred at 25° C. for 0.5 h, then was was quenched by addition of water (10 mL) and extracted with EA (10 mL×3). The combined organic layers were washed with brine, dried over anhydrous sodium sulfate, filtered and concentrated to give a residue. The residue was purified by prep-TLC (PE:EA=1:2) to give the title compound (30.0 mg, 41% yield) as a white solid. MS (ES+) $C_{16}H_{20}ClN_3O_2$ requires 321, found 322 [M+H]$^+$.

Step 4: 2-((8-Cyclopropoxy-5-(2-((2-hydroxyethyl)amino)propan-2-yl)-2,7-naphthyridin-3-yl)amino)-7,7-dimethyl-7,8-dihydro-5H-pyrano[4,3-b]pyridin-5-one BrettPhos (5.00 mg, 9.32 μmol), BrettPhos (Pd, G4) (8.58 mg, 9.32 μmol) and potassium acetate (22.9 mg, 233 μmol) were added to a mixture of 2-((2-(6-chloro-1-cyclopropoxy-2,7-naphthyridin-4-yl)propan-2-yl)amino)ethan-1-ol (30.0 mg, 93.2 μmol) and 2-amino-7,7-dimethyl-7,8-dihydro-5H-pyrano[4,3-b]pyridin-5-one (Intermediate 2)(26.9 mg, 140 μmol) in dioxane (3 mL). The reaction mixture was stirred at 80° C. for 2 h, then was concentrated to give a residue. The residue was purified by prep-TLC (EA:MeOH=10:1), then was further purified by prep-HPLC (column: Phenomenex Gemini NX-C18 (75*30 mm*3 um); mobile phase: [water (0.05% ammonia hydroxide v/v)-ACN]; B %: 33% 63%, 10 min) to give the title compound (6.70 mg, 15% yield) as a yellow solid. MS (ES+) $C_{26}H_{31}N_5O_4$ requires 477, found 478 $[M+H]^+$. $^1H$ NMR (400 MHz, $CD_3OD$): δ ppm 9.91 (s, 1H), 9.23 (s, 1H), 8.18-8.07 (m, 1H), 8.02 (s, 1H), 7.27-7.14 (m, 1H), 4.51-4.36 (m, 1H), 3.55-3.41 (m, 2H), 3.26 (s, 2H), 2.47-2.37 (m, 2H), 1.82-1.66 (m, 6H), 1.54 (s, 6H), 0.89 (s, 4H).

Example 16: (7S,8R)-2-((5-((R)-2-Amino-1-methoxypropan-2-yl)-8-cyclopropoxy-2,7-naphthyridin-3-yl)amino)-7,8-dimethyl-7,8-dihydro-5H-pyrano[4,3-b]pyridin-5-one and (7S,8R)-2-((5-((S)-2-amino-1-methoxypropan-2-yl)-8-cyclopropoxy-2,7-naphthyridin-3-yl)amino)-7,8-dimethyl-7,8-dihydro-5H-pyrano[4,3-b]pyridin-5-one (184)

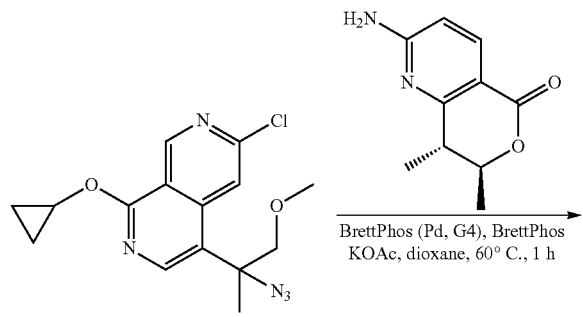

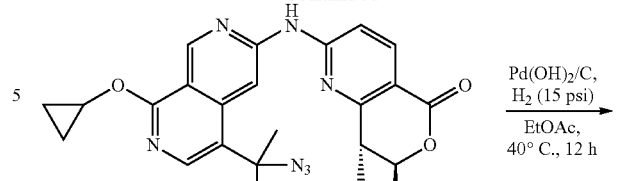

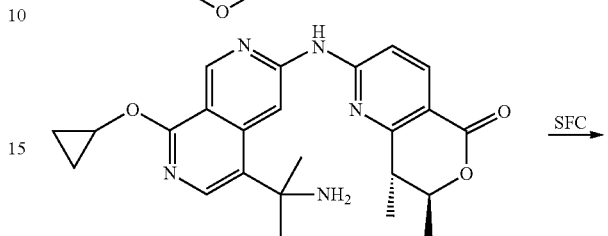

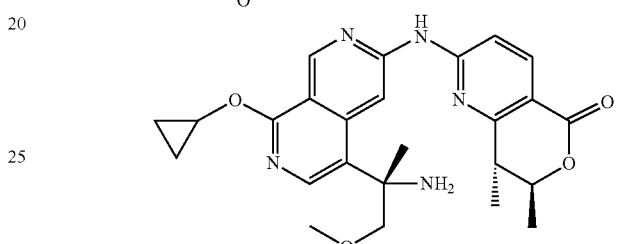

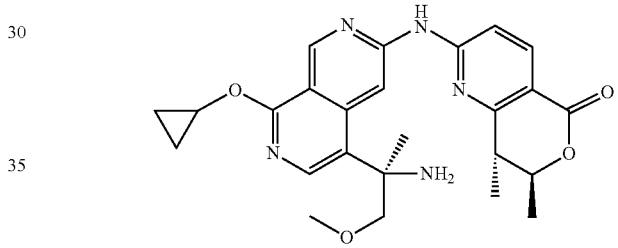

Steps 1-2: (7S,8R)-2-((5-(2-Amino-1-methoxypropan-2-yl)-8-cyclopropoxy-2,7-naphthyridin-3-yl)amino)-7,8-dimethyl-7,8-dihydro-5H-pyrano[4,3-b]pyridin-5-one The title compound was prepared from 4-(2-azido-1-methoxypropan-2-yl)-6-chloro-1-cyclopropoxy-2,7-naphthyridine (mixture of Intermediates 68 and 69 prior to separation (after Step 3) and (7S,8R)-2-amino-7,8-dimethyl-7,8-dihydro-5H-pyrano[4,3-b]pyridin-5-one (Intermediate 17) using a similar procedure as described in Steps 4 and 5 of Example 13.

Step 3: (7S,8R)-2-((5-((R)-2-Amino-1-methoxypropan-2-yl)-8-cyclopropoxy-2,7-naphthyridin-3-yl)amino)-7,8-dimethyl-7,8-dihydro-5H-pyrano[4,3-b]pyridin-5-one and (7S,8R)-2-((5-((S)-2-amino-1-methoxypropan-2-yl)-8-cyclopropoxy-2,7-naphthyridin-3-yl)amino)-7,8-dimethyl-7,8-dihydro-5H-pyrano[4,3-b]pyridin-5-one (7S,8R)-2-((5-(2-Amino-1-methoxypropan-2-yl)-8-cyclopropoxy-2,7-naphthyridin-3-yl)amino)-7,8-dimethyl-7,8-dihydro-5H-pyrano[4,3-b]pyridin-5-one (25.0 mg) was separated by SFC (column: Daicel Chiralpak AS (250 mm*30 mm, 10 um); mobile phase: [0.1% $NH_3H_2O$ MeOH]) to give (7S,8R)-2-((5-((R)-2-Amino-1-methoxypropan-2-yl)-8-cyclopropoxy-2,7-naphthyridin-3-yl) amino)-7,8-dimethyl-7,8-dihydro-5H-pyrano[4,3-b]pyridin-5-one or (7S,8R)-2-((5-((S)-2-amino-1-methoxypropan-2-yl)-8-cyclopropoxy-2,7-naphthyridin-3-yl)amino)-7,8-dimethyl-7,8-dihydro-5H-pyrano[4,3-b]pyridin-5-one (first eluting isomer, 8.00 mg, 32% yield) as a yellow solid and (7S,8R)-2-((5-((R)-2-Amino-1-methoxypropan-2-yl)-8-cyclopropoxy-2,7-naphthyridin-3-yl)amino)-7,8-dimethyl-7,8-dihydro-5H-pyrano[4,3-b]pyridin-5-one or (7S,8R)-2-((5-((S)-2-amino-1-methoxypropan-2-yl)-8-cyclopropoxy-2,7-naphthyridin-3-yl)amino)-7,8-dimethyl-7,8-dihydro-5H-pyrano[4,3-b]pyridin-5-one (second eluting isomer, 9.00 mg, 37% yield) as a yellow solid. MS (ES+) $C_{25}H_{29}N_5O_4$ requires 463, found 464 [M+H]$^+$. $^1$H-NMR (400 MHz, CD$_3$OD): δ ppm 9.24 (s, 1H), 9.20 (s, 1H), 8.19 (s, 1H), 8.13 (d, J=8.8 Hz, 1H), 7.29 (d, J=8.8 Hz, 1H), 4.69-4.63 (m, 1H), 4.45-4.43 (m, 1H), 3.97-3.95 (m, 1H), 3.83-3.81 (m, 1H), 3.35 (s, 3H), 3.06-2.99 (m, 1H), 1.74 (s, 3H), 1.52-1.46 (m, 6H), 0.93-0.87 (m, 4H).

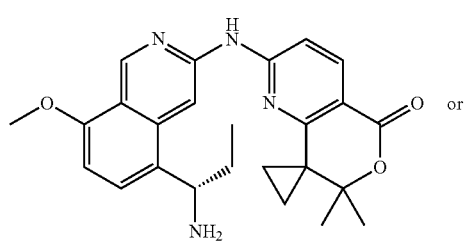 or

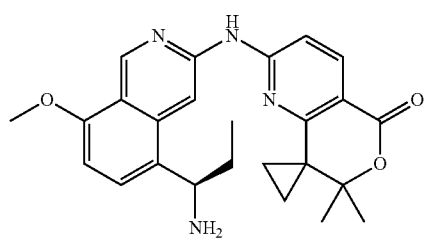

Example 17: (S)-2'-((5-(1-Aminopropyl)-8-methoxyisoquinolin-3-yl)amino)-7',7'-dimethyl-5'H,7'H-spiro[cyclopropane-1,8'-pyrano[4,3-b]pyridin]-5'-one or (R)-2'-((5-(1-aminopropyl)-8-methoxyisoquinolin-3-yl)amino)-7',7'-dimethyl-5'H,7'H-spiro[cyclopropane-1,8'-pyrano[4,3-b]pyridin]-5'-one (207)

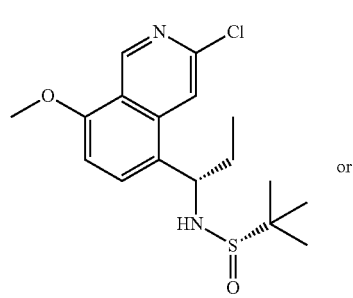 or

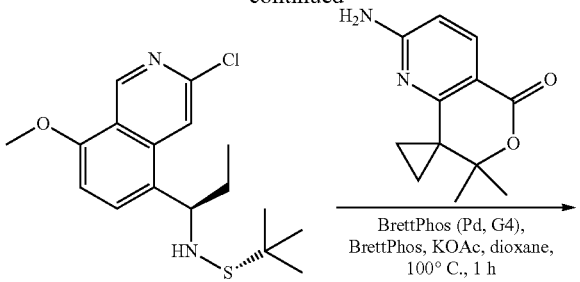
BrettPhos (Pd, G4), BrettPhos, KOAc, dioxane, 100° C., 1 h

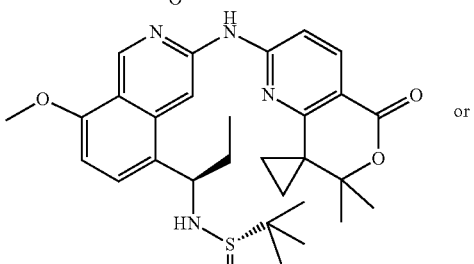 or

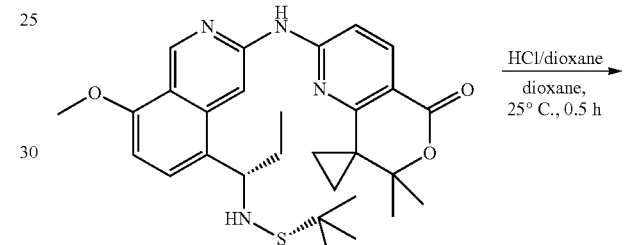
HCl/dioxane dioxane, 25° C., 0.5 h

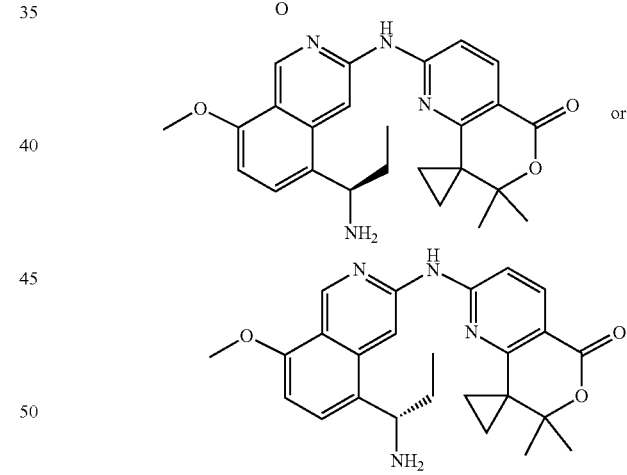 or

Step 1: (S)—N—((R)-1-(3-((7',7'-Dimethyl-5'-oxo-5'H,7'H-spiro[cyclopropane-1,8'-pyrano[4,3-b]pyridin]-2'-yl)amino)-8-methoxyisoquinolin-5-yl)propyl)-2-methylpropane-2-sulfinamide or (S)—N—((S)-1-(3-((7',7'-dimethyl-5'-oxo-5'H,7'H-spiro[cyclopropane-1,8'-pyrano[4,3-b]pyridin]-2'-yl)amino)-8-methoxyisoquinolin-5-yl)propyl)-2-methylpropane-2-sulfinamide A mixture of (S)—N—((S)-1-(3-chloro-8-methoxyisoquinolin-5-yl)propyl)-2-methylpropane-2-sulfinamide or (S)—N—((R)-1-(3-chloro-8-methoxyisoquinolin-5-yl)propyl)-2-methylpropane-2-sulfinamide (Intermediate 73, 20 mg, 56.4 umol), 2'-amino-7',7'-dimethyl-5'H,7'H-spiro[cyclopropane-1,8'-pyrano[4,3-b]pyridin]-5'-one (Intermediate 85)(14.8 mg, 67.6 umol), BrettPhos (6.05 mg, 11.3 umol), BrettPhos (Pd, G4) (5.19 mg, 5.64 umol) and potassium acetate (16.6 mg, 169 umol) in dioxane (2.5 mL) was degassed and purged with nitrogen 3 times. The reaction was stirred at 100° C. for 1 h, then was filtered and concentrated to give a residue. The residue was purified by prep-TLC (PE:EA=0:1) to give the title compound (20 mg, 65% yield) as a yellow solid. MS (ES+) $C_{29}H_{36}N_4O_4S$ requires 536, found 537 [M+H]+.

Step 2: (S)-2'-((5-(1-Aminopropyl)-8-methoxyisoquinolin-3-yl)amino)-7',7'-dimethyl-5'H,7'H-spiro[cyclopropane-1,8'-pyrano[4,3-b]pyridin]-5'-one or (R)-2'-((5-(1-aminopropyl)-8-methoxyisoquinolin-3-yl)amino)-7',7'-dimethyl-5'H,7'H-spiro[cyclopropane-1,8'-pyrano[4,3-b]pyridin]-5'-one HCl (4 M in dioxane, 9.32 uL) was added to a solution of (S)—N—((R)-1-(3-((7',7'-dimethyl-5'-oxo-5'H,7'H-spiro[cyclopropane-1,8'-pyrano[4,3-b]pyridin]-2'-yl)amino)-8-methoxyisoquinolin-5-yl)propyl)-2-methylpropane-2-sulfinamide or (S)—N—((S)-1-(3-((7',7'-dimethyl-5'-oxo-5'H,7'H-spiro[cyclopropane-1,8'-pyrano[4,3-b]pyridin]-2'-yl)amino)-8-methoxyisoquinolin-5-yl)propyl)-2-methylpropane-2-sulfinamide (product from previous step, 20 mg, 37.3 umol) in dioxane (1 mL). The reaction mixture was stirred at 25° C. for 0.5 h, then was concentrated to give a residue. The residue was purified by prep-HPLC (column: 3_Phenomenex Luna C18 75×30 mm×3 μm; mobile phase: [water (0.05% HCl)-ACN]; B %: 21%-41%, 6.5 min) to give the title compound (6.3 mg, 39% yield) as a white solid. MS (ES+) $C_{29}H_{36}N_4O_4S$ requires 432, found 433 [M+H]+. $^1$H NMR (400 MHz, CDCl$_3$): δ ppm 9.75-9.52 (m, 1H), 8.34 (d, J=8.8 Hz, 1H), 8.25 (s, 1H), 8.04 (d, J=8.4 Hz, 1H), 7.22 (d, J=2.0 Hz, 1H), 7.19 (d, J=0.8 Hz, 1H), 5.03-4.94 (m, 1H), 4.17 (s, 3H), 2.30-2.09 (m, 2H), 1.65-1.56 (m, 2H), 1.55-1.48 (m, 2H), 1.46 (s, 6H), 1.04-0.97 (m, 3H).

Example 18: (7S,8R)-2-((5-((R)-1-Amino-1-cyclopropylethyl)-8-((trans)-3-hydroxycyclobutoxy)-2,7-naphthyridin-3-yl)amino)-7,8-dimethyl-7,8-dihydro-5H-pyrano[4,3-b]pyridin-5-one and (7S,8R)-2-((5-((S)-1-amino-1-cyclopropylethyl)-8-((trans)-3-hydroxycyclobutoxy)-2,7-naphthyridin-3-yl)amino)-7,8-dimethyl-7,8-dihydro-5H-pyrano[4,3-b]pyridin-5-one (193)

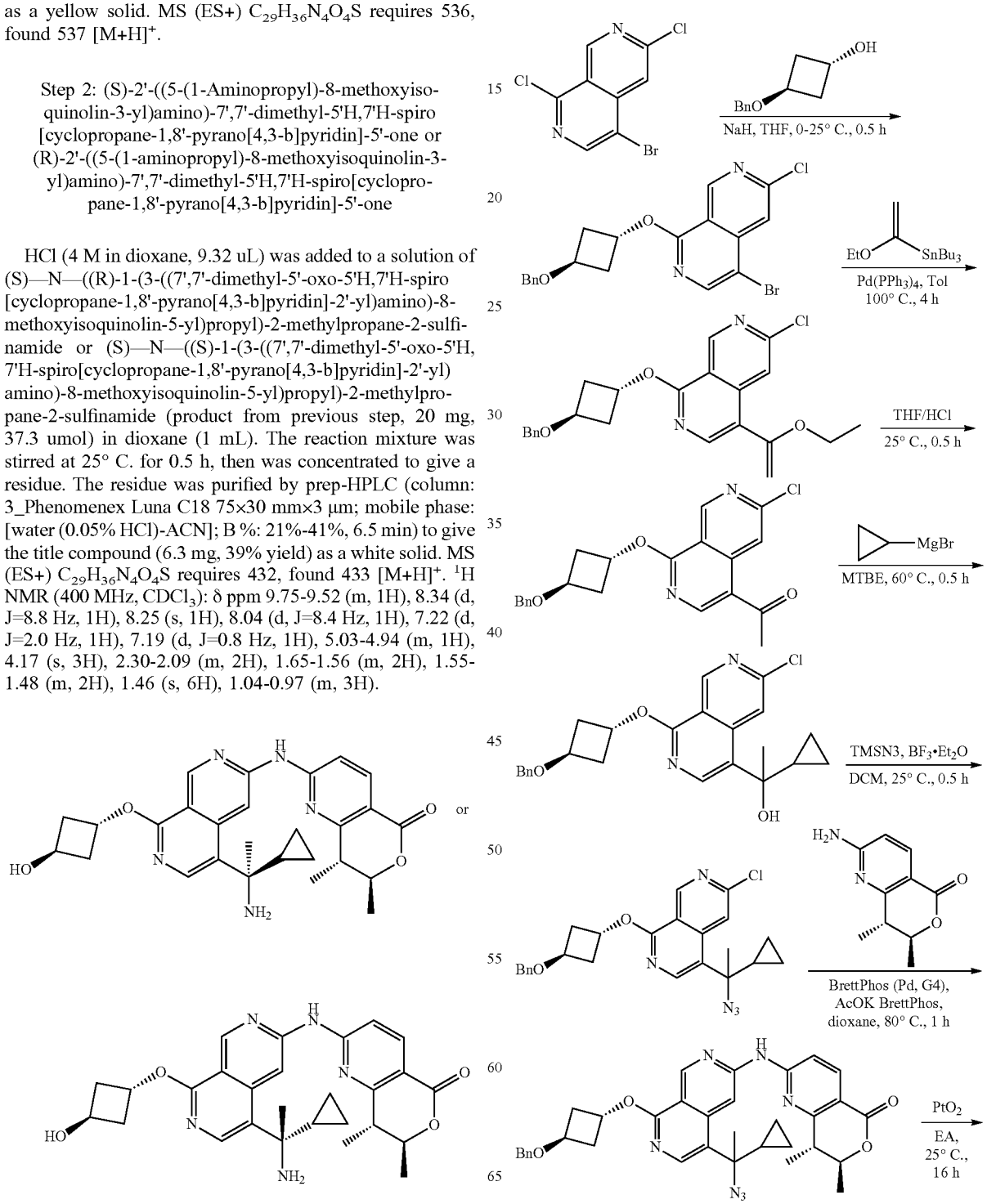

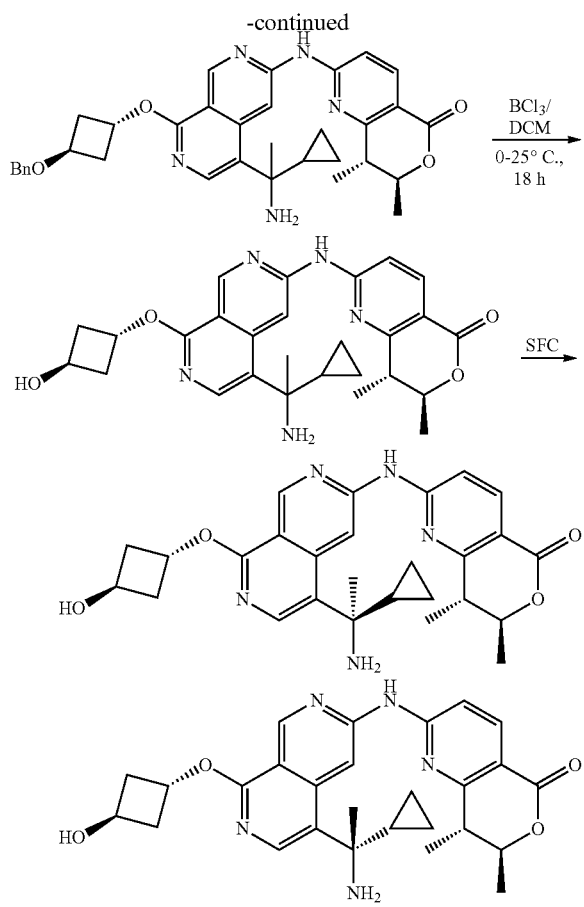

Steps 1-6: (7S,8R)-2-((5-(1-Azido-1-cyclopropyl-ethyl)-8-((trans)-3-(benzyloxy)cyclobutoxy)-2,7-naphthyridin-3-yl)amino)-7,8-dimethyl-7,8-dihydro-5H-pyrano[4,3-b]pyridin-5-one The title compound was prepared from 4-bromo-1,6-dichloro-2,7-naphthyridine and trans-3-(benzyloxy)cyclobutan-1-ol using a similar procedure as described in Steps 1-3 of Intermediate 33 and Steps 1,2, and 4 (except using Intermediate 17) of Example 3B. $^1$H NMR (400 MHz, CD$_3$OD): δ ppm 9.40 (s, 1H), 9.07 (d, J=14.4 Hz, 1H), 8.38 (d, J=10.0 Hz, 1H), 8.25 (d, J=8.8 Hz, 1H), 8.07-8.01 (m, 1H), 7.40-7.29 (m, 5H), 5.67-5.56 (m, 1H), 4.64-4.52 (m, 1H), 4.50 (s, 2H), 4.48-4.40 (m, 1H), 3.11-2.95 (m, 1H), 2.75-2.64 (m, 2H), 2.63-2.52 (m, 2H), 1.62-1.52 (m, 10H), 0.81-0.40 (m, 4H).

Step 7: (7S,8R)-2-((5-(1-Amino-1-cyclopropyl-ethyl)-8-((trans)-3-(benzyloxy)cyclobutoxy)-2,7-naphthyridin-3-yl)amino)-7,8-dimethyl-7,8-dihydro-5H-pyrano[4,3-b]pyridin-5-one To a solution of (7S,8R)-2-((5-(1-azido-1-cyclopropyl-ethyl)-8-((trans)-3-(benzyloxy)cyclobutoxy)-2,7-naphthyridin-3-yl)amino)-7,8-dimethyl-7,8-dihydro-5H-pyrano[4,3-b]pyridin-5-one (180 mg, 297 μmol) in EA (5 mL) was added platinum dioxide (54.0 mg, 238 μmol). The suspension was degassed under vacuum and purged with hydrogen several times. The mixture was stirred under hydrogen (15 psi) at 25° C. for 16 h, then was filtered and concentrated to give a residue. The residue was purified by flash silica gel chromatography (gradient elution, 0100% EA/PE) to give the title compound (75.0 mg, 44% yield) as a yellow solid.

Step 8: (7S,8R)-2-((5-(1-Amino-1-cyclopropyl-ethyl)-8-((trans)-3-hydroxycyclobutoxy)-2,7-naphthyridin-3-yl)amino)-7,8-dimethyl-7,8-dihydro-5H-pyrano[4,3-b]pyridin-5-one To a solution of (7S,8R)-2-((5-(1-amino-1-cyclopropyl-ethyl)-8-((trans)-3-(benzyloxy)cyclobutoxy)-2,7-naphthyridin-3-yl)amino)-7,8-dimethyl-7,8-dihydro-5H-pyrano[4,3-b]pyridin-5-one (60.0 mg, 104 μmol, 1 eq) in DCM (2 mL) was added boron trichloride (901 mg, 7.69 mmol) at 0° C. The mixture was stirred at 25° C. for 18 h, then was quenched with saturated aqueous sodium bicarbonate solution (10 mL) and extracted with DCM (10 mL×3). The combined organic layers were dried over anhydrous sodium sulfate, filtered and concentrated to give a residue. The residue was purified by prep-TLC (EA:MeOH=10:1) to give the title compound as a mixture of diastereomers. (20.0 mg, 40% yield). The mixture was separated by SFC (column: Daicel Chiralpak OD (250 mm*30 mm, 10 um); mobile phase: [0.1% NH$_3$H$_2$O MeOH]) to give (7S,8R)-2-((5-((R)-1-Amino-1-cyclopropylethyl)-8-((trans)-3-hydroxycyclobutoxy)-2,7-naphthyridin-3-yl)amino)-7,8-dimethyl-7,8-dihydro-5H-pyrano[4,3-b]pyridin-5-one or (7S,8R)-2-((5-((S)-1-amino-1-cyclopropylethyl)-8-((trans)-3-hydroxycyclobutoxy)-2,7-naphthyridin-3-yl)amino)-7,8-dimethyl-7,8-dihydro-5H-pyrano[4,3-b]pyridin-5-one (first eluting isomer, 10.0 mg, 50% yield) as a yellow solid and (7S,8R)-2-((5-((R)-1-Amino-1-cyclopropylethyl)-8-((trans)-3-hydroxycyclobutoxy)-2,7-naphthyridin-3-yl)amino)-7,8-dimethyl-7,8-dihydro-5H-pyrano[4,3-b]pyridin-5-one or (7S,8R)-2-((5-((S)-1-amino-1-cyclopropylethyl)-8-((trans)-3-hydroxycyclobutoxy)-2,7-naphthyridin-3-yl)amino)-7,8-dimethyl-7,8-dihydro-5H-pyrano[4,3-b]pyridin-5-one (second eluting isomer, 10.0 mg, 50%) as a yellow solid. MS (ES+) $C_{27}H_{31}N_5O_4$ requires 489, found 490 [M+H]$^+$.
$^1$H NMR (400 MHz, CD$_3$OD): δ ppm 9.40 (s, 1H), 9.01 (s, 1H), 8.16 (d, J=8.8 Hz, 1H), 8.09 (s, 1H), 7.41 (d, J=8.8 Hz, 1H), 5.64-5.53 (m, 1H), 4.70-4.55 (m, 2H), 3.06-2.94 (m, 1H), 2.65-2.45 (m, 4H), 1.80 (s, 3H), 1.65-1.56 (m, 1H), 1.51-1.44 (m, 6H), 0.79-0.48 (m, 4H).

Example 19: Inhibition of MAP4K$_1$ Biochemical Enzymatic Activity

MAP4K$_1$ (HPK1) and relevant off-target enzymatic activity was monitored using the Perkin Elmer electrophoretic mobility shift technology platform—the EZReader 2. Fluorescent labeled substrate peptide was incubated in the presence of kinase and ATP, and in the presence of dosed compound, such that each dose of compound resulted in a reflective proportion of the peptide to be phosphorylated. Within the linear, steady-state phase of the kinase enzymatic reaction, the mixed pool of phosphorylated (product) and non-phosphorylated (substrate) peptides was passed through the microfluidic system of the PerkinElmer EZ Reader 2, under an applied electric potential difference. The presence of the phosphate group on the product peptide provided a difference in mass and charge between that of the substrate peptide, resulting in a separation of the substrate and product pools in the sample (Perrin et al. 2010). As the product and substrate peptide mixture passes the lasers within the instrument, these pools are detected ($\lambda_{ex}$=488 nm, $\lambda_{ent}$=568 nm)

and resolved as separate peaks. The ratio between these peaks reflects the activity of the compound at that concentration, in that well, under those conditions.

Enzyme Activity Inhibition Assay Protocol:

Inhibitors were dissolved in 100% DMSO at a stock concentration of 10 mM. A 100×, 10-point, 4-fold serial dilution of each inhibitor was created in 100% DMSO either manually or on a Hamilton STAR liquid handler, starting at a relevant concentration, usually 1 mM. A volume of 0.130 µL of each concentration was transferred to the relevant wells of a 384-well plate (Greiner 781 201) in duplicate using a TTPLabtech Mosquito nano-litre dispenser. Using a Multidrop Combi, the remaining constituents of the kinase reaction were added to the 130 nL of dosed compound as follows (see table below for final reaction details):

Enzyme activity assays at the $^{APP}K_M$ for ATP or 1 mM ATP: In each well of a 384-well plate, 0.1-15 nM of untreated enzyme was incubated in a total of 13 µL of buffer (100 mM HEPES pH 7.5, 0.015% Brij 35, 10 mM MgCl$_2$, 1 mM DTT) with 1.5 µM fluorescent peptide and 20-1000 µM ATP, at 25° C., for 60-180 minutes in the presence or absence of a dosed concentration series of compound (1% DMSO final concentration). The kinase reactions were stopped by the addition of 70 µl of Stop buffer (100 mM HEPES pH 7.5, 0.015% Brij 35, 35 mM EDTA and 0.2% of Coating Reagent 3 (Caliper Lifesciences)). The plates were read on a Caliper EZReader 2 as described above.

TABLE 2

Kinase Reaction Conditions

| Enzyme (Source) | Enzyme Concentration | ATP Concentration | Substrate Peptide & Concentration | Kinase Reaction Time |
|---|---|---|---|---|
| HPK 1 (Invitrogen) | 0.5 nM | 26 µM | S6K2tide, 1.5 µM | 120 min. |
| HPK 1 (Invitrogen) | 0.25 nM | 1000 µM | S6K2tide, 1.5 µM | 120 min. |
| LCK (Invitrogen) | 12 nM | 26 µM | FL4tide, 1.5 µM | 60 min. |
| HGK (Invitrogen) | 0.1 nM | 50 µM | FL25tide, 1.5 µM | 60 min. |
| GLK (SignalChem) | 15 nM | 20 µM | PKAtide, 2 µM | 180 min. |

S6K$_2$tide; Carna Biosciences (5-FAM-Proprietary Sequence-CONH$_2$)

FL4tide; Perkin Elmer (5-FAM-EGIYGVLFKKK (SEQ ID NO: 1)-CONH$_2$)

FL25tide; Perkin Elmer (5-FAM-VDGKEIYNTIRRK (SEQ ID NO: 2)-CONH$_2$)

PKAtide; Anaspec Peptide Co. (5-FAM-GRTGRRNSI (SEQ ID NO: 3)-CONH$_2$)

Perrin D, Frémaux C, Shutes A. Capillary microfluidic electrophoretic mobility shift assays: application to enzymatic assays in drug discovery. Expert Opin Drug Discov. 2010, 5(1):51-63.

The results obtained ins these experiments for compounds prepared according to the examples are summarized in Table 3 below. For biochemical MAP4K$_1$ activity, the following designations are used: <0.30 nM=A; 0.31-1.0 nM=B; 1.1-10.0 nM=C; and >10.0 nM=D. For IL-2 measurement: <35.0 nM=A; 35.1-45.0 nM=B; 45.1-55.0=C nM; and >55.0 nM=D.

TABLE 3

| Compound No. | MAP4K1 IC$_{50}$ (nM) | MAP4K1 IC$_{50}$ (nM) | IL-2 EC$_{50}$ (nM) | IL-2 EC$_{50}$ (nM) |
|---|---|---|---|---|
| 1 | 21.35 | D | ND | ND |
| 2 | 1.60 | C | 18.9 | A |
| 3 | 0.36 | B | 108.3 | D |
| 4 | 0.42 | B | ND | ND |
| 5 | 0.37 | B | 37.1 | B |
| 6 | 3.31 | C | ND | ND |
| 7 | 0.91 | B | 21.7 | A |
| 8 | 11.14 | D | ND | ND |
| 9 | 0.55 | B | 21.1 | A |
| 10 | 2.73 | C | ND | ND |
| 11 | 0.33 | B | 10.9 | A |
| 12 | 0.31 | B | 11.0 | A |
| 13 | 0.29 | A | ND | ND |
| 14 | 0.64 | B | 51.0 | C |
| 15 | 0.68 | B | 30.9 | A |
| 16 | 2.50 | C | ND | ND |
| 17 | 4.02 | C | ND | ND |
| 18 | 0.40 | B | ND | ND |
| 19 | 0.30 | A | 27.3 | A |
| 20 | 0.73 | B | 51.1 | C |
| 21 | 0.85 | B | 48.7 | C |
| 22 | 0.50 | B | 36.6 | B |
| 23 | 0.11 | A | 4.9 | A |
| 24 | 0.47 | B | 11.3 | A |
| 25 | 0.29 | A | 3.3 | A |
| 26 | 0.55 | B | 14.0 | A |
| 27 | 0.30 | A | ND | ND |
| 28 | 0.67 | B | 31.4 | A |
| 29 | 3.98 | C | ND | ND |
| 30 | 3.57 | C | ND | ND |
| 31 | 5.88 | C | ND | ND |
| 32 | 11.46 | D | ND | ND |
| 33 | 0.13 | A | 9.3 | A |
| 34 | 0.24 | A | 45.6 | B |
| 35 | 0.41 | B | 23.5 | A |
| 36 | 0.17 | A | 15.3 | A |
| 37 | 0.14 | A | 1.9 | A |
| 38 | 0.20 | A | 5.8 | A |
| 39 | 0.85 | B | 16.2 | A |
| 40 | 0.15 | A | 4.0 | A |
| 41 | 0.57 | B | 22.7 | A |
| 42 | 0.86 | B | 13.6 | A |
| 43 | 0.23 | A | 8.3 | A |
| 44 | 1.20 | C | 22.0 | A |
| 45 | 1.03 | B | 70.3 | D |
| 46 | 0.94 | B | 34.3 | A |
| 47 | 13.58 | D | ND | ND |
| 48 | 1.72 | C | 135.5 | D |
| 49 | 1.01 | B | ND | ND |
| 50 | 52.56 | D | ND | ND |
| 51 | 0.26 | A | ND | ND |
| 52 | 0.33 | B | ND | ND |
| 53 | 0.36 | B | 17.2 | A |
| 54 | 0.25 | A | 9.3 | A |
| 55 | 0.18 | A | 11.6 | A |
| 56 | 0.10 | A | 6.6 | A |
| 57 | 0.16 | A | 5.1 | A |
| 58 | 0.39 | B | 20.4 | A |
| 59 | 3.35 | C | 56.7 | D |
| 60 | 0.18 | A | 10.3 | A |
| 61 | 0.15 | A | 3.5 | A |
| 62 | 0.55 | B | ND | ND |
| 63 | 6.46 | C | ND | ND |
| 64 | 0.44 | B | 42.9 | B |
| 65 | 0.56 | B | ND | ND |
| 66 | 0.18 | A | 8.1 | A |
| 67 | 0.12 | A | 6.2 | A |
| 68 | 0.27 | A | 29.5 | A |
| 69 | 0.88 | B | 52.8 | C |
| 70 | 0.35 | B | 20.6 | A |
| 71 | 0.11 | A | 7.9 | A |
| 72 | 0.41 | B | 35.5 | B |
| 73 | 0.22 | A | 23.7 | A |
| 74 | 0.12 | A | 22.2 | A |
| 75 | 0.09 | A | 7.3 | A |
| 76 | 0.12 | A | 6.5 | A |

TABLE 3-continued

| Compound No. | MAP4K1 IC$_{50}$ (nM) | MAP4K1 IC$_{50}$ (nM) | IL-2 EC$_{50}$ (nM) | IL-2 EC$_{50}$ (nM) |
|---|---|---|---|---|
| 77 | 0.65 | B | 32.5 | A |
| 78 | 0.19 | A | 11.6 | A |
| 79 | 0.26 | A | 9.3 | A |
| 80 | 0.08 | A | 4.1 | A |
| 81 | ND | ND | ND | ND |
| 82 | 0.16 | A | 20.8 | A |
| 83 | 0.19 | A | 28.7 | A |
| 84 | 1.32 | C | ND | ND |
| 85 | 0.22 | A | 36.1 | B |
| 86 | 2.03 | C | ND | ND |
| 87 | 0.44 | B | 31.6 | A |
| 88 | 0.16 | A | 11.5 | A |
| 89 | 5.12 | C | ND | ND |
| 90 | 3.42 | C | ND | ND |
| 91 | 0.10 | A | 15.1 | A |
| 92 | 0.25 | A | 15.4 | A |
| 93 | 3.65 | C | ND | ND |
| 94 | 0.14 | A | 23.5 | A |
| 95 | 4.54 | C | ND | ND |
| 96 | 0.14 | A | 9.4 | A |
| 97 | 0.36 | B | ND | ND |
| 98 | 19.1 | D | ND | ND |
| 99 | 0.13 | A | ND | ND |
| 100 | 2.60 | C | ND | ND |
| 101 | 0.11 | A | 20.8 | A |
| 102 | 1.87 | C | 28.7 | A |
| 103 | 0.11 | A | 3.1 | A |
| 104 | 0.13 | A | ND | ND |
| 105 | 2.09 | C | 50.6 | C |
| 106 | 0.61 | B | 41.3 | B |
| 107 | 0.62 | B | ND | ND |
| 108 | 0.98 | B | ND | ND |
| 109 | 0.21 | A | 9.8 | A |
| 110 | 0.55 | B | 33.9 | A |
| 111 | 16.77 | D | 2657 | D |
| 112 | 0.23 | A | 19.6 | A |
| 113 | 0.58 | B | 32.7 | A |
| 114 | 0.88 | B | 25.6 | A |
| 115 | 7.39 | D | 231.5 | D |
| 116 | 2.14 | C | 64.9 | D |
| 117 | 0.24 | A | 16.0 | A |
| 118 | 1.28 | C | 81.7 | D |
| 119 | 0.12 | A | ND | ND |
| 120 | 0.50 | B | ND | ND |
| 121 | 0.90 | B | ND | ND |
| 122 | 0.16 | A | ND | ND |
| 123 | 0.20 | A | 7.6 | A |
| 124 | 0.24 | A | 7.4 | A |
| 125 | 1.84 | C | ND | ND |
| 126 | ND | ND | ND | ND |
| 127 | 0.17 | A | 21.0 | A |
| 128 | 1.09 | C | ND | ND |
| 129 | 0.11 | A | ND | ND |
| 130 | 0.46 | B | ND | ND |
| 131 | 0.46 | B | 35.2 | B |
| 132 | 0.18 | A | 12.9 | A |
| 133 | 5.86 | C | 53.8 | C |
| 134 | 1.33 | C | ND | ND |
| 135 | 0.54 | B | 31.6 | A |
| 136 | 0.39 | B | 40.5 | B |
| 137 | 0.46 | B | ND | ND |
| 138 | 0.27 | A | 13.8 | A |
| 139 | 2.25 | C | ND | ND |
| 140 | 13.94 | D | ND | ND |
| 141 | 0.42 | B | 21.6 | A |
| 142 | 0.20 | A | ND | ND |
| 143 | 0.31 | B | ND | ND |
| 144 | 3.89 | C | ND | ND |
| 145 | 1.77 | C | ND | ND |
| 146 | 0.25 | A | 60.4 | D |
| 147 | 0.27 | A | 45.2 | B |
| 148 | 0.11 | A | ND | ND |
| 149 | 0.20 | A | ND | ND |
| 150 | 5.24 | C | ND | ND |
| 151 | 0.22 | A | 27.3 | A |
| 152 | 0.42 | B | 54.4 | D |
| 153 | 2.61 | C | ND | ND |
| 154 | 0.08 | A | 11.0 | A |
| 155 | 0.97 | B | 88.4 | D |
| 156 | 0.10 | A | 13.6 | A |
| 157 | 0.14 | A | 21.3 | A |
| 158 | 6.46 | C | ND | ND |
| 159 | 0.39 | B | 27.4 | A |
| 160 | 1.25 | C | ND | ND |
| 161 | 1.37 | C | ND | ND |
| 162 | 0.24 | A | ND | ND |
| 163 | 0.25 | A | ND | ND |
| 164 | 7.35 | C | ND | ND |
| 165 | 1.26 | C | ND | ND |
| 166 | 0.25 | A | 40.0 | B |
| 167 | 0.05 | A | 9.4 | A |
| 168 | 0.15 | A | 41.3 | B |
| 169 | 2.94 | C | ND | ND |
| 170 | 0.07 | A | 6.8 | A |
| 171 | 0.07 | A | 27.6 | A |
| 172 | 4.47 | C | 74.8 | D |
| 173 | 1.72 | C | ND | ND |
| 174 | 2.90 | C | 28.2 | A |
| 175 | 35.12 | D | ND | ND |
| 176 | 0.80 | B | 20.9 | A |
| 177 | 6.52 | C | ND | ND |
| 178 | 0.29 | A | 58.7 | D |
| 179 | 2.12 | C | ND | ND |
| 180 | 15.44 | D | ND | ND |
| 181 | 0.18 | A | 15.1 | A |
| 182 | 2.92 | C | 38.8 | B |
| 183 | 26.35 | D | 3.1 | A |
| 184 | 0.27 | A | 33.4 | A |
| 185 | 0.35 | B | ND | ND |
| 186 | 0.40 | B | ND | ND |
| 187 | 0.06 | A | ND | ND |
| 188 | 0.09 | A | 6.8 | A |
| 189 | 0.16 | A | 45.8 | C |
| 190 | 0.19 | A | ND | ND |
| 191 | 0.53 | B | ND | ND |
| 192 | 0.19 | A | 6.6 | A |
| 193 | 0.10 | A | ND | ND |
| 194 | 0.33 | B | ND | ND |
| 195 | 0.27 | A | ND | ND |
| 196 | 0.10 | A | 19.0 | A |
| 197 | 0.34 | B | ND | ND |
| 198 | 0.27 | A | ND | ND |
| 199 | 0.36 | B | ND | ND |
| 200 | 0.48 | B | ND | ND |
| 201 | 0.14 | A | ND | ND |
| 202 | 0.62 | B | ND | ND |
| 203 | 0.50 | B | ND | ND |
| 204 | 0.22 | A | 29.8 | A |
| 205 | 0.35 | B | 112.9 | D |
| 206 | 0.19 | A | ND | ND |
| 207 | 0.22 | A | ND | ND |
| 208 | 0.70 | B | 96.0 | D |
| 209 | 0.39 | B | ND | ND |
| 210 | 0.23 | A | 176.8 | D |

Example 20: T Cell Enhancement of Cytokines

Isolation and Expansion of T Cells from Whole Blood

T cells are isolated from whole blood of healthy donors by immunomagnetic negative selection following manufacture's protocol (StemCell Technologies, human T cell isolation kit). Purity of isolated cells is assessed by flow cytometry and yields 95-98% CD3$^+$ T cells. For expansion of T cells, 1×10$^6$ cells/well are plated in serum free cell expansion media (ThermoFisher) containing 30 U of recombinant human IL2 (R&D) and stimulated with 25 ul of CD3/CD28 beads (Invitrogen) in 24 well plates for 3-4 days. T cells are then expanded in 175 cm flasks and maintained at a cell density of 1 to 2.5×10⁶ cells/ml days by addition of ⅔ of fresh media every 2-3 days. After 10-14 days, cells are frozen in BamBanker freezing media (Thermo) and stored in liquid nitrogen. Phenotypic analysis of expanded T cells by flow cytometry, routinely shows 60% cells are CD8⁺ T cells upon freezing.

Cytokine Measurement

For IL2 measurement, expanded CD3⁺ T cells are dispensed at 100K cells/well (cultured in X-VIVO 10 Serum-free media) and are stimulated with plate-bound anti-CD3 and soluble anti-CD28 in the presence of vehicle or compound of the disclosure at various concentrations for 24 h. As outlined in the manufacturer's protocol (Cisbio), 16 µL of conditioned media is transferred to a white 384-well low volume plate. Following a 24 h incubation with the anti-IL2 antibodies, the homogenous time resolved fluorescence (HTRF) is measured.

Example 21: Inhibition of Anti-Tumor Activity in a Syngeneic Mouse Model

Generation of the MCA205 Syngeneic Xenograft Anti-Tumor Efficacy Study

Six to eight-week-old female, $C_{57}BL/6$ mice (Jackson Labs, Bar Harbor, Me.) are implanted subcutaneously on the left flank with 1×10⁶ MCA205 cells/mouse. After tumors reach an average volume of 50 mm³, mice are randomized into treatment groups, 10 mice per group, with tumors in the size range of 30-70 mm³. Compounds of the disclosure 10-30 mg/kg, anti-mouse PD-L1 mAb (B7H₁, clone #10F.9G2 Bio-X-cell, Lebanon, N.H.) and vehicle either alone or in different combinations are administered to tumor bearing mice. Reduction in tumor volume is measured [mm³] over time.

EQUIVALENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those skilled in the art will recognize or be able to ascertain using no more than routine experimentation, many equivalents to the specific embodiments of the disclosure described and claimed herein. Such equivalents are intended to be encompassed by the following claims.

What is claimed is:

1. A compound of formula I:

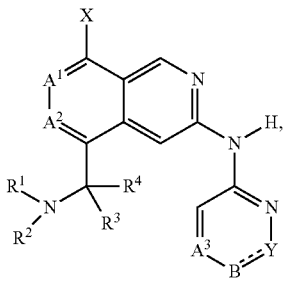

I or a pharmaceutically acceptable salt thereof,
wherein:
$A^1$ and $A^2$ are selected from N and CH;
$A^3$ is selected from CH and N;
X is selected from $C_{1-3}$ alkyl, $OR^6$, $NHR^7$ and halogen;
B is selected from $CR^{11}$ and N, Y is selected from N and $CR^{12}$, and the bond between Y and B is a double bond; or
B is C(O), Y is $NR^{14}$, and the bond between Y and B is a single bond; or Y and B taken together form a 5 to 7-membered heterocycle or $C_{5-6}$ cycloalkyl, and the bond between Y and B is a double bond, wherein said heterocycle or cycloalkyl is optionally substituted with 1-6 $R^8$;
each $R^8$ is independently selected from $C_{1-3}$ alkyl and OH, or
two $R^8$ attached to the same carbon form an oxo, or
two $R^8$ attached to the same carbon atom taken together with the carbon atom to which they are attached form a $C_{3-5}$ cycloalkyl, or
two $R^8$ attached to two adjacent carbon atoms taken together with the two adjacent carbon atoms to which they are attached form a $C_{3-6}$ cycloalkyl, wherein said alkyl and cycloalkyl are optionally substituted with 1-6 halogen;
$R^1$ and $R^2$ are each independently selected from hydrogen, $C_{1-4}$ alkyl, $C_{3-5}$ cycloalkyl, and 3 to 5-membered heterocycle, wherein said alkyl and cycloalkyl are optionally substituted with OH, $C_{1-6}$alkoxy or 1-6 halogen; or $R^1$ and $R^2$, taken together with the atoms to which they are attached, form a 4 to 6-membered heterocycle or $C_{3-6}$ cycloalkyl;
$R^3$ and $R^4$ are each independently selected from hydrogen, $C_{1-6}$ alkyl substituted with $OR^{16}$, $C_{1-6}$ alkyl, $C_{3-6}$ cycloalkyl and 4 to 6-membered heterocycle; or
$R^3$ and $R^4$, taken together with the atoms to which they are attached, form a $C_{3-6}$ cycloalkyl or 4 to 6-membered heterocycle; or
$R^1$ and $R^3$, taken together with the atoms to which they are attached, form a 3 to 6-membered heterocycle;
$R^6$ is selected from $C_{1-3}$ alkyl, $C_{3-6}$ cycloalkyl and 4 to 6-membered heterocycle, wherein said alkyl, cycloalkyl, and heterocycle are optionally substituted with 1-3 $R^9$;
$R^7$ is selected from hydrogen, $C_{1-3}$ alkyl, $C_{3-5}$ cycloalkyl and 4 to 6-membered heterocycle, wherein said alkyl, cycloalkyl, and heterocycle are optionally substituted with 1-3 $R^9$;
$R^9$ is selected from $C_{1-3}$ alkyl, $C_{3-6}$ cycloalkyl substituted with halogen, halogen, $C_{1-3}$ alkoxy, and OH;
$R^{11}$ is selected from hydrogen, COON, CN, halogen, and $C_{1-3}$ alkoxy;
$R^{12}$ is selected from $C_{1-5}$ alkyl, $C_{4-6}$ cycloalkyl, 3 to 6-membered heterocycle, $NHR^{13}$, $NR^{13}R^{13}$ and $OR^{13}$, wherein said alkyl, cycloalkyl or heterocycle is optionally substituted with OH, $NH_2$, 1-4 halogen or $R^{15}$;
each $R^{13}$ is independently selected from $C_{1-6}$ alkyl and $C_{3-6}$ cycloalkyl, wherein said alkyl or cycloalkyl is optionally substituted with halogen;
$R^{14}$ is selected from $C_{1-6}$ alkyl, $C_{3-6}$ cycloalkyl and 4 to 6-membered heterocycle, wherein said alkyl, cycloalkyl or heterocycle is optionally substituted with 1-6 halogen;
$R^{15}$ is OH, $C_{1-3}$ alkyl or $C_{3-5}$ cycloalkyl; and
$R^{16}$ is H or $C_{1-3}$ alkyl.

2. The compound of claim 1, or a pharmaceutically acceptable salt thereof,
wherein:
X is selected from $OR^6$, $NHR^7$ and halogen; and
$R^3$ and $R^4$ are each independently selected from hydrogen, $C_{1-6}$ alkyl substituted with OH, $C_{1-6}$ alkyl, $C_{3-6}$ cycloalkyl and 4 to 6-membered heterocycle; or
$R^3$ and $R^4$, taken together with the atoms to which they are attached, form a $C_{3-6}$ cycloalkyl or 4 to 6-membered heterocycle; or $R^1$ and $R^3$, taken together with the atoms to which they are attached, form a 3 to 6-membered heterocycle.

3. The compound of claim 2, wherein the compound is represented by Formula II, Formula III or Formula IV:

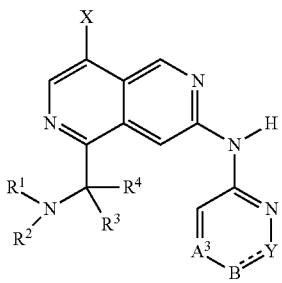

II

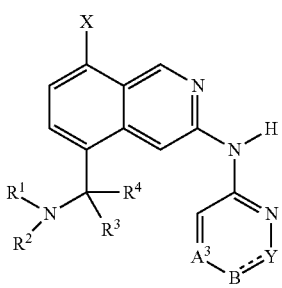

III

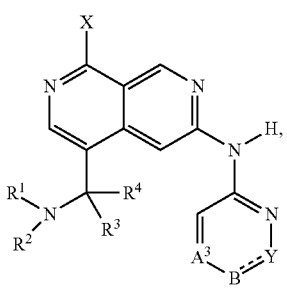

IV or a pharmaceutically acceptable salt thereof.

4. The compound of claim 3, wherein the compound is represented by Formula V or VI:

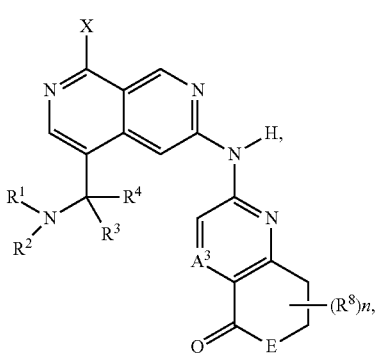

V

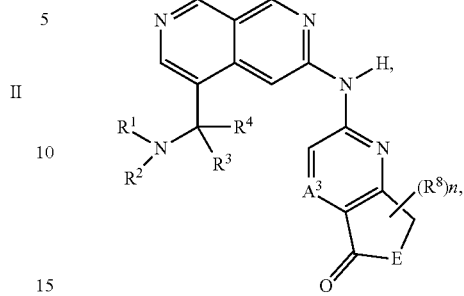

VI or a pharmaceutically acceptable salt thereof, wherein E is $CH_2$, NH, or O; $R^8$ is $C_{1-3}$ alkyl, and n is 0 to 4; two $R^8$ groups attached to the same carbon atom taken together with the carbon atom to which they attach form a $C_{3-5}$ cycloalkyl; or two $R^8$ groups attached to two adjacent carbon atoms taken together with the two adjacent carbon atoms to which they attached form a $C_{4-6}$ cycloalkyl.

5. The compound of claim 4, wherein the compound is represented by Formula V(B) or VI(B):

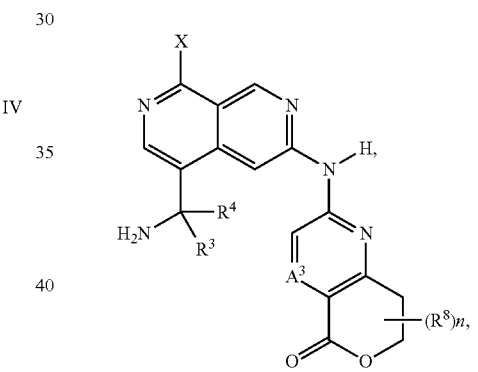

V(B)

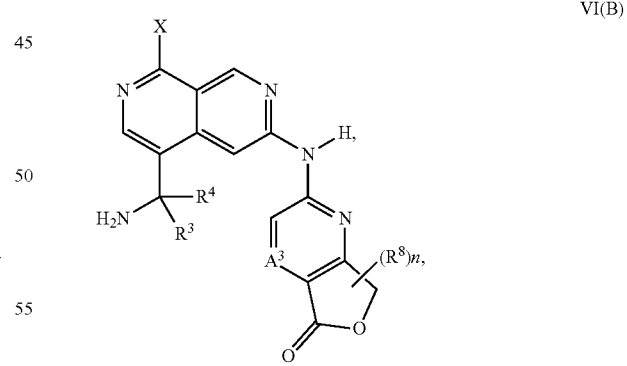

VI(B)

or a pharmaceutically acceptable salt thereof.

6. The compound of claim 5, or a pharmaceutically acceptable salt thereof, wherein $R^8$ is methyl and n is 0, 1, 2, 3, or 4.

7. The compound of claim 5, or a pharmaceutically acceptable salt thereof, wherein two $R^8$ attached to the same carbon atom taken together with the carbon atom to which they are attached form a cyclopropyl; or two $R^8$ attached to two adjacent carbon atoms taken together with the two adjacent carbon atoms to which they are attached form a cyclopentyl.

8. The compound of claim 3, wherein the compound is represented by Formula VII, VIII or IX:

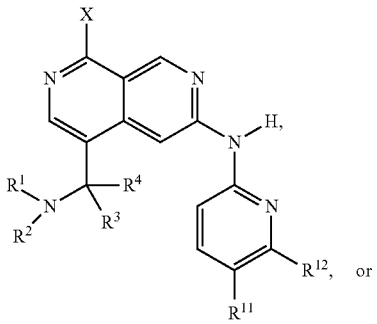

VII

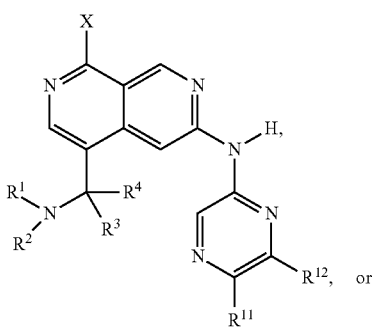

VIII

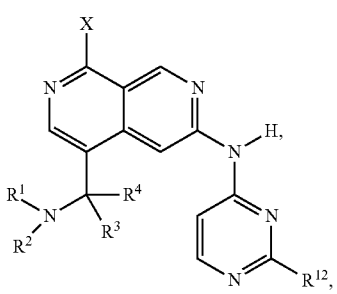

IX or a pharmaceutically acceptable salt thereof.

9. The compound of claim 8, or a pharmaceutically acceptable salt thereof, wherein:

$R^{11}$ is CN; and $R^{12}$ is selected from isopropyl, fluoropropyl, trifluoroisopropyl, isobutyl, tert-butyl, isopropyloxy, methylpyrrolidine, methylazetidine, and hydroxycyclohexyl.

10. The compound of claim 3, wherein the compound is represented by Formula X:

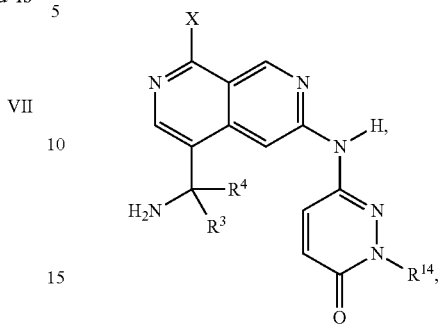

or a pharmaceutically acceptable salt thereof.

11. The compound of claim 10, or a pharmaceutically acceptable salt thereof, wherein $R^{14}$ is isobutyl.

12. The compound of claim 3, or a pharmaceutically acceptable salt thereof, wherein X is $OR^6$, and $R^6$ is selected from methyl, ethyl, propyl, isopropyl, trifluoroethyl, trifluoroisopropyl, difluoroethyl, difluoropropyl, difluoroisopropyl, oxetanyl, tetrahydrofuranyl, cyclobutyl, and cyclopropyl, wherein cyclopropyl is optionally substituted with methyl or one or two fluoro, wherein cyclobutyl is optionally substituted with OH, and wherein oxetanyl is optionally substituted with methyl.

13. The compound of claim 3, or a pharmaceutically acceptable salt thereof, wherein X is $NHR^7$, and $R^7$ is selected from methyl, ethyl, cyclopropyl and cyclobutyl.

14. The compound of claim 3, or a pharmaceutically acceptable salt thereof, wherein X is methyl.

15. The compound of claim 3, or a pharmaceutically acceptable salt thereof, wherein $R^3$ and $R^4$ are each independently selected from hydrogen, methyl, methyl substituted with $OCH_3$, ethyl, hydroxymethyl, cyclopropyl and cyclobutyl.

16. The compound of claim 1, wherein the compound is:

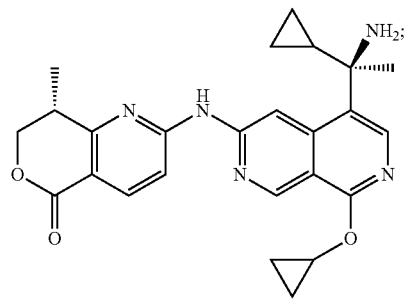 [SMILES: C[C@H]1COC(=O)c2ccc(Nc3cc4c([C@](C)(N)C5CC5)cnc(OC5CC5)c4cn3)nc21]

or a pharmaceutically acceptable salt thereof.

17. The compound of claim 1, wherein the compound is:

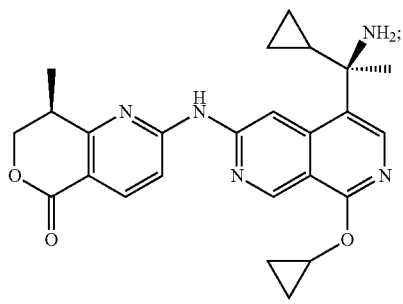 [SMILES: C[C@@H]1COC(=O)c2ccc(Nc3cc4c([C@](C)(N)C5CC5)cnc(OC5CC5)c4cn3)nc21]

or a pharmaceutically acceptable salt thereof.

18. The compound of claim 1, wherein the compound is:

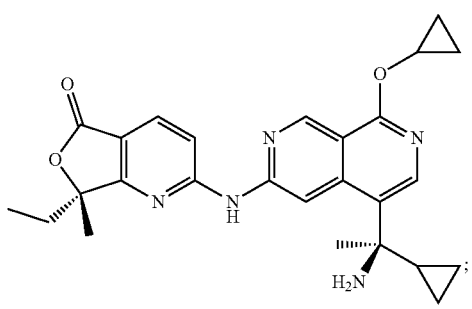 [SMILES: CC[C@]1(C)OC(=O)c2ccc(Nc3cc4c([C@](C)(N)C5CC5)cnc(OC5CC5)c4cn3)nc21]

or a pharmaceutically acceptable salt thereof.

19. The compound of claim 1, wherein the compound is:

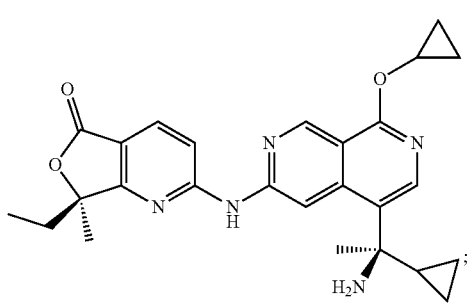 [SMILES: CC[C@@]1(C)OC(=O)c2ccc(Nc3cc4c([C@](C)(N)C5CC5)cnc(OC5CC5)c4cn3)nc21]

or a pharmaceutically acceptable salt thereof.

20. The compound of claim 1, wherein the compound is:

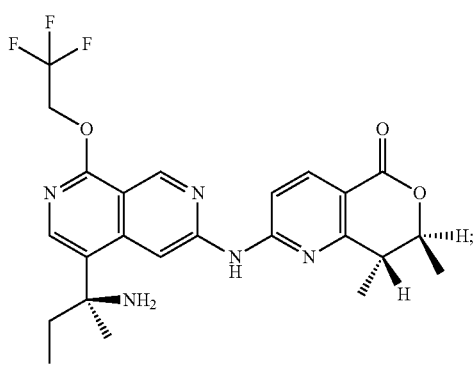

or a pharmaceutically acceptable salt thereof.

21. The compound of claim 1, wherein the compound is:

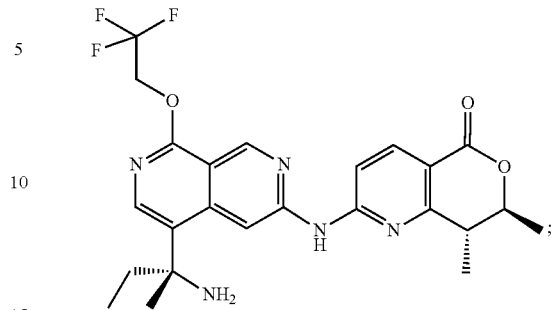

or a pharmaceutically acceptable salt thereof.

22. The compound of claim 1, wherein the compound is:

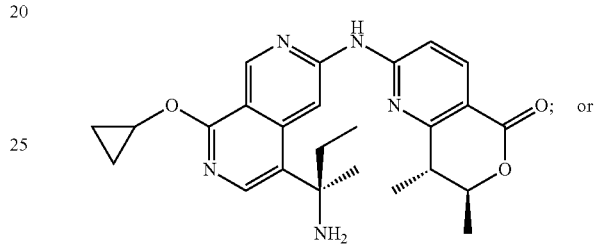

a pharmaceutically acceptable salt thereof.

23. The compound of claim 1, wherein the compound is:

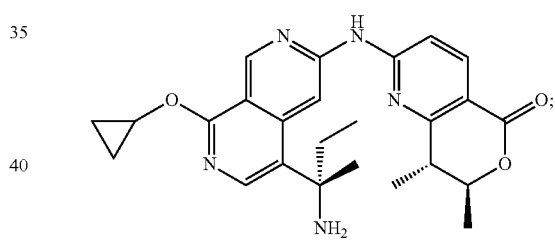

or a pharmaceutically acceptable salt thereof.

24. The compound of claim 1, wherein the compound is:

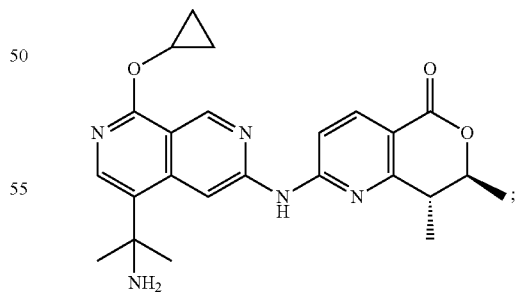

or a pharmaceutically acceptable salt thereof.

25. A pharmaceutical composition comprising the compound of claim 1, or a pharmaceutically acceptable salt thereof, and a pharmaceutically acceptable carrier or excipient.

* * * * *

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Glu Gly Ile Tyr Gly Val Leu Phe Lys Lys Lys
1               5                   10

<210> SEQ ID NO 2
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 2

Val Asp Gly Lys Glu Ile Tyr Asn Thr Ile Arg Arg Lys
1               5                   10

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Arg Thr Gly Arg Arg Asn Ser Ile
1               5
```